[19] United States Patent
Fischer

[11] Patent Number: 6,156,567
[45] Date of Patent: Dec. 5, 2000

[54] TRUNCATED TRANSCRIPTIONALLY ACTIVE CYTOMEGALOVIRUS PROMOTERS

[75] Inventor: Laurent Fischer, Albany, N.Y.

[73] Assignee: Merial, Lyons, France

[21] Appl. No.: 08/675,556

[22] Filed: Jul. 3, 1996

[51] Int. Cl.[7] ........................ A61K 39/235; C07H 21/04; C07K 14/075; C12N 5/16
[52] U.S. Cl. .................. 435/325; 435/235.1; 435/320.1; 424/199.1; 424/233.1; 536/24.1; 536/23.1; 514/44
[58] Field of Search ............................ 424/233.1, 199.1; 435/235.1, 325, 320.1; 536/24.1, 23.1; 514/44

[56] References Cited

U.S. PATENT DOCUMENTS

| | | | |
|---|---|---|---|
| 4,963,481 | 10/1990 | deVilliers | 435/69.1 |
| 5,122,458 | 6/1992 | Post et al. | 435/69.1 |
| 5,273,876 | 12/1993 | Hock et al. | |
| 5,585,237 | 12/1996 | Oppermann et al. | 435/6 |
| 5,616,326 | 4/1997 | Spibey | 424/199.1 |
| 5,641,662 | 6/1997 | Debs et al. | |

OTHER PUBLICATIONS

Ablett, R.E. and L.A. Baker. 1960. Veterinary Record, 72, 1202.

Bass, E.P., M.A. Gill and W.H. Beckenhauer. 1980. Evaluation of canine adenovirus type 2 as a replacement for infectious canine hepatatis vaccine. J. Am. Vet. Med. Assoc., 177, 234–242.

Bett, A.J., L. Prevec and F.L. Graham. 1993. Packaging capacity and stability of human adenovirus type 5 vectors. J. Virol., 67, 5911–5921.

Boshart, M., F. Weber, G. Jahn, K. Dorsh–Häsler, B. Fleckenstein and W. Schaffner. 1985. A very strong enhancer is located upstream of an immediate early gene of human cytomegalovirus. Cell, 41, 521–530.

Both, G.W., L.J. Lockett, V. Janardhana, S.J. Edwards, A.R. Bellamy, F.L. Graham, L. Prevec and M.E. Andrew. 1993. Protective immunity to rotavirus–induced diarrhoea is passively transferred to newborn mice from naive dams vaccinated with single dose of a recombinant adenovirus expressing rotavirus VP7sc. Virology, 193, 940–950.

Breker–Klassen, M., Yoo, D., Mittal, S.K., Sorden, S.D., Haines, D.M. and L.A. Babiuk. 1995. Recombinant type 5 adenovirus expressing bovine parainfluenza virus type 3 glycoproteins protect *Sigmodon hispidus* cotton rat from bovine parainfluenza virus type 3 infection. J. Virol., 69, 4308–4315.

Cavanagh, H.M.A., C.F. Gallagher and N. Spibey. 1991. A mutant of canine adenovirus type 2 with a duplication of the E1a region exhibits altered expression of early region 4. J. Gen. Virol., 72, 2121–2127.

Chanda, P.K., Natuk, R.J., B.B. Mason, B.M. Bhat, L. Greenberg, S.K. Dheer, K.L. Molnar–Kimber, S. Mizutani, M.D. Lubeck, A.R. Davis and P.P. Hung. 1990. High level expression of the envelope glycoprotein of the human immunodeficiency virus type I in presence of rev gene using helper–independent adenovirus type 7 recombinants. Virology, 175, 535–547.

Chengalvala, M., M.D. Lubeck, A.R. Davis, S. Mizutani, K. Molnar–Kimber, J. Morin, and P.P. Hung. 1991. Evaluation of adenovirus type 4 and type 7 recombinant hepatitis B vaccines in dogs. Vaccine, 9, 485–490.

Chengalvala, M.V., B.M. Bhat, R. Bhat, M.D. Lubeck, S. Mizutani, A.R. Davis and P.P. Hung. 1994. Immunogenicity of high expression adenovirus–hepatatis B virus recombinant vaccines in dogs. J. Gen. Virol., 75, 125–131.

Danskin, D. 1973. Isolation of canine adenovirus A26/61 (Toronto) using canine kidney (MDCK) cell line. The Veterinary Record, 126–127.

Darteil, R., Bublot, M., Laplace, E., J.–F. Bouquet, J.–C. Audonnet and M. Riviere. 1995. Herpesvirus of turkey recombinant viruses expressing infectious bursal disease virus (IBDV) VP2 immunogen induce protection against an IBDV virulent challenge in chickens. Virology 211, 481–490.

Dewar, R.L., V. Natarajan, M.B. Vasudevachari and N.P. Salzman. 1989. Synthesis and processing of human immunodeficiency virus type 1 envelope proteins encoded by recombinant human adenovirus. J. Virol., 63, 129–136.

Ditchfield, J., L.W. MacPerson and A. Zbitnew. 1962. Association of a canine adenovirus (Toronto A26/61) with an outbreak of laryngotracheitis ("kennel cough"). Can. Vet. Jour., 3, 238–247.

Dorsch–Häsler, K., G.M. Keil, F. Weber, M. Jasin, W. Schaffner and U.H. Koszinowski. 1985. A long and complex enhancer activates transcription of the gene coding for the highly abundant early mRNA in murine cytomegalovirus. Proc. Natl. Acad. Sci., 82, 8325–8329.

(List continued on next page.)

*Primary Examiner*—Frank C. Eisenschenk
*Assistant Examiner*—Phuong T. Bui
*Attorney, Agent, or Firm*—Frommer Lawerence & Haug, LLP; William S. Frommer; Thomas J. Kowalski

[57] ABSTRACT

Recombinant adenoviruses, methods of making them, uses for them, including in immunological, immunogenic, vaccine or therapeutic compositions, or, as a vector for cloning, replicating or expressing DNA and methods of using the compositions and vector, expression products from them, and uses for the expression products are provided. More particularly, recombinant canine adenoviruses (CAV) and methods of making them, uses for them, expression products from them, and uses for the expression products, including recombinant CAV2 viruses are provided. Additionally, truncated promoters, expression cassettes containing the promoters, and recombinant viruses and plasmids containing the promoters or expression cassettes are provided.

15 Claims, 97 Drawing Sheets

OTHER PUBLICATIONS

Edbauer, C., R. Weinberg, J. Taylor, A. Rey–Senelonge, J–F. Bouquet, P. Desmettre and E. Paoletti. 1990. Protection of chickens with a recombinant fowlpox virus expressing the newcastle disease virus hemagglutinin–neuraminidase gene. Virology, 179, 901–904.

Eloit, M. , P. Gilardi–Hebenstreit, B. Toma and M. Perricaudet. 1990. Construction of a defective adenovirus vector expressing the pseudorabies virus glycoprotein gp50 and its use as a live vaccine. J. Gen. Virol., 71, 2425–2431.

Fairchild, G.A. and D. Cohen. 1969. Serological study of a canine adenovirus (Toronto A26/61) infection in dogs. Am. J. Vet. Res., 30, 923–928.

Gallichan, W.S., D.C. Johnson, F.L. Graham and K.L. Rosenthal. 1993. Mucosal immunity and protection after intranasal immunization with recombinant adenovirus expressing herpes simplex virus glycoprotein B. J. of Infect. Dis. 168, 622–629.

Garcia–Sastre, A. and P. Palese. 1995. Influenza virus vectors. Biologicals, 23, 171–178.

Gillard, S., Spehner, D., Drillien, R., and Kirn, A., Proc. Natl. Acad. Sci. USA 83, 5573–5577 (1986).

Goebel, S.J., Johnson, G.P., Perkus, M.E., Davis, S.W., Winslow, J.P., Paoletii, E., Virology 179, 247–266 (1990a).

Goebel, S.J., G.P. Johnson, M.E. Perkus, S.W. Davis, J.P. Winslow and E. Paoletti, Virology 179, 517–563 (1990b).

Ginsberg, H.S. , U. Lundholm–Beauchamp, R.L. Horswood, B. Pernis, W.S.M. Wold, R.M. Chanock and G.A. Prince. 1989. Role of early region 3 (E3) in pathogenesis of adenovirus disease. Proc. Natl. Acad. Sci. USA, 86, 3823–3827.

Gibard, M., R. Altmeyer, S. van der Werf, C. Wychowski and A. Martin. 1995. The use of picornaviruses as vectors for the engineering of live recombinant vaccines. Biologicals, 23, 165–169.

Gorman, C.M., D. Gies, G. McCray and M. Huang. 1989. The human cytomegalovirus major immediate early promoter can be trans–activated by adenovirus early proteins. Virology, 171, 377–385.Graham, F.L. , L.A. Prevec, M. Scheider, G. Ghosh–Choudhury, M. McDermott, and D.C. Johnson. 1988. Cloning and expression of glycoprotein genes in human adenovirus vectors. In: Technological Advances in Vaccine Development, 243–253.

Graham, F. L., J. Smiley, W. C. Russell and R. Nairn. 1977. Characteristics of a human cell line transformed by human adenovirus 5. J. Gen. Virol., 36, 59–72.

Graham, F. L., J. Smiley, W.C. Russel and Nairn. 1977. Characteristics of a human cell line transformed by human adenovirus 5. J. Gen. Virol, 36, 59–72.

Grand, R. J. A. 1987. The structure and function of the adenovirus early region 1 proteins. Biochem. J. , 241, 25–38.

Haddada, H., B. Klonjkowski and M. Perricaudet. 1994. Adenoviral vectors of animal origin and use in gene therapy. Patent # W094/26914.

Haj–Ahmad, Y. and F.L. Graham. 1986. Development of a helper–independent human adenovirus vector and its use in the transfer of herpes simplex virus thymidine kinase gene. J. Virol., 57, 267–274.

Hsu, K.–H.L., M.D. Lubeck, B.M. Bhat, R.A. Bhat, B. Kostek, B.H. Selling, S. Mizutani; A.R. Davis and P.P. Hung. 1994. Efficacy of adenovirus–vectored syncytial virus vaccines in a new ferret model. Vaccine, 12, 607–612.

Imler, J–L. 1995. Adenovirus vectors as recombinant viral vaccines. Vaccine, 13, 1143–1151.

Imperiale, M., G. Akusjarvi and K. Leppard. 1995. Post–transcriptional control of adenovirus gene expression. Curr. Top. Microbiol. Immunol., 199, 139–171.

Johnson, D.C., G. Ghosh–Choudhury, J.R. Smiley, L. Fallis and F.L. Graham. 1988. Abundant expression of herpes simplex virus glycoprotein gB using an adenovirus vector. Virology, 164, 1–14.

Jouvenne, P., M. Dion and C. Hamelin. 1987. Cloning, physical mapping and cross–hybridization of the canine adenovirus types 1 and 2 genomes. Gene, 60, 21–28.

Kelly, T.J., Jr. and A.M. Lewis, Jr. 1973. Use of nondefective adenovirus–simian virus 40 hybrids for mapping the simian virus 40 genome. J. Virol., 12, 643–652.

Kit, M., S. Kit, S.P. Little, R.D. Di Marchi, and C. Gale. 1991. Bovine herpesvirus–1 (infectious bovine rhinotracheitis virus)–based viral vector which expresses foot–and–mouth disease epitopes. Vaccine, 9, 564–572.

Koptopoulos, G. and H. J. C. Cornwell. 1981. Veterinary bulletin, 51, 135–142.Lafemina, R.L, M.C. Pizzorno, J.D. Mosca and G.S. Hayward. 1989. Expression of the acidic nuclear immediate early protein (IE1) of human cytomegalovirus in stable cell lines and its preferential association with metaphase chromosomes. Virology, 172, 584–600.

Linne, T. 1992. Differences in E3 region of the canine adenovirus type 1 and type 2. Virus Research, 23, 119–133.

Lubeck, M.D. , A.R. Davis, M. Chengalvala, R.J. Natuk, J.E. Morin, K. Molnar–Kimber, B.B. Mason, B.M. Bhat, S. Mizutani, P.P. Hung and R.H. Purcell. 1989. Immunogenicity and efficacy testing in chimpanzees of an oral hepatitis B vaccine based on a live recombinant adenovirus. Proc. Natl. Acad. Sci. USA, 86, 6763–6767.

Lubeck, M.D. , R.J. Natuk, M. Chengalvala, P.K. Chanda, K.K. Murthy, S. Murthy, S. Mizutani, S.–G. Lee, M.S. Wade, B.M. Bhat, R. Bhat, S.K. Dheer, J.W. Eichberg, A.R. Davis and P.P. Hung. 1994. Immunogenicity of recombinant adenovirus–human immunodeficiency virus vaccines in chimpanzees following intranasal administration. AIDS. Res. Hum. Retr., 10, 1443–1449.

MaCartney, L. , H.M.A. Cavanagh and N. Spibey. 1988. Isolationof canine adenovirus–2 from foeces of dogs with enteric disease and its unambigous typing by restriction endonuclease mapping. Research in Veterinary Science, 44, 9–14.

McDermott, M.R., F.L. Graham, T. Hanke and D.C. Johnson. 1989. Protectiuon of mice against lethal challenge with.

Mettenleiter, T.C., B.G. Klupp, F. Weiland and N. Visser. 1994. Characterization of a quadruple glycoprotein–deleted pseudorabies virus mutant for use as a biologically safe live virus vaccine. 75, 1723–1733.herpes simplex by vaccination with an adenovirus vector expressing HSV glycoprotein B. Virology, 169, 244–247.

Mittal, S.K., A.J. Bett, L. Prevec and F.L. Graham. 1995b. Foreign gene expression by human adenovirus type 5–based vectors studied using firefly luciferase and bacterial β–galactosidase genes as reporters. Virology, 210, 226–230.

Mittal, S.K., L. Prevec, F.L. Graham and L.A. Babiuk. 1995a. Development of a bovine adenovirus type 3–based expression vector. J. Gen. Virol., 76, 93–102.

Morin, J.E. , M.D. Lubeck, J.E. Barton, A.J. Conley, A.R. Davis and P.P. Hung. 1987. Recombinant adenovirus induces antibody response to hepatatis B virus surface antigen in hamsters. Proc. Natl. Acad. Sci. USA, 84, 4626–4630.

Mueller, R.E., R.L. Muldoon and G.G. Jackson. 1969. Communicability of enteric live adenovirus type 4 vaccine in families. J. Infect. Dis., 119, 60–66.

Natuk, R.J., M.D. Lubeck, P.K. Chanda, M. Chengalvala, M.S. Wade, S.C.S. Murthy, J. Wilhelm, S.K. Vernon, S.K. Dheer, S. Mizutani, S.–G. Lee, K.K. Murthy, J.W. Eichberg, A.R. Davis and P.P. Hung. 1993. Immunogenicity of recombinant human adenovirus–human immunodeficiency virus vaccines in chimpanzees. AIDS. Res. Hum. Retr., 9, 395–404.

Nevins, J.R. 1993. Transcriptional activation by the adenovirus E1A prteins. Seminars in Virology, 4, 25–31.

Oualikene, W., P. Gonin and M. Eloit. 1994. Short and long term dissemination of deletion mutants of adenovirus in permissive (cotton rat) and non–permissive (mouse) species. J. Gen. Virol., 75, 2765–2768.

Perkus, M.E., Limbach, K., and Paoletti, E., J. Virol. 63, 3829–3836 (1989).

Perkus, M.E., J. Tartaglia and E. Paoletti. 1995. Poxvirus–based vaccine candidates for cancer, AIDS, and other infectious diseases. J. Leuk. Biol., 58, 1–13.

Perkus, M.E., E.B. Kauffman, J. Taylor, S. Mercer, D. Smith, J. Vanderhoeven, and E. Paoletti. 1993. Methodology of using vaccinia virus to express foreign genes in tissue culture. J. Tiss. Cult. Meth. 15:72–81.

Perricaudet, M. and L.D. Stratford–Perricaudet. 1995. Adenovirus–mediated in vivo gene therapy. In: Viruses in human gene therapy. Caroline Academic Press, 1–32.

Prevec, L., M. Schneider, K.L. Rosenthal, L.W. Belbeck, J.B. Derbyshire and F.L. Graham. 1989. Use of human adenovirus–based vectors for antigen expression in animals. J. Gen. Virol., 70, 429–434.

Ragot, T. , S. Finerty, P.E. Watkins, M. Perricaudet and A.J. Morgan. 1993. Replication–defective recombinant adenovirus expressing the Epstein–Barr virus (EBV) envelope glycoprotein gp340/220 induces protective immunity against EBV–induced lymphomas in cottontop tamarin. J. Gen. Virol., 74, 501–507.

Randrianarison–Jewtoukoff, V. and M. Perricaudet. 1995. Recombinant adenovirus as vaccines. Biologicals, 23, 145–157.

Robinson, A.J., H.B. Younghusband and A.J.D. Bellett. 1973. A circular DNA–protein complex from adenoviruses. Virology, 56, 54–69.

Ross, L.J.N., M.M. Binns, P. Tyers, J. Pastorek, V. Zelnik and S. Scott. 1993. Construction and properties of a turkey herpesvirus recombinant expressing the Marek's disease virus homolgue of glycoprotein B of herpes simplex virus. J. Gen. Virol. 74, 371–377.

Saito, I. , Y. Oya, K. Yamamoto, T. Yuasa and H. Shimojo. 1985. Construction of nondefective adenovirus type 5 bearing a 2.8 kilobase hepatatis B virus DNA near the right end of its genome. J. Virol. , 54, 711–719.

Schwartz, A.R., Y. Togo and R.B. Hornick. 1974. Clinical evaluation of live types 1, 2 and 5 adenovirus vaccines. Am. Rev. Resp. Dis., 109, 233–.

Sedegah, M., C.H. Chiang, W.R. Weiss, S. Mellouk, M.D. Cochran, R.A. Houghten, the late R.L. Beudoin, D. Smith, and S.L. Hoffman. 1992. recombinant pseudorabies virus carrying a plasmodium gene: herpesvirus as a new live viral vector for inducing T– and B–cell immunity. Vaccine, 10, 578–584.

Sharp, P. 1984. Adenovirus transcription. In: The adenovirus, Ed. H. S. Ginsberg, Plenun Press, New–York and London. pp. 173–204.

Spibey, N. and H.M.A. Cavanagh. 1989. Molecular cloning and restriction endonuclease mapping of two strains of canine adenovirus type 2. J. Gen. Virol., 70, 165–172.

Summer, J.W. , J.H. Shaddock, G.–J. Wu and G.M. Baer. 1988. Oral administration of an attenuated strain of canine adenovirus (type 2) to raccoons, foxes, shunk and mongoose. Am. J. Vet. Res., 49, 169–171.

Taylor, J., C. Trimarchi, R. Weinberg, B. Languet, F. Guillemin, P. Desmettre and E. Paoletti. 1991. Efficacy studies on a canarypox–rabies recombinant virus, Vaccine, 9, 190–193.

Thummel, C., R. Tjian, S.–L. Hu, and T. Grodzicker. 1983. Translational control of SV40 T antigen expressed from the adenovirus late promoter, Cell, 33, 455–464.

Top, Jr. F.H., R.A. Grossman, P.J. Bartelloni, H.E. Segal, B.A. Dudding, P.K. Russell and E.L. Buescher. 1971b. Immunization with live types 7 and 4 vaccines. I. Safety, infectivity, antigenicity and potency of adenovirus type 7 vaccine in humans. J. Inf. Dis., 124, 148–154.

Top, Jr., F.H. , E.L. Buescher, W.H. Bancroft and P K. Russell. 1971a. Immunization with live types 7 and 4 vaccines. II. Antibody response and protective effect against accutate respiratory disease due to adenovirus type 7. J. Inf. Dis., 124, 155–160.

Wesseling, J.G. , G.–J. Godeke, V.E.C.J. Schijns, L. Prevec, F.L. Graham, M.C. Horzinek and P.J.M. Rottier. 1993. Mouse hepatatis virus spike and nucleocapsid proteins expressed by adenovirus vectors protect mice against a lethal infection. J. Virol., 74, 2061–2069.

Wold, W.S.M. and L.R. Gooding. 1991. Minireview: Region E3 of adenovirus: A cassette of genes involved in host immunosurveillance and virus–cell interactions. Virology, 184, 1–8.

Xu, Z.Z., V. Krougliak, L. Prevec, F.L. Graham and G.W. Both. 1995. Investigation of promoter function in human and animal cells infected with human recombinant adenoviruses expressing rotovirus antigen VP7sc. J. Gen. Virol., 76, 1971–1980.

Zhang, Y. and R.J. Schneider. 1993. Adenovirus inhibition of cellular protein synthesis and the specific translation of late viral mRNAs. Seminars in Virology, 4, 229–236.

FIG. IA

```
   1 GGAAATTGTA AACGTTAATA TTTTGTTAAA ATTCGCGTTA AATTTTTGTT
  51 AAATCAGCTC ATTTTTTAAC CAATAGGCCG AAATCGGCAA AATCCCTTAT
 101 AAATCAAAAG AATAGACCGA GATAGGGTTG AGTGTTGTTC CAGTTTGGAA
 151 CAAGAGTCCA CTATTAAAGA ACGTGGACTC CAACGTCAAA GGGCGAAAAA
 201 CCGTCTATCA GGGCGATGGC CCACTACGTG AACCATCACC CTAATCAAGT
 251 TTTTTGGGGT CGAGGTGCCG TAAAGCACTA AATCGGAACC CTAAAGGGAG
 301 CCCCCGATTT AGAGCTTGAC GGGGAAAGCC GGCGAACGTG GCGAGAAAGG
 351 AAGGGAAGAA AGCGAAAGGA GCGGGCGCTA GGGCGCTGGC AAGTGTAGCG
 401 GTCACGCTGC GCGTAACCAC CACACCCGCC GCGCTTAATG CGCCGCTACA
 451 GGGCGCGTCG CGCCATTCGC CATTCAGGCT GCGCAACTGT TGGGAAGGGC
 501 GATCGGTGCG GGCCTCTTCG CTATTACGCC AGCTGGCGAA AGGGGGATGT
 551 GCTGCAAGGC GATTAAGTTG GGTAACGCCA GGGTTTTCCC AGTCACGACG
 601 TTGTAAAACG ACGGCCAGTG AATTGTAATA CGACTCACTA TAGGGCGAAT
 651 TGGGTACCGG GCCCCCCCTC GAGGTCGACG GTATCGATAA GCTTGCTCA
 701 ACAAATACTG TCAAGGACTC GAGTCCGGCT CTGACTGAGC AATGTCTAAA
 751 GAAATACCAA CCCCTTATAT GTGGAGCTAC CAACCGCAAA CGGGACACGC
 801 CGGCGCCTCC CAGGACTACT CCACCCAAAT GAATTGGTTT AGTGCTGGGC
 851 CATCAATGAT TAGTCAAGTT TATGGCATTA GAGACTTGCG CAACAAAGTT
 901 TTGATAACCC AGGCAGAAAT AACCAAAACT CCCAGAACAA TAATGGATCC
 951 GCCAATTTGG CCAGCTGCCA TGCTTGTTCA GGAAGCCGCC CCACCCAAAA
1001 CGGTCACTCT GCCCAGAAAC CACACCCTAG AACAGGCTAT GACCAACTCT
1051 GGGGCGCAGC TAGCGGGAGG ACGACAGCTG TGCCCCTCCC AAATAGGTAT
1101 AAAAAGCCCA GTGCTGGCTG GCACGGGCAT TCAGCTTAGC GAAGACATCC
1151 CCAGCGCCTC CTGGATCAGG CCCGACGGCA TATTCCAGCT AGGAGGGGGG
1201 TCTCGCTCGT CCTTCAGCCC AACGCAAGCA TTCCTCACCC TGCAACAGGC
1251 ATCCTCGACG CCGCGCGCAG GAGGCGTGGG CACCTACCAG TTTGTGCGCG
1301 AATTTGTGCC AGAGGTATAC CTTAACCCTT TTCAGGACC ACCGGACACC
1351 TTTCCTGATC AGTTCATTCC TAACTACGAC ATTGTAACCA ACTCTGTCGA
1401 TGGCTATGAC TGAGGAGAGC ATGGACCAGG TGGAGGTGAA CTGCCTGTGT
1451 GCTCAGCATG CCCAAACCTG CACGCGCCCT CGCTGCTTTG CAAAGGAGGG
1501 TTTATGTGCT AACTGGTTTT ACAACCCAGC ACTTGCCTTT GAAGGGTTTG
1551 ATATTCCAGA CTCTTACCAA GAGGGACACG GTGTGGACAT AGAAGTTAAG
1601 TGTTCCCACC ACTCCAGCAA ACTGTGCCAC AATGGCCATG ATATGATCTG
1651 CTCATACTCT CGCCTGGGAT CCCACATTAA CATAAGATGT ATTTGCAACA
1701 AGCCGCGGCC CCACATGAGC CTCATTGAGG CAGCCGTTC TATGTATAAC
1751 CTTAACTAGA TAATATTATT AAACTTGTTT TACAGCTACC ACCATAATGC
1801 GCTTCAGCTT CTTCATCGCC GCCGTTCTTT TCTGCACCAC AGGGGCCAGC
1851 AATGACATTG TGACTTGCTG CGCCCACACA CCTTGCCTCC TACACCTAGA
```

FIG. 1B

```
1901 AGTGGGCTTG GGGGCCAATG TCAGTTGGAT AAACTCTGAC ACAGGCCAGG
1951 CCCCGATTTG CCTCTCCAAT GGCATGTGCA ACGCTACCCA GCAAGGCCTG
2001 CAGTTTTCTG CAAACTTTTC TGAGGATGGC CTGTACATCG CCCTCATTAA
2051 GGAGAGCAAC TACGAGGGCG CTGAGCACTA CTACCTTGTC TATATTTATG
2101 GAGACTGCTA CCAAACTGCA AATGAGTCTG CCCACGGGCC TATTTCCAGG
2151 CCCCTCAACG AGATGCCTCT TCCAGCGTA ACCATAAATG CTTCCCTCTT
2201 CTATCCCGCC TTTCTGGAGC TGCCCCCACA GTACAGCAAT GACCTTAGCA
2251 ATGTGCGCTG GTATAAAGTA GACCCCAGCG GCTTCCAAGC CCAAAAAATC
2301 TCTAAAGTCA GAAGCGGAGG CAGAAAAGAG AACCTGCATC CCAACTGGGC
2351 CTTGGTTACC TATACTGGAG ACCTTCTTGT CTTGCATGTT TCGCCAAACA
2401 CCCTTGGACT GTGGCTGGCA GCCGTGCAGC ATCGCGGGG GCGCACTAAT
2451 TTCATTACCT TCAACATAAC TGTACCCAAC TGGCAACAAA ATCTAGTAAC
2501 CATATTTAAT CAACACGAGC CCCCAAAAAA GGGCGATAAT TATGAGGACA
2551 GTTTTATGGA ATGGACTCTG TTTAAAAAGC TCAAAAAAGG CTTATTTAGA
2601 GTAACTTGCA GAGCCAAGTC AATATTCCCA GAGTGCGTCC TCAACATCAC
2651 CCGCGACGGA ACTTTCCTGC TTATTGGGGA TAGCAAAAAG ACCCCCTATG
2701 TCATCCTGCT GCCCTTTTTT GCAAACCCCA AGAAGACAC TCCAATTTTA
2751 ATGGCCCTTA GCCATTCCAT GCCCGTCGCC ATACCTGACA CTGCAATGCC
2801 TATATATATT TCCATCATGT TTTTATTGT GGCCATGCTA GCCACCCTCA
2851 GCCTTCTAAT GGGACTAAAC AACAAAATCA GGCCCATGTA GCTTGTCAAA
2901 TAAACTTACC TAATTTTTGC TAAGACGTCT GGGTCCTGCG TTTCTATGTC
2951 CACCAAAGTC CCCTCTTCCC AGCTTTGGTA CTTCCACTTG TGCGCGCGAG
3001 CCAGCTTGCG GATGTGCTTG AAAGATAATG TGGTCTCTCC CAACAGCTTC
3051 CCGTTCACCA GCACCAGGGC CATGAAGCGG ACACGAAGAG CTCTACCTGC
3101 AAATTATGAC CCTGTATATC CATACGACGC CCCCGGGTCT TCCACACAAC
3151 CCCCTTTTTT TAATAACAAG CAAGGTCTCA CTGAGTCACC CCCAGGAACC
3201 CTGGCTGTCA ATGTTTCCCC TCCACTAACC TTTTCTACGT TAGGTGCCAT
3251 TAAACTTTCC ACAGGTCCCG GACTCACCCT CAACGAGGGC AAGTTACAAG
3301 CCAGCTTAGG GCCCGGCCTC ATCACAAATA CCGAGGGCCA AATCACTGTT
3351 GAAAATGTCA ACAAGGTTTT GTCTTTTACC TCCCCATTAC ATAAAAATGA
3401 AAACACTGTA TCCCTAGCGC TAGGAGATGG GTTAGAAGAT GAAAATGGCA
3451 CCCTTAAAGT GACCTTCCCT ACTCCCCCTC CCCCGCTACA ATTCTCCCCT
3501 CCCCTCACAA AAACAGGTGG TACTGTTTCC TTGCCCCTGC AAGACTCCAT
3551 GCAAGTGACA AATGGAAAAC TGGGCGTTAA GCTACCACCT ACGCACCTCC
3601 CTTGAAAAAA ACTGACCAGC AAGTTAGCCT CCAAGTAGGC TCGGGTCTCA
3651 CCGTGATTAA CGAACAGTTG CAAGCTGTCC AGCCTCCCGC AACCACCTAC
3701 AACGAGCCTC TTTCCAAAAC TGACAATTCT GTTTCTCTGC AAGTAGGTGC
3751 CGGCCTTGCC GTGCAGAGCG GACGTTTGGT GGCAACCCCT CCCCGCCTC
3801 TCACCTTTAC ATCACCCCTA GAAAAAAATG AAAACACAGT GTCGCTACAA
3851 GTAGGCGCGG GCTTGTCTGT ACAAACAAC GCCCTAGTAG CCACACCTCC
3901 CCCACCCTTA ACCTTTGCCT ATCCCTTAGT AAAAAATGAC AACCATGTAG
3951 CTCTAAGTGC TGGAAGTGGT TTAAGAATAT CTGGAGGCAG CCTCACGGTG
4001 GCCACTGGAC CTGGCCTTTC CCATCAAAAT GGAACAATAG GGCTGTAGT
4051 AGGTGCAGGC CTCAAGTTTG AAAACAATGC CATTCTTGCA AAACTAGGCA
4101 ACGGTCTAAC CATTAGAGAT GGCGCTATTG AAGCAACCCA ACCCCAGCT
4151 GCCCCATAA CACTGTGGAC AGGGCCTGGC CTAGCATTAA TGGCTTTATG
4201 TAATGACACT CCAGTAATTA GGTNCTTTAT ATGCCTAACC AGAGACAGCA
4251 ACTTAGTCAC AGTAAATGCT AGCTTTGTGG GAGAGGGGGG GTATCGAATA
4301 GTCAGCCCTA CCCAGTCACA ATTTAGCCTA ATTATGGAGT TTGATCAGTT
4351 TGGACAGCTT ATGTCCACAG GAAACATTAA CTCCACCACT ACTTGGGGAG
4401 AAAAGCCCTG GGGCAATAAC ACTGTACAGC CACGCCAAG CCACACCTGG
4451 AAACTGTGCA TGCCTAACAG AGAAGTTTAC TCCACTCCCG CCGCCACCAT
4501 CACCCGCTGT GGACTAGACA GCATTGCAGT CGACGGTGCC CAGCAGAAGT
```

FIG. IC

```
4551 ATCGACTGCA TGCTAATTAT TAACAAACCA AAAGGCGTTG CCACTTACAC
4601 CCTTACCTTT AGGTTTTTAA ACTTTAACAG ACTAAGCGGA GGTACCCTGT
4651 TTAAAACTGA TGTCTTAACC TTTACCTATG TAGGCGAAAA TCAATAAAAC
4701 CAGAAAAAAA TAAGGGGAAA AGCTTGATAT CGAATTCCTG CAGCCCGGGG
4751 GATCCACTAG TTCTAGAGCG GCCGCCACCG CGGTGGAGCT CCAGCTTTTG
4801 TTCCCTTTAG TGAGGGTTAA TTCCGAGCTT GGCGTAATCA TGGTCATAGC
4851 TGTTTCCTGT GTGAAATTGT TATCCGCTCA CAATTCCACA CAACATACGA
4901 GCCGGAAGCA TAAAGTGTAA AGCCTGGGGT GCCTAATGAG TGAGCTAACT
4951 CACATTAATT GCGTTGCGCT CACTGCCCGC TTTCCAGTCG GGAAACCTGT
5001 CGTGCCAGCT GCATTAATGA ATCGGCCAAC GCGCGGGGAG AGGCGGTTTG
5051 CGTATTGGGC GCTCTTCCGC TTCCTCGCTC ACTGACTCGC TGCGCTCGGT
5101 CGTTCGGCTG CGGCGAGCGG TATCAGCTCA CTCAAGGCG GTAATACGGT
5151 TATCCACAGA ATCAGGGGAT AACGCAGGAA AGAACATGTG AGCAAAAGGC
5201 CAGCAAAAGG CCAGGAACCG TAAAAAGGCC GCGTTGCTGG CGTTTTTCCA
5251 TAGGCTCCGC CCCCCTGACG AGCATCACAA AAATCGACGC TCAAGTCAGA
5301 GGTGGCGAAA CCCGACAGGA CTATAAAGAT ACCAGGCGTT TCCCCCTGGA
5351 AGCTCCCTCG TGCGCTCTCC TGTTCCGACC CTGCCGCTTA CCGGATACCT
5401 GTCCGCCTTT CTCCCTTCGG GAAGCGTGGC GCTTTCTCAT AGCTCACGCT
5451 GTAGGTATCT CAGTTCGGTG TAGGTCGTTC GCTCCAAGCT GGGCTGTGTG
5501 CACGAACCCC CCGTTCAGCC CGACCGCTGC GCCTTATCCG GTAACTATCG
5551 TCTTGAGTCC AACCCGGTAA GACACGACTT ATCGCCACTG GCAGCAGCCA
5601 CTGGTAACAG GATTAGCAGA GCGAGGTATG TAGGCGGTGC TACAGAGTTC
5651 TTGAAGTGGT GGCCTAACTA CGGCTACACT AGAAGGACAG TATTTGGTAT
5701 CTGCGCTCTG CTGAAGCCAG TTACCTTCGG AAAAAGAGTT GGTAGCTCTT
5751 GATCCGGCAA ACAAACCACC GCTGGTAGCG GTGGTTTTTT TGTTTGCAAG
5801 CAGCAGATTA CGCGCAGAAA AAAGGATCT CAAGAAGATC CTTTGATCTT
5851 TTCTACGGGG TCTGACGCTC AGTGGAACGA AAACTCACGT TAAGGGATTT
5901 TGGTCATGAG ATTATCAAAA AGGATCTTCA CCTAGATCCT TTTAAATTAA
5951 AAATGAAGTT TTAAATCAAT CTAAAGTATA TATGAGTAAA CTTGGTCTGA
6001 CAGTTACCAA TGCTTAATCA GTGAGGCACC TATCTCAGCG ATCTGTCTAT
6051 TTCGTTCATC CATAGTTGCC TGACTCCCCG TCGTGTAGAT AACTACGATA
6101 CGGGAGGGCT TACCATCTGG CCCCAGTGCT GCAATGATAC CGCGAGACCC
6151 ACGCTCACCG GCTCCAGATT TATCAGCAAT AAACCAGCCA GCCGGAAGGG
6201 CCGAGCGCAG AAGTGGTCCT GCAACTTTAT CCGCCTCCAT CCAGTCTATT
6251 AATTGTTGCC GGGAAGCTAG AGTAAGTAGT TCGCCAGTTA ATAGTTTGCG
6301 CAACGTTGTT GCCATTGCTA CAGGCATCGT GGTGTCACGC TCGTCGTTTG
6351 GTATGGCTTC ATTCAGCTCC GGTTCCCAAC GATCAAGGCG AGTTACATGA
6401 TCCCCCATGT TGTGCAAAAA AGCGGTTAGC TCCTTCGGTC CTCCGATCGT
6451 TGTCAGAAGT AAGTTGGCCG CAGTGTTATC ACTCATGGTT ATGGCAGCAC
6501 TGCATAATTC TCTTACTGTC ATGCCATCCG TAAGATGCTT TTCTGTGACT
6551 GGTGAGTACT CAACCAAGTC ATTCTGAGAA TAGTGTATGC GGCGACCGAG
6601 TTGCTCTTGC CCGGCGTCAA TACGGGATAA TACCGCGCCA CATAGCAGAA
6651 CTTTAAAAGT GCTCATCATT GGAAAACGTT CTTCGGGGCG AAAACTCTCA
6701 AGGATCTTAC CGCTGTTGAG ATCCAGTTCG ATGTAACCCA CTCGTGCACC
6751 CAACTGATCT TCAGCATCTT TTACTTTCAC CAGCGTTTCT GGGTGAGCAA
6801 AAACAGGAAG GCAAAATGCC GCAAAAAAGG GAATAAGGGC GACACGGAAA
6851 TGTTGAATAC TCATACTCTT CCTTTTTCAA TATTATTGAA GCATTTATCA
6901 GGGTTATTGT CTCATGAGCG GATACATATT TGAATGTATT TAGAAAAATA
6951 AACAAATAGG GGTTCCGCGC ACATTTCCCC GAAAAGTGCC ACCTG
```

E3 Region
726 to 2257

E3 ORF1
733 to 1067

E3 ORF2
1109 to 2203

E3 ORF3
1744 to 1208

FIG. 3A

```
   1 TCGACGGTAT CGATAAGCTT TGCTCAACAA ATACTGTCAA GGACTCGAGT
  51 CCGGCTCTGA CTGAGCAATG TCTAAAGAAA TACCAACCCC TTATATGTGG
 101 AGCTACCAAC CGCAAACGGG ACACGCCGGC GCCTCCCAGG ACTACTCCAC
 151 CCAAATGAAT TGGTTTAGTG CTGGGCCATC AATGATTAGT CAAGTTTATG
 201 GCATTAGAGA CTTGCGCAAC AAAGTTTTGA TAACCCAGGC AGAAATAACC
 251 AAAACTCCCA GAACAATAAT GGATCCGCCA ATTTGGCCAG CTGCCATGCT
 301 TGTTCAGGAA GCCGCCCAC CCAAAACGGT CACTCTGCCC AGAAACCACA
 351 CCCTAGAACA GGCTATGACC AACTCTGGGG CGCAGCTAGC GGGAGGACGA
 401 CAGCTGTGCC CCTCCCAAAT AGGTATAAAA AGCCCAGTGC TGGCTGGCAC
 451 GGGCATTCAG CTTAGCGAAG ACATCCCCAG CGCCTCCTGG ATCAGGCCCG
 501 ACGGCATATT CCAGCTAGGA GGGGGGTCTC GCTCGTCCTT CAGCCCAACG
 551 CAAGCATTCC TCACCCTGCA ACAGGCATCC TCGACGCCGC GCGCAGGAGG
 601 CGTGGGCACC TACCAGTTTG TGCGCAATT TGTGCCAGAG GTATACCTTA
 651 ACCCTTTTTC AGGACCACCG GACACCTTTC CTGATCAGTT CATTCCTAAC
 701 TACGACATTG TAACCAACTC TGTCGATGGC TATGACTGAG GAGAGCATGG
 751 ACCAGGTGGA GGTGAACTGC CTGTGTGCTC AGCATGCCCA AACCTGCACG
 801 CGCCCTCGCT GCTTTGCAAA GGAGGGTTTA TGTGCTAACT GGTTTTACAA
 851 CCCAGCACTT GCCTTTGAAG GGTTTGATAT TCCAGACTCT TACCAAGAGG
 901 GACACGGTGT GGACATAGAA GTTAAGTGTT CCCACCACTC CAGCAAACTG
 951 TGCCACAATG GCCATGATAT GATCTGCTCA TACTCTCGCC TGGGATCCCA
1001 CATTAACATA AGATGTATTT GCAACAAGCC GCGGCCCCAC ATGAGCCTCA
1051 TTGAGGCAGC CTGTTCTATG TATAACCTTA ACTAGATAAT ATTATTAAAC
1101 TTGTTTTACA GCTACCACCA TAATGCGCTT CAGCTTCTTC ATCGCCGCCG
1151 TTCTTTTCTG CACCACAGGG GCCAGCAATG ACATTGTGAC TTGCTGCGCC
1201 CACACACCTT GCCTCCTACA CCTAGAAGTG GGCTTGGGGG CCAATGTCAG
1251 TTGGATAAAC TCTGACACAG GCCAGGCCCC GATTTGCCTC TCCAATGGCA
1301 TGTGCAACGC TACCCAGCAA GGCCTGCAGT TTTCTGCAAA CTTTTCTGAG
1351 GATGGCCTGT ACATCGCCCT CATTAAGGAG AGCAACTACG AGGGCGCTGA
1401 GCACTACTAC CTTGTCTATA TTTATGGAGA CTGCTACCAA ACTGCAAATG
1451 AGTCTGCCCA CGGGCCTATT TCCAGGCCCC TCAAAGATCT GCTAATGGAA
1501 CGCGTATCGC TGCCCCACA GTACAGCAAT GACCTTAGCA ATGTGCGCTG
1551 GTATAAAGTA GACCCCAGCG GCTTCAAGC CCAAAAAATC TCTAAAGTCA
1601 GAAGCGGAGG CAGAAAAGAG AACCTGCATC CCAACTGGGC CTTGGTTACC
1651 TATACTGGAG ACCTTCTTGT CTTGCATGTT TCGCCAAACA CCCTTGGACT
1701 GTGGCTGGCA GCCGTGCAGC ATCGCGGGG GCGCACTAAT TTCATTACCT
1751 TCAACATAAC TGTACCCAAC TGGCAACAAA ATCTAGTAAC CATATTTAAT
1801 CAACACGAGC CCCCAAAAAA GGGCGATAAT TATGAGGACA GTTTATGGA
1851 ATGGACTCTG TTTAAAAAGC TCAAAAAGG CTTATTTAGA GTAACTTGCA
1901 GAGCCAAGTC AATATTCCCA GAGTGCGTCC TCAACATCAC CCGCGACGGA
1951 ACTTTCCTGC TTATTGGGGA TAGCAAAAAG ACCCCCTATG TCATCCTGCT
2001 GCCCTTTTTT GCAAACCCCA AAGAAGACAC TCCAATTTTA ATGGCCCTTA
2051 GCCATTCCAT GCCCGTCGCC ATACCTGACA CTGCAATGCC TATATATATT
2101 TCCATCATGT TTTTTATTGT GGCCATGCTA GCCACCCTCA GCCTTCTAAT
```

FIG.3B

```
2151 GGGACTAAAC AACAAAATCA GGCCCATGTA GCTTGTCAAA TAAACTTACC
2201 TAATTTTTGC TAAGACGTCT GGGTCCTGCG TTTCTATGTC CACCAAAGTC
2251 CCCTCTTCCC AGCTTTGGTA CTTCCACTTG TGCGCGCGAG CCAGCTTGCG
2301 GATGTGCTTG AAAGATAATG TGGTCTCTCC CAACAGCTTC CCGTTCACCA
2351 GCACCAGGGC CATGAAGCGG ACACGAAGAG CTCTACCTGC AAATTATGAC
2401 CCTGTATATC CATACGACGC CCCCGGGTCT TCCACACAAC CCCCTTTTTT
2451 TAATAACAAG CAAGGTCTCA CTGAGTCACC CCCAGGAACC CTGGCTGTCA
2501 ATGTTTCCCC TCCACTAACC TTTTCTACGT TAGGTGCCAT TAAACTTTCC
2551 ACAGGTCCCG GACTCACCCT CAACGAGGGC AAGTTACAAG CCAGCTTAGG
2601 GCCCGGCCTC ATCACAAATA CCGAGGGCCA AATCACTGTT GAAAATGTCA
2651 ACAAGGTTTT GTCTTTTACC TCCCCATTAC ATAAAAATGA AAACACTGTA
2701 TCCCTAGCGC TAGGAGATGG GTTAGAAGAT GAAAATGGCA CCCTTAAAGT
2751 GACCTTCCCT ACTCCCCCTC CCCCGCTACA ATTCTCCCCT CCCTCACAA
2801 AAACAGGTGG TACTGTTTCC TTGCCCCTGC AAGACTCCAT GCAAGTGACA
2851 AATGGAAAAC TGGGCGTTAA GCTACCACCT ACGCACCTCC CTTGAAAAAA
2901 ACTGACCAGC AAGTTAGCCT CCAAGTAGGC TCGGGTCTCA CCGTGATTAA
2951 CGAACAGTTG CAAGCTGTCC AGCCTCCCGC AACCACCTAC AACGAGCCTC
3001 TTTCCAAAAC TGACAATTCT GTTTCTCTGC AAGTAGGTGC CGGCCTTGCC
3051 GTGCAGAGCG GACGTTTGGT GGCAACCCCT CCCCCGCCTC TCACCTTTAC
3101 ATCACCCCTA GAAAAAATG AAAACACAGT GTCGCTACAA GTAGGCGCGG
3151 GCTTGTCTGT ACAAAACAAC GCCCTAGTAG CCACACCTCC CCCACCCTTA
3201 ACCTTTGCCT ATCCCTTAGT AAAAAATGAC AACCATGTAG CTCTAAGTGC
3251 TGGAAGTGGT TTAAGAATAT CTGGAGGCAG CCTCACGGTG GCCACTGGAC
3301 CTGGCCTTTC CCATCAAAAT GGAACAATAG GGCTGTAGT AGGTGCAGGC
3351 CTCAAGTTTG AAAACAATGC CATTCTTGCA AAACTAGGCA ACGGTCTAAC
3401 CATTAGAGAT GGCGCTATTG AAGCAACCCA ACCCCCAGCT GCCCCCATAA
3451 CACTGTGGAC AGGGCCTGGC CTAGCATTAA TGGCTTTATG TAATGACACT
3501 CCAGTAATTA GGTNCTTTAT ATGCCTAACC AGAGACAGCA ACTTAGTCAC
3551 AGTAAATGCT AGCTTTGTGG GAGAGGGGGG GTATCGAATA GTCAGCCCTA
3601 CCCAGTCACA ATTTAGCCTA ATTATGGAGT TTGATCAGTT TGGACAGCTT
3651 ATGTCCACAG GAAACATTAA CTCCACCACT ACTTGGGGAG AAAAGCCCTG
3701 GGGCAATAAC ACTGTACAGC CACGCCCAAG CCACACCTGG AAACTGTGCA
3751 TGCCTAACAG AGAAGTTTAC TCCACTCCCG CCGCCACCAT CACCCGCTGT
3801 GGACTAGACA GCATTGCAGT CGACGGTGCC CAGCAGAAGT ATCGACTGCA
3851 TGCTAATTAT TAACAAACCA AAAGGCGTTG CCACTTACAC CCTTACCTTT
3901 AGGTTTTTAA ACTTTAACAG ACTAAGCGGA GGTACCCTGT TTAAAACTGA
3951 TGTCTTAACC TTTACCTATG TAGGCGAAAA TCAATAAAAC CAGAAAAAAA
4001 TAAGGGGAAA AGCTTGATAT CGAATTCCTG CAGCCCGGGG GATCCACTAG
4051 TTCTAGAGCG GCCGCCACCG CGGTGGAGCT CCAGCTTTTG TTCCCTTTAG
4101 TGAGGGTTAA TTCCGAGCTT GGCGTAATCA TGGTCATAGC TGTTTCCTGT
4151 GTGAAATTGT TATCCGCTCA CAATTCCACA CAACATACGA GCCGGAAGCA
4201 TAAAGTGTAA AGCCTGGGGT GCCTAATGAG TGAGCTAACT CACATTAATT
4251 GCGTTGCGCT CACTGCCCGC TTTCCAGTCG GGAAACCTGT CGTGCCAGCT
4301 GCATTAATGA ATCGGCCAAC GCGCGGGGAG AGGCGGTTTG CGTATTGGGC
4351 GCTCTTCCGC TTCCTCGCTC ACTGACTCGC TGCGCTCGGT CGTTCGGCTG
4401 CGGCGAGCGG TATCAGCTCA CTCAAAGGCG GTAATACGGT TATCCACAGA
4451 ATCAGGGGAT AACGCAGGAA AGAACATGTG AGCAAAAGGC CAGCAAAAGG
4501 CCAGGAACCG TAAAAAGGCC GCGTTGCTGG CGTTTTTCCA TAGGCTCCGC
4551 CCCCCTGACG AGCATCACAA AAATCGACGC TCAAGTCAGA GGTGGCGAAA
4601 CCCGACAGGA CTATAAAGAT ACCAGGCGTT TCCCCCTGGA AGCTCCCTCG
4651 TGCGCTCTCC TGTTCCGACC CTGCCGCTTA CCGGATACCT GTCCGCCTTT
4701 CTCCCTTCGG GAAGCGTGGC GCTTTCTCAT AGCTCACGCT GTAGGTATCT
4751 CAGTTCGGTG TAGGTCGTTC GCTCCAAGCT GGGCTGTGTG CACGAACCCC
```

FIG.3C

```
4801 CCGTTCAGCC CGACCGCTGC GCCTTATCCG GTAACTATCG TCTTGAGTCC
4851 AACCCGGTAA GACACGACTT ATCGCCACTG GCAGCAGCCA CTGGTAACAG
4901 GATTAGCAGA GCGAGGTATG TAGGCGGTGC TACAGAGTTC TTGAAGTGGT
4951 GGCCTAACTA CGGCTACACT AGAAGGACAG TATTTGGTAT CTGCGCTCTG
5001 CTGAAGCCAG TTACCTTCGG AAAAAGAGTT GGTAGCTCTT GATCCGGCAA
5051 ACAAACCACC GCTGGTAGCG GTGGTTTTTT TGTTTGCAAG CAGCAGATTA
5101 CGCGCAGAAA AAAGGATCT CAAGAAGATC CTTTGATCTT TTCTACGGGG
5151 TCTGACGCTC AGTGGAACGA AAACTCACGT TAAGGGATTT TGGTCATGAG
5201 ATTATCAAAA AGGATCTTCA CCTAGATCCT TTTAAATTAA AAATGAAGTT
5251 TTAAATCAAT CTAAAGTATA TATGAGTAAA CTTGGTCTGA CAGTTACCAA
5301 TGCTTAATCA GTGAGGCACC TATCTCAGCG ATCTGTCTAT TTCGTTCATC
5351 CATAGTTGCC TGACTCCCCG TCGTGTAGAT AACTACGATA CGGGAGGGCT
5401 TACCATCTGG CCCCAGTGCT GCAATGATAC CGCGAGACCC ACGCTCACCG
5451 GCTCCAGATT TATCAGCAAT AAACCAGCCA GCCGGAAGGG CCGAGCGCAG
5501 AAGTGGTCCT GCAACTTTAT CCGCCTCCAT CCAGTCTATT AATTGTTGCC
5551 GGGAAGCTAG AGTAAGTAGT TCGCCAGTTA ATAGTTTGCG CAACGTTGTT
5601 GCCATTGCTA CAGGCATCGT GGTGTCACGC TCGTCGTTTG GTATGGCTTC
5651 ATTCAGCTCC GGTTCCCAAC GATCAAGGCG AGTTACATGA TCCCCCATGT
5701 TGTGCAAAAA AGCGGTTAGC TCCTTCGGTC CTCCGATCGT TGTCAGAAGT
5751 AAGTTGGCCG CAGTGTTATC ACTCATGGTT ATGGCAGCAC TGCATAATTC
5801 TCTTACTGTC ATGCCATCCG TAAGATGCTT TTCTGTGACT GGTGAGTACT
5851 CAACCAAGTC ATTCTGAGAA TAGTGTATGC GGCGACCGAG TTGCTCTTGC
5901 CCGGCGTCAA TACGGGATAA TACCGCGCCA CATAGCAGAA CTTTAAAAGT
5951 GCTCATCATT GGAAAACGTT CTTCGGGGCG AAAACTCTCA AGGATCTTAC
6001 CGCTGTTGAG ATCCAGTTCG ATGTAACCCA CTCGTGCACC CAACTGATCT
6051 TCAGCATCTT TTACTTTCAC CAGCGTTTCT GGGTGAGCAA AAACAGGAAG
6101 GCAAAATGCC GCAAAAAAGG GAATAAGGGC GACACGGAAA TGTTGAATAC
6151 TCATACTCTT CCTTTTTCAA TATTATTGAA GCATTTATCA GGGTTATTGT
6201 CTCATGAGCG GATACATATT TGAATGTATT TAGAAAAATA AACAAATAGG
6251 GGTTCCGCGC ACATTTCCCC GAAAAGTGCC ACCTGGGAAA TTGTAAACGT
6301 TAATATTTTG TTAAAATTCG CGTTAAATTT TTGTTAAATC AGCTCATTTT
6351 TTAACCAATA GGCCGAAATC GGCAAAATCC CTTATAAATC AAAAGAATAG
6401 ACCGAGATAG GGTTGAGTGT TGTTCCAGTT TGGAACAAGA GTCCACTATT
6451 AAAGAACGTG GACTCCAACG TCAAAGGGCG AAAAACCGTC TATCAGGGCG
6501 ATGGCCCACT ACGTGAACCA TCACCCTAAT CAAGTTTTTT GGGGTCGAGG
6551 TGCCGTAAAG CACTAAATCG GAACCCTAAA GGGAGCCCCC GATTTAGAGC
6601 TTGACGGGGA AAGCCGGCGA ACGTGGCGAG AAAGGAAGGG AAGAAAGCGA
6651 AAGGAGCGGG CGCTAGGGCG CTGGCAAGTG TAGCGGTCAC GCTGCGCGTA
6701 ACCACCACAC CCGCCGCGCT TAATGCGCCG CTACAGGGCG CGTCGCGCCA
6751 TTCGCCATTC AGGCTGCGCA ACTGTTGGGA AGGGCGATCG GTGCGGGCCT
6801 CTTCGCTATT ACGCCAGCTG GCGAAAGGGG GATGTGCTGC AAGGCGATTA
6851 AGTTGGGTAA CGCCAGGGTT TTCCCAGTCA CGACGTTGTA AAACGACGGC
6901 CAGTGAATTG TAATACGACT CACTATAGGG CGAATTGGGT ACCGGGCCCC
6951 CCCTCGAGG
``` pLF027 Backbone

Linker
23 bp
1471 to 1491

FIG.5A

```
   1 TTTGTTAAAA TTCGCGTTAA ATTTTTGTTA AATCAGCTCA TTTTTTAACC
  51 AATAGGCCGA AATCGGCAAA ATCCCTTATA AATCAAAAGA ATAGACCGAG
 101 ATAGGGTTGA GTGTTGTTCC AGTTTGGAAC AAGAGTCCAC TATTAAAGAA
 151 CGTGGACTCC AACGTCAAAG GGCGAAAAAC CGTCTATCAG GGCGATGGCC
 201 CACTACGTGA ACCATCACCC TAATCAAGTT TTTTGGGGTC GAGGTGCCGT
 251 AAAGCACTAA ATCGGAACCC TAAAGGGAGC CCCCGATTTA GAGCTTGACG
 301 GGGAAAGCCG GCGAACGTGG CGAGAAAGGA AGGGAAGAAA GCGAAAGGAG
 351 CGGGCGCTAG GCGCTGGCA AGTGTAGCGG TCACGCTGCG CGTAACCACC
 401 ACACCCGCCG CGCTTAATGC GCCGCTACAG GGCGCGTCGC GCCATTCGCC
 451 ATTCAGGCTG CGCAACTGTT GGGAAGGGCG ATCGGTGCGG GCCTCTTCGC
 501 TATTACGCCA GCTGGCGAAA GGGGGATGTG CTGCAAGGCG ATTAAGTTGG
 551 GTAACGCCAG GGTTTTCCCA GTCACGACGT TGTAAAACGA CGGCCAGTGA
 601 ATTGTAATAC GACTCACTAT AGGGCGAATT GGGTACCGGG CCCCCCCTCG
 651 AGGTCGACGG TATCGATAAG CTTTGCTCAA CAAATACTGT CAAGGACTCG
 701 AGTCCGGCTC TGACTGAGCA ATGTCTAAAG AAATACCAAC CCCTTATATG
 751 TGGAGCTACC AACCGCAAAC GGGACACGCC GGCGCCTCCC AGGACTACTC
 801 CACCCAAATG AATTGGTTTA GTGCTGGGCC ATCAATGATT AGTCAAGTTT
 851 ATGGCATTAG AGACTTGCGC AACAAAGTTT TGATAACCCA GGCAGAAATA
 901 ACCAAAACTC CCAGAACAAT AATGGATCCG CCAATTTGGC CAGCTGCCAT
 951 GCTTGTTCAG GAAGCCGCCC CACCCAAAAC GGTCACTCTG CCCAGAAACC
1001 ACACCCTAGA ACAGGCTATG ACCAACTCTG GGCGCAGCT AGCGGGAGGA
1051 CGACAGCTGT GCCCTCCCA AATAGGTATA AAAAGCCCAG TGCTGGCTGG
1101 CACGGGCATT CAGCTTAGCG AAGACATCCC CAGCGCCTCC TGGATCAGGC
1151 CCGACGGCAT ATTCCAGCTA GGAGGGGGGT CTCGCTCGTC CTTCAGCCCA
1201 ACGCAAGCAT TCCTCACCCT GCAACAGGCA TCCTCGACGC CGCGCGCAGG
1251 AGGCGTGGGC ACCTACCAGT TTGTGCGCGA ATTTGTGCCA GAGGTATACC
1301 TTAACCCTTT TCAGGACCA CCGGACACCT TTCCTGATCA GTTCATTCCT
1351 AACTACGACA TTGTAACCAA CTCTGTCGAT GGCTATGACT GAGGAGAGCA
1401 TGGACCAGGT GGAGGTGAAC TGCCTGTGTG CTCAGCATGC CCAAACCTGC
1451 ACGCGCCCTC GCTGCTTTGC AAAGGAGGGT TTATGTGCTA ACTGGTTTTA
1501 CAACCCAGCA CTTGCCTTTG AAGGGTTTGA TATTCCAGAC TCTTACCAAG
1551 AGGGACACGG TGTGGACATA GAAGTTAAGT GTTCCCACCA CTCCAGCAAA
1601 CTGTGCCACA ATGGCCATGA TATGATCTGC TCATACTCTC GCCTGGGATC
1651 CCACATTAAC ATAAGATGTA TTTGCAACAA GCCGCGGCCC CACATGAGCC
1701 TCATTGAGGC AGCCTGTTCT ATGTATAACC TTAACTAGAT AATATTATTA
1751 AACTTGTTTT ACAGCTACCA CCATAATGCG CTTCAGCTTC TTCATCGCCG
1801 CCGTTCTTTT CTGCACCACA GGGGCCAGCA ATGACATTGT GACTTGCTGC
1851 GCCCACACAC CTTGCCTCCT ACACCTAGAA GTGGGCTTGG GGCCAATGT
1901 CAGTTGGATA AACTCTGACA CAGGCCAGGC CCGATTTGC CTCTCCAATG
1951 GCATGTGCAA CGCTACCCAG CAAGGCCTGC AGTTTCTGC AAACTTTTCT
2001 GAGGATGGCC TGTACATCGC CCTCATTAAG GAGAGCAACT ACGAGGGCGC
2051 TGAGCACTAC TACCTTGTCT ATATTTATGG AGACTGCTAC CAAACTGCAA
2101 ATGAGTCTGC CCACGGGCCT ATTTCCAGGC CCCTCAAAGA TCTGTTAACC
```

FIG.5B

```
2151 CTAAGGCCAT GGCATATGTC GCGAGGCCAT CGTGGCCGCG GCCGCACGCG
2201 TATCGCTGCC CCCACAGTAC AGCAATGACC TTAGCAATGT GCGCTGGTAT
2251 AAAGTAGACC CCAGCGGCTT CCAAGCCCAA AAAATCTCTA AAGTCAGAAG
2301 CGGAGGCAGA AAAGAGAACC TGCATCCCAA CTGGGCCTTG GTTACCTATA
2351 CTGGAGACCT TCTTGTCTTG CATGTTTCGC CAAACACCCT TGGACTGTGG
2401 CTGGCAGCCG TGCAGCATCG CGGGGGGCGC ACTAATTTCA TTACCTTCAA
2451 CATAACTGTA CCCAACTGGC AACAAAATCT AGTAACCATA TTTAATCAAC
2501 ACGAGCCCCC AAAAAGGGC GATAATTATG AGGACAGTTT TATGGAATGG
2551 ACTCTGTTTA AAAAGCTCAA AAAAGGCTTA TTTAGAGTAA CTTGCAGAGC
2601 CAAGTCAATA TTCCCAGAGT GCGTCCTCAA CATCACCCGC GACGGAACTT
2651 TCCTGCTTAT TGGGGATAGC AAAAAGACCC CCTATGTCAT CCTGCTGCCC
2701 TTTTTTGCAA ACCCCAAAGA AGACACTCCA ATTTTAATGG CCCTTAGCCA
2751 TTCCATGCCC GTCGCCATAC CTGACACTGC AATGCCTATA TATATTTCCA
2801 TCATGTTTTT TATTGTGGCC ATGCTAGCCA CCCTCAGCCT TCTAATGGGA
2851 CTAAACAACA AAATCAGGCC CATGTAGCTT GTCAAATAAA CTTACCTAAT
2901 TTTTGCTAAG ACGTCTGGGT CCTGCGTTTC TATGTCCACC AAAGTCCCCT
2951 CTTCCCAGCT TTGGTACTTC CACTTGTGCG CGCGAGCCAG CTTGCGGATG
3001 TGCTTGAAAG ATAATGTGGT CTCTCCCAAC AGCTTCCCGT TCACCAGCAC
3051 CAGGGCCATG AAGCGGACAC GAAGAGCTCT ACCTGCAAAT TATGACCCTG
3101 TATATCCATA CGACGCCCCC GGGTCTTCCA CACAACCCCC TTTTTTTAAT
3151 AACAAGCAAG GTCTCACTGA GTCACCCCCA GGAACCCTGG CTGTCAATGT
3201 TTCCCCTCCA CTAACCTTTT CTACGTTAGG TGCCATTAAA CTTTCCACAG
3251 GTCCGGACT CACCCTCAAC GAGGGCAAGT TACAAGCCAG CTTAGGGCCC
3301 GGCCTCATCA CAAATACCGA GGGCCAAATC ACTGTTGAAA ATGTCAACAA
3351 GGTTTTGTCT TTTACCTCCC CATTACATAA AAATGAAAAC ACTGTATCCC
3401 TAGCGCTAGG AGATGGGTTA GAAGATGAAA ATGGCACCCT TAAAGTGACC
3451 TTCCCTACTC CCCCTCCCCC GCTACAATTC TCCCCTCCCC TCACAAAAAC
3501 AGGTGGTACT GTTTCCTTGC CCCTGCAAGA CTCCATGCAA GTGACAAATG
3551 GAAAACTGGG CGTTAAGCTA CCACCTACGC ACCTCCCTTG AAAAAAACTG
3601 ACCAGCAAGT TAGCCTCCAA GTAGGCTCGG GTCTCACCGT GATTAACGAA
3651 CAGTTGCAAG CTGTCCAGCC TCCCGCAACC ACCTACAACG AGCCTCTTTC
3701 CAAAACTGAC AATTCTGTTT CTCTGCAAGT AGGTGCCGGC CTTGCCGTGC
3751 AGAGCGGACG TTTGGTGGCA ACCCCTCCCC CGCCTCTCAC CTTTACATCA
3801 CCCCTAGAAA AAAATGAAAA CACAGTGTCG CTACAAGTAG GCGCGGGCTT
3851 GTCTGTACAA AACAACGCCC TAGTAGCCAC ACCTCCCCCA CCCTTAACCT
3901 TTGCCTATCC CTTAGTAAAA AATGACAACC ATGTAGCTCT AAGTGCTGGA
3951 AGTGGTTTAA GAATATCTGG AGGCAGCCTC ACGGTGGCCA CTGGACCTGG
4001 CCTTTCCCAT CAAAATGGAA CAATAGGGGC TGTAGTAGGT GCAGGCCTCA
4051 AGTTTGAAAA CAATGCCATT CTTGCAAAAC TAGGCAACGG TCTAACCATT
4101 AGAGATGGCG CTATTGAAGC AACCCAACCC CCAGCTGCCC CCATAACACT
4151 GTGGACAGGG CCTGGCCTAG CATTAATGGC TTTATGTAAT GACACTCCAG
4201 TAATTAGGTN CTTTATATGC CTAACCAGAG ACAGCAACTT AGTCACAGTA
4251 AATGCTAGCT TTGTGGGAGA GGGGGGGTAT CGAATAGTCA GCCCTACCCA
4301 GTCACAATTT AGCCTAATTA TGGAGTTTGA TCAGTTTGGA CAGCTTATGT
4351 CCACAGGAAA CATTAACTCC ACCACTACTT GGGGAGAAAA GCCCTGGGGC
4401 AATAACACTG TACAGCCACG CCCAAGCCAC ACCTGGAAAC TGTGCATGCC
4451 TAACAGAGAA GTTTACTCCA CTCCCGCCGC CACCATCACC CGCTGTGGAC
4501 TAGACAGCAT TGCAGTCGAC GGTGCCCAGC AGAAGTATCG ACTGCATGCT
4551 AATTATTAAC AAACCAAAAG GCGTTGCCAC TTACACCCTT ACCTTTAGGT
4601 TTTTAAACTT TAACAGACTA AGCGGAGGTA CCCTGTTTAA AACTGATGTC
4651 TTAACCTTTA CCTATGTAGG CGAAAATCAA TAAAACCAGA AAAAAATAAG
4701 GGGAAAAGCT TGATATCGAA TTCCTGCAGC CCGGGGGATC CACTAGTTCT
4751 AGAGCGGCCG CCACCGCGGT GGAGCTCCAG CTTTTGTTCC CTTTAGTGAG
```

FIG. 5C

```
4801 GGTTAATTCC GAGCTTGGCG TAATCATGGT CATAGCTGTT TCCTGTGTGA
4851 AATTGTTATC CGCTCACAAT TCCACACAAC ATACGAGCCG GAAGCATAAA
4901 GTGTAAAGCC TGGGGTGCCT AATGAGTGAG CTAACTCACA TTAATTGCGT
4951 TGCGCTCACT GCCCGCTTTC CAGTCGGGAA ACCTGTCGTG CCAGCTGCAT
5001 TAATGAATCG GCCAACGCGC GGGGAGAGGC GGTTTGCGTA TTGGGCGCTC
5051 TTCCGCTTCC TCGCTCACTG ACTCGCTGCG CTCGGTCGTT CGGCTGCGGC
5101 GAGCGGTATC AGCTCACTCA AAGGCGGTAA TACGGTTATC CACAGAATCA
5151 GGGGATAACG CAGGAAAGAA CATGTGAGCA AAAGGCCAGC AAAAGGCCAG
5201 GAACCGTAAA AAGGCCGCGT TGCTGGCGTT TTTCCATAGG CTCCGCCCCC
5251 CTGACGAGCA TCACAAAAAT CGACGCTCAA GTCAGAGGTG GCGAAACCCG
5301 ACAGGACTAT AAAGATACCA GGCGTTTCCC CCTGGAAGCT CCCTCGTGCG
5351 CTCTCCTGTT CCGACCCTGC CGCTTACCGG ATACCTGTCC GCCTTTCTCC
5401 CTTCGGGAAG CGTGGCGCTT TCTCATAGCT CACGCTGTAG GTATCTCAGT
5451 TCGGTGTAGG TCGTTCGCTC CAAGCTGGGC TGTGTGCACG AACCCCCCGT
5501 TCAGCCCGAC CGCTGCGCCT TATCCGGTAA CTATCGTCTT GAGTCCAACC
5551 CGGTAAGACA CGACTTATCG CCACTGGCAG CAGCCACTGG TAACAGGATT
5601 AGCAGAGCGA GGTATGTAGG CGGTGCTACA GAGTTCTTGA AGTGGTGGCC
5651 TAACTACGGC TACACTAGAA GGACAGTATT TGGTATCTGC GCTCTGCTGA
5701 AGCCAGTTAC CTTCGGAAAA AGAGTTGGTA GCTCTTGATC CGGCAAACAA
5751 ACCACCGCTG GTAGCGGTGG TTTTTTTGTT TGCAAGCAGC AGATTACGCG
5801 CAGAAAAAAA GGATCTCAAG AAGATCCTTT GATCTTTTCT ACGGGGTCTG
5851 ACGCTCAGTG GAACGAAAAC TCACGTTAAG GGATTTTGGT CATGAGATTA
5901 TCAAAAAGGA TCTTCACCTA GATCCTTTTA AATTAAAAAT GAAGTTTTAA
5951 ATCAATCTAA AGTATATATG AGTAAACTTG GTCTGACAGT TACCAATGCT
6001 TAATCAGTGA GGCACCTATC TCAGCGATCT GTCTATTTCG TTCATCCATA
6051 GTTGCCTGAC TCCCCGTCGT GTAGATAACT ACGATACGGG AGGGCTTACC
6101 ATCTGGCCCC AGTGCTGCAA TGATACCGCG AGACCCACGC TCACCGGCTC
6151 CAGATTTATC AGCAATAAAC CAGCCAGCCG AAGGGCCGA GCGCAGAAGT
6201 GGTCCTGCAA CTTTATCCGC CTCCATCCAG TCTATTAATT GTTGCCGGGA
6251 AGCTAGAGTA AGTAGTTCGC CAGTTAATAG TTTGCGCAAC GTTGTTGCCA
6301 TTGCTACAGG CATCGTGGTG TCACGCTCGT CGTTTGGTAT GGCTTCATTC
6351 AGCTCCGGTT CCCAACGATC AAGGCGAGTT ACATGATCCC CCATGTTGTG
6401 CAAAAAAGCG GTTAGCTCCT TCGGTCCTCC GATCGTTGTC AGAAGTAAGT
6451 TGGCCGCAGT GTTATCACTC ATGGTTATGG CAGCACTGCA TAATTCTCTT
6501 ACTGTCATGC CATCCGTAAG ATGCTTTTCT GTGACTGGTG AGTACTCAAC
6551 CAAGTCATTC TGAGAATAGT GTATGCGGCG ACCGAGTTGC TCTTGCCCGG
6601 CGTCAATACG GGATAATACC GCGCCACATA GCAGAACTTT AAAAGTGCTC
6651 ATCATTGGAA AACGTTCTTC GGGGCGAAAA CTCTCAAGGA TCTTACCGCT
6701 GTTGAGATCC AGTTCGATGT AACCCACTCG TGCACCCAAC TGATCTTCAG
6751 CATCTTTTAC TTTCACCAGC GTTTCTGGGT GAGCAAAAAC AGGAAGGCAA
6801 AATGCCGCAA AAAAGGGAAT AAGGGCGACA CGGAAATGTT GAATACTCAT
6851 ACTCTTCCTT TTTCAATATT ATTGAAGCAT TTATCAGGGT TATTGTCTCA
6901 TGAGCGGATA CATATTTGAA TGTATTTAGA AAAATAAACA AATAGGGGTT
6951 CCGCGCACAT TTCCCCGAAA AGTGCCACCT GGGAAATTGT AAACGTTAAT
7001 AT
``` pLF047A Backbone

Linker 63 bp

```
   1 ACTCATACTC TTCCTTTTTC AATATTATTG AAGCATTTAT CAGGGTTATT
  51 GTCTCATGAG CGGATACATA TTTGAATGTA TTTAGAAAAA TAAACAAATA
 101 GGGGTTCCGC GCACATTTCC CCGAAAAGTG CCACCTGGGA AATTGTAAAC
 151 GTTAATATTT TGTTAAAATT CGCGTTAAAT TTTTGTTAAA TCAGCTCATT
 201 TTTTAACCAA TAGGCCGAAA TCGGCAAAAT CCCTTATAAA TCAAAAGAAT
 251 AGACCGAGAT AGGGTTGAGT GTTGTTCCAG TTTGGAACAA GAGTCCACTA
 301 TTAAAGAACG TGGACTCCAA CGTCAAAGGG CGAAAAACCG TCTATCAGGG
 351 CGATGGCCCA CTACGTGAAC CATCACCCTA ATCAAGTTTT TTGGGGTCGA
 401 GGTGCCGTAA AGCACTAAAT CGGAACCCTA AAGGGAGCCC CCGATTTAGA
 451 GCTTGACGGG GAAAGCCGGC GAACGTGGCG AGAAAGGAAG GGAAGAAAGC
 501 GAAAGGAGCG GGCGCTAGGG CGCTGGCAAG TGTAGCGGTC ACGCTGCGCG
 551 TAACCACCAC ACCCGCCGCG CTTAATGCGC CGCTACAGGG CGCGTCGCGC
 601 CATTCGCCAT TCAGGCTGCG CAACTGTTGG GAAGGGCGAT CGGTGCGGGC
 651 CTCTTCGCTA TTACGCCAGC TGGCGAAAGG GGGATGTGCT GCAAGGCGAT
 701 TAAGTTGGGT AACGCCAGGG TTTTCCCAGT CACGACGTTG TAAAACGACG
 751 GCCAGTGAAT TGTAATACGA CTCACTATAG GCGAATTGGG TACCGGGCCC
 801 CCCCTCGAGG TCGACGGTAT CGATAAGCTT TGCTCAACAA ATACTGTCAA
 851 GGACTCGAGT CCGGCTCTGA CTGAGCAATG TCTAAAGAAA TACCAACCCC
 901 TTATATGTGG AGCTACCAAC CGCAAACGGG ACACGCCGGC GCCTCCCAGG
 951 ACTACTCCAC CCAAATGAAT TGGTTTAGTG CTGGGCCATC AATGATTAGT
1001 CAAGTTTATG GCATTAGAGA CTTGCGCAAC AAAGTTTTGA TAACCCAGGC
1051 AGAAATAACC AAAACTCCCA GAACAATAAT GGATCCGCCA ATTTGGCCAG
1101 CTGCCATGCT TGTTCAGGAA GCCGCCCCAC CCAAAACGGT CACTCTGCCC
1151 AGAAACCACA CCCTAGAACA GGCTATGACC AACTCTGGGG CGCAGCTAGC
1201 GGGAGGACGA CAGCTGTGCC CCTCCCAAAT AGGTATAAAA AGCCCAGTGC
1251 TGGCTGGCAC GGGCATTCAG CTTAGCGAAG ACATCCCCAG CGCCTCCTGG
1301 ATCAGGCCCG ACGGCATATT CCAGCTAGGA GGGGGGTCTC GCTCGTCCTT
1351 CAGCCCAACG CAAGCATTCC TCACCCTGCA ACAGGCATCC TCGACGCCGC
1401 GCGCAGGAGG CGTGGGCACC TACCAGTTTG TGCGCGAATT TGTGCCAGAG
1451 GTATACCTTA ACCCTTTTTC AGGACCACCG GACACCTTTC CTGATCAGTT
1501 CATTCCTAAC TACGACATTG TAACCAACTC TGTCGATGGC TATGACTGAG
1551 GAGAGCATGG ACCAGGTGGA GGTGAACTGC CTGTGTGCTC AGCATGCCCA
1601 AACCTGCACG CGCCCTCGCT GCTTTGCAAA GGAGGGTTTA TGTGCTAACT
1651 GGTTTTACAA CCCAGCACTT GCCTTTGAAG GGTTTGATAT TCCAGACTCT
1701 TACCAAGAGG GACACGGTGT GGACATAGAA GTTAAGTGTT CCCACCACTC
1751 CAGCAAACTG TGCCACAATG GCCATGATAT GATCTGCTCA TACTCTCGCC
1801 TGGGATCCCA CATTAACATA AGATGTATTT GCAACAAGCC GCGGCCCCAC
1851 ATGAGCCTCA TTGAGGCAGC CTGTTCTATG TATAACCTTA ACTAGATAAT
1901 ATTATTAAAC TTGTTTTACA GCTACCACCA TAATGCGCTT CAGCTTCTTC
1951 ATCGCCGCCG TTCTTTTCTG CACCACAGGG GCCAGCAATG ACATTGTGAC
2001 TTGCTGCGCC CACACACCTT GCCTCCTACA CCTAGAAGTG GGCTTGGGGG
2051 CCAATGTCAG TTGGATAAAC TCTGACACAG GCCAGGCCCC GATTTGCCTC
2101 TCCAATGGCA TGTGCAACGC TACCCAGCAA GGCCTGCAGT TTTCTGCAAA
2151 CTTTCTGAG GATGGCCTGT ACATCGCCCT CATTAAGGAG AGCAACTACG
```

FIG. 7B

```
2201 AGGGCGCTGA GCACTACTAC CTTGTCTATA TTTATGGAGA CTGCTACCAA
2251 ACTGCAAATG AGTCTGCCCA CGGGCCTATT TCCAGGCCCC TCAAAGATCT
2301 GTTAACCCTA AGGCCATGGC ATATGTCGCG AGGCCATCGT GGCCGCGGCC
2351 GCACGCGTGT CCTCAACATC ACCCGCGACG GAACTTTCCT GCTTATTGGG
2401 GATAGCAAAA AGACCCCCTA TGTCATCCTG CTGCCCTTTT TTGCAAACCC
2451 CAAAGAAGAC ACTCCAATTT TAATGGCCCT TAGCCATTCC ATGCCCGTCG
2501 CCATACCTGA CACTGCAATG CCTATATATA TTTCCATCAT GTTTTTTATT
2551 GTGGCCATGC TAGCCACCCT CAGCCTTCTA ATGGGACTAA ACAACAAAAT
2601 CAGGCCCATG TAGCTTGTCA AATAAACTTA CCTAATTTTT GCTAAGACG
2651 CTGGGTCCTG CGTTTCTATG TCCACCAAAG TCCCCTCTTC CCAGCTTTGG
2701 TACTTCCACT TGTGCGCGCG AGCCAGCTTG CGGATGTGCT TGAAAGATAA
2751 TGTGGTCTCT CCCAACAGCT TCCCGTTCAC CAGCACCAGG GCCATGAAGC
2801 GGACACGAAG AGCTCTACCT GCAAATTATG ACCCTGTATA TCCATACGAC
2851 GCCCCGGGT CTTCCACACA ACCCCCTTTT TTTAATAACA AGCAAGGTCT
2901 CACTGAGTCA CCCCCAGGAA CCCTGGCTGT CAATGTTTCC CCTCCACTAA
2951 CCTTTTCTAC GTTAGGTGCC ATTAAACTTT CCACAGGTCC CGGACTCACC
3001 CTCAACGAGG GCAAGTTACA AGCCAGCTTA GGGCCCGGCC TCATCACAAA
3051 TACCGAGGGC CAAATCACTG TTGAAAATGT CAACAAGGTT TTGTCTTTTA
3101 CCTCCCCATT ACATAAAAAT GAAACACTG TATCCCTAGC GCTAGGAGAT
3151 GGGTTAGAAG ATGAAAATGG CACCCTTAAA GTGACCTTCC CTACTCCCCC
3201 TCCCCGCTA CAATTCTCCC CTCCCCTCAC AAAAACAGGT GGTACTGTTT
3251 CCTTGCCCCT GCAAGACTCC ATGCAAGTGA CAAATGGAAA ACTGGGCGTT
3301 AAGCTACCAC CTACGCACCT CCCTTGAAAA AAACTGACCA GCAAGTTAGC
3351 CTCCAAGTAG GCTCGGGTCT CACCGTGATT AACGAACAGT TGCAAGCTGT
3401 CCAGCCTCCC GCAACCACCT ACAACGAGCC TCTTTCCAAA ACTGACAATT
3451 CTGTTTCTCT GCAAGTAGGT GCCGGCCTTG CCGTGCAGAG CGGACGTTTG
3501 GTGGCAACCC CTCCCCCGCC TCTCACCTTT ACATCACCCC TAGAAAAAAA
3551 TGAAAACACA GTGTCGCTAC AAGTAGGCGC GGGCTTGTCT GTACAAAACA
3601 ACGCCCTAGT AGCCACACCT CCCCCACCCT TAACCTTTGC CTATCCCTTA
3651 GTAAAAAATG ACAACCATGT AGCTCTAAGT GCTGGAAGTG GTTTAAGAAT
3701 ATCTGGAGGC AGCCTCACGG TGGCCACTGG ACCTGGCCTT TCCCATCAAA
3751 ATGGAACAAT AGGGGCTGTA GTAGGTGCAG GCCTCAAGTT TGAAAACAAT
3801 GCCATTCTTG CAAAACTAGG CAACGGTCTA ACCATTAGAG ATGGCGCTAT
3851 TGAAGCAACC CAACCCCCAG CTGCCCCAT AACACTGTGG ACAGGGCCTG
3901 GCCTAGCATT AATGGCTTTA TGTAATGACA CTCCAGTAAT TAGGTNCTTT
3951 ATATGCCTAA CCAGAGACAG CAACTTAGTC ACAGTAAATG CTAGCTTTGT
4001 GGGAGAGGGG GGGTATCGAA TAGTCAGCCC TACCCAGTCA CAATTTAGCC
4051 TAATTATGGA GTTTGATCAG TTTGGACAGC TTATGTCCAC AGGAAACATT
4101 AACTCCACCA CTACTTGGGG AGAAAGCCC TGGGCAATA ACACTGTACA
4151 GCCACGCCCA AGCCACACCT GGAAACTGTG CATGCCTAAC AGAGAAGTTT
4201 ACTCCACTCC CGCCGCCACC ATCACCCGCT GTGGACTAGA CAGCATTGCA
4251 GTCGACGGTG CCCAGCAGAA GTATCGACTG CATGCTAATT ATTAACAAAC
4301 CAAAAGGCGT TGCCACTTAC ACCCTTACCT TTAGGTTTTT AAACTTTAAC
4351 AGACTAAGCG GAGGTACCCT GTTTAAAACT GATGTCTTAA CCTTTACCTA
4401 TGTAGGCGAA AATCAATAAA ACCAGAAAAA AATAAGGGGA AAAGCTTGAT
4451 ATCGAATTCC TGCAGCCCGG GGATCCACT AGTTCTAGAG CGGCCGCCAC
4501 CGCGGTGGAG CTCCAGCTTT TGTTCCCTTT AGTGAGGGTT AATTCCGAGC
4551 TTGGCGTAAT CATGGTCATA GCTGTTTCCT GTGTGAAATT GTTATCCGCT
4601 CACAATTCCA CACAACATAC GAGCCGGAAG CATAAAGTGT AAAGCCTGGG
4651 GTGCCTAATG AGTGAGCTAA CTCACATTAA TTGCGTTGCG CTCACTGCCC
4701 GCTTTCCAGT CGGGAAACCT GTCGTGCCAG CTGCATTAAT GAATCGGCCA
4751 ACGCGCGGGG AGAGGCGGTT TGCGTATTGG GCGCTCTTCC GCTTCCTCGC
4801 TCACTGACTC GCTGCGCTCG GTCGTTCGGC TGCGGCGAGC GGTATCAGCT
```

FIG. 7C

```
4851 CACTCAAAGG CGGTAATACG GTTATCCACA GAATCAGGGG ATAACGCAGG
4901 AAAGAACATG TGAGCAAAAG GCCAGCAAAA GGCCAGGAAC CGTAAAAAGG
 4951 CCGCGTTGCT GGCGTTTTTC CATAGGCTCC GCCCCCCTGA CGAGCATCAC
5001 AAAAATCGAC GCTCAAGTCA GAGGTGGCGA AACCCGACAG GACTATAAAG
5051 ATACCAGGCG TTTCCCCCTG GAAGCTCCCT CGTGCGCTCT CCTGTTCCGA
5101 CCCTGCCGCT TACCGGATAC CTGTCCGCCT TTCTCCCTTC GGGAAGCGTG
5151 GCGCTTTCTC ATAGCTCACG CTGTAGGTAT CTCAGTTCGG TGTAGGTCGT
5201 TCGCTCCAAG CTGGGCTGTG TGCACGAACC CCCCGTTCAG CCCGACCGCT
5251 GCGCCTTATC CGGTAACTAT CGTCTTGAGT CCAACCCGGT AAGACACGAC
5301 TTATCGCCAC TGGCAGCAGC CACTGGTAAC AGGATTAGCA GAGCGAGGTA
5351 TGTAGGCGGT GCTACAGAGT TCTTGAAGTG GTGGCCTAAC TACGGCTACA
5401 CTAGAAGGAC AGTATTTGGT ATCTGCGCTC TGCTGAAGCC AGTTACCTTC
5451 GGAAAAAGAG TTGGTAGCTC TTGATCCGGC AAACAAACCA CCGCTGGTAG
5501 CGGTGGTTTT TTTGTTTGCA AGCAGCAGAT TACGCGCAGA AAAAAAGGAT
5551 CTCAAGAAGA TCCTTTGATC TTTTCTACGG GGTCTGACGC TCAGTGGAAC
5601 GAAAACTCAC GTTAAGGGAT TTTGGTCATG AGATTATCAA AAAGGATCTT
5651 CACCTAGATC CTTTTAAATT AAAAATGAAG TTTTAAATCA ATCTAAAGTA
5701 TATATGAGTA AACTTGGTCT GACAGTTACC AATGCTTAAT CAGTGAGGCA
5751 CCTATCTCAG CGATCTGTCT ATTTCGTTCA TCCATAGTTG CCTGACTCCC
5801 CGTCGTGTAG ATAACTACGA TACGGGAGGG CTTACCATCT GGCCCCAGTG
5851 CTGCAATGAT ACCGCGAGAC CCACGCTCAC CGGCTCCAGA TTTATCAGCA
5901 ATAAACCAGC CAGCCGGAAG GGCCGAGCGC AGAAGTGGTC CTGCAACTTT
5951 ATCCGCCTCC ATCCAGTCTA TTAATTGTTG CCGGGAAGCT AGAGTAAGTA
6001 GTTCGCCAGT TAATAGTTTG CGCAACGTTG TTGCCATTGC TACAGGCATC
6051 GTGGTGTCAC GCTCGTCGTT TGGTATGGCT TCATTCAGCT CCGGTTCCCA
6101 ACGATCAAGG CGAGTTACAT GATCCCCCAT GTTGTGCAAA AAAGCGGTTA
6151 GCTCCTTCGG TCCTCCGATC GTTGTCAGAA GTAAGTTGGC CGCAGTGTTA
6201 TCACTCATGG TTATGGCAGC ACTGCATAAT TCTCTTACTG TCATGCCATC
6251 CGTAAGATGC TTTTCTGTGA CTGGTGAGTA CTCAACCAAG TCATTCTGAG
6301 AATAGTGTAT GCGGCGACCG AGTTGCTCTT GCCCGGCGTC AATACGGGAT
6351 AATACCGCGC CACATAGCAG AACTTTAAAA GTGCTCATCA TTGGAAAACG
6401 TTCTTCGGGG CGAAAACTCT CAAGGATCTT ACCGCTGTTG AGATCCAGTT
6451 CGATGTAACC CACTCGTGCA CCCAACTGAT CTTCAGCATC TTTTACTTTC
6501 ACCAGCGTTT CTGGGTGAGC AAAAACAGGA AGGCAAAATG CCGCAAAAAA
6551 GGGAATAAGG GCGACACGGA AATGTTGAAT
``` pLF047A
Backbone

Partially deleted E3 region

722 to 1843

Linker 63 bp

```
   1 GTCGACGGTG CCCCCAGCAG AAGTATCGAC TGCATGCTAA TTATTAACAA
  51 ACCAAAAGGC GTTGCCACTT ACACCCTTAC CTTTAGGTTT TTAAACTTTA
 101 ACAGACTAAG CGGAGGTACC CTGTTTAAAA CTGATGTCTT AACCTTTACC
 151 TATGTAGGCG AAAATCAATA AAACCAGAAA AAAATAAGTT TAAAAGCTTT
 201 ATTTTTCATA CACGCGAGCG GTAAGGCTGC CGCCTTCAGG AAAAGTTACT
 251 CTGTAAACAG TTCTTTCACA ACAGCACAAA ACATAGGTAT TAGTTAACAG
 301 TTCATTTGGG CTATAATAAT ATACATTTTC TTGGGTGGCA AAGCAAGGGT
 351 CGGTAATCTC AACAAAACCA TCAACTGGAA TGCAAGAATA GTCCAGCACG
 401 GTGGGTTCAA TCTAAAAATG AAGAAACGCT GTTGAGGTTC ACTAAGCACA
 451 GGTTTTGAAT CTGTCGGCAG CGTCCATGCA TCATAGCTTG TCTCAAAGCA
 501 GATTGTCTTC TTTCCTCTGC CTTGGAAGTG GTTTGGTGAA GCACTACAGG
 551 TGTCTTTTCA ACCTCTTTCA GCACCCGCTC TATTACAGAT CTCACCCACA
 601 CAGCACAGTT TTTAAGAGAA CAATAGTTTT GAAGGCTACA AGATTTACAC
 651 TTAAGCACCA GCCAGTAATT ATAAGTGCTT TTAAGAACTA CCCCTAGCTC
 701 AGGGTTAATG CACCTTTTAA TGGCCTCCAT GCAGGCTTTA TGGACAGTTC
 751 TAAAAAAGA  CAGTCTAAAA TAAATGTAGT GAGTGTTTCT AAATATAATA
 801 CTCCCCACAT AGTTAATTTC ATCAGGCCTG CTAGAATTTA CAAACTCTCG
 851 GTACCACATA TACTTTTTAT TCATAGCCCC ACCCTTAATA AAGTCCTCAA
 901 TCACTTTCTG AACCACATGC TTGCTAGCCA TGCATTGTAA AGACAAGCTG
 951 TTAGCAGT   GACAGTGTAC TCGCCACGTT TGAGCCTCTG CCAGGCAGCA
1001 GTGCTTAGTT ACTATCAACT CAATACCCGC ATTGCATGTA AACCCCCCAA
1051 AGAGCAGTTT TTCATGCCTG TGTAGCACAT CATCCCACAA AATAGGAATT
1101 TCATAGCATA AAGCAAAGCA ATTACAATAT TTAGGAACTC TCACCACAGC
1151 AGTCACGTGA CATGTTGTCT CAGCAGTGCA GTTGCCTTCC ATCCTACAAT
1201 TATGAACAAA AACTAAACAC TTCTAACAAA GATACAGTGA CAATCTCCCT
1251 TCCTCTAAAA GCATTGTTTA CATTAGGGTG ATTATTAACA ACGTCAGAAA
1301 TTTCTTTAAT TAAAGTGCCT TTAAAATGTG CAAGAGCATC ATCATACTCA
1351 AAACCAAGCT GAGAGTAAAA GACCACCTTA AAAGTAATCC CAGGCTTGTT
1401 TTTATCAACA GCCTTAAACA TGCTTTCACA AAATATAGAA GCAGTAACAT
1451 CATCAATGGT GTCGAAGAGA AACTCCATAG GAGACTCCAG CATTGATCCA
1501 AGCTCTCTAA CAAAATCTTC CTCAAAATGA ATAATGCCCT TTACACAAAC
1551 GCGGGGCAGA CGATGGTGGG CCATCGCGTC AACCTGAAAC ACATTTTACA
1601 GTAAACAAAG CTAGCTCCGC AGTGGTAAAG TCATGCCCAT GGGTGAGGCC
1651 AAAATCCTTA AAAAGCTAT  CTAAGTAGTT GGTCATCCCC TCAGTTAAAA
1701 AGTTTTGCAG CTGGGTGGTG CATACCACAT AGTGCCAGCT TATAGCTACA
1751 AAGACCTGCA TCCCTCCTT  AGCAGACAGC TCTTGCACAC ACGCAGTAAC
1801 TATCCACCGC TTAAGAAAAG CTTAAGCCC  AGCGCACATA ACAGCTCCAA
1851 TGTTTTATC  CAAGGAGAGC AAAATTTCAG CAAGCGCAGG CTCAACAGTA
1901 ATAGTGAAGC AGAGGCATTT CAGACGAGGC TCACTAGCTG CAGTCGCCAT
1951 TTATGAGGTC TGCAATAAAA AACAACTCAT CAGCAGCTGA AAAAGTGCAC
2001 TTTGACCTCA TTAAGCCACT GCATATGCAA GTCCTCATCT ATGCCGCAGC
```

FIG. 9B

```
2051 CCAGACCCTC AATCCAGCCC CGAATGTACA CTTTAATAAG AGATTCAACC
2101 TCTTCTTTTA GCAAAGTACA CATGCTGTTT GGACTAGTAT ACACAATAGA
2151 AGTCACAATG AGGGGCCCGC TGTGGCTGGA AAGCCTGCGC ACAGCCCGAA
2201 GGTTAAAAAT GGACTGTAAC AGCATTGAAA CCCCGCGACA CAGGTCAGTC
2251 TCGCGGTCTT GATCTCTTAT TATAGCGACC AAATGGTCCT TCAGAGTGAT
2301 GTTGCACTCA TAGAAGTAGG CAGCTCCGGC AGCCATTCTG CAAAATAACA
2351 AAACACCACT AAGCATAGCA CCATCACCAA GCATGAAAAC AGGTAAAAAC
2401 AAAAGCAACA CTTACTTATT CAGCAGTCAC AAGAATGTTG GGCTCCCAAG
2451 TGACAGACAA GCCTAATGCA AGGTGGGCAC AGTCTCCGGA ATAAGTTGAC
2501 AAAAGTCACG CCGCAAAGCT TCCTGAAGAG AAACGGCGGT AGCCTGGATA
2551 TCTGCAACGG ACCCAAAACC TTCAGTGTCA CTTCCAATAA ACAGATAAAA
2601 CTCTAAATAG TCCCCACTTA AAACCGAAAC AGCCGCGGCA AAGGTAGGAC
2651 ACGGACGCAC TTCCTGAGCC CTAATAAGGC TAAACACCAC ACGGCGCAGT
2701 TCAGAAGGCA AAAGTCTGT AAGCTCTAGC TGAGCACACA CACTCTCCAC
2751 TAGACACTTG TGAAGCCTCA GACAAAACA TGCTCCCATA GACACTCCTA
2801 AAGCTGCCAT TGTACTCACG GACGGCTGGC TGTCAGAGGA GAGCTATGAG
2851 GATGAAATGC CAAGCACAGC GTTTATATAG TCCTCAAAGT AGGGCGTGTG
2901 GAAAACGAAA AGGAATATAA CGGGGCGTTT GAGGAAGTGG TGCCAAGTAC
2951 AGTCATAAAA TGTGGGCGCG TGGTAAATGT TAAGTGCAGT TTCCCTTTGG
3001 CGGTTGGCCC GGAAAGTTCA CAAAAAGTAC AGCACGTCCT TGTCACCGTG
3051 TCAACCACAA AACCACAAAT AGGCACAACG CCCAAAAACC CGGGGCGCCG
3101 GCCAAAAGTC CGCGGAACTC GCCCTGTCGT AAAACCACGC CTTTGACGTC
3151 ACTGGACATT CCCGTGGGAA CACCCTGACC AGGGCGTGAC CTGAACCTGA
3201 CCGTCCCATG ACCCCGCCCC TTGCAACACC CAAATTTAAG CCACACCTCT
3251 TTGTCCTGTA TATTATTGAT GATGGGGGA TCCACTAGTT CTAGAGCGGC
3301 CGCCACCGCG GTGGAGCTCC AGCTTTTGTT CCCTTTAGTG AGGGTTAATT
3351 CCGAGCTTGG CGTAATCATG GTCATAGCTG TTTCCTGTGT GAAATTGTTA
3401 TCCGCTCACA ATTCCACACA ACATACGAGC CGGAAGCATA AAGTGTAAAG
3451 CCTGGGGTGC CTAATGAGTG AGCTAACTCA CATTAATTGC GTTGCGCTCA
3501 CTGCCCGCTT TCCAGTCGGG AAACCTGTCG TGCCAGCTGC ATTAATGAAT
3551 CGGCCAACGC GCGGGGAGAG GCGGTTTGCG TATTGGGCGC TCTTCCGCTT
3601 CCTCGCTCAC TGACTCGCTG CGCTCGGTCG TTCGGCTGCG GCGAGCGGTA
3651 TCAGCTCACT CAAAGGCGGT AATACGGTTA TCCACAGAAT CAGGGGATAA
3701 CGCAGGAAAG AACATGTGAG CAAAAGGCCA GCAAAAGGCC AGGAACCGTA
3751 AAAAGGCCGC GTTGCTGGCG TTTTTCCATA GGCTCCGCCC CCCTGACGAG
3801 CATCACAAAA ATCGACGCTC AAGTCAGAGG TGGCGAAACC CGACAGGACT
3851 ATAAAGATAC CAGGCGTTTC CCCCTGGAAG CTCCCTCGTG CGCTCTCCTG
3901 TTCCGACCCT GCCGCTTACC GGATACCTGT CCGCCTTTCT CCCTTCGGGA
3951 AGCGTGGCGC TTTCTCATAG CTCACGCTGT AGGTATCTCA GTTCGGTGTA
4001 GGTCGTTCGC TCCAAGCTGG GCTGTGTGCA CGAACCCCCC GTTCAGCCCG
4051 ACCGCTGCGC CTTATCCGGT AACTATCGTC TTGAGTCCAA CCCGGTAAGA
4101 CACGACTTAT CGCCACTGGC AGCAGCCACT GGTAACAGGA TTAGCAGAGC
4151 GAGGTATGTA GGCGGTGCTA CAGAGTTCTT GAAGTGGTGG CCTAACTACG
4201 GCTACACTAG AAGGACAGTA TTTGGTATCT GCGCTCTGCT GAAGCCAGTT
4251 ACCTTCGGAA AAAGAGTTGG TAGCTCTTGA TCCGGCAAAC AAACCACCGC
4301 TGGTAGCGGT GGTTTTTTG TTTGCAAGCA GCAGATTACG CGCAGAAAAA
4351 AAGGATCTCA AGAAGATCCT TTGATCTTTT CTACGGGGTC TGACGCTCAG
4401 TGGAACGAAA ACTCACGTTA AGGGATTTTG GTCATGAGAT TATCAAAAAG
4451 GATCTTCACC TAGATCCTTT TAAATTAAAA ATGAAGTTTT AAATCAATCT
4501 AAAGTATATA TGAGTAAACT TGGTCTGACA GTTACCAATG CTTAATCAGT
4551 GAGGCACCTA TCTCAGCGAT CTGTCTATTT CGTTCATCCA TAGTTGCCTG
4601 ACTCCCCGTC GTGTAGATAA CTACGATACG GGAGGGCTTA CCATCTGGCC
4651 CCAGTGCTGC AATGATACCG CGAGACCCAC GCTCACCGGC TCCAGATTTA
```

FIG. 9C

```
4701 TCAGCAATAA ACCAGCCAGC CGGAAGGGCC GAGCGCAGAA GTGGTCCTGC
4751 AACTTTATCC GCCTCCATCC AGTCTATTAA TTGTTGCCGG GAAGCTAGAG
4801 TAAGTAGTTC GCCAGTTAAT AGTTTGCGCA ACGTTGTTGC CATTGCTACA
4851 GGCATCGTGG TGTCACGCTC GTCGTTTGGT ATGGCTTCAT TCAGCTCCGG
4901 TTCCCAACGA TCAAGGCGAG TTACATGATC CCCCATGTTG TGCAAAAAAG
4951 CGGTTAGCTC CTTCGGTCCT CCGATCGTTG TCAGAAGTAA GTTGGCCGCA
5001 GTGTTATCAC TCATGGTTAT GGCAGCACTG CATAATTCTC TTACTGTCAT
5051 GCCATCCGTA AGATGCTTTT CTGTGACTGG TGAGTACTCA ACCAAGTCAT
5101 TCTGAGAATA GTGTATGCGG CGACCGAGTT GCTCTTGCCC GGCGTCAATA
5151 CGGGATAATA CCGCGCCACA TAGCAGAACT TTAAAAGTGC TCATCATTGG
5201 AAAACGTTCT TCGGGGCGAA AACTCTCAAG GATCTTACCG CTGTTGAGAT
5251 CCAGTTCGAT GTAACCCACT CGTGCACCCA ACTGATCTTC AGCATCTTTT
5301 ACTTTCACCA GCGTTTCTGG GTGAGCAAAA ACAGGAAGGC AAAATGCCGC
5351 AAAAAAGGGA ATAAGGGCGA CACGGAAATG TTGAATACTC ATACTCTTCC
5401 TTTTTCAATA TTATTGAAGC ATTTATCAGG GTTATTGTCT CATGAGCGGA
5451 TACATATTTG AATGTATTTA GAAAAATAAA CAAATAGGGG TTCCGCGCAC
5501 ATTTCCCCGA AAAGTGCCAC CTGGGAAATT GTAAACGTTA ATATTTTGTT
5551 AAAATTCGCG TTAAATTTTT GTTAAATCAG CTCATTTTTT AACCAATAGG
5601 CCGAAATCGG CAAAATCCCT TATAAATCAA AAGAATAGAC CGAGATAGGG
5651 TTGAGTGTTG TTCCAGTTTG GAACAAGAGT CCACTATTAA AGAACGTGGA
5701 CTCCAACGTC AAAGGGCGAA AAACCGTCTA TCAGGGCGAT GGCCCACTAC
5751 GTGAACCATC ACCCTAATCA AGTTTTTTGG GGTCGAGGTG CCGTAAAGCA
5801 CTAAATCGGA ACCCTAAAGG GAGCCCCCGA TTTAGAGCTT GACGGGGAAA
5851 GCCGGCGAAC GTGGCGAGAA AGGAAGGGAA GAAAGCGAAA GGAGCGGGCG
5901 CTAGGGCGCT GGCAAGTGTA GCGGTCACGC TGCGCGTAAC CACCACACCC
5951 GCCGCGCTTA ATGCGCCGCT ACAGGGCGCG TCGCGCCATT CGCCATTCAG
6001 GCTGCGCAAC TGTTGGGAAG GGCGATCGGT GCGGGCCTCT TCGCTATTAC
6051 GCCAGCTGGC GAAAGGGGGA TGTGCTGCAA GGCGATTAAG TTGGGTAACG
6101 CCAGGGTTTT CCCAGTCACG ACGTTGTAAA ACGACGGCCA GTGAATTGTA
6151 ATACGACTCA CTATAGGGCG AATTGGGTAC CGGGCCCCCC CTCGAG
```

FIG. 11A

```
   1 TCGACGGTGC CCCCAGCAGA AGTATCGACT GCATGCTAAT TATTAACAAA
  51 CCAAAAGGCG TTGCCACTTA CACCCTTACC TTTAGGTTTT TAAACTTTAA
 101 CAGACTAAGC GGAGGTACCC TGTTTAAAAC TGATGTCTTA ACCTTTACCT
 151 ATGTAGGCGA AAATCAATAA AACCAGAAAA AAATAAGTTT AAAAGCTTTA
 201 TTTTTCATAC ACGCGAGCGG TAAGGCTGCC GCCTTCAGGA AAAGTTACTC
 251 TGTAAACAGT TCTTTCACAA CAGCACAAAA CATAGGTATT AGTTAACAGT
 301 TCATTTGGGC TATAATAATA TACATTTTCT TGGGTGGCAA AGCAAGGGTC
 351 GGTAATCTCA ACAAAACCAT CAACTGGAAT GCAAGAATAG TCCAGCACGG
 401 TGGGTTCAAT CTAAAAATGA AGAAACGCTG TTGAGGTTCA CTAAGCACAG
 451 GTTTTGAATC TGTCGGCAGC GTCCATGCAT CATAGCTTGT CTCAAAGCAG
 501 ATTGTCTTCT TTCCTCTGCC TTGGAAGTGG TTTGGTGAAG CACTACAGGT
 551 GTCTTTTCAA CCTCTTTCAG CACCCGCTCT ATTACAGATC TCACCCACAC
 601 AGCACAGTTT TTAAGAGAAC AATAGTTTTG AAGGCTACAA GATTTACACT
 651 TAAGCACCAG CCAGTAATTA TAAGTGCTTT TAAGAACTAC CCCTAGCTCA
 701 GGGTTAATGC ACCTTTTAAT GGCCTCCATG CAGGCTTTAT GGACAGTTCT
 751 AAAAAAAGAC AGTCTAAAAT AAATGTAGTG AGTGTTTCTA AATATAATAC
 801 TCCCCACATA GTTAATTTCA TCAGGCCTGC TAGAATTTAC AAACTCTCGG
 851 TACCACATAT ACTTTTTATT CATAGCCCCA CCCTTAATAA AGTCCTCAAT
 901 CACTTTCTGA ACCACATGCT TGCTAGCCAT GCATTGTAAA GACAAGCTGT
 951 TAGAGCAGTG ACAGTGTACT CGCCACGTTT GAGCCTCTGC CAGGCAGCAG
1001 TGCTTAGTTA CTATCAACTC AATACCCGCA TTGCATGTAA ACCCCCCAAA
1051 GAGCAGTTTT TCATGCCTGT GTAGCACATC ATCCCACAAA ATAGGAATTT
1101 CATAGCATAA AGCAAAGCAA TTACAATATT TAGGAACTCT CACCACAGCA
1151 GTCACGTGAC ATGTTGTCTC AGCAGTGCAG TTGCCTTCCA TCCTACAATT
1201 ATGAACAAAA ACTAAACACT TCTAACAAAG ATACAGTGAC AATCTCCCTT
1251 CCTCTAAAAG CATTGTTTAC ATTAGGGTGA TTATTAACAA CGTCAGAAAT
1301 TTCTTTAATT AAAGTGCCTT TAAAATGTGC AAGAGCATCA TCATACTCAA
1351 AACCAAGCTG AGAGTAAAAG ACCACCTTAA AAGTAATCCC AGGCTTGTTT
1401 TTATCAACAG CCTTAAACAT GCTTTCACAA AATATAGAAG CAGTAACATC
1451 ATCAATGGTG TCGAAGAGAA ACTCCATAGG AGACTCCAGC ATTGATCCAA
1501 GCTCTCTAAC AAAATCTTCC TCAAAATGAA TAATGCCCTT TACACAAACG
1551 CGGGGCAGAC GATGGTGGGC CATCGCGTCA ACCTGAAACA CATTTTACAG
1601 TAAACAAAGC TAGCTCCGCA GTGGTAAAGT CATGCCCATG GGTGAGGCCA
1651 AAATCCTTAA AAAAGCTATC TAAGTAGTTG GTCATCCCCT CAGTTAAAAA
1701 GTTTTGCAGC TGGGTGGTGC ATACCACATA GTGCCAGCTT ATAGCTACAA
1751 AGACCTGCAT CCCTCCTTA GCAGACAGCT CTTGCACACA CGCAGTAACT
1801 ATCCACCGCT TAAGAAAAGC TTAAGCCCA GCGCACATAA CAGCTCCAAT
1851 GTTTTATCC AAGGAGAGCA AAATTTCAGC AAGCGCAGGC TCAACAGTAA
1901 TAGTGAAGCA GAGGCATTTC AGACGAGGCT CACTAGCTGC AGTCGCCATT
1951 TATGAGGTCT GCAATAAAAA ACAACTCATC AGCAGCTGAA AAAGTGCACT
2001 TTGACCTCAT TAAGCCACTG CATATGCAAG TCCTCATCTA TGCCGCAGCC
2051 CAGACCCTCA ATCCAGCCCC GAATGTACAC TTTAATAAGA GATTCAACCT
2101 CTTCTTTTAG CAAAGTACAC ATGCTGTTTG GACTAGTATA CACAATAGAA
```

FIG. 11B

```
2151 GTCACAATGA GGGGCCCGCT GTGGCTGGAA AGCCTGCGCA CAGCCCGAAG
2201 GTTAAAAATG GACTGTAACA GCATTGAAAC CCCGCGACAC AGGTCAGTCT
2251 CGCGGTCTTG ATCTCTTATT ATAGCGACCA AATGGTCCTT CAGAGTGATG
2301 TTGCACTCAT AGAAGTAGGC AGCTCCGGCA GCCATTCTGC AAAATAACAA
2351 AACACCACTA AGCATAGCAC CATCACCAAG CATGAAAACA GGTAAAAACA
2401 AAAGCAACAC TTACTTATTC AGCAGTCACA AGAATGTTGG GCTCCCAAGT
2451 GACAGACAAG CCTAATGCAA GGTGGGCACA GTCTCCGGAA TAAGTTGACA
2501 AAAGTCACGC CGCAAAGCTT CCTGAAGAGA AACGGCGGTA GCCTGGATAT
2551 CTGCAACGGA CCCAAAACCT TCAGTGTCAC TTCCAATAAA CAGATAAAAC
2601 TCTAAATAGT CCCCACTTAA AACCGAAACA GCCGCGGCAA AGGTAGGACA
2651 CGGACGCACT TCCTGAGCCC TAATAAGGCT AAACACCACA CGGCGCAGTT
2701 CAGAAGGCAA AAAGTCTGTA AGCTCTAGCT GAGCACACAC ACTCTCCACT
2751 AGACACTTGT GAAGCCTCAG ACAAAAACAT GCTCCCATAG ACACTCCTAA
2801 AGCTGCCATT GTACTCACGG ACGGCTGGCT GTCAGAGGAG AGCTATGAGG
2851 ATGAAATGCC AAGCACAGCG TTTATATAGT CCTCAAAGTA GGGCGTGTGG
2901 AAAACGAAAA GGAATATAAC GGGGCGTTTG AGGAAGTGGT GCCAAGTACA
2951 GTCATAAAAT GTGGGCGCGT GGTAAATGTT AAGTGCAGTT TCCCTTTGGC
3001 GGTTGGCCCG GAAAGTTCAC AAAAAGTACA GCACGTCCTT GTCACCGTGT
3051 CAACCACAAA ACCACAAATA GGCACAACGC CCAAAAACCC ATCAAAGATG
3101 GTCCGGTTCT TGTACTCGGG CCATATATTC ATGTCCCCAG ACATCATAGT
3151 CAGCACCATT TTCTTCTCCT TTTGCCAGTA GATGCGAGTT TGTGCCAGCT
3201 CTTCAACAGA AACATTGTGA CCACAGGACA GCGTTGCCAC TTCTTTCACT
3251 TCCTTGGTCA CGTGGATAAC ACCTGAACAG AAGTGAGAAA GACCAGCCAG
3301 CACCAAGAGC TGAAAGAAAT TGAGGTATGG ACACTTGGAT GGTGATGTTC
3351 CCTGCCTCCG TGTGTGGCCC ATTACGATAC AAACTTAACG GATATCGGGG
3401 GCGCCGGCCA AAAGTCCGCG GAACTCGCCC TGTCGTAAAA CCACGCCTTT
3451 GACGTCACTG GACATTCCCG TGGGAACACC CTGACCAGGG CGTGACCTGA
3501 ACCTGACCGT CCCATGACCC CGCCCCTTGC AACACCCAAA TTTAAGCCAC
3551 ACCTCTTTGT CCTGTATATT ATTGATGATG GGGGATCCA CTAGTTCTAG
3601 AGCGGCCGCC ACCGCGGTGG AGCTCCAGCT TTTGTTCCCT TTAGTGAGGG
3651 TTAATTCCGA GCTTGGCGTA ATCATGGTCA TAGCTGTTTC CTGTGTGAAA
3701 TTGTTATCCG CTCACAATTC CACACAACAT ACGAGCCGGA AGCATAAAGT
3751 GTAAAGCCTG GGGTGCCTAA TGAGTGAGCT AACTCACATT AATTGCGTTG
3801 CGCTCACTGC CCGCTTTCCA GTCGGGAAAC CTGTCGTGCC AGCTGCATTA
3851 ATGAATCGGC CAACGCGCGG GGAGAGGCGG TTTGCGTATT GGGCGCTCTT
3901 CCGCTTCCTC GCTCACTGAC TCGCTGCGCT CGGTCGTTCG GCTGCGGCGA
3951 GCGGTATCAG CTCACTCAAA GGCGGTAATA CGGTTATCCA CAGAATCAGG
4001 GGATAACGCA GGAAAGAACA TGTGAGCAAA AGGCCAGCAA AAGGCCAGGA
4051 ACCGTAAAAA GGCCGCGTTG CTGGCGTTTT TCCATAGGCT CCGCCCCCCT
4101 GACGAGCATC ACAAAAATCG ACGCTCAAGT CAGAGGTGGC GAAACCCGAC
4151 AGGACTATAA AGATACCAGG CGTTTCCCCC TGGAAGCTCC CTCGTGCGCT
4201 CTCCTGTTCC GACCCTGCCG CTTACCGGAT ACCTGTCCGC CTTTCTCCCT
4251 TCGGGAAGCG TGGCGCTTTC TCATAGCTCA CGCTGTAGGT ATCTCAGTTC
4301 GGTGTAGGTC GTTCGCTCCA AGCTGGGCTG TGTGCACGAA CCCCCCGTTC
4351 AGCCCGACCG CTGCGCCTTA TCCGGTAACT ATCGTCTTGA GTCCAACCCG
4401 GTAAGACACG ACTTATCGCC ACTGGCAGCA GCCACTGGTA ACAGGATTAG
4451 CAGAGCGAGG TATGTAGGCG GTGCTACAGA GTTCTTGAAG TGGTGGCCTA
4501 ACTACGGCTA CACTAGAAGG ACAGTATTTG GTATCTGCGC TCTGCTGAAG
4551 CCAGTTACCT TCGGAAAAAG AGTTGGTAGC TCTTGATCCG GCAAACAAAC
4601 CACCGCTGGT AGCGGTGGTT TTTTGTTTG CAAGCAGCAG ATTACGCGCA
4651 GAAAAAAAGG ATCTCAAGAA GATCCTTTGA TCTTTTCTAC GGGGTCTGAC
4701 GCTCAGTGGA ACGAAAACTC ACGTTAAGGG ATTTTGGTCA TGAGATTATC
4751 AAAAAGGATC TTCACCTAGA TCCTTTTAAA TTAAAAATGA AGTTTTAAAT
```

FIG. 11C

```
4801 CAATCTAAAG TATATATGAG TAAACTTGGT CTGACAGTTA CCAATGCTTA
4851 ATCAGTGAGG CACCTATCTC AGCGATCTGT CTATTTCGTT CATCCATAGT
4901 TGCCTGACTC CCCGTCGTGT AGATAACTAC GATACGGGAG GGCTTACCAT
4951 CTGGCCCCAG TGCTGCAATG ATACCGCGAG ACCCACGCTC ACCGGCTCCA
5001 GATTTATCAG CAATAAACCA GCCAGCCGGA AGGGCCGAGC GCAGAAGTGG
5051 TCCTGCAACT TTATCCGCCT CCATCCAGTC TATTAATTGT TGCCGGGAAG
5101 CTAGAGTAAG TAGTTCGCCA GTTAATAGTT TGCGAACGT TGTTGCCATT
5151 GCTACAGGCA TCGTGGTGTC ACGCTCGTCG TTTGGTATGG CTTCATTCAG
5201 CTCCGGTTCC CAACGATCAA GGCGAGTTAC ATGATCCCCC ATGTTGTGCA
5251 AAAAAGCGGT TAGCTCCTTC GGTCCTCCGA TCGTTGTCAG AAGTAAGTTG
5301 GCCGCAGTGT TATCACTCAT GGTTATGCA GCACTGCATA ATTCTCTTAC
5351 TGTCATGCCA TCCGTAAGAT GCTTTTCTGT GACTGGTGAG TACTCAACCA
5401 AGTCATTCTG AGAATAGTGT ATGCGGCGAC CGAGTTGCTC TTGCCCGGCG
5451 TCAATACGGG ATAATACCGC GCCACATAGC AGAACTTTAA AAGTGCTCAT
5501 CATTGGAAAA CGTTCTTCGG GGCGAAAACT CTCAAGGATC TTACCGCTGT
5551 TGAGATCCAG TTCGATGTAA CCCACTCGTG CACCCAACTG ATCTTCAGCA
5601 TCTTTTACTT TCACCAGCGT TTCTGGGTGA GCAAAAACAG GAAGGCAAAA
5651 TGCCGCAAAA AAGGGAATAA GGGCGACACG GAAATGTTGA ATACTCATAC
5701 TCTTCCTTTT TCAATATTAT TGAAGCATTT ATCAGGGTTA TTGTCTCATG
5751 AGCGGATACA TATTTGAATG TATTTAGAAA AATAAACAAA TAGGGGTTCC
5801 GCGCACATTT CCCCGAAAAG TGCCACCTGG GAAATTGTAA ACGTTAATAT
5851 TTTGTTAAAA TTCGCGTTAA ATTTTTGTTA AATCAGCTCA TTTTTTAACC
5901 AATAGGCCGA AATCGGCAAA ATCCCTTATA AATCAAAAGA ATAGACCGAG
5951 ATAGGGTTGA GTGTTGTTCC AGTTTGGAAC AAGAGTCCAC TATTAAAGAA
6001 CGTGGACTCC AACGTCAAAG GGCGAAAAAC CGTCTATCAG GCGATGGCC
6051 CACTACGTGA ACCATCACCC TAATCAAGTT TTTTGGGGTC GAGGTGCCGT
6101 AAAGCACTAA ATCGGAACCC TAAAGGGAGC CCCCGATTTA GAGCTTGACG
6151 GGGAAAGCCG GCGAACGTGG CGAGAAAGGA AGGGAAGAAA GCGAAAGGAG
6201 CGGGCGCTAG GGCGCTGGCA AGTGTAGCGG TCACGCTGCG CGTAACCACC
6251 ACACCCGCCG CGCTTAATGC GCCGCTACAG GGCGCGTCGC GCCATTCGCC
6301 ATTCAGGCTG CGCAACTGTT GGGAAGGGCG ATCGGTGCGG GCCTCTTCGC
6351 TATTACGCCA GCTGGCGAAA GGGGGATGTG CTGCAAGGCG ATTAAGTTGG
6401 GTAACGCCAG GGTTTTCCCA GTCACGACGT TGTAAAACGA CGGCCAGTGA
6451 ATTGTAATAC GACTCACTAT AGGGCGAATT GGGTACCGGG CCCCCCCTCG
6501 AGG
```

FIG. 13A

```
   1 TAATGTCGTA ACAACTCCGC CCCGTTGACG CAAATGGGCG GTAGGCGTGT
  51 ACGGTGGGAG GTCTATATAA GCAGAGCTCG TTTAGTGAAC CGTCAGATCG
 101 CCTGGAGACG CCATCCACGC TGTTTTGACC TCCATAGAAG ACACCGGCTG
 151 CAGGTCGACT CTAGAGGATC TGAGCTTGGC GAGATTTTCA GGAGCTAAGG
 201 AAGCTAAAAT GGAGAAAAAA ATCACTGGAT ATACCACCGT TGATATATCC
 251 CAATGGCATC GTAAAGAACA TTTTGAGGCA TTTCAGTCAG TTGCTCAATG
 301 TACCTATAAC CAGACCGTTC AGCTGGATAT TACGGCCTTT TTAAAGACCG
 351 TAAAGAAAAA TAAGCACAAG TTTTATCCGG CCTTTATTCA CATTCTTGCC
 401 CGCCTGATGA ATGCTCATCC GGAATTCCGT ATGGCAATGA AAGACGGTGA
 451 GCTGGTGATA TGGGATAGTG TTCACCCTTG TTACACCGTT TTCCATGAGC
 501 AAACTGAAAC GTTTTCATCG CTCTGGAGTG AATACCACGA CGATTTCCGG
 551 CAGTTTCTAC ACATATATTC GCAAGATGTG GCGTGTTACG GTGAAAACCT
 601 GGCCTATTTC CCTAAAGGGT TTATTGAGAA TATGTTTTTC GTCTCAGCCA
 651 ATCCCTGGGT GAGTTTCACC AGTTTTGATT TAAACGTGGC CAATATGGAC
 701 AACTTCTTCG CCCCCGTTTT CACCATGGGC AAATATTATA CGCAAGGCGA
 751 CAAGGTGCTG ATGCCGCTGG CGATTCAGGT TCATCATGCC GTCTGTGATG
 801 GCTTCCATGT CGGCAGAATG CTTAATGAAT TACAACAGTA CTGCGATGAG
 851 TGGCAGGGCG GGGCGTAATT TTTTTAAGGC AGTTATTGGT GCCCTTAAAC
 901 GCCTGGTGCT ACGCCTGAAT AAGTGATAAT AAGCGGATGA ATGGCAGAAA
 951 TTCGCCGGAT CTTTGTGAAG GAACCTTACT TCTGTGGTGT GACATAATTG
1001 GACAAACTAC CTACAGAGAT TTAAAGCTCT AAGGTAAATA TAAAATTTTT
1051 AAGTGTATAA TGTGTTAAAC TACTGATTCT AATTGTTTGT GTATTTAGA
1101 TTCCAACCTA TGGAACTGAT GAATGGGAGC AGTGGTGGAA TGCCTTTAAT
1151 GAGGAAAACC TGTTTTGCTC AGAAGAAATG CCATCTAGTG ATGATGAGGC
1201 TACTGCTGAC TCTCAACATT CTACTCCTCC AAAAAAGAAG AGAAAGGTAG
1251 AAGACCCCAA GGACTTTCCT TCAGAATTGC TAAGTTTTTT GAGTCATGCT
1301 GTGTTTAGTA ATAGAACTCT TGCTTGCTTT GCTATTTACA CCACAAAGGA
1351 AAAAGCTGCA CTGCTATACA AGAAAATTAT GGAAAAATAT TCTGTAACCT
1401 TTATAAGTAG GCATAACAGT TATAATCATA ACATACTGTT TTTTCTTACT
1451 CCACACAGGC ATAGAGTGTC TGCTATTAAT AACTATGCTC AAAAATTGTG
1501 TACCTTTAGC TTTTTAATTT GTAAAGGGGT TAATAAGGAA TATTTGATGT
1551 ATAGTGCCTT GACTAGAGAT CATAATCAGC CATACCACAT TTGTAGAGGT
1601 TTTACTTGCT TTAAAAAACC TCCCACACCT CCCCCTGAAC CTGAAACATA
1651 AAATGAATGC AATTGTTGTT GTTAACTTGT TTATTGCAGC TTATAATGGT
1701 TACAAATAAA GCAATAGCAT CACAAATTTC ACAAATAAAG CATTTTTTTC
1751 ACTGCATTCT AGTTGTGGTT TGTCCAAACT CATCAATGTA TCTTATCATG
```

FIG. 13B

```
1801 TCTGGATCCC CCGGAATTCA CTGGCCGTCG TTTTACAACG TCGTGACTGG
1851 GAAAACCCTG GCGTTACCCA ACTTAATCGC CTTGCAGCAC ATCCCCCCTT
1901 CGCCAGCTGG CGTAATAGCG AAGAGGCCCG CACCGATCGC CCTTCCCAAC
1951 AGTTGCGCAG CCTGAATGGC GAATGGCGCC TGATGCGGTA TTTTCTCCTT
2001 ACGCATCTGT GCGGTATTTC ACACCGCATA TGGTGCACTC TCAGTACAAT
2051 CTGCTCTGAT GCCGCATAGT TAAGCCAGTA CACTCCGCTA TCGCTACGTG
2101 ACTGGGTCAT GGCTGCGCCC CGACACCCGC CAACACCCGC TGACGCGCCC
2151 TGACGGGCTT GTCTGCTCCC GGCATCCGCT TACAGACAAG CTGTGACCGT
2201 CTCCGGGAGC TGCATGTGTC AGAGGTTTTC ACCGTCATCA CCGAAACGCG
2251 CGAGGCAGTT CTTGAAGACG AAAGGGCCTC GTGATACGCC TATTTTTATA
2301 GGTTAATGTC ATGATAATAA TGGTTTCTTA GACGTCAGGT GGCACTTTTC
2351 GGGGAAATGT GCGCGGAACC CCTATTTGTT TATTTTTCTA AATACATTCA
2401 AATATGTATC CGCTCATGAG ACAATAACCC TGATAAATGC TTCAATAATA
2451 TTGAAAAAGG AAGAGTATGA GTATTCAACA TTTCCGTGTC GCCCTTATTC
2501 CCTTTTTTGC GGCATTTGC CTTCCTGTTT TTGCTCACCC AGAAACGCTG
2551 GTGAAAGTAA AAGATGCTGA AGATCAGTTG GGTGCACGAG TGGGTTACAT
2601 CGAACTGGAT CTCAACAGCG GTAAGATCCT TGAGAGTTTT CGCCCCGAAG
2651 AACGTTTTCC AATGATGAGC ACTTTTAAAG TTCTGCTATG TGGCGCGGTA
2701 TTATCCCGTA TTGACGCCGG GCAAGAGCAA CTCGGTCGCC GCATACACTA
2751 TTCTCAGAAT GACTTGGTTG AGTACTCACC AGTCACAGAA AAGCATCTTA
2801 CGGATGGCAT GACAGTAAGA GAATTATGCA GTGCTGCCAT AACCATGAGT
2851 GATAACACTG CGGCCAACTT ACTTCTGACA ACGATCGGAG GACCGAAGGA
2901 GCTAACCGCT TTTTTGCACA ACATGGGGGA TCATGTAACT CGCCTTGATC
2951 GTTGGGAACC GGAGCTGAAT GAAGCCATAC CAAACGACGA GCGTGACACC
3001 ACGATGCCTG TAGCAATGGC AACAACGTTG CGCAAACTAT TAACTGGCGA
3051 ACTACTTACT CTAGCTTCCC GGCAACAATT AATAGACTGG ATGGAGGCGG
3101 ATAAAGTTGC AGGACCACTT CTGCGCTCGG CCCTTCCGGC TGGCTGGTTT
3151 ATTGCTGATA AATCTGGAGC CGGTGAGCGT GGGTCTCGCG GTATCATTGC
3201 AGCACTGGGG CCAGATGGTA AGCCCTCCCG TATCGTAGTT ATCTACACGA
3251 CGGGGAGTCA GGCAACTATG GATGAACGAA ATAGACAGAT CGCTGAGATA
3301 GGTGCCTCAC TGATTAAGCA TTGGTAACTG TCAGACCAAG TTTACTCATA
3351 TATACTTTAG ATTGATTTAA AACTTCATTT TTAATTTAAA AGGATCTAGG
3401 TGAAGATCCT TTTTGATAAT CTCATGACCA AAATCCCTTA ACGTGAGTTT
3451 TCGTTCCACT GAGCGTCAGA CCCCGTAGAA AAGATCAAAG GATCTTCTTG
3501 AGATCCTTTT TTTCTGCGCG TAATCTGCTG CTTGCAAACA AAAAAACCAC
3551 CGCTACCAGC GGTGGTTTGT TTGCCGGATC AAGAGCTACC AACTCTTTTT
3601 CCGAAGGTAA CTGGCTTCAG CAGAGCGCAG ATACCAAATA CTGTCCTTCT
3651 AGTGTAGCCG TAGTTAGGCC ACCACTTCAA GAACTCTGTA GCACCGCCTA
3701 CATACCTCGC TCTGCTAATC CTGTTACCAG TGGCTGCTGC CAGTGGCGAT
3751 AAGTCGTGTC TTACCGGGTT GGACTCAAGA CGATAGTTAC CGGATAAGGC
3801 GCAGCGGTCG GGCTGAACGG GGGGTTCGTG CACACAGCCC AGCTTGGAGC
3851 GAACGACCTA CACCGAACTG AGATACCTAC AGCGTGAGCA TTGAGAAAGC
3901 GCCACGCTTC CCGAAGGGAG AAAGGCGGAC AGGTATCCGG TAAGCGGCAG
3951 GGTCGGAACA GGAGAGCGCA CGAGGGAGCT TCCAGGGGGA AACGCCTGGT
4001 ATCTTTATAG TCCTGTCGGG TTTCGCCACC TCTGACTTGA GCGTCGATTT
4051 TTGTGATGCT CGTCAGGGGG GCGGAGCCTA TGGAAAAACG CCAGCAACGC
4101 GGCCTTTTTA CGGTTCCTGG CCTTTTGCTG GCCTTTTGCT CACATGTTCT
4151 TTCCTGCGTT ATCCCCTGAT TCTGTGGATA ACCGTATTAC CGCCTTTGAG
4201 TGAGCTGATA CCGCTCGCCG CAGCCGAACG ACCGAGCGCA GCGAGTCAGT
4251 GAGCGAGGAA GCGGAAGAGC GCCAATACGC AAACCGCCTC TCCCCGCGCG
```

FIG.13C

```
4301 TTGGCCGATT CATTAATGCA GCTGGCACGA CAGGTTTCCC GACTGGAAAG
4351 CGGGCAGTGA GCGCAACGCA ATTAATGTGA GTTACCTCAC TCATTAGGCA
4401 CCCCAGGCTT TACACTTTAT GCTTCCGGCT CGTATGTTGT GTGGAATTGT
4451 GAGCGGATAA CAATTTCACA CAGGAAACAG CTATGACCAT GATTACGCC
     AGCT
```

FIG. 15A

```
   1 TAATGTCGTA ACAACTCCGC CCCGTTGACG CAAATGGGCG GTAGGCGTGT
  51 ACGGTGGGAG GTCTATATAA GCAGAGCTCG TTTAGTGAAC CGTCAGATCG
 101 CCTGGAGACG CCATCCACGC TGTTTTGACC TCCATAGAAG ACACCGGCTG
 151 CAGGTCGACT CTAGAGGATC TGAGCTTGGC GAGATTTTCA GGAGCTAAGG
 201 AAGCTAAAAT GGAGAAAAAA ATCACTGGAT ATACCACCGT TGATATATCC
 251 CAATGGCATC GTAAAGAACA TTTTGAGGCA TTTCAGTCAG TTGCTCAATG
 301 TACCTATAAC CAGACCGTTC AGCTGGATAT TACGGCCTTT TTAAAGACCG
 351 TAAAGAAAAA TAAGCACAAG TTTTATCCGG CCTTTATTCA CATTCTTGCC
 401 CGCCTGATGA ATGCTCATCC GGAATTCCGT ATGGCAATGA AAGACGGTGA
 451 GCTGGTGATA TGGGATAGTG TTCACCCTTG TTACACCGTT TTCCATGAGC
 501 AAACTGAAAC GTTTTCATCG CTCTGGAGTG AATACCACGA CGATTTCCGG
 551 CAGTTTCTAC ACATATATTC GCAAGATGTG GCGTGTTACG GTGAAAACCT
 601 GGCCTATTTC CCTAAAGGGT TTATTGAGAA TATGTTTTTC GTCTCAGCCA
 651 ATCCCTGGGT GAGTTTCACC AGTTTTGATT TAAACGTGGC CAATATGGAC
 701 AACTTCTTCG CCCCGTTTT CACCATGGGC AAATATTATA CGCAAGGCGA
 751 CAAGGTGCTG ATGCCGCTGG CGATTCAGGT TCATCATGCC GTCTGTGATG
 801 GCTTCCATGT CGGCAGAATG CTTAATGAAT TACAACAGTA CTGCGATGAG
 851 TGGCAGGGCG GGGCGTAATT TTTTAAGCC GCGGCGTGAT TAATCAGCCA
 901 TACCACATTT GTAGAGGTTT TACTTGCTTT AAAAAACCTC CCACACCTCC
 951 CCCTGAACCT GAAACATAAA ATGAATGCAA TTGTTGTTGT TAACTTGTTT
1001 ATTGCAGCTT ATAATGGTTA CAAATAAAGC AATAGCATCA CAAATTTCAC
1051 AAATAAAGCA TTTTTTTCAC TGCATTCTAG TTGTGGTTTG TCCAAACTCA
1101 TCAATGTATC TTATCATGTC TGGATCCCCC GGAATTCACT GGCCGTCGTT
1151 TTACAACGTC GTGACTGGGA AAACCCTGGC GTTACCCAAC TTAATCGCCT
1201 TGCAGCACAT CCCCCCTTCG CCAGCTGGCG TAATAGCGAA GAGGCCCGCA
1251 CCGATCGCCC TTCCCAACAG TTGCGCAGCC TGAATGGCGA ATGGCGCCTG
1301 ATGCGGTATT TTCTCCTTAC GCATCTGTGC GGTATTTCAC ACCGCATATG
1351 GTGCACTCTC AGTACAATCT GCTCTGATGC CGCATAGTTA AGCCAGTACA
1401 CTCCGCTATC GCTACGTGAC TGGGTCATGG CTGCGCCCCG ACACCCGCCA
1451 ACACCCGCTG ACGCGCCCTG ACGGGCTTGT CTGCTCCCGG CATCCGCTTA
1501 CAGACAAGCT GTGACCGTCT CCGGGAGCTG CATGTGTCAG AGGTTTTCAC
1551 CGTCATCACC GAAACGCGCG AGGCAGTTCT TGAAGACGAA AGGGCCTCGT
1601 GATACGCCTA TTTTTATAGG TTAATGTCAT GATAATAATG GTTTCTTAGA
1651 CGTCAGGTGG CACTTTTCGG GGAAATGTGC GCGGAACCCC TATTTGTTTA
1701 TTTTTCTAAA TACATTCAAA TATGTATCCG CTCATGAGAC AATAACCCTG
1751 ATAAATGCTT CAATAATATT GAAAAGGAA GAGTATGAGT ATTCAACATT
1801 TCCGTGTCGC CCTTATTCCC TTTTTGCGG CATTTTGCCT TCCTGTTTTT
1851 GCTCACCCAG AAACGCTGGT GAAAGTAAAA GATGCTGAAG ATCAGTTGGG
1901 TGCACGAGTG GGTTACATCG AACTGGATCT CAACAGCGGT AAGATCCTTG
1951 AGAGTTTTCG CCCCGAAGAA CGTTTTCCAA TGATGAGCAC TTTTAAAGTT
2001 CTGCTATGTG GCGCGGTATT ATCCCGTATT GACGCCGGGC AAGAGCAACT
```

FIG. 15B

```
2051 CGGTCGCCGC ATACACTATT CTCAGAATGA CTTGGTTGAG TACTCACCAG
2101 TCACAGAAAA GCATCTTACG GATGGCATGA CAGTAAGAGA ATTATGCAGT
2151 GCTGCCATAA CCATGAGTGA TAACACTGCG GCCAACTTAC TTCTGACAAC
2201 GATCGGAGGA CCGAAGGAGC TAACCGCTTT TTTGCACAAC ATGGGGATC
2251 ATGTAACTCG CCTTGATCGT TGGGAACCGG AGCTGAATGA AGCCATACCA
2301 AACGACGAGC GTGACACCAC GATGCCTGTA GCAATGGCAA CAACGTTGCG
2351 CAAACTATTA ACTGGCGAAC TACTTACTCT AGCTTCCCGG CAACAATTAA
2401 TAGACTGGAT GGAGGCGGAT AAAGTTGCAG GACCACTTCT GCGCTCGGCC
2451 CTTCCGGCTG GCTGGTTTAT TGCTGATAAA TCTGGAGCCG GTGAGCGTGG
2501 GTCTCGCGGT ATCATTGCAG CACTGGGGCC AGATGGTAAG CCCTCCCGTA
2551 TCGTAGTTAT CTACACGACG GGGAGTCAGG CAACTATGGA TGAACGAAAT
2601 AGACAGATCG CTGAGATAGG TGCCTCACTG ATTAAGCATT GGTAACTGTC
2651 AGACCAAGTT TACTCATATA TACTTTAGAT TGATTTAAAA CTTCATTTTT
2701 AATTTAAAAG GATCTAGGTG AAGATCCTTT TTGATAATCT CATGACCAAA
2751 ATCCCTTAAC GTGAGTTTTC GTTCCACTGA GCGTCAGACC CCGTAGAAAA
2801 GATCAAAGGA TCTTCTTGAG ATCCTTTTTT TCTGCGCGTA ATCTGCTGCT
2851 TGCAAACAAA AAAACCACCG CTACCAGCGG TGGTTTGTTT GCCGGATCAA
2901 GAGCTACCAA CTCTTTTTCC GAAGGTAACT GGCTTCAGCA GAGCGCAGAT
2951 ACCAAATACT GTCCTTCTAG TGTAGCCGTA GTTAGGCCAC CACTTCAAGA
3001 ACTCTGTAGC ACCGCCTACA TACCTCGCTC TGCTAATCCT GTTACCAGTG
3051 GCTGCTGCCA GTGGCGATAA GTCGTGTCTT ACCGGGTTGG ACTCAAGACG
3101 ATAGTTACCG GATAAGGCGC AGCGGTCGGG CTGAACGGGG GGTTCGTGCA
3151 CACAGCCCAG CTTGGAGCGA ACGACCTACA CCGAACTGAG ATACCTACAG
3201 CGTGAGCATT GAGAAAGCGC CACGCTTCCC GAAGGGAGAA AGGCGGACAG
3251 GTATCCGGTA AGCGGCAGGG TCGAACAGG AGAGCGCACG AGGGAGCTTC
3301 CAGGGGGAAA CGCCTGGTAT CTTTATAGTC CTGTCGGGTT TCGCCACCTC
3351 TGACTTGAGC GTCGATTTTT GTGATGCTCG TCAGGGGGGC GGAGCCTATG
3401 GAAAAACGCC AGCAACGCGG CCTTTTTACG GTTCCTGGCC TTTTGCTGGC
3451 CTTTTGCTCA CATGTTCTTT CCTGCGTTAT CCCCTGATTC TGTGGATAAC
3501 CGTATTACCG CCTTTGAGTG AGCTGATACC GCTCGCCGCA GCCGAACGAC
3551 CGAGCGCAGC GAGTCAGTGA GCGAGGAAGC GGAAGAGCGC CAATACGCAA
3601 ACCGCCTCTC CCCGCGCGTT GGCCGATTCA TTAATGCAGC TGGCACGACA
3651 GGTTTCCCGA CTGGAAAGCG GGCAGTGAGC GCAACGCAAT TAATGTGAGT
3701 TACCTCACTC ATTAGGCACC CCAGGCTTTA CACTTTATGC TTCCGGCTCG
3751 TATGTTGTGT GGAATTGTGA GCGGATAACA ATTTCACACA GGAAACAGCT
3801 ATGACCATGA TTACGCCAAG CT
```

FIG. 17A

```
   1 TAATGTCGTA ACAACTCCGC CCCGTTGACG CAAATGGGCG GTAGGCGTGT
  51 ACGGTGGGAG GTCTATATAA GCAGAGCTCG TTTAGTGAAC CGTCAGATCG
 101 CCTGGAGACG CCATCCACGC TGTTTTGACC TCCATAGAAG ACACCGGCTG
 151 CAGACTCTCT TCCGCATCGC TGTCTGCGAG GGCCAGCTGT TGGGCTCGCG
 201 GTTGAGGACA AACTCTTCGC GGTCTTTCCA GTACTCTTGG ATCGGAAACC
 251 CGTCGGCCTC CGAACGGTAC TCCGCCACCG AGGGACCTGA GCGAGTCCGC
 301 ATCGACCGGA TCGGAAAACC TCTCGAGAAA GGCGTCTAAC CAGTCACAGT
 351 CGCAAGTCTA GAGGATCTGA GCTTGGCGAG ATTTTCAGGA GCTAAGGAAG
 401 CTAAAATGGA GAAAAAATC ACTGGATATA CCACCGTTGA TATATCCCAA
 451 TGGCATCGTA AAGAACATTT TGAGGCATTT CAGTCAGTTG CTCAATGTAC
 501 CTATAACCAG ACCGTTCAGC TGGATATTAC GGCCTTTTTA AAGACCGTAA
 551 AGAAAAATAA GCACAAGTTT TATCCGGCCT TTATTCACAT TCTTGCCCGC
 601 CTGATGAATG CTCATCCGGA ATTCCGTATG GCAATGAAAG ACGGTGAGCT
 651 GGTGATATGG GATAGTGTTC ACCCTTGTTA CACCGTTTTC CATGAGCAAA
 701 CTGAAACGTT TTCATCGCTC TGGAGTGAAT ACCACGACGA TTTCCGGCAG
 751 TTTCTACACA TATATTCGCA AGATGTGGCG TGTTACGGTG AAAACCTGGC
 801 CTATTTCCCT AAAGGGTTTA TTGAGAATAT GTTTTCGTC TCAGCCAATC
 851 CCTGGGTGAG TTTCACCAGT TTTGATTTAA ACGTGGCCAA TATGGACAAC
 901 TTCTTCGCCC CCGTTTTCAC CATGGGCAAA TATTATACGC AAGGCGACAA
 951 GGTGCTGATG CCGCTGGCGA TTCAGGTTCA TCATGCCGTC TGTGATGGCT
1001 TCCATGTCGG CAGAATGCTT AATGAATTAC AACAGTACTG CGATGAGTGG
1051 CAGGGCGGGG CGTAACCGCG GCGTGATTAA TCAGCCATAC CACATTTGTA
1101 GAGGTTTTAC TTGCTTTAAA AAACCTCCCA CACCTCCCCC TGAACCTGAA
1151 ACATAAAATG AATGCAATTG TTGTTGTTAA CTTGTTTATT GCAGCTTATA
1201 ATGGTTACAA ATAAAGCAAT AGCATCACAA ATTTCACAAA TAAAGCATTT
1251 TTTTCACTGC ATTCTAGTTG TGGTTTGTCC AAACTCATCA ATGTATCTTA
1301 TCATGTCTGG ATCCCCGGA ATTCACTGGC CGTCGTTTTA CAACGTCGTG
1351 ACTGGGAAAA CCCTGGCGTT ACCCAACTTA ATCGCCTTGC AGCACATCCC
1401 CCCTTCGCCA GCTGGCGTAA TAGCGAAGAG GCCCGCACCG ATCGCCCTTC
1451 CCAACAGTTG CGCAGCCTGA ATGGCGAATG GCGCCTGATG CGGTATTTTC
1501 TCCTTACGCA TCTGTGCGGT ATTTCACACC GCATATGGTG CACTCTCAGT
1551 ACAATCTGCT CTGATGCCGC ATAGTTAAGC CAGTACACTC CGCTATCGCT
1601 ACGTGACTGG GTCATGGCTG CGCCCCGACA CCCGCCAACA CCCGCTGACG
1651 CGCCCTGACG GGCTTGTCTG CTCCCGGCAT CCGCTTACAG ACAAGCTGTG
1701 ACCGTCTCCG GGAGCTGCAT GTGTCAGAGG TTTTCACCGT CATCACCGAA
1751 ACGCGCGAGG CAGTTCTTGA AGACGAAAGG GCCTCGTGAT ACGCCTATTT
1801 TTATAGGTTA ATGTCATGAT AATAATGGTT TCTTAGACGT CAGGTGGCAC
1851 TTTTCGGGGA AATGTGCGCG GAACCCCTAT TTGTTTATTT TTCTAAATAC
```

FIG. 17B

```
1901 ATTCAAATAT GTATCCGCTC ATGAGACAAT AACCCTGATA AATGCTTCAA
1951 TAATATTGAA AAAGGAAGAG TATGAGTATT CAACATTTCC GTGTCGCCCT
2001 TATTCCCTTT TTTGCGGCAT TTTGCCTTCC TGTTTTGCT CACCCAGAAA
2051 CGCTGGTGAA AGTAAAAGAT GCTGAAGATC AGTTGGGTGC ACGAGTGGGT
2101 TACATCGAAC TGGATCTCAA CAGCGGTAAG ATCCTTGAGA GTTTTCGCCC
2151 CGAAGAACGT TTTCCAATGA TGAGCACTTT TAAAGTTCTG CTATGTGGCG
2201 CGGTATTATC CCGTATTGAC GCCGGGCAAG AGCAACTCGG TCGCCGCATA
2251 CACTATTCTC AGAATGACTT GGTTGAGTAC TCACCAGTCA CAGAAAAGCA
2301 TCTTACGGAT GGCATGACAG TAAGAGAATT ATGCAGTGCT GCCATAACCA
2351 TGAGTGATAA CACTGCGGCC AACTTACTTC TGACAACGAT CGGAGGACCG
2401 AAGGAGCTAA CCGCTTTTTT GCACAACATG GGGGATCATG TAACTCGCCT
2451 TGATCGTTGG GAACCGGAGC TGAATGAAGC CATACCAAAC GACGAGCGTG
2501 ACACCACGAT GCCTGTAGCA ATGGCAACAA CGTTGCGCAA ACTATTAACT
2551 GGCGAACTAC TTACTCTAGC TTCCCGGCAA CAATTAATAG ACTGGATGGA
2601 GGCGGATAAA GTTGCAGGAC CACTTCTGCG CTCGGCCCTT CCGGCTGGCT
2651 GGTTTATTGC TGATAAATCT GGAGCCGGTG AGCGTGGGTC TCGCGGTATC
2701 ATTGCAGCAC TGGGGCCAGA TGGTAAGCCC TCCCGTATCG TAGTTATCTA
2751 CACGACGGGG AGTCAGGCAA CTATGGATGA ACGAAATAGA CAGATCGCTG
2801 AGATAGGTGC CTCACTGATT AAGCATTGGT AACTGTCAGA CCAAGTTTAC
2851 TCATATATAC TTTAGATTGA TTTAAAACTT CATTTTTAAT TTAAAAGGAT
2901 CTAGGTGAAG ATCCTTTTTG ATAATCTCAT GACCAAAATC CCTTAACGTG
2951 AGTTTTCGTT CCACTGAGCG TCAGACCCCG TAGAAAAGAT CAAAGGATCT
3001 TCTTGAGATC CTTTTTTTCT GCGCGTAATC TGCTGCTTGC AAACAAAAAA
3051 ACCACCGCTA CCAGCGGTGG TTTGTTTGCC GGATCAAGAG CTACCAACTC
3101 TTTTTCCGAA GGTAACTGGC TTCAGCAGAG CGCAGATACC AAATACTGTC
3151 CTTCTAGTGT AGCCGTAGTT AGGCCACCAC TTCAAGAACT CTGTAGCACC
3201 GCCTACATAC CTCGCTCTGC TAATCCTGTT ACCAGTGGCT GCTGCCAGTG
3251 GCGATAAGTC GTGTCTTACC GGGTTGGACT CAAGACGATA GTTACCGGAT
3301 AAGGCGCAGC GGTCGGGCTG AACGGGGGGT TCGTGCACAC AGCCCAGCTT
3351 GGAGCGAACG ACCTACACCG AACTGAGATA CCTACAGCGT GAGCATTGAG
3401 AAAGCGCCAC GCTTCCCGAA GGGAGAAAGG CGGACAGGTA TCCGGTAAGC
3451 GGCAGGGTCG GAACAGGAGA GCGCACGAGG GAGCTTCCAG GGGGAAACGC
3501 CTGGTATCTT TATAGTCCTG TCGGGTTTCG CCACCTCTGA CTTGAGCGTC
3551 GATTTTTGTG ATGCTCGTCA GGGGGGCGGA GCCTATGGAA AAACGCCAGC
3601 AACGCGGCCT TTTTACGGTT CCTGGCCTTT TGCTGGCCTT TTGCTCACAT
3651 GTTCTTTCCT GCGTTATCCC CTGATTCTGT GGATAACCGT ATTACCGCCT
3701 TTGAGTGAGC TGATACCGCT CGCCGCAGCC GAACGACCGA GCGCAGCGAG
3751 TCAGTGAGCG AGGAAGCGGA AGAGCGCCAA TACGCAAACC GCCTCTCCCC
3801 GCGCGTTGGC CGATTCATTA ATGCAGCTGG CACGACAGGT TTCCCGACTG
3851 GAAAGCGGGC AGTGAGCGCA ACGCAATTAA TGTGAGTTAC CTCACTCATT
3901 AGGCACCCCA GGCTTTACAC TTTATGCTTC CGGCTCGTAT GTTGTGTGGA
3951 ATTGTGAGCG GATAACAATT TCACACAGGA AACAGCTATG ACCATGATTA
4001 CGCCAAGCT
```

FIG. 19A

```
   1 TAATGTCGTA ACAACTCCGC CCCGTTGACG CAAATGGGCG GTAGGCGTGT
  51 ACGGTGGGAG GTCTATATAA GCAGAGCTCG TTTAGTGAAC CGTCTGCAGA
 101 CTCTCTTCCG CATCGCTGTC TGCGAGGGCC AGCTGTTGGG CTCGCGGTTG
 151 AGGACAAACT CTTCGCGGTC TTTCCAGTAC TCTTGGATCG GAAACCCGTC
 201 GGCCTCCGAA CGGTACTCCG CCACCGAGGG ACCTGAGCGA GTCCGCATCG
 251 ACCGGATCGG AAAACCTCTC GAGAAAGGCG TCTAACCAGT CACAGTCGCA
 301 AGTCTAGAGG ATCTGAGCTT GGCGAGATTT TCAGGAGCTA AGGAAGCTAA
 351 AATGGAGAAA AAAATCACTG GATATACCAC CGTTGATATA TCCCAATGGC
 401 ATCGTAAAGA ACATTTTGAG GCATTTCAGT CAGTTGCTCA ATGTACCTAT
 451 AACCAGACCG TTCAGCTGGA TATTACGGCC TTTTTAAAGA CCGTAAAGAA
 501 AAATAAGCAC AAGTTTTATC CGGCCTTTAT TCACATTCTT GCCCGCCTGA
 551 TGAATGCTCA TCCGGAATTC CGTATGGCAA TGAAAGACGG TGAGCTGGTG
 601 ATATGGGATA GTGTTCACCC TTGTTACACC GTTTTCCATG AGCAAACTGA
 651 AACGTTTTCA TCGCTCTGGA GTGAATACCA CGACGATTTC CGGCAGTTTC
 701 TACACATATA TTCGCAAGAT GTGGCGTGTT ACGGTGAAAA CCTGGCCTAT
 751 TTCCCTAAAG GGTTTATTGA GAATATGTTT TTCGTCTCAG CCAATCCCTG
 801 GGTGAGTTTC ACCAGTTTTG ATTTAAACGT GGCCAATATG GACAACTTCT
 851 TCGCCCCCGT TTTCACCATG GGCAAATATT ATACGCAAGG CGACAAGGTG
 901 CTGATGCCGC TGGCGATTCA GGTTCATCAT GCCGTCTGTG ATGGCTTCCA
 951 TGTCGGCAGA ATGCTTAATG AATTACAACA GTACTGCGAT GAGTGGCAGG
1001 GCGGGGCGTA ACCGCGGCGT GATTAATCAG CCATACCACA TTTGTAGAGG
1051 TTTTACTTGC TTTAAAAAAC CTCCCACACC TCCCCCTGAA CCTGAAACAT
1101 AAAATGAATG CAATTGTTGT TGTTAACTTG TTTATTGCAG CTTATAATGG
1151 TTACAAATAA AGCAATAGCA TCACAAATTT CACAAATAAA GCATTTTTTT
1201 CACTGCATTC TAGTTGTGGT TTGTCCAAAC TCATCAATGT ATCTTATCAT
1251 GTCTGGATCC CCCGGAATTC ACTGGCCGTC GTTTTACAAC GTCGTGACTG
1301 GGAAAACCCT GGCGTTACCC AACTTAATCG CCTTGCAGCA CATCCCCCCT
1351 TCGCCAGCTG GCGTAATAGC GAAGAGGCCC GCACCGATCG CCCTTCCCAA
1401 CAGTTGCGCA GCCTGAATGG CGAATGGCGC CTGATGCGGT ATTTTCTCCT
1451 TACGCATCTG TGCGGTATTT CACACCGCAT ATGGTGCACT CTCAGTACAA
1501 TCTGCTCTGA TGCCGCATAG TTAAGCCAGT ACACTCCGCT ATCGCTACGT
1551 GACTGGGTCA TGGCTGCGCC CCGACACCCG CCAACACCCG CTGACGCGCC
1601 CTGACGGGCT TGTCTGCTCC CGGCATCCGC TTACAGACAA GCTGTGACCG
1651 TCTCCGGGAG CTGCATGTGT CAGAGGTTTT CACCGTCATC ACCGAAACGC
1701 GCGAGGCAGT TCTTGAAGAC GAAAGGGCCT CGTGATACGC CTATTTTTAT
1751 AGGTTAATGT CATGATAATA ATGGTTTCTT AGACGTCAGG TGGCACTTTT
1801 CGGGGAAATG TGCGCGGAAC CCCTATTTGT TTATTTTTCT AAATACATTC
1851 AAATATGTAT CCGCTCATGA GACAATAACC CTGATAAATG CTTCAATAAT
```

FIG. 19B

```
1901 ATTGAAAAAG GAAGAGTATG AGTATTCAAC ATTTCCGTGT CGCCCTTATT
1951 CCCTTTTTTG CGGCATTTTG CCTTCCTGTT TTTGCTCACC CAGAAACGCT
2001 GGTGAAAGTA AAAGATGCTG AAGATCAGTT GGGTGCACGA GTGGGTTACA
2051 TCGAACTGGA TCTCAACAGC GGTAAGATCC TTGAGAGTTT TCGCCCCGAA
2101 GAACGTTTTC CAATGATGAG CACTTTTAAA GTTCTGCTAT GTGGCGCGGT
2151 ATTATCCCGT ATTGACGCCG GGCAAGAGCA ACTCGGTCGC CGCATACACT
2201 ATTCTCAGAA TGACTTGGTT GAGTACTCAC CAGTCACAGA AAAGCATCTT
2251 ACGGATGGCA TGACAGTAAG AGAATTATGC AGTGCTGCCA TAACCATGAG
2301 TGATAACACT GCGGCCAACT TACTTCTGAC AACGATCGGA GGACCGAAGG
2351 AGCTAACCGC TTTTTTGCAC AACATGGGGG ATCATGTAAC TCGCCTTGAT
2401 CGTTGGGAAC CGGAGCTGAA TGAAGCCATA CCAAACGACG AGCGTGACAC
2451 CACGATGCCT GTAGCAATGG CAACAACGTT GCGCAAACTA TTAACTGGCG
2501 AACTACTTAC TCTAGCTTCC CGGCAACAAT TAATAGACTG GATGGAGGCG
2551 GATAAAGTTG CAGGACCACT TCTGCGCTCG GCCCTTCCGG CTGGCTGGTT
2601 TATTGCTGAT AAATCTGGAG CCGGTGAGCG TGGGTCTCGC GGTATCATTG
2651 CAGCACTGGG GCCAGATGGT AAGCCCTCCC GTATCGTAGT TATCTACACG
2701 ACGGGGAGTC AGGCAACTAT GGATGAACGA AATAGACAGA TCGCTGAGAT
2751 AGGTGCCTCA CTGATTAAGC ATTGGTAACT GTCAGACCAA GTTTACTCAT
2801 ATATACTTTA GATTGATTTA AAACTTCATT TTTAATTTAA AAGGATCTAG
2851 GTGAAGATCC TTTTTGATAA TCTCATGACC AAAATCCCTT AACGTGAGTT
2901 TTCGTTCCAC TGAGCGTCAG ACCCCGTAGA AAAGATCAAA GGATCTTCTT
2951 GAGATCCTTT TTTTCTGCGC GTAATCTGCT GCTTGCAAAC AAAAAAACCA
3001 CCGCTACCAG CGGTGGTTTG TTTGCCGGAT CAAGAGCTAC CAACTCTTTT
3051 TCCGAAGGTA ACTGGCTTCA GCAGAGCGCA GATACCAAAT ACTGTCCTTC
3101 TAGTGTAGCC GTAGTTAGGC CACCACTTCA AGAACTCTGT AGCACCGCCT
3151 ACATACCTCG CTCTGCTAAT CCTGTTACCA GTGGCTGCTG CCAGTGGCGA
3201 TAAGTCGTGT CTTACCGGGT TGGACTCAAG ACGATAGTTA CCGGATAAGG
3251 CGCAGCGGTC GGGCTGAACG GGGGGTTCGT GCACACAGCC CAGCTTGGAG
3301 CGAACGACCT ACACCGAACT GAGATACCTA CAGCGTGAGC ATTGAGAAAG
3351 CGCCACGCTT CCCGAAGGGA GAAAGGCGGA CAGGTATCCG GTAAGCGGCA
3401 GGGTCGGAAC AGGAGAGCGC ACGAGGGAGC TTCCAGGGGG AAACGCCTGG
3451 TATCTTTATA GTCCTGTCGG GTTTCGCCAC CTCTGACTTG AGCGTCGATT
3501 TTTGTGATGC TCGTCAGGGG GCGGAGCCT ATGGAAAAAC GCCAGCAACG
3551 CGGCCTTTTT ACGGTTCCTG GCCTTTTGCT GGCCTTTTGC TCACATGTTC
3601 TTTCCTGCGT TATCCCCTGA TTCTGTGGAT AACCGTATTA CCGCCTTTGA
3651 GTGAGCTGAT ACCGCTCGCC GCAGCCGAAC GACCGAGCGC AGCGAGTCAG
3701 TGAGCGAGGA AGCGGAAGAG CGCCAATACG CAAACCGCCT CTCCCCGCGC
3751 GTTGGCCGAT TCATTAATGC AGCTGGCACG ACAGGTTTCC CGACTGGAAA
3801 GCGGGCAGTG AGCGCAACGC AATTAATGTG AGTTACCTCA CTCATTAGGC
3851 ACCCCAGGCT TTACACTTTA TGCTTCCGGC TCGTATGTTG TGTGGAATTG
3901 TGAGCGGATA ACAATTTCAC ACAGGAAACA GCTATGACCA TGATTACGCC
3951 AAGCT
```

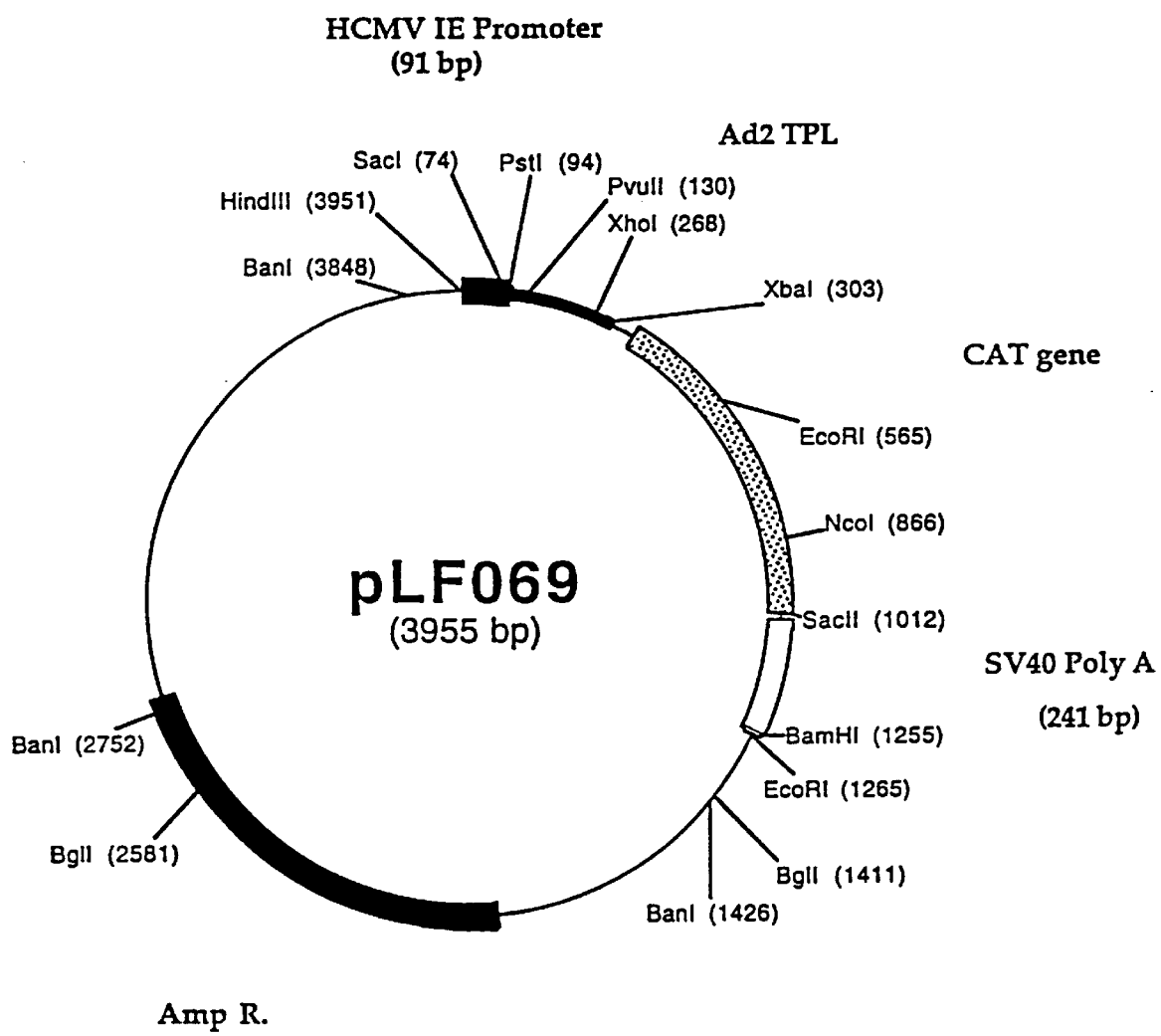

FIG.21A

```
   1 TAATGTCGTA ACAACTCCGC CCCGTTGACG CAAATGGGCG GTAGGCGTGT
  51 ACGGTGGGAG GTCTATATAA GCAGAGCTCG TTTAGTGAAC CGTCTGCAGA
 101 CTCTCTTCCG CATCGCTGTC TGCGAGGGCC AGCTGTTGGG CTCGCGGTTG
 151 AGGACAAACT CTTCGCGGTC TTTCCAGTAC TCTTGGATCG GAAACCCGTC
 201 GGCCTCCGAA CGGTACTCCG CCACCGAGGG ACCTGAGCGA GTCCGCATCG
 251 ACCGGATCGG AAAACCTCTC GAGAAAGGCG TCTAACCAGT CACAGTCGCA
 301 AGTCTAGAGG ATCTGAGCTT GGCGAGATTT TCAGGAGCTA AGGAAGCTAA
 351 AATGGAGAAA AAAATCACTG GATATACCAC CGTTGATATA TCCCAATGGC
 401 ATCGTAAAGA ACATTTTGAG GCATTTCAGT CAGTTGCTCA ATGTACCTAT
 451 AACCAGACCG TTCAGCTGGA TATTACGGCC TTTTTAAAGA CCGTAAAGAA
 501 AAATAAGCAC AAGTTTTATC CGGCCTTTAT TCACATTCTT GCCCGCCTGA
 551 TGAATGCTCA TCCGGAATTC CGTATGGCAA TGAAAGACGG TGAGCTGGTG
 601 ATATGGGATA GTGTTCACCC TTGTTACACC GTTTTCCATG AGCAAACTGA
 651 AACGTTTTCA TCGCTCTGGA GTGAATACCA CGACGATTTC CGGCAGTTTC
 701 TACACATATA TTCGCAAGAT GTGGCGTGTT ACGGTGAAAA CCTGGCCTAT
 751 TTCCCTAAAG GGTTTATTGA GAATATGTTT TCGTCTCAG CCAATCCCTG
 801 GGTGAGTTTC ACCAGTTTTG ATTTAAACGT GGCCAATATG GACAACTTCT
 851 TCGCCCCCGT TTTCACCATG GGCAAATATT ATACGCAAGG CGACAAGGTG
 901 CTGATGCCGC TGGCGATTCA GGTTCATCAT GCCGTCTGTG ATGGCTTCCA
 951 TGTCGGCAGA ATGCTTAATG AATTACAACA GTACTGCGAT GAGTGGCAGG
1001 GCGGGGCGTA ACCGCGGAAT TGTTGTTGTT AACTTGTTTA TTGCAGCTTA
1051 TAATGGTTAC AAATAAAGCA ATAGCATCAC AAATTTCACA AATAAAGCAT
1101 TTTTTCACT GCATTCTAGT TGTGGTTTGT CCAAACTCAT CAATGTATCT
1151 TATCATGTCT GGATCCCCG GAATTCACTG GCCGTCGTTT ACAACGTCG
1201 TGACTGGGAA AACCCTGGCG TTACCCAACT TAATCGCCTT GCAGCACATC
1251 CCCCCTTCGC CAGCTGGCGT AATAGCGAAG AGGCCCGCAC CGATCGCCCT
1301 TCCCAACAGT TGCGCAGCCT GAATGGCGAA TGGCGCCTGA TGCGGTATTT
1351 TCTCCTTACG CATCTGTGCG GTATTTCACA CCGCATATGG TGCACTCTCA
1401 GTACAATCTG CTCTGATGCC GCATAGTTAA GCCAGTACAC TCCGCTATCG
1451 CTACGTGACT GGGTCATGGC TGCGCCCCGA CACCCGCCAA CACCCGCTGA
1501 CGCGCCCTGA CGGGCTTGTC TGCTCCCGGC ATCCGCTTAC AGACAAGCTG
1551 TGACCGTCTC CGGGAGCTGC ATGTGTCAGA GGTTTTCACC GTCATCACCG
1601 AAACGCGCGA GGCAGTTCTT GAAGACGAAA GGGCCTCGTG ATACGCCTAT
1651 TTTTATAGGT TAATGTCATG ATAATAATGG TTTCTTAGAC GTCAGGTGGC
1701 ACTTTTCGGG GAAATGTGCG CGGAACCCCT ATTTGTTTAT TTTTCTAAAT
1751 ACATTCAAAT ATGTATCCGC TCATGAGACA ATAACCCTGA TAAATGCTTC
1801 AATAATATTG AAAAAGGAAG AGTATGAGTA TTCAACATTT CCGTGTCGCC
1851 CTTATTCCCT TTTTGCGGC ATTTGCCTT CCTGTTTTTG CTCACCCAGA
```

FIG. 2IB

```
1901 AACGCTGGTG AAAGTAAAAG ATGCTGAAGA TCAGTTGGGT GCACGAGTGG
1951 GTTACATCGA ACTGGATCTC AACAGCGGTA AGATCCTTGA GAGTTTTCGC
2001 CCCGAAGAAC GTTTTCCAAT GATGAGCACT TTTAAAGTTC TGCTATGTGG
2051 CGCGGTATTA TCCCGTATTG ACGCCGGGCA AGAGCAACTC GGTCGCCGCA
2101 TACACTATTC TCAGAATGAC TTGGTTGAGT ACTCACCAGT CACAGAAAAG
2151 CATCTTACGG ATGGCATGAC AGTAAGAGAA TTATGCAGTG CTGCCATAAC
2201 CATGAGTGAT AACACTGCGG CCAACTTACT TCTGACAACG ATCGGAGGAC
2251 CGAAGGAGCT AACCGCTTTT TTGCACAACA TGGGGGATCA TGTAACTCGC
2301 CTTGATCGTT GGGAACCGGA GCTGAATGAA GCCATACCAA ACGACGAGCG
2351 TGACACCACG ATGCCTGTAG CAATGGCAAC AACGTTGCGC AAACTATTAA
2401 CTGGCGAACT ACTTACTCTA GCTTCCCGGC AACAATTAAT AGACTGGATG
2451 GAGGCGGATA AAGTTGCAGG ACCACTTCTG CGCTCGGCCC TTCCGGCTGG
2501 CTGGTTTATT GCTGATAAAT CTGGAGCCGG TGAGCGTGGG TCTCGCGGTA
2551 TCATTGCAGC ACTGGGGCCA GATGGTAAGC CCTCCCGTAT CGTAGTTATC
2601 TACACGACGG GGAGTCAGGC AACTATGGAT GAACGAAATA GACAGATCGC
2651 TGAGATAGGT GCCTCACTGA TTAAGCATTG GTAACTGTCA GACCAAGTTT
2701 ACTCATATAT ACTTTAGATT GATTTAAAAC TTCATTTTTA ATTTAAAGG
2751 ATCTAGGTGA AGATCCTTTT TGATAATCTC ATGACCAAAA TCCCTTAACG
2801 TGAGTTTTCG TTCCACTGAG CGTCAGACCC CGTAGAAAAG ATCAAAGGAT
2851 CTTCTTGAGA TCCTTTTTTT CTGCGCGTAA TCTGCTGCTT GCAAACAAAA
2901 AAACCACCGC TACCAGCGGT GGTTTGTTTG CCGGATCAAG AGCTACCAAC
2951 TCTTTTTCCG AAGGTAACTG GCTTCAGCAG AGCGCAGATA CCAAATACTG
3001 TCCTTCTAGT GTAGCCGTAG TTAGGCCACC ACTTCAAGAA CTCTGTAGCA
3051 CCGCCTACAT ACCTCGCTCT GCTAATCCTG TTACCAGTGG CTGCTGCCAG
3101 TGGCGATAAG TCGTGTCTTA CCGGGTTGGA CTCAAGACGA TAGTTACCGG
3151 ATAAGGCGCA GCGGTCGGGC TGAACGGGGG GTTCGTGCAC ACAGCCCAGC
3201 TTGGAGCGAA CGACCTACAC CGAACTGAGA TACCTACAGC GTGAGCATTG
3251 AGAAAGCGCC ACGCTTCCCG AAGGGAGAAA GGCGGACAGG TATCCGGTAA
3301 GCGGCAGGGT CGGAACAGGA GAGCGCACGA GGGAGCTTCC AGGGGGAAAC
3351 GCCTGGTATC TTTATAGTCC TGTCGGGTTT CGCCACCTCT GACTTGAGCG
3401 TCGATTTTTG TGATGCTCGT CAGGGGGGCG GAGCCTATGG AAAAACGCCA
3451 GCAACGCGGC CTTTTTACGG TTCCTGGCCT TTTGCTGGCC TTTTGCTCAC
3501 ATGTTCTTTC CTGCGTTATC CCTGATTCT GTGGATAACC GTATTACCGC
3551 CTTTGAGTGA GCTGATACCG CTCGCCGCAG CCGAACGACC GAGCGCAGCG
3601 AGTCAGTGAG CGAGGAAGCG GAAGAGCGCC AATACGCAAA CCGCCTCTCC
3651 CCGCGCGTTG GCCGATTCAT TAATGCAGCT GGCACGACAG GTTTCCCGAC
3701 TGGAAAGCGG GCAGTGAGCG CAACGCAATT AATGTGAGTT ACCTCACTCA
3751 TTAGGCACCC CAGGCTTTAC ACTTTATGCT TCCGGCTCGT ATGTTGTGTG
3801 GAATTGTGAG CGGATAACAA TTTCACACAG GAAACAGCTA TGACCATGAT
3851 TACGCCAAGC T
```

FIG. 23A

```
   1 TAATGTCGTA ACAACTCCGC CCCGTTGACG CAAATGGGCG GTAGGCGTGT
  51 ACGGTGGGAG GTCTATATAA GCAGAGCTCG TTTAGTGAAC CGTCTGCAGA
 101 CTCTCTTCCG CATCGCTGTC TGCGAGGGCC AGCTGTTGGG CTCGCGGTTG
 151 AGGACAAACT CTTCGCGGTC TTTCCAGTAC TCTTGGATCG GAAACCCGTC
 201 GGCCTCCGAA CGGTACTCCG CCACCGAGGG ACCTGAGCGA GTCCGCATCG
 251 ACCGGATCGG AAAACCTCTC GAGAAAGGCG TCTAACCAGT CACAGTCGCA
 301 AGTCTAGAGG ATCTGAGCTT GGCGAGATTT TCAGGAGCTA AGGAAGCTAA
 351 AATGGAGAAA AAAATCACTG GATATACCAC CGTTGATATA TCCCAATGGC
 401 ATCGTAAAGA ACATTTTGAG GCATTTCAGT CAGTTGCTCA ATGTACCTAT
 451 AACCAGACCG TTCAGCTGGA TATTACGGCC TTTTTAAAGA CCGTAAAGAA
 501 AAATAAGCAC AAGTTTTATC CGGCCTTTAT TCACATTCTT GCCCGCCTGA
 551 TGAATGCTCA TCCGGAATTC CGTATGGCAA TGAAAGACGG TGAGCTGGTG
 601 ATATGGGATA GTGTTCACCC TTGTTACACC GTTTTCCATG AGCAAACTGA
 651 AACGTTTTCA TCGCTCTGGA GTGAATACCA CGACGATTTC CGGCAGTTTC
 701 TACACATATA TTCGCAAGAT GTGGCGTGTT ACGGTGAAAA CCTGGCCTAT
 751 TTCCCTAAAG GGTTTATTGA GAATATGTTT TTCGTCTCAG CCAATCCCTG
 801 GGTGAGTTTC ACCAGTTTTG ATTTAAACGT GGCCAATATG GACAACTTCT
 851 TCGCCCCCGT TTTCACCATG GGCAAATATT ATACGCAAGG CGACAAGGTG
 901 CTGATGCCGC TGGCGATTCA GGTTCATCAT GCCGTCTGTG ATGGCTTCCA
 951 TGTCGGCAGA ATGCTTAATG AATTACAACA GTACTGCGAT GAGTGGCAGG
1001 GCGGGGCGTA ACCGCGGAAT TGTTGTTGTT AACTTGTTTA TTGCAGCTTA
1051 TAATGGTTAC AAATAAAGCA ATAGCATCAC AAATTTCACA AATAAAGCAT
1101 TTTTTTCACT GCATTCTAGT TGTGGTTTGT CCAAACTCAT CAATGTATCT
1151 TATCATGTCT GGATAACGCC CAAAAACCCG GGGACGATGA TCCCCCGGAA
1201 TTCACTGGCC GTCGTTTTAC AACGTCGTGA CTGGGAAAAC CCTGGCGTTA
1251 CCCAACTTAA TCGCCTTGCA GCACATCCCC CCTTCGCCAG CTGGCGTAAT
1301 AGCGAAGAGG CCCGCACCGA TCGCCCTTCC CAACAGTTGC GCAGCCTGAA
1351 TGGCGAATGG CGCCTGATGC GGTATTTTCT CCTTACGCAT CTGTGCGGTA
1401 TTTCACACCG CATATGGTGC ACTCTCAGTA CAATCTGCTC TGATGCCGCA
1451 TAGTTAAGCC AGTACACTCC GCTATCGCTA CGTGACTGGG TCATGGCTGC
1501 GCCCCGACAC CCGCCAACAC CCGCTGACGC GCCCTGACGG GCTTGTCTGC
1551 TCCCGGCATC CGCTTACAGA CAAGCTGTGA CCGTCTCCGG GAGCTGCATG
1601 TGTCAGAGGT TTTCACCGTC ATCACCGAAA CGCGCGAGGC AGTTCTTGAA
1651 GACGAAAGGG CCTCGTGATA CGCCTATTTT TATAGGTTAA TGTCATGATA
1701 ATAATGGTTT CTTAGACGTC AGGTGGCACT TTTCGGGGAA ATGTGCGCGG
1751 AACCCCTATT TGTTTATTTT TCTAAATACA TTCAAATATG TATCCGCTCA
```

FIG. 23B

```
1801 TGAGACAATA ACCCTGATAA ATGCTTCAAT AATATTGAAA AAGGAAGAGT
1851 ATGAGTATTC AACATTTCCG TGTCGCCCTT ATTCCCTTTT TTGCGGCATT
1901 TTGCCTTCCT GTTTTTGCTC ACCCAGAAAC GCTGGTGAAA GTAAAAGATG
1951 CTGAAGATCA GTTGGGTGCA CGAGTGGGTT ACATCGAACT GGATCTCAAC
2001 AGCGGTAAGA TCCTTGAGAG TTTTCGCCCC GAAGAACGTT TTCCAATGAT
2051 GAGCACTTTT AAAGTTCTGC TATGTGGCGC GGTATTATCC CGTATTGACG
2101 CCGGGCAAGA GCAACTCGGT CGCCGCATAC ACTATTCTCA GAATGACTTG
2151 GTTGAGTACT CACCAGTCAC AGAAAAGCAT CTTACGGATG CATGACAGT
2201 AAGAGAATTA TGCAGTGCTG CCATAACCAT GAGTGATAAC ACTGCGGCCA
2251 ACTTACTTCT GACAACGATC GGAGGACCGA AGGAGCTAAC CGCTTTTTTG
2301 CACAACATGG GGGATCATGT AACTCGCCTT GATCGTTGGG AACCGGAGCT
2351 GAATGAAGCC ATACCAAACG ACGAGCGTGA CACCACGATG CCTGTAGCAA
2401 TGGCAACAAC GTTGCGCAAA CTATTAACTG GCGAACTACT TACTCTAGCT
2451 TCCCGGCAAC AATTAATAGA CTGGATGGAG GCGGATAAAG TTGCAGGACC
2501 ACTTCTGCGC TCGGCCCTTC CGGCTGGCTG GTTTATTGCT GATAAATCTG
2551 GAGCCGGTGA GCGTGGGTCT CGCGGTATCA TTGCAGCACT GGGGCCAGAT
2601 GGTAAGCCCT CCCGTATCGT AGTTATCTAC ACGACGGGGA GTCAGGCAAC
2651 TATGGATGAA CGAAATAGAC AGATCGCTGA GATAGGTGCC TCACTGATTA
2701 AGCATTGGTA ACTGTCAGAC CAAGTTTACT CATATATACT TTAGATTGAT
2751 TTAAAACTTC ATTTTTAATT TAAAAGGATC TAGGTGAAGA TCCTTTTTGA
2801 TAATCTCATG ACCAAAATCC CTTAACGTGA GTTTTCGTTC CACTGAGCGT
2851 CAGACCCCGT AGAAAAGATC AAAGGATCTT CTTGAGATCC TTTTTTTCTG
2901 CGCGTAATCT GCTGCTTGCA AACAAAAAAA CCACCGCTAC CAGCGGTGGT
2951 TTGTTTGCCG GATCAAGAGC TACCAACTCT TTTTCCGAAG GTAACTGGCT
3001 TCAGCAGAGC GCAGATACCA AATACTGTCC TTCTAGTGTA GCCGTAGTTA
3051 GGCCACCACT TCAAGAACTC TGTAGCACCG CCTACATACC TCGCTCTGCT
3101 AATCCTGTTA CCAGTGGCTG CTGCCAGTGG CGATAAGTCG TGTCTTACCG
3151 GGTTGGACTC AAGACGATAG TTACCGGATA AGGCGCAGCG GTCGGGCTGA
3201 ACGGGGGGTT CGTGCACACA GCCCAGCTTG GAGCGAACGA CCTACACCGA
3251 ACTGAGATAC CTACAGCGTG AGCATTGAGA AAGCGCCACG CTTCCCGAAG
3301 GGAGAAAGGC GGACAGGTAT CCGGTAAGCG GCAGGGTCGG AACAGGAGAG
3351 CGCACGAGGG AGCTTCCAGG GGGAAACGCC TGGTATCTTT ATAGTCCTGT
3401 CGGGTTTCGC CACCTCTGAC TTGAGCGTCG ATTTTTGTGA TGCTCGTCAG
3451 GGGGCGGAG CCTATGGAAA AACGCCAGCA ACGCGGCCTT TTTACGGTTC
3501 CTGGCCTTTT GCTGGCCTTT TGCTCACATG TTCTTTCCTG CGTTATCCCC
3551 TGATTCTGTG GATAACCGTA TTACCGCCTT TGAGTGAGCT GATACCGCTC
3601 GCCGCAGCCG AACGACCGAG CGCAGCGAGT CAGTGAGCGA GGAAGCGGAA
3651 GAGCGCCAAT ACGCAAACCG CCTCTCCCCG CGCGTTGGCC GATTCATTAA
3701 TGCAGCTGGC ACGACAGGTT TCCCGACTGG AAAGCGGGCA GTGAGCGCAA
3751 CGCAATTAAT GTGAGTTACC TCACTCATTA GGCACCCCAG GCTTTACACT
3801 TTATGCTTCC GGCTCGTATG TTGTGTGGAA TTGTGAGCGG ATAACAATTT
3851 CACACAGGAA ACAGCTATGA CCATGATTAC GCCAAGCT
```

FIG. 25A

```
   1 TAATGTCGTA ACAACTCCGC CCCGTTGACG CAAATGGGCG GTAGGCGTGT
  51 ACGGTGGGAG GTCTATATAA GCAGAGCTCG TTTAGTGAAC CGTCTGCAGA
 101 CTCTCTTCCG CATCGCTGTC TGCGAGGGCC AGCTGTTGGG CTCGCGGTTG
 151 AGGACAAACT CTTCGCGGTC TTTCCAGTAC TCTTGGATCG GAAACCCGTC
 201 GGCCTCCGAA CGGTACTCCG CCACCGAGGG ACCTGAGCGA GTCCGCATCG
 251 ACCGGATCGG AAAACCTCTC GAGAAAGGCG TCTAACCAGT CACAGTCGCA
 301 AGTCTAGAGG ATCTGAGCTT GGCGAGATTT TCAGGAGCTA AGGAAGCTAA
 351 AATGGAGAAA AAAATCACTG GATATACCAC CGTTGATATA TCCCAATGGC
 401 ATCGTAAAGA ACATTTTGAG GCATTTCAGT CAGTTGCTCA ATGTACCTAT
 451 AACCAGACCG TTCAGCTGGA TATTACGGCC TTTTTAAAGA CCGTAAAGAA
 501 AAATAAGCAC AAGTTTTATC CGGCCTTTAT TCACATTCTT GCCCGCCTGA
 551 TGAATGCTCA TCCGGAATTC CGTATGGCAA TGAAAGACGG TGAGCTGGTG
 601 ATATGGGATA GTGTTCACCC TTGTTACACC GTTTTCCATG AGCAAACTGA
 651 AACGTTTTCA TCGCTCTGGA GTGAATACCA CGACGATTTC CGGCAGTTTC
 701 TACACATATA TTCGCAAGAT GTGGCGTGTT ACGGTGAAAA CCTGGCCTAT
 751 TTCCCTAAAG GGTTTATTGA GAATATGTTT TTCGTCTCAG CCAATCCCTG
 801 GGTGAGTTTC ACCAGTTTTG ATTTAAACGT GGCCAATATG GACAACTTCT
 851 TCGCCCCCGT TTTCACCATG GGCAAATATT ATACGCAAGG CGACAAGGTG
 901 CTGATGCCGC TGGCGATTCA GGTTCATCAT GCCGTCTGTG ATGGCTTCCA
 951 TGTCGGCAGA ATGCTTAATG AATTACAACA GTACTGCGAT GAGTGGCAGG
1001 GCGGGGCGTA ACCGCGGAAT TGTTGTTGTT AACTTGTTTA TTGCAGCTTA
1051 TAATGGTTAC AAATAAAGCA ATAGCATCAC AAATTTCACA AATAAAGCAT
1101 TTTTTTCACT GCATTCTAGT TGTGGTTTGT CCAAACTCAT CAATGTATCT
1151 TATCATGTCT GGATAACGCC AAAAACCCG GGGCGCCGGC AAAAGTCCG
1201 CGGAACTCGC CCTGTCGTAA AACCACGCCT TGACGTCAC TGGACATTCC
1251 CGTGGGAACA CCCTGACCAG GGCGTGACCT GAACCTGACC GTCCATGAC
1301 CCCGCCCCTT GCAACACCCA AATTTAAGCC ACACCTCTTT GTCCTGTATA
1351 TTATTGATGA TGGGGGGATC CACTAGTTCT AGAGCGGCCG CCACCGCGGT
1401 GGAGCTCCAG CTTTTGTTCC CTTTAGTGAG GGTTAATTCC GAGCTTGGCG
1451 TAATCATGGT CATAGCTGTT TCCTGTGTGA AATTGTTATC CGCTCACAAT
1501 TCCACACAAC ATACGAGCCG GAAGCATAAA GTGTAAAGCC TGGGGTGCCT
1551 AATGAGTGAG CTAACTCACA TTAATTGCGT TGCGCTCACT GCCCGCTTTC
1601 CAGTCGGGAA ACCTGTCGTG CCAGCTGCAT TAATGAATCG GCCAACGCGC
1651 GGGGAGAGGC GGTTTGCGTA TTGGGCGCTC TTCCGCTTCC TCGCTCACTG
1701 ACTCGCTGCG CTCGGTCGTT CGGCTGCGGC GAGCGGTATC AGCTCACTCA
1751 AAGGCGGTAA TACGGTTATC CACAGAATCA GGGGATAACG CAGGAAAGAA
1801 CATGTGAGCA AAAGGCCAGC AAAAGGCCAG GAACCGTAAA AAGGCCGCGT
1851 TGCTGGCGTT TTTCCATAGG CTCCGCCCCC CTGACGAGCA TCACAAAAAT
1901 CGACGCTCAA GTCAGAGGTG GCGAAACCCG ACAGGACTAT AAAGATACCA
1951 GGCGTTTCCC CCTGGAAGCT CCCTCGTGCG CTCTCCTGTT CCGACCCTGC
```

FIG.25B

```
2001 CGCTTACCGG ATACCTGTCC GCCTTTCTCC CTTCGGGAAG CGTGGCGCTT
2051 TCTCATAGCT CACGCTGTAG GTATCTCAGT TCGGTGTAGG TCGTTCGCTC
2101 CAAGCTGGGC TGTGTGCACG AACCCCCGT TCAGCCCGAC CGCTGCGCCT
2151 TATCCGGTAA CTATCGTCTT GAGTCCAACC CGGTAAGACA CGACTTATCG
2201 CCACTGGCAG CAGCCACTGG TAACAGGATT AGCAGAGCGA GGTATGTAGG
2251 CGGTGCTACA GAGTTCTTGA AGTGGTGGCC TAACTACGGC TACACTAGAA
2301 GGACAGTATT TGGTATCTGC GCTCTGCTGA AGCCAGTTAC CTTCGGAAAA
2351 AGAGTTGGTA GCTCTTGATC CGGCAAACAA ACCACCGCTG GTAGCGGTGG
2401 TTTTTTTGTT TGCAAGCAGC AGATTACGCG CAGAAAAAAA GGATCTCAAG
2451 AAGATCCTTT GATCTTTCT ACGGGGTCTG ACGCTCAGTG AACGAAAAC
2501 TCACGTTAAG GGATTTTGGT CATGAGATTA TCAAAAGGA TCTTCACCTA
2551 GATCCTTTTA AATTAAAAAT GAAGTTTTAA ATCAATCTAA AGTATATATG
2601 AGTAAACTTG GTCTGACAGT TACCAATGCT TAATCAGTGA GGCACCTATC
2651 TCAGCGATCT GTCTATTTCG TTCATCCATA GTTGCCTGAC TCCCCGTCGT
2701 GTAGATAACT ACGATACGGG AGGGCTTACC ATCTGGCCCC AGTGCTGCAA
2751 TGATACCGCG AGACCCACGC TCACCGGCTC CAGATTTATC AGCAATAAAC
2801 CAGCCAGCCG GAAGGGCCGA GCGCAGAAGT GGTCCTGCAA CTTTATCCGC
2851 CTCCATCCAG TCTATTAATT GTTGCCGGGA AGCTAGAGTA AGTAGTTCGC
2901 CAGTTAATAG TTTGCGCAAC GTTGTTGCCA TTGCTACAGG CATCGTGGTG
2951 TCACGCTCGT CGTTTGGTAT GGCTTCATTC AGCTCCGGTT CCCAACGATC
3001 AAGGCGAGTT ACATGATCCC CCATGTTGTG CAAAAAAGCG GTTAGCTCCT
3051 TCGGTCCTCC GATCGTTGTC AGAAGTAAGT TGGCCGCAGT GTTATCACTC
3101 ATGGTTATGG CAGCACTGCA TAATTCTCTT ACTGTCATGC CATCCGTAAG
3151 ATGCTTTTCT GTGACTGGTG AGTACTCAAC CAAGTCATTC TGAGAATAGT
3201 GTATGCGGCG ACCGAGTTGC TCTTGCCCGG CGTCAATACG GGATAATACC
3251 GCGCCACATA GCAGAACTTT AAAAGTGCTC ATCATTGGAA AACGTTCTTC
3301 GGGGCGAAAA CTCTCAAGGA TCTTACCGCT GTTGAGATCC AGTTCGATGT
3351 AACCCACTCG TGCACCCAAC TGATCTTCAG CATCTTTTAC TTTCACCAGC
3401 GTTTCTGGGT GAGCAAAAAC AGGAAGGCAA AATGCCGCAA AAAAGGGAAT
3451 AAGGGCGACA CGGAAATGTT GAATACTCAT ACTCTTCCTT TTTCAATATT
3501 ATTGAAGCAT TTATCAGGGT TATTGTCTCA TGAGCGGATA CATATTTGAA
3551 TGTATTTAGA AAAATAAACA AATAGGGGTT CCGCGCACAT TTCCCCGAAA
3601 AGTGCCACCT GGGAAATTGT AAACGTTAAT ATTTTGTTAA AATTCGCGTT
3651 AAATTTTTGT TAAATCAGCT CATTTTTTAA CCAATAGGCC GAAATCGGCA
3701 AAATCCCTTA TAAATCAAAA GAATAGACCG AGATAGGGTT GAGTGTTGTT
3751 CCAGTTTGGA ACAAGAGTCC ACTATTAAAG AACGTGGACT CCAACGTCAA
3801 AGGGCGAAAA ACCGTCTATC AGGGCGATGG CCCACTACGT GAACCATCAC
3851 CCTAATCAAG TTTTTTGGGG TCGAGGTGCC GTAAAGCACT AAATCGGAAC
3901 CCTAAAGGGA GCCCCCGATT TAGAGCTTGA CGGGGAAAGC CGGCGAACGT
3951 GGCGAGAAAG GAAGGGAAGA AAGCGAAAGG AGCGGGCGCT AGGGCGCTGG
4001 CAAGTGTAGC GGTCACGCTG CGCGTAACCA CCACACCCGC CGCGCTTAAT
4051 GCGCCGCTAC AGGGCGCGTC GCGCCATTCG CCATTCAGGC TGCGCAACTG
4101 TTGGGAAGGG CGATCGGTGC GGGCCTCTTC GCTATTACGC CAGCTGGCGA
4151 AAGGGGGATG TGCTGCAAGG CGATTAAGTT GGGTAACGCC AGGGTTTTCC
4201 CAGTCACGAC GTTGTAAAAC GACGGCCAGT GAATTGTAAT ACGACTCACT
4251 ATAGGGCGAA TTGGGTACCG GCCCCCCCT CGAGGTCGAC GGTGCCCCCA
4301 GCAGAAGTAT CGACTGCATG CTAATTATTA ACAAACCAAA AGGCGTTGCC
4351 ACTTACACCC TTACCTTTAG GTTTTAAAC TTAACAGAC TAAGCGGAGG
4401 TACCCTGTTT AAAACTGATG TCTTAACCTT TACCTATGTA GGCGAAAATC
4451 AATAAAACCA GAAAAAATA AGTTTAAAAG CTTTATTTTT CATACACGCG
4501 AGCGGTAAGG CTGCCGCCTT CAGGAAAAGT TACTCTGTAA ACAGTTCTTT
4551 CACAACAGCA CAAAACATAG GTATTAGTTA ACAGTTCATT TGGGCTATAA
4601 TAATATACAT TTTCTTGGGT GGCAAAGCAA GGGTCGGTAA TCTCAACAAA
```

FIG. 25C

```
4651 ACCATCAACT GGAATGCAAG AATAGTCCAG CACGGTGGGT TCAATCTAAA
4701 AATGAAGAAA CGCTGTTGAG GTTCACTAAG CACAGGTTTT GAATCTGTCG
4751 GCAGCGTCCA TGCATCATAG CTTGTCTCAA AGCAGATTGT CTTCTTTCCT
4801 CTGCCTTGGA AGTGGTTTGG TGAAGCACTA CAGGTGTCTT TTCAACCTCT
4851 TTCAGCACCC GCTCTATTAC AGATCTCACC CACACAGCAC AGTTTTAAG
4901 AGAACAATAG TTTTGAAGGC TACAAGATTT ACACTTAAGC ACCAGCCAGT
4951 AATTATAAGT GCTTTTAAGA ACTACCCCTA GCTCAGGGTT AATGCACCTT
5001 TTAATGGCCT CCATGCAGGC TTTATGGACA GTTCTAAAAA AAGACAGTCT
5051 AAAATAAATG TAGTGAGTGT TTCTAAATAT AATACTCCCC ACATAGTTAA
5101 TTTCATCAGG CCTGCTAGAA TTTACAAACT CTCGGTACCA CATATACTTT
5151 TTATTCATAG CCCCACCCTT AATAAAGTCC TCAATCACTT TCTGAACCAC
5201 ATGCTTGCTA GCCATGCATT GTAAAGACAA GCTGTTAGAG CAGTGACAGT
5251 GTACTCGCCA CGTTTGAGCC TCTGCCAGGC AGCAGTGCTT AGTTACTATC
5301 AACTCAATAC CCGCATTGCA TGTAAACCCC CAAAGAGCA GTTTTCATG
5351 CCTGTGTAGC ACATCATCCC ACAAAATAGG AATTTCATAG CATAAAGCAA
5401 AGCAATTACA ATATTTAGGA ACTCTCACCA CAGCAGTCAC GTGACATGTT
5451 GTCTCAGCAG TGCAGTTGCC TTCCATCCTA CAATTATGAA CAAAAACTAA
5501 ACACTTCTAA CAAAGATACA GTGACAATCT CCCTTCCTCT AAAAGCATTG
5551 TTTACATTAG GGTGATTATT AACAACGTCA GAAATTTCTT TAATTAAAGT
5601 GCCTTTAAAA TGTGCAAGAG CATCATCATA CTCAAAACCA AGCTGAGAGT
5651 AAAAGACCAC CTTAAAAGTA ATCCCAGGCT TGTTTTATC AACAGCCTTA
5701 AACATGCTTT CACAAAATAT AGAAGCAGTA ACATCATCAA TGGTGTCGAA
5751 GAGAAACTCC ATAGGAGACT CCAGCATTGA TCCAAGCTCT CTAACAAAAT
5801 CTTCCTCAAA ATGAATAATG CCCTTTACAC AAACGCGGGG CAGACGATGG
5851 TGGGCCATCG CGTCAACCTG AAACACATTT TACAGTAAAC AAAGCTAGCT
5901 CCGCAGTGGT AAAGTCATGC CCATGGGTGA GGCCAAAATC CTTAAAAAAG
5951 CTATCTAAGT AGTTGGTCAT CCCCTCAGTT AAAAAGTTTT GCAGCTGGGT
6001 GGTGCATACC ACATAGTGCC AGCTTATAGC TACAAAGACC TGCATCCCCT
6051 CCTTAGCAGA CAGCTCTTGC ACACACGCAG TAACTATCCA CCGCTTAAGA
6101 AAAGCTTTAA GCCCAGCGCA CATAACAGCT CCAATGTTTT TATCCAAGGA
6151 GAGCAAAATT TCAGCAAGCG CAGGCTCAAC AGTAATAGTG AAGCAGAGGC
6201 ATTTCAGACG AGGCTCACTA GCTGCAGTCG CCATTTATGA GGTCTGCAAT
6251 AAAAAACAAC TCATCAGCAG CTGAAAAAGT GCACTTTGAC CTCATTAAGC
6301 CACTGCATAT GCAAGTCCTC ATCTATGCCG CAGCCCAGAC CCTCAATCCA
6351 GCCCCGAATG TACACTTTAA TAAGAGATTC AACCTCTTCT TTTAGCAAAG
6401 TACACATGCT GTTTGGACTA GTATACACAA TAGAAGTCAC AATGAGGGGC
6451 CCGCTGTGGC TGGAAAGCCT GCGCACAGCC CGAAGGTTAA AAATGGACTG
6501 TAACAGCATT GAAACCCCGC GACACAGGTC AGTCTCGCGG TCTTGATCTC
6551 TTATTATAGC GACCAAATGG TCCTTCAGAG TGATGTTGCA CTCATAGAAG
6601 TAGGCAGCTC CGGCAGCCAT TCTGCAAAAT AACAAAACAC CACTAAGCAT
6651 AGCACCATCA CCAAGCATGA AAACAGGTAA AAACAAAAGC AACACTTACT
6701 TATTCAGCAG TCACAAGAAT GTTGGGCTCC CAAGTGACAG ACAAGCCTAA
6751 TGCAAGGTGG GCACAGTCTC CGGAATAAGT TGACAAAAGT CACGCCGCAA
6801 AGCTTCCTGA AGAGAAACGG CGGTAGCCTG GATATCTGCA ACGGACCCAA
6851 AACCTTCAGT GTCACTTCCA ATAAACAGAT AAAACTCTAA ATAGTCCCCA
6901 CTTAAAACCG AAACAGCCGC GGCAAAGGTA GGACACGGAC GCACTTCCTG
6951 AGCCCTAATA AGGCTAAACA CCACACGGCG CAGTTCAGAA GGCAAAAAGT
7001 CTGTAAGCTC TAGCTGAGCA CACACACTCT CCACTAGACA CTTGTGAAGC
7051 CTCAGACAAA AACATGCTCC CATAGACACT CCTAAAGCTG CCATTGTACT
7101 CACGGACGGC TGGCTGTCAG AGGAGAGCTA TGAGGATGAA ATGCCAAGCA
7151 CAGCGTTTAT ATAGTCCTCA AAGTAGGGCG TGTGGAAAAC GAAAAGGAAT
7201 ATAACGGGGC GTTTGAGGAA GTGGTGCCAA GTACAGTCAT AAAATGTGGG
7251 CGCGTGGTAA ATGTTAAGTG CAGTTTCCCT TTGGCGGTTG GCCCGGAAAG
7301 TTCACAAAAA GTACAGCACG TCCTTGTCAC CGTGTCAACC ACAAAACCAC
7351 AAATAGGCAC AACGCCCAAA AACCCAGCT
```

FIG. 27A

```
   1 GTCGACGGTG CCCCCAGCAG AAGTATCGAC TGCATGCTAA TTATTAACAA
  51 ACCAAAAGGC GTTGCCACTT ACACCCTTAC CTTTAGGTTT TTAAACTTTA
 101 ACAGACTAAG CGGAGGTACC CTGTTTAAAA CTGATGTCTT AACCTTTACC
 151 TATGTAGGCG AAAATCAATA AAACCAGAAA AAAATAAGTT TAAAAGCTTT
 201 ATTTTTCATA CACGCGAGCG GTAAGGCTGC CGCCTTCAGG AAAAGTTACT
 251 CTGTAAACAG TTCTTTCACA ACAGCACAAA ACATAGGTAT TAGTTAACAG
 301 TTCATTTGGG CTATAATAAT ATACATTTTC TTGGGTGGCA AAGCAAGGGT
 351 CGGTAATCTC AACAAAACCA TCAACTGGAA TGCAAGAATA GTCCAGCACG
 401 GTGGGTTCAA TCTAAAAATG AAGAAACGCT GTTGAGGTTC ACTAAGCACA
 451 GGTTTTGAAT CTGTCGGCAG CGTCCATGCA TCATAGCTTG TCTCAAAGCA
 501 GATTGTCTTC TTTCCTCTGC CTTGGAAGTG GTTTGGTGAA GCACTACAGG
 551 TGTCTTTTCA ACCTCTTTCA GCACCCGCTC TATTACAGAT CTCACCCACA
 601 CAGCACAGTT TTAAGAGAA CAATAGTTTT GAAGGCTACA AGATTTACAC
 651 TTAAGCACCA GCCAGTAATT ATAAGTGCTT TTAAGAACTA CCCCTAGCTC
 701 AGGGTTAATG CACCTTTTAA TGGCCTCCAT GCAGGCTTTA TGGACAGTTC
 751 TAAAAAAGA CAGTCTAAAA TAAATGTAGT GAGTGTTTCT AAATATAATA
 801 CTCCCCACAT AGTTAATTTC ATCAGGCCTG CTAGAATTTA CAAACTCTCG
 851 GTACCACATA TACTTTTTAT TCATAGCCCC ACCCTTAATA AAGTCCTCAA
 901 TCACTTTCTG AACCACATGC TTGCTAGCCA TGCATTGTAA AGACAAGCTG
 951 TTAGAGCAGT GACAGTGTAC TCGCCACGTT TGAGCCTCTG CCAGGCAGCA
1001 GTGCTTAGTT ACTATCAACT CAATACCCGC ATTGCATGTA AACCCCCCAA
1051 AGAGCAGTTT TTCATGCCTG TGTAGCACAT CATCCCACAA AATAGGAATT
1101 TCATAGCATA AAGCAAAGCA ATTACAATAT TTAGGAACTC TCACCACAGC
1151 AGTCACGTGA CATGTTGTCT CAGCAGTGCA GTTGCCTTCC ATCCTACAAT
1201 TATGAACAAA AACTAAACAC TTCTAACAAA GATACAGTGA CAATCTCCCT
1251 TCCTCTAAAA GCATTGTTTA CATTAGGGTG ATTATTAACA ACGTCAGAAA
1301 TTTCTTTAAT TAAAGTGCCT TTAAAATGTG CAAGAGCATC ATCATACTCA
1351 AAACCAAGCT GAGAGTAAAA GACCACCTTA AAAGTAATCC CAGGCTTGTT
1401 TTTATCAACA GCCTTAAACA TGCTTTCACA AAATATAGAA GCAGTAACAT
1451 CATCAATGGT GTCGAAGAGA AACTCCATAG GAGACTCCAG CATTGATCCA
1501 AGCTCTCTAA CAAAATCTTC CTCAAAATGA ATAATGCCCT TTACACAAAC
1551 GCGGGGCAGA CGATGGTGGG CCATCGCGTC AACCTGAAAC ACATTTTACA
1601 GTAAACAAAG CTAGCTCCGC AGTGGTAAAG TCATGCCCAT GGGTGAGGCC
1651 AAAATCCTTA AAAAGCTAT CTAAGTAGTT GGTCATCCCC TCAGTTAAAA
1701 AGTTTTGCAG CTGGGTGGTG CATACCACAT AGTGCCAGCT TATAGCTACA
1751 AAGACCTGCA TCCCCTCCTT AGCAGACAGC TCTTGCACAC ACGCAGTAAC
1801 TATCCACCGC TTAAGAAAAG CTTAAGCCC AGCGCACATA ACAGCTCCAA
1851 TGTTTTTATC CAAGGAGAGC AAAATTTCAG CAAGCGCAGG CTCAACAGTA
1901 ATAGTGAAGC AGAGGCATTT CAGACGAGGC TCACTAGCTG CAGTCGCCAT
1951 TTATGAGGTC TGCAATAAAA AACAACTCAT CAGCAGCTGA AAAAGTGCAC
```

FIG. 27B

```
2001 TTTGACCTCA TTAAGCCACT GCATATGCAA GTCCTCATCT ATGCCGCAGC
2051 CCAGACCCTC AATCCAGCCC CGAATGTACA CTTTAATAAG AGATTCAACC
2101 TCTTCTTTTA GCAAAGTACA CATGCTGTTT GGACTAGTAT ACACAATAGA
2151 AGTCACAATG AGGGGCCCGC TGTGGCTGGA AAGCCTGCGC ACAGCCCGAA
2201 GGTTAAAAAT GGACTGTAAC AGCATTGAAA CCCCGCGACA CAGGTCAGTC
2251 TCGCGGTCTT GATCTCTTAT TATAGCGACC AAATGGTCCT TCAGAGTGAT
2301 GTTGCACTCA TAGAAGTAGG CAGCTCCGGC AGCCATTCTG CAAAATAACA
2351 AAACACCACT AAGCATAGCA CCATCACCAA GCATGAAAAC AGGTAAAAAC
2401 AAAAGCAACA CTTACTTATT CAGCAGTCAC AAGAATGTTG GGCTCCCAAG
2451 TGACAGACAA GCCTAATGCA AGGTGGGCAC AGTCTCCGGA ATAAGTTGAC
2501 AAAAGTCACG CCGCAAAGCT TCCTGAAGAG AAACGGCGGT AGCCTGGATA
2551 TCTGCAACGG ACCCAAAACC TTCAGTGTCA CTTCCAATAA ACAGATAAAA
2601 CTCTAAATAG TCCCCACTTA AAACCGAAAC AGCCGCGGCA AAGGTAGGAC
2651 ACGGACGCAC TTCCTGAGCC CTAATAAGGC TAAACACCAC ACGGCGCAGT
2701 TCAGAAGGCA AAAGTCTGT AAGCTCTAGC TGAGCACACA CACTCTCCAC
2751 TAGACACTTG TGAAGCCTCA GACAAAAACA TGCTCCCATA GACACTCCTA
2801 AAGCTGCCAT TGTACTCACG GACGGCTGGC TGTCAGAGGA GAGCTATGAG
2851 GATGAAATGC CAAGCACAGC GTTTATATAG TCCTCAAAGT AGGGCGTGTG
2901 GAAAACGAAA AGGAATATAA CGGGGCGTTT GAGGAAGTGG TGCCAAGTAC
2951 AGTCATAAAA TGTGGGCGCG TGGTAAATGT TAAGTGCAGT TTCCCTTTGG
3001 CGGTTGGCCC GGAAAGTTCA CAAAAAGTAC AGCACGTCCT TGTCACCGTG
3051 TCAACCACAA AACCACAAAT AGGCACAACG CCCAAAAACC CGGGTCGACA
3101 CGCGTGAATT CACCGGTTCG CGAAACGCCC AAAAACCCGG GGCGCCGGCC
3151 AAAAGTCCGC GGAACTCGCC CTGTCGTAAA ACCACGCCTT TGACGTCACT
3201 GGACATTCCC GTGGGAACAC CCTGACCAGG GCGTGACCTG AACCTGACCG
3251 TCCCATGACC CCGCCCCTTG CAACACCCAA ATTTAAGCCA CACCTCTTTG
3301 TCCTGTATAT TATTGATGAT GGGGGGATCC ACTAGTTCTA GAGCGGCCGC
3351 CACCGCGGTG GAGCTCCAGC TTTTGTTCCC TTTAGTGAGG GTTAATTCCG
3401 AGCTTGGCGT AATCATGGTC ATAGCTGTTT CCTGTGTGAA ATTGTTATCC
3451 GCTCACAATT CCACACAACA TACGAGCCGG AAGCATAAAG TGTAAAGCCT
3501 GGGGTGCCTA ATGAGTGAGC TAACTCACAT TAATTGCGTT GCGCTCACTG
3551 CCCGCTTTCC AGTCGGGAAA CCTGTCGTGC CAGCTGCATT AATGAATCGG
3601 CCAACGCGCG GGGAGAGGCG GTTTGCGTAT TGGGCGCTCT TCCGCTTCCT
3651 CGCTCACTGA CTCGCTGCGC TCGGTCGTTC GGCTGCGGCG AGCGGTATCA
3701 GCTCACTCAA AGGCGGTAAT ACGGTTATCC ACAGAATCAG GGGATAACGC
3751 AGGAAAGAAC ATGTGAGCAA AAGGCCAGCA AAAGGCCAGG AACCGTAAAA
3801 AGGCCGCGTT GCTGGCGTTT TTCCATAGGC TCCGCCCCCC TGACGAGCAT
3851 CACAAAAATC GACGCTCAAG TCAGAGGTGG CGAAACCCGA CAGGACTATA
3901 AAGATACCAG GCGTTTCCCC CTGGAAGCTC CCTCGTGCGC TCTCCTGTTC
3951 CGACCCTGCC GCTTACCGGA TACCTGTCCG CCTTTCTCCC TTCGGGAAGC
4001 GTGGCGCTTT CTCATAGCTC ACGCTGTAGG TATCTCAGTT CGGTGTAGGT
4051 CGTTCGCTCC AAGCTGGGCT GTGTGCACGA ACCCCCGTT CAGCCCGACC
4101 GCTGCGCCTT ATCCGGTAAC TATCGTCTTG AGTCCAACCC GGTAAGACAC
4151 GACTTATCGC CACTGGCAGC AGCCACTGGT AACAGGATTA GCAGAGCGAG
4201 GTATGTAGGC GGTGCTACAG AGTTCTTGAA GTGGTGGCCT AACTACGGCT
4251 ACACTAGAAG GACAGTATTT GGTATCTGCG CTCTGCTGAA GCCAGTTACC
4301 TTCGGAAAAA GAGTTGGTAG CTCTTGATCC GGCAAACAAA CCACCGCTGG
4351 TAGCGGTGGT TTTTTTGTTT GCAAGCAGCA GATTACGCGC AGAAAAAAAG
4401 GATCTCAAGA AGATCCTTTG ATCTTTTCTA CGGGGTCTGA CGCTCAGTGG
4451 AACGAAAACT CACGTTAAGG GATTTTGGTC ATGAGATTAT CAAAAAGGAT
4501 CTTCACCTAG ATCCTTTTAA ATTAAAAATG AAGTTTTAAA TCAATCTAAA
4551 GTATATATGA GTAAACTTGG TCTGACAGTT ACCAATGCTT AATCAGTGAG
4601 GCACCTATCT CAGCGATCTG TCTATTTCGT TCATCCATAG TTGCCTGACT
```

FIG. 27C

```
4651 CCCCGTCGTG TAGATAACTA CGATACGGGA GGGCTTACCA TCTGGCCCCA
4701 GTGCTGCAAT GATACCGCGA GACCCACGCT CACCGGCTCC AGATTTATCA
4751 GCAATAAACC AGCCAGCCGG AAGGGCCGAG CGCAGAAGTG GTCCTGCAAC
4801 TTTATCCGCC TCCATCCAGT CTATTAATTG TTGCCGGGAA GCTAGAGTAA
4851 GTAGTTCGCC AGTTAATAGT TTGCGCAACG TTGTTGCCAT TGCTACAGGC
4901 ATCGTGGTGT CACGCTCGTC GTTTGGTATG GCTTCATTCA GCTCCGGTTC
4951 CCAACGATCA AGGCGAGTTA CATGATCCCC CATGTTGTGC AAAAAAGCGG
5001 TTAGCTCCTT CGGTCCTCCG ATCGTTGTCA GAAGTAAGTT GGCCGCAGTG
5051 TTATCACTCA TGGTTATGGC AGCACTGCAT AATTCTCTTA CTGTCATGCC
5101 ATCCGTAAGA TGCTTTTCTG TGACTGGTGA GTACTCAACC AAGTCATTCT
5151 GAGAATAGTG TATGCGGCGA CCGAGTTGCT CTTGCCCGGC GTCAATACGG
5201 GATAATACCG CGCCACATAG CAGAACTTTA AAAGTGCTCA TCATTGGAAA
5251 ACGTTCTTCG GGGCGAAAAC TCTCAAGGAT CTTACCGCTG TTGAGATCCA
5301 GTTCGATGTA ACCCACTCGT GCACCCAACT GATCTTCAGC ATCTTTTACT
5351 TTCACCAGCG TTTCTGGGTG AGCAAAAACA GGAAGGCAAA ATGCCGCAAA
5401 AAAGGGAATA AGGGCGACAC GGAAATGTTG AATACTCATA CTCTTCCTTT
5451 TTCAATATTA TTGAAGCATT TATCAGGGTT ATTGTCTCAT GAGCGGATAC
5501 ATATTTGAAT GTATTTAGAA AAATAAACAA ATAGGGGTTC CGCGCACATT
5551 TCCCCGAAAA GTGCCACCTG GAAATTGTA AACGTTAATA TTTTGTTAAA
5601 ATTCGCGTTA AATTTTTGTT AAATCAGCTC ATTTTTTAAC CAATAGGCCG
5651 AAATCGGCAA AATCCCTTAT AAATCAAAAG AATAGACCGA GATAGGGTTG
5701 AGTGTTGTTC CAGTTTGGAA CAAGAGTCCA CTATTAAAGA ACGTGGACTC
5751 CAACGTCAAA GGGCGAAAAA CCGTCTATCA GGGCGATGGC CCACTACGTG
5801 AACCATCACC CTAATCAAGT TTTTTGGGGT CGAGGTGCCG TAAAGCACTA
5851 AATCGGAACC CTAAAGGGAG CCCCCGATTT AGAGCTTGAC GGGGAAAGCC
5901 GGCGAACGTG GCGAGAAAGG AAGGGAAGAA AGCGAAAGGA GCGGGCGCTA
5951 GGGCGCTGGC AAGTGTAGCG GTCACGCTGC GCGTAACCAC CACACCCGCC
6001 GCGCTTAATG CGCCGCTACA GGGCGCGTCG CGCCATTCGC CATTCAGGCT
6051 GCGCAACTGT TGGGAAGGGC GATCGGTGCG GGCCTCTTCG CTATTACGCC
6101 AGCTGGCGAA AGGGGGATGT GCTGCAAGGC GATTAAGTTG GGTAACGCCA
6151 GGGTTTTCCC AGTCACGACG TTGTAAAACG ACGGCCAGTG AATTGTAATA
6201 CGACTCACTA TAGGGCGAAT TGGGTACCGG GCCCCCCTC GAG·
```

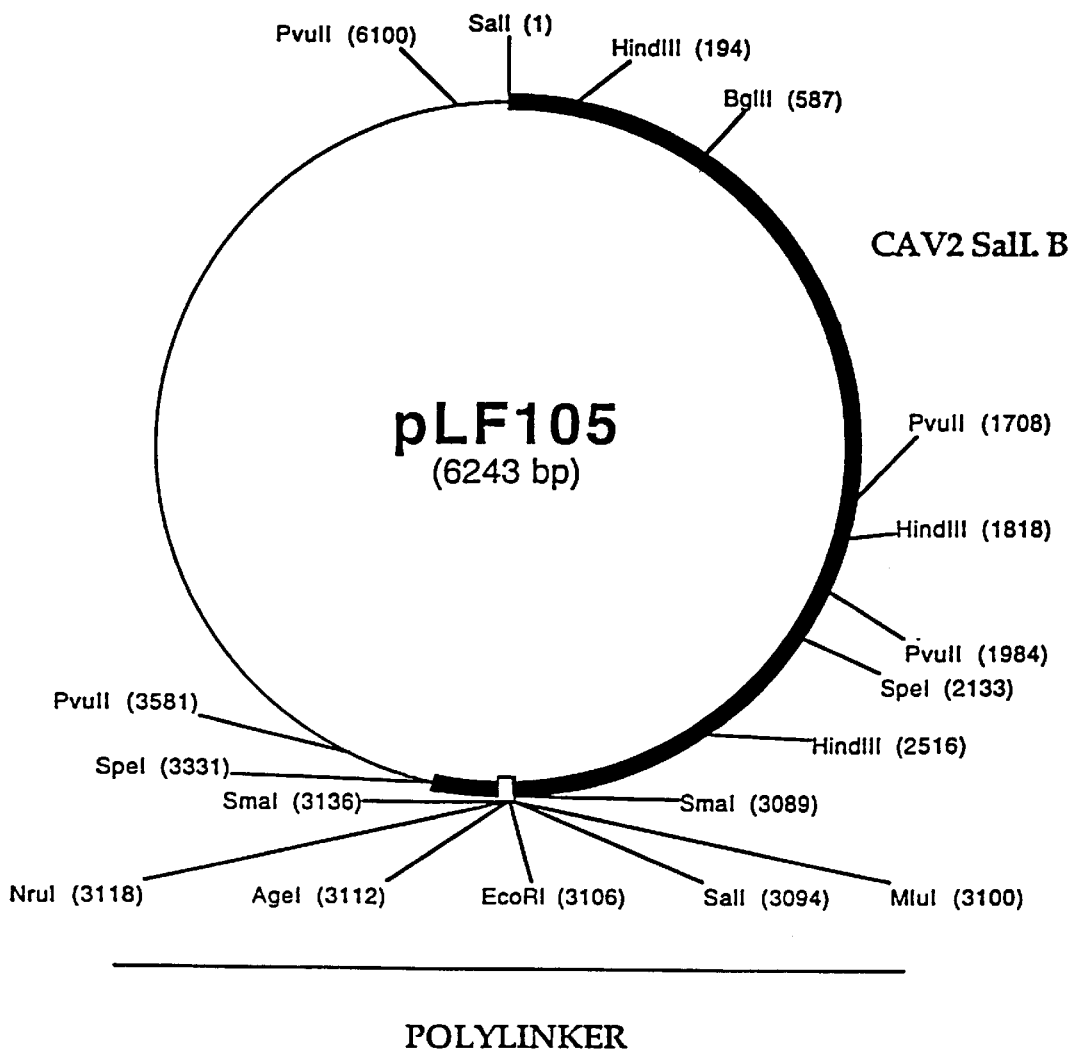

FIG. 29A

```
   1 AAGCTTTGCT CAACAAATAC TGTCAAGGAC TCGAGTCCGG CTCTGACTGA
  51 GCAATGTCTA AAGAAATACC AACCCCTTAT ATGTGGAGCT ACCAACCGCA
 101 AACGGGACAC GCCGGCGCCT CCCAGGACTA CTCCACCCAA ATGAATTGGT
 151 TTAGTGCTGG GCCATCAATG ATTAGTCAAG TTTATGGCAT TAGAGACTTG
 201 CGCAACAAAG TTTTGATAAC CCAGGCAGAA ATAACCAAAA CTCCCAGAAC
 251 AATAATGGAT CCGCCAATTT GGCCAGCTGC CATGCTTGTT CAGGAAGCCG
 301 CCCCACCCAA AACGGTCACT CTGCCCAGAA ACCACACCCT AGAACAGGCT
 351 ATGACCAACT CTGGGGCGCA GCTAGCGGGA GGACGACAGC TGTGCCCCTC
 401 CCAAATAGGT ATAAAAGCC CAGTGCTGGC TGGCACGGGC ATTCAGCTTA
 451 GCGAAGACAT CCCCAGCGCC TCCTGGATCA GGCCCGACGG CATATTCCAG
 501 CTAGGAGGGG GGTCTCGCTC GTCCTTCAGC CCAACGCAAG CATTCCTCAC
 551 CCTGCAACAG GCATCCTCGA CGCCGCGCGC AGGAGGCGTG GGCACCTACC
 601 AGTTTGTGCG CGAATTTGTG CCAGAGGTAT ACCTTAACCC TTTTTCAGGA
 651 CCACCGGACA CCTTTCCTGA TCAGTTCATT CCTAACTACG ACATTGTAAC
 701 CAACTCTGTC GATGGCTATG ACTGAGGAGA GCATGGACCA GGTGGAGGTG
 751 AACTGCCTGT GTGCTCAGCA TGCCCAAACC TGCACGCGCC CTCGCTGCTT
 801 TGCAAAGGAG GGTTTATGTG CTAACTGGTT TTACAACCCA GCACTTGCCT
 851 TTGAAGGGTT TGATATTCCA GACTCTTACC AAGAGGGACA CGGTGTGGAC
 901 ATAGAAGTTA AGTGTTCCCA CCACTCCAGC AAACTGTGCC ACAATGGCCA
 951 TGATATGATC TGCTCATACT CTCGCCTGGG ATCCCACATT AACATAAGAT
1001 GTATTTGCAA CAAGCCGCGG CCCCACATGA GCCTCATTGA GGCAGCCTGT
1051 TCTATGTATA ACCTTAACTA GATAATATTA TTAAACTTGT TTACAGCTA
1101 CCACCATAAT GCGCTTCAGC TTCTTCATCG CCGCCGTTCT TTTCTGCACC
1151 ACAGGGGCCA GCAATGACAT TGTGACTTGC TGCGCCCACA CACCTTGCCT
1201 CCTACACCTA GAAGTGGGCT TGGGGGCCAA TGTCAGTTGG ATAAACTCTG
1251 ACACAGGCCA GGCCCCGATT TGCCTCTCCA ATGGCATGTG CAACGCTACC
1301 CAGCAAGGCC TGCAGTTTTC TGCAAACTTT TCTGAGGATG CCTGTACAT
1351 CGCCCTCATT AAGGAGAGCA ACTACGAGGG CGCTGAGCAC TACTACCTTG
1401 TCTATATTTA TGGAGACTGC TACCAAACTG CAAATGAGTC TGCCCACGGG
1451 CCTATTTCCA GGCCCCTCAA AGATCTGTTA TTAGTGATAT CAAAGATGGT
1501 CCGGTTCTTG TACTCGGGCC ATATATTCAT GTCCCCAGAC ATCATAGTCA
1551 GCACCATTTT CTTCTCCTTT TGCCAGTAGA TGCGAGTTTG TGCCAGCTCT
1601 TCAACAGAAA CATTGTGACC ACAGGACAGC GTTGCCACTT CTTTCACTTC
1651 CTTGGTCACG TGGATAACAC CTGAACAGAA GTGAGAAAGA CCAGCCAGCA
1701 CCAAGAGCTG AAAGAAATTG AGGTATGGAC ACTTGGATGG TGATGTTCCC
1751 TGCCTCCGTG TGTGGCCCAT ACGCGTCCCT CAGCCTTCTA ATGGGACTAA
1801 ACAACAAAAT CAGGCCCATG TAGCTTGTCA ATAAACTTA CCTAATTTTT
1851 GCTAAGACG CTGGGTCCTG CGTTTCTATG TCCACCAAAG TCCCCTCTTC
1901 CCAGCTTTGG TACTTCCACT TGTGCGCGCG AGCCAGCTTG CGGATGTGCT
1951 TGAAAGATAA TGTGGTCTCT CCCAACAGCT TCCCGTTCAC CAGCACCAGG
2001 GCCATGAAGC GGACACGAAG AGCTCTACCT GCAAATTATG ACCCTGTATA
2051 TCCATACGAC GCCCCCGGGT CTTCCACACA ACCCCCTTTT TTAATAACA
2101 AGCAAGGTCT CACTGAGTCA CCCCCAGGAA CCCTGGCTGT CAATGTTTCC
```

FIG. 29B

```
2151 CCTCCACTAA CCTTTTCTAC GTTAGGTGCC ATTAAACTTT CCACAGGTCC
2201 CGGACTCACC CTCAACGAGG GCAAGTTACA AGCCAGCTTA GGGCCCGGCC
2251 TCATCACAAA TACCGAGGGC CAAATCACTG TTGAAAATGT CAACAAGGTT
2301 TTGTCTTTTA CCTCCCCATT ACATAAAAAT GAAAACACTG TATCCCTAGC
2351 GCTAGGAGAT GGGTTAGAAG ATGAAAATGG CACCCTTAAA GTGACCTTCC
2401 CTACTCCCCC TCCCCCGCTA CAATTCTCCC CTCCCCTCAC AAAAACAGGT
2451 GGTACTGTTT CCTTGCCCCT GCAAGACTCC ATGCAAGTGA CAAATGGAAA
2501 ACTGGGCGTT AAGCTACCAC CTACGCACCT CCCTTGAAAA AAACTGACCA
2551 GCAAGTTAGC CTCCAAGTAG GCTCGGGTCT CACCGTGATT AACGAACAGT
2601 TGCAAGCTGT CCAGCCTCCC GCAACCACCT ACAACGAGCC TCTTTCCAAA
2651 ACTGACAATT CTGTTTCTCT GCAAGTAGGT GCCGGCCTTG CCGTGCAGAG
2701 CGGACGTTTG GTGGCAACCC CTCCCCCGCC TCTCACCTTT ACATCACCCC
2751 TAGAAAAAAA TGAAAACACA GTGTCGCTAC AAGTAGGCGC GGGCTTGTCT
2801 GTACAAAACA ACGCCCTAGT AGCCACACCT CCCCCACCCT TAACCTTTGC
2851 CTATCCCTTA GTAAAAATG ACAACCATGT AGCTCTAAGT GCTGGAAGTG
2901 GTTTAAGAAT ATCTGGAGGC AGCCTACGG TGGCCACTGG ACCTGGCCTT
2951 TCCCATCAAA ATGGAACAAT AGGGGCTGTA GTAGGTGCAG GCCTCAAGTT
3001 TGAAAACAAT GCCATTCTTG CAAAACTAGG CAACGGTCTA ACCATTAGAG
3051 ATGGCGCTAT TGAAGCAACC CAACCCCCAG CTGCCCCAT AACACTGTGG
3101 ACAGCGCCTG GCCTAGCATT AATGGCTTTA TGTAATGACA CTCCAGTAAT
3151 TAGGTNCTTT ATATGCCTAA CCAGAGACAG CAACTTAGTC ACAGTAAATG
3201 CTAGCTTTGT GGGAGAGGGG GGGTATCGAA TAGTCAGCCC TACCCAGTCA
3251 CAATTTAGCC TAATTATGGA GTTTGATCAG TTTGGACAGC TTATGTCCAC
3301 AGGAAACATT AACTCCACCA CTACTTGGGG AGAAAAGCCC TGGGGCAATA
3351 ACACTGTACA GCCACGCCCA AGCCACACCT GGAAACTGTG CATGCCTAAC
3401 AGAGAAGTTT ACTCCACTCC CGCCGCCACC ATCACCCGCT GTGGACTAGA
3451 CAGCATTGCA GTCGACGGTG CCCAGCAGAA GTATCGACTG CATGCTAATT
3501 ATTAACAAAC CAAAAGGCGT TGCCACTTAC ACCCTTACCT TTAGGTTTTT
3551 AAACTTTAAC AGACTAAGCG GAGGTACCCT GTTTAAAACT GATGTCTTAA
3601 CCTTTACCTA TGTAGGCGAA AATCAATAAA ACCAGAAAAA AATAAGGGGA
3651 AAAGCTTGAT ATCGAATTCC TGCAGCCCGG GGATCCACT AGTTCTAGAG
3701 CGGCCGCCAC CGCGGTGGAG CTCCAGCTTT TGTTCCCTTT AGTGAGGGTT
3751 AATTCCGAGC TTGGCGTAAT CATGGTCATA GCTGTTTCCT GTGTGAAATT
3801 GTTATCCGCT CACAATTCCA CACAACATAC GAGCCGGAAG CATAAAGTGT
3851 AAAGCCTGGG GTGCCTAATG AGTGAGCTAA CTCACATTAA TTGCGTTGCG
3901 CTCACTGCCC GCTTTCCAGT CGGGAAACCT GTCGTGCCAG CTGCATTAAT
3951 GAATCGGCCA ACGCGCGGGG AGAGGCGGTT TGCGTATTGG GCGCTCTTCC
4001 GCTTCCTCGC TCACTGACTC GCTGCGCTCG GTCGTTCGGC TGCGGCGAGC
4051 GGTATCAGCT CACTCAAAGG CGGTAATACG GTTATCCACA GAATCAGGGG
4101 ATAACGCAGG AAAGAACATG TGAGCAAAAG GCCAGCAAAA GGCCAGGAAC
4151 CGTAAAAAGG CCGCGTTGCT GGCGTTTTTC CATAGGCTCC GCCCCCTGA
4201 CGAGCATCAC AAAAATCGAC GCTCAAGTCA GAGGTGGCGA AACCCGACAG
4251 GACTATAAAG ATACCAGGCG TTTCCCCCTG GAAGCTCCCT CGTGCGCTCT
4301 CCTGTTCCGA CCCTGCCGCT TACCGGATAC CTGTCCGCCT TTCTCCCTTC
4351 GGGAAGCGTG GCGCTTTCTC ATAGCTCACG CTGTAGGTAT CTCAGTTCGG
4401 TGTAGGTCGT TCGCTCCAAG CTGGGCTGTG TGCACGAACC CCCGTTCAG
4451 CCCGACCGCT GCGCCTTATC CGGTAACTAT CGTCTTGAGT CCAACCCGGT
4501 AAGACACGAC TTATCGCCAC TGGCAGCAGC CACTGGTAAC AGGATTAGCA
4551 GAGCGAGGTA TGTAGGCGGT GCTACAGAGT TCTTGAAGTG GTGGCCTAAC
4601 TACGGCTACA CTAGAAGGAC AGTATTTGGT ATCTGCGCTC TGCTGAAGCC
4651 AGTTACCTTC GGAAAAGAG TTGGTAGCTC TTGATCCGGC AAACAAACCA
4701 CCGCTGGTAG CGGTGGTTTT TTGTTTGCA AGCAGCAGAT TACGCGCAGA
4751 AAAAAGGAT CTCAAGAAGA TCCTTTGATC TTTTCTACGG GGTCTGACGC
```

FIG. 29C

```
4801 TCAGTGGAAC GAAAACTCAC GTTAAGGGAT TTTGGTCATG AGATTATCAA
4851 AAAGGATCTT CACCTAGATC CTTTTAAATT AAAAATGAAG TTTTAAATCA
4901 ATCTAAAGTA TATATGAGTA AACTTGGTCT GACAGTTACC AATGCTTAAT
4951 CAGTGAGGCA CCTATCTCAG CGATCTGTCT ATTTCGTTCA TCCATAGTTG
5001 CCTGACTCCC CGTCGTGTAG ATAACTACGA TACGGGAGGG CTTACCATCT
5051 GGCCCCAGTG CTGCAATGAT ACCGCGAGAC CCACGCTCAC CGGCTCCAGA
5101 TTTATCAGCA ATAAACCAGC CAGCCGGAAG GGCCGAGCGC AGAAGTGGTC
5151 CTGCAACTTT ATCCGCCTCC ATCCAGTCTA TTAATTGTTG CCGGGAAGCT
5201 AGAGTAAGTA GTTCGCCAGT TAATAGTTTG CGCAACGTTG TTGCCATTGC
5251 TACAGGCATC GTGGTGTCAC GCTCGTCGTT TGGTATGGCT TCATTCAGCT
5301 CCGGTTCCCA ACGATCAAGG CGAGTTACAT GATCCCCCAT GTTGTGCAAA
5351 AAAGCGGTTA GCTCCTTCGG TCCTCCGATC GTTGTCAGAA GTAAGTTGGC
5401 CGCAGTGTTA TCACTCATGG TTATGGCAGC ACTGCATAAT TCTCTTACTG
5451 TCATGCCATC CGTAAGATGC TTTTCTGTGA CTGGTGAGTA CTCAACCAAG
5501 TCATTCTGAG AATAGTGTAT GCGGCGACCG AGTTGCTCTT GCCCGGCGTC
5551 AATACGGGAT AATACCGCGC CACATAGCAG AACTTTAAAA GTGCTCATCA
5601 TTGGAAAACG TTCTTCGGGG CGAAAACTCT CAAGGATCTT ACCGCTGTTG
5651 AGATCCAGTT CGATGTAACC CACTCGTGCA CCCAACTGAT CTTCAGCATC
5701 TTTTACTTTC ACCAGCGTTT CTGGGTGAGC AAAAACAGGA AGGCAAAATG
5751 CCGCAAAAAA GGGAATAAGG GCGACACGGA AATGTTGAAT ACTCATACTC
5801 TTCCTTTTTC AATATTATTG AAGCATTTAT CAGGGTTATT GTCTCATGAG
5851 CGGATACATA TTTGAATGTA TTTAGAAAAA TAAACAAATA GGGGTTCCGC
5901 GCACATTTCC CCGAAAAGTG CCACCTGGGA AATTGTAAAC GTTAATATTT
5951 TGTTAAAATT CGCGTTAAAT TTTTGTTAAA TCAGCTCATT TTTTAACCAA
6001 TAGGCCGAAA TCGGCAAAAT CCCTTATAAA TCAAAAGAAT AGACCGAGAT
6051 AGGGTTGAGT GTTGTTCCAG TTTGGAACAA GAGTCCACTA TTAAAGAACG
6101 TGGACTCCAA CGTCAAAGGG CGAAAAACCG TCTATCAGGG CGATGGCCCA
6151 CTACGTGAAC CATCACCCTA ATCAAGTTTT TTGGGGTCGA GGTGCCGTAA
6201 AGCACTAAAT CGGAACCCTA AAGGGAGCCC CCGATTTAGA GCTTGACGGG
6251 GAAAGCCGGC GAACGTGGCG AGAAAGGAAG GAAGAAAGC GAAAGGAGCG
6301 GCGCTAGGG CGCTGGCAAG TGTAGCGGTC ACGCTGCGCG TAACCACCAC
6351 ACCCGCCGCG CTTAATGCGC CGCTACAGGG CGCGTCGCGC CATTCGCCAT
6401 TCAGGCTGCG CAACTGTTGG GAAGGGCGAT CGGTGCGGGC CTCTTCGCTA
6451 TTACGCCAGC TGGCGAAAGG GGGATGTGCT GCAAGGCGAT TAAGTTGGGT
6501 AACGCCAGGG TTTTCCCAGT CACGACGTTG TAAAACGACG GCCAGTGAAT
6551 TGTAATACGA CTCACTATAG GCGAATTGG GTACCGGGCC CCCCCTCGAG
6601 GTCGACGGTA TCGAT
``` pLF086 Backbone

Partially deleted E3 region

726 to 1877

Linker 305 bp

```
   1 AAGCTTTGCT CAACAAATAC TGTCAAGGAC TCGAGTCCGG CTCTGACTGA
  51 GCAATGTCTA AAGAAATACC AACCCCTTAT ATGTGGAGCT ACCAACCGCA
 101 AACGGGACAC GCCGGCGCCT CCCAGGACTA CTCCACCCAA ATGAATTGGT
 151 TTAGTGCTGG GCCATCAATG ATTAGTCAAG TTTATGGCAT TAGAGACTTG
 201 CGCAACAAAG TTTTGATAAC CCAGGCAGAA ATAACCAAAA CTCCCAGAAC
 251 AATAATGGAT CCGCCAATTT GGCCAGCTGC CATGCTTGTT CAGGAAGCCG
 301 CCCCACCCAA AACGGTCACT CTGCCCAGAA ACCACACCCT AGAACAGGCT
 351 ATGACCAACT CTGGGGCGCA GCTAGCGGGA GGACGACAGC TGTGCCCCTC
 401 CCAAATAGGT ATAAAAGCC CAGTGCTGGC TGGCACGGGC ATTCAGCTTA
 451 GCGAAGACAT CCCCAGCGCC TCCTGGATCA GGCCCGACGG CATATTCCAG
 501 CTAGGAGGGG GGTCTCGCTC GTCCTTCAGC CCAACGCAAG CATTCCTCAC
 551 CCTGCAACAG GCATCCTCGA CGCCGCGCGC AGGAGGCGTG GGCACCTACC
 601 AGTTTGTGCG CGAATTTGTG CCAGAGGTAT ACCTTAACCC TTTTTCAGGA
 651 CCACCGGACA CCTTTCCTGA TCAGTTCATT CCTAACTACG ACATTGTAAC
 701 CAACTCTGTC GATGGCTATG ACTGAGGAGA GCATGGACCA GGTGGAGGTG
 751 AACTGCCTGT GTGCTCAGCA TGCCCAAACC TGCACGCGCC CTCGCTGCTT
 801 TGCAAAGGAG GGTTTATGTG CTAACTGGTT TTACAACCCA GCACTTGCCT
 851 TTGAAGGGTT TGATATTCCA GACTCTTACC AAGAGGGACA CGGTGTGGAC
 901 ATAGAAGTTA AGTGTTCCCA CCACTCCAGC AAACTGTGCC ACAATGGCCA
 951 TGATATGATC TGCTCATACT CTCGCCTGGG ATCCCACATT AACATAAGAT
1001 GTATTTGCAA CAAGCCGCGG CCCCACATGA GCCTCATTGA GGCAGCCTGT
1051 TCTATGTATA ACCTTAACTA GATAATATTA TTAAACTTGA TACGCGTATG
1101 GCAGAAGGAT TTGCAGCCAA TAGACAATGG ATAGGACCAG AAGAAGCTGA
1151 AGAGTTATTA GATTTTGATA TAGCAACACA AATGAGTGAA GAAGGACCAC
1201 TAAATCCAGG AGTAAACCCA TTTAGGGTAC CTGGAATAAC AGAAAAAGAA
1251 AAGCAAAACT ACTGTAACAT ATTACAACCT AAGTTACAAG ATCTAAGGAA
1301 CGAAATTCAA GAGGTAAAAC TGGAAGAAGG AAATGCAGGT AAGTTTAGAA
1351 GAGCAAGATT TTTAAGGTAT TCTGATGAAC AAGTATTGTC CCTGGTTACG
1401 CGTGTCCTCA ACATCACCCG CGACGGAACT TTCCTGCTTA TTGGGGATAG
1451 CAAAAAGACC CCCTATGTCA TCCTGCTGCC CTTTTTTGCA AACCCCAAAG
1501 AAGACACTCC AATTTTAATG GCCCTTAGCC ATTCCATGCC CGTCGCCATA
1551 CCTGACACTG CAATGCCTAT ATATATTTCC ATCATGTTTT TTATTGTGGC
1601 CATGCTAGCC ACCCTCAGCC TTCTAATGGG ACTAAACAAC AAAATCAGGC
1651 CCATGTAGCT TGTCAAATAA ACTTACCTAA TTTTTGCTAA GACGCTGGGT
1701 CCTGCGTTTC TATGTCCACC AAAGTCCCCT CTTCCCAGCT TTGGTACTTC
1751 CACTTGTGCG CGCGAGCCAG CTTGCGGATG TGCTTGAAAG ATAATGTGGT
1801 CTCTCCCAAC AGCTTCCCGT TCACCAGCAC CAGGGCCATG AAGCGGACAC
1851 GAAGAGCTCT ACCTGCAAAT TATGACCCTG TATATCCATA CGACGCCCCC
1901 GGGTCTTCCA CACAACCCCC TTTTTTAAT AACAAGCAAG GTCTCACTGA
1951 GTCACCCCCA GGAACCCTGG CTGTCAATGT TCCCCTCCA CTAACCTTTT
2001 CTACGTTAGG TGCCATTAAA CTTTCCACAG GTCCCGGACT CACCCTCAAC
2051 GAGGGCAAGT TACAAGCCAG CTTAGGGCCC GGCCTCATCA CAAATACCGA
2101 GGGCCAAATC ACTGTTGAAA ATGTCAACAA GGTTTTGTCT TTTACCTCCC
```

FIG. 31B

```
2151 CATTACATAA AAATGAAAAC ACTGTATCCC TAGCGCTAGG AGATGGGTTA
2201 GAAGATGAAA ATGGCACCCT TAAAGTGACC TTCCCTACTC CCCCTCCCCC
2251 GCTACAATTC TCCCCTCCCC TCACAAAAAC AGGTGGTACT GTTTCCTTGC
2301 CCCTGCAAGA CTCCATGCAA GTGACAAATG GAAAACTGGG CGTTAAGCTA
2351 CCACCTACGC ACCTCCTTG AAAAAAACTG ACCAGCAAGT TAGCCTCCAA
2401 GTAGGCTCGG GTCTCACCGT GATTAACGAA CAGTTGCAAG CTGTCCAGCC
2451 TCCCGCAACC ACCTACAACG AGCCTCTTTC CAAAACTGAC AATTCTGTTT
2501 CTCTGCAAGT AGGTGCCGGC CTTGCCGTGC AGAGCGGACG TTTGGTGGCA
2551 ACCCCTCCCC CGCCTCTCAC CTTTACATCA CCCCTAGAAA AAAATGAAAA
2601 CACAGTGTCG CTACAAGTAG GCGCGGGCTT GTCTGTACAA AACAACGCCC
2651 TAGTAGCCAC ACCTCCCCCA CCCTTAACCT TGCCTATCC CTTAGTAAAA
2701 AATGACAACC ATGTAGCTCT AAGTGCTGGA AGTGGTTTAA GAATATCTGG
2751 AGGCAGCCTC ACGGTGGCCA CTGGACCTGG CCTTTCCCAT CAAAATGGAA
2801 CAATAGGGGC TGTAGTAGGT GCAGGCCTCA AGTTTGAAAA CAATGCCATT
2851 CTTGCAAAAC TAGGCAACGG TCTAACCATT AGAGATGGCG CTATTGAAGC
2901 AACCCAACCC CCAGCTGCCC CCATAACACT GTGGACAGGG CCTGGCCTAG
2951 CATTAATGGC TTTATGTAAT GACACTCCAG TAATTAGGTN CTTTATATGC
3001 CTAACCAGAG ACAGCAACTT AGTCACAGTA AATGCTAGCT TTGTGGGAGA
3051 GGGGGGGTAT CGAATAGTCA GCCCTACCCA GTCACAATTT AGCCTAATTA
3101 TGGAGTTTGA TCAGTTTGGA CAGCTTATGT CCACAGGAAA CATTAACTCC
3151 ACCACTACTT GGGGAGAAAA GCCCTGGGGC AATAACACTG TACAGCCACG
3201 CCCAAGCCAC ACCTGGAAAC TGTGCATGCC TAACAGAGAA GTTTACTCCA
3251 CTCCCGCCGC CACCATCACC CGCTGTGGAC TAGACAGCAT TGCAGTCGAC
3301 GGTGCCCAGC AGAAGTATCG ACTGCATGCT AATTATTAAC AAACCAAAAG
3351 GCGTTGCCAC TTACACCCTT ACCTTTAGGT TTTTAAACTT TAACAGACTA
3401 AGCGGAGGTA CCCTGTTTAA AACTGATGTC TTAACCTTTA CCTATGTAGG
3451 CGAAAATCAA TAAAACCAGA AAAAATAAG GGGAAAAGCT TGATATCGAA
3501 TTCCTGCAGC CCGGGGGATC CACTAGTTCT AGAGCGGCCG CCACCGCGGT
3551 GGAGCTCCAG CTTTTGTTCC CTTTAGTGAG GGTTAATTCC GAGCTTGGCG
3601 TAATCATGGT CATAGCTGTT TCCTGTGTGA AATTGTTATC CGCTCACAAT
3651 TCCACACAAC ATACGAGCCG GAAGCATAAA GTGTAAAGCC TGGGGTGCCT
3701 AATGAGTGAG CTAACTCACA TTAATTGCGT TGCGCTCACT GCCCGCTTTC
3751 CAGTCGGGAA ACCTGTCGTG CCAGCTGCAT TAATGAATCG GCCAACGCGC
3801 GGGGAGAGGC GGTTTGCGTA TTGGGCGCTC TTCCGCTTCC TCGCTCACTG
3851 ACTCGCTGCG CTCGGTCGTT CGGCTGCGGC GAGCGGTATC AGCTCACTCA
3901 AAGGCGGTAA TACGGTTATC CACAGAATCA GGGGATAACG CAGGAAAGAA
3951 CATGTGAGCA AAAGGCCAGC AAAAGGCCAG GAACCGTAAA AAGGCCGCGT
4001 TGCTGGCGTT TTTCCATAGG CTCCGCCCCC CTGACGAGCA TCACAAAAAT
4051 CGACGCTCAA GTCAGAGGTG GCGAAACCCG ACAGGACTAT AAAGATACCA
4101 GGCGTTTCCC CCTGGAAGCT CCCTCGTGCG CTCTCCTGTT CCGACCCTGC
4151 CGCTTACCGG ATACCTGTCC GCCTTTCTCC CTTCGGGAAG CGTGGCGCTT
4201 TCTCATAGCT CACGCTGTAG GTATCTCAGT TCGGTGTAGG TCGTTCGCTC
4251 CAAGCTGGGC TGTGTGCACG AACCCCCCGT TCAGCCCGAC CGCTGCGCCT
4301 TATCCGGTAA CTATCGTCTT GAGTCCAACC CGGTAAGACA CGACTTATCG
4351 CCACTGGCAG CAGCCACTGG TAACAGGATT AGCAGAGCGA GGTATGTAGG
4401 CGGTGCTACA GAGTTCTTGA AGTGGTGGCC TAACTACGGC TACACTAGAA
4451 GGACAGTATT TGGTATCTGC GCTCTGCTGA AGCCAGTTAC CTTCGGAAAA
4501 AGAGTTGGTA GCTCTTGATC CGGCAAACAA ACCACCGCTG GTAGCGGTGG
4551 TTTTTTTGTT TGCAAGCAGC AGATTACGCG CAGAAAAAAA GGATCTCAAG
4601 AAGATCCTTT GATCTTTTCT ACGGGGTCTG ACGCTCAGTG GAACGAAAAC
4651 TCACGTTAAG GGATTTTGGT CATGAGATTA TCAAAAGGA TCTTCACCTA
4701 GATCCTTTTA AATTAAAAAT GAAGTTTTAA ATCAATCTAA AGTATATATG
4751 AGTAAACTTG GTCTGACAGT TACCAATGCT TAATCAGTGA GGCACCTATC
```

FIG. 31C

```
4801 TCAGCGATCT GTCTATTTCG TTCATCCATA GTTGCCTGAC TCCCCGTCGT
4851 GTAGATAACT ACGATACGGG AGGGCTTACC ATCTGGCCCC AGTGCTGCAA
4901 TGATACCGCG AGACCCACGC TCACCGGCTC CAGATTTATC AGCAATAAAC
4951 CAGCCAGCCG GAAGGGCCGA GCGCAGAAGT GGTCCTGCAA CTTTATCCGC
5001 CTCCATCCAG TCTATTAATT GTTGCCGGGA AGCTAGAGTA AGTAGTTCGC
5051 CAGTTAATAG TTTGCGCAAC GTTGTTGCCA TTGCTACAGG CATCGTGGTG
5101 TCACGCTCGT CGTTTGGTAT GGCTTCATTC AGCTCCGGTT CCCAACGATC
5151 AAGGCGAGTT ACATGATCCC CCATGTTGTG CAAAAAAGCG GTTAGCTCCT
5201 TCGGTCCTCC GATCGTTGTC AGAAGTAAGT TGGCCGCAGT GTTATCACTC
5251 ATGGTTATGG CAGCACTGCA TAATTCTCTT ACTGTCATGC CATCCGTAAG
5301 ATGCTTTTCT GTGACTGGTG AGTACTCAAC CAAGTCATTC TGAGAATAGT
5351 GTATGCGGCG ACCGAGTTGC TCTTGCCCGG CGTCAATACG GGATAATACC
5401 GCGCCACATA GCAGAACTTT AAAAGTGCTC ATCATTGGAA AACGTTCTTC
5451 GGGGCGAAAA CTCTCAAGGA TCTTACCGCT GTTGAGATCC AGTTCGATGT
5501 AACCCACTCG TGCACCCAAC TGATCTTCAG CATCTTTTAC TTTCACCAGC
5551 GTTTCTGGGT GAGCAAAAAC AGGAAGGCAA AATGCCGCAA AAAAGGGAAT
5601 AAGGGCGACA CGGAAATGTT GAATACTCAT ACTCTTCCTT TTTCAATATT
5651 ATTGAAGCAT TTATCAGGGT TATTGTCTCA TGAGCGGATA CATATTTGAA
5701 TGTATTTAGA AAAATAAACA AATAGGGGTT CCGCGCACAT TTCCCCGAAA
5751 AGTGCCACCT GGGAAATTGT AAACGTTAAT ATTTTGTTAA AATTCGCGTT
5801 AAATTTTTGT TAAATCAGCT CATTTTTTAA CCAATAGGCC GAAATCGGCA
5851 AAATCCCTTA TAAATCAAAA GAATAGACCG AGATAGGGTT GAGTGTTGTT
5901 CCAGTTTGGA ACAAGAGTCC ACTATTAAAG AACGTGGACT CCAACGTCAA
5951 AGGGCGAAAA ACCGTCTATC AGGGCGATGG CCCACTACGT GAACCATCAC
6001 CCTAATCAAG TTTTTTGGGG TCGAGGTGCC GTAAAGCACT AAATCGGAAC
6051 CCTAAAGGGA GCCCCCGATT TAGAGCTTGA CGGGGAAAGC CGGCGAACGT
6101 GGCGAGAAAG GAAGGGAAGA AAGCGAAAGG AGCGGGCGCT AGGGCGCTGG
6151 CAAGTGTAGC GGTCACGCTG CGCGTAACCA CCACACCCGC CGCGCTTAAT
6201 GCGCCGCTAC AGGGCGCGTC GCGCCATTCG CCATTCAGGC TGCGCAACTG
6251 TTGGGAAGGG CGATCGGTGC GGGCCTCTTC GCTATTACGC CAGCTGGCGA
6301 AAGGGGGATG TGCTGCAAGG CGATTAAGTT GGGTAACGCC AGGGTTTTCC
6351 CAGTCACGAC GTTGTAAAAC GACGGCCAGT GAATTGTAAT ACGACTCACT
6401 ATAGGCGAA TTGGGTACCG GCCCCCCCT CGAGGTCGAC GGTATCGAT
``` pLF086 Backbone

Partially deleted E3 region
726 to 1712

Linker
311 bp

```
   1 AAGCTTTGCT CAACAAATAC TGTCAAGGAC TCGAGTCCGG CTCTGACTGA
  51 GCAATGTCTA AAGAAATACC AACCCCTTAT ATGTGGAGCT ACCAACCGCA
 101 AACGGGACAC GCCGGCGCCT CCCAGGACTA CTCCACCCAA ATGAATTGGT
 151 TTAGTGCTGG GCCATCAATG ATTAGTCAAG TTTATGGCAT TAGAGACTTG
 201 CGCAACAAAG TTTTGATAAC CCAGGCAGAA ATAACCAAAA CTCCCAGAAC
 251 AATAATGGAT CCGCCAATTT GGCCAGCTGC CATGCTTGTT CAGGAAGCCG
 301 CCCCACCCAA AACGGTCACT CTGCCCAGAA ACCACACCCT AGAACAGGCT
 351 ATGACCAACT CTGGGGCGCA GCTAGCGGGA GGACGACAGC TGTGCCCCTC
 401 CCAAATAGGT ATAAAAGCC CAGTGCTGGC TGGCACGGGC ATTCAGCTTA
 451 GCGAAGACAT CCCCAGCGCC TCCTGGATCA GGCCCGACGG CATATTCCAG
 501 CTAGGAGGGG GGTCTCGCTC GTCCTTCAGC CAACGCAAG CATTCCTCAC
 551 CCTGCAACAG GCATCCTCGA CGCCGCGCGC AGGAGGCGTG GCACCTACC
 601 AGTTTGTGCG CGAATTGTG CCAGAGGTAT ACCTTAACCC TTTTTCAGGA
 651 CCACCGGACA CCTTTCCTGA TCAGTTCATT CCTAACTACG ACATTGTAAC
 701 CAACTCTGTC GATGGCTATG ACTGAGGAGA GCATGGACCA GGTGGAGGTG
 751 AACTGCCTGT GTGCTCAGCA TGCCCAAACC TGCACGCGCC CTCGCTGCTT
 801 TGCAAAGGAG GGTTTATGTG CTAACTGGTT TTACAACCCA GCACTTGCCT
 851 TTGAAGGGTT TGATATTCCA GACTCTTACC AAGAGGGACA CGGTGTGTAA
 901 ATGGGCCACA CACGGAGGCA GGAACATCA CCATCCAAGT GTCCATACCT
 951 CAATTTCTTT CAGCTCTTGG TGCTGGCTGG TCTTTCTCAC TTCTGTTCAG
1001 GTGTTATCCA CGTGACCAAG GAAGTGAAAG AAGTGGCAAC GCTGTCCTGT
1051 GGTCACAATG TTTCTGTTGA AGAGCTGGCA CAAACTCGCA TCTACTGGCA
1101 AAAGGAGAAG AAAATGGTGC TGACTATGAT GTCTGGGAC ATGAATATAT
1151 GGCCCGAGTA CAAGAACCGG ACCATCTTTG ATATCACTAA TAACACGCGT
1201 GTCCTCAACA TCACCCGCGA CGGAACTTTC CTGCTTATTG GGGATAGCAA
1251 AAAGACCCCC TATGTCATCC TGCTGCCCTT TTTTGCAAAC CCCAAAGAAG
1301 ACACTCCAAT TTTAATGGCC CTTAGCCATT CCATGCCCGT CGCCATACCT
1351 GACACTGCAA TGCCTATATA TATTTCCATC ATGTTTTTTA TTGTGGCCAT
1401 GCTAGCCACC CTCAGCCTTC TAATGGGACT AAACAACAAA ATCAGGCCCA
1451 TGTAGCTTGT CAAATAAACT TACCTAATTT TTGCTAAGAC GCTGGGTCCT
1501 GCGTTTCTAT GTCCACCAAA GTCCCTCTT CCCAGCTTTG GTACTTCCAC
1551 TTGTGCGCGC GAGCCAGCTT GCGGATGTGC TTGAAAGATA ATGTGGTCTC
1601 TCCCAACAGC TTCCCGTTCA CCAGCACCAG GGCCATGAAG CGGACACGAA
1651 GAGCTCTACC TGCAAATTAT GACCCTGTAT ATCCATACGA CGCCCCGGG
1701 TCTTCCACAC AACCCCCTTT TTTAATAAC AAGCAAGGTC TCACTGAGTC
1751 ACCCCAGGA ACCCTGGCTG TCAATGTTTC CCTCCACTA ACCTTTTCTA
1801 CGTTAGGTGC CATTAAACTT TCCACAGGTC CCGGACTAC CCTCAACGAG
1851 GGCAAGTTAC AAGCCAGCTT AGGGCCCGGC CTCATCACAA ATACCGAGGG
1901 CCAAATCACT GTTGAAAATG TCAACAAGGT TTTGTCTTTT ACCTCCCCAT
1951 TACATAAAAA TGAAAACACT GTATCCCTAG CGCTAGGAGA TGGGTTAGAA
2001 GATGAAAATG GCACCCTTAA AGTGACCTTC CCTACTCCCC CTCCCCCGCT
2051 ACAATTCTCC CCTCCCCTCA CAAAACAGG TGGTACTGTT TCCTTGCCCC
2101 TGCAAGACTC CATGCAAGTG ACAAATGGAA AACTGGGCGT TAAGCTACCA
```

FIG. 33B

```
2151 CCTACGCACC TCCCTTGAAA AAAACTGACC AGCAAGTTAG CCTCCAAGTA
2201 GGCTCGGGTC TCACCGTGAT TAACGAACAG TTGCAAGCTG TCCAGCCTCC
2251 CGCAACCACC TACAACGAGC CTCTTTCCAA AACTGACAAT TCTGTTTCTC
2301 TGCAAGTAGG TGCCGGCCTT GCCGTGCAGA GCGGACGTTT GGTGGCAACC
2351 CCTCCCCCGC CTCTCACCTT TACATCACCC CTAGAAAAAA ATGAAAACAC
2401 AGTGTCGCTA CAAGTAGGCG CGGGCTTGTC TGTACAAAAC AACGCCCTAG
2451 TAGCCACACC TCCCCCACCC TTAACCTTTG CCTATCCCTT AGTAAAAAAT
2501 GACAACCATG TAGCTCTAAG TGCTGGAAGT GGTTTAAGAA TATCTGGAGG
2551 CAGCCTCACG GTGGCCACTG GACCTGGCCT TTCCCATCAA AATGGAACAA
2601 TAGGGCTGT AGTAGGTGCA GGCCTCAAGT TTGAAAACAA TGCCATTCTT
2651 GCAAAACTAG GCAACGGTCT AACCATTAGA GATGGCGCTA TTGAAGCAAC
2701 CCAACCCCCA GCTGCCCCCA TAACACTGTG GACAGGGCCT GGCCTAGCAT
2751 TAATGGCTTT ATGTAATGAC ACTCCAGTAA TTAGGTNGTT TATATGCCTA
2801 ACCAGAGACA GCAACTTAGT CACAGTAAAT GCTAGCTTTG TGGGAGAGGG
2851 GGGGTATCGA ATAGTCAGCC CTACCCAGTC ACAATTTAGC CTAATTATGG
2901 AGTTTGATCA GTTTGGACAG CTTATGTCCA CAGGAAACAT TAACTCCACC
2951 ACTACTTGGG GAGAAAAGCC CTGGGCAAT AACACTGTAC AGCCACGCCC
3001 AAGCCACACC TGGAAACTGT GCATGCCTAA CAGAGAAGTT TACTCCACTC
3051 CCGCCGCCAC CATCACCCGC TGTGGACTAG ACAGCATTGC AGTCGACGGT
3101 GCCCAGCAGA AGTATCGACT GCATGCTAAT TATTAACAAA CCAAAAGGCG
3151 TTGCCACTTA CACCCTTACC TTTAGGTTTT TAAACTTTAA CAGACTAAGC
3201 GGAGGTACCC TGTTTAAAAC TGATGTCTTA ACCTTTACCT ATGTAGGCGA
3251 AAATCAATAA AACCAGAAAA AAATAAGGGG AAAAGCTTGA TATCGAATTC
3301 CTGCAGCCCG GGGGATCCAC TAGTTCTAGA GCGGCCGCCA CCGCGGTGGA
3351 GCTCCAGCTT TTGTTCCCTT TAGTGAGGGT TAATTCCGAG CTTGGCGTAA
3401 TCATGGTCAT AGCTGTTTCC TGTGTGAAAT TGTTATCCGC TCACAATTCC
3451 ACACAACATA CGAGCCGGAA GCATAAAGTG TAAAGCCTGG GGTGCCTAAT
3501 GAGTGAGCTA ACTCACATTA ATTGCGTTGC GCTCACTGCC CGCTTTCCAG
3551 TCGGGAAACC TGTCGTGCCA GCTGCATTAA TGAATCGGCC AACGCGCGGG
3601 GAGAGGCGGT TTGCGTATTG GGCGCTCTTC CGCTTCCTCG CTCACTGACT
3651 CGCTGCGCTC GGTCGTTCGG CTGCGGCGAG CGGTATCAGC TCACTCAAAG
3701 GCGGTAATAC GGTTATCCAC AGAATCAGGG GATAACGCAG GAAAGAACAT
3751 GTGAGCAAAA GGCCAGCAAA AGGCCAGGAA CCGTAAAAAG GCCGCGTTGC
3801 TGGCGTTTTT CCATAGGCTC CGCCCCCCTG ACGAGCATCA CAAAAATCGA
3851 CGCTCAAGTC AGAGGTGGCG AAACCCGACA GGACTATAAA GATACCAGGC
3901 GTTTCCCCCT GGAAGCTCCC TCGTGCGCTC TCCTGTTCCG ACCCTGCCGC
3951 TTACCGGATA CCTGTCCGCC TTTCTCCCTT CGGGAAGCGT GGCGCTTTCT
4001 CATAGCTCAC GCTGTAGGTA TCTCAGTTCG GTGTAGGTCG TTCGCTCCAA
4051 GCTGGGCTGT GTGCACGAAC CCCCCGTTCA GCCCGACCGC TGCGCCTTAT
4101 CCGGTAACTA TCGTCTTGAG TCCAACCCGG TAAGACACGA CTTATCGCCA
4151 CTGGCAGCAG CCACTGGTAA CAGGATTAGC AGAGCGAGGT ATGTAGGCGG
4201 TGCTACAGAG TTCTTGAAGT GGTGGCCTAA CTACGGCTAC ACTAGAAGGA
4251 CAGTATTTGG TATCTGCGCT CTGCTGAAGC CAGTTACCTT CGGAAAAGA
4301 GTTGGTAGCT CTTGATCCGG CAAACAAACC ACCGCTGGTA GCGGTGGTTT
4351 TTTTGTTTGC AAGCAGCAGA TTACGCGCAG AAAAAAAGGA TCTCAAGAAG
4401 ATCCTTTGAT CTTTTCTACG GGTCTGACG CTCAGTGGAA CGAAAACTCA
4451 CGTTAAGGGA TTTTGGTCAT GAGATTATCA AAAAGGATCT TCACCTAGAT
4501 CCTTTTAAAT TAAAAATGAA GTTTTAAATC AATCTAAAGT ATATATGAGT
4551 AAACTTGGTC TGACAGTTAC CAATGCTTAA TCAGTGAGGC ACCTATCTCA
4601 GCGATCTGTC TATTTCGTTC ATCCATAGTT GCCTGACTCC CCGTCGTGTA
4651 GATAACTACG ATACGGGAGG GCTTACCATC TGGCCCCAGT GCTGCAATGA
4701 TACCGCGAGA CCCACGCTCA CCGGCTCCAG ATTTATCAGC AATAAACCAG
4751 CCAGCCGGAA GGGCCGAGCG CAGAAGTGGT CCTGCAACTT TATCCGCCTC
```

FIG. 33C

```
4801 CATCCAGTCT ATTAATTGTT GCCGGGAAGC TAGAGTAAGT AGTTCGCCAG
4851 TTAATAGTTT GCGCAACGTT GTTGCCATTG CTACAGGCAT CGTGGTGTCA
4901 CGCTCGTCGT TTGGTATGGC TTCATTCAGC TCCGGTTCCC AACGATCAAG
4951 GCGAGTTACA TGATCCCCCA TGTTGTGCAA AAAAGCGGTT AGCTCCTTCG
5001 GTCCTCCGAT CGTTGTCAGA AGTAAGTTGG CCGCAGTGTT ATCACTCATG
5051 GTTATGGCAG CACTGCATAA TTCTCTTACT GTCATGCCAT CCGTAAGATG
5101 CTTTTCTGTG ACTGGTGAGT ACTCAACCAA GTCATTCTGA GAATAGTGTA
5151 TGCGGCGACC GAGTTGCTCT TGCCCGGCGT CAATACGGGA TAATACCGCG
5201 CCACATAGCA GAACTTTAAA AGTGCTCATC ATTGGAAAAC GTTCTTCGGG
5251 GCGAAAACTC TCAAGGATCT TACCGCTGTT GAGATCCAGT TCGATGTAAC
5301 CCACTCGTGC ACCCAACTGA TCTTCAGCAT CTTTTACTTT CACCAGCGTT
5351 TCTGGGTGAG CAAAAACAGG AAGGCAAAAT GCCGCAAAAA AGGGAATAAG
5401 GGCGACACGG AAATGTTGAA TACTCATACT CTTCCTTTTT CAATATTATT
5451 GAAGCATTTA TCAGGGTTAT TGTCTCATGA GCGGATACAT ATTTGAATGT
5501 ATTTAGAAAA ATAAACAAAT AGGGGTTCCG CGCACATTTC CCCGAAAAGT
5551 GCCACCTGGG AAATTGTAAA CGTTAATATT TTGTTAAAAT TCGCGTTAAA
5601 TTTTTGTTAA ATCAGCTCAT TTTTTAACCA ATAGGCCGAA ATCGGCAAAA
5651 TCCCTTATAA ATCAAAAGAA TAGACCGAGA TAGGGTTGAG TGTTGTTCCA
5701 GTTTGGAACA AGAGTCCACT ATTAAAGAAC GTGGACTCCA ACGTCAAAGG
5751 GCGAAAAACC GTCTATCAGG GCGATGGCCC ACTACGTGAA CCATCACCCT
5801 AATCAAGTTT TTTGGGGTCG AGGTGCCGTA AAGCACTAAA TCGGAACCCT
5851 AAAGGGAGCC CCCGATTTAG AGCTTGACGG GGAAAGCCGG CGAACGTGGC
5901 GAGAAAGGAA GGGAAGAAAG CGAAAGGAGC GGGCGCTAGG GCGCTGGCAA
5951 GTGTAGCGGT CACGCTGCGC GTAACCACCA CACCCGCCGC GCTTAATGCG
6001 CCGCTACAGG GCGCGTCGCG CCATTCGCCA TTCAGGCTGC GCAACTGTTG
6051 GGAAGGGCGA TCGGTGCGGG CCTCTTCGCT ATTACGCCAG CTGGCGAAAG
6101 GGGGATGTGC TGCAAGGCGA TTAAGTTGGG TAACGCCAGG GTTTTCCCAG
6151 TCACGACGTT GTAAAACGAC GGCCAGTGAA TTGTAATACG ACTCACTATA
6201 GGCGAATTG  GGTACCGGGC CCCCCCTCGA GGTCGACGGT ATCGAT
``` pLF086 Backbone

Partially deleted E3 region
726 to 1509

Linker
302 bp
898 to 1200

FIG.35A

```
   1 AAGCTTTGCT CAACAAATAC TGTCAAGGAC TCGAGTCCGG CTCTGACTGA
  51 GCAATGTCTA AAGAAATACC AACCCCTTAT ATGTGGAGCT ACCAACCGCA
 101 AACGGGACAC GCCGGCGCCT CCCAGGACTA CTCCACCCAA ATGAATTGGT
 151 TTAGTGCTGG GCCATCAATG ATTAGTCAAG TTTATGGCAT TAGAGACTTG
 201 CGCAACAAAG TTTTGATAAC CCAGGCAGAA ATAACCAAAA CTCCCAGAAC
 251 AATAATGGAT CCGCCAATTT GGCCAGCTGC CATGCTTGTT CAGGAAGCCG
 301 CCCCACCCAA AACGGTCACT CTGCCCAGAA ACCACACCCT AGAACAGGCT
 351 ATGACCAACT CTGGGGCGCA GCTAGCGGGA GGACGACAGC TGTGCCCCTC
 401 CCAAATAGGT ATAAAAGCC CAGTGCTGGC TGGCACGGGC ATTCAGCTTA
 451 GCGAAGACAT CCCCAGCGCC TCCTGGATCA GGCCCGACGG CATATTCCAG
 501 CTAGGAGGGG GGTCTCGCTC GTCCTTCAGC CAACGCAAG CATTCCTCAC
 551 CCTGCAACAG GCATCCTCGA CGCCGCGCGC AGGAGGCGTG GCACCTACC
 601 AGTTTGTGCG CGAATTTGTG CCAGAGGTAT ACCTTAACCC TTTTTCAGGA
 651 CCACCGGACA CCTTTCCTGA TCAGTTCATT CCTAACTACG ACATTGTAAC
 701 CAACTCTGTC GATGGCTATG ACTGAGGAGA GCATGGACCA GGTGGAGGTG
 751 AACTGCCTGT GTGCTCAGCA TGCCCAAACC TGCACGCGCC CTCGCTGCTT
 801 TGCAAAGGAG GGTTTATGTG CTAACTGGTT TTACAACCCA GCACTTGCCT
 851 TTGAAGGGTT TGATATTCCA GACTCTTACC AAGAGGGACA CGGTGTGTAG
 901 ATGGGTTGTT CTGTGGAGAA TGTTGGACAG TGTAAAGTAT GCTGCCAGGG
 951 GCGTCCGCGA CTGACCAAGT GAAAACATCA TTGTAATAGG AGTTTGTTCT
1001 CCATGTCTCT TGTTGGTCTA CCTGTTGGGG TGGTCCGCCA ATCCCTGCTG
1051 TTGCAATCGA TGCGGATGAA TTTTCTGCAG TGATCACGCT GGTAGTGGCC
1101 ACAACGCCAG GATCCATGCC ATCAGTCGTA GTTCCAGGAA CTGATGCTGT
1151 GGTGGCAGTG CCCGCTGCTT CGCCTTGCGG CGCTGCACGG GCTTTGCCCT
1201 CTAACGCGTC CCTCAGCCTT CTAATGGGAC TAAACAACAA AATCAGGCCC
1251 ATGTAGCTTG TCAAATAAAC TTACCTAATT TTTGCTAAGA CGCTGGGTC
1301 CTGCGTTTCT ATGTCCACCA AAGTCCCCTC TTCCCAGCTT TGGTACTTCC
1351 ACTTGTGCGC GCGAGCCAGC TTGCGGATGT GCTTGAAAGA TAATGTGGTC
1401 TCTCCCAACA GCTTCCGTT CACCAGCACC AGGGCCATGA AGCGGACACG
1451 AAGAGCTCTA CCTGCAAATT ATGACCCTGT ATATCCATAC GACGCCCCG
1501 GGTCTTCCAC ACAACCCCCT TTTTTAATA ACAAGCAAGG TCTCACTGAG
1551 TCACCCCCAG GAACCCTGGC TGTCAATGTT TCCCCTCCAC TAACCTTTTC
1601 TACGTTAGGT GCCATTAAAC TTTCCACAGG TCCCGGACTC ACCCTCAACG
1651 AGGGCAAGTT ACAAGCCAGC TTAGGGCCCG GCCTCATCAC AAATACCGAG
1701 GGCCAAATCA CTGTTGAAAA TGTCAACAAG GTTTTGTCTT TTACCTCCCC
1751 ATTACATAAA AATGAAAACA CTGTATCCCT AGCGCTAGGA GATGGGTTAG
1801 AAGATGAAAA TGGCACCCTT AAAGTGACCT TCCCTACTCC CCCTCCCCG
1851 CTACAATTCT CCCCTCCCCT CACAAAAACA GGTGGTACTG TTTCCTTGCC
1901 CCTGCAAGAC TCCATGCAAG TGACAAATGG AAAACTGGGC GTTAAGCTAC
1951 CACCTACGCA CCTCCCTTGA AAAAAACTGA CCAGCAAGTT AGCCTCCAAG
2001 TAGGCTCGGG TCTCACCGTG ATTAACGAAC AGTTGCAAGC TGTCCAGCCT
2051 CCCGCAACCA CCTACAACGA GCCTCTTTCC AAAACTGACA ATTCTGTTTC
2101 TCTGCAAGTA GGTGCCGGCC TTGCCGTGCA GAGCGGACGT TTGGTGGCAA
```

FIG. 35B

```
2151 CCCCTCCCCC GCCTCTCACC TTTACATCAC CCCTAGAAAA AAATGAAAAC
2201 ACAGTGTCGC TACAAGTAGG CGCGGGCTTG TCTGTACAAA ACAACGCCCT
2251 AGTAGCCACA CCTCCCCCAC CCTTAACCTT TGCCTATCCC TTAGTAAAAA
2301 ATGACAACCA TGTAGCTCTA AGTGCTGGAA GTGGTTTAAG AATATCTGGA
2351 GGCAGCCTCA CGGTGGCCAC TGGACCTGGC CTTTCCCATC AAAATGGAAC
2401 AATAGGGGCT GTAGTAGGTG CAGGCCTCAA GTTTGAAAAC AATGCCATTC
2451 TTGCAAAACT AGGCAACGGT CTAACCATTA GAGATGGCGC TATTGAAGCA
2501 ACCCAACCCC CAGCTGCCCC CATAACACTG TGGACAGGGC CTGGCCTAGC
2551 ATTAATGGCT TTATGTAATG ACACTCCAGT AATTAGGTNC TTTATATGCC
2601 TAACCAGAGA CAGCAACTTA GTCACAGTAA ATGCTAGCTT TGTGGGAGAG
2651 GGGGGGTATC GAATAGTCAG CCCTACCCAG TCACAATTTA GCCTAATTAT
2701 GGAGTTTGAT CAGTTTGGAC AGCTTATGTC CACAGGAAAC ATTAACTCCA
2751 CCACTACTTG GGGAGAAAAG CCCTGGGGCA ATAACACTGT ACAGCCACGC
2801 CCAAGCCACA CCTGGAAACT GTGCATGCCT AACAGAGAAG TTTACTCCAC
2851 TCCCGCCGCC ACCATCACCC GCTGTGGACT AGACAGCATT GCAGTCGACG
2901 GTGCCCAGCA GAAGTATCGA CTGCATGCTA ATTATTAACA AACCAAAAGG
2951 CGTTGCCACT TACACCCTTA CCTTTAGGTT TTTAAACTTT AACAGACTAA
3001 GCGGAGGTAC CCTGTTTAAA ACTGATGTCT TAACCTTTAC CTATGTAGGC
3051 GAAAATCAAT AAAACCAGAA AAAAATAAGG GGAAAAGCTT GATATCGAAT
3101 TCCTGCAGCC CGGGGGATCC ACTAGTTCTA GAGCGGCCGC CACCGCGGTG
3151 GAGCTCCAGC TTTTGTTCCC TTTAGTGAGG GTTAATTCCG AGCTTGGCGT
3201 AATCATGGTC ATAGCTGTTT CCTGTGTGAA ATTGTTATCC GCTCACAATT
3251 CCACACAACA TACGAGCCGG AAGCATAAAG TGTAAAGCCT GGGGTGCCTA
3301 ATGAGTGAGC TAACTCACAT TAATTGCGTT GCGCTCACTG CCCGCTTTCC
3351 AGTCGGGAAA CCTGTCGTGC CAGCTGCATT AATGAATCGG CCAACGCGCG
3401 GGGAGAGGCG GTTTGCGTAT TGGGCGCTCT TCCGCTTCCT CGCTCACTGA
3451 CTCGCTGCGC TCGGTCGTTC GGCTGCGGCG AGCGGTATCA GCTCACTCAA
3501 AGGCGGTAAT ACGGTTATCC ACAGAATCAG GGGATAACGC AGGAAAGAAC
3551 ATGTGAGCAA AAGGCCAGCA AAAGGCCAGG AACCGTAAAA AGGCCGCGTT
3601 GCTGGCGTTT TTCCATAGGC TCCGCCCCCC TGACGAGCAT CACAAAAATC
3651 GACGCTCAAG TCAGAGGTGG CGAAACCCGA CAGGACTATA AAGATACCAG
3701 GCGTTTCCCC CTGGAAGCTC CCTCGTGCGC TCTCCTGTTC CGACCCTGCC
3751 GCTTACCGGA TACCTGTCCG CCTTTCTCCC TTCGGGAAGC GTGGCGCTTT
3801 CTCATAGCTC ACGCTGTAGG TATCTCAGTT CGGTGTAGGT CGTTCGCTCC
3851 AAGCTGGGCT GTGTGCACGA ACCCCCCGTT CAGCCCGACC GCTGCGCCTT
3901 ATCCGGTAAC TATCGTCTTG AGTCCAACCC GGTAAGACAC GACTTATCGC
3951 CACTGGCAGC AGCCACTGGT AACAGGATTA GCAGAGCGAG GTATGTAGGC
4001 GGTGCTACAG AGTTCTTGAA GTGGTGGCCT AACTACGGCT ACACTAGAAG
4051 GACAGTATTT GGTATCTGCG CTCTGCTGAA GCCAGTTACC TTCGGAAAAA
4101 GAGTTGGTAG CTCTTGATCC GGCAAACAAA CCACCGCTGG TAGCGGTGGT
4151 TTTTTTGTTT GCAAGCAGCA GATTACGCGC AGAAAAAAAG GATCTCAAGA
4201 AGATCCTTTG ATCTTTTCTA CGGGGTCTGA CGCTCAGTGG AACGAAAACT
4251 CACGTTAAGG GATTTTGGTC ATGAGATTAT CAAAAAGGAT CTTCACCTAG
4301 ATCCTTTTAA ATTAAAAATG AAGTTTTAAA TCAATCTAAA GTATATATGA
4351 GTAAACTTGG TCTGACAGTT ACCAATGCTT AATCAGTGAG GCACCTATCT
4401 CAGCGATCTG TCTATTTCGT TCATCCATAG TTGCCTGACT CCCCGTCGTG
4451 TAGATAACTA CGATACGGGA GGGCTTACCA TCTGGCCCCA GTGCTGCAAT
4501 GATACCGCGA GACCCACGCT CACCGGCTCC AGATTTATCA GCAATAAACC
4551 AGCCAGCCGG AAGGGCCGAG CGCAGAAGTG GTCCTGCAAC TTTATCCGCC
4601 TCCATCCAGT CTATTAATTG TTGCCGGGAA GCTAGAGTAA GTAGTTCGCC
4651 AGTTAATAGT TTGCGCAACG TTGTTGCCAT TGCTACAGGC ATCGTGGTGT
4701 CACGCTCGTC GTTTGGTATG GCTTCATTCA GCTCCGGTTC CCAACGATCA
4751 AGGCGAGTTA CATGATCCCC CATGTTGTGC AAAAAAGCGG TTAGCTCCTT
```

FIG. 35C

```
4801 CGGTCCTCCG ATCGTTGTCA GAAGTAAGTT GGCCGCAGTG TTATCACTCA
4851 TGGTTATGGC AGCACTGCAT AATTCTCTTA CTGTCATGCC ATCCGTAAGA
4901 TGCTTTTCTG TGACTGGTGA GTACTCAACC AAGTCATTCT GAGAATAGTG
4951 TATGCGGCGA CCGAGTTGCT CTTGCCCGGC GTCAATACGG GATAATACCG
5001 CGCCACATAG CAGAACTTTA AAAGTGCTCA TCATTGGAAA ACGTTCTTCG
5051 GGGCGAAAAC TCTCAAGGAT CTTACCGCTG TTGAGATCCA GTTCGATGTA
5101 ACCCACTCGT GCACCCAACT GATCTTCAGC ATCTTTTACT TTCACCAGCG
5151 TTTCTGGGTG AGCAAAAACA GGAAGGCAAA ATGCCGCAAA AAAGGGAATA
5201 AGGGCGACAC GGAAATGTTG AATACTCATA CTCTTCCTTT TTCAATATTA
5251 TTGAAGCATT TATCAGGGTT ATTGTCTCAT GAGCGGATAC ATATTTGAAT
5301 GTATTTAGAA AAATAAACAA ATAGGGGTTC CGCGCACATT TCCCCGAAAA
5351 GTGCCACCTG GGAAATTGTA AACGTTAATA TTTTGTTAAA ATTCGCGTTA
5401 AATTTTTGTT AAATCAGCTC ATTTTTTAAC CAATAGGCCG AAATCGGCAA
5451 AATCCCTTAT AAATCAAAAG AATAGACCGA GATAGGGTTG AGTGTTGTTC
5501 CAGTTTGGAA CAAGAGTCCA CTATTAAAGA ACGTGGACTC CAACGTCAAA
5551 GGGCGAAAAA CCGTCTATCA GGGCGATGGC CCACTACGTG AACCATCACC
5601 CTAATCAAGT TTTTTGGGGT CGAGGTGCCG TAAAGCACTA AATCGGAACC
5651 CTAAAGGGAG CCCCCGATTT AGAGCTTGAC GGGGAAAGCC GGCGAACGTG
5701 GCGAGAAAGG AAGGGAAGAA AGCGAAAGGA GCGGGCGCTA GGGCGCTGGC
5751 AAGTGTAGCG GTCACGCTGC GCGTAACCAC CACACCCGCC GCGCTTAATG
5801 CGCCGCTACA GGGCGCGTCG CGCCATTCGC CATTCAGGCT GCGCAACTGT
5851 TGGGAAGGGC GATCGGTGCG GCCTCTTCG CTATTACGCC AGCTGGCGAA
5901 AGGGGGATGT GCTGCAAGGC GATTAAGTTG GGTAACGCCA GGGTTTTCCC
5951 AGTCACGACG TTGTAAAACG ACGGCCAGTG AATTGTAATA CGACTCACTA
6001 TAGGCGAAT TGGGTACCGG GCCCCCCCTC GAGGTCGACG GTATCGAT
``` pLF086 Backbone

Partially deleted E3 region
726 to 1310

Linker 311 bp

```
   1 AAGCTTTCGC GATATCCGTT AAGTTTGTAT CGTAATGCTC CCCTACCAAG
  51 ACAAGGTGGG TGCCTTCTAC AAGGATAATG CAAGAGCCAA TTCAACCAAG
 101 CTGTCCTTAG TGACAGAAGG ACATGGGGGC AGGAGACCAC CTTATTTGTT
 151 GTTTGTCCTT CTCATCTTAT TGGTTGGTAT CCTGGCCTTG CTTGCTATCA
 201 CTGGAGTTCG ATTTCACCAA GTATCAACTA GTAATATGGA ATTTAGCAGA
 251 TTGCTGAAAG AGGATATGGA GAAATCAGAG GCCGTACATC ACCAAGTCAT
 301 AGATGTCTTG ACACCGCTCT TCAAGATTAT TGGAGATGAG ATTGGGTTAC
 351 GGTTGCCACA AAAGCTAAAC GAGATCAAAC AATTTATCCT TCAAAAGACA
 401 AATTTCTTCA ATCCGAACAG AGAATTCGAC TTCCGCGATC TCCACTGGTG
 451 CATTAACCCG CCTAGTACGG TCAAGGTGAA TTTTACTAAT TACTGTGAGT
 501 CAATTGGGAT CAGAAAAGCT ATTGCATCGG CAGCAAATCC TATCCTTTTA
 551 TCAGCCCTAT CTGGGGGCAG AGGTGACATA TTCCCACCAC ACAGATGCAG
 601 TGGAGCTACT ACTTCAGTAG GCAAAGTTTT CCCCCTATCA GTCTCATTAT
 651 CCATGTCTTT GATCTCAAGA ACCTCAGAGG TAATCAATAT GCTGACCGCT
 701 ATCTCAGACG GCGTGTATGG CAAAACTTAC TTGCTAGTGC CTGATGATAT
 751 AGAAAGAGAG TTCGACACTC GAGAGATTCG AGTCTTTGAA ATAGGGTTCA
 801 TCAAAAGGTG GCTGAATGAC ATGCCATTAC TCCAAACAAC CAACTATATG
 851 GTACTCCCGA AGAATTCCAA AGCCAAGGTA TGTACTATAG CAGTGGGTGA
 901 GTTGACACTG GCTTCCTTGT GTGTAGAAGA GAGCACTGTA TTATTATATC
 951 ATGACAGCAG TGGTTCACAA GATGGTATTC TAGTAGTGAC ACTGGGGATA
1001 TTTTGGGCAA CACCTATGGA TCACATTGAG GAAGTGATAC CTGTCGCTCA
1051 CCCATCAATG AAGAAAATAC ATATAACAAA CCACCGTGGT TTTATAAAAG
1101 ATTCAATTGC AACCTGGATG GTGCCTGCCC TGGCCTCTGA GAAACAAGAA
1151 GAACAAAAAG GTTGTCTGGA GTCAGCTTGT CAAAGAAAAA CCTACCCCAT
1201 GTGCAACCAA GCGTCATGGG AACCCTTCGG AGGAAGACAG TTGCCATCTT
1251 ATGGGCGGTT GACATTACCT CTAGATGCAA GTGTTGACCT TCAACTTAAC
1301 ATATCGTTCA CATACGGTCC GGTTATACTG AATGGAGATG GTATGGATTA
1351 TTATGAAAGC CCACTTTTGA ACTCCGGATG GCTTACCATT CCCCCCAAAG
1401 ACGGAACAAT CTCTGGATTG ATAAACAAAG CAGGTAGAGG AGACCAGTTC
1451 ACTGTACTCC CCATGTGTT AACATTTGCG CCCAGGGAAT CAAGTGGAAA
1501 TTGTTATTTA CCTATTCAAA CATCTCAAAT TAGAGATAGA GATGTCCTCA
1551 TTGAGTCCAA TATAGTGGTG TTGCCTACAC AGAGTATTAG ATATGTCATA
1601 GCAACGTATG ACATATCACG AAGTGATCAT GCTATTGTTT ATTATGTTTA
1651 TGACCCAATC CGGACGATTT CTTATACGCA CCCATTTAGA CTAACTACCA
1701 AGGGTAGACC TGATTTCCTA AGGATTGAAT GTTTTGTGTG GGATGACAAT
1751 TTGTGGTGTC ACCAATTTTA CAGATTCGAG GCTGACATCG CCAACTCTAC
1801 AACCAGTGTT GAGAATTTAG TCCGTATAAG ATTCTCATGT AACCGTTAAA
1851 ATCCCTGACA GTATGATGAT ACACATCTCA ATTGGCCTTA GGCATGATAA
1901 CTGCGGTGAG AAATCCCTTA CAGACGATTG AATTAAACCA TCTCTAGCAT
1951 TATAAAAAAA CTAAGGATCC AAGATCCTTT TAGCCATGGA CTCTGTATCA
2001 GTGAACCAGA TTCTATACCC TGAGGTCCAT CTAGATAGCC CAATTGTAAC
2051 CAATAAGCTA GTATCTATTT TAGAATACGC ACGAATTAGA CATAACTATC
```

FIG. 37B

```
2101 AGCTCCTTGA TACAAGATTA GTGCGTAATA TCAAAGAGAG AATTTCAGAA
2151 GGGTTCTCAA ACCAGATGAT CATTAGGATC CACTAGTTCT AGAGCGGCCG
2201 CCACCGCGGT GGAGCTCCAG CTTTTGTTCC CTTTAGTGAG GGTTAATTCC
2251 GAGCTTGGCG TAATCATGGT CATAGCTGTT TCCTGTGTGA AATTGTTATC
2301 CGCTCACAAT TCCACACAAC ATACGAGCCG GAAGCATAAA GTGTAAAGCC
2351 TGGGGTGCCT AATGAGTGAG CTAACTCACA TTAATTGCGT TGCGCTCACT
2401 GCCCGCTTTC CAGTCGGGAA ACCTGTCGTG CCAGCTGCAT TAATGAATCG
2451 GCCAACGCGC GGGGAGAGGC GGTTTGCGTA TTGGGCGCTC TTCCGCTTCC
2501 TCGCTCACTG ACTCGCTGCG CTCGTCGTT CGGCTGCGGC GAGCGGTATC
2551 AGCTCACTCA AAGGCGGTAA TACGGTTATC CACAGAATCA GGGGATAACG
2601 CAGGAAAGAA CATGTGAGCA AAAGGCCAGC AAAAGGCCAG GAACCGTAAA
2651 AAGGCCGCGT TGCTGGCGTT TTTCCATAGG CTCCGCCCCC CTGACGAGCA
2701 TCACAAAAAT CGACGCTCAA GTCAGAGGTG GCGAAACCCG ACAGGACTAT
2751 AAAGATACCA GGCGTTTCCC CCTGGAAGCT CCCTCGTGCG CTCTCCTGTT
2801 CCGACCCTGC CGCTTACCGG ATACCTGTCC GCCTTTCTCC CTTCGGGAAG
2851 CGTGGCGCTT TCTCATAGCT CACGCTGTAG GTATCTCAGT TCGGTGTAGG
2901 TCGTTCGCTC CAAGCTGGGC TGTGTGCACG AACCCCCCGT TCAGCCCGAC
2951 CGCTGCGCCT TATCCGGTAA CTATCGTCTT GAGTCCAACC CGGTAAGACA
3001 CGACTTATCG CCACTGGCAG CAGCCACTGG TAACAGGATT AGCAGAGCGA
3051 GGTATGTAGG CGGTGCTACA GAGTTCTTGA AGTGGTGGCC TAACTACGGC
3101 TACACTAGAA GGACAGTATT TGGTATCTGC GCTCTGCTGA AGCCAGTTAC
3151 CTTCGGAAAA AGAGTTGGTA GCTCTTGATC CGGCAAACAA ACCACCGCTG
3201 GTAGCGGTGG TTTTTTTGTT TGCAAGCAGC AGATTACGCG CAGAAAAAAA
3251 GGATCTCAAG AAGATCCTTT GATCTTTTCT ACGGGGTCTG ACGCTCAGTG
3301 GAACGAAAAC TCACGTTAAG GGATTTTGGT CATGAGATTA TCAAAAAGGA
3351 TCTTCACCTA GATCCTTTTA AATTAAAAAT GAAGTTTTAA ATCAATCTAA
3401 AGTATATATG AGTAAACTTG GTCTGACAGT TACCAATGCT TAATCAGTGA
3451 GGCACCTATC TCAGCGATCT GTCTATTTCG TTCATCCATA GTTGCCTGAC
3501 TCCCCGTCGT GTAGATAACT ACGATACGGG AGGGCTTACC ATCTGGCCCC
3551 AGTGCTGCAA TGATACCGCG AGACCCACGC TCACCGGCTC CAGATTTATC
3601 AGCAATAAAC CAGCCAGCCG GAAGGGCCGA GCGCAGAAGT GGTCCTGCAA
3651 CTTTATCCGC CTCCATCCAG TCTATTAATT GTTGCCGGGA AGCTAGAGTA
3701 AGTAGTTCGC CAGTTAATAG TTTGCGCAAC GTTGTTGCCA TTGCTACAGG
3751 CATCGTGGTG TCACGCTCGT CGTTTGGTAT GGCTTCATTC AGCTCCGGTT
3801 CCCAACGATC AAGGCGAGTT ACATGATCCC CCATGTTGTG CAAAAAAGCG
3851 GTTAGCTCCT TCGGTCCTCC GATCGTTGTC AGAAGTAAGT TGGCCGCAGT
3901 GTTATCACTC ATGGTTATGG CAGCACTGCA TAATTCTCTT ACTGTCATGC
3951 CATCCGTAAG ATGCTTTTCT GTGACTGGTG AGTACTCAAC CAAGTCATTC
4001 TGAGAATAGT GTATGCGGCG ACCGAGTTGC TCTTGCCCGG CGTCAATACG
4051 GGATAATACC GCGCCACATA GCAGAACTTT AAAAGTGCTC ATCATTGGAA
4101 AACGTTCTTC GGGGCGAAAA CTCTCAAGGA TCTTACCGCT GTTGAGATCC
4151 AGTTCGATGT AACCCACTCG TGCACCCAAC TGATCTTCAG CATCTTTTAC
4201 TTTCACCAGC GTTTCTGGGT GAGCAAAAAC AGGAAGGCAA AATGCCGCAA
4251 AAAAGGGAAT AAGGGCGACA CGGAAATGTT GAATACTCAT ACTCTTCCTT
4301 TTTCAATATT ATTGAAGCAT TTATCAGGGT TATTGTCTCA TGAGCGGATA
4351 CATATTTGAA TGTATTTAGA AAAATAAACA AATAGGGGTT CCGCGCACAT
4401 TTCCCCGAAA AGTGCCACCT GGGAAATTGT AAACGTTAAT ATTTTGTTAA
4451 AATTCGCGTT AAATTTTTGT TAAATCAGCT CATTTTTTAA CCAATAGGCC
4501 GAAATCGGCA AAATCCCTTA TAAATCAAAA GAATAGACCG AGATAGGGTT
4551 GAGTGTTGTT CCAGTTTGGA ACAAGAGTCC ACTATTAAAG AACGTGGACT
4601 CCAACGTCAA AGGGCGAAAA ACCGTCTATC AGGGCGATGG CCCACTACGT
4651 GAACCATCAC CCTAATCAAG TTTTTTGGGG TCGAGGTGCC GTAAAGCACT
4701 AAATCGGAAC CCTAAAGGGA GCCCCCGATT TAGAGCTTGA CGGGGAAAGC
```

FIG.37C

```
4751 CGGCGAACGT GGCGAGAAAG GAAGGGAAGA AAGCGAAAGG AGCGGGCGCT
4801 AGGGCGCTGG CAAGTGTAGC GGTCACGCTG CGCGTAACCA CCACACCCGC
4851 CGCGCTTAAT GCGCCGCTAC AGGGCGCGTC GCGCCATTCG CCATTCAGGC
4901 TGCGCAACTG TTGGGAAGGG CGATCGGTGC GGGCCTCTTC GCTATTACGC
4951 CAGCTGGCGA AAGGGGGATG TGCTGCAAGG CGATTAAGTT GGGTAACGCC
5001 AGGGTTTTCC CAGTCACGAC GTTGTAAAAC GACGGCCAGT GAATTGTAAT
5051 ACGACTCACT ATAGGGCGAA TTGGGTACCG GGCCCCCCCT CGAGGTCGAC
5101 GGTATCGAT
```

FIG. 38 pBSSK+  Vaccinia H6 Promoter #7 to 37

- AccI (5095)
- XhoI (5089)
- KpnI (5074)
- HindIII (1)
- NruI (7)
- SpeI (227)
- EcoRI (422)
- XhoI (768)
- EcoRI (862)

CDV-HA Gene #35 to 2175 pLF043 (5109 bp)

- XbaI (1270)
- AccI (1704)

Stop Codon #1847

- BamHI (1965)
- XbaI (2030)
- SacI (2212)
- SacII (2204)
- XbaI (2188)
- SpeI (2182)
- BamHI (2176)

FIG. 39A

```
   1 AAGCTTAATG TCGTAACAAC TCCGCCCCGT TGACGCAAAT GGGCGGTAGG
  51 CGTGTACGGT GGGAGGTCTA TATAAGCAGA GCTCGTTTAG TGAACCGTCT
 101 GCAGACTCTC TTCCGCATCG CTGTCTGCGA GGGCCAGCTG TTGGGCTCGC
 151 GGTTGAGGAC AAACTCTTCG CGGTCTTTCC AGTACTCTTG GATCGGAAAC
 201 CCGTCGGCCT CCGAACGGTA CTCCGCCACC GAGGGACCTG AGCGAGTCCG
 251 CATCGACCGG ATCGGAAAAC CTCTCGAGAA AGGCGTCTAA CCAGTCACAG
 301 TCGCAAGTCT AGAATGCTCC CCTACCAAGA CAAGGTGGGT GCCTTCTACA
 351 AGGATAATGC AAGAGCCAAT TCAACCAAGC TGTCCTTAGT GACAGAAGGA
 401 CATGGGGGCA GGAGACCACC TTATTTGTTG TTTGTCCTTC TCATCTTATT
 451 GGTTGGTATC CTGGCCTTGC TTGCTATCAC TGGAGTTCGA TTTCACCAAG
 501 TATCAACTAG TAATATGGAA TTTAGCAGAT TGCTGAAAGA GGATATGGAG
 551 AAATCAGAGG CCGTACATCA CCAAGTCATA GATGTCTTGA CACCGCTCTT
 601 CAAGATTATT GGAGATGAGA TTGGGTTACG GTTGCCACAA AAGCTAAACG
 651 AGATCAAACA ATTTATCCTT CAAAAGACAA ATTTCTTCAA TCCGAACAGA
 701 GAATTCGACT TCCGCGATCT CCACTGGTGC ATTAACCCGC CTAGTACGGT
 751 CAAGGTGAAT TTTACTAATT ACTGTGAGTC AATTGGGATC AGAAAAGCTA
 801 TTGCATCGGC AGCAAATCCT ATCCTTTTAT CAGCCCATCT GGGGGCAGA
 851 GGTGACATAT TCCCACCACA CAGATGCAGT GGAGCTACTA CTTCAGTAGG
 901 CAAAGTTTTC CCCCTATCAG TCTCATTATC CATGTCTTTG ATCTCAAGAA
 951 CCTCAGAGGT AATCAATATG CTGACCGCTA TCTCAGACGG CGTGTATGGC
1001 AAAACTTACT TGCTAGTGCC TGATGATATA GAAAGAGAGT TCGACACTCG
1051 AGAGATTCGA GTCTTTGAAA TAGGGTTCAT CAAAAGGTGG CTGAATGACA
1101 TGCCATTACT CCAAACAACC AACTATATGG TACTCCCGAA GAATTCCAAA
1151 GCCAAGGTAT GTACTATAGC AGTGGGTGAG TTGACACTGG CTTCCTTGTG
1201 TGTAGAAGAG AGCACTGTAT TATTATATCA TGACAGCAGT GGTTCACAAG
1251 ATGGTATTCT AGTAGTGACA CTGGGGATAT TTTGGGCAAC ACCTATGGAT
1301 CACATTGAGG AAGTGATACC TGTCGCTCAC CCATCAATGA AGAAAATACA
1351 TATAACAAAC CACCGTGGTT TTATAAAAGA TTCAATTGCA ACCTGGATGG
1401 TGCCTGCCCT GGCCTCTGAG AAACAAGAAG AACAAAAAGG TTGTCTGGAG
1451 TCAGCTTGTC AAAGAAAAAC CTACCCCATG TGCAACCAAG CGTCATGGGA
1501 ACCCTTCGGA GGAAGACAGT TGCCATCTTA TGGGCGGTTG ACATTACCTC
1551 TAGATGCAAG TGTTGACCTT CAACTTAACA TATCGTTCAC ATACGGTCCG
1601 GTTATACTGA ATGGAGATGG TATGGATTAT TATGAAAGCC CACTTTTGAA
1651 CTCCGGATGG CTTACCATTC CCCCAAAGA CGGAACAATC TCTGGATTGA
1701 TAAACAAAGC AGGTAGAGGA GACCAGTTCA CTGTACTCCC CCATGTGTTA
1751 ACATTTGCGC CCAGGGAATC AAGTGGAAAT TGTTATTTAC CTATTCAAAC
1801 ATCTCAAATT AGAGATAGAG ATGTCCTCAT TGAGTCCAAT ATAGTGGTGT
1851 TGCCTACACA GAGTATTAGA TATGTCATAG CAACGTATGA CATATCACGA
1901 AGTGATCATG CTATTGTTTA TTATGTTTAT GACCCAATCC GGACGATTTC
1951 TTATACGCAC CCATTTAGAC TAACTACCAA GGGTAGACCT GATTTCCTAA
2001 GGATTGAATG TTTTGTGTGG GATGACAATT TGTGGTGTCA CCAATTTTAC
2051 AGATTCGAGG CTGACATCGC CAACTCTACA ACCAGTGTTG AGAATTTAGT
2101 CCGTATAAGA TTCTCATGTA ACCGTTAACC GCGGCGTGAT TAATCAGCCA
```

FIG. 39B

```
2151 TACCACATTT GTAGAGGTTT TACTTGCTTT AAAAAACCTC CCACACCTCC
2201 CCCTGAACCT GAAACATAAA ATGAATGCAA TTGTTGTTGT TAACTTGTTT
2251 ATTGCAGCTT ATAATGGTTA CAAATAAAGC AATAGCATCA CAAATTTCAC
2301 AAATAAAGCA TTTTTTTCAC TGCATTCTAG TTGTGGTTTG TCCAAACTCA
2351 TCAATGTATC TTATCATGTC TGGATCCCCC GGAATTCACT GGCCGTCGTT
2401 TTACAACGTC GTGACTGGGA AAACCCTGGC GTTACCCAAC TTAATCGCCT
2451 TGCAGCACAT CCCCCCTTCG CCAGCTGGCG TAATAGCGAA GAGGCCCGCA
2501 CCGATCGCCC TTCCCAACAG TTGCGCAGCC TGAATGGCGA ATGGCGCCTG
2551 ATGCGGTATT TTCTCCTTAC GCATCTGTGC GGTATTTCAC ACCGCATATG
2601 GTGCACTCTC AGTACAATCT GCTCTGATGC CGCATAGTTA AGCCAGTACA
2651 CTCCGCTATC GCTACGTGAC TGGGTCATGG CTGCGCCCCG ACACCCGCCA
2701 ACACCCGCTG ACGCGCCCTG ACGGGCTTGT CTGCTCCCGG CATCCGCTTA
2751 CAGACAAGCT GTGACCGTCT CCGGGAGCTG CATGTGTCAG AGGTTTTCAC
2801 CGTCATCACC GAAACGCGCG AGGCAGTTCT TGAAGACGAA AGGGCCTCGT
2851 GATACGCCTA TTTTTATAGG TTAATGTCAT GATAATAATG GTTTCTTAGA
2901 CGTCAGGTGG CACTTTTCGG GGAAATGTGC GCGGAACCCC TATTTGTTTA
2951 TTTTTCTAAA TACATTCAAA TATGTATCCG CTCATGAGAC AATAACCCTG
3001 ATAAATGCTT CAATAATATT GAAAAAGGAA GAGTATGAGT ATTCAACATT
3051 TCCGTGTCGC CCTTATTCCC TTTTTTGCGG CATTTGCCT TCCTGTTTTT
3101 GCTCACCCAG AAACGCTGGT GAAAGTAAAA GATGCTGAAG ATCAGTTGGG
3151 TGCACGAGTG GGTTACATCG AACTGGATCT CAACAGCGGT AAGATCCTTG
3201 AGAGTTTTCG CCCCGAAGAA CGTTTTCCAA TGATGAGCAC TTTTAAAGTT
3251 CTGCTATGTG GCGCGGTATT ATCCCGTATT GACGCCGGGC AAGAGCAACT
3301 CGGTCGCCGC ATACACTATT CTCAGAATGA CTTGGTTGAG TACTCACCAG
3351 TCACAGAAAA GCATCTTACG GATGGCATGA CAGTAAGAGA ATTATGCAGT
3401 GCTGCCATAA CCATGAGTGA TAACACTGCG GCCAACTTAC TTCTGACAAC
3451 GATCGGAGGA CCGAAGGAGC TAACCGCTTT TTTGCACAAC ATGGGGGATC
3501 ATGTAACTCG CCTTGATCGT TGGGAACCGG AGCTGAATGA AGCCATACCA
3551 AACGACGAGC GTGACACCAC GATGCCTGTA GCAATGGCAA CAACGTTGCG
3601 CAAACTATTA ACTGGCGAAC TACTTACTCT AGCTTCCCGG CAACAATTAA
3651 TAGACTGGAT GGAGGCGGAT AAAGTTGCAG GACCACTTCT GCGCTCGGCC
3701 CTTCCGGCTG GCTGGTTTAT TGCTGATAAA TCTGGAGCCG GTGAGCGTGG
3751 GTCTCGCGGT ATCATTGCAG CACTGGGGCC AGATGGTAAG CCCTCCCGTA
3801 TCGTAGTTAT CTACACGACG GGGAGTCAGG CAACTATGGA TGAACGAAAT
3851 AGACAGATCG CTGAGATAGG TGCCTCACTG ATTAAGCATT GGTAACTGTC
3901 AGACCAAGTT TACTCATATA TACTTTAGAT TGATTTAAAA CTTCATTTTT
3951 AATTTAAAAG GATCTAGGTG AAGATCCTTT TTGATAATCT CATGACCAAA
4001 ATCCCTTAAC GTGAGTTTTC GTTCCACTGA GCGTCAGACC CCGTAGAAAA
4051 GATCAAAGGA TCTTCTTGAG ATCCTTTTTT TCTGCGCGTA ATCTGCTGCT
4101 TGCAAACAAA AAAACCACCG CTACCAGCGG TGGTTTGTTT GCCGGATCAA
4151 GAGCTACCAA CTCTTTTTCC GAAGGTAACT GGCTTCAGCA GAGCGCAGAT
4201 ACCAAATACT GTCCTTCTAG TGTAGCCGTA GTTAGGCCAC CACTTCAAGA
4251 ACTCTGTAGC ACCGCCTACA TACCTCGCTC TGCTAATCCT GTTACCAGTG
4301 GCTGCTGCCA GTGGCGATAA GTCGTGTCTT ACCGGGTTGG ACTCAAGACG
4351 ATAGTTACCG GATAAGGCGC AGCGGTCGGG CTGAACGGGG GGTTCGTGCA
4401 CACAGCCCAG CTTGGAGCGA ACGACCTACA CCGAACTGAG ATACCTACAG
4451 CGTGAGCATT GAGAAAGCGC CACGCTTCCC GAAGGGAGAA AGGCGGACAG
4501 GTATCCGGTA AGCGGCAGGG TCGGAACAGG AGAGCGCACG AGGGAGCTTC
4551 CAGGGGGAAA CGCCTGGTAT CTTTATAGTC CTGTCGGGTT TCGCCACCTC
4601 TGACTTGAGC GTCGATTTTT GTGATGCTCG TCAGGGGGC GGAGCCTATG
4651 GAAAAACGCC AGCAACGCGG CCTTTTTACG GTTCCTGGCC TTTTGCTGGC
4701 CTTTTGCTCA CATGTTCTTT CCTGCGTTAT CCCCTGATTC TGTGGATAAC
4751 CGTATTACCG CCTTTGAGTG AGCTGATACC GCTCGCCGCA GCCGAACGAC
```

FIG.39C

```
4801 CGAGCGCAGC GAGTCAGTGA GCGAGGAAGC GGAAGAGCGC CAATACGCAA
4851 ACCGCCTCTC CCCGCGCGTT GGCCGATTCA TTAATGCAGC TGGCACGACA
4901 GGTTTCCCGA CTGGAAAGCG GGCAGTGAGC GCAACGCAAT TAATGTGAGT
4951 TACCTCACTC ATTAGGCACC CCAGGCTTTA CACTTTATGC TTCCGGCTCG
5001 TATGTTGTGT GGAATTGTGA GCGGATAACA ATTTCACACA GGAAACAGCT
5051 ATGACCATGA TTACGCC
```

FIG. 41A

```
   1 TCGACGGTGC CCCCAGCAGA AGTATCGACT GCATGCTAAT TATTAACAAA
  51 CCAAAAGGCG TTGCCACTTA CACCCTTACC TTTAGGTTTT TAAACTTTAA
 101 CAGACTAAGC GGAGGTACCC TGTTTAAAAC TGATGTCTTA ACCTTTACCT
 151 ATGTAGGCGA AAATCAATAA AACCAGAAAA AAATAAGTTT AAAAGCTTTA
 201 TTTTTCATAC ACGCGAGCGG TAAGGCTGCC GCCTTCAGGA AAAGTTACTC
 251 TGTAAACAGT TCTTTCACAA CAGCACAAAA CATAGGTATT AGTTAACAGT
 301 TCATTTGGGC TATAATAATA TACATTTTCT TGGGTGGCAA AGCAAGGGTC
 351 GGTAATCTCA ACAAAACCAT CAACTGGAAT GCAAGAATAG TCCAGCACGG
 401 TGGGTTCAAT CTAAAAATGA AGAAACGCTG TTGAGGTTCA CTAAGCACAG
 451 GTTTTGAATC TGTCGGCAGC GTCCATGCAT CATAGCTTGT CTCAAAGCAG
 501 ATTGTCTTCT TTCCTCTGCC TTGGAAGTGG TTTGGTGAAG CACTACAGGT
 551 GTCTTTTCAA CCTCTTTCAG CACCCGCTCT ATTACAGATC TCACCCACAC
 601 AGCACAGTTT TTAAGAGAAC AATAGTTTTG AAGGCTACAA GATTTACACT
 651 TAAGCACCAG CCAGTAATTA TAAGTGCTTT TAAGAACTAC CCCTAGCTCA
 701 GGGTTAATGC ACCTTTTAAT GGCCTCCATG CAGGCTTTAT GGACAGTTCT
 751 AAAAAAAGAC AGTCTAAAAT AAATGTAGTG AGTGTTTCTA AATATAATAC
 801 TCCCCACATA GTTAATTTCA TCAGGCCTGC TAGAATTTAC AAACTCTCGG
 851 TACCACATAT ACTTTTTATT CATAGCCCCA CCCTTAATAA AGTCCTCAAT
 901 CACTTTCTGA ACCACATGCT TGCTAGCCAT GCATTGTAAA GACAAGCTGT
 951 TAGAGCAGTG ACAGTGTACT CGCCACGTTT GAGCCTCTGC CAGGCAGCAG
1001 TGCTTAGTTA CTATCAACTC AATACCCGCA TTGCATGTAA ACCCCCAAA
1051 GAGCAGTTTT TCATGCCTGT GTAGCACATC ATCCCACAAA ATAGGAATTT
1101 CATAGCATAA AGCAAAGCAA TTACAATATT TAGGAACTCT CACCACAGCA
1151 GTCACGTGAC ATGTTGTCTC AGCAGTGCAG TTGCCTTCCA TCCTACAATT
1201 ATGAACAAAA ACTAAACACT TCTAACAAAG ATACAGTGAC AATCTCCCTT
1251 CCTCTAAAAG CATTGTTTAC ATTAGGGTGA TTATTAACAA CGTCAGAAAT
1301 TTCTTTAATT AAAGTGCCTT TAAAATGTGC AAGAGCATCA TCATACTCAA
1351 AACCAAGCTG AGAGTAAAAG ACCACCTTAA AAGTAATCCC AGGCTTGTTT
1401 TTATCAACAG CCTTAAACAT GCTTTCACAA AATATAGAAG CAGTAACATC
1451 ATCAATGGTG TCGAAGAGAA ACTCCATAGG AGACTCCAGC ATTGATCCAA
1501 GCTCTCTAAC AAAATCTTCC TCAAAATGAA TAATGCCCTT TACACAAACG
1551 CGGGGCAGAC GATGGTGGGC CATCGCGTCA ACCTGAAACA CATTTTACAG
1601 TAAACAAAGC TAGCTCCGCA GTGGTAAAGT CATGCCCATG GGTGAGGCCA
1651 AAATCCTTAA AAAAGCTATC TAAGTAGTTG GTCATCCCCT CAGTTAAAAA
1701 GTTTTGCAGC TGGGTGGTGC ATACCACATA GTGCCAGCTT ATAGCTACAA
1751 AGACCTGCAT CCCCTCCTTA GCAGACAGCT CTTGCACACA CGCAGTAACT
1801 ATCCACCGCT TAAGAAAGC TTTAAGCCCA GCGCACATAA CAGCTCCAAT
1851 GTTTTATCC AAGGAGAGCA AAATTTCAGC AAGCGCAGGC TCAACAGTAA
1901 TAGTGAAGCA GAGGCATTTC AGACGAGGCT CACTAGCTGC AGTCGCCATT
1951 TATGAGGTCT GCAATAAAAA ACAACTCATC AGCAGCTGAA AAAGTGCACT
2001 TTGACCTCAT TAAGCCACTG CATATGCAAG TCCTCATCTA TGCCGCAGCC
2051 CAGACCCTCA ATCCAGCCCC GAATGTACAC TTAATAAGA GATTCAACCT
2101 CTTCTTTTAG CAAAGTACAC ATGCTGTTTG GACTAGTATA CACAATAGAA
```

FIG. 4IB

```
2151 GTCACAATGA GGGGCCCGCT GTGGCTGGAA AGCCTGCGCA CAGCCCGAAG
2201 GTTAAAAATG GACTGTAACA GCATTGAAAC CCCGCGACAC AGGTCAGTCT
2251 CGCGGTCTTG ATCTCTTATT ATAGCGACCA AATGGTCCTT CAGAGTGATG
2301 TTGCACTCAT AGAAGTAGGC AGCTCCGGCA GCCATTCTGC AAAATAACAA
2351 AACACCACTA AGCATAGCAC CATCACCAAG CATGAAAACA GGTAAAAACA
2401 AAAGCAACAC TTACTTATTC AGCAGTCACA AGAATGTTGG GCTCCCAAGT
2451 GACAGACAAG CCTAATGCAA GGTGGGCACA GTCTCCGGAA TAAGTTGACA
2501 AAAGTCACGC CGCAAAGCTT CCTGAAGAGA AACGGCGGTA GCCTGGATAT
2551 CTGCAACGGA CCCAAAACCT TCAGTGTCAC TTCCAATAAA CAGATAAAAC
2601 TCTAAATAGT CCCCACTTAA AACCGAAACA GCCGCGGCAA AGGTAGGACA
2651 CGGACGCACT TCCTGAGCCC TAATAAGGCT AAACACCACA CGGCGCAGTT
2701 CAGAAGGCAA AAAGTCTGTA AGCTCTAGCT GAGCACACAC ACTCTCCACT
2751 AGACACTTGT GAAGCCTCAG ACAAAAACAT GCTCCCATAG ACACTCCTAA
2801 AGCTGCCATT GTACTCACGG ACGGCTGGCT GTCAGAGGAG AGCTATGAGG
2851 ATGAAATGCC AAGCACAGCG TTTATATAGT CCTCAAAGTA GGGCGTGTGG
2901 AAAACGAAAA GGAATATAAC GGGGCGTTTG AGGAAGTGGT GCCAAGTACA
2951 GTCATAAAAT GTGGGCGCGT GGTAAATGTT AAGTGCAGTT TCCCTTTGGC
3001 GGTTGGCCCG GAAAGTTCAC AAAAAGTACA GCACGTCCTT GTCACCGTGT
3051 CAACCACAAA ACCACAAATA GGCACAACGC CAAAAACCC GGGTCGACAC
3101 GCGTGAATTC ACCGGTTCGA GCTTAATGTC GTAACAACTC CGCCCCGTTG
3151 ACGCAAATGG GCGGTAGGCG TGTACGGTGG GAGGTCTATA TAAGCAGAGC
3201 TCGTTTAGTG AACCGTCTGC AGACTCTCTT CCGCATCGCT GTCTGCGAGG
3251 GCCAGCTGTT GGGCTCGCGG TTGAGGACAA ACTCTTCGCG GTCTTTCCAG
3301 TACTCTTGGA TCGGAAACCC GTCGGCCTCC GAACGGTACT CCGCCACCGA
3351 GGGACCTGAG CGAGTCCGCA TCGACCGGAT CGGAAAACCT CTCGAGAAAG
3401 GCGTCTAACC AGTCACAGTC GCAAGTCTAG AATGCTCCCC TACCAAGACA
3451 AGGTGGGTGC CTTCTACAAG GATAATGCAA GAGCCAATTC AACCAAGCTG
3501 TCCTTAGTGA CAGAAGGACA TGGGGGCAGG AGACCACCTT ATTTGTTGTT
3551 TGTCCTTCTC ATCTTATTGG TTGGTATCCT GGCCTTGCTT GCTATCACTG
3601 GAGTTCGATT TCACCAAGTA TCAACTAGTA ATATGGAATT TAGCAGATTG
3651 CTGAAAGAGG ATATGGAGAA ATCAGAGGCC GTACATCACC AAGTCATAGA
3701 TGTCTTGACA CCGCTCTTCA AGATTATTGG AGATGAGATT GGGTTACGGT
3751 TGCCACAAAA GCTAAACGAG ATCAAACAAT TTATCCTTCA AAAGACAAAT
3801 TTCTTCAATC CGAACAGAGA ATTCGACTTC CGCGATCTCC ACTGGTGCAT
3851 TAACCCGCCT AGTACGGTCA AGGTGAATTT TACTAATTAC TGTGAGTCAA
3901 TTGGGATCAG AAAAGCTATT GCATCGGCAG CAAATCCTAT CCTTTTATCA
3951 GCCCTATCTG GGGGCAGAGG TGACATATTC CCACCACACA GATGCAGTGG
4001 AGCTACTACT TCAGTAGGCA AAGTTTTCCC CCTATCAGTC TCATTATCCA
4051 TGTCTTTGAT CTCAAGAACC TCAGAGGTAA TCAATATGCT GACCGCTATC
4101 TCAGACGGCG TGTATGGCAA AACTTACTTG CTAGTGCCTG ATGATATAGA
4151 AAGAGAGTTC GACACTCGAG AGATTCGAGT CTTTGAAATA GGGTTCATCA
4201 AAAGGTGGCT GAATGACATG CCATTACTCC AAACAACCAA CTATATGGTA
4251 CTCCCGAAGA ATTCCAAAGC CAAGGTATGT ACTATAGCAG TGGGTGAGTT
4301 GACACTGGCT TCCTTGTGTG TAGAAGAGAG CACTGTATTA TTATATCATG
4351 ACAGCAGTGG TTCACAAGAT GGTATTCTAG TAGTGACACT GGGGATATTT
4401 TGGGCAACAC CTATGGATCA CATTGAGGAA GTGATACCTG TCGCTCACCC
4451 ATCAATGAAG AAAATACATA TAACAAACCA CCGTGGTTTT ATAAAAGATT
4501 CAATTGCAAC CTGGATGGTG CCTGCCCTGG CCTCTGAGAA ACAAGAAGAA
4551 CAAAAAGGTT GTCTGGAGTC AGCTTGTCAA AGAAAAACCT ACCCCATGTG
4601 CAACCAAGCG TCATGGGAAC CCTTCGGAGG AAGACAGTTG CCATCTTATG
4651 GGCGGTTGAC ATTACCTCTA GATGCAAGTG TTGACCTTCA ACTTAACATA
4701 TCGTTCACAT ACGGTCCGGT TATACTGAAT GGAGATGGTA TGGATTATTA
4751 TGAAAGCCCA CTTTTGAACT CCGGATGGCT TACCATTCCC CCCAAAGACG
```

FIG. 4IC

```
4801 GAACAATCTC TGGATTGATA AACAAAGCAG GTAGAGGAGA CCAGTTCACT
4851 GTACTCCCCC ATGTGTTAAC ATTTGCGCCC AGGGAATCAA GTGGAAATTG
4901 TTATTTACCT ATTCAAACAT CTCAAATTAG AGATAGAGAT GTCCTCATTG
4951 AGTCCAATAT AGTGGTGTTG CCTACACAGA GTATTAGATA TGTCATAGCA
5001 ACGTATGACA TATCACGAAG TGATCATGCT ATTGTTTATT ATGTTTATGA
5051 CCCAATCCGG ACGATTTCTT ATACGCACCC ATTTAGACTA ACTACCAAGG
5101 GTAGACCTGA TTTCCTAAGG ATTGAATGTT TTGTGTGGGA TGACAATTTG
5151 TGGTGTCACC AATTTTACAG ATTCGAGGCT GACATCGCCA ACTCTACAAC
5201 CAGTGTTGAG AATTTAGTCC GTATAAGATT CTCATGTAAC CGTTAACCGC
5251 GGCGTGATTA ATCAGCCATA CCACATTTGT AGAGGTTTTA CTTGCTTTAA
5301 AAAACCTCCC ACACCTCCCC CTGAACCTGA AACATAAAAT GAATGCAATT
5351 GTTGTTGTTA ACTTGTTTAT TGCAGCTTAT AATGGTTACA AATAAAGCAA
5401 TAGCATCACA AATTTCACAA ATAAAGCATT TTTTCACTG CATTCTAGTT
5451 GTGGTTTGTC CAAACTCATC AATGTATCTT ATCATGTCTG GATCCGAAAC
5501 GCCCAAAAAC CCGGGGCGCC GGCCAAAAGT CCGCGGAACT CGCCCTGTCG
5551 TAAAACCACG CCTTTGACGT CACTGGACAT TCCCGTGGGA ACACCCTGAC
5601 CAGGGCGTGA CCTGAACCTG ACCGTCCCAT GACCCCGCCC CTTGCAACAC
5651 CCAAATTTAA GCCACACCTC TTTGTCCTGT ATATTATTGA TGATGGGGGG
5701 ATCCACTAGT TCTAGAGCGG CCGCCACCGC GGTGGAGCTC CAGCTTTTGT
5751 TCCCTTTAGT GAGGGTTAAT TCCGAGCTTG GCGTAATCAT GGTCATAGCT
5801 GTTTCCTGTG TGAAATTGTT ATCCGCTCAC AATTCCACAC AACATACGAG
5851 CCGGAAGCAT AAAGTGTAAA GCCTGGGGTG CCTAATGAGT GAGCTAACTC
5901 ACATTAATTG CGTTGCGCTC ACTGCCCGCT TTCCAGTCGG GAAACCTGTC
5951 GTGCCAGCTG CATTAATGAA TCGGCCAACG CGCGGGGAGA GGCGGTTTGC
6001 GTATTGGGCG CTCTTCCGCT TCCTCGCTCA CTGACTCGCT GCGCTCGGTC
6051 GTTCGGCTGC GGCGAGCGGT ATCAGCTCAC TCAAAGGCGG TAATACGGTT
6101 ATCCACAGAA TCAGGGGATA ACGCAGGAAA GAACATGTGA GCAAAAGGCC
6151 AGCAAAAGGC CAGGAACCGT AAAAAGGCCG CGTTGCTGGC GTTTTTCCAT
6201 AGGCTCCGCC CCCCTGACGA GCATCACAAA AATCGACGCT CAAGTCAGAG
6251 GTGGCGAAAC CCGACAGGAC TATAAAGATA CCAGGCGTTT CCCCCTGGAA
6301 GCTCCCTCGT GCGCTCTCCT GTTCCGACCC TGCCGCTTAC CGGATACCTG
6351 TCCGCCTTTC TCCCTTCGGG AAGCGTGGCG CTTTCTCATA GCTCACGCTG
6401 TAGGTATCTC AGTTCGGTGT AGGTCGTTCG CTCCAAGCTG GGCTGTGTGC
6451 ACGAACCCCC CGTTCAGCCC GACCGCTGCG CCTTATCCGG TAACTATCGT
6501 CTTGAGTCCA ACCCGGTAAG ACACGACTTA TCGCCACTGG CAGCAGCCAC
6551 TGGTAACAGG ATTAGCAGAG CGAGGTATGT AGGCGGTGCT ACAGAGTTCT
6601 TGAAGTGGTG GCCTAACTAC GGCTACACTA GAAGGACAGT ATTTGGTATC
6651 TGCGCTCTGC TGAAGCCAGT TACCTTCGGA AAAAGAGTTG GTAGCTCTTG
6701 ATCCGGCAAA CAAACCACCG CTGGTAGCGG TGGTTTTTTT GTTTGCAAGC
6751 AGCAGATTAC GCGCAGAAAA AAAGGATCTC AAGAAGATCC TTTGATCTTT
6801 TCTACGGGGT CTGACGCTCA GTGGAACGAA AACTCACGTT AAGGGATTTT
6851 GGTCATGAGA TTATCAAAAA GGATCTTCAC CTAGATCCTT TTAAATTAAA
6901 AATGAAGTTT TAAATCAATC TAAAGTATAT ATGAGTAAAC TTGGTCTGAC
6951 AGTTACCAAT GCTTAATCAG TGAGGCACCT ATCTCAGCGA TCTGTCTATT
7001 TCGTTCATCC ATAGTTGCCT GACTCCCCGT CGTGTAGATA ACTACGATAC
7051 GGGAGGGCTT ACCATCTGGC CCCAGTGCTG CAATGATACC GCGAGACCCA
7101 CGCTCACCGG CTCCAGATTT ATCAGCAATA AACCAGCCAG CCGGAAGGGC
7151 CGAGCGCAGA AGTGGTCCTG CAACTTTATC CGCCTCCATC CAGTCTATTA
7201 ATTGTTGCCG GGAAGCTAGA GTAAGTAGTT CGCCAGTTAA TAGTTTGCGC
7251 AACGTTGTTG CCATTGCTAC AGGCATCGTG GTGTCACGCT CGTCGTTTGG
7301 TATGGCTTCA TTCAGCTCCG GTTCCCAACG ATCAAGGCGA GTTACATGAT
7351 CCCCCATGTT GTGCAAAAAA GCGGTTAGCT CCTTCGGTCC TCCGATCGTT
7401 GTCAGAAGTA AGTTGGCCGC AGTGTTATCA CTCATGGTTA TGGCAGCACT
```

FIG. 41D

```
7451 GCATAATTCT CTTACTGTCA TGCCATCCGT AAGATGCTTT TCTGTGACTG
7501 GTGAGTACTC AACCAAGTCA TTCTGAGAAT AGTGTATGCG GCGACCGAGT
7551 TGCTCTTGCC CGGCGTCAAT ACGGGATAAT ACCGCGCCAC ATAGCAGAAC
7601 TTTAAAAGTG CTCATCATTG GAAAACGTTC TTCGGGGCGA AAACTCTCAA
7651 GGATCTTACC GCTGTTGAGA TCCAGTTCGA TGTAACCCAC TCGTGCACCC
7701 AACTGATCTT CAGCATCTTT TACTTTCACC AGCGTTTCTG GGTGAGCAAA
7751 AACAGGAAGG CAAAATGCCG CAAAAAAGGG AATAAGGGCG ACACGGAAAT
7801 GTTGAATACT CATACTCTTC CTTTTTCAAT ATTATTGAAG CATTTATCAG
7851 GGTTATTGTC TCATGAGCGG ATACATATTT GAATGTATTT AGAAAAATAA
7901 ACAAATAGGG GTTCCGCGCA CATTTCCCCG AAAAGTGCCA CCTGGGAAAT
7951 TGTAAACGTT AATATTTTGT TAAAATTCGC GTTAAATTTT TGTTAAATCA
8001 GCTCATTTTT TAACCAATAG GCCGAAATCG GCAAAATCCC TTATAAATCA
8051 AAAGAATAGA CCGAGATAGG GTTGAGTGTT GTTCCAGTTT GGAACAAGAG
8101 TCCACTATTA AAGAACGTGG ACTCCAACGT CAAAGGGCGA AAAACCGTCT
8151 ATCAGGGCGA TGGCCCACTA CGTGAACCAT CACCCTAATC AAGTTTTTTG
8201 GGGTCGAGGT GCCGTAAAGC ACTAAATCGG AACCCTAAAG GGAGCCCCCG
8251 ATTTAGAGCT TGACGGGGAA AGCCGGCGAA CGTGGCGAGA AAGGAAGGGA
8301 AGAAAGCGAA AGGAGCGGGC GCTAGGGCGC TGGCAAGTGT AGCGGTCACG
8351 CTGCGCGTAA CCACCACACC CGCCGCGCTT AATGCCGCC TACAGGGCGC
8401 GTCGCGCCAT TCGCCATTCA GGCTGCGCAA CTGTTGGGAA GGGCGATCGG
8451 TGCGGGCCTC TTCGCTATTA CGCCAGCTGG CGAAAGGGGG ATGTGCTGCA
8501 AGGCGATTAA GTTGGGTAAC GCCAGGGTTT TCCCAGTCAC GACGTTGTAA
8551 AACGACGGCC AGTGAATTGT AATACGACTC ACTATAGGGC GAATTGGGTA
8601 CCGGGCCCCC CCTCGAGG
```

FIG.43A

```
   1 TCGCGATATC CGTTAAGTTT GTATCGTAAA TGCACAAGGG AATCCCCAAA
  51 AGCTCCAAAA CCCAAACACA TACCCAACAA GACCGCCCCC CACAACCCAG
 101 CACCGAACTC GAAGAGACCA GGACCTCCCG AGCACGACAC AGCACAACAT
 151 CAGCTCAGCG ATCCACGCAC TACGATCCTC GAACATCGGA CAGACCCGTC
 201 TCCTACACCA TGAACAGGAC CAGGTCCCGC AAGCAAACCA GCCACAGATT
 251 GAAGAACATC CCAGTTCACG GAAACCACGA GGCCACCATC CAGCACATAC
 301 CAGAGAGTGT CTCAAAAGGA GCGAGATCCC AGATCGAAAG GCGGCAACCC
 351 AATGCAATCA ACTCAGGCTC TCATTGCACC TGGTTAGTCC TGTGGTGCCT
 401 CGGAATGGCC AGTCTCTTTC TTTGTTCCAA GGCTCAGATA CATTGGAATA
 451 ATTTGTCAAC TATTGGGATT ATCGGGACTG ATAGTGTCCA TTACAAGATC
 501 ATGACTAGGC CCAGTCACCA GTACTTGGTC ATAAAACTGA TGCCTAATGT
 551 TTCACTTATA GAGAATTGTA CCAAAGCAGA ATTAGGTGAG TATGAGAAAT
 601 TATTGAATTC AGTCCTCGAA CCAATCAACC AAGCTTTGAC TCTAATGACC
 651 AAGAATGTGA AGCCCCTGCA GTCATTAGGG TCAGGTAGGA GACAAAGGCG
 701 TTTTGCAGGA GTGGTACTTG CAGGTGTAGC TTTAGGAGTG GCTACAGCTG
 751 CACAAATCAC TGCAGGAATA GCTTTACATC AATCCAACCT CAATGCTCAA
 801 GCAATCCAAT CTCTTAGAAC CAGCCTTGAA CAGTCTAACA AGCTATAGA
 851 AGAAATTAGG GAGGCTACCC AAGAAACCGT CATTGCCGTT CAGGGAGTCC
 901 AGGACTACGT CAACAACGAA CTCGTCCCTG CCATGCAACA TATGTCATGT
 951 GAATTAGTTG GCAGAGATT AGGGTTAAGA CTGCTTCGGT ATTATACTGA
1001 GTTGTTGTCA ATATTTGGCC CGAGTTTACG TGACCCTATT TCAGCCGAGA
1051 TATCAATTCA GGCACTGATT TATGCTCTTG GAGGAGAAAT TCATAAGATA
1101 CTTGGGAAGT TGGGATATTC TGGAAGTGAT ATGATTGCAA TCTTGGAGAG
1151 TCGGGGGATA AAAACAAAAA TAACTCATGT TGATCTTCCC GGGAAATTCA
1201 TCATCCTAAG TATCTCATAC CCAACTTTAT CAGAAGTCAA GGGGGTTATA
1251 GTCCACAGAC TGGAAGCGGT TCTTACAAC ATAGGATCAC AAGAGTGGTA
1301 CACCACTGTC CCGAGGTATA TTGCAACTAA TGGTTACTTA ATATCTAATT
1351 TTGATGAGTC ATCTTGTGTA TTCGTCTCAG AGTCAGCCAT TTGTAGCCAG
1401 AACTCCCTGT ATCCCATGAG CCCACTCTTA CAACAATGTA TTAGGGGCGA
1451 CACTTCATCT TGTGCTCGGA CCTTGGTATC TGGGACTATG GGCAACAAAT
1501 TTATTCTGTC AAAAGGTAAT ATCGTCGCAA ATTGTGCTTC TATACTATGT
1551 AAGTGTTATA GCACAAGCAC AATTATTAAT CAGAGTCCTG ATAAGTTGCT
1601 GACATTCATT GCCTCCGATA CCTGCCCACT GGTTGAAATA GATGGTGCTA
1651 CTATCCAAGT TGGAGGCAGG CAATACCCTG ATATGGTATA CGAAGGCAAA
1701 GTTGCCTTAG GCCCTGCTAT ATCACTTGAT AGGTTAGATG TAGGTACAAA
1751 CTTAGGGAAC GCCCTTAAGA AACTGGATGA TGCTAAGGTA CTGATAGACT
1801 CCTCTAACCA GATCCTTGAG ACGGTTAGGC GCTCTTCCTT CAATTTTGGC
1851 AGTCTCCTCA GCGTTCCTAT ATTAAGTTGT ACAGCCCTGG CTTTGTTGTT
1901 GCTGATTTAC TGTTGTAAAA GACGCTACCA ACAGACACTC AAGCAGCATA
1951 CTAAGGTCGA TCCGGCATTT AAACCTGATC TAACTGGAAC TTCGAAATCC
2001 TATGTGAGAT CACACTGACT CGAGATCCAC TAGTTCTAGA GCGGCCGCCA
2051 CCGCGGTGGA GCTCCAGCTT TTGTTCCCTT TAGTGAGGGT TAATTCCGAG
2101 CTTGGCGTAA TCATGGTCAT AGCTGTTTCC TGTGTGAAAT TGTTATCCGC
```

FIG. 43B

```
2151 TCACAATTCC ACACAACATA CGAGCCGGAA GCATAAAGTG TAAAGCCTGG
2201 GGTGCCTAAT GAGTGAGCTA ACTCACATTA ATTGCGTTGC GCTCACTGCC
2251 CGCTTTCCAG TCGGGAAACC TGTCGTGCCA GCTGCATTAA TGAATCGGCC
2301 AACGCGCGGG GAGAGGCGGT TTGCGTATTG GGCGCTCTTC CGCTTCCTCG
2351 CTCACTGACT CGCTGCGCTC GGTCGTTCGG CTGCGGCGAG CGGTATCAGC
2401 TCACTCAAAG GCGGTAATAC GGTTATCCAC AGAATCAGGG GATAACGCAG
2451 GAAAGAACAT GTGAGCAAAA GGCCAGCAAA AGGCCAGGAA CCGTAAAAAG
2501 GCCGCGTTGC TGGCGTTTTT CCATAGGCTC CGCCCCCCTG ACGAGCATCA
2551 CAAAAATCGA CGCTCAAGTC AGAGGTGGCG AAACCCGACA GGACTATAAA
2601 GATACCAGGC GTTTCCCCCT GGAAGCTCCC TCGTGCGCTC TCCTGTTCCG
2651 ACCCTGCCGC TTACCGGATA CCTGTCCGCC TTTCTCCCTT CGGGAAGCGT
2701 GGCGCTTTCT CATAGCTCAC GCTGTAGGTA TCTCAGTTCG GTGTAGGTCG
2751 TTCGCTCCAA GCTGGGCTGT GTGCACGAAC CCCCCGTTCA GCCCGACCGC
2801 TGCGCCTTAT CCGGTAACTA TCGTCTTGAG TCCAACCCGG TAAGACACGA
2851 CTTATCGCCA CTGGCAGCAG CCACTGGTAA CAGGATTAGC AGAGCGAGGT
2901 ATGTAGGCGG TGCTACAGAG TTCTTGAAGT GGTGGCCTAA CTACGGCTAC
2951 ACTAGAAGGA CAGTATTTGG TATCTGCGCT CTGCTGAAGC CAGTTACCTT
3001 CGGAAAAAGA GTTGGTAGCT CTTGATCCGG CAAACAAACC ACCGCTGGTA
3051 GCGGTGGTTT TTTTGTTTGC AAGCAGCAGA TTACGCGCAG AAAAAAAGGA
3101 TCTCAAGAAG ATCCTTTGAT CTTTTCTACG GGGTCTGACG CTCAGTGGAA
3151 CGAAAACTCA CGTTAAGGGA TTTTGGTCAT GAGATTATCA AAAAGGATCT
3201 TCACCTAGAT CCTTTTAAAT TAAAAATGAA GTTTTAAATC AATCTAAAGT
3251 ATATATGAGT AAACTTGGTC TGACAGTTAC CAATGCTTAA TCAGTGAGGC
3301 ACCTATCTCA GCGATCTGTC TATTTCGTTC ATCCATAGTT GCCTGACTCC
3351 CCGTCGTGTA GATAACTACG ATACGGGAGG GCTTACCATC TGGCCCCAGT
3401 GCTGCAATGA TACCGCGAGA CCCACGCTCA CCGGCTCCAG ATTTATCAGC
3451 AATAAACCAG CCAGCCGGAA GGGCCGAGCG CAGAAGTGGT CCTGCAACTT
3501 TATCCGCCTC CATCCAGTCT ATTAATTGTT GCCGGGAAGC TAGAGTAAGT
3551 AGTTCGCCAG TTAATAGTTT GCGCAACGTT GTTGCCATTG CTACAGGCAT
3601 CGTGGTGTCA CGCTCGTCGT TTGGTATGGC TTCATTCAGC TCCGGTTCCC
3651 AACGATCAAG GCGAGTTACA TGATCCCCCA TGTTGTGCAA AAAAGCGGTT
3701 AGCTCCTTCG GTCCTCCGAT CGTTGTCAGA AGTAAGTTGG CCGCAGTGTT
3751 ATCACTCATG GTTATGGCAG CACTGCATAA TTCTCTTACT GTCATGCCAT
3801 CCGTAAGATG CTTTTCTGTG ACTGGTGAGT ACTCAACCAA GTCATTCTGA
3851 GAATAGTGTA TGCGGCGACC GAGTTGCTCT TGCCCGGCGT CAATACGGGA
3901 TAATACCGCG CCACATAGCA GAACTTTAAA AGTGCTCATC ATTGGAAAAC
3951 GTTCTTCGGG GCGAAAACTC TCAAGGATCT TACCGCTGTT GAGATCCAGT
4001 TCGATGTAAC CCACTCGTGC ACCCAACTGA TCTTCAGCAT CTTTTACTTT
4051 CACCAGCGTT TCTGGGTGAG CAAAAACAGG AAGGCAAAAT GCCGCAAAAA
4101 AGGGAATAAG GGCGACACGG AAATGTTGAA TACTCATACT CTTCCTTTTT
4151 CAATATTATT GAAGCATTTA TCAGGGTTAT TGTCTCATGA GCGGATACAT
4201 ATTTGAATGT ATTTAGAAAA ATAAACAAAT AGGGGTTCCG CGCACATTTC
4251 CCCGAAAAGT GCCACCTGGG AAATTGTAAA CGTTAATATT TTGTTAAAAT
4301 TCGCGTTAAA TTTTTGTTAA ATCAGCTCAT TTTTTAACCA ATAGGCCGAA
4351 ATCGGCAAAA TCCCTTATAA ATCAAAAGAA TAGACCGAGA TAGGGTTGAG
4401 TGTTGTTCCA GTTTGGAACA AGAGTCCACT ATTAAAGAAC GTGGACTCCA
4451 ACGTCAAAGG GCGAAAAACC GTCTATCAGG GCGATGGCCC ACTACGTGAA
4501 CCATCACCCT AATCAAGTTT TTTGGGGTCG AGGTGCCGTA AAGCACTAAA
4551 TCGGAACCCT AAAGGGAGCC CCCGATTTAG AGCTTGACGG GGAAAGCCGG
4601 CGAACGTGGC GAGAAAGGAA GGGAAGAAAG CGAAAGGAGC GGGCGCTAGG
4651 GCGCTGGCAA GTGTAGCGGT CACGCTGCGC GTAACCACCA CACCCGCCGC
4701 GCTTAATGCG CCGCTACAGG GCGCGTCGCG CCATTCGCCA TTCAGGCTGC
4751 GCAACTGTTG GGAAGGGCGA TCGGTGCGGG CCTCTTCGCT ATTACGCCAG
```

FIG. 43C

```
4801 CTGGCGAAAG GGGGATGTGC TGCAAGGCGA TTAAGTTGGG TAACGCCAGG
4851 GTTTTCCCAG TCACGACGTT GTAAAACGAC GGCCAGTGAA TTGTAATACG
4901 ACTCACTATA GGGCGAATTG GGTACCGGGC CCCCCCTCGA GGTCGACGGT
4951 ATCGATAAGC TTGAT
```

FIG. 44 pBSSK+

Xhol (4936)
HindIII (4957)
EcoRV (5)
PvuII (4798)
CelII (153)
HindIII (631)
PvuII (745)
NdeI (939)
EcoRV (1049)
BfrI (1764)
SpeI (2029)
XbaI (2035)
NotI (2041)
KspI (2051)
SacI (2059)
PvuII (2279)

pLF108
(4965 bp)

CDV F1 gene
bp#30 to 2018

FIG. 45A

```
   1 AAGCTTAATG TCGTAACAAC TCCGCCCCGT TGACGCAAAT GGGCGGTAGG
  51 CGTGTACGGT GGGAGGTCTA TATAAGCAGA GCTCGTTTAG TGAACCGTCT
 101 GCAGACTCTC TTCCGCATCG CTGTCTGCGA GGGCCAGCTG TTGGGCTCGC
 151 GGTTGAGGAC AAACTCTTCG CGGTCTTTCC AGTACTCTTG GATCGGAAAC
 201 CCGTCGGCCT CCGAACGGTA CTCCGCCACC GAGGGACCTG AGCGAGTCCG
 251 CATCGACCGG ATCGGAAAAC CTCTCGAGAA AGGCGTCTAA CCAGTCACAG
 301 TCGCAAGTCT AGAATGCACA AGGGAATCCC CAAAAGCTCC AAAACCCAAA
 351 CACATACCCA ACAAGACCGC CCCCACAAC CCAGCACCGA ACTCGAAGAG
 401 ACCAGGACCT CCCGAGCACG ACACAGCACA ACATCAGCTC AGCGATCCAC
 451 GCACTACGAT CCTCGAACAT CGGACAGACC CGTCTCCTAC ACCATGAACA
 501 GGACCAGGTC CCGCAAGCAA ACCAGCCACA GATTGAAGAA CATCCCAGTT
 551 CACGGAAACC ACGAGGCCAC CATCCAGCAC ATACCAGAGA GTGTCTCAAA
 601 AGGAGCGAGA TCCCAGATCG AAAGGCGGCA ACCCAATGCA ATCAACTCAG
 651 GCTCTCATTG CACCTGGTTA GTCCTGTGGT GCCTCGGAAT GGCCAGTCTC
 701 TTTCTTTGTT CCAAGGCTCA GATACATTGG AATAATTTGT CAACTATTGG
 751 GATTATCGGG ACTGATAGTG TCCATTACAA GATCATGACT AGGCCCAGTC
 801 ACCAGTACTT GGTCATAAAA CTGATGCCTA ATGTTTCACT TATAGAGAAT
 851 TGTACCAAAG CAGAATTAGG TGAGTATGAG AAATTATTGA ATTCAGTCCT
 901 CGAACCAATC AACCAAGCTT TGACTCTAAT GACCAAGAAT GTGAAGCCCC
 951 TGCAGTCATT AGGGTCAGGT AGGAGACAAA GGCGTTTTGC AGGAGTGGTA
1001 CTTGCAGGTG TAGCTTTAGG AGTGGCTACA GCTGCACAAA TCACTGCAGG
1051 AATAGCTTTA CATCAATCCA ACCTCAATGC TCAAGCAATC CAATCTCTTA
1101 GAACCAGCCT TGAACAGTCT AACAAAGCTA TAGAAGAAAT TAGGGAGGCT
1151 ACCCAAGAAA CCGTCATTGC CGTTCAGGGA GTCCAGGACT ACGTCAACAA
1201 CGAACTCGTC CCTGCCATGC AACATATGTC ATGTGAATTA GTTGGGCAGA
1251 GATTAGGGTT AAGACTGCTT CGGTATTATA CTGAGTTGTT GTCAATATTT
1301 GGCCCGAGTT TACGTGACCC TATTTCAGCC GAGATATCAA TTCAGGCACT
1351 GATTTATGCT CTTGGAGGAG AAATTCATAA GATACTTGGG AAGTTGGGAT
1401 ATTCTGGAAG TGATATGATT GCAATCTTGG AGAGTCGGGG GATAAAAACA
1451 AAAATAACTC ATGTTGATCT TCCCGGGAAA TTCATCATCC TAAGTATCTC
1501 ATACCCAACT TTATCAGAAG TCAAGGGGGT TATAGTCCAC AGACTGGAAG
1551 CGGTTTCTTA CAACATAGGA TCACAAGAGT GGTACACCAC TGTCCCGAGG
1601 TATATTGCAA CTAATGGTTA CTTAATATCT AATTTTGATG AGTCATCTTG
1651 TGTATTCGTC TCAGAGTCAG CCATTTGTAG CCAGAACTCC CTGTATCCCA
1701 TGAGCCCACT CTTACAACAA TGTATTAGGG GCGACACTTC ATCTTGTGCT
1751 CGGACCTTGG TATCTGGGAC TATGGGCAAC AAATTTATTC TGTCAAAAGG
1801 TAATATCGTC GCAAATTGTG CTTCTATACT ATGTAAGTGT TATAGCACAA
1851 GCACAATTAT TAATCAGAGT CCTGATAAGT TGCTGACATT CATTGCCTCC
1901 GATACCTGCC CACTGGTTGA AATAGATGGT GCTACTATCC AAGTTGGAGG
1951 CAGGCAATAC CCTGATATGG TATACGAAGG CAAAGTTGCC TTAGGCCCTG
2001 CTATATCACT TGATAGGTTA GATGTAGGTA CAAACTTAGG GAACGCCCTT
2051 AAGAAACTGG ATGATGCTAA GGTACTGATA GACTCCTCTA ACCAGATCCT
2101 TGAGACGGTT AGGCGCTCTT CCTTCAATTT TGGCAGTCTC CTCAGCGTTC
```

FIG. 45B

```
2151 CTATATTAAG TTGTACAGCC CTGGCTTTGT TGTTGCTGAT TTACTGTTGT
2201 AAAAGACGCT ACCAACAGAC ACTCAAGCAG CATACTAAGG TCGATCCGGC
2251 ATTTAAACCT GATCTAACTG GAACTTCGAA ATCCTATGTG AGATCACACT
2301 GACCGCGGCG TGATTAATCA GCCATACCAC ATTTGTAGAG GTTTTACTTG
2351 CTTTAAAAAA CCTCCCACAC CTCCCCCTGA ACCTGAAACA TAAAATGAAT
2401 GCAATTGTTG TTGTTAACTT GTTTATTGCA GCTTATAATG GTTACAAATA
2451 AAGCAATAGC ATCACAAATT TCACAAATAA AGCATTTTTT TCACTGCATT
2501 CTAGTTGTGG TTTGTCCAAA CTCATCAATG TATCTTATCA TGTCTGGATC
2551 CCCCGGAATT CACTGGCCGT CGTTTTACAA CGTCGTGACT GGGAAAACCC
2601 TGGCGTTACC CAACTTAATC GCCTTGCAGC ACATCCCCCC TTCGCCAGCT
2651 GGCGTAATAG CGAAGAGGCC CGCACCGATC GCCCTTCCCA ACAGTTGCGC
2701 AGCCTGAATG GCGAATGGCG CCTGATGCGG TATTTTCTCC TTACGCATCT
2751 GTGCGGTATT TCACACCGCA TATGGTGCAC TCTCAGTACA ATCTGCTCTG
2801 ATGCCGCATA GTTAAGCCAG TACACTCCGC TATCGCTACG TGACTGGGTC
2851 ATGGCTGCGC CCCGACACCC GCCAACACCC GCTGACGCGC CCTGACGGGC
2901 TTGTCTGCTC CCGGCATCCG CTTACAGACA AGCTGTGACC GTCTCCGGA
2951 GCTGCATGTG TCAGAGGTTT TCACCGTCAT CACCGAAACG CGCGAGGCAG
3001 TTCTTGAAGA CGAAAGGGCC TCGTGATACG CCTATTTTTA TAGGTTAATG
3051 TCATGATAAT AATGGTTTCT TAGACGTCAG GTGGCACTTT TCGGGGAAAT
3101 GTGCGCGGAA CCCCTATTTG TTTATTTTTC TAAATACATT CAAATATGTA
3151 TCCGCTCATG AGACAATAAC CCTGATAAAT GCTTCAATAA TATTGAAAAA
3201 GGAAGAGTAT GAGTATTCAA CATTTCCGTG TCGCCCTTAT TCCCTTTTTT
3251 GCGGCATTTT GCCTTCCTGT TTTTGCTCAC CCAGAAACGC TGGTGAAAGT
3301 AAAAGATGCT GAAGATCAGT TGGGTGCACG AGTGGGTTAC ATCGAACTGG
3351 ATCTCAACAG CGGTAAGATC CTTGAGAGTT TTCGCCCCGA AGAACGTTTT
3401 CCAATGATGA GCACTTTTAA AGTTCTGCTA TGTGGCGCGG TATTATCCCG
3451 TATTGACGCC GGGCAAGAGC AACTCGGTCG CCGCATACAC TATTCTCAGA
3501 ATGACTTGGT TGAGTACTCA CCAGTCACAG AAAAGCATCT TACGGATGGC
3551 ATGACAGTAA GAGAATTATG CAGTGCTGCC ATAACCATGA GTGATAACAC
3601 TGCGGCCAAC TTACTTCTGA CAACGATCGG AGGACCGAAG GAGCTAACCG
3651 CTTTTTTGCA CAACATGGGG GATCATGTAA CTCGCCTTGA TCGTTGGGAA
3701 CCGGAGCTGA ATGAAGCCAT ACCAAACGAC GAGCGTGACA CCACGATGCC
3751 TGTAGCAATG GCAACAACGT TGCGCAAACT ATTAACTGGC GAACTACTTA
3801 CTCTAGCTTC CCGGCAACAA TTAATAGACT GGATGGAGGC GGATAAAGTT
3851 GCAGGACCAC TTCTGCGCTC GGCCCTTCCG GCTGGCTGGT TTATTGCTGA
3901 TAAATCTGGA GCCGGTGAGC GTGGGTCTCG CGGTATCATT GCAGCACTGG
3951 GGCCAGATGG TAAGCCCTCC CGTATCGTAG TTATCTACAC GACGGGGAGT
4001 CAGGCAACTA TGGATGAACG AAATAGACAG ATCGCTGAGA TAGGTGCCTC
4051 ACTGATTAAG CATTGGTAAC TGTCAGACCA AGTTTACTCA TATATACTTT
4101 AGATTGATTT AAAACTTCAT TTTTAATTTA AAAGGATCTA GGTGAAGATC
4151 CTTTTTGATA ATCTCATGAC CAAAATCCCT TAACGTGAGT TTTCGTTCCA
4201 CTGAGCGTCA GACCCCGTAG AAAAGATCAA AGGATCTTCT TGAGATCCTT
4251 TTTTTCTGCG CGTAATCTGC TGCTTGCAAA CAAAAAAACC ACCGCTACCA
4301 GCGGTGGTTT GTTTGCCGGA TCAAGAGCTA CCAACTCTTT TTCCGAAGGT
4351 AACTGGCTTC AGCAGAGCGC AGATACCAAA TACTGTCCTT CTAGTGTAGC
4401 CGTAGTTAGG CCACCACTTC AAGAACTCTG TAGCACCGCC TACATACCTC
4451 GCTCTGCTAA TCCTGTTACC AGTGGCTGCT GCCAGTGGCG ATAAGTCGTG
4501 TCTTACCGGG TTGGACTCAA GACGATAGTT ACCGGATAAG GCGCAGCGGT
4551 CGGGCTGAAC GGGGGGTTCG TGCACACAGC CCAGCTTGGA GCGAACGACC
4601 TACACCGAAC TGAGATACCT ACAGCGTGAG CATTGAGAAA GCGCCACGCT
4651 TCCCGAAGGG AGAAAGGCGG ACAGGTATCC GGTAAGCGGC AGGGTCGGAA
4701 CAGGAGAGCG CACGAGGGAG CTTCCAGGGG GAAACGCCTG GTATCTTTAT
4751 AGTCCTGTCG GGTTTCGCCA CCTCTGACTT GAGCGTCGAT TTTTGTGATG
```

FIG. 45C

```
4801 CTCGTCAGGG GGGCGGAGCC TATGGAAAAA CGCCAGCAAC GCGGCCTTTT
4851 TACGGTTCCT GGCCTTTTGC TGGCCTTTTG CTCACATGTT CTTTCCTGCG
4901 TTATCCCCTG ATTCTGTGGA TAACCGTATT ACCGCCTTTG AGTGAGCTGA
4951 TACCGCTCGC CGCAGCCGAA CGACCGAGCG CAGCGAGTCA GTGAGCGAGG
5001 AAGCGGAAGA GCGCCAATAC GCAAACCGCC TCTCCCCGCG CGTTGGCCGA
5051 TTCATTAATG CAGCTGGCAC GACAGGTTTC CCGACTGGAA AGCGGGCAGT
5101 GAGCGCAACG CAATTAATGT GAGTTACCTC ACTCATTAGG CACCCCAGGC
5151 TTTACACTTT ATGCTTCCGG CTCGTATGTT GTGTGGAATT GTGAGCGGAT
5201 AACAATTTCA CACAGGAAAC AGCTATGACC ATGATTACGC C
```

FIG. 47A

```
   1 AAGCTTAATG TCGTAACAAC TCCGCCCCGT TGACGCAAAT GGGCGGTAGG
  51 CGTGTACGGT GGGAGGTCTA TATAAGCAGA GCTCGTTTAG TGAACCGTCT
 101 GCAGACTCTC TTCCGCATCG CTGTCTGCGA GGGCCAGCTG TTGGGCTCGC
 151 GGTTGAGGAC AAACTCTTCG CGGTCTTTCC AGTACTCTTG GATCGGAAAC
 201 CCGTCGGCCT CCGAACGGTA CTCCGCCACC GAGGGACCTG AGCGAGTCCG
 251 CATCGACCGG ATCGGAAAAC CTCTCGAGAA AGGCGTCTAA CCAGTCACAG
 301 TCGCAAGTCT AGAATGCACA AGGGAATCCC CAAAAGCTCC AAAACCCAAA
 351 CACATACCCA ACAAGACCGC CCCCACAAC CCAGCACCGA ACTCGAAGAG
 401 ACCAGGACCT CCCGAGCACG ACACAGCACA ACATCAGCTC AGCGATCCAC
 451 GCACTACGAT CCTCGAACAT CGGACAGACC CGTCTCCTAC ACCATGAACA
 501 GGACCAGGTC CCGCAAGCAA ACCAGCCACA GATTGAAGAA CATCCCAGTT
 551 CACGGAAACC ACGAGGCCAC CATCCAGCAC ATACCAGAGA GTGTCTCAAA
 601 AGGAGCGAGA TCCCAGATCG AAAGGCGGCA ACCCAATGCA ATCAACTCAG
 651 GCTCTCATTG CACCTGGTTA GTCCTGTGGT GCCTCGGAAT GGCCAGTCTC
 701 TTTCTTTGTT CCAAGGCTCA GATACATTGG AATAATTTGT CAACTATTGG
 751 GATTATCGGG ACTGATAGTG TCCATTACAA GATCATGACT AGGCCCAGTC
 801 ACCAGTACTT GGTCATAAAA CTGATGCCTA ATGTTTCACT TATAGAGAAT
 851 TGTACCAAAG CAGAATTAGG TGAGTATGAG AAATTATTGA ATTCAGTCCT
 901 CGAACCAATC AACCAAGCTT TGACTCTAAT GACCAAGAAT GTGAAGCCCC
 951 TGCAGTCATT AGGGTCAGGT AGGAGACAAA GGCGTTTTGC AGGAGTGGTA
1001 CTTGCAGGTG TAGCTTTAGG AGTGGCTACA GCTGCACAAA TCACTGCAGG
1051 AATAGCTTTA CATCAATCCA ACCTCAATGC TCAAGCAATC CAATCTCTTA
1101 GAACCAGCCT TGAACAGTCT AACAAAGCTA TAGAAGAAAT TAGGGAGGCT
1151 ACCCAAGAAA CCGTCATTGC CGTTCAGGGA GTCCAGGACT ACGTCAACAA
1201 CGAACTCGTC CCTGCCATGC AACATATGTC ATGTGAATTA GTTGGGCAGA
1251 GATTAGGGTT AAGACTGCTT CGGTATTATA CTGAGTTGTT GTCAATATTT
1301 GGCCCGAGTT TACGTGACCC TATTTCAGCC GAGATATCAA TTCAGGCACT
1351 GATTTATGCT CTTGGAGGAG AAATTCATAA GATACTTGGG AAGTTGGGAT
1401 ATTCTGGAAG TGATATGATT GCAATCTTGG AGAGTCGGGG GATAAAAACA
1451 AAAATAACTC ATGTTGATCT TCCCGGGAAA TTCATCATCC TAAGTATCTC
1501 ATACCCAACT TTATCAGAAG TCAAGGGGGT TATAGTCCAC AGACTGGAAG
1551 CGGTTTCTTA CAACATAGGA TCACAAGAGT GGTACACCAC TGTCCCGAGG
1601 TATATTGCAA CTAATGGTTA CTTAATATCT AATTTTGATG AGTCATCTTG
1651 TGTATTCGTC TCAGAGTCAG CCATTTGTAG CCAGAACTCC CTGTATCCCA
1701 TGAGCCCACT CTTACAACAA TGTATTAGGG GCGACACTTC ATCTTGTGCT
1751 CGGACCTTGG TATCTGGGAC TATGGGCAAC AAATTTATTC TGTCAAAAGG
1801 TAATATCGTC GCAAATTGTG CTTCTATACT ATGTAAGTGT TATAGCACAA
1851 GCACAATTAT TAATCAGAGT CCTGATAAGT TGCTGACATT CATTGCCTCC
1901 GATACCTGCC CACTGGTTGA AATAGATGGT GCTACTATCC AAGTTGGAGG
1951 CAGGCAATAC CCTGATATGG TATACGAAGG CAAAGTTGCC TTAGGCCCTG
2001 CTATATCACT TGATAGGTTA GATGTAGGTA CAAACTTAGG GAACGCCCTT
2051 AAGAAACTGG ATGATGCTAA GGTACTGATA GACTCCTCTA ACCAGATCCT
2101 TGACACGGTT AGGCGCTCTT CCTTCAATTT TGGCAGTCTC CTCAGCGTTC
2151 CTATATTAAG TTGTACAGCC CTGGCTTTGT TGTTGCTGAT TTACTGTTGT
2201 AAAAGACGCT ACCAACAGAC ACTCAAGCAG CATACTAAGG TCGATCCGGC
```

FIG. 47B

```
2251 ATTTAAACCT GATCTAACTG GAACTTCGAA ATCCTATGTG AGATCACACT
2301 GACCGCGGAA TTGTTGTTGT TAACTTGTTT ATTGCAGCTT ATAATGGTTA
2351 CAAATAAAGC AATAGCATCA CAAATTTCAC AAATAAAGCA TTTTTTTCAC
2401 TGCATTCTAG TTGTGGTTTG TCCAAACTCA TCAATGTATC TTATCATGTC
2451 TGGATCCCCC GGAATTCACT GGCCGTCGTT TTACAACGTC GTGACTGGGA
2501 AAACCCTGGC GTTACCCAAC TTAATCGCCT TGCAGCACAT CCCCCCTTCG
2551 CCAGCTGGCG TAATAGCGAA GAGGCCCGCA CCGATCGCCC TTCCCAACAG
2601 TTGCGCAGCC TGAATGGCGA ATGGCGCCTG ATGCGGTATT TTCTCCTTAC
2651 GCATCTGTGC GGTATTTCAC ACCGCATATG GTGCACTCTC AGTACAATCT
2701 GCTCTGATGC CGCATAGTTA AGCCAGTACA CTCCGCTATC GCTACGTGAC
2751 TGGGTCATGG CTGCGCCCCG ACACCCGCCA ACACCCGCTG ACGCGCCTG
2801 ACGGGCTTGT CTGCTCCCGG CATCCGCTTA CAGACAAGCT GTGACCGTCT
2851 CCGGGAGCTG CATGTGTCAG AGGTTTTCAC CGTCATCACC GAAACGCGCG
2901 AGGCAGTTCT TGAAGACGAA AGGGCCTCGT GATACGCCTA TTTTTATAGG
2951 TTAATGTCAT GATAATAATG GTTTCTTAGA CGTCAGGTGG CACTTTTCGG
3001 GGAAATGTGC GCGGAACCCC TATTTGTTTA TTTTTCTAAA TACATTCAAA
3051 TATGTATCCG CTCATGAGAC AATAACCCTG ATAAATGCTT CAATAATATT
3101 GAAAAAGGAA GAGTATGAGT ATTCAACATT TCCGTGTCGC CCTTATTCCC
3151 TTTTTGCGG CATTTTGCCT TCCTGTTTTT GCTCACCCAG AAACGCTGGT
3201 GAAAGTAAAA GATGCTGAAG ATCAGTTGGG TGCACGAGTG GGTTACATCG
3251 AACTGGATCT CAACAGCGGT AAGATCCTTG AGAGTTTTCG CCCCGAAGAA
3301 CGTTTTCCAA TGATGAGCAC TTTTAAAGTT CTGCTATGTG GCGCGGTATT
3351 ATCCCGTATT GACGCCGGGC AAGAGCAACT CGGTCGCCGC ATACACTATT
3401 CTCAGAATGA CTTGGTTGAG TACTCACCAG TCACAGAAAA GCATCTTACG
3451 GATGGCATGA CAGTAAGAGA ATTATGCAGT GCTGCCATAA CCATGAGTGA
3501 TAACACTGCG GCCAACTTAC TTCTGACAAC GATCGGAGGA CCGAAGGAGC
3551 TAACCGCTTT TTTGCACAAC ATGGGGATC ATGTAACTCG CCTTGATCGT
3601 TGGGAACCGG AGCTGAATGA AGCCATACCA AACGACGAGC GTGACACCAC
3651 GATGCCTGTA GCAATGGCAA CAACGTTGCG CAAACTATTA ACTGGCGAAC
3701 TACTTACTCT AGCTTCCCGG CAACAATTAA TAGACTGGAT GGAGGCGGAT
3751 AAAGTTGCAG GACCACTTCT GCGCTCGGCC CTTCCGGCTG GCTGGTTTAT
3801 TGCTGATAAA TCTGGAGCCG GTGAGCGTGG GTCTCGCGGT ATCATTGCAG
3851 CACTGGGGCC AGATGGTAAG CCCTCCCGTA TCGTAGTTAT CTACACGACG
3901 GGGAGTCAGG CAACTATGGA TGAACGAAAT AGACAGATCG CTGAGATAGG
3951 TGCCTCACTG ATTAAGCATT GGTAACTGTC AGACCAAGTT TACTCATATA
4001 TACTTTAGAT TGATTTAAAA CTTCATTTTT AATTTAAAAG GATCTAGGTG
4051 AAGATCCTTT TTGATAATCT CATGACCAAA ATCCCTTAAC GTGAGTTTTC
4101 GTTCCACTGA GCGTCAGACC CCGTAGAAAA GATCAAAGGA TCTTCTTGAG
4151 ATCCTTTTTT TCTGCGCGTA ATCTGCTGCT TGCAAACAAA AAAACCACCG
4201 CTACCAGCGG TGGTTTGTTT GCCGGATCAA GAGCTACCAA CTCTTTTTCC
4251 GAAGGTAACT GGCTTCAGCA GAGCGCAGAT ACCAAATACT GTCCTTCTAG
4301 TGTAGCCGTA GTTAGGCCAC CACTTCAAGA ACTCTGTAGC ACCGCCTACA
4351 TACCTCGCTC TGCTAATCCT GTTACCAGTG GCTGCTGCCA GTGGCGATAA
4401 GTCGTGTCTT ACCGGGTTGG ACTCAAGACG ATAGTTACCG GATAAGGCGC
4451 AGCGGTCGGG CTGAACGGGG GGTTCGTGCA CACAGCCCAG CTTGGAGCGA
4501 ACGACCTACA CCGAACTGAG ATACCTACAG CGTGAGCATT GAGAAAGCGC
4551 CACGCTTCCC GAAGGGAGAA AGGCGGACAG GTATCCGGTA AGCGGCAGGG
4601 TCGGAACAGG AGAGCGCACG AGGGAGCTTC CAGGGGGAAA CGCCTGGTAT
4651 CTTTATAGTC CTGTCGGGTT TCGCCACCTC TGACTTGAGC GTCGATTTTT
4701 GTGATGCTCG TCAGGGGGC GGAGCCTATG GAAAAACGCC AGCAACGCGG
4751 CCTTTTTACG GTTCCTGGCC TTTTGCTGGC CTTTTGCTCA CATGTTCTTT
4801 CCTGCGTTAT CCCCTGATTC TGTGGATAAC CGTATTACCG CCTTTGAGTG
4851 AGCTGATACC GCTCGCCGCA GCCGAACGAC CGAGCGCAGC GAGTCAGTGA
```

FIG.47C

```
4901 GCGAGGAAGC GGAAGAGCGC CAATACGCAA ACCGCCTCTC CCCGCGCGTT
4951 GGCCGATTCA TTAATGCAGC TGGCACGACA GGTTTCCCGA CTGGAAAGCG
5001 GGCAGTGAGC GCAACGCAAT TAATGTGAGT TACCTCACTC ATTAGGCACC
5051 CCAGGCTTTA CACTTTATGC TTCCGGCTCG TATGTTGTGT GGAATTGTGA
5101 GCGGATAACA ATTTCACACA GGAAACAGCT ATGACCATGA TTACGCC
```

FIG. 49A

```
   1 GTCGACGGTG CCCCCAGCAG AAGTATCGAC TGCATGCTAA TTATTAACAA
  51 ACCAAAAGGC GTTGCCACTT ACACCCTTAC CTTTAGGTTT TTAAACTTTA
 101 ACAGACTAAG CGGAGGTACC CTGTTTAAAA CTGATGTCTT AACCTTTACC
 151 TATGTAGGCG AAAATCAATA AAACCAGAAA AAAATAAGTT TAAAAGCTTT
 201 ATTTTTCATA CACGCGAGCG GTAAGGCTGC CGCCTTCAGG AAAAGTTACT
 251 CTGTAAACAG TTCTTTCACA ACAGCACAAA ACATAGGTAT TAGTTAACAG
 301 TTCATTTGGG CTATAATAAT ATACATTTTC TTGGGTGGCA AAGCAAGGGT
 351 CGGTAATCTC AACAAAACCA TCAACTGGAA TGCAAGAATA GTCCAGCACG
 401 GTGGGTTCAA TCTAAAAATG AAGAAACGCT GTTGAGGTTC ACTAAGCACA
 451 GGTTTTGAAT CTGTCGGCAG CGTCCATGCA TCATAGCTTG TCTCAAAGCA
 501 GATTGTCTTC TTTCCTCTGC CTTGGAAGTG GTTTGGTGAA GCACTACAGG
 551 TGTCTTTTCA ACCTCTTTCA GCACCCGCTC TATTACAGAT CTCACCCACA
 601 CAGCACAGTT TTAAGAGAA CAATAGTTTT GAAGGCTACA AGATTTACAC
 651 TTAAGCACCA GCCAGTAATT ATAAGTGCTT TTAAGAACTA CCCCTAGCTC
 701 AGGGTTAATG CACCTTTTAA TGGCCTCCAT GCAGGCTTTA TGGACAGTTC
 751 TAAAAAAAGA CAGTCTAAAA TAAATGTAGT GAGTGTTTCT AAATATAATA
 801 CTCCCCACAT AGTTAATTTC ATCAGGCCTG CTAGAATTTA CAAACTCTCG
 851 GTACCACATA TACTTTTTAT TCATAGCCCC ACCCTTAATA AAGTCCTCAA
 901 TCACTTTCTG AACCACATGC TTGCTAGCCA TGCATTGTAA AGACAAGCTG
 951 TTAGAGCAGT GACAGTGTAC TCGCCACGTT TGAGCCTCTG CCAGGCAGCA
1001 GTGCTTAGTT ACTATCAACT CAATACCCGC ATTGCATGTA AACCCCCCAA
1051 AGAGCAGTTT TTCATGCCTG TGTAGCACAT CATCCCACAA AATAGGAATT
1101 TCATAGCATA AAGCAAAGCA ATTACAATAT TTAGGAACTC TCACCACAGC
1151 AGTCACGTGA CATGTTGTCT CAGCAGTGCA GTTGCCTTCC ATCCTACAAT
1201 TATGAACAAA AACTAAACAC TTCTAACAAA GATACAGTGA CAATCTCCCT
1251 TCCTCTAAAA GCATTGTTTA CATTAGGGTG ATTATTAACA ACGTCAGAAA
1301 TTTCTTTAAT TAAAGTGCCT TTAAAATGTG CAAGAGCATC ATCATACTCA
1351 AAACCAAGCT GAGAGTAAAA GACCACCTTA AAAGTAATCC CAGGCTTGTT
1401 TTTATCAACA GCCTTAAACA TGCTTTCACA AAATATAGAA GCAGTAACAT
1451 CATCAATGGT GTCGAAGAGA AACTCCATAG GAGACTCCAG CATTGATCCA
1501 AGCTCTCTAA CAAAATCTTC CTCAAAATGA ATAATGCCCT TTACACAAAC
1551 GCGGGGCAGA CGATGGTGGG CCATCGCGTC AACCTGAAAC ACATTTTACA
1601 GTAAACAAAG CTAGCTCCGC AGTGGTAAAG TCATGCCCAT GGGTGAGGCC
1651 AAAATCCTTA AAAAGCTAT CTAAGTAGTT GGTCATCCCC TCAGTTAAAA
1701 AGTTTGCAG CTGGGTGGTG CATACCACAT AGTGCCAGCT TATAGCTACA
1751 AAGACCTGCA TCCCTCCTT AGCAGACAGC TCTTGCACAC ACGCAGTAAC
1801 TATCCACCGC TTAAGAAAG CTTAAGCCC AGCGCACATA ACAGCTCCAA
1851 TGTTTTTATC CAAGGAGAGC AAAATTTCAG CAAGCGCAGG CTCAACAGTA
1901 ATAGTGAAGC AGAGGCATTT CAGACGAGGC TCACTAGCTG CAGTCGCCAT
1951 TTATGAGGTC TGCAATAAAA AACAACTCAT CAGCAGCTGA AAAAGTGCAC
2001 TTTGACCTCA TTAAGCCACT GCATATGCAA GTCCTCATCT ATGCCGCAGC
2051 CCAGACCCTC AATCCAGCCC CGAATGTACA CTTTAATAAG AGATTCAACC
2101 TCTTCTTTTA GCAAAGTACA CATGCTGTTT GGACTAGTAT ACACAATAGA
```

FIG.49B

```
2151 AGTCACAATG AGGGGCCCGC TGTGGCTGGA AAGCCTGCGC ACAGCCCGAA
2201 GGTTAAAAAT GGACTGTAAC AGCATTGAAA CCCCGCGACA CAGGTCAGTC
2251 TCGCGGTCTT GATCTCTTAT TATAGCGACC AAATGGTCCT TCAGAGTGAT
2301 GTTGCACTCA TAGAAGTAGG CAGCTCCGGC AGCCATTCTG CAAAATAACA
2351 AAACACCACT AAGCATAGCA CCATCACCAA GCATGAAAAC AGGTAAAAAC
2401 AAAAGCAACA CTTACTTATT CAGCAGTCAC AAGAATGTTG GGCTCCCAAG
2451 TGACAGACAA GCCTAATGCA AGGTGGGCAC AGTCTCCGGA ATAAGTTGAC
2501 AAAAGTCACG CCGCAAAGCT TCCTGAAGAG AAACGGCGGT AGCCTGGATA
2551 TCTGCAACGG ACCCAAAACC TTCAGTGTCA CTTCCAATAA ACAGATAAAA
2601 CTCTAAATAG TCCCCACTTA AAACCGAAAC AGCCGCGGCA AAGGTAGGAC
2651 ACGGACGCAC TTCCTGAGCC CTAATAAGGC TAAACACCAC ACGGCGCAGT
2701 TCAGAAGGCA AAAGTCTGT AAGCTCTAGC TGAGCACACA CACTCTCCAC
2751 TAGACACTTG TGAAGCCTCA GACAAAAACA TGCTCCCATA GACACTCCTA
2801 AAGCTGCCAT TGTACTCACG GACGGCTGGC TGTCAGAGGA GAGCTATGAG
2851 GATGAAATGC CAAGCACAGC GTTTATATAG TCCTCAAAGT AGGGCGTGTG
2901 GAAAACGAAA AGGAATATAA CGGGGCGTTT GAGGAAGTGG TGCCAAGTAC
2951 AGTCATAAAA TGTGGGCGCG TGGTAAATGT TAAGTGCAGT TTCCCTTTGG
3001 CGGTTGGCCC GGAAAGTTCA CAAAAAGTAC AGCACGTCCT TGTCACCGTG
3051 TCAACCACAA AACCACAAAT AGGCACAACG CCCAAAAACC CGGGTCGACA
3101 CGCGTGAATT CACCGGTTCG AGCTTAATGT CGTAACAACT CCGCCCCGTT
3151 GACGCAAATG GGCGGTAGGC GTGTACGGTG GGAGGTCTAT ATAAGCAGAG
3201 CTCGTTTAGT GAACCGTCTG CAGACTCTCT TCCGCATCGC TGTCTGCGAG
3251 GGCCAGCTGT TGGGCTCGCG GTTGAGGACA AACTCTTCGC GGTCTTTCCA
3301 GTACTCTTGG ATCGGAAACC CGTCGGCCTC CGAACGGTAC TCCGCCACCG
3351 AGGGACCTGA GCGAGTCCGC ATCGACCGGA TCGGAAAACC TCTCGAGAAA
3401 GGCGTCTAAC CAGTCACAGT CGCAAGTCTA GAATGCACAA GGGAATCCCC
3451 AAAAGCTCCA AAACCCAAAC ACATACCCAA CAAGACCGCC CCCCACAACC
3501 CAGCACCGAA CTCGAAGAGA CCAGGACCTC CCGAGCACGA CACAGCACAA
3551 CATCAGCTCA GCGATCCACG CACTACGATC CTCGAACATC GGACAGACCC
3601 GTCTCCTACA CCATGAACAG GACCAGGTCC CGCAAGCAAA CCAGCCACAG
3651 ATTGAAGAAC ATCCCAGTTC ACGGAAACCA CGAGGCCACC ATCCAGCACA
3701 TACCAGAGAG TGTCTCAAAA GGAGCGAGAT CCCAGATCGA AAGGCGGCAA
3751 CCCAATGCAA TCAACTCAGG CTCTCATTGC ACCTGGTTAG TCCTGTGGTG
3801 CCTCGGAATG GCCAGTCTCT TTCTTTGTTC CAAGGCTCAG ATACATTGGA
3851 ATAATTTGTC AACTATTGGG ATTATCGGGA CTGATAGTGT CCATTACAAG
3901 ATCATGACTA GGCCCAGTCA CCAGTACTTG GTCATAAAAC TGATGCCTAA
3951 TGTTTCACTT ATAGAGAATT GTACCAAAGC AGAATTAGGT GAGTATGAGA
4001 AATTATTGAA TTCAGTCCTC GAACCAATCA ACCAAGCTTT GACTCTAATG
4051 ACCAAGAATG TGAAGCCCCT GCAGTCATTA GGGTCAGGTA GGAGACAAAG
4101 GCGTTTTGCA GGAGTGGTAC TTGCAGGTGT AGCTTTAGGA GTGGCTACAG
4151 CTGCACAAAT CACTGCAGGA ATAGCTTTAC ATCAATCCAA CCTCAATGCT
4201 CAAGCAATCC AATCTCTTAG AACCAGCCTT GAACAGTCTA ACAAAGCTAT
4251 AGAAGAAATT AGGGAGGCTA CCCAAGAAAC CGTCATTGCC GTTCAGGGAG
4301 TCCAGGACTA CGTCAACAAC GAACTCGTCC CTGCCATGCA ACATATGTCA
4351 TGTGAATTAG TTGGGCAGAG ATTAGGGTTA AGACTGCTTC GGTATTATAC
4401 TGAGTTGTTG TCAATATTTG GCCCGAGTTT ACGTGACCCT ATTTCAGCCG
4451 AGATATCAAT TCAGGCACTG ATTTATGCTC TTGGAGGAGA AATTCATAAG
4501 ATACTTGGGA AGTTGGGATA TTCTGGAAGT GATATGATTG CAATCTTGGA
4551 GAGTCGGGGG ATAAAAACAA AAATAACTCA TGTTGATCTT CCCGGGAAAT
4601 TCATCATCCT AAGTATCTCA TACCCAACTT TATCAGAAGT CAAGGGGGTT
4651 ATAGTCCACA GACTGGAAGC GGTTCTTAC AACATAGGAT CACAAGAGTG
4701 GTACACCACT GTCCCGAGGT ATATTGCAAC TAATGGTTAC TTAATATCTA
4751 ATTTTGATGA GTCATCTTGT GTATTCGTCT CAGAGTCAGC CATTTGTAGC
```

FIG. 49C

```
4801 CAGAACTCCC TGTATCCCAT GAGCCCACTC TTACAACAAT GTATTAGGGG
4851 CGACACTTCA TCTTGTGCTC GGACCTTGGT ATCTGGGACT ATGGGCAACA
4901 AATTTATTCT GTCAAAAGGT AATATCGTCG CAAATTGTGC TTCTATACTA
4951 TGTAAGTGTT ATAGCACAAG CACAATTATT AATCAGAGTC CTGATAAGTT
5001 GCTGACATTC ATTGCCTCCG ATACCTGCCC ACTGGTTGAA ATAGATGGTG
5051 CTACTATCCA AGTTGGAGGC AGGCAATACC CTGATATGGT ATACGAAGGC
5101 AAAGTTGCCT TAGGCCCTGC TATATCACTT GATAGGTTAG ATGTAGGTAC
5151 AAACTTAGGG AACGCCCTTA AGAAACTGGA TGATGCTAAG GTACTGATAG
5201 ACTCCTCTAA CCAGATCCTT GAGACGGTTA GGCGCTCTTC CTTCAATTTT
5251 GGCAGTCTCC TCAGCGTTCC TATATTAAGT TGTACAGCCC TGGCTTTGTT
5301 GTTGCTGATT TACTGTTGTA AAAGACGCTA CCAACAGACA CTCAAGCAGC
5351 ATACTAAGGT CGATCCGGCA TTTAAACCTG ATCTAACTGG AACTTCGAAA
5401 TCCTATGTGA GATCACACTG ACCGCGGCGT GATTAATCAG CCATACCACA
5451 TTTGTAGAGG TTTTACTTGC TTTAAAAAAC CTCCCACACC TCCCCCTGAA
5501 CCTGAAACAT AAAATGAATG CAATTGTTGT TGTTAACTTG TTTATTGCAG
5551 CTTATAATGG TTACAAATAA AGCAATAGCA TCACAAATTT CACAAATAAA
5601 GCATTTTTTT CACTGCATTC TAGTTGTGGT TTGTCCAAAC TCATCAATGT
5651 ATCTTATCAT GTCTGGATCC GAAACGCCCA AAAACCCGGG GCGCCGGCCA
5701 AAAGTCCGCG GAACTCGCCC TGTCGTAAAA CCACGCCTTT GACGTCACTG
5751 GACATTCCCG TGGGAACACC CTGACCAGGG CGTGACCTGA ACCTGACCGT
5801 CCCATGACCC CGCCCCTTGC AACACCCAAA TTTAAGCCAC ACCTCTTTGT
5851 CCTGTATATT ATTGATGATG GGGGATCCA CTAGTTCTAG AGCGGCCGCC
5901 ACCGCGGTGG AGCTCCAGCT TTTGTTCCCT TTAGTGAGGG TTAATTCCGA
5951 GCTTGGCGTA ATCATGGTCA TAGCTGTTTC CTGTGTGAAA TTGTTATCCG
6001 CTCACAATTC CACACAACAT ACGAGCCGGA AGCATAAAGT GTAAAGCCTG
6051 GGGTGCCTAA TGAGTGAGCT AACTCACATT AATTGCGTTG CGCTCACTGC
6101 CCGCTTTCCA GTCGGGAAAC CTGTCGTGCC AGCTGCATTA ATGAATCGGC
6151 CAACGCGCGG GGAGAGGCGG TTTGCGTATT GGGCGCTCTT CCGCTTCCTC
6201 GCTCACTGAC TCGCTGCGCT CGGTCGTTCG GCTGCGGCGA GCGGTATCAG
6251 CTCACTCAAA GGCGGTAATA CGGTTATCCA CAGAATCAGG GGATAACGCA
6301 GGAAAGAACA TGTGAGCAAA AGGCCAGCAA AAGGCCAGGA ACCGTAAAAA
6351 GGCCGCGTTG CTGGCGTTTT TCCATAGGCT CCGCCCCCCT GACGAGCATC
6401 ACAAAAATCG ACGCTCAAGT CAGAGGTGGC GAAACCCGAC AGGACTATAA
6451 AGATACCAGG CGTTTCCCCC TGGAAGCTCC CTCGTGCGCT CTCCTGTTCC
6501 GACCCTGCCG CTTACCGGAT ACCTGTCCGC CTTTCTCCCT TCGGGAAGCG
6551 TGGCGCTTTC TCATAGCTCA CGCTGTAGGT ATCTCAGTTC GGTGTAGGTC
6601 GTTCGCTCCA AGCTGGGCTG TGTGCACGAA CCCCCCGTTC AGCCCGACCG
6651 CTGCGCCTTA TCCGGTAACT ATCGTCTTGA GTCCAACCCG GTAAGACACG
6701 ACTTATCGCC ACTGGCAGCA GCCACTGGTA ACAGGATTAG CAGAGCGAGG
6751 TATGTAGGCG GTGCTACAGA GTTCTTGAAG TGGTGGCCTA ACTACGGCTA
6801 CACTAGAAGG ACAGTATTTG GTATCTGCGC TCTGCTGAAG CCAGTTACCT
6851 TCGGAAAAAG AGTTGGTAGC TCTTGATCCG GCAAACAAAC CACCGCTGGT
6901 AGCGGTGGTT TTTTTGTTTG CAAGCAGCAG ATTACGCGCA GAAAAAAAGG
6951 ATCTCAAGAA GATCCTTTGA TCTTTTCTAC GGGGTCTGAC GCTCAGTGGA
7001 ACGAAAACTC ACGTTAAGGG ATTTTGGTCA TGAGATTATC AAAAAGGATC
7051 TTCACCTAGA TCCTTTTAAA TTAAAAATGA AGTTTTAAAT CAATCTAAAG
7101 TATATATGAG TAAACTTGGT CTGACAGTTA CCAATGCTTA ATCAGTGAGG
7151 CACCTATCTC AGCGATCTGT CTATTTCGTT CATCCATAGT TGCCTGACTC
7201 CCCGTCGTGT AGATAACTAC GATACGGGAG GGCTTACCAT CTGGCCCCAG
7251 TGCTGCAATG ATACCGCGAG ACCCACGCTC ACCGGCTCCA GATTTATCAG
7301 CAATAAACCA GCCAGCCGGA AGGGCCGAGC GCAGAAGTGG TCCTGCAACT
7351 TTATCCGCCT CCATCCAGTC TATTAATTGT TGCCGGGAAG CTAGAGTAAG
7401 TAGTTCGCCA GTTAATAGTT TGCGCAACGT TGTTGCCATT GCTACAGGCA
```

FIG. 49D

```
7451 TCGTGGTGTC ACGCTCGTCG TTTGGTATGG CTTCATTCAG CTCCGGTTCC
7501 CAACGATCAA GGCGAGTTAC ATGATCCCCC ATGTTGTGCA AAAAAGCGGT
7551 TAGCTCCTTC GGTCCTCCGA TCGTTGTCAG AAGTAAGTTG GCCGCAGTGT
7601 TATCACTCAT GGTTATGGCA GCACTGCATA ATTCTCTTAC TGTCATGCCA
7651 TCCGTAAGAT GCTTTTCTGT GACTGGTGAG TACTCAACCA AGTCATTCTG
7701 AGAATAGTGT ATGCGGCGAC CGAGTTGCTC TTGCCCGGCG TCAATACGGG
7751 ATAATACCGC GCCACATAGC AGAACTTTAA AAGTGCTCAT CATTGGAAAA
7801 CGTTCTTCGG GGCGAAAACT CTCAAGGATC TTACCGCTGT TGAGATCCAG
7851 TTCGATGTAA CCCACTCGTG CACCCAACTG ATCTTCAGCA TCTTTTACTT
7901 TCACCAGCGT TTCTGGGTGA GCAAAAACAG GAAGGCAAAA TGCCGCAAAA
7951 AAGGGAATAA GGGCGACACG GAAATGTTGA ATACTCATAC TCTTCCTTTT
8001 TCAATATTAT TGAAGCATTT ATCAGGGTTA TTGTCTCATG AGCGGATACA
8051 TATTTGAATG TATTTAGAAA AATAAACAAA TAGGGGTTCC GCGCACATTT
8101 CCCCGAAAAG TGCCACCTGG GAAATTGTAA ACGTTAATAT TTTGTTAAAA
8151 TTCGCGTTAA ATTTTTGTTA AATCAGCTCA TTTTTTAACC AATAGGCCGA
8201 AATCGGCAAA ATCCCTTATA AATCAAAAGA ATAGACCGAG ATAGGGTTGA
8251 GTGTTGTTCC AGTTTGGAAC AAGAGTCCAC TATTAAAGAA CGTGGACTCC
8301 AACGTCAAAG GGCGAAAAAC CGTCTATCAG GGCGATGGCC CACTACGTGA
8351 ACCATCACCC TAATCAAGTT TTTTGGGGTC GAGGTGCCGT AAAGCACTAA
8401 ATCGGAACCC TAAAGGGAGC CCCCGATTTA GAGCTTGACG GGGAAAGCCG
8451 GCGAACGTGG CGAGAAAGGA AGGGAAGAAA GCGAAAGGAG CGGGCGCTAG
8501 GGCGCTGGCA AGTGTAGCGG TCACGCTGCG CGTAACCACC ACACCCGCCG
8551 CGCTTAATGC GCCGCTACAG GGCGCGTCGC GCCATTCGCC ATTCAGGCTG
8601 CGCAACTGTT GGGAAGGGCG ATCGGTGCGG GCCTCTTCGC TATTACGCCA
8651 GCTGGCGAAA GGGGGATGTG CTGCAAGGCG ATTAAGTTGG GTAACGCCAG
8701 GGTTTTCCCA GTCACGACGT TGTAAAACGA CGGCCAGTGA ATTGTAATAC
8751 GACTCACTAT AGGGCGAATT GGGTACCGGG CCCCCCCTCG AG
```

FIG. 50

SalI.B Left Arm
1-3091 pLF105 background pLF130A (8792 bp)

XhoI (8787)
SalI (1)
HindIII (194)
BglII (587)
HindIII (1818)
SpeI (2133)
HindIII (2516)
SalI (3094)
SacI (3198)
PstI (3218)
XhoI (3392)
XbaI (3427)
HindIII (4034)
CelII (3556)
BfrI (5167)
KspI (5422)
SpeI (5880)
BamHI (5874)
XbaI (5886)
NotI (5892)

SalI.B Right Arm
5688-5870

CDV F1 Expression Cassette
3126-5669

SEQUENCE LISTING (1) GENERAL INFORMATION:

(iii) NUMBER OF SEQUENCES: 120

(2) INFORMATION FOR SEQ ID NO:1:

(i) SEQUENCE CHARACTERISTICS:
        (A) LENGTH: 6994 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
GGAAATTGTA AACGTTAATA TTTTGTTAAA ATTCGCGTTA AATTTTTGTT AAATCAGCTC      60
ATTTTTTAAC CAATAGGCCG AAATCGGCAA AATCCCTTAT AAATCAAAAG AATAGACCGA     120
GATAGGGTTG AGTGTTGTTC CAGTTTGGAA CAAGAGTCCA CTATTAAAGA ACGTGGACTC     180
CAACGTCAAA GGGCGAAAAA CCGTCTATCA GGGCGATGGC CCACTACGTG AACCATCACC     240
CTAATCAAGT TTTTTGGGGT CGAGGTGCCG TAAAGCACTA AATCGGAACC CTAAAGGGAG     300
CCCCCGATTT AGAGCTTGAC GGGGAAAGCC GGCGAACGTG GCGAGAAAGG AAGGGAAGAA     360
AGCGAAAGGA GCGGGCGCTA GGGCGCTGGC AAGTGTAGCG GTCACGCTGC GCGTAACCAC     420
CACACCCGCC GCGCTTAATG CGCCGCTACA GGGCGCGTCG CGCCATTCGC CATTCAGGCT     480
GCGCAACTGT TGGGAAGGGC GATCGGTGCG GGCCTCTTCG CTATTACGCC AGCTGGCGAA     540
AGGGGGATGT GCTGCAAGGC GATTAAGTTG GGTAACGCCA GGGTTTTCCC AGTCACGACG     600
TTGTAAAACG ACGGCCAGTG AATTGTAATA CGACTCACTA TAGGGCGAAT TGGGTACCGG     660
GCCCCCCCTC GAGGTCGACG GTATCGATAA GCTTGCTCA ACAAATACTG TCAAGGACTC      720
GAGTCCGGCT CTGACTGAGC AATGTCTAAA GAAATACCAA CCCCTTATAT GTGGAGCTAC     780
CAACCGCAAA CGGGACACGC CGGCGCCTCC CAGGACTACT CCACCCAAAT GAATTGGTTT     840
AGTGCTGGGC CATCAATGAT TAGTCAAGTT TATGGCATTA GAGACTTGCG CAACAAAGTT     900
TTGATAACCC AGGCAGAAAT AACCAAAACT CCCAGAACAA TAATGGATCC GCCAATTTGG     960
CCAGCTGCCA TGCTTGTTCA GGAAGCCGCC CCACCCAAAA CGGTCACTCT GCCCAGAAAC    1020
CACACCCTAG AACAGGCTAT GACCAACTCT GGGGCGCAGC TAGCGGGAGG ACGACAGCTG    1080
TGCCCCTCCC AAATAGGTAT AAAAAGCCCA GTGCTGGCTG GCACGGGCAT TCAGCTTAGC    1140
GAAGACATCC CCAGCGCCTC CTGGATCAGG CCCGACGGCA TATTCCAGCT AGGAGGGGGG    1200
TCTCGCTCGT CCTTCAGCCC AACGCAAGCA TTCCTCACCC TGCAACAGGC ATCCTCGACG    1260
CCGCGCGCAG GAGGCGTGGG CACCTACCAG TTTGTGCGCG AATTTGTGCC AGAGGTATAC    1320
CTTAACCCTT TTTCAGGACC ACCGGACACC TTTCCTGATC AGTTCATTCC TAACTACGAC    1380
ATTGTAACCA ACTCTGTCGA TGGCTATGAC TGAGGAGAGC ATGGACCAGG TGGAGGTGAA    1440
CTGCCTGTGT GCTCAGCATG CCCAAACCTG CACGCGCCCT CGCTGCTTTG CAAAGGAGGG    1500
TTTATGTGCT AACTGGTTTT ACAACCCAGC ACTTGCCTTT GAAGGGTTTG ATATTCCAGA    1560
CTCTTACCAA GAGGGACACG GTGTGGACAT AGAAGTTAAG TGTTCCCACC ACTCCAGCAA    1620
ACTGTGCCAC AATGGCCATG ATATGATCTG CTCATACTCT CGCCTGGGAT CCCACATTAA    1680
CATAAGATGT ATTTGCAACA AGCCGCGGCC CCACATGAGC CTCATTGAGG CAGCCTGTTC    1740
TATGTATAAC CTTAACTAGA TAATATTATT AAACTTGTTT TACAGCTACC ACCATAATGC    1800
GCTTCAGCTT CTTCATCGCC GCCGTTCTTT TCTGCACCAC AGGGGCCAGC AATGACATTG    1860
TGACTTGCTG CGCCCACACA CCTTGCCTCC TACACCTAGA AGTGGGCTTG GGGGCCAATG    1920
TCAGTTGGAT AAACTCTGAC ACAGGCCAGG CCCCGATTTG CCTCTCCAAT GGCATGTGCA    1980
ACGCTACCCA GCAAGGCCTG CAGTTTTCTG CAAACTTTTC TGAGGATGGC CTGTACATCG    2040
CCCTCATTAA GGAGAGCAAC TACGAGGGCG CTGAGCACTA CTACCTTGTC TATATTTATG    2100
GAGACTGCTA CCAAACTGCA AATGAGTCTG CCCACGGGCC TATTTCCAGG CCCCTCAACG    2160
AGATGCCTCT TCCCAGCGTA ACCATAAATG CTTCCCTCTT CTATCCCGCC TTTCTGGAGC    2220
TGCCCCCACA GTACAGCAAT GACCTTAGCA ATGTGCGCTG GTATAAAGTA GACCCCAGCG    2280
```

```
                                      -continued
GCTTCCAAGC CCAAAAAATC TCTAAAGTCA GAAGCGGAGG CAGAAAAGAG AACCTGCATC    2340

CCAACTGGGC CTTGGTTACC TATACTGGAG ACCTTCTTGT CTTGCATGTT TCGCCAAACA    2400

CCCTTGGACT GTGGCTGGCA GCCGTGCAGC ATCGCGGGGG GCGCACTAAT TTCATTACCT    2460

TCAACATAAC TGTACCCAAC TGGCAACAAA ATCTAGTAAC CATATTTAAT CAACACGAGC    2520

CCCCAAAAAA GGGCGATAAT TATGAGGACA GTTTTATGGA ATGGACTCTG TTTAAAAAGC    2580

TCAAAAAAGG CTTATTTAGA GTAACTTGCA GAGCCAAGTC AATATTCCCA GAGTGCGTCC    2640

TCAACATCAC CCGCGACGGA ACTTTCCTGC TTATTGGGGA TAGCAAAAAG ACCCCCTATG    2700

TCATCCTGCT GCCCTTTTTT GCAAACCCCA AAGAAGACAC TCCAATTTTA ATGGCCCTTA    2760

GCCATTCCAT GCCCGTCGCC ATACCTGACA CTGCAATGCC TATATATATT TCCATCATGT    2820

TTTTTATTGT GGCCATGCTA GCCACCCTCA GCCTTCTAAT GGGACTAAAC AACAAAATCA    2880

GGCCCATGTA GCTTGTCAAA TAAACTTACC TAATTTTTGC TAAGACGTCT GGGTCCTGCG    2940

TTTCTATGTC CACCAAAGTC CCCTCTTCCC AGCTTTGGTA CTTCCACTTG TGCGCGCGAG    3000

CCAGCTTGCG GATGTGCTTG AAAGATAATG TGGTCTCTCC CAACAGCTTC CCGTTCACCA    3060

GCACCAGGGC CATGAAGCGG ACACGAAGAG CTCTACCTGC AAATTATGAC CCTGTATATC    3120

CATACGACGC CCCCGGGTCT TCCACACAAC CCCCTTTTTT TAATAACAAG CAAGGTCTCA    3180

CTGAGTCACC CCCAGGAACC CTGGCTGTCA ATGTTTCCCC TCCACTAACC TTTTCTACGT    3240

TAGGTGCCAT TAAACTTTCC ACAGGTCCCG GACTCACCCT CAACGAGGGC AAGTTACAAG    3300

CCAGCTTAGG GCCCGGCCTC ATCACAAATA CCGAGGGCCA AATCACTGTT GAAAATGTCA    3360

ACAAGGTTTT GTCTTTTACC TCCCCATTAC ATAAAAATGA AAACACTGTA TCCCTAGCGC    3420

TAGGAGATGG GTTAGAAGAT GAAAATGGCA CCCTTAAAGT GACCTTCCCT ACTCCCCCTC    3480

CCCCGCTACA ATTCTCCCCT CCCCTCACAA AAACAGGTGG TACTGTTTCC TTGCCCCTGC    3540

AAGACTCCAT GCAAGTGACA AATGGAAAAC TGGGCGTTAA GCTACCACCT ACGCACCTCC    3600

CTTGAAAAAA ACTGACCAGC AAGTTAGCCT CCAAGTAGGC TCGGGTCTCA CCGTGATTAA    3660

CGAACAGTTG CAAGCTGTCC AGCCTCCCGC AACCACCTAC AACGAGCCTC TTTCAAAAC     3720

TGACAATTCT GTTTCTCTGC AAGTAGGTGC CGGCCTTGCC GTGCAGAGCG ACGTTTGGT     3780

GGCAACCCCT CCCCCGCCTC TCACCTTTAC ATCACCCCTA GAAAAAAATG AAAACACAGT    3840

GTCGCTACAA GTAGGCGCGG GCTTGTCTGT ACAAAACAAC GCCCTAGTAG CCACACCTCC    3900

CCCACCCTTA ACCTTTGCCT ATCCCTTAGT AAAAAATGAC AACCATGTAG CTCTAAGTGC    3960

TGGAAGTGGT TTAAGAATAT CTGGAGGCAG CCTCACGGTG GCCACTGGAC CTGGCCTTTC    4020

CCATCAAAAT GGAACAATAG GGGCTGTAGT AGGTGCAGGC CTCAAGTTTG AAAACAATGC    4080

CATTCTTGCA AAACTAGGCA ACGGTCTAAC CATTAGAGAT GGCGCTATTG AAGCAACCCA    4140

ACCCCCAGCT GCCCCCATAA CACTGTGGAC AGGGCCTGGC CTAGCATTAA TGGCTTTATG    4200

TAATGACACT CCAGTAATTA GGTCTTTATA TGCCTAACCA GAGACAGCAA CTTAGTCACA    4260

GTAAATGCTA GCTTTGTGGG AGAGGGGGGG TATCGAATAG TCAGCCCTAC CCAGTCACAA    4320

TTTAGCCTAA TTATGGAGTT TGATCAGTTT GGACAGCTTA TGTCCACAGG AAACATTAAC    4380

TCCACCACTA CTTGGGGAGA AAAGCCCTGG GGCAATAACA CTGTACAGCC ACGCCCAAGC    4440

CACACCTGGA AACTGTGCAT GCCTAACAGA GAAGTTTACT CCACTCCCGC CGCCACCATC    4500

ACCCGCTGTG GACTAGACAG CATTGCAGTC GACGGTGCCC AGCAGAAGTA TCGACTGCAT    4560

GCTAATTATT AACAAACCAA AAGGCGTTGC CACTTACACC CTTACCTTTA GGTTTTTAAA    4620

CTTTAACAGA CTAAGCGGAG GTACCCTGTT TAAAACTGAT GTCTTAACCT TTACCTATGT    4680
```

-continued

```
AGGCGAAAAT CAATAAAACC AGAAAAAAAT AAGGGGAAAA GCTTGATATC GAATTCCTGC       4740

AGCCCGGGGG ATCCACTAGT TCTAGAGCGG CCGCCACCGC GGTGGAGCTC CAGCTTTTGT       4800

TCCCTTTAGT GAGGGTTAAT TCCGAGCTTG GCGTAATCAT GGTCATAGCT GTTTCCTGTG       4860

TGAAATTGTT ATCCGCTCAC AATTCCACAC AACATACGAG CCGGAAGCAT AAAGTGTAAA       4920

GCCTGGGGTG CCTAATGAGT GAGCTAACTC ACATTAATTG CGTTGCGCTC ACTGCCCGCT       4980

TTCCAGTCGG GAAACCTGTC GTGCCAGCTG CATTAATGAA TCGGCCAACG CGCGGGGAGA       5040

GGCGGTTTGC GTATTGGGCG CTCTTCCGCT TCCTCGCTCA CTGACTCGCT GCGCTCGGTC       5100

GTTCGGCTGC GGCGAGCGGT ATCAGCTCAC TCAAAGGCGG TAATACGGTT ATCCACAGAA       5160

TCAGGGGATA ACGCAGGAAA GAACATGTGA GCAAAAGGCC AGCAAAAGGC CAGGAACCGT       5220

AAAAAGGCCG CGTTGCTGGC GTTTTTCCAT AGGCTCCGCC CCCCTGACGA GCATCACAAA       5280

AATCGACGCT CAAGTCAGAG GTGGCGAAAC CCGACAGGAC TATAAAGATA CCAGGCGTTT       5340

CCCCCTGGAA GCTCCCTCGT GCGCTCTCCT GTTCCGACCC TGCCGCTTAC CGGATACCTG       5400

TCCGCCTTTC TCCCTTCGGG AAGCGTGGCG CTTTCTCATA GCTCACGCTG TAGGTATCTC       5460

AGTTCGGTGT AGGTCGTTCG CTCCAAGCTG GGCTGTGTGC ACGAACCCCC CGTTCAGCCC       5520

GACCGCTGCG CCTTATCCGG TAACTATCGT CTTGAGTCCA ACCCGGTAAG ACACGACTTA       5580

TCGCCACTGG CAGCAGCCAC TGGTAACAGG ATTAGCAGAG CGAGGTATGT AGGCGGTGCT       5640

ACAGAGTTCT TGAAGTGGTG GCCTAACTAC GGCTACACTA GAAGGACAGT ATTTGGTATC       5700

TGCGCTCTGC TGAAGCCAGT TACCTTCGGA AAAAGAGTTG GTAGCTCTTG ATCCGGCAAA       5760

CAAACCACCG CTGGTAGCGG TGGTTTTTTT GTTTGCAAGC AGCAGATTAC GCGCAGAAAA       5820

AAAGGATCTC AAGAAGATCC TTTGATCTTT TCTACGGGGT CTGACGCTCA GTGGAACGAA       5880

AACTCACGTT AAGGGATTTT GGTCATGAGA TTATCAAAAA GGATCTTCAC CTAGATCCTT       5940

TTAAATTAAA AATGAAGTTT TAAATCAATC TAAAGTATAT ATGAGTAAAC TTGGTCTGAC       6000

AGTTACCAAT GCTTAATCAG TGAGGCACCT ATCTCAGCGA TCTGTCTATT TCGTTCATCC       6060

ATAGTTGCCT GACTCCCCGT CGTGTAGATA ACTACGATAC GGGAGGGCTT ACCATCTGGC       6120

CCCAGTGCTG CAATGATACC GCGAGACCCA CGCTCACCGG CTCCAGATTT ATCAGCAATA       6180

AACCAGCCAG CCGGAAGGGC CGAGCGCAGA AGTGGTCCTG CAACTTTATC CGCCTCCATC       6240

CAGTCTATTA ATTGTTGCCG GGAAGCTAGA GTAAGTAGTT CGCCAGTTAA TAGTTTGCGC       6300

AACGTTGTTG CCATTGCTAC AGGCATCGTG GTGTCACGCT CGTCGTTTGG TATGGCTTCA       6360

TTCAGCTCCG GTTCCCAACG ATCAAGGCGA GTTACATGAT CCCCCATGTT GTGCAAAAAA       6420

GCGGTTAGCT CCTTCGGTCC TCCGATCGTT GTCAGAAGTA AGTTGGCCGC AGTGTTATCA       6480

CTCATGGTTA TGGCAGCACT GCATAATTCT CTTACTGTCA TGCCATCCGT AAGATGCTTT       6540

TCTGTGACTG GTGAGTACTC AACCAAGTCA TTCTGAGAAT AGTGTATGCG GCGACCGAGT       6600

TGCTCTTGCC CGGCGTCAAT ACGGGATAAT ACCGCGCCAC ATAGCAGAAC TTTAAAAGTG       6660

CTCATCATTG GAAAACGTTC TTCGGGGCGA AAACTCTCAA GGATCTTACC GCTGTTGAGA       6720

TCCAGTTCGA TGTAACCCAC TCGTGCACCC AACTGATCTT CAGCATCTTT TACTTTCACC       6780

AGCGTTTCTG GGTGAGCAAA AACAGGAAGG CAAAATGCCG CAAAAAAGGG AATAAGGGCG       6840

ACACGGAAAT GTTGAATACT CATACTCTTC CTTTTTCAAT ATTATTGAAG CATTTATCAG       6900

GGTTATTGTC TCATGAGCGG ATACATATTT GAATGTATTT AGAAAAATAA ACAAATAGGG       6960

GTTCCGCGCA CATTTCCCCG AAAAGTGCCA CCTG                                  6994
```

(2) INFORMATION FOR SEQ ID NO:2:

(i) SEQUENCE CHARACTERISTICS:
        (A) LENGTH: 6958 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
TCGACGGTAT CGATAAGCTT TGCTCAACAA ATACTGTCAA GGACTCGAGT CCGGCTCTGA     60

CTGAGCAATG TCTAAAGAAA TACCAACCCC TTATATGTGG AGCTACCAAC CGCAAACGGG    120

ACACGCCGGC GCCTCCCAGG ACTACTCCAC CCAAATGAAT TGGTTTAGTG CTGGGCCATC    180

AATGATTAGT CAAGTTTATG CATTAGAGA CTTGCGCAAC AAAGTTTTGA TAACCCAGGC     240

AGAAATAACC AAAACTCCCA GAACAATAAT GGATCCGCCA ATTTGGCCAG CTGCCATGCT    300

TGTTCAGGAA GCCGCCCCAC CCAAAACGGT CACTCTGCCC AGAAACCACA CCCTAGAACA    360

GGCTATGACC AACTCTGGGG CGCAGCTAGC GGGAGGACGA CAGCTGTGCC CCTCCCAAAT    420

AGGTATAAAA AGCCCAGTGC TGGCTGGCAC GGGCATTCAG CTTAGCGAAG ACATCCCCAG    480

CGCCTCCTGG ATCAGGCCCG ACGGCATATT CCAGCTAGGA GGGGGGTCTC GCTCGTCCTT    540

CAGCCCAACG CAAGCATTCC TCACCCTGCA ACAGGCATCC TCGACGCCGC GCGCAGGAGG    600

CGTGGGCACC TACCAGTTTG TGCGCGAATT TGTGCCAGAG GTATACCTTA ACCCTTTTTC    660

AGGACCACCG GACACCTTTC CTGATCAGTT CATTCCTAAC TACGACATTG TAACCAACTC    720

TGTCGATGGC TATGACTGAG GAGAGCATGG ACCAGGTGGA GGTGAACTGC CTGTGTGCTC    780

AGCATGCCCA AACCTGCACG CGCCCTCGCT GCTTTGCAAA GGAGGGTTTA TGTGCTAACT    840

GGTTTTACAA CCCAGCACTT GCCTTTGAAG GGTTTGATAT TCCAGACTCT TACCAAGAGG    900

GACACGGTGT GGACATAGAA GTTAAGTGTT CCCACCACTC CAGCAAACTG TGCCACAATG    960

GCCATGATAT GATCTGCTCA TACTCTCGCC TGGGATCCCA CATTAACATA AGATGTATTT   1020

GCAACAAGCC GCGGCCCCAC ATGAGCCTCA TTGAGGCAGC CTGTTCTATG TATAACCTTA   1080

ACTAGATAAT ATTATTAAAC TTGTTTTACA GCTACCACCA TAATGCGCTT CAGCTTCTTC   1140

ATCGCCGCCG TTCTTTTCTG CACCACAGGG GCCAGCAATG ACATTGTGAC TTGCTGCGCC   1200

CACACACCTT GCCTCCTACA CCTAGAAGTG GGCTTGGGGG CCAATGTCAG TTGGATAAAC   1260

TCTGACACAG GCCAGGCCCC GATTTGCCTC TCCAATGGCA TGTGCAACGC TACCCAGCAA   1320

GGCCTGCAGT TTTCTGCAAA CTTTTCTGAG GATGGCCTGT ACATCGCCCT CATTAAGGAG   1380

AGCAACTACG AGGGCGCTGA GCACTACTAC CTTGTCTATA TTTATGGAGA CTGCTACCAA   1440

ACTGCAAATG AGTCTGCCCA CGGGCCTATT TCCAGGCCCC TCAAAGATCT GCTAATGGAA   1500

CGCGTATCGC TGCCCCCACA GTACAGCAAT GACCTTAGCA ATGTGCGCTG GTATAAAGTA   1560

GACCCCAGCG GCTTCCAAGC CCAAAAAATC TCTAAAGTCA GAAGCGGAGG CAGAAAAGAG   1620

AACCTGCATC CCAACTGGGC CTTGGTTACC TATACTGGAG ACCTTCTTGT CTTGCATGTT   1680

TCGCCAAACA CCCTTGGACT GTGGCTGGCA GCCGTGCAGC ATCGCGGGGG CGCACTAAT    1740

TTCATTACCT TCAACATAAC TGTACCCAAC TGGCAACAAA ATCTAGTAAC CATATTTAAT   1800

CAACACGAGC CCCAAAAAAA GGGCGATAAT TATGAGGACA GTTTTATGGA ATGGACTCTG   1860

TTTAAAAAGC TCAAAAAAGG CTTATTTAGA GTAACTTGCA GAGCCAAGTC AATATTCCCA   1920

GAGTGCGTCC TCAACATCAC CCGCGACGGA ACTTTCCTGC TTATTGGGGA TAGCAAAAAG   1980
```

-continued

```
ACCCCCTATG TCATCCTGCT GCCCTTTTTT GCAAACCCCA AGAAGACAC  TCCAATTTTA    2040

ATGGCCCTTA GCCATTCCAT GCCCGTCGCC ATACCTGACA CTGCAATGCC TATATATATT    2100

TCCATCATGT TTTTTATTGT GGCCATGCTA GCCACCCTCA GCCTTCTAAT GGGACTAAAC    2160

AACAAAATCA GGCCCATGTA GCTTGTCAAA TAAACTTACC TAATTTTTGC TAAGACGTCT    2220

GGGTCCTGCG TTTCTATGTC CACCAAAGTC CCCTCTTCCC AGCTTTGGTA CTTCCACTTG    2280

TGCGCGCGAG CCAGCTTGCG GATGTGCTTG AAAGATAATG TGGTCTCTCC CAACAGCTTC    2340

CCGTTCACCA GCACCAGGGC CATGAAGCGG ACACGAAGAG CTCTACCTGC AAATTATGAC    2400

CCTGTATATC CATACGACGC CCCCGGGTCT TCCACACAAC CCCCTTTTTT TAATAACAAG    2460

CAAGGTCTCA CTGAGTCACC CCCAGGAACC CTGGCTGTCA ATGTTTCCCC TCCACTAACC    2520

TTTTCTACGT TAGGTGCCAT TAAACTTTCC ACAGGTCCCG GACTCACCCT CAACGAGGGC    2580

AAGTTACAAG CCAGCTTAGG GCCCGGCCTC ATCACAAATA CCGAGGGCCA AATCACTGTT    2640

GAAAATGTCA ACAAGGTTTT GTCTTTTACC TCCCCATTAC ATAAAAATGA AAACACTGTA    2700

TCCCTAGCGC TAGGAGATGG GTTAGAAGAT GAAAATGGCA CCCTTAAAGT GACCTTCCCT    2760

ACTCCCCCTC CCCCGCTACA ATTCTCCCCT CCCCTCACAA AAACAGGTGG TACTGTTTCC    2820

TTGCCCCTGC AAGACTCCAT GCAAGTGACA AATGGAAAAC TGGGCGTTAA GCTACCACCT    2880

ACGCACCTCC CTTGAAAAAA ACTGACCAGC AAGTTAGCCT CCAAGTAGGC TCGGGTCTCA    2940

CCGTGATTAA CGAACAGTTG CAAGCTGTCC AGCCTCCCGC AACCACCTAC AACGAGCCTC    3000

TTTCCAAAAC TGACAATTCT GTTTCTCTGC AAGTAGGTGC CGGCCTTGCC GTGCAGAGCG    3060

GACGTTTGGT GGCAACCCCT CCCCCGCCTC TCACCTTTAC ATCACCCCTA GAAAAAAATG    3120

AAAACACAGT GTCGCTACAA GTAGGCGCGG GCTTGTCTGT ACAAAACAAC GCCCTAGTAG    3180

CCACACCTCC CCCACCCTTA ACCTTTGCCT ATCCCTTAGT AAAAAATGAC AACCATGTAG    3240

CTCTAAGTGC TGGAAGTGGT TTAAGAATAT CTGGAGGCAG CCTCACGGTG GCCACTGGAC    3300

CTGGCCTTTC CCATCAAAAT GGAACAATAG GGGCTGTAGT AGGTGCAGGC CTCAAGTTTG    3360

AAAACAATGC CATTCTTGCA AAACTAGGCA ACGGTCTAAC CATTAGAGAT GGCGCTATTG    3420

AAGCAACCCA ACCCCAGCT  GCCCCCATAA CACTGTGGAC AGGGCCTGGC CTAGCATTAA    3480

TGGCTTTATG TAATGACACT CCAGTAATTA GGTCTTTATA TGCCTAACCA GAGACAGCAA    3540

CTTAGTCACA GTAAATGCTA GCTTTGTGGG AGAGGGGGG  TATCGAATAG TCAGCCCTAC    3600

CCAGTCACAA TTTAGCCTAA TTATGGAGTT TGATCAGTTT GGACAGCTTA TGTCCACAGG    3660

AAACATTAAC TCCACCACTA CTTGGGGAGA AAAGCCCTGG GGCAATAACA CTGTACAGCC    3720

ACGCCCAAGC CACACCTGGA AACTGTGCAT GCCTAACAGA GAAGTTTACT CCACTCCCGC    3780

CGCCACCATC ACCCGCTGTG GACTAGACAG CATTGCAGTC GACGGTGCCC AGCAGAAGTA    3840

TCGACTGCAT GCTAATTATT AACAAACCAA AAGGCGTTGC CACTTACACC CTTACCTTTA    3900

GGTTTTTAAA CTTTAACAGA CTAAGCGGAG GTACCCTGTT TAAAACTGAT GTCTTAACCT    3960

TTACCTATGT AGGCGAAAAT CAATAAAACC AGAAAAAAAT AAGGGGAAAA GCTTGATATC    4020

GAATTCCTGC AGCCCGGGGG ATCCACTAGT TCTAGAGCGG CCGCCACCGC GGTGGAGCTC    4080

CAGCTTTTGT TCCCTTTAGT GAGGGTTAAT TCCGAGCTTG GCGTAATCAT GGTCATAGCT    4140

GTTTCCTGTG TGAAATTGTT ATCCGCTCAC AATTCCACAC AACATACGAG CCGGAAGCAT    4200

AAAGTGTAAA GCCTGGGGTG CCTAATGAGT GAGCTAACTC ACATTAATTG CGTTGCGCTC    4260

ACTGCCCGCT TTCCAGTCGG GAAACCTGTC GTGCCAGCTG CATTAATGAA TCGGCCAACG    4320

CGCGGGGAGA GGCGGTTTGC GTATTGGGCG CTCTTCCGCT TCCTCGCTCA CTGACTCGCT    4380
```

```
GCGCTCGGTC GTTCGGCTGC GGCGAGCGGT ATCAGCTCAC TCAAAGGCGG TAATACGGTT    4440

ATCCACAGAA TCAGGGGATA ACGCAGGAAA GAACATGTGA GCAAAAGGCC AGCAAAAGGC    4500

CAGGAACCGT AAAAAGGCCG CGTTGCTGGC GTTTTTCCAT AGGCTCCGCC CCCCTGACGA    4560

GCATCACAAA AATCGACGCT CAAGTCAGAG GTGGCGAAAC CCGACAGGAC TATAAAGATA    4620

CCAGGCGTTT CCCCCTGGAA GCTCCCTCGT GCGCTCTCCT GTTCCGACCC TGCCGCTTAC    4680

CGGATACCTG TCCGCCTTTC TCCCTTCGGG AAGCGTGGCG CTTTCTCATA GCTCACGCTG    4740

TAGGTATCTC AGTTCGGTGT AGGTCGTTCG CTCCAAGCTG GGCTGTGTGC ACGAACCCCC    4800

CGTTCAGCCC GACCGCTGCG CCTTATCCGG TAACTATCGT CTTGAGTCCA ACCCGGTAAG    4860

ACACGACTTA TCGCCACTGG CAGCAGCCAC TGGTAACAGG ATTAGCAGAG CGAGGTATGT    4920

AGGCGGTGCT ACAGAGTTCT TGAAGTGGTG GCCTAACTAC GGCTACACTA GAAGGACAGT    4980

ATTTGGTATC TGCGCTCTGC TGAAGCCAGT TACCTTCGGA AAAAGAGTTG GTAGCTCTTG    5040

ATCCGGCAAA CAAACCACCG CTGGTAGCGG TGGTTTTTTT GTTTGCAAGC AGCAGATTAC    5100

GCGCAGAAAA AAAGGATCTC AAGAAGATCC TTTGATCTTT TCTACGGGGT CTGACGCTCA    5160

GTGGAACGAA AACTCACGTT AAGGGATTTT GGTCATGAGA TTATCAAAAA GGATCTTCAC    5220

CTAGATCCTT TTAAATTAAA AATGAAGTTT TAAATCAATC TAAAGTATAT ATGAGTAAAC    5280

TTGGTCTGAC AGTTACCAAT GCTTAATCAG TGAGGCACCT ATCTCAGCGA TCTGTCTATT    5340

TCGTTCATCC ATAGTTGCCT GACTCCCCGT CGTGTAGATA ACTACGATAC GGGAGGGCTT    5400

ACCATCTGGC CCCAGTGCTG CAATGATACC GCGAGACCCA CGCTCACCGG CTCCAGATTT    5460

ATCAGCAATA AACCAGCCAG CCGGAAGGGC CGAGCGCAGA AGTGGTCCTG CAACTTTATC    5520

CGCCTCCATC CAGTCTATTA ATTGTTGCCG GGAAGCTAGA GTAAGTAGTT CGCCAGTTAA    5580

TAGTTTGCGC AACGTTGTTG CCATTGCTAC AGGCATCGTG GTGTCACGCT CGTCGTTTGG    5640

TATGGCTTCA TTCAGCTCCG GTTCCCAACG ATCAAGGCGA GTTACATGAT CCCCCATGTT    5700

GTGCAAAAAA GCGGTTAGCT CCTTCGGTCC TCCGATCGTT GTCAGAAGTA AGTTGGCCGC    5760

AGTGTTATCA CTCATGGTTA TGGCAGCACT GCATAATTCT CTTACTGTCA TGCCATCCGT    5820

AAGATGCTTT TCTGTGACTG GTGAGTACTC AACCAAGTCA TTCTGAGAAT AGTGTATGCG    5880

GCGACCGAGT TGCTCTTGCC CGGCGTCAAT ACGGGATAAT ACCGCGCCAC ATAGCAGAAC    5940

TTTAAAAGTG CTCATCATTG GAAAACGTTC TTCGGGGCGA AAACTCTCAA GGATCTTACC    6000

GCTGTTGAGA TCCAGTTCGA TGTAACCCAC TCGTGCACCC AACTGATCTT CAGCATCTTT    6060

TACTTTCACC AGCGTTTCTG GGTGAGCAAA AACAGGAAGG CAAAATGCCG CAAAAAAGGG    6120

AATAAGGGCG ACACGGAAAT GTTGAATACT CATACTCTTC CTTTTTCAAT ATTATTGAAG    6180

CATTTATCAG GGTTATTGTC TCATGAGCGG ATACATATTT GAATGTATTT AGAAAAATAA    6240

ACAAATAGGG GTTCCGCGCA CATTTCCCCG AAAAGTGCCA CCTGGGAAAT TGTAAACGTT    6300

AATATTTTGT TAAAATTCGC GTTAAATTTT TGTTAAATCA GCTCATTTTT TAACCAATAG    6360

GCCGAAATCG GCAAAATCCC TTATAAATCA AAAGAATAGA CCGAGATAGG GTTGAGTGTT    6420

GTTCCAGTTT GGAACAAGAG TCCACTATTA AAGAACGTGG ACTCCAACGT CAAAGGGCGA    6480

AAAACCGTCT ATCAGGGCGA TGGCCCACTA CGTGAACCAT CACCCTAATC AAGTTTTTTG    6540

GGGTCGAGGT GCCGTAAAGC ACTAAATCGG AACCCTAAAG GGAGCCCCCG ATTTAGAGCT    6600

TGACGGGGAA AGCCGGCGAA CGTGGCGAGA AAGGAAGGGA AGAAAGCGAA AGGAGCGGGC    6660

GCTAGGGCGC TGGCAAGTGT AGCGGTCACG CTGCGCGTAA CCACCACACC CGCCGCGCTT    6720
```

```
AATGCGCCGC TACAGGGCGC GTCGCGCCAT TCGCCATTCA GGCTGCGCAA CTGTTGGGAA       6780

GGGCGATCGG TGCGGGCCTC TTCGCTATTA CGCCAGCTGG CGAAAGGGGG ATGTGCTGCA       6840

AGGCGATTAA GTTGGGTAAC GCCAGGGTTT TCCCAGTCAC GACGTTGTAA AACGACGGCC       6900

AGTGAATTGT AATACGACTC ACTATAGGGC GAATTGGGTA CCGGGCCCCC CCTCGAGG        6958

(2) INFORMATION FOR SEQ ID NO:3:

(i) SEQUENCE CHARACTERISTICS:
        (A) LENGTH: 7001 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TTTGTTAAAA TTCGCGTTAA ATTTTTGTTA AATCAGCTCA TTTTTTAACC AATAGGCCGA         60

AATCGGCAAA ATCCCTTATA AATCAAAAGA ATAGACCGAG ATAGGGTTGA GTGTTGTTCC        120

AGTTTGGAAC AAGAGTCCAC TATTAAAGAA CGTGGACTCC AACGTCAAAG GGCGAAAAAC        180

CGTCTATCAG GGCGATGGCC CACTACGTGA ACCATCACCC TAATCAAGTT TTTTGGGGTC        240

GAGGTGCCGT AAAGCACTAA ATCGGAACCC TAAAGGGAGC CCCCGATTTA GAGCTTGACG        300

GGGAAAGCCG GCGAACGTGG CGAGAAAGGA AGGGAAGAAA GCGAAAGGAG CGGGCGCTAG        360

GGCGCTGGCA AGTGTAGCGG TCACGCTGCG CGTAACCACC ACACCCGCCG CGCTTAATGC        420

GCCGCTACAG GGCGCGTCGC GCCATTCGCC ATTCAGGCTG CGCAACTGTT GGGAAGGGCG        480

ATCGGTGCGG GCCTCTTCGC TATTACGCCA GCTGGCGAAA GGGGGATGTG CTGCAAGGCG        540

ATTAAGTTGG GTAACGCCAG GGTTTTCCCA GTCACGACGT TGTAAAACGA CGGCCAGTGA        600

ATTGTAATAC GACTCACTAT AGGGCGAATT GGGTACCGGG CCCCCCCTCG AGGTCGACGG        660

TATCGATAAG CTTTGCTCAA CAAATACTGT CAAGGACTCG AGTCCGGCTC TGACTGAGCA        720

ATGTCTAAAG AAATACCAAC CCCTTATATG TGGAGCTACC AACCGCAAAC GGGACACGCC        780

GGCGCCTCCC AGGACTACTC CACCCAAATG AATTGGTTTA GTGCTGGGCC ATCAATGATT        840

AGTCAAGTTT ATGGCATTAG AGACTTGCGC AACAAAGTTT TGATAACCCA GGCAGAAATA        900

ACCAAAACTC CCAGAACAAT AATGGATCCG CCAATTTGGC CAGCTGCCAT GCTTGTTCAG        960

GAAGCCGCCC CACCCAAAAC GGTCACTCTG CCCAGAAACC ACACCCTAGA ACAGGCTATG       1020

ACCAACTCTG GGGCGCAGCT AGCGGGAGGA CGACAGCTGT GCCCCTCCCA AATAGGTATA       1080

AAAAGCCCAG TGCTGGCTGG CACGGGCATT CAGCTTAGCG AAGACATCCC CAGCGCCTCC       1140

TGGATCAGGC CCGACGGCAT ATTCCAGCTA GGAGGGGGGT CTCGCTCGTC CTTCAGCCCA       1200

ACGCAAGCAT TCCTCACCCT GCAACAGGCA TCCTCGACGC CGCGCGCAGG AGGCGTGGGC       1260

ACCTACCAGT TTGTGCGCGA ATTTGTGCCA GAGGTATACC TTAACCCTTT TTCAGGACCA       1320

CCGGACACCT TTCCTGATCA GTTCATTCCT AACTACGACA TTGTAACCAA CTCTGTCGAT       1380

GGCTATGACT GAGGAGAGCA TGGACCAGGT GGAGGTGAAC TGCCTGTGTG CTCAGCATGC       1440

CCAAACCTGC ACGCGCCCTC GCTGCTTTGC AAAGGAGGGT TTATGTGCTA ACTGGTTTTA       1500

CAACCCAGCA CTTGCCTTTG AAGGGTTTGA TATTCCAGAC TCTTACCAAG AGGGACACGG       1560

TGTGGACATA GAAGTTAAGT GTTCCCACCA CTCCAGCAAA CTGTGCCACA ATGGCCATGA       1620

TATGATCTGC TCATACTCTC GCCTGGGATC CCACATTAAC ATAAGATGTA TTTGCAACAA       1680

GCCGCGGCCC CACATGAGCC TCATTGAGGC AGCCTGTTCT ATGTATAACC TTAACTAGAT       1740
```

```
AATATTATTA AACTTGTTTT ACAGCTACCA CCATAATGCG CTTCAGCTTC TTCATCGCCG    1800

CCGTTCTTTT CTGCACCACA GGGGCCAGCA ATGACATTGT GACTTGCTGC GCCCACACAC    1860

CTTGCCTCCT ACACCTAGAA GTGGGCTTGG GGGCCAATGT CAGTTGGATA AACTCTGACA    1920

CAGGCCAGGC CCCGATTTGC CTCTCCAATG GCATGTGCAA CGCTACCCAG CAAGGCCTGC    1980

AGTTTTCTGC AAACTTTTCT GAGGATGGCC TGTACATCGC CCTCATTAAG GAGAGCAACT    2040

ACGAGGGCGC TGAGCACTAC TACCTTGTCT ATATTTATGG AGACTGCTAC CAAACTGCAA    2100

ATGAGTCTGC CCACGGGCCT ATTTCCAGGC CCCTCAAAGA TCTGTTAACC CTAAGGCCAT    2160

GGCATATGTC GCGAGGCCAT CGTGGCCGCG GCCGCACGCG TATCGCTGCC CCCACAGTAC    2220

AGCAATGACC TTAGCAATGT GCGCTGGTAT AAAGTAGACC CCAGCGGCTT CCAAGCCCAA    2280

AAAATCTCTA AAGTCAGAAG CGGAGGCAGA AAAGAGAACC TGCATCCCAA CTGGGCCTTG    2340

GTTACCTATA CTGGAGACCT TCTTGTCTTG CATGTTTCGC CAAACACCCT TGGACTGTGG    2400

CTGGCAGCCG TGCAGCATCG CGGGGGGCGC ACTAATTTCA TTACCTTCAA CATAACTGTA    2460

CCCAACTGGC AACAAAATCT AGTAACCATA TTTAATCAAC ACGAGCCCCC AAAAAAGGGC    2520

GATAATTATG AGGACAGTTT TATGGAATGG ACTCTGTTTA AAAAGCTCAA AAAAGGCTTA    2580

TTTAGAGTAA CTTGCAGAGC CAAGTCAATA TTCCCAGAGT GCGTCCTCAA CATCACCCGC    2640

GACGGAACTT TCCTGCTTAT TGGGGATAGC AAAAAGACCC CCTATGTCAT CCTGCTGCCC    2700

TTTTTTGCAA ACCCCAAAGA AGACACTCCA ATTTTAATGG CCCTTAGCCA TTCCATGCCC    2760

GTCGCCATAC CTGACACTGC AATGCCTATA TATATTTCCA TCATGTTTTT TATTGTGGCC    2820

ATGCTAGCCA CCCTCAGCCT TCTAATGGGA CTAAACAACA AAATCAGGCC CATGTAGCTT    2880

GTCAAATAAA CTTACCTAAT TTTTGCTAAG ACGTCTGGGT CCTGCGTTTC TATGTCCACC    2940

AAAGTCCCCT CTTCCCAGCT TTGGTACTTC CACTTGTGCG CGCGAGCCAG CTTGCGGATG    3000

TGCTTGAAAG ATAATGTGGT CTCTCCCAAC AGCTTCCCGT TCACCAGCAC CAGGGCCATG    3060

AAGCGGACAC GAAGAGCTCT ACCTGCAAAT TATGACCCTG TATATCCATA CGACGCCCCC    3120

GGGTCTTCCA CACAACCCCC TTTTTTTAAT AACAAGCAAG GTCTCACTGA GTCACCCCCA    3180

GGAACCCTGG CTGTCAATGT TTCCCCTCCA CTAACCTTTT CTACGTTAGG TGCCATTAAA    3240

CTTTCCACAG GTCCCGGACT CACCCTCAAC GAGGGCAAGT TACAAGCCAG CTTAGGGCCC    3300

GGCCTCATCA CAAATACCGA GGGCCAAATC ACTGTTGAAA ATGTCAACAA GGTTTTGTCT    3360

TTTACCTCCC CATTACATAA AAATGAAAAC ACTGTATCCC TAGCGCTAGG AGATGGGTTA    3420

GAAGATGAAA ATGGCACCCT TAAAGTGACC TTCCCTACTC CCCCTCCCCC GCTACAATTC    3480

TCCCCTCCCC TCACAAAAAC AGGTGGTACT GTTTCCTTGC CCCTGCAAGA CTCCATGCAA    3540

GTGACAAATG GAAAACTGGG CGTTAAGCTA CCACCTACGC ACCTCCCTTG AAAAAAACTG    3600

ACCAGCAAGT TAGCCTCCAA GTAGGCTCGG GTCTCACCGT GATTAACGAA CAGTTGCAAG    3660

CTGTCCAGCC TCCCGCAACC ACCTACAACG AGCCTCTTTC CAAAACTGAC AATTCTGTTT    3720

CTCTGCAAGT AGGTGCCGGC CTTGCCGTGC AGAGCGGACG TTTGGTGGCA ACCCCTCCCC    3780

CGCCTCTCAC CTTTACATCA CCCCTAGAAA AAAATGAAAA CACAGTGTCG CTACAAGTAG    3840

GCGCGGGCTT GTCTGTACAA AACAACGCCC TAGTAGCCAC ACCTCCCCCA CCCTTAACCT    3900

TTGCCTATCC CTTAGTAAAA AATGACAACC ATGTAGCTCT AAGTGCTGGA AGTGGTTTAA    3960

GAATATCTGG AGGCAGCCTC ACGGTGGCCA CTGGACCTGG CCTTTCCCAT CAAAATGGAA    4020

CAATAGGGGC TGTAGTAGGT GCAGGCCTCA AGTTTGAAAA CAATGCCATT CTTGCAAAAC    4080

TAGGCAACGG TCTAACCATT AGAGATGGCG CTATTGAAGC AACCCAACCC CCAGCTGCCC    4140
```

```
CCATAACACT GTGGACAGGG CCTGGCCTAG CATTAATGGC TTTATGTAAT GACACTCCAG    4200

TAATTAGGTC TTTATATGCC TAACCAGAGA CAGCAACTTA GTCACAGTAA ATGCTAGCTT    4260

TGTGGGAGAG GGGGGGTATC GAATAGTCAG CCCTACCCAG TCACAATTTA GCCTAATTAT    4320

GGAGTTTGAT CAGTTTGGAC AGCTTATGTC CACAGGAAAC ATTAACTCCA CCACTACTTG    4380

GGGAGAAAAG CCCTGGGGCA ATAACACTGT ACAGCCACGC CCAAGCCACA CCTGGAAACT    4440

GTGCATGCCT AACAGAGAAG TTTACTCCAC TCCCGCCGCC ACCATCACCC GCTGTGGACT    4500

AGACAGCATT GCAGTCGACG GTGCCCAGCA GAAGTATCGA CTGCATGCTA ATTATTAACA    4560

AACCAAAAGG CGTTGCCACT TACACCCTTA CCTTTAGGTT TTTAAACTTT AACAGACTAA    4620

GCGGAGGTAC CCTGTTTAAA ACTGATGTCT TAACCTTTAC CTATGTAGGC GAAAATCAAT    4680

AAAACCAGAA AAAAATAAGG GGAAAAGCTT GATATCGAAT TCCTGCAGCC CGGGGGATCC    4740

ACTAGTTCTA GAGCGGCCGC CACCGCGGTG GAGCTCCAGC TTTTGTTCCC TTTAGTGAGG    4800

GTTAATTCCG AGCTTGGCGT AATCATGGTC ATAGCTGTTT CCTGTGTGAA ATTGTTATCC    4860

GCTCACAATT CCACACAACA TACGAGCCGG AAGCATAAAG TGTAAAGCCT GGGGTGCCTA    4920

ATGAGTGAGC TAACTCACAT TAATTGCGTT GCGCTCACTG CCCGCTTTCC AGTCGGGAAA    4980

CCTGTCGTGC CAGCTGCATT AATGAATCGG CCAACGCGCG GGGAGAGGCG GTTTGCGTAT    5040

TGGGCGCTCT TCCGCTTCCT CGCTCACTGA CTCGCTGCGC TCGGTCGTTC GGCTGCGGCG    5100

AGCGGTATCA GCTCACTCAA AGGCGGTAAT ACGGTTATCC ACAGAATCAG GGGATAACGC    5160

AGGAAAGAAC ATGTGAGCAA AAGGCCAGCA AAAGGCCAGG AACCGTAAAA AGGCCGCGTT    5220

GCTGGCGTTT TTCCATAGGC TCCGCCCCCC TGACGAGCAT CACAAAAATC GACGCTCAAG    5280

TCAGAGGTGG CGAAACCCGA CAGGACTATA AAGATACCAG GCGTTTCCCC CTGGAAGCTC    5340

CCTCGTGCGC TCTCCTGTTC CGACCCTGCC GCTTACCGGA TACCTGTCCG CCTTTCTCCC    5400

TTCGGGAAGC GTGGCGCTTT CTCATAGCTC ACGCTGTAGG TATCTCAGTT CGGTGTAGGT    5460

CGTTCGCTCC AAGCTGGGCT GTGTGCACGA ACCCCCCGTT CAGCCCGACC GCTGCGCCTT    5520

ATCCGGTAAC TATCGTCTTG AGTCCAACCC GGTAAGACAC GACTTATCGC CACTGGCAGC    5580

AGCCACTGGT AACAGGATTA GCAGAGCGAG GTATGTAGGC GGTGCTACAG AGTTCTTGAA    5640

GTGGTGGCCT AACTACGGCT ACACTAGAAG GACAGTATTT GGTATCTGCG CTCTGCTGAA    5700

GCCAGTTACC TTCGGAAAAA GAGTTGGTAG CTCTTGATCC GGCAAACAAA CCACCGCTGG    5760

TAGCGGTGGT TTTTTTGTTT GCAAGCAGCA GATTACGCGC AGAAAAAAAG GATCTCAAGA    5820

AGATCCTTTG ATCTTTTCTA CGGGGTCTGA CGCTCAGTGG AACGAAAACT CACGTTAAGG    5880

GATTTTGGTC ATGAGATTAT CAAAAAGGAT CTTCACCTAG ATCCTTTTAA ATTAAAAATG    5940

AAGTTTTAAA TCAATCTAAA GTATATATGA GTAAACTTGG TCTGACAGTT ACCAATGCTT    6000

AATCAGTGAG GCACCTATCT CAGCGATCTG TCTATTTCGT TCATCCATAG TTGCCTGACT    6060

CCCCGTCGTG TAGATAACTA CGATACGGGA GGGCTTACCA TCTGGCCCCA GTGCTGCAAT    6120

GATACCGCGA GACCCACGCT CACCGGCTCC AGATTTATCA GCAATAAACC AGCCAGCCGG    6180

AAGGGCCGAG CGCAGAAGTG GTCCTGCAAC TTTATCCGCC TCCATCCAGT CTATTAATTG    6240

TTGCCGGGAA GCTAGAGTAA GTAGTTCGCC AGTTAATAGT TTGCGCAACG TTGTTGCCAT    6300

TGCTACAGGC ATCGTGGTGT CACGCTCGTC GTTTGGTATG GCTTCATTCA GCTCCGGTTC    6360

CCAACGATCA AGGCGAGTTA CATGATCCCC CATGTTGTGC AAAAAAGCGG TTAGCTCCTT    6420

CGGTCCTCCG ATCGTTGTCA GAAGTAAGTT GGCCGCAGTG TTATCACTCA TGGTTATGGC    6480
```

```
AGCACTGCAT AATTCTCTTA CTGTCATGCC ATCCGTAAGA TGCTTTTCTG TGACTGGTGA    6540

GTACTCAACC AAGTCATTCT GAGAATAGTG TATGCGGCGA CCGAGTTGCT CTTGCCCGGC    6600

GTCAATACGG GATAATACCG CGCCACATAG CAGAACTTTA AAAGTGCTCA TCATTGGAAA    6660

ACGTTCTTCG GGGCGAAAAC TCTCAAGGAT CTTACCGCTG TTGAGATCCA GTTCGATGTA    6720

ACCCACTCGT GCACCCAACT GATCTTCAGC ATCTTTTACT TTCACCAGCG TTTCTGGGTG    6780

AGCAAAAACA GGAAGGCAAA ATGCCGCAAA AAGGGAATA AGGGCGACAC GGAAATGTTG    6840

AATACTCATA CTCTTCCTTT TTCAATATTA TTGAAGCATT TATCAGGGTT ATTGTCTCAT    6900

GAGCGGATAC ATATTTGAAT GTATTTAGAA AAATAAACAA ATAGGGGTTC CGCGCACATT    6960

TCCCCGAAAA GTGCCACCTG GGAAATTGTA AACGTTAATA T                       7001
```

(2) INFORMATION FOR SEQ ID NO:4:

(i) SEQUENCE CHARACTERISTICS:
        (A) LENGTH: 6578 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
ACTCATACTC TTCCTTTTTC AATATTATTG AAGCATTTAT CAGGGTTATT GTCTCATGAG      60

CGGATACATA TTTGAATGTA TTTAGAAAAA TAAACAAATA GGGGTTCCGC GCACATTTCC     120

CCGAAAAGTG CCACCTGGGA AATTGTAAAC GTTAATATTT TGTTAAAATT CGCGTTAAAT     180

TTTTGTTAAA TCAGCTCATT TTTTAACCAA TAGGCCGAAA TCGGCAAAAT CCCTTATAAA     240

TCAAAAGAAT AGACCGAGAT AGGGTTGAGT GTTGTTCCAG TTTGGAACAA GAGTCCACTA     300

TTAAAGAACG TGGACTCCAA CGTCAAAGGG CGAAAAACCG TCTATCAGGG CGATGGCCCA     360

CTACGTGAAC CATCACCCTA ATCAAGTTTT TTGGGGTCGA GGTGCCGTAA AGCACTAAAT     420

CGGAACCCTA AAGGGAGCCC CCGATTTAGA GCTTGACGGG GAAAGCCGGC GAACGTGGCG     480

AGAAAGGAAG GGAAGAAAGC GAAAGGAGCG GGCGCTAGGG CGCTGGCAAG TGTAGCGGTC     540

ACGCTGCGCG TAACCACCAC ACCCGCCGCG CTTAATGCGC CGCTACAGGG CGCGTCGCGC     600

CATTCGCCAT TCAGGCTGCG CAACTGTTGG GAAGGGCGAT CGGTGCGGGC CTCTTCGCTA     660

TTACGCCAGC TGGCGAAAGG GGGATGTGCT GCAAGGCGAT TAAGTTGGGT AACGCCAGGG     720

TTTTCCCAGT CACGACGTTG TAAAACGACG GCCAGTGAAT TGTAATACGA CTCACTATAG     780

GCGAATTGGG TACCGGGCCC CCCCTCGAGG TCGACGGTAT CGATAAGCTT TGCTCAACAA     840

ATACTGTCAA GGACTCGAGT CCGGCTCTGA CTGAGCAATG TCTAAAGAAA TACCAACCCC     900

TTATATGTGG AGCTACCAAC CGCAAACGGG ACACGCCGGC GCCTCCCAGG ACTACTCCAC     960

CCAAATGAAT TGGTTTAGTG CTGGGCCATC AATGATTAGT CAAGTTTATG GCATTAGAGA    1020

CTTGCGCAAC AAAGTTTTGA TAACCCAGGC AGAAATAACC AAAACTCCCA GAACAATAAT    1080

GGATCCGCCA ATTTGGCCAG CTGCCATGCT TGTTCAGGAA GCCGCCCCAC CCAAAACGGT    1140

CACTCTGCCC AGAAACCACA CCCTAGAACA GGCTATGACC AACTCTGGGG CGCAGCTAGC    1200

GGGAGGACGA CAGCTGTGCC CCTCCCAAAT AGGTATAAAA AGCCCAGTGC TGGCTGGCAC    1260

GGGCATTCAG CTTAGCGAAG ACATCCCCAG CGCCTCCTGG ATCAGGCCCG ACGGCATATT    1320

CCAGCTAGGA GGGGGGTCTC GCTCGTCCTT CAGCCCAACG CAAGCATTCC TCACCCTGCA    1380

ACAGGCATCC TCGACGCCGC GCGCAGGAGG CGTGGGCACC TACCAGTTTG TGCGCGAATT    1440
```

-continued

```
TGTGCCAGAG GTATACCTTA ACCCTTTTTC AGGACCACCG GACACCTTTC CTGATCAGTT    1500

CATTCCTAAC TACGACATTG TAACCAACTC TGTCGATGGC TATGACTGAG GAGAGCATGG    1560

ACCAGGTGGA GGTGAACTGC CTGTGTGCTC AGCATGCCCA AACCTGCACG CGCCCTCGCT    1620

GCTTTGCAAA GGAGGGTTTA TGTGCTAACT GGTTTTACAA CCCAGCACTT GCCTTTGAAG    1680

GGTTTGATAT TCCAGACTCT TACCAAGAGG GACACGGTGT GGACATAGAA GTTAAGTGTT    1740

CCCACCACTC CAGCAAACTG TGCCACAATG GCCATGATAT GATCTGCTCA TACTCTCGCC    1800

TGGGATCCCA CATTAACATA AGATGTATTT GCAACAAGCC GCGGCCCCAC ATGAGCCTCA    1860

TTGAGGCAGC CTGTTCTATG TATAACCTTA ACTAGATAAT ATTATTAAAC TTGTTTTACA    1920

GCTACCACCA TAATGCGCTT CAGCTTCTTC ATCGCCGCCG TTCTTTTCTG CACCACAGGG    1980

GCCAGCAATG ACATTGTGAC TTGCTGCGCC CACACACCTT GCCTCCTACA CCTAGAAGTG    2040

GGCTTGGGGG CCAATGTCAG TTGGATAAAC TCTGACACAG GCCAGGCCCC GATTTGCCTC    2100

TCCAATGGCA TGTGCAACGC TACCCAGCAA GGCCTGCAGT TTTCTGCAAA CTTTTCTGAG    2160

GATGGCCTGT ACATCGCCCT CATTAAGGAG AGCAACTACG AGGGCGCTGA GCACTACTAC    2220

CTTGTCTATA TTTATGGAGA CTGCTACCAA ACTGCAAATG AGTCTGCCCA CGGGCCTATT    2280

TCCAGGCCCC TCAAAGATCT GTTAACCCTA AGGCCATGGC ATATGTCGCG AGGCCATCGT    2340

GGCCGCGGCC GCACGCGTGT CCTCAACATC ACCCGCGACG GAACTTTCCT GCTTATTGGG    2400

GATAGCAAAA AGACCCCCTA TGTCATCCTG CTGCCCTTTT TTGCAAACCC CAAAGAAGAC    2460

ACTCCAATTT TAATGGCCCT TAGCCATTCC ATGCCCGTCG CCATACCTGA CACTGCAATG    2520

CCTATATATA TTTCCATCAT GTTTTTTATT GTGGCCATGC TAGCCACCCT CAGCCTTCTA    2580

ATGGGACTAA ACAACAAAAT CAGGCCCATG TAGCTTGTCA AATAAACTTA CCTAATTTTT    2640

GCTAAGACGC TGGGTCCTGC GTTTCTATGT CCACCAAAGT CCCCTCTTCC CAGCTTTGGT    2700

ACTTCCACTT GTGCGCGCGA GCCAGCTTGC GGATGTGCTT GAAAGATAAT GTGGTCTCTC    2760

CCAACAGCTT CCCGTTCACC AGCACCAGGG CCATGAAGCG GACACGAAGA GCTCTACCTG    2820

CAAATTATGA CCCTGTATAT CCATACGACG CCCCCGGGTC TTCCACACAA CCCCCTTTTT    2880

TTAATAACAA GCAAGGTCTC ACTGAGTCAC CCCCAGGAAC CCTGGCTGTC AATGTTTCCC    2940

CTCCACTAAC CTTTTCTACG TTAGGTGCCA TTAAACTTTC CACAGGTCCC GGACTCACCC    3000

TCAACGAGGG CAAGTTACAA GCCAGCTTAG GGCCCGGCCT CATCACAAAT ACCGAGGGCC    3060

AAATCACTGT TGAAAATGTC AACAAGGTTT TGTCTTTTAC CTCCCCATTA CATAAAAATG    3120

AAAACACTGT ATCCCTAGCG CTAGGAGATG GGTTAGAAGA TGAAAATGGC ACCCTTAAAG    3180

TGACCTTCCC TACTCCCCCT CCCCCGCTAC AATTCTCCCC TCCCCTCACA AAAACAGGTG    3240

GTACTGTTTC CTTGCCCCTG CAAGACTCCA TGCAAGTGAC AAATGGAAAA CTGGGCGTTA    3300

AGCTACCACC TACGCACCTC CCTTGAAAAA AACTGACCAG CAAGTTAGCC TCCAAGTAGG    3360

CTCGGGTCTC ACCGTGATTA ACGAACAGTT GCAAGCTGTC CAGCCTCCCG CAACCACCTA    3420

CAACGAGCCT CTTTCCAAAA CTGACAATTC TGTTTCTCTG CAAGTAGGTG CCGGCCTTGC    3480

CGTGCAGAGC GGACGTTTGG TGGCAACCCC TCCCCCGCCT CTCACCTTTA CATCACCCCT    3540

AGAAAAAAAT GAAAACACAG TGTCGCTACA AGTAGGCGCG GGCTTGTCTG TACAAAACAA    3600

CGCCCTAGTA GCCACACCTC CCCCACCCTT AACCTTTGCC TATCCCTTAG TAAAAAATGA    3660

CAACCATGTA GCTCTAAGTG CTGGAAGTGG TTTAAGAATA TCTGGAGGCA GCCTCACGGT    3720

GGCCACTGGA CCTGGCCTTT CCCATCAAAA TGGAACAATA GGGGCTGTAG TAGGTGCAGG    3780

CCTCAAGTTT GAAAACAATG CCATTCTTGC AAAACTAGGC AACGGTCTAA CCATTAGAGA    3840
```

```
TGGCGCTATT GAAGCAACCC AACCCCCAGC TGCCCCCATA ACACTGTGGA CAGGGCCTGG    3900

CCTAGCATTA ATGGCTTTAT GTAATGACAC TCCAGTAATT AGGTCTTTAT ATGCCTAACC    3960

AGAGACAGCA ACTTAGTCAC AGTAAATGCT AGCTTTGTGG GAGAGGGGG  GTATCGAATA    4020

GTCAGCCCTA CCCAGTCACA ATTTAGCCTA ATTATGGAGT TTGATCAGTT TGGACAGCTT    4080

ATGTCCACAG GAAACATTAA CTCCACCACT ACTTGGGGAG AAAAGCCCTG GGGCAATAAC    4140

ACTGTACAGC CACGCCCAAG CCACACCTGG AAACTGTGCA TGCCTAACAG AGAAGTTTAC    4200

TCCACTCCCG CCGCCACCAT CACCCGCTGT GGACTAGACA GCATTGCAGT CGACGGTGCC    4260

CAGCAGAAGT ATCGACTGCA TGCTAATTAT TAACAAACCA AAAGGCGTTG CCACTTACAC    4320

CCTTACCTTT AGGTTTTTAA ACTTTAACAG ACTAAGCGGA GGTACCCTGT TTAAAACTGA    4380

TGTCTTAACC TTTACCTATG TAGGCGAAAA TCAATAAAAC CAGAAAAAAA TAAGGGGAAA    4440

AGCTTGATAT CGAATTCCTG CAGCCCGGGG GATCCACTAG TTCTAGAGCG GCCGCCACCG    4500

CGGTGGAGCT CCAGCTTTTG TTCCCTTTAG TGAGGGTTAA TTCCGAGCTT GGCGTAATCA    4560

TGGTCATAGC TGTTTCCTGT GTGAAATTGT TATCCGCTCA CAATTCCACA CAACATACGA    4620

GCCGGAAGCA TAAAGTGTAA AGCCTGGGGT GCCTAATGAG TGAGCTAACT CACATTAATT    4680

GCGTTGCGCT CACTGCCCGC TTTCCAGTCG GGAAACCTGT CGTGCCAGCT GCATTAATGA    4740

ATCGGCCAAC GCGCGGGGAG AGGCGGTTTG CGTATTGGGC GCTCTTCCGC TTCCTCGCTC    4800

ACTGACTCGC TGCGCTCGGT CGTTCGGCTG CGGCGAGCGG TATCAGCTCA CTCAAAGGCG    4860

GTAATACGGT TATCCACAGA ATCAGGGGAT AACGCAGGAA AGAACATGTG AGCAAAAGGC    4920

CAGCAAAAGG CCAGGAACCG TAAAAAGGCC GCGTTGCTGG CGTTTTTCCA TAGGCTCCGC    4980

CCCCCTGACG AGCATCACAA AAATCGACGC TCAAGTCAGA GGTGGCGAAA CCCGACAGGA    5040

CTATAAAGAT ACCAGGCGTT TCCCCCTGGA AGCTCCCTCG TGCGCTCTCC TGTTCCGACC    5100

CTGCCGCTTA CCGGATACCT GTCCGCCTTT CTCCCTTCGG GAAGCGTGGC GCTTTCTCAT    5160

AGCTCACGCT GTAGGTATCT CAGTTCGGTG TAGGTCGTTC GCTCCAAGCT GGGCTGTGTG    5220

CACGAACCCC CCGTTCAGCC CGACCGCTGC GCCTTATCCG GTAACTATCG TCTTGAGTCC    5280

AACCCGGTAA GACACGACTT ATCGCCACTG GCAGCAGCCA CTGGTAACAG GATTAGCAGA    5340

GCGAGGTATG TAGGCGGTGC TACAGAGTTC TTGAAGTGGT GGCCTAACTA CGGCTACACT    5400

AGAAGGACAG TATTTGGTAT CTGCGCTCTG CTGAAGCCAG TTACCTTCGG AAAAAGAGTT    5460

GGTAGCTCTT GATCCGGCAA ACAAACCACC GCTGGTAGCG GTGGTTTTTT TGTTTGCAAG    5520

CAGCAGATTA CGCGCAGAAA AAAAGGATCT CAAGAAGATC CTTTGATCTT TTCTACGGGG    5580

TCTGACGCTC AGTGGAACGA AAACTCACGT TAAGGGATTT TGGTCATGAG ATTATCAAAA    5640

AGGATCTTCA CCTAGATCCT TTTAAATTAA AAATGAAGTT TTAAATCAAT CTAAAGTATA    5700

TATGAGTAAA CTTGGTCTGA CAGTTACCAA TGCTTAATCA GTGAGGCACC TATCTCAGCG    5760

ATCTGTCTAT TTCGTTCATC CATAGTTGCC TGACTCCCCG TCGTGTAGAT AACTACGATA    5820

CGGGAGGGCT TACCATCTGG CCCCAGTGCT GCAATGATAC CGCGAGACCC ACGCTCACCG    5880

GCTCCAGATT TATCAGCAAT AAACCAGCCA GCCGGAAGGG CCGAGCGCAG AAGTGGTCCT    5940

GCAACTTTAT CCGCCTCCAT CCAGTCTATT AATTGTTGCC GGGAAGCTAG AGTAAGTAGT    6000

TCGCCAGTTA ATAGTTTGCG CAACGTTGTT GCCATTGCTA CAGGCATCGT GGTGTCACGC    6060

TCGTCGTTTG GTATGGCTTC ATTCAGCTCC GGTTCCCAAC GATCAAGGCG AGTTACATGA    6120

TCCCCCATGT TGTGCAAAAA AGCGGTTAGC TCCTTCGGTC CTCCGATCGT TGTCAGAAGT    6180
```

-continued

```
AAGTTGGCCG CAGTGTTATC ACTCATGGTT ATGGCAGCAC TGCATAATTC TCTTACTGTC      6240

ATGCCATCCG TAAGATGCTT TTCTGTGACT GGTGAGTACT CAACCAAGTC ATTCTGAGAA      6300

TAGTGTATGC GGCGACCGAG TTGCTCTTGC CCGGCGTCAA TACGGGATAA TACCGCGCCA      6360

CATAGCAGAA CTTTAAAAGT GCTCATCATT GGAAAACGTT CTTCGGGGCG AAAACTCTCA      6420

AGGATCTTAC CGCTGTTGAG ATCCAGTTCG ATGTAACCCA CTCGTGCACC CAACTGATCT      6480

TCAGCATCTT TTACTTTCAC CAGCGTTTCT GGGTGAGCAA AAACAGGAAG GCAAAATGCC      6540

GCAAAAAAGG GAATAAGGGC GACACGGAAA TGTTGAAT                              6578

(2) INFORMATION FOR SEQ ID NO:5:

(i) SEQUENCE CHARACTERISTICS:
        (A) LENGTH: 6196 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GTCGACGGTG CCCCCAGCAG AAGTATCGAC TGCATGCTAA TTATTAACAA ACCAAAAGGC        60

GTTGCCACTT ACACCCTTAC CTTTAGGTTT TAAACTTTA ACAGACTAAG CGGAGGTACC       120

CTGTTTAAAA CTGATGTCTT AACCTTTACC TATGTAGGCG AAAATCAATA AAACCAGAAA      180

AAAATAAGTT TAAAAGCTTT ATTTTTCATA CACGCGAGCG GTAAGGCTGC CGCCTTCAGG      240

AAAAGTTACT CTGTAAACAG TTCTTTCACA ACAGCACAAA ACATAGGTAT TAGTTAACAG      300

TTCATTTGGG CTATAATAAT ATACATTTTC TTGGGTGGCA AAGCAAGGGT CGGTAATCTC      360

AACAAAACCA TCAACTGGAA TGCAAGAATA GTCCAGCACG GTGGGTTCAA TCTAAAAATG      420

AAGAAACGCT GTTGAGGTTC ACTAAGCACA GGTTTTGAAT CTGTCGGCAG CGTCCATGCA      480

TCATAGCTTG TCTCAAAGCA GATTGTCTTC TTTCCTCTGC CTTGGAAGTG GTTTGGTGAA      540

GCACTACAGG TGTCTTTTCA ACCTCTTTCA GCACCCGCTC TATTACAGAT CTCACCCACA      600

CAGCACAGTT TTTAAGAGAA CAATAGTTTT GAAGGCTACA AGATTTACAC TTAAGCACCA      660

GCCAGTAATT ATAAGTGCTT TTAAGAACTA CCCCTAGCTC AGGGTTAATG CACCTTTTAA      720

TGGCCTCCAT GCAGGCTTTA TGGACAGTTC TAAAAAAGA CAGTCTAAAA TAAATGTAGT      780

GAGTGTTTCT AAATATAATA CTCCCCACAT AGTTAATTTC ATCAGGCCTG CTAGAATTTA      840

CAAACTCTCG GTACCACATA TACTTTTTAT TCATAGCCCC ACCCTTAATA AAGTCCTCAA      900

TCACTTTCTG AACCACATGC TTGCTAGCCA TGCATTGTAA AGACAAGCTG TTAGAGCAGT      960

GACAGTGTAC TCGCCACGTT TGAGCCTCTG CCAGGCAGCA GTGCTTAGTT ACTATCAACT     1020

CAATACCCGC ATTGCATGTA AACCCCCCAA AGAGCAGTTT TTCATGCCTG TGTAGCACAT     1080

CATCCCACAA AATAGGAATT TCATAGCATA AAGCAAAGCA ATTACAATAT TTAGGAACTC     1140

TCACCACAGC AGTCACGTGA CATGTTGTCT CAGCAGTGCA GTTGCCTTCC ATCCTACAAT     1200

TATGAACAAA AACTAAACAC TTCTAACAAA GATCAGTGA CAATCTCCCT TCCTCTAAAA     1260

GCATTGTTTA CATTAGGGTG ATTATTAACA ACGTCAGAAA TTTCTTTAAT TAAAGTGCCT     1320

TTAAAATGTG CAAGAGCATC ATCATACTCA AAACCAAGCT GAGAGTAAAA GACCACCTTA     1380

AAAGTAATCC CAGGCTTGTT TTTATCAACA GCCTTAAACA TGCTTTCACA AAATATAGAA     1440

GCAGTAACAT CATCAATGGT GTCGAAGAGA AACTCCATAG GAGACTCCAG CATTGATCCA     1500

AGCTCTCTAA CAAAATCTTC CTCAAAATGA ATAATGCCCT TTACACAAAC GCGGGGCAGA     1560
```

-continued

```
CGATGGTGGG CCATCGCGTC AACCTGAAAC ACATTTTACA GTAAACAAAG CTAGCTCCGC    1620

AGTGGTAAAG TCATGCCCAT GGGTGAGGCC AAAATCCTTA AAAAAGCTAT CTAAGTAGTT    1680

GGTCATCCCC TCAGTTAAAA AGTTTTGCAG CTGGGTGGTG CATACCACAT AGTGCCAGCT    1740

TATAGCTACA AAGACCTGCA TCCCCTCCTT AGCAGACAGC TCTTGCACAC ACGCAGTAAC    1800

TATCCACCGC TTAAGAAAAG CTTTAAGCCC AGCGCACATA ACAGCTCCAA TGTTTTTATC    1860

CAAGGAGAGC AAAATTTCAG CAAGCGCAGG CTCAACAGTA ATAGTGAAGC AGAGGCATTT    1920

CAGACGAGGC TCACTAGCTG CAGTCGCCAT TTATGAGGTC TGCAATAAAA AACAACTCAT    1980

CAGCAGCTGA AAAAGTGCAC TTTGACCTCA TTAAGCCACT GCATATGCAA GTCCTCATCT    2040

ATGCCGCAGC CCAGACCCTC AATCCAGCCC CGAATGTACA CTTTAATAAG AGATTCAACC    2100

TCTTCTTTTA GCAAAGTACA CATGCTGTTT GGACTAGTAT ACACAATAGA AGTCACAATG    2160

AGGGGCCCGC TGTGGCTGGA AAGCCTGCGC ACAGCCCGAA GGTTAAAAAT GGACTGTAAC    2220

AGCATTGAAA CCCCGCGACA CAGGTCAGTC TCGCGGTCTT GATCTCTTAT TATAGCGACC    2280

AAATGGTCCT TCAGAGTGAT GTTGCACTCA TAGAAGTAGG CAGCTCCGGC AGCCATTCTG    2340

CAAAATAACA AAACACCACT AAGCATAGCA CCATCACCAA GCATGAAAAC AGGTAAAAAC    2400

AAAAGCAACA CTTACTTATT CAGCAGTCAC AAGAATGTTG GGCTCCCAAG TGACAGACAA    2460

GCCTAATGCA AGGTGGGCAC AGTCTCCGGA ATAAGTTGAC AAAAGTCACG CCGCAAAGCT    2520

TCCTGAAGAG AAACGGCGGT AGCCTGGATA TCTGCAACGG ACCCAAAACC TTCAGTGTCA    2580

CTTCCAATAA ACAGATAAAA CTCTAAATAG TCCCCACTTA AAACCGAAAC AGCCGCGGCA    2640

AAGGTAGGAC ACGGACGCAC TTCCTGAGCC CTAATAAGGC TAAACACCAC ACGGCGCAGT    2700

TCAGAAGGCA AAAAGTCTGT AAGCTCTAGC TGAGCACACA CACTCTCCAC TAGACACTTG    2760

TGAAGCCTCA GACAAAAACA TGCTCCCATA GACACTCCTA AAGCTGCCAT TGTACTCACG    2820

GACGGCTGGC TGTCAGAGGA GAGCTATGAG GATGAAATGC CAAGCACAGC GTTTATATAG    2880

TCCTCAAAGT AGGGCGTGTG GAAAACGAAA AGGAATATAA CGGGGCGTTT GAGGAAGTGG    2940

TGCCAAGTAC AGTCATAAAA TGTGGGCGCG TGGTAAATGT TAAGTGCAGT TTCCCTTTGG    3000

CGGTTGGCCC GGAAAGTTCA CAAAAAGTAC AGCACGTCCT TGTCACCGTG TCAACCACAA    3060

AACCACAAAT AGGCACAACG CCCAAAAACC CGGGGCGCCG GCCAAAAGTC CGCGGAACTC    3120

GCCCTGTCGT AAAACCACGC CTTTGACGTC ACTGGACATT CCCGTGGGAA CACCCTGACC    3180

AGGGCGTGAC CTGAACCTGA CCGTCCCATG ACCCCGCCCC TTGCAACACC CAAATTTAAG    3240

CCACACCTCT TTGTCCTGTA TATTATTGAT GATGGGGGA TCCACTAGTT CTAGAGCGGC     3300

CGCCACCGCG GTGGAGCTCC AGCTTTTGTT CCCTTTAGTG AGGGTTAATT CCGAGCTTGG    3360

CGTAATCATG GTCATAGCTG TTTCCTGTGT GAAATTGTTA TCCGCTCACA ATTCCACACA    3420

ACATACGAGC CGGAAGCATA AAGTGTAAAG CCTGGGGTGC CTAATGAGTG AGCTAACTCA    3480

CATTAATTGC GTTGCGCTCA CTGCCCGCTT TCCAGTCGGG AAACCTGTCG TGCCAGCTGC    3540

ATTAATGAAT CGGCCAACGC GCGGGGAGAG GCGGTTTGCG TATTGGGCGC TCTTCCGCTT    3600

CCTCGCTCAC TGACTCGCTG CGCTCGGTCG TTCGGCTGCG GCGAGCGGTA TCAGCTCACT    3660

CAAAGGCGGT AATACGGTTA TCCACAGAAT CAGGGGATAA CGCAGGAAAG AACATGTGAG    3720

CAAAAGGCCA GCAAAAGGCC AGGAACCGTA AAAAGGCCGC GTTGCTGGCG TTTTTCCATA    3780

GGCTCCGCCC CCCTGACGAG CATCACAAAA ATCGACGCTC AAGTCAGAGG TGGCGAAACC    3840

CGACAGGACT ATAAAGATAC CAGGCGTTTC CCCCTGGAAG CTCCCTCGTG CGCTCTCCTG    3900

TTCCGACCCT GCCGCTTACC GGATACCTGT CCGCCTTTCT CCCTTCGGGA AGCGTGGCGC    3960
```

```
TTTCTCATAG CTCACGCTGT AGGTATCTCA GTTCGGTGTA GGTCGTTCGC TCCAAGCTGG    4020

GCTGTGTGCA CGAACCCCCC GTTCAGCCCG ACCGCTGCGC CTTATCCGGT AACTATCGTC    4080

TTGAGTCCAA CCCGGTAAGA CACGACTTAT CGCCACTGGC AGCAGCCACT GGTAACAGGA    4140

TTAGCAGAGC GAGGTATGTA GGCGGTGCTA CAGAGTTCTT GAAGTGGTGG CCTAACTACG    4200

GCTACACTAG AAGGACAGTA TTTGGTATCT GCGCTCTGCT GAAGCCAGTT ACCTTCGGAA    4260

AAAGAGTTGG TAGCTCTTGA TCCGGCAAAC AAACCACCGC TGGTAGCGGT GGTTTTTTTG    4320

TTTGCAAGCA GCAGATTACG CGCAGAAAAA AAGGATCTCA AGAAGATCCT TTGATCTTTT    4380

CTACGGGGTC TGACGCTCAG TGGAACGAAA ACTCACGTTA AGGGATTTTG GTCATGAGAT    4440

TATCAAAAAG GATCTTCACC TAGATCCTTT TAAATTAAAA ATGAAGTTTT AAATCAATCT    4500

AAAGTATATA TGAGTAAACT TGGTCTGACA GTTACCAATG CTTAATCAGT GAGGCACCTA    4560

TCTCAGCGAT CTGTCTATTT CGTTCATCCA TAGTTGCCTG ACTCCCCGTC GTGTAGATAA    4620

CTACGATACG GGAGGGCTTA CCATCTGGCC CCAGTGCTGC AATGATACCG CGAGACCCAC    4680

GCTCACCGGC TCCAGATTTA TCAGCAATAA ACCAGCCAGC CGGAAGGGCC GAGCGCAGAA    4740

GTGGTCCTGC AACTTTATCC GCCTCCATCC AGTCTATTAA TTGTTGCCGG GAAGCTAGAG    4800

TAAGTAGTTC GCCAGTTAAT AGTTTGCGCA ACGTTGTTGC CATTGCTACA GGCATCGTGG    4860

TGTCACGCTC GTCGTTTGGT ATGGCTTCAT TCAGCTCCGG TTCCCAACGA TCAAGGCGAG    4920

TTACATGATC CCCCATGTTG TGCAAAAAAG CGGTTAGCTC CTTCGGTCCT CCGATCGTTG    4980

TCAGAAGTAA GTTGGCCGCA GTGTTATCAC TCATGGTTAT GGCAGCACTG CATAATTCTC    5040

TTACTGTCAT GCCATCCGTA AGATGCTTTT CTGTGACTGG TGAGTACTCA ACCAAGTCAT    5100

TCTGAGAATA GTGTATGCGG CGACCGAGTT GCTCTTGCCC GGCGTCAATA CGGGATAATA    5160

CCGCGCCACA TAGCAGAACT TTAAAAGTGC TCATCATTGG AAAACGTTCT TCGGGGCGAA    5220

AACTCTCAAG GATCTTACCG CTGTTGAGAT CCAGTTCGAT GTAACCCACT CGTGCACCCA    5280

ACTGATCTTC AGCATCTTTT ACTTTCACCA GCGTTTCTGG GTGAGCAAAA ACAGGAAGGC    5340

AAAATGCCGC AAAAAAGGGA ATAAGGGCGA CACGGAAATG TTGAATACTC ATACTCTTCC    5400

TTTTTCAATA TTATTGAAGC ATTTATCAGG GTTATTGTCT CATGAGCGGA TACATATTTG    5460

AATGTATTTA GAAAAATAAA CAAATAGGGG TTCCGCGCAC ATTTCCCCGA AAAGTGCCAC    5520

CTGGGAAATT GTAAACGTTA ATATTTTGTT AAAATTCGCG TTAAATTTTT GTTAAATCAG    5580

CTCATTTTTT AACCAATAGG CCGAAATCGG CAAAATCCCT TATAAATCAA AAGAATAGAC    5640

CGAGATAGGG TTGAGTGTTG TTCCAGTTTG GAACAAGAGT CCACTATTAA AGAACGTGGA    5700

CTCCAACGTC AAAGGGCGAA AAACCGTCTA TCAGGGCGAT GGCCCACTAC GTGAACCATC    5760

ACCCTAATCA AGTTTTTTGG GGTCGAGGTG CCGTAAAGCA CTAAATCGGA ACCCTAAAGG    5820

GAGCCCCCGA TTTAGAGCTT GACGGGGAAA GCCGGCGAAC GTGGCGAGAA AGGAAGGGAA    5880

GAAAGCGAAA GGAGCGGGCG CTAGGGCGCT GGCAAGTGTA GCGGTCACGC TGCGCGTAAC    5940

CACCACACCC GCCGCGCTTA ATGCGCCGCT ACAGGGCGCG TCGCGCCATT CGCCATTCAG    6000

GCTGCGCAAC TGTTGGGAAG GGCGATCGGT GCGGGCCTCT TCGCTATTAC GCCAGCTGGC    6060

GAAAGGGGGA TGTGCTGCAA GGCGATTAAG TTGGGTAACG CCAGGGTTTT CCCAGTCACG    6120

ACGTTGTAAA ACGACGGCCA GTGAATTGTA ATACGACTCA CTATAGGGCG AATTGGGTAC    6180

CGGGCCCCCC CTCGAG                                                   6196
```

(2) INFORMATION FOR SEQ ID NO:6:

(i) SEQUENCE CHARACTERISTICS:
    (A) LENGTH: 6503 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:6:

```
TCGACGGTGC CCCCAGCAGA AGTATCGACT GCATGCTAAT TATTAACAAA CCAAAAGGCG    60
TTGCCACTTA CACCCTTACC TTTAGGTTTT TAAACTTTAA CAGACTAAGC GGAGGTACCC   120
TGTTTAAAAC TGATGTCTTA ACCTTTACCT ATGTAGGCGA AAATCAATAA AACCAGAAAA   180
AAATAAGTTT AAAAGCTTTA TTTTTCATAC ACGCGAGCGG TAAGGCTGCC GCCTTCAGGA   240
AAAGTTACTC TGTAAACAGT TCTTTCACAA CAGCACAAAA CATAGGTATT AGTTAACAGT   300
TCATTTGGGC TATAATAATA TACATTTTCT TGGGTGGCAA AGCAAGGGTC GGTAATCTCA   360
ACAAAACCAT CAACTGGAAT GCAAGAATAG TCCAGCACGG TGGGTTCAAT CTAAAAATGA   420
AGAAACGCTG TTGAGGTTCA CTAAGCACAG GTTTTGAATC TGTCGGCAGC GTCCATGCAT   480
CATAGCTTGT CTCAAAGCAG ATTGTCTTCT TTCCTCTGCC TTGGAAGTGG TTTGGTGAAG   540
CACTACAGGT GTCTTTTCAA CCTCTTTCAG CACCCGCTCT ATTACAGATC TCACCCACAC   600
AGCACAGTTT TTAAGAGAAC AATAGTTTTG AAGGCTACAA GATTTACACT TAAGCACCAG   660
CCAGTAATTA TAAGTGCTTT TAAGAACTAC CCCTAGCTCA GGGTTAATGC ACCTTTTAAT   720
GGCCTCCATG CAGGCTTTAT GGACAGTTCT AAAAAAAGAC AGTCTAAAAT AAATGTAGTG   780
AGTGTTTCTA AATATAATAC TCCCCACATA GTTAATTTCA TCAGGCCTGC TAGAATTTAC   840
AAACTCTCGG TACCACATAT ACTTTTTATT CATAGCCCCA CCCTTAATAA AGTCCTCAAT   900
CACTTTCTGA ACCACATGCT TGCTAGCCAT GCATTGTAAA GACAAGCTGT TAGAGCAGTG   960
ACAGTGTACT CGCCACGTTT GAGCCTCTGC CAGGCAGCAG TGCTTAGTTA CTATCAACTC  1020
AATACCCGCA TTGCATGTAA ACCCCCCAAA GAGCAGTTTT TCATGCCTGT GTAGCACATC  1080
ATCCCACAAA ATAGGAATTT CATAGCATAA AGCAAAGCAA TTACAATATT TAGGAACTCT  1140
CACCACAGCA GTCACGTGAC ATGTTGTCTC AGCAGTGCAG TTGCCTTCCA TCCTACAATT  1200
ATGAACAAAA ACTAAACACT TCTAACAAAG ATACAGTGAC AATCTCCCTT CCTCTAAAAG  1260
CATTGTTTAC ATTAGGGTGA TTATTAACAA CGTCAGAAAT TTCTTTAATT AAAGTGCCTT  1320
TAAAATGTGC AAGAGCATCA TCATACTCAA AACCAAGCTG AGAGTAAAAG ACCACCTTAA  1380
AAGTAATCCC AGGCTTGTTT TTATCAACAG CCTTAAACAT GCTTTCACAA AATATAGAAG  1440
CAGTAACATC ATCAATGGTG TCGAAGAGAA ACTCCATAGG AGACTCCAGC ATTGATCCAA  1500
GCTCTCTAAC AAAATCTTCC TCAAAATGAA TAATGCCCTT TACACAAACG CGGGGCAGAC  1560
GATGGTGGGC CATCGCGTCA ACCTGAAACA CATTTTACAG TAAACAAAGC TAGCTCCGCA  1620
GTGGTAAAGT CATGCCCATG GGTGAGGCCA AAATCCTTAA AAAAGCTATC TAAGTAGTTG  1680
GTCATCCCCT CAGTTAAAAA GTTTTGCAGC TGGGTGGTGC ATACCACATA GTGCCAGCTT  1740
ATAGCTACAA AGACCTGCAT CCCCTCCTTA GCAGACAGCT CTTGCACACA CGCAGTAACT  1800
ATCCACCGCT TAAGAAAAGC TTTAAGCCCA GCGCACATAA CAGCTCCAAT GTTTTTATCC  1860
AAGGAGAGCA AAATTTCAGC AAGCGCAGGC TCAACAGTAA TAGTGAAGCA GAGGCATTTC  1920
AGACGAGGCT CACTAGCTGC AGTCGCCATT TATGAGGTCT GCAATAAAAA ACAACTCATC  1980
AGCAGCTGAA AAAGTGCACT TTGACCTCAT TAAGCCACTG CATATGCAAG TCCTCATCTA  2040
```

```
TGCCGCAGCC CAGACCCTCA ATCCAGCCCC GAATGTACAC TTTAATAAGA GATTCAACCT    2100

CTTCTTTTAG CAAAGTACAC ATGCTGTTTG GACTAGTATA CACAATAGAA GTCACAATGA    2160

GGGGCCCGCT GTGGCTGGAA AGCCTGCGCA CAGCCCGAAG GTTAAAAATG GACTGTAACA    2220

GCATTGAAAC CCCGCGACAC AGGTCAGTCT CGCGGTCTTG ATCTCTTATT ATAGCGACCA    2280

AATGGTCCTT CAGAGTGATG TTGCACTCAT AGAAGTAGGC AGCTCCGGCA GCCATTCTGC    2340

AAAATAACAA AACACCACTA AGCATAGCAC CATCACCAAG CATGAAAACA GGTAAAAACA    2400

AAAGCAACAC TTACTTATTC AGCAGTCACA AGAATGTTGG GCTCCCAAGT GACAGACAAG    2460

CCTAATGCAA GGTGGGCACA GTCTCCGGAA TAAGTTGACA AAAGTCACGC CGCAAAGCTT    2520

CCTGAAGAGA AACGGCGGTA GCCTGGATAT CTGCAACGGA CCCAAAACCT TCAGTGTCAC    2580

TTCCAATAAA CAGATAAAAC TCTAAATAGT CCCCACTTAA AACCGAAACA GCCGCGGCAA    2640

AGGTAGGACA CGGACGCACT TCCTGAGCCC TAATAAGGCT AAACACCACA CGGCGCAGTT    2700

CAGAAGGCAA AAAGTCTGTA AGCTCTAGCT GAGCACACAC ACTCTCCACT AGACACTTGT    2760

GAAGCCTCAG ACAAAAACAT GCTCCCATAG ACACTCCTAA AGCTGCCATT GTACTCACGG    2820

ACGGCTGGCT GTCAGAGGAG AGCTATGAGG ATGAAATGCC AAGCACAGCG TTTATATAGT    2880

CCTCAAAGTA GGGCGTGTGG AAAACGAAAA GGAATATAAC GGGGCGTTTG AGGAAGTGGT    2940

GCCAAGTACA GTCATAAAAT GTGGGCGCGT GGTAAATGTT AAGTGCAGTT TCCCTTTGGC    3000

GGTTGGCCCG GAAAGTTCAC AAAAAGTACA GCACGTCCTT GTCACCGTGT CAACCACAAA    3060

ACCACAAATA GGCACAACGC CCAAAAACCC ATCAAAGATG GTCCGGTTCT TGTACTCGGG    3120

CCATATATTC ATGTCCCCAG ACATCATAGT CAGCACCATT TTCTTCTCCT TTTGCCAGTA    3180

GATGCGAGTT TGTGCCAGCT CTTCAACAGA AACATTGTGA CCACAGGACA GCGTTGCCAC    3240

TTCTTTCACT TCCTTGGTCA CGTGGATAAC ACCTGAACAG AAGTGAGAAA GACCAGCCAG    3300

CACCAAGAGC TGAAAGAAAT TGAGGTATGG ACACTTGGAT GGTGATGTTC CCTGCCTCCG    3360

TGTGTGGCCC ATTACGATAC AAACTTAACG GATATCGGGG GCGCCGGCCA AAAGTCCGCG    3420

GAACTCGCCC TGTCGTAAAA CCACGCCTTT GACGTCACTG GACATTCCCG TGGGAACACC    3480

CTGACCAGGG CGTGACCTGA ACCTGACCGT CCCATGACCC CGCCCCTTGC AACACCCAAA    3540

TTTAAGCCAC ACCTCTTTGT CCTGTATATT ATTGATGATG GGGGGATCCA CTAGTTCTAG    3600

AGCGGCCGCC ACCGCGGTGG AGCTCCAGCT TTTGTTCCCT TTAGTGAGGG TTAATTCCGA    3660

GCTTGGCGTA ATCATGGTCA TAGCTGTTTC CTGTGTGAAA TTGTTATCCG CTCACAATTC    3720

CACACAACAT ACGAGCCGGA AGCATAAAGT GTAAAGCCTG GGGTGCCTAA TGAGTGAGCT    3780

AACTCACATT AATTGCGTTG CGCTCACTGC CCGCTTTCCA GTCGGGAAAC CTGTCGTGCC    3840

AGCTGCATTA ATGAATCGGC CAACGCGCGG GGAGAGGCGG TTTGCGTATT GGGCGCTCTT    3900

CCGCTTCCTC GCTCACTGAC TCGCTGCGCT CGGTCGTTCG GCTGCGGCGA GCGGTATCAG    3960

CTCACTCAAA GGCGGTAATA CGGTTATCCA CAGAATCAGG GGATAACGCA GGAAAGAACA    4020

TGTGAGCAAA AGGCCAGCAA AAGGCCAGGA ACCGTAAAAA GGCCGCGTTG CTGGCGTTTT    4080

TCCATAGGCT CCGCCCCCCT GACGAGCATC ACAAAAATCG ACGCTCAAGT CAGAGGTGGC    4140

GAAACCCGAC AGGACTATAA AGATACCAGG CGTTTCCCCC TGGAAGCTCC CTCGTGCGCT    4200

CTCCTGTTCC GACCCTGCCG CTTACCGGAT ACCTGTCCGC CTTTCTCCCT TCGGGAAGCG    4260

TGGCGCTTTC TCATAGCTCA CGCTGTAGGT ATCTCAGTTC GGTGTAGGTC GTTCGCTCCA    4320

AGCTGGGCTG TGTGCACGAA CCCCCCGTTC AGCCCGACCG CTGCGCCTTA TCCGGTAACT    4380

ATCGTCTTGA GTCCAACCCG GTAAGACACG ACTTATCGCC ACTGGCAGCA GCCACTGGTA    4440
```

-continued

```
ACAGGATTAG CAGAGCGAGG TATGTAGGCG GTGCTACAGA GTTCTTGAAG TGGTGGCCTA      4500

ACTACGGCTA CACTAGAAGG ACAGTATTTG GTATCTGCGC TCTGCTGAAG CCAGTTACCT      4560

TCGGAAAAAG AGTTGGTAGC TCTTGATCCG GCAAACAAAC CACCGCTGGT AGCGGTGGTT      4620

TTTTTGTTTG CAAGCAGCAG ATTACGCGCA GAAAAAAGG ATCTCAAGAA GATCCTTTGA       4680

TCTTTTCTAC GGGGTCTGAC GCTCAGTGGA ACGAAAACTC ACGTTAAGGG ATTTTGGTCA      4740

TGAGATTATC AAAAAGGATC TTCACCTAGA TCCTTTTAAA TTAAAAATGA AGTTTTAAAT      4800

CAATCTAAAG TATATATGAG TAAACTTGGT CTGACAGTTA CCAATGCTTA ATCAGTGAGG      4860

CACCTATCTC AGCGATCTGT CTATTTCGTT CATCCATAGT TGCCTGACTC CCCGTCGTGT      4920

AGATAACTAC GATACGGGAG GGCTTACCAT CTGGCCCCAG TGCTGCAATG ATACCGCGAG      4980

ACCCACGCTC ACCGGCTCCA GATTTATCAG CAATAAACCA GCCAGCCGGA AGGGCCGAGC      5040

GCAGAAGTGG TCCTGCAACT TTATCCGCCT CCATCCAGTC TATTAATTGT TGCCGGGAAG     5100

CTAGAGTAAG TAGTTCGCCA GTTAATAGTT TGCGCAACGT TGTTGCCATT GCTACAGGCA     5160

TCGTGGTGTC ACGCTCGTCG TTTGGTATGG CTTCATTCAG CTCCGGTTCC CAACGATCAA     5220

GGCGAGTTAC ATGATCCCCC ATGTTGTGCA AAAAAGCGGT TAGCTCCTTC GGTCCTCCGA     5280

TCGTTGTCAG AAGTAAGTTG GCCGCAGTGT TATCACTCAT GGTTATGGCA GCACTGCATA     5340

ATTCTCTTAC TGTCATGCCA TCCGTAAGAT GCTTTTCTGT GACTGGTGAG TACTCAACCA     5400

AGTCATTCTG AGAATAGTGT ATGCGGCGAC CGAGTTGCTC TTGCCCGGCG TCAATACGGG     5460

ATAATACCGC GCCACATAGC AGAACTTTAA AAGTGCTCAT CATTGGAAAA CGTTCTTCGG     5520

GGCGAAAACT CTCAAGGATC TTACCGCTGT TGAGATCCAG TTCGATGTAA CCCACTCGTG     5580

CACCCAACTG ATCTTCAGCA TCTTTTACTT TCACCAGCGT TTCTGGGTGA GCAAAAACAG     5640

GAAGGCAAAA TGCCGCAAAA AAGGGAATAA GGGCGACACG GAAATGTTGA ATACTCATAC     5700

TCTTCCTTTT TCAATATTAT TGAAGCATTT ATCAGGGTTA TTGTCTCATG AGCGGATACA     5760

TATTTGAATG TATTTAGAAA AATAAACAAA TAGGGGTTCC GCGCACATTT CCCCGAAAAG     5820

TGCCACCTGG GAAATTGTAA ACGTTAATAT TTTGTTAAAA TTCGCGTTAA ATTTTTGTTA     5880

AATCAGCTCA TTTTTTAACC AATAGGCCGA AATCGGCAAA ATCCCTTATA AATCAAAAGA     5940

ATAGACCGAG ATAGGGTTGA GTGTTGTTCC AGTTTGGAAC AAGAGTCCAC TATTAAAGAA     6000

CGTGGACTCC AACGTCAAAG GGCGAAAAAC CGTCTATCAG GGCGATGGCC CACTACGTGA     6060

ACCATCACCC TAATCAAGTT TTTTGGGGTC GAGGTGCCGT AAAGCACTAA ATCGGAACCC     6120

TAAAGGGAGC CCCCGATTTA GAGCTTGACG GGGAAAGCCG GCGAACGTGG CGAGAAAGGA     6180

AGGGAAGAAA GCGAAAGGAG CGGGCGCTAG GGCGCTGGCA AGTGTAGCGG TCACGCTGCG     6240

CGTAACCACC ACACCCGCCG CGCTTAATGC GCCGCTACAG GGCGCGTCGC GCCATTCGCC     6300

ATTCAGGCTG CGCAACTGTT GGGAAGGGCG ATCGGTGCGG GCCTCTTCGC TATTACGCCA     6360

GCTGGCGAAA GGGGGATGTG CTGCAAGGCG ATTAAGTTGG GTAACGCCAG GGTTTTCCCA     6420

GTCACGACGT TGTAAAACGA CGGCCAGTGA ATTGTAATAC GACTCACTAT AGGGCGAATT     6480

GGGTACCGGG CCCCCCCTCG AGG                                             6503
```

(2) INFORMATION FOR SEQ ID NO:7:

(i) SEQUENCE CHARACTERISTICS:
        (A) LENGTH: 4503 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
TAATGTCGTA ACAACTCCGC CCCGTTGACG CAAATGGGCG GTAGGCGTGT ACGGTGGGAG      60
GTCTATATAA GCAGAGCTCG TTTAGTGAAC CGTCAGATCG CCTGGAGACG CCATCCACGC     120
TGTTTTGACC TCCATAGAAG ACACCGGCTG CAGGTCGACT CTAGAGGATC TGAGCTTGGC     180
GAGATTTTCA GGAGCTAAGG AAGCTAAAAT GGAGAAAAAA ATCACTGGAT ATACCACCGT     240
TGATATATCC CAATGGCATC GTAAAGAACA TTTTGAGGCA TTTCAGTCAG TTGCTCAATG     300
TACCTATAAC CAGACCGTTC AGCTGGATAT TACGGCCTTT TTAAAGACCG TAAAGAAAAA     360
TAAGCACAAG TTTTATCCGG CCTTTATTCA CATTCTTGCC CGCCTGATGA ATGCTCATCC     420
GGAATTCCGT ATGGCAATGA AAGACGGTGA GCTGGTGATA TGGGATAGTG TTCACCCTTG     480
TTACACCGTT TTCATGAGC AAACTGAAAC GTTTTCATCG CTCTGGAGTG AATACCACGA     540
CGATTTCCGG CAGTTTCTAC ACATATATTC GCAAGATGTG GCGTGTTACG GTGAAAACCT     600
GGCCTATTTC CCTAAAGGGT TTATTGAGAA TATGTTTTTC GTCTCAGCCA ATCCCTGGGT     660
GAGTTTCACC AGTTTTGATT TAAACGTGGC CAATATGGAC AACTTCTTCG CCCCCGTTTT     720
CACCATGGGC AAATATTATA CGCAAGGCGA CAAGGTGCTG ATGCCGCTGG CGATTCAGGT     780
TCATCATGCC GTCTGTGATG GCTTCCATGT CGGCAGAATG CTTAATGAAT TACAACAGTA     840
CTGCGATGAG TGGCAGGGCG GGGCGTAATT TTTTTAAGGC AGTTATTGGT GCCCTTAAAC     900
GCCTGGTGCT ACGCCTGAAT AAGTGATAAT AAGCGGATGA ATGGCAGAAA TTCGCCGGAT     960
CTTTGTGAAG GAACCTTACT TCTGTGGTGT GACATAATTG GACAAACTAC CTACAGAGAT    1020
TTAAAGCTCT AAGGTAAATA TAAAATTTTT AAGTGTATAA TGTGTTAAAC TACTGATTCT    1080
AATTGTTTGT GTATTTTAGA TTCCAACCTA TGGAACTGAT GAATGGGAGC AGTGGTGGAA    1140
TGCCTTTAAT GAGGAAAACC TGTTTTGCTC AGAAGAAATG CCATCTAGTG ATGATGAGGC    1200
TACTGCTGAC TCTCAACATT CTACTCCTCC AAAAAAGAAG AGAAAGGTAG AAGACCCCAA    1260
GGACTTTCCT TCAGAATTGC TAAGTTTTTT GAGTCATGCT GTGTTTAGTA ATAGAACTCT    1320
TGCTTGCTTT GCTATTTACA CCACAAAGGA AAAAGCTGCA CTGCTATACA AGAAAATTAT    1380
GGAAAAATAT TCTGTAACCT TTATAAGTAG GCATAACAGT TATAATCATA ACATACTGTT    1440
TTTTCTTACT CCACACAGGC ATAGAGTGTC TGCTATTAAT AACTATGCTC AAAAATTGTG    1500
TACCTTTAGC TTTTTAATTT GTAAAGGGGT TAATAAGGAA TATTTGATGT ATAGTGCCTT    1560
GACTAGAGAT CATAATCAGC CATACCACAT TTGTAGAGGT TTTACTTGCT TTAAAAAACC    1620
TCCCACACCT CCCCCTGAAC CTGAAACATA AAATGAATGC AATTGTTGTT GTTAACTTGT    1680
TTATTGCAGC TTATAATGGT TACAAATAAA GCAATAGCAT CACAAATTTC ACAAATAAAG    1740
CATTTTTTTC ACTGCATTCT AGTTGTGGTT TGTCCAAACT CATCAATGTA TCTTATCATG    1800
TCTGGATCCC CCGGAATTCA CTGGCCGTCG TTTTACAACG TCGTGACTGG GAAAACCCTG    1860
GCGTTACCCA ACTTAATCGC CTTGCAGCAC ATCCCCCCTT CGCCAGCTGG CGTAATAGCG    1920
AAGAGGCCCG CACCGATCGC CCTTCCCAAC AGTTGCGCAG CCTGAATGGC GAATGGCGCC    1980
TGATGCGGTA TTTTCTCCTT ACGCATCTGT GCGGTATTTC ACACCGCATA TGGTGCACTC    2040
TCAGTACAAT CTGCTCTGAT GCCGCATAGT TAAGCCAGTA CACTCCGCTA TCGCTACGTG    2100
ACTGGGTCAT GGCTGCGCCC CGACACCCGC CAACACCCGC TGACGCGCCC TGACGGGCTT    2160
GTCTGCTCCC GGCATCCGCT TACAGACAAG CTGTGACCGT CTCCGGGAGC TGCATGTGTC    2220
```

-continued

```
AGAGGTTTTC ACCGTCATCA CCGAAACGCG CGAGGCAGTT CTTGAAGACG AAAGGGCCTC      2280

GTGATACGCC TATTTTTATA GGTTAATGTC ATGATAATAA TGGTTTCTTA GACGTCAGGT      2340

GGCACTTTTC GGGGAAATGT GCGCGGAACC CCTATTTGTT TATTTTTCTA AATACATTCA      2400

AATATGTATC CGCTCATGAG ACAATAACCC TGATAAATGC TTCAATAATA TTGAAAAAGG      2460

AAGAGTATGA GTATTCAACA TTTCCGTGTC GCCCTTATTC CCTTTTTTGC GGCATTTTGC      2520

CTTCCTGTTT TTGCTCACCC AGAAACGCTG GTGAAAGTAA AAGATGCTGA AGATCAGTTG      2580

GGTGCACGAG TGGGTTACAT CGAACTGGAT CTCAACAGCG GTAAGATCCT TGAGAGTTTT      2640

CGCCCCGAAG AACGTTTTCC AATGATGAGC ACTTTTAAAG TTCTGCTATG TGGCGCGGTA      2700

TTATCCCGTA TTGACGCCGG GCAAGAGCAA CTCGGTCGCC GCATACACTA TTCTCAGAAT      2760

GACTTGGTTG AGTACTCACC AGTCACAGAA AAGCATCTTA CGGATGGCAT GACAGTAAGA      2820

GAATTATGCA GTGCTGCCAT AACCATGAGT GATAACACTG CGGCCAACTT ACTTCTGACA      2880

ACGATCGGAG GACCGAAGGA GCTAACCGCT TTTTTGCACA ACATGGGGGA TCATGTAACT      2940

CGCCTTGATC GTTGGGAACC GGAGCTGAAT GAAGCCATAC CAAACGACGA GCGTGACACC      3000

ACGATGCCTG TAGCAATGGC AACAACGTTG CGCAAACTAT TAACTGGCGA ACTACTTACT      3060

CTAGCTTCCC GGCAACAATT AATAGACTGG ATGGAGGCGG ATAAAGTTGC AGGACCACTT      3120

CTGCGCTCGG CCCTTCCGGC TGGCTGGTTT ATTGCTGATA AATCTGGAGC CGGTGAGCGT      3180

GGGTCTCGCG GTATCATTGC AGCACTGGGG CCAGATGGTA AGCCCTCCCG TATCGTAGTT      3240

ATCTACACGA CGGGGAGTCA GGCAACTATG GATGAACGAA ATAGACAGAT CGCTGAGATA      3300

GGTGCCTCAC TGATTAAGCA TTGGTAACTG TCAGACCAAG TTTACTCATA TATACTTTAG      3360

ATTGATTTAA AACTTCATTT TTAATTTAAA AGGATCTAGG TGAAGATCCT TTTTGATAAT      3420

CTCATGACCA AAATCCCTTA ACGTGAGTTT TCGTTCCACT GAGCGTCAGA CCCCGTAGAA      3480

AAGATCAAAG GATCTTCTTG AGATCCTTTT TTTCTGCGCG TAATCTGCTG CTTGCAAACA      3540

AAAAAACCAC CGCTACCAGC GGTGGTTTGT TTGCCGGATC AAGAGCTACC AACTCTTTTT      3600

CCGAAGGTAA CTGGCTTCAG CAGAGCGCAG ATACCAAATA CTGTCCTTCT AGTGTAGCCG      3660

TAGTTAGGCC ACCACTTCAA GAACTCTGTA GCACCGCCTA CATACCTCGC TCTGCTAATC      3720

CTGTTACCAG TGGCTGCTGC CAGTGGCGAT AAGTCGTGTC TTACCGGGTT GGACTCAAGA      3780

CGATAGTTAC CGGATAAGGC GCAGCGGTCG GGCTGAACGG GGGGTTCGTG CACACAGCCC      3840

AGCTTGGAGC GAACGACCTA CACCGAACTG AGATACCTAC AGCGTGAGCA TTGAGAAAGC      3900

GCCACGCTTC CCGAAGGGAG AAAGGCGGAC AGGTATCCGG TAAGCGGCAG GGTCGGAACA      3960

GGAGAGCGCA CGAGGGAGCT TCCAGGGGGA AACGCCTGGT ATCTTTATAG TCCTGTCGGG      4020

TTTCGCCACC TCTGACTTGA GCGTCGATTT TTGTGATGCT CGTCAGGGGG GCGGAGCCTA      4080

TGGAAAAACG CCAGCAACGC GGCCTTTTTA CGGTTCCTGG CCTTTTGCTG GCCTTTTGCT      4140

CACATGTTCT TTCCTGCGTT ATCCCCTGAT TCTGTGGATA ACCGTATTAC CGCCTTTGAG      4200

TGAGCTGATA CCGCTCGCCG CAGCCGAACG ACCGAGCGCA GCGAGTCAGT GAGCGAGGAA      4260

GCGGAAGAGC GCCAATACGC AAACCGCCTC TCCCCGCGCG TTGGCCGATT CATTAATGCA      4320

GCTGGCACGA CAGGTTTCCC GACTGGAAAG CGGGCAGTGA GCGCAACGCA ATTAATGTGA      4380

GTTACCTCAC TCATTAGGCA CCCCAGGCTT TACACTTTAT GCTTCCGGCT CGTATGTTGT      4440

GTGGAATTGT GAGCGGATAA CAATTTCACA CAGGAAACAG CTATGACCAT GATTACGCCA      4500

GCT                                                                  4503
```

(2) INFORMATION FOR SEQ ID NO:8:

(i) SEQUENCE CHARACTERISTICS:
        (A) LENGTH: 3822 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
TAATGTCGTA ACAACTCCGC CCCGTTGACG CAAATGGGCG GTAGGCGTGT ACGGTGGGAG      60

GTCTATATAA GCAGAGCTCG TTTAGTGAAC CGTCAGATCG CCTGGAGACG CCATCCACGC     120

TGTTTTGACC TCCATAGAAG ACACCGGCTG CAGGTCGACT CTAGAGGATC TGAGCTTGGC     180

GAGATTTTCA GGAGCTAAGG AAGCTAAAAT GGAGAAAAAA ATCACTGGAT ATACCACCGT     240

TGATATATCC CAATGGCATC GTAAAGAACA TTTTGAGGCA TTTCAGTCAG TTGCTCAATG     300

TACCTATAAC CAGACCGTTC AGCTGGATAT TACGGCCTTT TTAAAGACCG TAAAGAAAAA     360

TAAGCACAAG TTTTATCCGG CCTTTATTCA CATTCTTGCC CGCCTGATGA ATGCTCATCC     420

GGAATTCCGT ATGGCAATGA AAGACGGTGA GCTGGTGATA TGGGATAGTG TTCACCCTTG     480

TTACACCGTT TTCCATGAGC AAACTGAAAC GTTTTCATCG CTCTGGAGTG AATACCACGA     540

CGATTTCCGG CAGTTTCTAC ACATATATTC GCAAGATGTG GCGTGTTACG GTGAAAACCT     600

GGCCTATTTC CCTAAAGGGT TTATTGAGAA TATGTTTTTC GTCTCAGCCA ATCCCTGGGT     660

GAGTTTCACC AGTTTTGATT TAAACGTGGC CAATATGGAC AACTTCTTCG CCCCCGTTTT     720

CACCATGGGC AAATATTATA CGCAAGGCGA CAAGGTGCTG ATGCCGCTGG CGATTCAGGT     780

TCATCATGCC GTCTGTGATG GCTTCCATGT CGGCAGAATG CTTAATGAAT TACAACAGTA     840

CTGCGATGAG TGGCAGGGCG GGGCGTAATT TTTTTAAGCC GCGGCGTGAT TAATCAGCCA     900

TACCACATTT GTAGAGGTTT TACTTGCTTT AAAAAACCTC CCACACCTCC CCCTGAACCT     960

GAAACATAAA ATGAATGCAA TTGTTGTTGT TAACTTGTTT ATTGCAGCTT ATAATGGTTA    1020

CAAATAAAGC AATAGCATCA CAAATTTCAC AAATAAAGCA TTTTTTTCAC TGCATTCTAG    1080

TTGTGGTTTG TCCAAACTCA TCAATGTATC TTATCATGTC TGGATCCCCC GGAATTCACT    1140

GGCCGTCGTT TTACAACGTC GTGACTGGGA AAACCCTGGC GTTACCCAAC TTAATCGCCT    1200

TGCAGCACAT CCCCCCTTCG CCAGCTGGCG TAATAGCGAA GAGGCCCGCA CCGATCGCCC    1260

TTCCCAACAG TTGCGCAGCC TGAATGGCGA ATGGCGCCTG ATGCGGTATT TTCTCCTTAC    1320

GCATCTGTGC GGTATTTCAC ACCGCATATG GTGCACTCTC AGTACAATCT GCTCTGATGC    1380

CGCATAGTTA AGCCAGTACA CTCCGCTATC GCTACGTGAC TGGGTCATGG CTGCGCCCCG    1440

ACACCCGCCA ACACCCGCTG ACGCGCCCTG ACGGGCTTGT CTGCTCCCGG CATCCGCTTA    1500

CAGACAAGCT GTGACCGTCT CCGGGAGCTG CATGTGTCAG AGGTTTTCAC CGTCATCACC    1560

GAAACGCGCG AGGCAGTTCT TGAAGACGAA AGGGCCTCGT GATACGCCTA TTTTTATAGG    1620

TTAATGTCAT GATAATAATG GTTTCTTAGA CGTCAGGTGG CACTTTTCGG GGAAATGTGC    1680

GCGGAACCCC TATTTGTTTA TTTTTCTAAA TACATTCAAA TATGTATCCG CTCATGAGAC    1740

AATAACCCTG ATAAATGCTT CAATAATATT GAAAAAGGAA GAGTATGAGT ATTCAACATT    1800

TCCGTGTCGC CCTTATTCCC TTTTTTGCGG CATTTTGCCT TCCTGTTTTT GCTCACCCAG    1860

AAACGCTGGT GAAAGTAAAA GATGCTGAAG ATCAGTTGGG TGCACGAGTG GGTTACATCG    1920

AACTGGATCT CAACAGCGGT AAGATCCTTG AGAGTTTTCG CCCCGAAGAA CGTTTTCCAA    1980

TGATGAGCAC TTTTAAAGTT CTGCTATGTG GCGCGGTATT ATCCCGTATT GACGCCGGGC    2040
```

```
AAGAGCAACT CGGTCGCCGC ATACACTATT CTCAGAATGA CTTGGTTGAG TACTCACCAG    2100

TCACAGAAAA GCATCTTACG GATGGCATGA CAGTAAGAGA ATTATGCAGT GCTGCCATAA    2160

CCATGAGTGA TAACACTGCG GCCAACTTAC TTCTGACAAC GATCGGAGGA CCGAAGGAGC    2220

TAACCGCTTT TTTGCACAAC ATGGGGATC ATGTAACTCG CCTTGATCGT TGGGAACCGG     2280

AGCTGAATGA AGCCATACCA AACGACGAGC GTGACACCAC GATGCCTGTA GCAATGGCAA    2340

CAACGTTGCG CAAACTATTA ACTGGCGAAC TACTTACTCT AGCTTCCCGG CAACAATTAA    2400

TAGACTGGAT GGAGGCGGAT AAAGTTGCAG GACCACTTCT GCGCTCGGCC CTTCCGGCTG    2460

GCTGGTTTAT TGCTGATAAA TCTGGAGCCG GTGAGCGTGG GTCTCGCGGT ATCATTGCAG    2520

CACTGGGGCC AGATGGTAAG CCCTCCCGTA TCGTAGTTAT CTACACGACG GGGAGTCAGG    2580

CAACTATGGA TGAACGAAAT AGACAGATCG CTGAGATAGG TGCCTCACTG ATTAAGCATT    2640

GGTAACTGTC AGACCAAGTT TACTCATATA TACTTTAGAT TGATTTAAAA CTTCATTTTT    2700

AATTTAAAAG GATCTAGGTG AAGATCCTTT TTGATAATCT CATGACCAAA ATCCCTTAAC    2760

GTGAGTTTTC GTTCCACTGA GCGTCAGACC CCGTAGAAAA GATCAAAGGA TCTTCTTGAG    2820

ATCCTTTTTT TCTGCGCGTA ATCTGCTGCT TGCAAACAAA AAAACCACCG CTACCAGCGG    2880

TGGTTTGTTT GCCGGATCAA GAGCTACCAA CTCTTTTTCC GAAGGTAACT GGCTTCAGCA    2940

GAGCGCAGAT ACCAAATACT GTCCTTCTAG TGTAGCCGTA GTTAGGCCAC CACTTCAAGA    3000

ACTCTGTAGC ACCGCCTACA TACCTCGCTC TGCTAATCCT GTTACCAGTG GCTGCTGCCA    3060

GTGGCGATAA GTCGTGTCTT ACCGGGTTGG ACTCAAGACG ATAGTTACCG GATAAGGCGC    3120

AGCGGTCGGG CTGAACGGGG GGTTCGTGCA CACAGCCCAG CTTGGAGCGA ACGACCTACA    3180

CCGAACTGAG ATACCTACAG CGTGAGCATT GAGAAAGCGC CACGCTTCCC GAAGGGAGAA    3240

AGGCGGACAG GTATCCGGTA AGCGGCAGGG TCGGAACAGG AGAGCGCACG AGGGAGCTTC    3300

CAGGGGGAAA CGCCTGGTAT CTTTATAGTC CTGTCGGGTT TCGCCACCTC TGACTTGAGC    3360

GTCGATTTTT GTGATGCTCG TCAGGGGGGC GGAGCCTATG GAAAAACGCC AGCAACGCGG    3420

CCTTTTTACG GTTCCTGGCC TTTTGCTGGC CTTTTGCTCA CATGTTCTTT CCTGCGTTAT    3480

CCCCTGATTC TGTGGATAAC CGTATTACCG CCTTTGAGTG AGCTGATACC GCTCGCCGCA    3540

GCCGAACGAC CGAGCGCAGC GAGTCAGTGA GCGAGGAAGC GGAAGAGCGC CAATACGCAA    3600

ACCGCCTCTC CCCGCGCGTT GGCCGATTCA TTAATGCAGC TGGCACGACA GGTTTCCCGA    3660

CTGGAAAGCG GGCAGTGAGC GCAACGCAAT TAATGTGAGT TACCTCACTC ATTAGGCACC    3720

CCAGGCTTTA CACTTTATGC TTCCGGCTCG TATGTTGTGT GGAATTGTGA GCGGATAACA    3780

ATTTCACACA GGAAACAGCT ATGACCATGA TTACGCCAAG CT                       3822
```

(2) INFORMATION FOR SEQ ID NO:9:

(i) SEQUENCE CHARACTERISTICS:
        (A) LENGTH: 4009 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
TAATGTCGTA ACAACTCCGC CCCGTTGACG CAAATGGGCG GTAGGCGTGT ACGGTGGGAG     60

GTCTATATAA GCAGAGCTCG TTTAGTGAAC CGTCAGATCG CCTGGAGACG CCATCCACGC    120

TGTTTTGACC TCCATAGAAG ACACCGGCTG CAGACTCTCT TCCGCATCGC TGTCTGCGAG    180
```

| | |
|---|---|
| GGCCAGCTGT TGGGCTCGCG GTTGAGGACA AACTCTTCGC GGTCTTTCCA GTACTCTTGG | 240 |
| ATCGGAAACC CGTCGGCCTC CGAACGGTAC TCCGCCACCG AGGGACCTGA GCGAGTCCGC | 300 |
| ATCGACCGGA TCGGAAAACC TCTCGAGAAA GGCGTCTAAC CAGTCACAGT CGCAAGTCTA | 360 |
| GAGGATCTGA GCTTGGCGAG ATTTTCAGGA GCTAAGGAAG CTAAAATGGA GAAAAAAATC | 420 |
| ACTGGATATA CCACCGTTGA TATATCCCAA TGGCATCGTA AGAACATTT TGAGGCATTT | 480 |
| CAGTCAGTTG CTCAATGTAC CTATAACCAG ACCGTTCAGC TGGATATTAC GGCCTTTTTA | 540 |
| AAGACCGTAA AGAAAAATAA GCACAAGTTT TATCCGGCCT TTATTCACAT TCTTGCCCGC | 600 |
| CTGATGAATG CTCATCCGGA ATTCCGTATG GCAATGAAAG ACGGTGAGCT GGTGATATGG | 660 |
| GATAGTGTTC ACCCTTGTTA CACCGTTTTC CATGAGCAAA CTGAAACGTT TTCATCGCTC | 720 |
| TGGAGTGAAT ACCACGACGA TTTCCGGCAG TTTCTACACA TATATTCGCA AGATGTGGCG | 780 |
| TGTTACGGTG AAAACCTGGC CTATTTCCCT AAAGGGTTTA TTGAGAATAT GTTTTTCGTC | 840 |
| TCAGCCAATC CCTGGGTGAG TTTCACCAGT TTTGATTTAA ACGTGGCCAA TATGGACAAC | 900 |
| TTCTTCGCCC CCGTTTTCAC CATGGGCAAA TATTATACGC AAGGCGACAA GGTGCTGATG | 960 |
| CCGCTGGCGA TTCAGGTTCA TCATGCCGTC TGTGATGGCT TCCATGTCGG CAGAATGCTT | 1020 |
| AATGAATTAC AACAGTACTG CGATGAGTGG CAGGGCGGGG CGTAACCGCG GCGTGATTAA | 1080 |
| TCAGCCATAC CACATTTGTA GAGGTTTTAC TTGCTTTAAA AAACCTCCCA CACCTCCCCC | 1140 |
| TGAACCTGAA ACATAAAATG AATGCAATTG TTGTTGTTAA CTTGTTTATT GCAGCTTATA | 1200 |
| ATGGTTACAA ATAAAGCAAT AGCATCACAA ATTTCACAAA TAAAGCATTT TTTTCACTGC | 1260 |
| ATTCTAGTTG TGGTTTGTCC AAACTCATCA ATGTATCTTA TCATGTCTGG ATCCCCCGGA | 1320 |
| ATTCACTGGC CGTCGTTTTA CAACGTCGTG ACTGGGAAAA CCCTGGCGTT ACCCAACTTA | 1380 |
| ATCGCCTTGC AGCACATCCC CCCTTCGCCA GCTGGCGTAA TAGCGAAGAG GCCCGCACCG | 1440 |
| ATCGCCCTTC CCAACAGTTG CGCAGCCTGA ATGGCGAATG GCGCCTGATG CGGTATTTTC | 1500 |
| TCCTTACGCA TCTGTGCGGT ATTTCACACC GCATATGGTG CACTCTCAGT ACAATCTGCT | 1560 |
| CTGATGCCGC ATAGTTAAGC CAGTACACTC CGCTATCGCT ACGTGACTGG GTCATGGCTG | 1620 |
| CGCCCCGACA CCCGCCAACA CCCGCTGACG CGCCCTGACG GGCTTGTCTG CTCCCGGCAT | 1680 |
| CCGCTTACAG ACAAGCTGTG ACCGTCTCCG GGAGCTGCAT GTGTCAGAGG TTTTCACCGT | 1740 |
| CATCACCGAA ACGCGCGAGG CAGTTCTTGA AGACGAAAGG GCCTCGTGAT ACGCCTATTT | 1800 |
| TTATAGGTTA ATGTCATGAT AATAATGGTT TCTTAGACGT CAGGTGGCAC TTTTCGGGGA | 1860 |
| AATGTGCGCG GAACCCCTAT TTGTTTATTT TTCTAAATAC ATTCAAATAT GTATCCGCTC | 1920 |
| ATGAGACAAT AACCCTGATA AATGCTTCAA TAATATTGAA AAAGGAAGAG TATGAGTATT | 1980 |
| CAACATTTCC GTGTCGCCCT TATTCCCTTT TTTGCGGCAT TTTGCCTTCC TGTTTTTGCT | 2040 |
| CACCCAGAAA CGCTGGTGAA AGTAAAAGAT GCTGAAGATC AGTTGGGTGC ACGAGTGGGT | 2100 |
| TACATCGAAC TGGATCTCAA CAGCGGTAAG ATCCTTGAGA GTTTTCGCCC CGAAGAACGT | 2160 |
| TTTCCAATGA TGAGCACTTT TAAAGTTCTG CTATGTGGCG CGGTATTATC CCGTATTGAC | 2220 |
| GCCGGGCAAG AGCAACTCGG TCGCCGCATA CACTATTCTC AGAATGACTT GGTTGAGTAC | 2280 |
| TCACCAGTCA CAGAAAAGCA TCTTACGGAT GGCATGACAG TAAGAGAATT ATGCAGTGCT | 2340 |
| GCCATAACCA TGAGTGATAA CACTGCGGCC AACTTACTTC TGACAACGAT CGGAGGACCG | 2400 |
| AAGGAGCTAA CCGCTTTTTT GCACAACATG GGGGATCATG TAACTCGCCT TGATCGTTGG | 2460 |
| GAACCGGAGC TGAATGAAGC CATACCAAAC GACGAGCGTG ACACCACGAT GCCTGTAGCA | 2520 |

```
ATGGCAACAA CGTTGCGCAA ACTATTAACT GGCGAACTAC TTACTCTAGC TTCCCGGCAA    2580

CAATTAATAG ACTGGATGGA GGCGGATAAA GTTGCAGGAC CACTTCTGCG CTCGGCCCTT    2640

CCGGCTGGCT GGTTTATTGC TGATAAATCT GGAGCCGGTG AGCGTGGGTC TCGCGGTATC    2700

ATTGCAGCAC TGGGGCCAGA TGGTAAGCCC TCCCGTATCG TAGTTATCTA CACGACGGGG    2760

AGTCAGGCAA CTATGGATGA ACGAAATAGA CAGATCGCTG AGATAGGTGC CTCACTGATT    2820

AAGCATTGGT AACTGTCAGA CCAAGTTTAC TCATATATAC TTTAGATTGA TTTAAAACTT    2880

CATTTTTAAT TTAAAAGGAT CTAGGTGAAG ATCCTTTTTG ATAATCTCAT GACCAAAATC    2940

CCTTAACGTG AGTTTTCGTT CCACTGAGCG TCAGACCCCG TAGAAAAGAT CAAAGGATCT    3000

TCTTGAGATC CTTTTTTTCT GCGCGTAATC TGCTGCTTGC AAACAAAAAA ACCACCGCTA    3060

CCAGCGGTGG TTTGTTTGCC GGATCAAGAG CTACCAACTC TTTTTCCGAA GGTAACTGGC    3120

TTCAGCAGAG CGCAGATACC AAATACTGTC CTTCTAGTGT AGCCGTAGTT AGGCCACCAC    3180

TTCAAGAACT CTGTAGCACC GCCTACATAC CTCGCTCTGC TAATCCTGTT ACCAGTGGCT    3240

GCTGCCAGTG GCGATAAGTC GTGTCTTACC GGGTTGGACT CAAGACGATA GTTACCGGAT    3300

AAGGCGCAGC GGTCGGGCTG AACGGGGGGT TCGTGCACAC AGCCCAGCTT GGAGCGAACG    3360

ACCTACACCG AACTGAGATA CCTACAGCGT GAGCATTGAG AAAGCGCCAC GCTTCCCGAA    3420

GGGAGAAAGG CGGACAGGTA TCCGGTAAGC GGCAGGGTCG GAACAGGAGA GCGCACGAGG    3480

GAGCTTCCAG GGGGAAACGC CTGGTATCTT TATAGTCCTG TCGGGTTTCG CCACCTCTGA    3540

CTTGAGCGTC GATTTTTGTG ATGCTCGTCA GGGGGGCGGA GCCTATGGAA AAACGCCAGC    3600

AACGCGGCCT TTTTACGGTT CCTGGCCTTT TGCTGGCCTT TTGCTCACAT GTTCTTTCCT    3660

GCGTTATCCC CTGATTCTGT GGATAACCGT ATTACCGCCT TTGAGTGAGC TGATACCGCT    3720

CGCCGCAGCC GAACGACCGA GCGCAGCGAG TCAGTGAGCG AGGAAGCGGA AGAGCGCCAA    3780

TACGCAAACC GCCTCTCCCC GCGCGTTGGC CGATTCATTA ATGCAGCTGG CACGACAGGT    3840

TTCCCGACTG GAAAGCGGGC AGTGAGCGCA ACGCAATTAA TGTGAGTTAC CTCACTCATT    3900

AGGCACCCCA GGCTTTACAC TTTATGCTTC CGGCTCGTAT GTTGTGTGGA ATTGTGAGCG    3960

GATAACAATT TCACACAGGA AACAGCTATG ACCATGATTA CGCCAAGCT              4009

(2) INFORMATION FOR SEQ ID NO:10:

(i) SEQUENCE CHARACTERISTICS:
        (A) LENGTH: 3955 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TAATGTCGTA ACAACTCCGC CCCGTTGACG CAAATGGGCG GTAGGCGTGT ACGGTGGGAG     60

GTCTATATAA GCAGAGCTCG TTTAGTGAAC CGTCTGCAGA CTCTCTTCCG CATCGCTGTC    120

TGCGAGGGCC AGCTGTTGGG CTCGCGGTTG AGGACAAACT CTTCGCGGTC TTTCCAGTAC    180

TCTTGGATCG GAAACCCGTC GGCCTCCGAA CGGTACTCCG CCACCGAGGG ACCTGAGCGA    240

GTCCGCATCG ACCGGATCGG AAAACCTCTC GAGAAAGGCG TCTAACCAGT CACAGTCGCA    300

AGTCTAGAGG ATCTGAGCTT GGCGAGATTT TCAGGAGCTA AGGAAGCTAA AATGGAGAAA    360

AAAATCACTG GATATACCAC CGTTGATATA TCCCAATGGC ATCGTAAAGA ACATTTTGAG    420

GCATTTCAGT CAGTTGCTCA ATGTACCTAT AACCAGACCG TTCAGCTGGA TATTACGGCC    480
```

```
-continued

TTTTTAAAGA CCGTAAAGAA AAATAAGCAC AAGTTTTATC CGGCCTTTAT TCACATTCTT    540

GCCCGCCTGA TGAATGCTCA TCCGGAATTC CGTATGGCAA TGAAAGACGG TGAGCTGGTG    600

ATATGGGATA GTGTTCACCC TTGTTACACC GTTTTCCATG AGCAAACTGA AACGTTTTCA    660

TCGCTCTGGA GTGAATACCA CGACGATTTC CGGCAGTTTC TACACATATA TTCGCAAGAT    720

GTGGCGTGTT ACGGTGAAAA CCTGGCCTAT TTCCCTAAAG GGTTTATTGA GAATATGTTT    780

TTCGTCTCAG CCAATCCCTG GGTGAGTTTC ACCAGTTTTG ATTTAAACGT GGCCAATATG    840

GACAACTTCT TCGCCCCCGT TTTCACCATG GGCAAATATT ATACGCAAGG CGACAAGGTG    900

CTGATGCCGC TGGCGATTCA GGTTCATCAT GCCGTCTGTG ATGGCTTCCA TGTCGGCAGA    960

ATGCTTAATG AATTACAACA GTACTGCGAT GAGTGGCAGG GCGGGGCGTA ACCGCGGCGT   1020

GATTAATCAG CCATACCACA TTTGTAGAGG TTTTACTTGC TTTAAAAAAC CTCCCACACC   1080

TCCCCCTGAA CCTGAAACAT AAAATGAATG CAATTGTTGT TGTTAACTTG TTTATTGCAG   1140

CTTATAATGG TTACAAATAA AGCAATAGCA TCACAAATTT CACAAATAAA GCATTTTTTT   1200

CACTGCATTC TAGTTGTGGT TTGTCCAAAC TCATCAATGT ATCTTATCAT GTCTGGATCC   1260

CCCGGAATTC ACTGGCCGTC GTTTTACAAC GTCGTGACTG GGAAAACCCT GGCGTTACCC   1320

AACTTAATCG CCTTGCAGCA CATCCCCCCT TCGCCAGCTG GCGTAATAGC GAAGAGGCCC   1380

GCACCGATCG CCCTTCCCAA CAGTTGCGCA GCCTGAATGG CGAATGGCGC CTGATGCGGT   1440

ATTTTCTCCT TACGCATCTG TGCGGTATTT CACACCGCAT ATGGTGCACT CTCAGTACAA   1500

TCTGCTCTGA TGCCGCATAG TTAAGCCAGT ACACTCCGCT ATCGCTACGT GACTGGGTCA   1560

TGGCTGCGCC CCGACACCCG CCAACACCCG CTGACGCGCC CTGACGGGCT TGTCTGCTCC   1620

CGGCATCCGC TTACAGACAA GCTGTGACCG TCTCCGGGAG CTGCATGTGT CAGAGGTTTT   1680

CACCGTCATC ACCGAAACGC GCGAGGCAGT TCTTGAAGAC GAAAGGGCCT CGTGATACGC   1740

CTATTTTTAT AGGTTAATGT CATGATAATA ATGGTTTCTT AGACGTCAGG TGGCACTTTT   1800

CGGGGAAATG TGCGCGGAAC CCCTATTTGT TTATTTTTCT AAATACATTC AAATATGTAT   1860

CCGCTCATGA GACAATAACC CTGATAAATG CTTCAATAAT ATTGAAAAAG GAAGAGTATG   1920

AGTATTCAAC ATTTCCGTGT CGCCCTTATT CCCTTTTTTG CGGCATTTTG CCTTCCTGTT   1980

TTTGCTCACC CAGAAACGCT GGTGAAAGTA AAAGATGCTG AAGATCAGTT GGGTGCACGA   2040

GTGGGTTACA TCGAACTGGA TCTCAACAGC GGTAAGATCC TTGAGAGTTT TCGCCCCGAA   2100

GAACGTTTTC CAATGATGAG CACTTTTAAA GTTCTGCTAT GTGGCGCGGT ATTATCCCGT   2160

ATTGACGCCG GGCAAGAGCA ACTCGGTCGC CGCATACACT ATTCTCAGAA TGACTTGGTT   2220

GAGTACTCAC CAGTCACAGA AAAGCATCTT ACGGATGGCA TGACAGTAAG AGAATTATGC   2280

AGTGCTGCCA TAACCATGAG TGATAACACT GCGGCCAACT TACTTCTGAC AACGATCGGA   2340

GGACCGAAGG AGCTAACCGC TTTTTTGCAC AACATGGGGG ATCATGTAAC TCGCCTTGAT   2400

CGTTGGGAAC CGGAGCTGAA TGAAGCCATA CCAAACGACG AGCGTGACAC CACGATGCCT   2460

GTAGCAATGG CAACAACGTT GCGCAAACTA TTAACTGGCG AACTACTTAC TCTAGCTTCC   2520

CGGCAACAAT TAATAGACTG GATGGAGGCG GATAAAGTTG CAGGACCACT TCTGCGCTCG   2580

GCCCTTCCGG CTGGCTGGTT TATTGCTGAT AAATCTGGAG CCGGTGAGCG TGGGTCTCGC   2640

GGTATCATTG CAGCACTGGG GCCAGATGGT AAGCCCTCCC GTATCGTAGT TATCTACACG   2700

ACGGGGAGTC AGGCAACTAT GGATGAACGA AATAGACAGA TCGCTGAGAT AGGTGCCTCA   2760

CTGATTAAGC ATTGGTAACT GTCAGACCAA GTTTACTCAT ATATACTTTA GATTGATTTA   2820

AAACTTCATT TTTAATTTAA AAGGATCTAG GTGAAGATCC TTTTTGATAA TCTCATGACC   2880
```

```
AAAATCCCTT AACGTGAGTT TCGTTCCAC TGAGCGTCAG ACCCCGTAGA AAAGATCAAA     2940

GGATCTTCTT GAGATCCTTT TTTTCTGCGC GTAATCTGCT GCTTGCAAAC AAAAAAACCA    3000

CCGCTACCAG CGGTGGTTTG TTTGCCGGAT CAAGAGCTAC CAACTCTTTT TCCGAAGGTA    3060

ACTGGCTTCA GCAGAGCGCA GATACCAAAT ACTGTCCTTC TAGTGTAGCC GTAGTTAGGC    3120

CACCACTTCA AGAACTCTGT AGCACCGCCT ACATACCTCG CTCTGCTAAT CCTGTTACCA    3180

GTGGCTGCTG CCAGTGGCGA TAAGTCGTGT CTTACCGGGT TGGACTCAAG ACGATAGTTA    3240

CCGGATAAGG CGCAGCGGTC GGGCTGAACG GGGGGTTCGT GCACACAGCC CAGCTTGGAG    3300

CGAACGACCT ACACCGAACT GAGATACCTA CAGCGTGAGC ATTGAGAAAG CGCCACGCTT    3360

CCCGAAGGGA GAAAGGCGGA CAGGTATCCG GTAAGCGGCA GGGTCGGAAC AGGAGAGCGC    3420

ACGAGGGAGC TTCCAGGGGG AAACGCCTGG TATCTTTATA GTCCTGTCGG GTTTCGCCAC    3480

CTCTGACTTG AGCGTCGATT TTTGTGATGC TCGTCAGGGG GGCGGAGCCT ATGGAAAAAC    3540

GCCAGCAACG CGGCCTTTTT ACGGTTCCTG GCCTTTTGCT GGCCTTTTGC TCACATGTTC    3600

TTTCCTGCGT TATCCCCTGA TTCTGTGGAT AACCGTATTA CCGCCTTTGA GTGAGCTGAT    3660

ACCGCTCGCC GCAGCCGAAC GACCGAGCGC AGCGAGTCAG TGAGCGAGGA AGCGGAAGAG    3720

CGCCAATACG CAAACCGCCT CTCCCCGCGC GTTGGCCGAT TCATTAATGC AGCTGGCACG    3780

ACAGGTTTCC CGACTGGAAA GCGGGCAGTG AGCGCAACGC AATTAATGTG AGTTACCTCA    3840

CTCATTAGGC ACCCCAGGCT TTACACTTTA TGCTTCCGGC TCGTATGTTG TGTGGAATTG    3900

TGAGCGGATA ACAATTTCAC ACAGGAAACA GCTATGACCA TGATTACGCC AAGCT          3955

(2) INFORMATION FOR SEQ ID NO:11:

(i) SEQUENCE CHARACTERISTICS:
        (A) LENGTH: 3861 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TAATGTCGTA ACAACTCCGC CCCGTTGACG CAAATGGGCG GTAGGCGTGT ACGGTGGGAG      60

GTCTATATAA GCAGAGCTCG TTTAGTGAAC CGTCTGCAGA CTCTCTTCCG CATCGCTGTC     120

TGCGAGGGCC AGCTGTTGGG CTCGCGGTTG AGGACAAACT CTTCGCGGTC TTTCCAGTAC     180

TCTTGGATCG GAAACCCGTC GGCCTCCGAA CGGTACTCCG CCACCGAGGG ACCTGAGCGA     240

GTCCGCATCG ACCGGATCGG AAAACCTCTC GAGAAAGGCG TCTAACCAGT CACAGTCGCA     300

AGTCTAGAGG ATCTGAGCTT GGCGAGATTT TCAGGAGCTA AGGAAGCTAA AATGGAGAAA     360

AAAATCACTG GATATACCAC CGTTGATATA TCCCAATGGC ATCGTAAAGA ACATTTTGAG     420

GCATTTCAGT CAGTTGCTCA ATGTACCTAT AACCAGACCG TTCAGCTGGA TATTACGGCC     480

TTTTTAAAGA CCGTAAAGAA AAATAAGCAC AAGTTTTATC CGGCCTTTAT TCACATTCTT     540

GCCCGCCTGA TGAATGCTCA TCCGGAATTC CGTATGGCAA TGAAAGACGG TGAGCTGGTG     600

ATATGGGATA GTGTTCACCC TTGTTACACC GTTTTCCATG AGCAAACTGA AACGTTTTCA     660

TCGCTCTGGA GTGAATACCA CGACGATTTC CGGCAGTTTC TACACATATA TTCGCAAGAT     720

GTGGCGTGTT ACGGTGAAAA CCTGGCCTAT TTCCCTAAAG GGTTTATTGA GAATATGTTT     780

TTCGTCTCAG CCAATCCCTG GGTGAGTTTC ACCAGTTTTG ATTTAAACGT GGCCAATATG     840

GACAACTTCT TCGCCCCCGT TTTCACCATG GGCAAATATT ATACGCAAGG CGACAAGGTG     900
```

-continued

```
CTGATGCCGC TGGCGATTCA GGTTCATCAT GCCGTCTGTG ATGGCTTCCA TGTCGGCAGA    960

ATGCTTAATG AATTACAACA GTACTGCGAT GAGTGGCAGG GCGGGGCGTA ACCGCGGAAT   1020

TGTTGTTGTT AACTTGTTTA TTGCAGCTTA TAATGGTTAC AAATAAAGCA ATAGCATCAC   1080

AAATTTCACA AATAAAGCAT TTTTTTCACT GCATTCTAGT TGTGGTTTGT CCAAACTCAT   1140

CAATGTATCT TATCATGTCT GGATCCCCCG GAATTCACTG GCCGTCGTTT TACAACGTCG   1200

TGACTGGGAA AACCCTGGCG TTACCCAACT TAATCGCCTT GCAGCACATC CCCCCTTCGC   1260

CAGCTGGCGT AATAGCGAAG AGGCCCGCAC CGATCGCCCT TCCCAACAGT TGCGCAGCCT   1320

GAATGGCGAA TGGCGCCTGA TGCGGTATTT TCTCCTTACG CATCTGTGCG GTATTTCACA   1380

CCGCATATGG TGCACTCTCA GTACAATCTG CTCTGATGCC GCATAGTTAA GCCAGTACAC   1440

TCCGCTATCG CTACGTGACT GGGTCATGGC TGCGCCCCGA CACCCGCCAA CACCCGCTGA   1500

CGCGCCCTGA CGGGCTTGTC TGCTCCCGGC ATCCGCTTAC AGACAAGCTG TGACCGTCTC   1560

CGGGAGCTGC ATGTGTCAGA GGTTTTCACC GTCATCACCG AAACGCGCGA GGCAGTTCTT   1620

GAAGACGAAA GGGCCTCGTG ATACGCCTAT TTTTATAGGT TAATGTCATG ATAATAATGG   1680

TTTCTTAGAC GTCAGGTGGC ACTTTTCGGG GAAATGTGCG CGGAACCCCT ATTTGTTTAT   1740

TTTTCTAAAT ACATTCAAAT ATGTATCCGC TCATGAGACA ATAACCCTGA TAAATGCTTC   1800

AATAATATTG AAAAAGGAAG AGTATGAGTA TTCAACATTT CCGTGTCGCC CTTATTCCCT   1860

TTTTTGCGGC ATTTTGCCTT CCTGTTTTTG CTCACCCAGA AACGCTGGTG AAAGTAAAAG   1920

ATGCTGAAGA TCAGTTGGGT GCACGAGTGG GTTACATCGA ACTGGATCTC AACAGCGGTA   1980

AGATCCTTGA GAGTTTTCGC CCCGAAGAAC GTTTTCCAAT GATGAGCACT TTTAAAGTTC   2040

TGCTATGTGG CGCGGTATTA TCCCGTATTG ACGCCGGGCA AGAGCAACTC GGTCGCCGCA   2100

TACACTATTC TCAGAATGAC TTGGTTGAGT ACTCACCAGT CACAGAAAAG CATCTTACGG   2160

ATGGCATGAC AGTAAGAGAA TTATGCAGTG CTGCCATAAC CATGAGTGAT AACACTGCGG   2220

CCAACTTACT TCTGACAACG ATCGGAGGAC CGAAGGAGCT AACCGCTTTT TTGCACAACA   2280

TGGGGGATCA TGTAACTCGC CTTGATCGTT GGGAACCGGA GCTGAATGAA GCCATACCAA   2340

ACGACGAGCG TGACACCACG ATGCCTGTAG CAATGGCAAC AACGTTGCGC AAACTATTAA   2400

CTGGCGAACT ACTTACTCTA GCTTCCCGGC AACAATTAAT AGACTGGATG GAGGCGGATA   2460

AAGTTGCAGG ACCACTTCTG CGCTCGGCCC TTCCGGCTGG CTGGTTTATT GCTGATAAAT   2520

CTGGAGCCGG TGAGCGTGGG TCTCGCGGTA TCATTGCAGC ACTGGGGCCA GATGGTAAGC   2580

CCTCCCGTAT CGTAGTTATC TACACGACGG GGAGTCAGGC AACTATGGAT GAACGAAATA   2640

GACAGATCGC TGAGATAGGT GCCTCACTGA TTAAGCATTG GTAACTGTCA GACCAAGTTT   2700

ACTCATATAT ACTTTAGATT GATTTAAAAC TTCATTTTTA ATTTAAAAGG ATCTAGGTGA   2760

AGATCCTTTT TGATAATCTC ATGACCAAAA TCCCTTAACG TGAGTTTTCG TTCCACTGAG   2820

CGTCAGACCC CGTAGAAAAG ATCAAAGGAT CTTCTTGAGA TCCTTTTTTT CTGCGCGTAA   2880

TCTGCTGCTT GCAAACAAAA AAACCACCGC TACCAGCGGT GGTTTGTTTG CCGGATCAAG   2940

AGCTACCAAC TCTTTTTCCG AAGGTAACTG GCTTCAGCAG AGCGCAGATA CCAAATACTG   3000

TCCTTCTAGT GTAGCCGTAG TTAGGCCACC ACTTCAAGAA CTCTGTAGCA CCGCCTACAT   3060

ACCTCGCTCT GCTAATCCTG TTACCAGTGG CTGCTGCCAG TGGCGATAAG TCGTGTCTTA   3120

CCGGGTTGGA CTCAAGACGA TAGTTACCGG ATAAGGCGCA GCGGTCGGGC TGAACGGGGG   3180

GTTCGTGCAC ACAGCCCAGC TTGGAGCGAA CGACCTACAC CGAACTGAGA TACCTACAGC   3240
```

-continued

```
GTGAGCATTG AGAAAGCGCC ACGCTTCCCG AAGGGAGAAA GGCGGACAGG TATCCGGTAA     3300

GCGGCAGGGT CGGAACAGGA GAGCGCACGA GGGAGCTTCC AGGGGGAAAC GCCTGGTATC     3360

TTTATAGTCC TGTCGGGTTT CGCCACCTCT GACTTGAGCG TCGATTTTTG TGATGCTCGT     3420

CAGGGGGGCG GAGCCTATGG AAAAACGCCA GCAACGCGGC CTTTTTACGG TTCCTGGCCT     3480

TTTGCTGGCC TTTTGCTCAC ATGTTCTTTC CTGCGTTATC CCCTGATTCT GTGGATAACC     3540

GTATTACCGC CTTTGAGTGA GCTGATACCG CTCGCCGCAG CCGAACGACC GAGCGCAGCG     3600

AGTCAGTGAG CGAGGAAGCG GAAGAGCGCC AATACGCAAA CCGCCTCTCC CCGCGCGTTG     3660

GCCGATTCAT TAATGCAGCT GGCACGACAG GTTTCCCGAC TGGAAAGCGG GCAGTGAGCG     3720

CAACGCAATT AATGTGAGTT ACCTCACTCA TTAGGCACCC CAGGCTTTAC ACTTTATGCT     3780

TCCGGCTCGT ATGTTGTGTG GAATTGTGAG CGGATAACAA TTTCACACAG GAAACAGCTA     3840

TGACCATGAT TACGCCAAGC T                                              3861
```

(2) INFORMATION FOR SEQ ID NO:12:

(i) SEQUENCE CHARACTERISTICS:
        (A) LENGTH: 3888 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
TAATGTCGTA ACAACTCCGC CCCGTTGACG CAAATGGGCG GTAGGCGTGT ACGGTGGGAG       60

GTCTATATAA GCAGAGCTCG TTTAGTGAAC CGTCTGCAGA CTCTCTTCCG CATCGCTGTC      120

TGCGAGGGCC AGCTGTTGGG CTCGCGGTTG AGGACAAACT CTTCGCGGTC TTTCCAGTAC      180

TCTTGGATCG GAAACCCGTC GGCCTCCGAA CGGTACTCCG CCACCGAGGG ACCTGAGCGA      240

GTCCGCATCG ACCGGATCGG AAAACCTCTC GAGAAAGGCG TCTAACCAGT CACAGTCGCA      300

AGTCTAGAGG ATCTGAGCTT GGCGAGATTT TCAGGAGCTA AGGAAGCTAA AATGGAGAAA      360

AAAATCACTG GATATACCAC CGTTGATATA TCCCAATGGC ATCGTAAAGA ACATTTTGAG      420

GCATTTCAGT CAGTTGCTCA ATGTACCTAT AACCAGACCG TTCAGCTGGA TATTACGGCC      480

TTTTTAAAGA CCGTAAAGAA AAATAAGCAC AAGTTTTATC CGGCCTTTAT TCACATTCTT      540

GCCCGCCTGA TGAATGCTCA TCCGGAATTC CGTATGGCAA TGAAAGACGG TGAGCTGGTG      600

ATATGGGATA GTGTTCACCC TTGTTACACC GTTTTCCATG AGCAAACTGA AACGTTTTCA      660

TCGCTCTGGA GTGAATACCA CGACGATTTC CGGCAGTTTC TACACATATA TTCGCAAGAT      720

GTGGCGTGTT ACGGTGAAAA CCTGGCCTAT TTCCCTAAAG GGTTTATTGA GAATATGTTT      780

TTCGTCTCAG CCAATCCCTG GGTGAGTTTC ACCAGTTTTG ATTTAAACGT GGCCAATATG      840

GACAACTTCT TCGCCCCCGT TTTCACCATG GGCAAATATT ATACGCAAGG CGACAAGGTG      900

CTGATGCCGC TGGCGATTCA GGTTCATCAT GCCGTCTGTG ATGGCTTCCA TGTCGGCAGA      960

ATGCTTAATG AATTACAACA GTACTGCGAT GAGTGGCAGG GCGGGGCGTA ACCGCGGAAT     1020

TGTTGTTGTT AACTTGTTTA TTGCAGCTTA TAATGGTTAC AAATAAAGCA ATAGCATCAC     1080

AAATTTCACA AATAAAGCAT TTTTTTCACT GCATTCTAGT TGTGGTTTGT CCAAACTCAT     1140

CAATGTATCT TATCATGTCT GGATAACGCC CAAAACCCG GGGACGATGA TCCCCCGGAA      1200

TTCACTGGCC GTCGTTTTAC AACGTCGTGA CTGGGAAAAC CCTGGCGTTA CCCAACTTAA     1260

TCGCCTTGCA GCACATCCCC CCTTCGCCAG CTGGCGTAAT AGCGAAGAGG CCCGCACCGA     1320
```

-continued

```
TCGCCCTTCC CAACAGTTGC GCAGCCTGAA TGGCGAATGG CGCCTGATGC GGTATTTTCT    1380
CCTTACGCAT CTGTGCGGTA TTTCACACCG CATATGGTGC ACTCTCAGTA CAATCTGCTC    1440
TGATGCCGCA TAGTTAAGCC AGTACACTCC GCTATCGCTA CGTGACTGGG TCATGGCTGC    1500
GCCCCGACAC CCGCCAACAC CCGCTGACGC GCCCTGACGG GCTTGTCTGC TCCCGGCATC    1560
CGCTTACAGA CAAGCTGTGA CCGTCTCCGG GAGCTGCATG TGTCAGAGGT TTTCACCGTC    1620
ATCACCGAAA CGCGCGAGGC AGTTCTTGAA GACGAAAGGG CCTCGTGATA CGCCTATTTT    1680
TATAGGTTAA TGTCATGATA ATAATGGTTT CTTAGACGTC AGGTGGCACT TTTCGGGGAA    1740
ATGTGCGCGG AACCCCTATT TGTTTATTTT TCTAAATACA TTCAAATATG TATCCGCTCA    1800
TGAGACAATA ACCCTGATAA ATGCTTCAAT AATATTGAAA AAGGAAGAGT ATGAGTATTC    1860
AACATTTCCG TGTCGCCCTT ATTCCCTTTT TTGCGGCATT TTGCCTTCCT GTTTTTGCTC    1920
ACCCAGAAAC GCTGGTGAAA GTAAAAGATG CTGAAGATCA GTTGGGTGCA CGAGTGGGTT    1980
ACATCGAACT GGATCTCAAC AGCGGTAAGA TCCTTGAGAG TTTTCGCCCC GAAGAACGTT    2040
TTCCAATGAT GAGCACTTTT AAAGTTCTGC TATGTGGCGC GGTATTATCC CGTATTGACG    2100
CCGGGCAAGA GCAACTCGGT CGCCGCATAC ACTATTCTCA GAATGACTTG GTTGAGTACT    2160
CACCAGTCAC AGAAAAGCAT CTTACGGATG GCATGACAGT AAGAGAATTA TGCAGTGCTG    2220
CCATAACCAT GAGTGATAAC ACTGCGGCCA ACTTACTTCT GACAACGATC GGAGGACCGA    2280
AGGAGCTAAC CGCTTTTTTG CACAACATGG GGGATCATGT AACTCGCCTT GATCGTTGGG    2340
AACCGGAGCT GAATGAAGCC ATACCAAACG ACGAGCGTGA CACCACGATG CCTGTAGCAA    2400
TGGCAACAAC GTTGCGCAAA CTATTAACTG GCGAACTACT TACTCTAGCT TCCCGGCAAC    2460
AATTAATAGA CTGGATGGAG GCGGATAAAG TTGCAGGACC ACTTCTGCGC TCGGCCCTTC    2520
CGGCTGGCTG GTTTATTGCT GATAAATCTG GAGCCGGTGA GCGTGGGTCT CGCGGTATCA    2580
TTGCAGCACT GGGGCCAGAT GGTAAGCCCT CCCGTATCGT AGTTATCTAC ACGACGGGGA    2640
GTCAGGCAAC TATGGATGAA CGAAATAGAC AGATCGCTGA GATAGGTGCC TCACTGATTA    2700
AGCATTGGTA ACTGTCAGAC CAAGTTTACT CATATATACT TTAGATTGAT TTAAAACTTC    2760
ATTTTTAATT TAAAAGGATC TAGGTGAAGA TCCTTTTTGA TAATCTCATG ACCAAAATCC    2820
CTTAACGTGA GTTTTCGTTC CACTGAGCGT CAGACCCCGT AGAAAAGATC AAAGGATCTT    2880
CTTGAGATCC TTTTTTTCTG CGCGTAATCT GCTGCTTGCA AACAAAAAAA CCACCGCTAC    2940
CAGCGGTGGT TTGTTTGCCG GATCAAGAGC TACCAACTCT TTTTCCGAAG GTAACTGGCT    3000
TCAGCAGAGC GCAGATACCA AATACTGTCC TTCTAGTGTA GCCGTAGTTA GGCCACCACT    3060
TCAAGAACTC TGTAGCACCG CCTACATACC TCGCTCTGCT AATCCTGTTA CCAGTGGCTG    3120
CTGCCAGTGG CGATAAGTCG TGTCTTACCG GGTTGGACTC AAGACGATAG TTACCGGATA    3180
AGGCGCAGCG GTCGGGCTGA ACGGGGGGTT CGTGCACACA GCCCAGCTTG GAGCGAACGA    3240
CCTACACCGA ACTGAGATAC CTACAGCGTG AGCATTGAGA AAGCGCCACG CTTCCCGAAG    3300
GGAGAAAGGC GGACAGGTAT CCGGTAAGCG GCAGGGTCGG AACAGGAGAG CGCACGAGGG    3360
AGCTTCCAGG GGGAAACGCC TGGTATCTTT ATAGTCCTGT CGGGTTTCGC CACCTCTGAC    3420
TTGAGCGTCG ATTTTTGTGA TGCTCGTCAG GGGGCGGAG CCTATGGAAA AACGCCAGCA    3480
ACGCGGCCTT TTTACGGTTC CTGGCCTTTT GCTGGCCTTT TGCTCACATG TTCTTTCCTG    3540
CGTTATCCCC TGATTCTGTG GATAACCGTA TTACCGCCTT TGAGTGAGCT GATACCGCTC    3600
GCCGCAGCCG AACGACCGAG CGCAGCGAGT CAGTGAGCGA GGAAGCGGAA GAGCGCCAAT    3660
ACGCAAACCG CCTCTCCCCG CGCGTTGGCC GATTCATTAA TGCAGCTGGC ACGACAGGTT    3720
```

```
TCCCGACTGG AAAGCGGGCA GTGAGCGCAA CGCAATTAAT GTGAGTTACC TCACTCATTA      3780

GGCACCCCAG GCTTTACACT TTATGCTTCC GGCTCGTATG TTGTGTGGAA TTGTGAGCGG      3840

ATAACAATTT CACACAGGAA ACAGCTATGA CCATGATTAC GCCAAGCT                  3888
```

(2) INFORMATION FOR SEQ ID NO:13:

(i) SEQUENCE CHARACTERISTICS:
        (A) LENGTH: 7379 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
TAATGTCGTA ACAACTCCGC CCCGTTGACG CAAATGGGCG GTAGGCGTGT ACGGTGGGAG        60

GTCTATATAA GCAGAGCTCG TTTAGTGAAC CGTCTGCAGA CTCTCTTCCG CATCGCTGTC       120

TGCGAGGGCC AGCTGTTGGG CTCGCGGTTG AGGACAAACT CTTCGCGGTC TTTCCAGTAC       180

TCTTGGATCG GAAACCCGTC GGCCTCCGAA CGGTACTCCG CCACCGAGGG ACCTGAGCGA       240

GTCCGCATCG ACCGGATCGG AAAACCTCTC GAGAAAGGCG TCTAACCAGT CACAGTCGCA       300

AGTCTAGAGG ATCTGAGCTT GGCGAGATTT TCAGGAGCTA AGGAAGCTAA AATGGAGAAA       360

AAAATCACTG GATATACCAC CGTTGATATA TCCCAATGGC ATCGTAAAGA ACATTTTGAG       420

GCATTTCAGT CAGTTGCTCA ATGTACCTAT AACCAGACCG TTCAGCTGGA TATTACGGCC       480

TTTTTAAAGA CCGTAAAGAA AAATAAGCAC AAGTTTTATC CGGCCTTTAT TCACATTCTT       540

GCCCGCCTGA TGAATGCTCA TCCGGAATTC CGTATGGCAA TGAAAGACGG TGAGCTGGTG       600

ATATGGGATA GTGTTCACCC TTGTTACACC GTTTTCCATG AGCAAACTGA AACGTTTTCA       660

TCGCTCTGGA GTGAATACCA CGACGATTTC CGGCAGTTTC TACACATATA TTCGCAAGAT       720

GTGGCGTGTT ACGGTGAAAA CCTGGCCTAT TTCCCTAAAG GGTTTATTGA GAATATGTTT       780

TTCGTCTCAG CCAATCCCTG GGTGAGTTTC ACCAGTTTTG ATTTAAACGT GGCCAATATG       840

GACAACTTCT TCGCCCCCGT TTTCACCATG GGCAAATATT ATACGCAAGG CGACAAGGTG       900

CTGATGCCGC TGGCGATTCA GGTTCATCAT GCCGTCTGTG ATGGCTTCCA TGTCGGCAGA       960

ATGCTTAATG AATTACAACA GTACTGCGAT GAGTGGCAGG GCGGGGCGTA ACCGCGGAAT      1020

TGTTGTTGTT AACTTGTTTA TTGCAGCTTA TAATGGTTAC AAATAAAGCA ATAGCATCAC      1080

AAATTTCACA AATAAAGCAT TTTTTTCACT GCATTCTAGT TGTGGTTTGT CCAAACTCAT      1140

CAATGTATCT TATCATGTCT GGATAACGCC CAAAAACCCG GGGCGCCGGC AAAAGTCCG       1200

CGGAACTCGC CCTGTCGTAA AACCACGCCT TTGACGTCAC TGGACATTCC CGTGGGAACA      1260

CCCTGACCAG GGCGTGACCT GAACCTGACC GTCCCATGAC CCCGCCCCTT GCAACACCCA      1320

AATTTAAGCC ACACCTCTTT GTCCTGTATA TTATTGATGA TGGGGGGATC CACTAGTTCT      1380

AGAGCGGCCG CCACCGCGGT GGAGCTCCAG CTTTTGTTCC CTTTAGTGAG GGTTAATTCC      1440

GAGCTTGGCG TAATCATGGT CATAGCTGTT TCCTGTGTGA AATTGTTATC CGCTCACAAT      1500

TCCACACAAC ATACGAGCCG GAAGCATAAA GTGTAAAGCC TGGGGTGCCT AATGAGTGAG      1560

CTAACTCACA TTAATTGCGT TGCGCTCACT GCCCGCTTTC CAGTCGGGAA ACCTGTCGTG      1620

CCAGCTGCAT TAATGAATCG GCCAACGCGC GGGGAGAGGC GGTTTGCGTA TTGGGCGCTC      1680

TTCCGCTTCC TCGCTCACTG ACTCGCTGCG CTCGGTCGTT CGGCTGCGGC GAGCGGTATC      1740

AGCTCACTCA AAGGCGGTAA TACGGTTATC CACAGAATCA GGGGATAACG CAGGAAAGAA      1800
```

-continued

| | | | | | |
|---|---|---|---|---|---|
| CATGTGAGCA | AAAGGCCAGC | AAAAGGCCAG | GAACCGTAAA | AAGGCCGCGT | TGCTGGCGTT | 1860 |
| TTTCCATAGG | CTCCGCCCCC | CTGACGAGCA | TCACAAAAAT | CGACGCTCAA | GTCAGAGGTG | 1920 |
| GCGAAACCCG | ACAGGACTAT | AAAGATACCA | GGCGTTTCCC | CCTGGAAGCT | CCCTCGTGCG | 1980 |
| CTCTCCTGTT | CCGACCCTGC | CGCTTACCGG | ATACCTGTCC | GCCTTTCTCC | CTTCGGGAAG | 2040 |
| CGTGGCGCTT | TCTCATAGCT | CACGCTGTAG | GTATCTCAGT | TCGGTGTAGG | TCGTTCGCTC | 2100 |
| CAAGCTGGGC | TGTGTGCACG | AACCCCCCGT | TCAGCCCGAC | CGCTGCGCCT | TATCCGGTAA | 2160 |
| CTATCGTCTT | GAGTCCAACC | CGGTAAGACA | CGACTTATCG | CCACTGGCAG | CAGCCACTGG | 2220 |
| TAACAGGATT | AGCAGAGCGA | GGTATGTAGG | CGGTGCTACA | GAGTTCTTGA | AGTGGTGGCC | 2280 |
| TAACTACGGC | TACACTAGAA | GGACAGTATT | TGGTATCTGC | GCTCTGCTGA | AGCCAGTTAC | 2340 |
| CTTCGGAAAA | AGAGTTGGTA | GCTCTTGATC | CGGCAAACAA | ACCACCGCTG | GTAGCGGTGG | 2400 |
| TTTTTTTGTT | TGCAAGCAGC | AGATTACGCG | CAGAAAAAAA | GGATCTCAAG | AAGATCCTTT | 2460 |
| GATCTTTTCT | ACGGGGTCTG | ACGCTCAGTG | GAACGAAAAC | TCACGTTAAG | GGATTTTGGT | 2520 |
| CATGAGATTA | TCAAAAAGGA | TCTTCACCTA | GATCCTTTTA | AATTAAAAAT | GAAGTTTTAA | 2580 |
| ATCAATCTAA | AGTATATATG | AGTAAACTTG | GTCTGACAGT | TACCAATGCT | TAATCAGTGA | 2640 |
| GGCACCTATC | TCAGCGATCT | GTCTATTTCG | TTCATCCATA | GTTGCCTGAC | TCCCCGTCGT | 2700 |
| GTAGATAACT | ACGATACGGG | AGGGCTTACC | ATCTGGCCCC | AGTGCTGCAA | TGATACCGCG | 2760 |
| AGACCCACGC | TCACCGGCTC | CAGATTTATC | AGCAATAAAC | CAGCCAGCCG | GAAGGGCCGA | 2820 |
| GCGCAGAAGT | GGTCCTGCAA | CTTTATCCGC | CTCCATCCAG | TCTATTAATT | GTTGCCGGGA | 2880 |
| AGCTAGAGTA | AGTAGTTCGC | CAGTTAATAG | TTTGCGCAAC | GTTGTTGCCA | TTGCTACAGG | 2940 |
| CATCGTGGTG | TCACGCTCGT | CGTTTGGTAT | GGCTTCATTC | AGCTCCGGTT | CCCAACGATC | 3000 |
| AAGGCGAGTT | ACATGATCCC | CCATGTTGTG | CAAAAAAGCG | GTTAGCTCCT | TCGGTCCTCC | 3060 |
| GATCGTTGTC | AGAAGTAAGT | TGGCCGCAGT | GTTATCACTC | ATGGTTATGG | CAGCACTGCA | 3120 |
| TAATTCTCTT | ACTGTCATGC | CATCCGTAAG | ATGCTTTTCT | GTGACTGGTG | AGTACTCAAC | 3180 |
| CAAGTCATTC | TGAGAATAGT | GTATGCGGCG | ACCGAGTTGC | TCTTGCCCGG | CGTCAATACG | 3240 |
| GGATAATACC | GCGCCACATA | GCAGAACTTT | AAAAGTGCTC | ATCATTGGAA | AACGTTCTTC | 3300 |
| GGGGCGAAAA | CTCTCAAGGA | TCTTACCGCT | GTTGAGATCC | AGTTCGATGT | AACCCACTCG | 3360 |
| TGCACCCAAC | TGATCTTCAG | CATCTTTTAC | TTTCACCAGC | GTTTCTGGGT | GAGCAAAAAC | 3420 |
| AGGAAGGCAA | AATGCCGCAA | AAAAGGGAAT | AAGGGCGACA | CGGAAATGTT | GAATACTCAT | 3480 |
| ACTCTTCCTT | TTTCAATATT | ATTGAAGCAT | TTATCAGGGT | TATTGTCTCA | TGAGCGGATA | 3540 |
| CATATTTGAA | TGTATTTAGA | AAAATAAACA | AATAGGGGTT | CCGCGCACAT | TTCCCCGAAA | 3600 |
| AGTGCCACCT | GGGAAATTGT | AAACGTTAAT | ATTTTGTTAA | AATTCGCGTT | AAATTTTTGT | 3660 |
| TAAATCAGCT | CATTTTTTAA | CCAATAGGCC | GAAATCGGCA | AAATCCCTTA | TAAATCAAAA | 3720 |
| GAATAGACCG | AGATAGGGTT | GAGTGTTGTT | CCAGTTTGGA | ACAAGAGTCC | ACTATTAAAG | 3780 |
| AACGTGGACT | CCAACGTCAA | AGGGCGAAAA | ACCGTCTATC | AGGGCGATGG | CCCACTACGT | 3840 |
| GAACCATCAC | CCTAATCAAG | TTTTTTGGGG | TCGAGGTGCC | GTAAAGCACT | AAATCGGAAC | 3900 |
| CCTAAAGGGA | GCCCCCGATT | TAGAGCTTGA | CGGGGAAAGC | CGGCGAACGT | GGCGAGAAAG | 3960 |
| GAAGGGAAGA | AAGCGAAAGG | AGCGGGCGCT | AGGGCGCTGG | CAAGTGTAGC | GGTCACGCTG | 4020 |
| CGCGTAACCA | CCACACCCGC | CGCGCTTAAT | GCGCCGCTAC | AGGGCGCGTC | GCGCCATTCG | 4080 |
| CCATTCAGGC | TGCGCAACTG | TTGGGAAGGG | CGATCGGTGC | GGGCCTCTTC | GCTATTACGC | 4140 |

```
CAGCTGGCGA AAGGGGGATG TGCTGCAAGG CGATTAAGTT GGGTAACGCC AGGGTTTTCC     4200

CAGTCACGAC GTTGTAAAAC GACGGCCAGT GAATTGTAAT ACGACTCACT ATAGGGCGAA     4260

TTGGGTACCG GGCCCCCCCT CGAGGTCGAC GGTGCCCCCA GCAGAAGTAT CGACTGCATG     4320

CTAATTATTA ACAAACCAAA AGGCGTTGCC ACTTACACCC TTACCTTTAG GTTTTTAAAC     4380

TTTAACAGAC TAAGCGGAGG TACCCTGTTT AAAACTGATG TCTTAACCTT TACCTATGTA     4440

GGCGAAAATC AATAAAACCA GAAAAAAATA AGTTTAAAAG CTTTATTTTT CATACACGCG     4500

AGCGGTAAGG CTGCCGCCTT CAGGAAAAGT TACTCTGTAA ACAGTTCTTT CACAACAGCA     4560

CAAAACATAG GTATTAGTTA ACAGTTCATT TGGGCTATAA TAATATACAT TTTCTTGGGT     4620

GGCAAAGCAA GGGTCGGTAA TCTCAACAAA ACCATCAACT GGAATGCAAG AATAGTCCAG     4680

CACGGTGGGT TCAATCTAAA AATGAAGAAA CGCTGTTGAG GTTCACTAAG CACAGGTTTT     4740

GAATCTGTCG GCAGCGTCCA TGCATCATAG CTTGTCTCAA AGCAGATTGT CTTCTTTCCT     4800

CTGCCTTGGA AGTGGTTTGG TGAAGCACTA CAGGTGTCTT TTCAACCTCT TTCAGCACCC     4860

GCTCTATTAC AGATCTCACC CACACAGCAC AGTTTTTAAG AGAACAATAG TTTTGAAGGC     4920

TACAAGATTT ACACTTAAGC ACCAGCCAGT AATTATAAGT GCTTTTAAGA ACTACCCCTA     4980

GCTCAGGGTT AATGCACCTT TTAATGGCCT CCATGCAGGC TTTATGGACA GTTCTAAAAA     5040

AAGACAGTCT AAAATAAATG TAGTGAGTGT TTCTAAATAT AATACTCCCC ACATAGTTAA     5100

TTTCATCAGG CCTGCTAGAA TTTACAAACT CTCGGTACCA CATATACTTT TTATTCATAG     5160

CCCCACCCTT AATAAAGTCC TCAATCACTT TCTGAACCAC ATGCTTGCTA GCCATGCATT     5220

GTAAAGACAA GCTGTTAGAG CAGTGACAGT GTACTCGCCA CGTTTGAGCC TCTGCCAGGC     5280

AGCAGTGCTT AGTTACTATC AACTCAATAC CCGCATTGCA TGTAAACCCC CCAAAGAGCA     5340

GTTTTTCATG CCTGTGTAGC ACATCATCCC ACAAAATAGG AATTTCATAG CATAAAGCAA     5400

AGCAATTACA ATATTTAGGA ACTCTCACCA CAGCAGTCAC GTGACATGTT GTCTCAGCAG     5460

TGCAGTTGCC TTCCATCCTA CAATTATGAA CAAAAACTAA ACACTTCTAA CAAAGATACA     5520

GTGACAATCT CCCTTCCTCT AAAAGCATTG TTTACATTAG GGTGATTATT AACAACGTCA     5580

GAAATTTCTT TAATTAAAGT GCCTTTAAAA TGTGCAAGAG CATCATCATA CTCAAAACCA     5640

AGCTGAGAGT AAAAGACCAC CTTAAAAGTA ATCCCAGGCT TGTTTTTATC AACAGCCTTA     5700

AACATGCTTT CACAAAATAT AGAAGCAGTA ACATCATCAA TGGTGTCGAA GAGAAACTCC     5760

ATAGGAGACT CCAGCATTGA TCCAAGCTCT CTAACAAAAT CTTCCTCAAA ATGAATAATG     5820

CCCTTTACAC AAACGCGGGG CAGACGATGG TGGGCCATCG CGTCAACCTG AAACACATTT     5880

TACAGTAAAC AAAGCTAGCT CCGCAGTGGT AAAGTCATGC CCATGGGTGA GGCCAAAATC     5940

CTTAAAAAAG CTATCTAAGT AGTTGGTCAT CCCCTCAGTT AAAAAGTTTT GCAGCTGGGT     6000

GGTGCATACC ACATAGTGCC AGCTTATAGC TACAAAGACC TGCATCCCCT CCTTAGCAGA     6060

CAGCTCTTGC ACACACGCAG TAACTATCCA CCGCTTAAGA AAAGCTTTAA GCCCAGCGCA     6120

CATAACAGCT CCAATGTTTT TATCCAAGGA GAGCAAAATT TCAGCAAGCG CAGGCTCAAC     6180

AGTAATAGTG AAGCAGAGGC ATTTCAGACG AGGCTCACTA GCTGCAGTCG CCATTTATGA     6240

GGTCTGCAAT AAAAAACAAC TCATCAGCAG CTGAAAAAGT GCACTTTGAC CTCATTAAGC     6300

CACTGCATAT GCAAGTCCTC ATCTATGCCG CAGCCCAGAC CCTCAATCCA GCCCCGAATG     6360

TACACTTTAA TAAGAGATTC AACCTCTTCT TTTAGCAAAG TACACATGCT GTTTGGACTA     6420

GTATACACAA TAGAAGTCAC AATGAGGGGC CCGCTGTGGC TGGAAAGCCT GCGCACAGCC     6480

CGAAGGTTAA AAATGGACTG TAACAGCATT GAAACCCCGC GACACAGGTC AGTCTCGCGG     6540
```

-continued

```
TCTTGATCTC TTATTATAGC GACCAAATGG TCCTTCAGAG TGATGTTGCA CTCATAGAAG      6600

TAGGCAGCTC CGGCAGCCAT TCTGCAAAAT AACAAAACAC CACTAAGCAT AGCACCATCA      6660

CCAAGCATGA AAACAGGTAA AAACAAAAGC AACACTTACT TATTCAGCAG TCACAAGAAT      6720

GTTGGGCTCC CAAGTGACAG ACAAGCCTAA TGCAAGGTGG GCACAGTCTC CGGAATAAGT      6780

TGACAAAAGT CACGCCGCAA AGCTTCCTGA AGAGAAACGG CGGTAGCCTG GATATCTGCA      6840

ACGGACCCAA AACCTTCAGT GTCACTTCCA ATAAACAGAT AAAACTCTAA ATAGTCCCCA      6900

CTTAAAACCG AAACAGCCGC GGCAAAGGTA GGACACGGAC GCACTTCCTG AGCCCTAATA      6960

AGGCTAAACA CCACACGGCG CAGTTCAGAA GGCAAAAAGT CTGTAAGCTC TAGCTGAGCA      7020

CACACACTCT CCACTAGACA CTTGTGAAGC CTCAGACAAA AACATGCTCC CATAGACACT      7080

CCTAAAGCTG CCATTGTACT CACGGACGGC TGGCTGTCAG AGGAGAGCTA TGAGGATGAA      7140

ATGCCAAGCA CAGCGTTTAT ATAGTCCTCA AGTAGGGCG TGTGGAAAAC GAAAAGGAAT       7200

ATAACGGGGC GTTTGAGGAA GTGGTGCCAA GTACAGTCAT AAAATGTGGG CGCGTGGTAA      7260

ATGTTAAGTG CAGTTTCCCT TTGGCGGTTG GCCCGGAAAG TTCACAAAAA GTACAGCACG      7320

TCCTTGTCAC CGTGTCAACC ACAAAACCAC AAATAGGCAC AACGCCCAAA AACCCAGCT      7379
```

(2) INFORMATION FOR SEQ ID NO:14:

(i) SEQUENCE CHARACTERISTICS:
        (A) LENGTH: 6243 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
GTCGACGGTG CCCCCAGCAG AAGTATCGAC TGCATGCTAA TTATTAACAA ACCAAAAGGC        60

GTTGCCACTT ACACCCTTAC CTTTAGGTTT TTAAACTTTA ACAGACTAAG CGGAGGTACC       120

CTGTTTAAAA CTGATGTCTT AACCTTTACC TATGTAGGCG AAAATCAATA AAACCAGAAA       180

AAAATAAGTT TAAAAGCTTT ATTTTTCATA CACGCGAGCG GTAAGGCTGC CGCCTTCAGG       240

AAAAGTTACT CTGTAAACAG TTCTTTCACA ACAGCACAAA ACATAGGTAT TAGTTAACAG       300

TTCATTTGGG CTATAATAAT ATACATTTTC TTGGGTGGCA AAGCAAGGGT CGGTAATCTC       360

AACAAAACCA TCAACTGGAA TGCAAGAATA GTCCAGCACG GTGGGTTCAA TCTAAAAATG       420

AAGAAACGCT GTTGAGGTTC ACTAAGCACA GGTTTTGAAT CTGTCGGCAG CGTCCATGCA       480

TCATAGCTTG TCTCAAAGCA GATTGTCTTC TTTCCTCTGC CTTGGAAGTG GTTTGGTGAA       540

GCACTACAGG TGTCTTTTCA ACCTCTTTCA GCACCCGCTC TATTACAGAT CTCACCCACA       600

CAGCACAGTT TTTAAGAGAA CAATAGTTTT GAAGGCTACA AGATTTACAC TTAAGCACCA       660

GCCAGTAATT ATAAGTGCTT TTAAGAACTA CCCCTAGCTC AGGGTTAATG CACCTTTTAA       720

TGGCCTCCAT GCAGGCTTTA TGGACAGTTC TAAAAAAAGA CAGTCTAAAA TAAATGTAGT       780

GAGTGTTTCT AAATATAATA CTCCCCACAT AGTTAATTTC ATCAGGCCTG CTAGAATTTA       840

CAAACTCTCG GTACCACATA TACTTTTTAT TCATAGCCCC ACCCTTAATA AAGTCCTCAA       900

TCACTTTCTG AACCACATGC TTGCTAGCCA TGCATTGTAA AGACAAGCTG TTAGAGCAGT       960

GACAGTGTAC TCGCCACGTT TGAGCCTCTG CCAGGCAGCA GTGCTTAGTT ACTATCAACT      1020

CAATACCCGC ATTGCATGTA AACCCCCCAA AGAGCAGTTT TTCATGCCTG TGTAGCACAT      1080

CATCCCACAA AATAGGAATT TCATAGCATA AAGCAAAGCA ATTACAATAT TTAGGAACTC      1140
```

-continued

```
TCACCACAGC AGTCACGTGA CATGTTGTCT CAGCAGTGCA GTTGCCTTCC ATCCTACAAT    1200

TATGAACAAA AACTAAACAC TTCTAACAAA GATACAGTGA CAATCTCCCT TCCTCTAAAA    1260

GCATTGTTTA CATTAGGGTG ATTATTAACA ACGTCAGAAA TTTCTTTAAT TAAAGTGCCT    1320

TTAAAATGTG CAAGAGCATC ATCATACTCA AAACCAAGCT GAGAGTAAAA GACCACCTTA    1380

AAAGTAATCC CAGGCTTGTT TTTATCAACA GCCTTAAACA TGCTTTCACA AAATATAGAA    1440

GCAGTAACAT CATCAATGGT GTCGAAGAGA AACTCCATAG GAGACTCCAG CATTGATCCA    1500

AGCTCTCTAA CAAAATCTTC CTCAAAATGA ATAATGCCCT TTACACAAAC GCGGGGCAGA    1560

CGATGGTGGG CCATCGCGTC AACCTGAAAC ACATTTTACA GTAAACAAAG CTAGCTCCGC    1620

AGTGGTAAAG TCATGCCCAT GGGTGAGGCC AAAATCCTTA AAAAAGCTAT CTAAGTAGTT    1680

GGTCATCCCC TCAGTTAAAA AGTTTTGCAG CTGGGTGGTG CATACCACAT AGTGCCAGCT    1740

TATAGCTACA AAGACCTGCA TCCCCTCCTT AGCAGACAGC TCTTGCACAC ACGCAGTAAC    1800

TATCCACCGC TTAAGAAAAG CTTTAAGCCC AGCGCACATA ACAGCTCCAA TGTTTTTATC    1860

CAAGGAGAGC AAAATTTCAG CAAGCGCAGG CTCAACAGTA ATAGTGAAGC AGAGGCATTT    1920

CAGACGAGGC TCACTAGCTG CAGTCGCCAT TTATGAGGTC TGCAATAAAA AACAACTCAT    1980

CAGCAGCTGA AAAAGTGCAC TTTGACCTCA TTAAGCCACT GCATATGCAA GTCCTCATCT    2040

ATGCCGCAGC CCAGACCCTC AATCCAGCCC CGAATGTACA CTTTAATAAG AGATTCAACC    2100

TCTTCTTTTA GCAAAGTACA CATGCTGTTT GGACTAGTAT ACACAATAGA AGTCACAATG    2160

AGGGGCCCGC TGTGGCTGGA AAGCCTGCGC ACAGCCCGAA GGTTAAAAAT GGACTGTAAC    2220

AGCATTGAAA CCCCGCGACA CAGGTCAGTC TCGCGGTCTT GATCTCTTAT TATAGCGACC    2280

AAATGGTCCT TCAGAGTGAT GTTGCACTCA TAGAAGTAGG CAGCTCCGGC AGCCATTCTG    2340

CAAAATAACA AAACACCACT AAGCATAGCA CCATCACCAA GCATGAAAAC AGGTAAAAAC    2400

AAAAGCAACA CTTACTTATT CAGCAGTCAC AAGAATGTTG GGCTCCCAAG TGACAGACAA    2460

GCCTAATGCA AGGTGGGCAC AGTCTCCGGA ATAAGTTGAC AAAAGTCACG CCGCAAAGCT    2520

TCCTGAAGAG AAACGGCGGT AGCCTGGATA TCTGCAACGG ACCCAAAACC TTCAGTGTCA    2580

CTTCCAATAA ACAGATAAAA CTCTAAATAG TCCCCACTTA AAACCGAAAC AGCCGCGGCA    2640

AAGGTAGGAC ACGGACGCAC TTCCTGAGCC CTAATAAGGC TAAACACCAC ACGGCGCAGT    2700

TCAGAAGGCA AAAAGTCTGT AAGCTCTAGC TGAGCACACA CACTCTCCAC TAGACACTTG    2760

TGAAGCCTCA GACAAAAACA TGCTCCCATA GACACTCCTA AAGCTGCCAT TGTACTCACG    2820

GACGGCTGGC TGTCAGAGGA GAGCTATGAG GATGAAATGC CAAGCACAGC GTTTATATAG    2880

TCCTCAAAGT AGGGCGTGTG GAAAACGAAA AGGAATATAA CGGGGCGTTT GAGGAAGTGG    2940

TGCCAAGTAC AGTCATAAAA TGTGGGCGCG TGGTAAATGT TAAGTGCAGT TTCCCTTTGG    3000

CGGTTGGCCC GGAAAGTTCA CAAAAAGTAC AGCACGTCCT TGTCACCGTG TCAACCACAA    3060

AACCACAAAT AGGCACAACG CCCAAAAACC CGGGTCGACA CGCGTGAATT CACCGGTTCG    3120

CGAAACGCCC AAAAACCCGG GGCGCCGGCC AAAAGTCCGC GGAACTCGCC CTGTCGTAAA    3180

ACCACGCCTT TGACGTCACT GGACATTCCC GTGGGAACAC CCTGACCAGG GCGTGACCTG    3240

AACCTGACCG TCCCATGACC CCGCCCCTTG CAACACCCAA ATTAAGCCA CACCTCTTTG    3300

TCCTGTATAT TATTGATGAT GGGGGGATCC ACTAGTTCTA GAGCGGCCGC CACCGCGGTG    3360

GAGCTCCAGC TTTTGTTCCC TTTAGTGAGG GTTAATTCCG AGCTTGGCGT AATCATGGTC    3420

ATAGCTGTTT CCTGTGTGAA ATTGTTATCC GCTCACAATT CCACACAACA TACGAGCCGG    3480
```

```
AAGCATAAAG TGTAAAGCCT GGGGTGCCTA ATGAGTGAGC TAACTCACAT TAATTGCGTT     3540

GCGCTCACTG CCCGCTTTCC AGTCGGGAAA CCTGTCGTGC CAGCTGCATT AATGAATCGG     3600

CCAACGCGCG GGGAGAGGCG GTTTGCGTAT TGGGCGCTCT TCCGCTTCCT CGCTCACTGA     3660

CTCGCTGCGC TCGGTCGTTC GGCTGCGGCG AGCGGTATCA GCTCACTCAA AGGCGGTAAT     3720

ACGGTTATCC ACAGAATCAG GGGATAACGC AGGAAAGAAC ATGTGAGCAA AAGGCCAGCA     3780

AAAGGCCAGG AACCGTAAAA AGGCCGCGTT GCTGGCGTTT TTCCATAGGC TCCGCCCCCC     3840

TGACGAGCAT CACAAAAATC GACGCTCAAG TCAGAGGTGG CGAAACCCGA CAGGACTATA     3900

AAGATACCAG GCGTTTCCCC CTGGAAGCTC CCTCGTGCGC TCTCCTGTTC CGACCCTGCC     3960

GCTTACCGGA TACCTGTCCG CCTTTCTCCC TTCGGGAAGC GTGGCGCTTT CTCATAGCTC     4020

ACGCTGTAGG TATCTCAGTT CGGTGTAGGT CGTTCGCTCC AAGCTGGGCT GTGTGCACGA     4080

ACCCCCCGTT CAGCCCGACC GCTGCGCCTT ATCCGGTAAC TATCGTCTTG AGTCCAACCC     4140

GGTAAGACAC GACTTATCGC CACTGGCAGC AGCCACTGGT AACAGGATTA GCAGAGCGAG     4200

GTATGTAGGC GGTGCTACAG AGTTCTTGAA GTGGTGGCCT AACTACGGCT ACACTAGAAG     4260

GACAGTATTT GGTATCTGCG CTCTGCTGAA GCCAGTTACC TTCGGAAAAA GAGTTGGTAG     4320

CTCTTGATCC GGCAAACAAA CCACCGCTGG TAGCGGTGGT TTTTTTGTTT GCAAGCAGCA     4380

GATTACGCGC AGAAAAAAAG GATCTCAAGA AGATCCTTTG ATCTTTTCTA CGGGGTCTGA     4440

CGCTCAGTGG AACGAAAACT CACGTTAAGG GATTTTGGTC ATGAGATTAT CAAAAAGGAT     4500

CTTCACCTAG ATCCTTTTAA ATTAAAAATG AAGTTTTAAA TCAATCTAAA GTATATATGA     4560

GTAAACTTGG TCTGACAGTT ACCAATGCTT AATCAGTGAG GCACCTATCT CAGCGATCTG     4620

TCTATTTCGT TCATCCATAG TTGCCTGACT CCCCGTCGTG TAGATAACTA CGATACGGGA     4680

GGGCTTACCA TCTGGCCCCA GTGCTGCAAT GATACCGCGA GACCCACGCT CACCGGCTCC     4740

AGATTTATCA GCAATAAACC AGCCAGCCGG AAGGGCCGAG CGCAGAAGTG GTCCTGCAAC     4800

TTTATCCGCC TCCATCCAGT CTATTAATTG TTGCCGGGAA GCTAGAGTAA GTAGTTCGCC     4860

AGTTAATAGT TTGCGCAACG TTGTTGCCAT TGCTACAGGC ATCGTGGTGT CACGCTCGTC     4920

GTTTGGTATG GCTTCATTCA GCTCCGGTTC CCAACGATCA AGGCGAGTTA CATGATCCCC     4980

CATGTTGTGC AAAAAAGCGG TTAGCTCCTT CGGTCCTCCG ATCGTTGTCA GAAGTAAGTT     5040

GGCCGCAGTG TTATCACTCA TGGTTATGGC AGCACTGCAT AATTCTCTTA CTGTCATGCC     5100

ATCCGTAAGA TGCTTTTCTG TGACTGGTGA GTACTCAACC AAGTCATTCT GAGAATAGTG     5160

TATGCGGCGA CCGAGTTGCT CTTGCCCGGC GTCAATACGG GATAATACCG CGCCACATAG     5220

CAGAACTTTA AAAGTGCTCA TCATTGGAAA ACGTTCTTCG GGGCGAAAAC TCTCAAGGAT     5280

CTTACCGCTG TTGAGATCCA GTTCGATGTA ACCCACTCGT GCACCCAACT GATCTTCAGC     5340

ATCTTTTACT TTCACCAGCG TTTCTGGGTG AGCAAAAACA GGAAGGCAAA ATGCCGCAAA     5400

AAAGGGAATA AGGGCGACAC GGAAATGTTG AATACTCATA CTCTTCCTTT TTCAATATTA     5460

TTGAAGCATT TATCAGGGTT ATTGTCTCAT GAGCGGATAC ATATTTGAAT GTATTTAGAA     5520

AAATAAACAA ATAGGGGTTC CGCGCACATT TCCCCGAAAA GTGCCACCTG GGAAATTGTA     5580

AACGTTAATA TTTTGTTAAA ATTCGCGTTA AATTTTTGTT AAATCAGCTC ATTTTTTAAC     5640

CAATAGGCCG AAATCGGCAA AATCCCTTAT AAATCAAAAG AATAGACCGA GATAGGGTTG     5700

AGTGTTGTTC CAGTTTGGAA CAAGAGTCCA CTATTAAAGA ACGTGGACTC CAACGTCAAA     5760

GGGCGAAAAA CCGTCTATCA GGGCGATGGC CCACTACGTG AACCATCACC CTAATCAAGT     5820

TTTTTGGGGT CGAGGTGCCG TAAAGCACTA AATCGGAACC CTAAAGGGAG CCCCCGATTT     5880
```

-continued

| | |
|---|---|
| AGAGCTTGAC GGGGAAAGCC GGCGAACGTG GCGAGAAAGG AAGGGAAGAA AGCGAAAGGA | 5940 |
| GCGGGCGCTA GGGCGCTGGC AAGTGTAGCG GTCACGCTGC GCGTAACCAC CACACCCGCC | 6000 |
| GCGCTTAATG CGCCGCTACA GGGCGCGTCG CGCCATTCGC CATTCAGGCT GCGCAACTGT | 6060 |
| TGGGAAGGGC GATCGGTGCG GGCCTCTTCG CTATTACGCC AGCTGGCGAA AGGGGGATGT | 6120 |
| GCTGCAAGGC GATTAAGTTG GGTAACGCCA GGGTTTTCCC AGTCACGACG TTGTAAAACG | 6180 |
| ACGGCCAGTG AATTGTAATA CGACTCACTA TAGGGCGAAT TGGGTACCGG GCCCCCCCTC | 6240 |
| GAG | 6243 |

(2) INFORMATION FOR SEQ ID NO:15:

(i) SEQUENCE CHARACTERISTICS:
        (A) LENGTH: 6612 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

| | |
|---|---|
| AAGCTTTGCT CAACAAATAC TGTCAAGGAC TCGAGTCCGG CTCTGACTGA GCAATGTCTA | 60 |
| AAGAAATACC AACCCCTTAT ATGTGGAGCT ACCAACCGCA AACGGACAC GCCGGCGCCT | 120 |
| CCCAGGACTA CTCCACCCAA ATGAATTGGT TTAGTGCTGG GCCATCAATG ATTAGTCAAG | 180 |
| TTTATGGCAT TAGAGACTTG CGCAACAAAG TTTTGATAAC CCAGGCAGAA ATAACCAAAA | 240 |
| CTCCCAGAAC AATAATGGAT CCGCCAATTT GGCCAGCTGC CATGCTTGTT CAGGAAGCCG | 300 |
| CCCCACCCAA AACGGTCACT CTGCCCAGAA ACCACACCCT AGAACAGGCT ATGACCAACT | 360 |
| CTGGGGCGCA GCTAGCGGGA GGACGACAGC TGTGCCCCTC CCAAATAGGT ATAAAAAGCC | 420 |
| CAGTGCTGGC TGGCACGGGC ATTCAGCTTA GCGAAGACAT CCCCAGCGCC TCCTGGATCA | 480 |
| GGCCCGACGG CATATTCCAG CTAGGAGGGG GGTCTCGCTC GTCCTTCAGC CCAACGCAAG | 540 |
| CATTCCTCAC CCTGCAACAG GCATCCTCGA CGCCGCGCGC AGGAGGCGTG GGCACCTACC | 600 |
| AGTTTGTGCG CGAATTTGTG CCAGAGGTAT ACCTTAACCC TTTTTCAGGA CCACCGGACA | 660 |
| CCTTTCCTGA TCAGTTCATT CCTAACTACG ACATTGTAAC CAACTCTGTC GATGGCTATG | 720 |
| ACTGAGGAGA GCATGGACCA GGTGGAGGTG AACTGCCTGT GTGCTCAGCA TGCCCAAACC | 780 |
| TGCACGCGCC CTCGCTGCTT TGCAAAGGAG GGTTTATGTG CTAACTGGTT TTACAACCCA | 840 |
| GCACTTGCCT TTGAAGGGTT TGATATTCCA GACTCTTACC AAGAGGGACA CGGTGTGGAC | 900 |
| ATAGAAGTTA AGTGTTCCCA CCACTCCAGC AAACTGTGCC ACAATGGCCA TGATATGATC | 960 |
| TGCTCATACT CTCGCCTGGG ATCCCACATT AACATAAGAT GTATTTGCAA CAAGCCGCGG | 1020 |
| CCCCACATGA GCCTCATTGA GGCAGCCTGT TCTATGTATA ACCTTAACTA GATAATATTA | 1080 |
| TTAAACTTGT TTTACAGCTA CCACCATAAT GCGCTTCAGC TTCTTCATCG CCGCCGTTCT | 1140 |
| TTTCTGCACC ACAGGGGCCA GCAATGACAT TGTGACTTGC TGCGCCCACA CACCTTGCCT | 1200 |
| CCTACACCTA GAAGTGGGCT TGGGGGCCAA TGTCAGTTGG ATAAACTCTG ACACAGGCCA | 1260 |
| GGCCCCGATT TGCCTCTCCA ATGGCATGTG CAACGCTACC CAGCAAGGCC TGCAGTTTTC | 1320 |
| TGCAAACTTT TCTGAGGATG GCCTGTACAT CGCCCTCATT AAGGAGAGCA ACTACGAGGG | 1380 |
| CGCTGAGCAC TACTACCTTG TCTATATTTA TGGAGACTGC TACCAAACTG CAAATGAGTC | 1440 |
| TGCCCACGGG CCTATTTCCA GGCCCCTCAA AGATCTGTTA TTAGTGATAT CAAAGATGGT | 1500 |
| CCGGTTCTTG TACTCGGGCC ATATATTCAT GTCCCCAGAC ATCATAGTCA GCACCATTTT | 1560 |

```
CTTCTCCTTT TGCCAGTAGA TGCGAGTTTG TGCCAGCTCT TCAACAGAAA CATTGTGACC    1620

ACAGGACAGC GTTGCCACTT CTTTCACTTC CTTGGTCACG TGGATAACAC CTGAACAGAA    1680

GTGAGAAAGA CCAGCCAGCA CCAAGAGCTG AAAGAAATTG AGGTATGGAC ACTTGGATGG    1740

TGATGTTCCC TGCCTCCGTG TGTGGCCCAT ACGCGTCCCT CAGCCTTCTA ATGGGACTAA    1800

ACAACAAAAT CAGGCCCATG TAGCTTGTCA AATAAACTTA CCTAATTTTT GCTAAGACGC    1860

TGGGTCCTGC GTTTCTATGT CCACCAAAGT CCCCTCTTCC CAGCTTTGGT ACTTCCACTT    1920

GTGCGCGCGA GCCAGCTTGC GGATGTGCTT GAAAGATAAT GTGGTCTCTC CCAACAGCTT    1980

CCCGTTCACC AGCACCAGGG CCATGAAGCG GACACGAAGA GCTCTACCTG CAAATTATGA    2040

CCCTGTATAT CCATACGACG CCCCCGGGTC TTCCACACAA CCCCCTTTTT TTAATAACAA    2100

GCAAGGTCTC ACTGAGTCAC CCCCAGGAAC CCTGGCTGTC AATGTTTCCC CTCCACTAAC    2160

CTTTTCTACG TTAGGTGCCA TTAAACTTTC CACAGGTCCC GGACTCACCC TCAACGAGGG    2220

CAAGTTACAA GCCAGCTTAG GGCCCGGCCT CATCACAAAT ACCGAGGGCC AAATCACTGT    2280

TGAAAATGTC AACAAGGTTT TGTCTTTTAC CTCCCCATTA CATAAAAATG AAAACACTGT    2340

ATCCCTAGCG CTAGGAGATG GGTTAGAAGA TGAAATGGC ACCCTTAAAG TGACCTTCCC     2400

TACTCCCCCT CCCCCGCTAC AATTCTCCCC TCCCCTCACA AAAACAGGTG GTACTGTTTC    2460

CTTGCCCCTG CAAGACTCCA TGCAAGTGAC AAATGGAAAA CTGGGCGTTA AGCTACCACC    2520

TACGCACCTC CCTTGAAAAA AACTGACCAG CAAGTTAGCC TCCAAGTAGG CTCGGGTCTC    2580

ACCGTGATTA ACGAACAGTT GCAAGCTGTC CAGCCTCCCG CAACCACCTA CAACGAGCCT    2640

CTTTCCAAAA CTGACAATTC TGTTTCTCTG CAAGTAGGTG CCGGCCTTGC CGTGCAGAGC    2700

GGACGTTTGG TGGCAACCCC TCCCCCGCCT CTCACCTTTA CATCACCCCT AGAAAAAAAT    2760

GAAAACACAG TGTCGCTACA AGTAGGCGCG GGCTTGTCTG TACAAAACAA CGCCCTAGTA    2820

GCCACACCTC CCCCACCCTT AACCTTTGCC TATCCCTTAG TAAAAAATGA CAACCATGTA    2880

GCTCTAAGTG CTGGAAGTGG TTTAAGAATA TCTGGAGGCA GCCTCACGGT GGCCACTGGA    2940

CCTGGCCTTT CCCATCAAAA TGGAACAATA GGGGCTGTAG TAGGTGCAGG CCTCAAGTTT    3000

GAAAACAATG CCATTCTTGC AAAACTAGGC AACGGTCTAA CCATTAGAGA TGGCGCTATT    3060

GAAGCAACCC AACCCCCAGC TGCCCCCATA ACACTGTGGA CAGGGCCTGG CCTAGCATTA    3120

ATGGCTTTAT GTAATGACAC TCCAGTAATT AGGTCTTTAT ATGCCTAACC AGAGACAGCA    3180

ACTTAGTCAC AGTAAATGCT AGCTTTGTGG GAGAGGGGG GTATCGAATA GTCAGCCCTA     3240

CCCAGTCACA ATTTAGCCTA ATTATGGAGT TTGATCAGTT TGGACAGCTT ATGTCCACAG    3300

GAAACATTAA CTCCACCACT ACTTGGGGAG AAAAGCCCTG GGGCAATAAC ACTGTACAGC    3360

CACGCCCAAG CCACACCTGG AAACTGTGCA TGCCTAACAG AGAAGTTTAC TCCACTCCCG    3420

CCGCCACCAT CACCCGCTGT GGACTAGACA GCATTGCAGT CGACGGTGCC CAGCAGAAGT    3480

ATCGACTGCA TGCTAATTAT TAACAAACCA AAAGGCGTTG CCACTTACAC CCTTACCTTT    3540

AGGTTTTTAA ACTTTAACAG ACTAAGCGGA GGTACCCTGT TTAAAACTGA TGTCTTAACC    3600

TTTACCTATG TAGGCGAAAA TCAATAAAAC CAGAAAAAAA TAAGGGGAAA AGCTTGATAT    3660

CGAATTCCTG CAGCCCGGGG GATCCACTAG TTCTAGAGCG GCCGCCACCG CGGTGGAGCT    3720

CCAGCTTTTG TTCCCTTTAG TGAGGGTTAA TTCCGAGCTT GGCGTAATCA TGGTCATAGC    3780

TGTTTCCTGT GTGAAATTGT TATCCGCTCA CAATTCCACA CAACATACGA GCCGGAAGCA    3840

TAAAGTGTAA AGCCTGGGGT GCCTAATGAG TGAGCTAACT CACATTAATT GCGTTGCGCT    3900
```

```
CACTGCCCGC TTTCCAGTCG GGAAACCTGT CGTGCCAGCT GCATTAATGA ATCGGCCAAC    3960

GCGCGGGGAG AGGCGGTTTG CGTATTGGGC GCTCTTCCGC TTCCTCGCTC ACTGACTCGC    4020

TGCGCTCGGT CGTTCGGCTG CGGCGAGCGG TATCAGCTCA CTCAAAGGCG GTAATACGGT    4080

TATCCACAGA ATCAGGGGAT AACGCAGGAA AGAACATGTG AGCAAAAGGC CAGCAAAAGG    4140

CCAGGAACCG TAAAAAGGCC GCGTTGCTGG CGTTTTTCCA TAGGCTCCGC CCCCCTGACG    4200

AGCATCACAA AAATCGACGC TCAAGTCAGA GGTGGCGAAA CCCGACAGGA CTATAAAGAT    4260

ACCAGGCGTT TCCCCCTGGA AGCTCCCTCG TGCGCTCTCC TGTTCCGACC CTGCCGCTTA    4320

CCGGATACCT GTCCGCCTTT CTCCCTTCGG GAAGCGTGGC GCTTTCTCAT AGCTCACGCT    4380

GTAGGTATCT CAGTTCGGTG TAGGTCGTTC GCTCCAAGCT GGGCTGTGTG CACGAACCCC    4440

CCGTTCAGCC CGACCGCTGC GCCTTATCCG GTAACTATCG TCTTGAGTCC AACCCGGTAA    4500

GACACGACTT ATCGCCACTG GCAGCAGCCA CTGGTAACAG GATTAGCAGA GCGAGGTATG    4560

TAGGCGGTGC TACAGAGTTC TTGAAGTGGT GGCCTAACTA CGGCTACACT AGAAGGACAG    4620

TATTTGGTAT CTGCGCTCTG CTGAAGCCAG TTACCTTCGG AAAAAGAGTT GGTAGCTCTT    4680

GATCCGGCAA ACAAACCACC GCTGGTAGCG GTGGTTTTTT TGTTTGCAAG CAGCAGATTA    4740

CGCGCAGAAA AAAAGGATCT CAAGAAGATC CTTTGATCTT TTCTACGGGG TCTGACGCTC    4800

AGTGGAACGA AAACTCACGT TAAGGGATTT TGGTCATGAG ATTATCAAAA AGGATCTTCA    4860

CCTAGATCCT TTTAAATTAA AAATGAAGTT TTAAATCAAT CTAAAGTATA TATGAGTAAA    4920

CTTGGTCTGA CAGTTACCAA TGCTTAATCA GTGAGGCACC TATCTCAGCG ATCTGTCTAT    4980

TTCGTTCATC CATAGTTGCC TGACTCCCCG TCGTGTAGAT AACTACGATA CGGGAGGGCT    5040

TACCATCTGG CCCCAGTGCT GCAATGATAC CGCGAGACCC ACGCTCACCG GCTCCAGATT    5100

TATCAGCAAT AAACCAGCCA GCCGGAAGGG CCGAGCGCAG AAGTGGTCCT GCAACTTTAT    5160

CCGCCTCCAT CCAGTCTATT AATTGTTGCC GGGAAGCTAG AGTAAGTAGT TCGCCAGTTA    5220

ATAGTTTGCG CAACGTTGTT GCCATTGCTA CAGGCATCGT GGTGTCACGC TCGTCGTTTG    5280

GTATGGCTTC ATTCAGCTCC GGTTCCCAAC GATCAAGGCG AGTTACATGA TCCCCCATGT    5340

TGTGCAAAAA AGCGGTTAGC TCCTTCGGTC CTCCGATCGT TGTCAGAAGT AAGTTGGCCG    5400

CAGTGTTATC ACTCATGGTT ATGGCAGCAC TGCATAATTC TCTTACTGTC ATGCCATCCG    5460

TAAGATGCTT TTCTGTGACT GGTGAGTACT CAACCAAGTC ATTCTGAGAA TAGTGTATGC    5520

GGCGACCGAG TTGCTCTTGC CCGGCGTCAA TACGGGATAA TACCGCGCCA CATAGCAGAA    5580

CTTTAAAAGT GCTCATCATT GGAAAACGTT CTTCGGGGCG AAAACTCTCA AGGATCTTAC    5640

CGCTGTTGAG ATCCAGTTCG ATGTAACCCA CTCGTGCACC CAACTGATCT TCAGCATCTT    5700

TTACTTTCAC CAGCGTTTCT GGGTGAGCAA AAACAGGAAG GCAAAATGCC GCAAAAAAGG    5760

GAATAAGGGC GACACGGAAA TGTTGAATAC TCATACTCTT CCTTTTTCAA TATTATTGAA    5820

GCATTTATCA GGGTTATTGT CTCATGAGCG GATACATATT TGAATGTATT TAGAAAAATA    5880

AACAAATAGG GGTTCCGCGC ACATTTCCCC GAAAAGTGCC ACCTGGGAAA TTGTAAACGT    5940

TAATATTTTG TTAAAATTCG CGTTAAATTT TTGTTAAATC AGCTCATTTT TTAACCAATA    6000

GGCCGAAATC GGCAAAATCC CTTATAAATC AAAAGAATAG ACCGAGATAG GGTTGAGTGT    6060

TGTTCCAGTT TGGAACAAGA GTCCACTATT AAAGAACGTG GACTCCAACG TCAAAGGGCG    6120

AAAAACCGTC TATCAGGGCG ATGGCCCACT ACGTGAACCA TCACCCTAAT CAAGTTTTTT    6180

GGGGTCGAGG TGCCGTAAAG CACTAAATCG GAACCCTAAA GGGAGCCCCC GATTTAGAGC    6240

TTGACGGGGA AAGCCGGCGA ACGTGGCGAG AAAGGAAGGG AAGAAAGCGA AAGGAGCGGG    6300
```

-continued

```
CGCTAGGGCG CTGGCAAGTG TAGCGGTCAC GCTGCGCGTA ACCACCACAC CCGCCGCGCT      6360

TAATGCGCCG CTACAGGGCG CGTCGCGCCA TTCGCCATTC AGGCTGCGCA ACTGTTGGGA      6420

AGGGCGATCG GTGCGGGCCT CTTCGCTATT ACGCCAGCTG GCGAAAGGGG GATGTGCTGC      6480

AAGGCGATTA AGTTGGGTAA CGCCAGGGTT TTCCCAGTCA CGACGTTGTA AAACGACGGC      6540

CAGTGAATTG TAATACGACT CACTATAGGC GAATTGGGTA CCGGGCCCCC CCTCGAGGTC      6600

GACGGTATCG AT                                                         6612
```

(2) INFORMATION FOR SEQ ID NO:16:

(i) SEQUENCE CHARACTERISTICS:
        (A) LENGTH: 6447 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
AAGCTTTGCT CAACAAATAC TGTCAAGGAC TCGAGTCCGG CTCTGACTGA GCAATGTCTA        60

AAGAAATACC AACCCCTTAT ATGTGGAGCT ACCAACCGCA AACGGGACAC GCCGGCGCCT       120

CCCAGGACTA CTCCACCCAA ATGAATTGGT TTAGTGCTGG GCCATCAATG ATTAGTCAAG       180

TTTATGGCAT TAGAGACTTG CGCAACAAAG TTTTGATAAC CCAGGCAGAA ATAACCAAAA       240

CTCCCAGAAC AATAATGGAT CCGCCAATTT GGCCAGCTGC CATGCTTGTT CAGGAAGCCG       300

CCCCACCCAA AACGGTCACT CTGCCCAGAA ACCACACCCT AGAACAGGCT ATGACCAACT       360

CTGGGGCGCA GCTAGCGGGA GGACGACAGC TGTGCCCCTC CCAAATAGGT ATAAAAAGCC       420

CAGTGCTGGC TGGCACGGGC ATTCAGCTTA GCGAAGACAT CCCCAGCGCC TCCTGGATCA       480

GGCCCGACGG CATATTCCAG CTAGGAGGGG GGTCTCGCTC GTCCTTCAGC CAACGCAAG        540

CATTCCTCAC CCTGCAACAG GCATCCTCGA CGCCGCGCGC AGGAGGCGTG GGCACCTACC       600

AGTTTGTGCG CGAATTTGTG CCAGAGGTAT ACCTTAACCC TTTTTCAGGA CCACCGGACA       660

CCTTTCCTGA TCAGTTCATT CCTAACTACG ACATTGTAAC CAACTCTGTC GATGGCTATG       720

ACTGAGGAGA GCATGGACCA GGTGGAGGTG AACTGCCTGT GTGCTCAGCA TGCCCAAACC       780

TGCACGCGCC CTCGCTGCTT TGCAAAGGAG GGTTTATGTG CTAACTGGTT TTACAACCCA       840

GCACTTGCCT TTGAAGGGTT TGATATTCCA GACTCTTACC AAGAGGGACA CGGTGTGGAC       900

ATAGAAGTTA AGTGTTCCCA CCACTCCAGC AAACTGTGCC ACAATGGCCA TGATATGATC       960

TGCTCATACT CTCGCCTGGG ATCCCACATT AACATAAGAT GTATTTGCAA CAAGCCGCGG      1020

CCCCACATGA GCCTCATTGA GGCAGCCTGT TCTATGTATA ACCTTAACTA GATAATATTA      1080

TTAAACTTGA TACGCGTATG GCAGAAGGAT TTGCAGCCAA TAGACAATGG ATAGGACCAG      1140

AAGAAGCTGA AGAGTTATTA GATTTTGATA TAGCAACACA AATGAGTGAA GAAGGACCAC      1200

TAAATCCAGG AGTAAACCCA TTTAGGGTAC CTGGAATAAC AGAAAAAGAA AAGCAAAACT      1260

ACTGTAACAT ATTACAACCT AAGTTACAAG ATCTAAGGAA CGAAATTCAA GAGGTAAAAC      1320

TGGAAGAAGG AAATGCAGGT AAGTTTAGAA GAGCAAGATT TTTAAGGTAT TCTGATGAAC      1380

AAGTATTGTC CCTGGTTACG CGTGTCCTCA ACATCACCCG CGACGGAACT TTCCTGCTTA      1440

TTGGGGATAG CAAAAAGACC CCCTATGTCA TCCTGCTGCC CTTTTTTGCA AACCCCAAAG      1500

AAGACACTCC AATTTTAATG GCCCTTAGCC ATTCCATGCC CGTCGCCATA CCTGACACTG      1560

CAATGCCTAT ATATATTTCC ATCATGTTTT TTATTGTGGC CATGCTAGCC ACCCTCAGCC      1620
```

```
TTCTAATGGG ACTAAACAAC AAAATCAGGC CCATGTAGCT TGTCAAATAA ACTTACCTAA      1680

TTTTTGCTAA GACGCTGGGT CCTGCGTTTC TATGTCCACC AAAGTCCCCT CTTCCCAGCT      1740

TTGGTACTTC CACTTGTGCG CGCGAGCCAG CTTGCGGATG TGCTTGAAAG ATAATGTGGT      1800

CTCTCCCAAC AGCTTCCCGT TCACCAGCAC CAGGGCCATG AAGCGGACAC GAAGAGCTCT      1860

ACCTGCAAAT TATGACCCTG TATATCCATA CGACGCCCCC GGGTCTTCCA CACAACCCCC      1920

TTTTTTTAAT AACAAGCAAG GTCTCACTGA GTCACCCCCA GGAACCCTGG CTGTCAATGT      1980

TTCCCCTCCA CTAACCTTTT CTACGTTAGG TGCCATTAAA CTTTCCACAG GTCCCGGACT      2040

CACCCTCAAC GAGGGCAAGT TACAAGCCAG CTTAGGGCCC GGCCTCATCA CAAATACCGA      2100

GGGCCAAATC ACTGTTGAAA ATGTCAACAA GGTTTTGTCT TTTACCTCCC CATTACATAA      2160

AAATGAAAAC ACTGTATCCC TAGCGCTAGG AGATGGGTTA AAGATGAAA ATGGCACCCT       2220

TAAAGTGACC TTCCCTACTC CCCCTCCCCC GCTACAATTC TCCCCTCCCC TCACAAAAAC      2280

AGGTGGTACT GTTTCCTTGC CCCTGCAAGA CTCCATGCAA GTGACAAATG GAAAACTGGG      2340

CGTTAAGCTA CCACCTACGC ACCTCCCTTG AAAAAAACTG ACCAGCAAGT TAGCCTCCAA      2400

GTAGGCTCGG GTCTCACCGT GATTAACGAA CAGTTGCAAG CTGTCCAGCC TCCCGCAACC      2460

ACCTACAACG AGCCTCTTTC CAAAACTGAC AATTCTGTTT CTCTGCAAGT AGGTGCCGGC      2520

CTTGCCGTGC AGAGCGGACG TTTGGTGGCA ACCCCTCCCC CGCCTCTCAC CTTTACATCA      2580

CCCCTAGAAA AAAATGAAAA CACAGTGTCG CTACAAGTAG GCGCGGGCTT GTCTGTACAA      2640

AACAACGCCC TAGTAGCCAC ACCTCCCCCA CCCTTAACCT TTGCCTATCC CTTAGTAAAA      2700

AATGACAACC ATGTAGCTCT AAGTGCTGGA AGTGGTTTAA GAATATCTGG AGGCAGCCTC      2760

ACGGTGGCCA CTGGACCTGG CCTTTCCCAT CAAAATGGAA CAATAGGGGC TGTAGTAGGT      2820

GCAGGCCTCA AGTTTGAAAA CAATGCCATT CTTGCAAAAC TAGGCAACGG TCTAACCATT      2880

AGAGATGGCG CTATTGAAGC AACCCAACCC CCAGCTGCCC CCATAACACT GTGGACAGGG      2940

CCTGGCCTAG CATTAATGGC TTTATGTAAT GACACTCCAG TAATTAGGTC TTTATATGCC      3000

TAACCAGAGA CAGCAACTTA GTCACAGTAA ATGCTAGCTT TGTGGGAGAG GGGGGGTATC      3060

GAATAGTCAG CCCTACCCAG TCACAATTTA GCCTAATTAT GGAGTTTGAT CAGTTTGGAC      3120

AGCTTATGTC CACAGGAAAC ATTAACTCCA CCACTACTTG GGGAGAAAAG CCCTGGGGCA      3180

ATAACACTGT ACAGCCACGC CCAAGCCACA CCTGGAAACT GTGCATGCCT AACAGAGAAG      3240

TTTACTCCAC TCCCGCCGCC ACCATCACCC GCTGTGGACT AGACAGCATT GCAGTCGACG      3300

GTGCCCAGCA GAAGTATCGA CTGCATGCTA ATTATTAACA AACCAAAAGG CGTTGCCACT      3360

TACACCCTTA CCTTTAGGTT TTTAAACTTT AACAGACTAA GCGGAGGTAC CCTGTTTAAA      3420

ACTGATGTCT TAACCTTTAC CTATGTAGGC GAAAATCAAT AAAACCAGAA AAAAATAAGG      3480

GGAAAAGCTT GATATCGAAT TCCTGCAGCC CGGGGGATCC ACTAGTTCTA GAGCGGCCGC      3540

CACCGCGGTG GAGCTCCAGC TTTTGTTCCC TTTAGTGAGG GTTAATTCCG AGCTTGGCGT      3600

AATCATGGTC ATAGCTGTTT CCTGTGTGAA ATTGTTATCC GCTCACAATT CCACACAACA      3660

TACGAGCCGG AAGCATAAAG TGTAAAGCCT GGGGTGCCTA ATGAGTGAGC TAACTCACAT      3720

TAATTGCGTT GCGCTCACTG CCCGCTTTCC AGTCGGGAAA CCTGTCGTGC CAGCTGCATT      3780

AATGAATCGG CCAACGCGCG GGGAGAGGCG GTTTGCGTAT TGGGCGCTCT TCCGCTTCCT      3840

CGCTCACTGA CTCGCTGCGC TCGGTCGTTC GGCTGCGGCG AGCGGTATCA GCTCACTCAA      3900

AGGCGGTAAT ACGGTTATCC ACAGAATCAG GGGATAACGC AGGAAAGAAC ATGTGAGCAA      3960
```

-continued

```
AAGGCCAGCA AAAGGCCAGG AACCGTAAAA AGGCCGCGTT GCTGGCGTTT TTCCATAGGC    4020
TCCGCCCCCC TGACGAGCAT CACAAAAATC GACGCTCAAG TCAGAGGTGG CGAAACCCGA    4080
CAGGACTATA AAGATACCAG GCGTTTCCCC CTGGAAGCTC CCTCGTGCGC TCTCCTGTTC    4140
CGACCCTGCC GCTTACCGGA TACCTGTCCG CCTTTCTCCC TTCGGGAAGC GTGGCGCTTT    4200
CTCATAGCTC ACGCTGTAGG TATCTCAGTT CGGTGTAGGT CGTTCGCTCC AAGCTGGGCT    4260
GTGTGCACGA ACCCCCCGTT CAGCCCGACC GCTGCGCCTT ATCCGGTAAC TATCGTCTTG    4320
AGTCCAACCC GGTAAGACAC GACTTATCGC CACTGGCAGC AGCCACTGGT AACAGGATTA    4380
GCAGAGCGAG GTATGTAGGC GGTGCTACAG AGTTCTTGAA GTGGTGGCCT AACTACGGCT    4440
ACACTAGAAG GACAGTATTT GGTATCTGCG CTCTGCTGAA GCCAGTTACC TTCGGAAAAA    4500
GAGTTGGTAG CTCTTGATCC GGCAAACAAA CCACCGCTGG TAGCGGTGGT TTTTTTGTTT    4560
GCAAGCAGCA GATTACGCGC AGAAAAAAAG GATCTCAAGA AGATCCTTTG ATCTTTTCTA    4620
CGGGGTCTGA CGCTCAGTGG AACGAAAACT CACGTTAAGG GATTTTGGTC ATGAGATTAT    4680
CAAAAAGGAT CTTCACCTAG ATCCTTTTAA ATTAAAAATG AAGTTTTAAA TCAATCTAAA    4740
GTATATATGA GTAAACTTGG TCTGACAGTT ACCAATGCTT AATCAGTGAG GCACCTATCT    4800
CAGCGATCTG TCTATTTCGT TCATCCATAG TTGCCTGACT CCCCGTCGTG TAGATAACTA    4860
CGATACGGGA GGGCTTACCA TCTGGCCCCA GTGCTGCAAT GATACCGCGA GACCCACGCT    4920
CACCGGCTCC AGATTTATCA GCAATAAACC AGCCAGCCGG AAGGGCCGAG CGCAGAAGTG    4980
GTCCTGCAAC TTTATCCGCC TCCATCCAGT CTATTAATTG TTGCCGGGAA GCTAGAGTAA    5040
GTAGTTCGCC AGTTAATAGT TTGCGCAACG TTGTTGCCAT TGCTACAGGC ATCGTGGTGT    5100
CACGCTCGTC GTTTGGTATG GCTTCATTCA GCTCCGGTTC CCAACGATCA AGGCGAGTTA    5160
CATGATCCCC CATGTTGTGC AAAAAAGCGG TTAGCTCCTT CGGTCCTCCG ATCGTTGTCA    5220
GAAGTAAGTT GGCCGCAGTG TTATCACTCA TGGTTATGGC AGCACTGCAT AATTCTCTTA    5280
CTGTCATGCC ATCCGTAAGA TGCTTTTCTG TGACTGGTGA GTACTCAACC AAGTCATTCT    5340
GAGAATAGTG TATGCGGCGA CCGAGTTGCT CTTGCCCGGC GTCAATACGG GATAATACCG    5400
CGCCACATAG CAGAACTTTA AAAGTGCTCA TCATTGGAAA ACGTTCTTCG GGGCGAAAAC    5460
TCTCAAGGAT CTTACCGCTG TTGAGATCCA GTTCGATGTA ACCCACTCGT GCACCCAACT    5520
GATCTTCAGC ATCTTTTACT TTCACCAGCG TTTCTGGGTG AGCAAAAACA GGAAGGCAAA    5580
ATGCCGCAAA AAAGGGAATA AGGGCGACAC GGAAATGTTG AATACTCATA CTCTTCCTTT    5640
TTCAATATTA TTGAAGCATT TATCAGGGTT ATTGTCTCAT GAGCGGATAC ATATTTGAAT    5700
GTATTTAGAA AAATAAACAA ATAGGGGTTC CGCGCACATT TCCCCGAAAA GTGCCACCTG    5760
GGAAATTGTA AACGTTAATA TTTTGTTAAA ATTCGCGTTA AATTTTTGTT AAATCAGCTC    5820
ATTTTTTAAC CAATAGGCCG AAATCGGCAA AATCCCTTAT AAATCAAAAG AATAGACCGA    5880
GATAGGGTTG AGTGTTGTTC CAGTTTGGAA CAAGAGTCCA CTATTAAAGA ACGTGGACTC    5940
CAACGTCAAA GGGCGAAAAA CCGTCTATCA GGGCGATGGC CCACTACGTG AACCATCACC    6000
CTAATCAAGT TTTTTGGGGT CGAGGTGCCG TAAAGCACTA AATCGGAACC CTAAAGGGAG    6060
CCCCCGATTT AGAGCTTGAC GGGGAAAGCC GGCGAACGTG GCGAGAAAGG AAGGGAAGAA    6120
AGCGAAAGGA GCGGGCGCTA GGGCGCTGGC AAGTGTAGCG GTCACGCTGC GCGTAACCAC    6180
CACACCCGCC GCGCTTAATG CGCCGCTACA GGGCGCGTCG CGCCATTCGC CATTCAGGCT    6240
GCGCAACTGT TGGGAAGGGC GATCGGTGCG GGCCTCTTCG CTATTACGCC AGCTGGCGAA    6300
AGGGGGATGT GCTGCAAGGC GATTAAGTTG GGTAACGCCA GGGTTTTCCC AGTCACGACG    6360
```

(2) INFORMATION FOR SEQ ID NO:17:

(i) SEQUENCE CHARACTERISTICS:
        (A) LENGTH: 6244 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
TTGTAAAACG ACGGCCAGTG AATTGTAATA CGACTCACTA TAGGCGAATT GGGTACCGGG      6420
CCCCCCCTCG AGGTCGACGG TATCGAT                                         6447

AAGCTTTGCT CAACAAATAC TGTCAAGGAC TCGAGTCCGG CTCTGACTGA GCAATGTCTA       60
AAGAAATACC AACCCTTAT ATGTGGAGCT ACCAACCGCA AACGGGACAC GCCGGCGCCT        120
CCCAGGACTA CTCCACCCAA ATGAATTGGT TTAGTGCTGG GCCATCAATG ATTAGTCAAG       180
TTTATGGCAT TAGAGACTTG CGCAACAAAG TTTTGATAAC CCAGGCAGAA ATAACCAAAA       240
CTCCCAGAAC AATAATGGAT CCGCCAATTT GGCCAGCTGC CATGCTTGTT CAGGAAGCCG       300
CCCCACCCAA AACGGTCACT CTGCCCAGAA ACCACACCCT AGAACAGGCT ATGACCAACT       360
CTGGGGCGCA GCTAGCGGGA GGACGACAGC TGTGCCCCTC CCAAATAGGT ATAAAAAGCC       420
CAGTGCTGGC TGGCACGGGC ATTCAGCTTA GCGAAGACAT CCCCAGCGCC TCCTGGATCA       480
GGCCCGACGG CATATTCCAG CTAGGAGGGG GGTCTCGCTC GTCCTTCAGC CCAACGCAAG       540
CATTCCTCAC CCTGCAACAG GCATCCTCGA CGCCGCGCGC AGGAGGCGTG GGCACCTACC       600
AGTTTGTGCG CGAATTTGTG CCAGAGGTAT ACCTTAACCC TTTTTCAGGA CCACCGGACA       660
CCTTTCCTGA TCAGTTCATT CCTAACTACG ACATTGTAAC CAACTCTGTC GATGGCTATG       720
ACTGAGGAGA GCATGGACCA GGTGGAGGTG AACTGCCTGT GTGCTCAGCA TGCCCAAACC       780
TGCACGCGCC CTCGCTGCTT TGCAAAGGAG GGTTTATGTG CTAACTGGTT TTACAACCCA       840
GCACTTGCCT TTGAAGGGTT TGATATTCCA GACTCTTACC AAGAGGGACA CGGTGTGTAA       900
ATGGGCCACA CACGGAGGCA GGAACATCA CCATCCAAGT GTCCATACCT CAATTTCTTT       960
CAGCTCTTGG TGCTGGCTGG TCTTTCTCAC TTCTGTTCAG GTGTTATCCA CGTGACCAAG      1020
GAAGTGAAAG AAGTGGCAAC GCTGTCCTGT GGTCACAATG TTTCTGTTGA AGAGCTGGCA      1080
CAAACTCGCA TCTACTGGCA AAAGGAGAAG AAAATGGTGC TGACTATGAT GTCTGGGGAC      1140
ATGAATATAT GGCCCGAGTA CAAGAACCGG ACCATCTTTG ATATCACTAA TAACACGCGT      1200
GTCCTCAACA TCACCCGCGA CGGAACTTTC CTGCTTATTG GGGATAGCAA AAAGACCCCC      1260
TATGTCATCC TGCTGCCCTT TTTTGCAAAC CCCAAAGAAG ACACTCCAAT TTTAATGGCC      1320
CTTAGCCATT CCATGCCCGT CGCCATACCT GACACTGCAA TGCCTATATA TATTTCCATC      1380
ATGTTTTTTA TTGTGGCCAT GCTAGCCACC CTCAGCCTTC TAATGGGACT AAACAACAAA      1440
ATCAGGCCCA TGTAGCTTGT CAAATAAACT TACCTAATTT TTGCTAAGAC GCTGGGTCCT      1500
GCGTTTCTAT GTCCACCAAA GTCCCCTCTT CCCAGCTTTG GTACTTCCAC TTGTGCGCGC      1560
GAGCCAGCTT GCGGATGTGC TTGAAAGATA ATGTGGTCTC TCCCAACAGC TTCCCGTTCA      1620
CCAGCACCAG GGCCATGAAG CGGACACGAA GAGCTCTACC TGCAAATTAT GACCCTGTAT      1680
ATCCATACGA CGCCCCCGGG TCTTCCACAC AACCCCCTTT TTTTAATAAC AAGCAAGGTC      1740
TCACTGAGTC ACCCCCAGGA ACCCTGGCTG TCAATGTTTC CCCTCCACTA ACCTTTTCTA      1800
CGTTAGGTGC CATTAAACTT TCCACAGGTC CCGGACTCAC CCTCAACGAG GGCAAGTTAC      1860
```

```
AAGCCAGCTT AGGGCCCGGC CTCATCACAA ATACCGAGGG CCAAATCACT GTTGAAAATG    1920

TCAACAAGGT TTTGTCTTTT ACCTCCCCAT TACATAAAAA TGAAAACACT GTATCCCTAG    1980

CGCTAGGAGA TGGGTTAGAA GATGAAAATG GCACCCTTAA AGTGACCTTC CCTACTCCCC    2040

CTCCCCCGCT ACAATTCTCC CCTCCCCTCA CAAAAACAGG TGGTACTGTT TCCTTGCCCC    2100

TGCAAGACTC CATGCAAGTG ACAAATGGAA AACTGGGCGT TAAGCTACCA CCTACGCACC    2160

TCCCTTGAAA AAAACTGACC AGCAAGTTAG CCTCCAAGTA GGCTCGGGTC TCACCGTGAT    2220

TAACGAACAG TTGCAAGCTG TCCAGCCTCC CGCAACCACC TACAACGAGC CTCTTTCCAA    2280

AACTGACAAT TCTGTTTCTC TGCAAGTAGG TGCCGGCCTT GCCGTGCAGA GCGGACGTTT    2340

GGTGGCAACC CCTCCCCCGC CTCTCACCTT TACATCACCC CTAGAAAAAA ATGAAAACAC    2400

AGTGTCGCTA CAAGTAGGCG CGGGCTTGTC TGTACAAAAC AACGCCCTAG TAGCCACACC    2460

TCCCCCACCC TTAACCTTTG CCTATCCCTT AGTAAAAAAT GACAACCATG TAGCTCTAAG    2520

TGCTGGAAGT GGTTTAAGAA TATCTGGAGG CAGCCTCACG GTGGCCACTG GACCTGGCCT    2580

TTCCCATCAA AATGGAACAA TAGGGGCTGT AGTAGGTGCA GGCCTCAAGT TTGAAAACAA    2640

TGCCATTCTT GCAAAACTAG GCAACGGTCT AACCATTAGA GATGGCGCTA TTGAAGCAAC    2700

CCAACCCCCA GCTGCCCCCA TAACACTGTG GACAGGGCCT GGCCTAGCAT TAATGGCTTT    2760

ATGTAATGAC ACTCCAGTAA TTAGGTCTTT ATATGCCTAA CCAGAGACAG CAACTTAGTC    2820

ACAGTAAATG CTAGCTTTGT GGGAGAGGGG GGGTATCGAA TAGTCAGCCC TACCCAGTCA    2880

CAATTTAGCC TAATTATGGA GTTTGATCAG TTTGGACAGC TTATGTCCAC AGGAAACATT    2940

AACTCCACCA CTACTTGGGG AGAAAAGCCC TGGGGCAATA ACACTGTACA GCCACGCCCA    3000

AGCCACACCT GGAAACTGTG CATGCCTAAC AGAGAAGTTT ACTCCACTCC CGCCGCCACC    3060

ATCACCCGCT GTGGACTAGA CAGCATTGCA GTCGACGGTG CCCAGCAGAA GTATCGACTG    3120

CATGCTAATT ATTAACAAAC CAAAAGGCGT TGCCACTTAC ACCCTTACCT TTAGGTTTTT    3180

AAACTTTAAC AGACTAAGCG GAGGTACCCT GTTTAAAACT GATGTCTTAA CCTTTACCTA    3240

TGTAGGCGAA AATCAATAAA ACCAGAAAAA AATAAGGGGA AAAGCTTGAT ATCGAATTCC    3300

TGCAGCCCGG GGGATCCACT AGTTCTAGAG CGGCCGCCAC CGCGGTGGAG CTCCAGCTTT    3360

TGTTCCCTTT AGTGAGGGTT AATTCCGAGC TTGGCGTAAT CATGGTCATA GCTGTTTCCT    3420

GTGTGAAATT GTTATCCGCT CACAATTCCA CACAACATAC GAGCCGGAAG CATAAAGTGT    3480

AAAGCCTGGG GTGCCTAATG AGTGAGCTAA CTCACATTAA TTGCGTTGCG CTCACTGCCC    3540

GCTTTCCAGT CGGGAAACCT GTCGTGCCAG CTGCATTAAT GAATCGGCCA ACGCGCGGGG    3600

AGAGGCGGTT TGCGTATTGG GCGCTCTTCC GCTTCCTCGC TCACTGACTC GCTGCGCTCG    3660

GTCGTTCGGC TGCGGCGAGC GGTATCAGCT CACTCAAAGG CGGTAATACG GTTATCCACA    3720

GAATCAGGGG ATAACGCAGG AAAGAACATG TGAGCAAAAG GCCAGCAAAA GGCCAGGAAC    3780

CGTAAAAAGG CCGCGTTGCT GGCGTTTTTC CATAGGCTCC GCCCCCCTGA CGAGCATCAC    3840

AAAAATCGAC GCTCAAGTCA GAGGTGGCGA AACCCGACAG GACTATAAAG ATACCAGGCG    3900

TTTCCCCCTG GAAGCTCCCT CGTGCGCTCT CCTGTTCCGA CCCTGCCGCT TACCGGATAC    3960

CTGTCCGCCT TTCTCCCTTC GGGAAGCGTG GCGCTTTCTC ATAGCTCACG CTGTAGGTAT    4020

CTCAGTTCGG TGTAGGTCGT TCGCTCCAAG CTGGGCTGTG TGCACGAACC CCCCGTTCAG    4080

CCCGACCGCT GCGCCTTATC CGGTAACTAT CGTCTTGAGT CCAACCCGGT AAGACACGAC    4140

TTATCGCCAC TGGCAGCAGC CACTGGTAAC AGGATTAGCA GAGCGAGGTA TGTAGGCGGT    4200
```

```
GCTACAGAGT TCTTGAAGTG GTGGCCTAAC TACGGCTACA CTAGAAGGAC AGTATTTGGT      4260

ATCTGCGCTC TGCTGAAGCC AGTTACCTTC GGAAAAAGAG TTGGTAGCTC TTGATCCGGC      4320

AAACAAACCA CCGCTGGTAG CGGTGGTTTT TTTGTTTGCA AGCAGCAGAT TACGCGCAGA      4380

AAAAAAGGAT CTCAAGAAGA TCCTTTGATC TTTTCTACGG GGTCTGACGC TCAGTGGAAC      4440

GAAAACTCAC GTTAAGGGAT TTTGGTCATG AGATTATCAA AAAGGATCTT CACCTAGATC      4500

CTTTTAAATT AAAAATGAAG TTTTAAATCA ATCTAAAGTA TATATGAGTA AACTTGGTCT      4560

GACAGTTACC AATGCTTAAT CAGTGAGGCA CCTATCTCAG CGATCTGTCT ATTTCGTTCA      4620

TCCATAGTTG CCTGACTCCC CGTCGTGTAG ATAACTACGA TACGGGAGGG CTTACCATCT      4680

GGCCCCAGTG CTGCAATGAT ACCGCGAGAC CCACGCTCAC CGGCTCCAGA TTTATCAGCA      4740

ATAAACCAGC CAGCCGGAAG GGCCGAGCGC AGAAGTGGTC CTGCAACTTT ATCCGCCTCC      4800

ATCCAGTCTA TTAATTGTTG CCGGGAAGCT AGAGTAAGTA GTTCGCCAGT TAATAGTTTG      4860

CGCAACGTTG TTGCCATTGC TACAGGCATC GTGGTGTCAC GCTCGTCGTT TGGTATGGCT      4920

TCATTCAGCT CCGGTTCCCA ACGATCAAGG CGAGTTACAT GATCCCCCAT GTTGTGCAAA      4980

AAAGCGGTTA GCTCCTTCGG TCCTCCGATC GTTGTCAGAA GTAAGTTGGC CGCAGTGTTA      5040

TCACTCATGG TTATGGCAGC ACTGCATAAT TCTCTTACTG TCATGCCATC CGTAAGATGC      5100

TTTTCTGTGA CTGGTGAGTA CTCAACCAAG TCATTCTGAG AATAGTGTAT GCGGCGACCG      5160

AGTTGCTCTT GCCCGGCGTC AATACGGGAT AATACCGCGC CACATAGCAG AACTTTAAAA      5220

GTGCTCATCA TTGGAAAACG TTCTTCGGGG CGAAAACTCT CAAGGATCTT ACCGCTGTTG      5280

AGATCCAGTT CGATGTAACC CACTCGTGCA CCCAACTGAT CTTCAGCATC TTTTACTTTC      5340

ACCAGCGTTT CTGGGTGAGC AAAAACAGGA AGGCAAAATG CCGCAAAAAA GGGAATAAGG      5400

GCGACACGGA AATGTTGAAT ACTCATACTC TTCCTTTTTC AATATTATTG AAGCATTTAT      5460

CAGGGTTATT GTCTCATGAG CGGATACATA TTTGAATGTA TTTAGAAAAA TAAACAAATA      5520

GGGGTTCCGC GCACATTTCC CCGAAAAGTG CCACCTGGGA AATTGTAAAC GTTAATATTT      5580

TGTTAAAATT CGCGTTAAAT TTTTGTTAAA TCAGCTCATT TTTTAACCAA TAGGCCGAAA      5640

TCGGCAAAAT CCCTTATAAA TCAAAAGAAT AGACCGAGAT AGGGTTGAGT GTTGTTCCAG      5700

TTTGAACAA GAGTCCACTA TTAAAGAACG TGGACTCCAA CGTCAAAGGG CGAAAAACCG       5760

TCTATCAGGG CGATGGCCCA CTACGTGAAC CATCACCCTA ATCAAGTTTT TTGGGGTCGA      5820

GGTGCCGTAA AGCACTAAAT CGGAACCCTA AAGGGAGCCC CCGATTTAGA GCTTGACGGG      5880

GAAAGCCGGC GAACGTGGCG AGAAAGGAAG GGAAGAAAGC GAAAGGAGCG GGCGCTAGGG     5940

CGCTGGCAAG TGTAGCGGTC ACGCTGCGCG TAACCACCAC ACCCGCCGCG CTTAATGCGC      6000

CGCTACAGGG CGCGTCGCGC CATTCGCCAT TCAGGCTGCG CAACTGTTGG GAAGGGCGAT      6060

CGGTGCGGGC CTCTTCGCTA TTACGCCAGC TGGCGAAAGG GGGATGTGCT GCAAGGCGAT      6120

TAAGTTGGGT AACGCCAGGG TTTTCCCAGT CACGACGTTG TAAAACGACG GCCAGTGAAT      6180

TGTAATACGA CTCACTATAG GCGAATTGGG TACCGGGCCC CCCCTCGAGG TCGACGGTAT      6240

CGAT                                                                  6244
```

(2) INFORMATION FOR SEQ ID NO:18:

(i) SEQUENCE CHARACTERISTICS:
        (A) LENGTH: 6045 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

| | | | | | |
|---|---|---|---|---|---|
| AAGCTTTGCT | CAACAAATAC | TGTCAAGGAC | TCGAGTCCGG | CTCTGACTGA | GCAATGTCTA | 60 |
| AAGAAATACC | AACCCCTTAT | ATGTGGAGCT | ACCAACCGCA | AACGGGACAC | GCCGGCGCCT | 120 |
| CCCAGGACTA | CTCCACCCAA | ATGAATTGGT | TTAGTGCTGG | GCCATCAATG | ATTAGTCAAG | 180 |
| TTTATGGCAT | TAGAGACTTG | CGCAACAAAG | TTTTGATAAC | CCAGGCAGAA | ATAACCAAAA | 240 |
| CTCCCAGAAC | AATAATGGAT | CCGCCAATTT | GGCCAGCTGC | CATGCTTGTT | CAGGAAGCCG | 300 |
| CCCCACCCAA | AACGGTCACT | CTGCCCAGAA | ACCACACCCT | AGAACAGGCT | ATGACCAACT | 360 |
| CTGGGGCGCA | GCTAGCGGGA | GGACGACAGC | TGTGCCCCTC | CCAAATAGGT | ATAAAAAGCC | 420 |
| CAGTGCTGGC | TGGCACGGGC | ATTCAGCTTA | GCGAAGACAT | CCCCAGCGCC | TCCTGGATCA | 480 |
| GGCCCGACGG | CATATTCCAG | CTAGGAGGGG | GGTCTCGCTC | GTCCTTCAGC | CCAACGCAAG | 540 |
| CATTCCTCAC | CCTGCAACAG | GCATCCTCGA | CGCCGCGCGC | AGGAGGCGTG | GGCACCTACC | 600 |
| AGTTTGTGCG | CGAATTTGTG | CCAGAGGTAT | ACCTTAACCC | TTTTTCAGGA | CCACCGGACA | 660 |
| CCTTTCCTGA | TCAGTTCATT | CCTAACTACG | ACATTGTAAC | CAACTCTGTC | GATGGCTATG | 720 |
| ACTGAGGAGA | GCATGGACCA | GGTGGAGGTG | AACTGCCTGT | GTGCTCAGCA | TGCCCAAACC | 780 |
| TGCACGCGCC | CTCGCTGCTT | TGCAAAGGAG | GGTTTATGTG | CTAACTGGTT | TTACAACCCA | 840 |
| GCACTTGCCT | TTGAAGGGTT | TGATATTCCA | GACTCTTACC | AAGAGGGACA | CGGTGTGTAG | 900 |
| ATGGGTTGTT | CTGTGGAGAA | TGTTGGACAG | TGTAAAGTAT | GCTGCCAGGG | GCGTCCGCGA | 960 |
| CTGACCAAGT | GAAAACATCA | TTGTAATAGG | AGTTTGTTCT | CCATGTCTCT | TGTTGGTCTA | 1020 |
| CCTGTTGGGG | TGGTCCGCCA | ATCCCTGCTG | TTGCAATCGA | TGCGGATGAA | TTTTCTGCAG | 1080 |
| TGATCACGCT | GGTAGTGGCC | ACAACGCCAG | GATCCATGCC | ATCAGTCGTA | GTTCCAGGAA | 1140 |
| CTGATGCTGT | GGTGGCAGTG | CCCGCTGCTT | CGCCTTGCGG | CGCTGCACGG | GCTTTGCCCT | 1200 |
| CTAACGCGTC | CCTCAGCCTT | CTAATGGGAC | TAAACAACAA | AATCAGGCCC | ATGTAGCTTG | 1260 |
| TCAAATAAAC | TTACCTAATT | TTTGCTAAGA | CGCTGGGTCC | TGCGTTTCTA | TGTCCACCAA | 1320 |
| AGTCCCCTCT | TCCCAGCTTT | GGTACTTCCA | CTTGTGCGCG | CGAGCCAGCT | TGCGGATGTG | 1380 |
| CTTGAAAGAT | AATGTGGTCT | CTCCCAACAG | CTTCCCGTTC | ACCAGCACCA | GGGCCATGAA | 1440 |
| GCGGACACGA | AGAGCTCTAC | CTGCAAATTA | TGACCCTGTA | TATCCATACG | ACGCCCCCGG | 1500 |
| GTCTTCCACA | CAACCCCCTT | TTTTTAATAA | CAAGCAAGGT | CTCACTGAGT | CACCCCCAGG | 1560 |
| AACCCTGGCT | GTCAATGTTT | CCCCTCCACT | AACCTTTTCT | ACGTTAGGTG | CCATTAAACT | 1620 |
| TTCCACAGGT | CCCGGACTCA | CCCTCAACGA | GGGCAAGTTA | CAAGCCAGCT | TAGGGCCCGG | 1680 |
| CCTCATCACA | AATACCGAGG | GCCAAATCAC | TGTTGAAAAT | GTCAACAAGG | TTTTGTCTTT | 1740 |
| TACCTCCCCA | TTACATAAAA | ATGAAAACAC | TGTATCCCTA | GCGCTAGGAG | ATGGGTTAGA | 1800 |
| AGATGAAAAT | GGCACCCTTA | AAGTGACCTT | CCCTACTCCC | CCTCCCCCGC | TACAATTCTC | 1860 |
| CCCTCCCCTC | ACAAAAACAG | GTGGTACTGT | TTCCTTGCCC | CTGCAAGACT | CCATGCAAGT | 1920 |
| GACAAATGGA | AAACTGGGCG | TTAAGCTACC | ACCTACGCAC | CTCCCTTGAA | AAAAACTGAC | 1980 |
| CAGCAAGTTA | GCCTCCAAGT | AGGCTCGGGT | CTCACCGTGA | TTAACGAACA | GTTGCAAGCT | 2040 |
| GTCCAGCCTC | CCGCAACCAC | CTACAACGAG | CCTCTTTCCA | AAACTGACAA | TTCTGTTTCT | 2100 |
| CTGCAAGTAG | GTGCCGGCCT | TGCCGTGCAG | AGCGGACGTT | TGGTGGCAAC | CCCTCCCCCG | 2160 |
| CCTCTCACCT | TTACATCACC | CCTAGAAAAA | AATGAAAACA | CAGTGTCGCT | ACAAGTAGGC | 2220 |
| GCGGGCTTGT | CTGTACAAAA | CAACGCCCTA | GTAGCCACAC | CTCCCCCACC | CTTAACCTTT | 2280 |

```
GCCTATCCCT TAGTAAAAAA TGACAACCAT GTAGCTCTAA GTGCTGGAAG TGGTTTAAGA    2340

ATATCTGGAG GCAGCCTCAC GGTGGCCACT GGACCTGGCC TTTCCCATCA AAATGGAACA    2400

ATAGGGGCTG TAGTAGGTGC AGGCCTCAAG TTTGAAAACA ATGCCATTCT TGCAAAACTA    2460

GGCAACGGTC TAACCATTAG AGATGGCGCT ATTGAAGCAA CCCAACCCCC AGCTGCCCCC    2520

ATAACACTGT GGACAGGGCC TGGCCTAGCA TTAATGGCTT TATGTAATGA CACTCCAGTA    2580

ATTAGGTCTT TATATGCCTA ACCAGAGACA GCAACTTAGT CACAGTAAAT GCTAGCTTTG    2640

TGGGAGAGGG GGGGTATCGA ATAGTCAGCC CTACCCAGTC ACAATTTAGC CTAATTATGG    2700

AGTTTGATCA GTTTGGACAG CTTATGTCCA CAGGAAACAT TAACTCCACC ACTACTTGGG    2760

GAGAAAAGCC CTGGGGCAAT AACACTGTAC AGCCACGCCC AAGCCACACC TGGAAACTGT    2820

GCATGCCTAA CAGAGAAGTT TACTCCACTC CCGCCGCCAC CATCACCCGC TGTGGACTAG    2880

ACAGCATTGC AGTCGACGGT GCCCAGCAGA AGTATCGACT GCATGCTAAT TATTAACAAA    2940

CCAAAAGGCG TTGCCACTTA CACCCTTACC TTTAGGTTTT TAAACTTTAA CAGACTAAGC    3000

GGAGGTACCC TGTTTAAAAC TGATGTCTTA ACCTTTACCT ATGTAGGCGA AAATCAATAA    3060

AACCAGAAAA AAATAAGGGG AAAAGCTTGA TATCGAATTC CTGCAGCCCG GGGATCCAC    3120

TAGTTCTAGA GCGGCCGCCA CCGCGGTGGA GCTCCAGCTT TGTTCCCTT TAGTGAGGGT    3180

TAATTCCGAG CTTGGCGTAA TCATGGTCAT AGCTGTTTCC TGTGTGAAAT TGTTATCCGC    3240

TCACAATTCC ACACAACATA CGAGCCGGAA GCATAAAGTG TAAAGCCTGG GGTGCCTAAT    3300

GAGTGAGCTA ACTCACATTA ATTGCGTTGC GCTCACTGCC CGCTTTCCAG TCGGGAAACC    3360

TGTCGTGCCA GCTGCATTAA TGAATCGGCC AACGCGCGGG GAGAGGCGGT TTGCGTATTG    3420

GGCGCTCTTC CGCTTCCTCG CTCACTGACT CGCTGCGCTC GGTCGTTCGG CTGCGGCGAG    3480

CGGTATCAGC TCACTCAAAG GCGGTAATAC GGTTATCCAC AGAATCAGGG GATAACGCAG    3540

GAAAGAACAT GTGAGCAAAA GGCCAGCAAA AGGCCAGGAA CCGTAAAAAG GCCGCGTTGC    3600

TGGCGTTTTT CCATAGGCTC CGCCCCCCTG ACGAGCATCA CAAAAATCGA CGCTCAAGTC    3660

AGAGGTGGCG AAACCCGACA GGACTATAAA GATACCAGGC GTTTCCCCCT GGAAGCTCCC    3720

TCGTGCGCTC TCCTGTTCCG ACCCTGCCGC TTACCGGATA CCTGTCCGCC TTTCTCCCTT    3780

CGGGAAGCGT GGCGCTTTCT CATAGCTCAC GCTGTAGGTA TCTCAGTTCG GTGTAGGTCG    3840

TTCGCTCCAA GCTGGGCTGT GTGCACGAAC CCCCCGTTCA GCCCGACCGC TGCGCCTTAT    3900

CCGGTAACTA TCGTCTTGAG TCCAACCCGG TAAGACACGA CTTATCGCCA CTGGCAGCAG    3960

CCACTGGTAA CAGGATTAGC AGAGCGAGGT ATGTAGGCGG TGCTACAGAG TTCTTGAAGT    4020

GGTGGCCTAA CTACGGCTAC ACTAGAAGGA CAGTATTTGG TATCTGCGCT CTGCTGAAGC    4080

CAGTTACCTT CGGAAAAAGA GTTGGTAGCT CTTGATCCGG CAAACAAACC ACCGCTGGTA    4140

GCGGTGGTTT TTTTGTTTGC AAGCAGCAGA TTACGCGCAG AAAAAAAGGA TCTCAAGAAG    4200

ATCCTTTGAT CTTTTCTACG GGGTCTGACG CTCAGTGGAA CGAAAACTCA CGTTAAGGGA    4260

TTTTGGTCAT GAGATTATCA AAAAGGATCT TCACCTAGAT CCTTTTAAAT TAAAAATGAA    4320

GTTTTAAATC AATCTAAAGT ATATATGAGT AAACTTGGTC TGACAGTTAC CAATGCTTAA    4380

TCAGTGAGGC ACCTATCTCA GCGATCTGTC TATTTCGTTC ATCCATAGTT GCCTGACTCC    4440

CCGTCGTGTA GATAACTACG ATACGGGAGG GCTTACCATC TGGCCCCAGT GCTGCAATGA    4500

TACCGCGAGA CCCACGCTCA CCGGCTCCAG ATTTATCAGC AATAAACCAG CCAGCCGGAA    4560

GGGCCGAGCG CAGAAGTGGT CCTGCAACTT TATCCGCCTC CATCCAGTCT ATTAATTGTT    4620
```

```
GCCGGGAAGC TAGAGTAAGT AGTTCGCCAG TTAATAGTTT GCGCAACGTT GTTGCCATTG    4680

CTACAGGCAT CGTGGTGTCA CGCTCGTCGT TTGGTATGGC TTCATTCAGC TCCGGTTCCC    4740

AACGATCAAG GCGAGTTACA TGATCCCCCA TGTTGTGCAA AAAAGCGGTT AGCTCCTTCG    4800

GTCCTCCGAT CGTTGTCAGA AGTAAGTTGG CCGCAGTGTT ATCACTCATG GTTATGGCAG    4860

CACTGCATAA TTCTCTTACT GTCATGCCAT CCGTAAGATG CTTTTCTGTG ACTGGTGAGT    4920

ACTCAACCAA GTCATTCTGA GAATAGTGTA TGCGGCGACC GAGTTGCTCT TGCCCGGCGT    4980

CAATACGGGA TAATACCGCG CCACATAGCA GAACTTTAAA AGTGCTCATC ATTGGAAAAC    5040

GTTCTTCGGG GCGAAAACTC TCAAGGATCT TACCGCTGTT GAGATCCAGT TCGATGTAAC    5100

CCACTCGTGC ACCCAACTGA TCTTCAGCAT CTTTTACTTT CACCAGCGTT TCTGGGTGAG    5160

CAAAAACAGG AAGGCAAAAT GCCGCAAAAA AGGGAATAAG GGCGACACGG AAATGTTGAA    5220

TACTCATACT CTTCCTTTTT CAATATTATT GAAGCATTTA TCAGGGTTAT TGTCTCATGA    5280

GCGGATACAT ATTTGAATGT ATTTAGAAAA ATAAACAAAT AGGGGTTCCG CGCACATTTC    5340

CCCGAAAAGT GCCACCTGGG AAATTGTAAA CGTTAATATT TTGTTAAAAT TCGCGTTAAA    5400

TTTTTGTTAA ATCAGCTCAT TTTTTAACCA ATAGGCCGAA ATCGGCAAAA TCCCTTATAA    5460

ATCAAAAGAA TAGACCGAGA TAGGGTTGAG TGTTGTTCCA GTTTGGAACA AGAGTCCACT    5520

ATTAAAGAAC GTGGACTCCA ACGTCAAAGG GCGAAAAACC GTCTATCAGG GCGATGGCCC    5580

ACTACGTGAA CCATCACCCT AATCAAGTTT TTTGGGGTCG AGGTGCCGTA AAGCACTAAA    5640

TCGGAACCCT AAAGGGAGCC CCCGATTTAG AGCTTGACGG GGAAAGCCGG CGAACGTGGC    5700

GAGAAAGGAA GGGAAGAAAG CGAAAGGAGC GGGCGCTAGG GCGCTGGCAA GTGTAGCGGT    5760

CACGCTGCGC GTAACCACCA CACCCGCCGC GCTTAATGCG CCGCTACAGG GCGCGTCGCG    5820

CCATTCGCCA TTCAGGCTGC GCAACTGTTG GGAAGGGCGA TCGGTGCGGG CCTCTTCGCT    5880

ATTACGCCAG CTGGCGAAAG GGGGATGTGC TGCAAGGCGA TTAAGTTGGG TAACGCCAGG    5940

GTTTTCCCAG TCACGACGTT GTAAAACGAC GGCCAGTGAA TTGTAATACG ACTCACTATA    6000

GGCGAATTGG GTACCGGGCC CCCCCTCGAG GTCGACGGTA TCGAT                    6045

(2) INFORMATION FOR SEQ ID NO:19:

(i) SEQUENCE CHARACTERISTICS:
        (A) LENGTH: 5109 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

AAGCTTTCGC GATATCCGTT AAGTTTGTAT CGTAATGCTC CCCTACCAAG ACAAGGTGGG      60

TGCCTTCTAC AAGGATAATG CAAGAGCCAA TTCAACCAAG CTGTCCTTAG TGACAGAAGG     120

ACATGGGGC AGGAGACCAC CTTATTTGTT GTTTGTCCTT CTCATCTTAT TGGTTGGTAT     180

CCTGGCCTTG CTTGCTATCA CTGGAGTTCG ATTTCACCAA GTATCAACTA GTAATATGGA    240

ATTTAGCAGA TTGCTGAAAG AGGATATGGA GAAATCAGAG GCCGTACATC ACCAAGTCAT    300

AGATGTCTTG ACACCGCTCT TCAAGATTAT TGGAGATGAG ATTGGGTTAC GGTTGCCACA    360

AAAGCTAAAC GAGATCAAAC AATTTATCCT TCAAAAGACA AATTTCTTCA ATCCGAACAG    420

AGAATTCGAC TTCCGCGATC TCCACTGGTG CATTAACCCG CCTAGTACGG TCAAGGTGAA    480

TTTTACTAAT TACTGTGAGT CAATTGGGAT CAGAAAAGCT ATTGCATCGG CAGCAAATCC    540
```

```
                                                                 -continued

TATCCTTTTA TCAGCCCTAT CTGGGGGCAG AGGTGACATA TTCCCACCAC ACAGATGCAG     600

TGGAGCTACT ACTTCAGTAG GCAAAGTTTT CCCCCTATCA GTCTCATTAT CCATGTCTTT     660

GATCTCAAGA ACCTCAGAGG TAATCAATAT GCTGACCGCT ATCTCAGACG GCGTGTATGG     720

CAAAACTTAC TTGCTAGTGC CTGATGATAT AGAAAGAGAG TTCGACACTC GAGAGATTCG     780

AGTCTTTGAA ATAGGGTTCA TCAAAAGGTG GCTGAATGAC ATGCCATTAC TCCAAACAAC     840

CAACTATATG GTACTCCCGA AGAATTCCAA AGCCAAGGTA TGTACTATAG CAGTGGGTGA     900

GTTGACACTG GCTTCCTTGT GTGTAGAAGA GAGCACTGTA TTATTATATC ATGACAGCAG     960

TGGTTCACAA GATGGTATTC TAGTAGTGAC ACTGGGGATA TTTTGGGCAA CACCTATGGA    1020

TCACATTGAG GAAGTGATAC CTGTCGCTCA CCCATCAATG AAGAAAATAC ATATAACAAA    1080

CCACCGTGGT TTTATAAAAG ATTCAATTGC AACCTGGATG GTGCCTGCCC TGGCCTCTGA    1140

GAAACAAGAA GAACAAAAAG GTTGTCTGGA GTCAGCTTGT CAAAGAAAAA CCTACCCCAT    1200

GTGCAACCAA GCGTCATGGG AACCCTTCGG AGGAAGACAG TTGCCATCTT ATGGGCGGTT    1260

GACATTACCT CTAGATGCAA GTGTTGACCT TCAACTTAAC ATATCGTTCA CATACGGTCC    1320

GGTTATACTG AATGGAGATG GTATGGATTA TTATGAAAGC CCACTTTTGA ACTCCGGATG    1380

GCTTACCATT CCCCCCAAAG ACGGAACAAT CTCTGGATTG ATAAACAAAG CAGGTAGAGG    1440

AGACCAGTTC ACTGTACTCC CCCATGTGTT AACATTTGCG CCCAGGGAAT CAAGTGGAAA    1500

TTGTTATTTA CCTATTCAAA CATCTCAAAT TAGAGATAGA GATGTCCTCA TTGAGTCCAA    1560

TATAGTGGTG TTGCCTACAC AGAGTATTAG ATATGTCATA GCAACGTATG ACATATCACG    1620

AAGTGATCAT GCTATTGTTT ATTATGTTTA TGACCCAATC CGGACGATTT CTTATACGCA    1680

CCCATTTAGA CTAACTACCA AGGGTAGACC TGATTTCCTA AGGATTGAAT GTTTTGTGTG    1740

GGATGACAAT TTGTGGTGTC ACCAATTTTA CAGATTCGAG GCTGACATCG CCAACTCTAC    1800

AACCAGTGTT GAGAATTTAG TCCGTATAAG ATTCTCATGT AACCGTTAAA ATCCCTGACA    1860

GTATGATGAT ACACATCTCA ATTGGCCTTA GGCATGATAA CTGCGGTGAG AAATCCCTTA    1920

CAGACGATTG AATTAAACCA TCTCTAGCAT TATAAAAAAA CTAAGGATCC AAGATCCTTT    1980

TAGCCATGGA CTCTGTATCA GTGAACCAGA TTCTATACCC TGAGGTCCAT CTAGATAGCC    2040

CAATTGTAAC CAATAAGCTA GTATCTATTT TAGAATACGC ACGAATTAGA CATAACTATC    2100

AGCTCCTTGA TACAAGATTA GTGCGTAATA TCAAAGAGAG AATTTCAGAA GGGTTCTCAA    2160

ACCAGATGAT CATTAGGATC CACTAGTTCT AGAGCGGCCG CCACCGCGGT GGAGCTCCAG    2220

CTTTTGTTCC CTTTAGTGAG GGTTAATTCC GAGCTTGGCG TAATCATGGT CATAGCTGTT    2280

TCCTGTGTGA AATTGTTATC CGCTCACAAT TCCACACAAC ATACGAGCCG GAAGCATAAA    2340

GTGTAAAGCC TGGGGTGCCT AATGAGTGAG CTAACTCACA TTAATTGCGT TGCGCTCACT    2400

GCCCGCTTTC CAGTCGGGAA ACCTGTCGTG CCAGCTGCAT TAATGAATCG GCCAACGCGC    2460

GGGGAGAGGC GGTTTGCGTA TTGGGCGCTC TTCCGCTTCC TCGCTCACTG ACTCGCTGCG    2520

CTCGGTCGTT CGGCTGCGGC GAGCGGTATC AGCTCACTCA AAGGCGGTAA TACGGTTATC    2580

CACAGAATCA GGGGATAACG CAGGAAAGAA CATGTGAGCA AAAGGCCAGC AAAAGGCCAG    2640

GAACCGTAAA AAGGCCGCGT TGCTGGCGTT TTTCCATAGG CTCCGCCCCC CTGACGAGCA    2700

TCACAAAAAT CGACGCTCAA GTCAGAGGTG GCGAAACCCG ACAGGACTAT AAAGATACCA    2760

GGCGTTTCCC CCTGGAAGCT CCCTCGTGCG CTCTCCTGTT CCGACCCTGC CGCTTACCGG    2820

ATACCTGTCC GCCTTTCTCC CTTCGGGAAG CGTGGCGCTT TCTCATAGCT CACGCTGTAG    2880

GTATCTCAGT TCGGTGTAGG TCGTTCGCTC CAAGCTGGGC TGTGTGCACG AACCCCCCGT    2940
```

```
TCAGCCCGAC CGCTGCGCCT TATCCGGTAA CTATCGTCTT GAGTCCAACC CGGTAAGACA      3000

CGACTTATCG CCACTGGCAG CAGCCACTGG TAACAGGATT AGCAGAGCGA GGTATGTAGG      3060

CGGTGCTACA GAGTTCTTGA AGTGGTGGCC TAACTACGGC TACACTAGAA GGACAGTATT      3120

TGGTATCTGC GCTCTGCTGA AGCCAGTTAC CTTCGGAAAA AGAGTTGGTA GCTCTTGATC      3180

CGGCAAACAA ACCACCGCTG GTAGCGGTGG TTTTTTTGTT TGCAAGCAGC AGATTACGCG      3240

CAGAAAAAAA GGATCTCAAG AAGATCCTTT GATCTTTTCT ACGGGGTCTG ACGCTCAGTG      3300

GAACGAAAAC TCACGTTAAG GGATTTTGGT CATGAGATTA TCAAAAGGA TCTTCACCTA       3360

GATCCTTTTA AATTAAAAAT GAAGTTTTAA ATCAATCTAA AGTATATATG AGTAAACTTG      3420

GTCTGACAGT TACCAATGCT TAATCAGTGA GGCACCTATC TCAGCGATCT GTCTATTTCG      3480

TTCATCCATA GTTGCCTGAC TCCCCGTCGT GTAGATAACT ACGATACGGG AGGGCTTACC      3540

ATCTGGCCCC AGTGCTGCAA TGATACCGCG AGACCCACGC TCACCGGCTC CAGATTTATC      3600

AGCAATAAAC CAGCCAGCCG GAAGGGCCGA GCGCAGAAGT GGTCCTGCAA CTTTATCCGC      3660

CTCCATCCAG TCTATTAATT GTTGCCGGGA AGCTAGAGTA AGTAGTTCGC CAGTTAATAG      3720

TTTGCGCAAC GTTGTTGCCA TTGCTACAGG CATCGTGGTG TCACGCTCGT CGTTTGGTAT      3780

GGCTTCATTC AGCTCCGGTT CCCAACGATC AAGGCGAGTT ACATGATCCC CCATGTTGTG      3840

CAAAAAAGCG GTTAGCTCCT TCGGTCCTCC GATCGTTGTC AGAAGTAAGT TGGCCGCAGT      3900

GTTATCACTC ATGGTTATGG CAGCACTGCA TAATTCTCTT ACTGTCATGC CATCCGTAAG      3960

ATGCTTTTCT GTGACTGGTG AGTACTCAAC CAAGTCATTC TGAGAATAGT GTATGCGGCG      4020

ACCGAGTTGC TCTTGCCCGG CGTCAATACG GGATAATACC GCGCCACATA GCAGAACTTT      4080

AAAAGTGCTC ATCATTGGAA AACGTTCTTC GGGGCGAAAA CTCTCAAGGA TCTTACCGCT      4140

GTTGAGATCC AGTTCGATGT AACCCACTCG TGCACCCAAC TGATCTTCAG CATCTTTTAC      4200

TTTCACCAGC GTTTCTGGGT GAGCAAAAAC AGGAAGGCAA AATGCCGCAA AAAAGGGAAT      4260

AAGGGCGACA CGGAAATGTT GAATACTCAT ACTCTTCCTT TTTCAATATT ATTGAAGCAT      4320

TTATCAGGGT TATTGTCTCA TGAGCGGATA CATATTTGAA TGTATTTAGA AAAATAAACA      4380

AATAGGGGTT CCGCGCACAT TTCCCCGAAA AGTGCCACCT GGGAAATTGT AAACGTTAAT      4440

ATTTTGTTAA AATTCGCGTT AAATTTTTGT TAAATCAGCT CATTTTTTAA CCAATAGGCC      4500

GAAATCGGCA AAATCCCTTA TAAATCAAAA GAATAGACCG AGATAGGGTT GAGTGTTGTT      4560

CCAGTTTGGA ACAAGAGTCC ACTATTAAAG AACGTGGACT CCAACGTCAA AGGGCGAAAA      4620

ACCGTCTATC AGGGCGATGG CCCACTACGT GAACCATCAC CCTAATCAAG TTTTTTGGGG      4680

TCGAGGTGCC GTAAAGCACT AAATCGGAAC CCTAAAGGGA GCCCCCGATT TAGAGCTTGA      4740

CGGGGAAAGC CGGCGAACGT GGCGAGAAAG GAAGGGAAGA AAGCGAAAGG AGCGGGCGCT      4800

AGGGCGCTGG CAAGTGTAGC GGTCACGCTG CGCGTAACCA CCACACCCGC CGCGCTTAAT      4860

GCGCCGCTAC AGGGCGCGTC GCGCCATTCG CCATTCAGGC TGCGCAACTG TTGGGAAGGG      4920

CGATCGGTGC GGGCCTCTTC GCTATTACGC CAGCTGGCGA AAGGGGGATG TGCTGCAAGG      4980

CGATTAAGTT GGGTAACGCC AGGGTTTTCC CAGTCACGAC GTTGTAAAAC GACGGCCAGT      5040

GAATTGTAAT ACGACTCACT ATAGGGCGAA TTGGGTACCG GCCCCCCCT CGAGGTCGAC       5100

GGTATCGAT                                                              5109
```

(2) INFORMATION FOR SEQ ID NO:20:

(i) SEQUENCE CHARACTERISTICS:

(A) LENGTH: 5067 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
AAGCTTAATG TCGTAACAAC TCCGCCCCGT TGACGCAAAT GGGCGGTAGG CGTGTACGGT      60

GGGAGGTCTA TATAAGCAGA GCTCGTTTAG TGAACCGTCT GCAGACTCTC TTCCGCATCG     120

CTGTCTGCGA GGGCCAGCTG TTGGGCTCGC GGTTGAGGAC AAACTCTTCG CGGTCTTTCC     180

AGTACTCTTG GATCGGAAAC CCGTCGGCCT CCGAACGGTA CTCCGCCACC GAGGGACCTG     240

AGCGAGTCCG CATCGACCGG ATCGGAAAAC CTCTCGAGAA AGGCGTCTAA CCAGTCACAG     300

TCGCAAGTCT AGAATGCTCC CCTACCAAGA CAAGGTGGGT GCCTTCTACA AGGATAATGC     360

AAGAGCCAAT TCAACCAAGC TGTCCTTAGT GACAGAAGGA CATGGGGCA GGAGACCACC      420

TTATTTGTTG TTTGTCCTTC TCATCTTATT GGTTGGTATC CTGGCCTTGC TTGCTATCAC     480

TGGAGTTCGA TTTCACCAAG TATCAACTAG TAATATGGAA TTTAGCAGAT TGCTGAAAGA     540

GGATATGGAG AAATCAGAGG CCGTACATCA CCAAGTCATA GATGTCTTGA CACCGCTCTT     600

CAAGATTATT GGAGATGAGA TTGGGTTACG GTTGCCACAA AAGCTAAACG AGATCAAACA     660

ATTTATCCTT CAAAAGACAA ATTTCTTCAA TCCGAACAGA GAATTCGACT TCCGCGATCT     720

CCACTGGTGC ATTAACCCGC CTAGTACGGT CAAGGTGAAT TTTACTAATT ACTGTGAGTC     780

AATTGGGATC AGAAAAGCTA TTGCATCGGC AGCAAATCCT ATCCTTTTAT CAGCCCTATC     840

TGGGGGCAGA GGTGACATAT TCCCACCACA CAGATGCAGT GGAGCTACTA CTTCAGTAGG     900

CAAAGTTTTC CCCCTATCAG TCTCATTATC CATGTCTTTG ATCTCAAGAA CCTCAGAGGT     960

AATCAATATG CTGACCGCTA TCTCAGACGG CGTGTATGGC AAAACTTACT TGCTAGTGCC    1020

TGATGATATA GAAAGAGAGT TCGACACTCG AGAGATTCGA GTCTTTGAAA TAGGGTTCAT    1080

CAAAAGGTGG CTGAATGACA TGCCATTACT CCAAACAACC AACTATATGG TACTCCCGAA    1140

GAATTCCAAA GCCAAGGTAT GTACTATAGC AGTGGGTGAG TTGACACTGG CTTCCTTGTG    1200

TGTAGAAGAG AGCACTGTAT TATTATATCA TGACAGCAGT GGTTCACAAG ATGGTATTCT    1260

AGTAGTGACA CTGGGGATAT TTTGGGCAAC ACCTATGGAT CACATTGAGG AAGTGATACC    1320

TGTCGCTCAC CCATCAATGA AGAAAATACA TATAACAAAC CACCGTGGTT TTATAAAAGA    1380

TTCAATTGCA ACCTGGATGG TGCCTGCCCT GGCCTCTGAG AAACAAGAAG AACAAAAAGG    1440

TTGTCTGGAG TCAGCTTGTC AAAGAAAAAC CTACCCCATG TGCAACCAAG CGTCATGGGA    1500

ACCCTTCGGA GGAAGACAGT TGCCATCTTA TGGGCGGTTG ACATTACCTC TAGATGCAAG    1560

TGTTGACCTT CAACTTAACA TATCGTTCAC ATACGGTCCG GTTATACTGA ATGGAGATGG    1620

TATGGATTAT TATGAAAGCC CACTTTTGAA CTCCGGATGG CTTACCATTC CCCCAAAGA     1680

CGGAACAATC TCTGGATTGA TAAACAAAGC AGGTAGAGGA GACCAGTTCA CTGTACTCCC    1740

CCATGTGTTA ACATTTGCGC CCAGGGAATC AAGTGGAAAT TGTTATTTAC CTATTCAAAC    1800

ATCTCAAATT AGAGATAGAG ATGTCCTCAT TGAGTCCAAT ATAGTGGTGT TGCCTACACA    1860

GAGTATTAGA TATGTCATAG CAACGTATGA CATATCACGA AGTGATCATG CTATTGTTTA    1920

TTATGTTTAT GACCCAATCC GGACGATTTC TTATACGCAC CCATTTAGAC TAACTACCAA    1980

GGGTAGACCT GATTTCCTAA GGATTGAATG TTTTGTGTGG GATGACAATT TGTGGTGTCA    2040

CCAATTTTAC AGATTCGAGG CTGACATCGC CAACTCTACA ACCAGTGTTG AGAATTTAGT    2100
```

-continued

```
CCGTATAAGA TTCTCATGTA ACCGTTAACC GCGGCGTGAT TAATCAGCCA TACCACATTT    2160
GTAGAGGTTT TACTTGCTTT AAAAAACCTC CCACACCTCC CCCTGAACCT GAAACATAAA    2220
ATGAATGCAA TTGTTGTTGT TAACTTGTTT ATTGCAGCTT ATAATGGTTA CAAATAAAGC    2280
AATAGCATCA CAAATTTCAC AAATAAAGCA TTTTTTTCAC TGCATTCTAG TTGTGGTTTG    2340
TCCAAACTCA TCAATGTATC TTATCATGTC TGGATCCCCC GGAATTCACT GGCCGTCGTT    2400
TTACAACGTC GTGACTGGGA AAACCCTGGC GTTACCCAAC TTAATCGCCT TGCAGCACAT    2460
CCCCCCTTCG CCAGCTGGCG TAATAGCGAA GAGGCCCGCA CCGATCGCCC TTCCCAACAG    2520
TTGCGCAGCC TGAATGGCGA ATGGCGCCTG ATGCGGTATT TTCTCCTTAC GCATCTGTGC    2580
GGTATTTCAC ACCGCATATG GTGCACTCTC AGTACAATCT GCTCTGATGC CGCATAGTTA    2640
AGCCAGTACA CTCCGCTATC GCTACGTGAC TGGGTCATGG CTGCGCCCCG ACACCCGCCA    2700
ACACCCGCTG ACGCGCCCTG ACGGGCTTGT CTGCTCCCGG CATCCGCTTA CAGACAAGCT    2760
GTGACCGTCT CCGGGAGCTG CATGTGTCAG AGGTTTTCAC CGTCATCACC GAAACGCGCG    2820
AGGCAGTTCT TGAAGACGAA AGGGCCTCGT GATACGCCTA TTTTTATAGG TTAATGTCAT    2880
GATAATAATG GTTTCTTAGA CGTCAGGTGG CACTTTTCGG GGAAATGTGC GCGGAACCCC    2940
TATTTGTTTA TTTTTCTAAA TACATTCAAA TATGTATCCG CTCATGAGAC AATAACCCTG    3000
ATAAATGCTT CAATAATATT GAAAAAGGAA GAGTATGAGT ATTCAACATT TCCGTGTCGC    3060
CCTTATTCCC TTTTTTGCGG CATTTTGCCT TCCTGTTTTT GCTCACCCAG AAACGCTGGT    3120
GAAAGTAAAA GATGCTGAAG ATCAGTTGGG TGCACGAGTG GGTTACATCG AACTGGATCT    3180
CAACAGCGGT AAGATCCTTG AGAGTTTTCG CCCCGAAGAA CGTTTTCCAA TGATGAGCAC    3240
TTTTAAAGTT CTGCTATGTG GCGCGGTATT ATCCCGTATT GACGCCGGGC AAGAGCAACT    3300
CGGTCGCCGC ATACACTATT CTCAGAATGA CTTGGTTGAG TACTCACCAG TCACAGAAAA    3360
GCATCTTACG GATGGCATGA CAGTAAGAGA ATTATGCAGT GCTGCCATAA CCATGAGTGA    3420
TAACACTGCG GCCAACTTAC TTCTGACAAC GATCGGAGGA CCGAAGGAGC TAACCGCTTT    3480
TTTGCACAAC ATGGGGGATC ATGTAACTCG CCTTGATCGT TGGGAACCGG AGCTGAATGA    3540
AGCCATACCA AACGACGAGC GTGACACCAC GATGCCTGTA GCAATGGCAA CAACGTTGCG    3600
CAAACTATTA ACTGGCGAAC TACTTACTCT AGCTTCCCGG CAACAATTAA TAGACTGGAT    3660
GGAGGCGGAT AAAGTTGCAG GACCACTTCT GCGCTCGGCC CTTCCGGCTG GCTGGTTTAT    3720
TGCTGATAAA TCTGGAGCCG GTGAGCGTGG GTCTCGCGGT ATCATTGCAG CACTGGGGCC    3780
AGATGGTAAG CCCTCCCGTA TCGTAGTTAT CTACACGACG GGGAGTCAGG CAACTATGGA    3840
TGAACGAAAT AGACAGATCG CTGAGATAGG TGCCTCACTG ATTAAGCATT GGTAACTGTC    3900
AGACCAAGTT TACTCATATA TACTTTAGAT TGATTTAAAA CTTCATTTTT AATTTAAAAG    3960
GATCTAGGTG AAGATCCTTT TTGATAATCT CATGACCAAA ATCCCTTAAC GTGAGTTTTC    4020
GTTCCACTGA GCGTCAGACC CCGTAGAAAA GATCAAAGGA TCTTCTTGAG ATCCTTTTTT    4080
TCTGCGCGTA ATCTGCTGCT TGCAAACAAA AAAACCACCG CTACCAGCGG TGGTTTGTTT    4140
GCCGGATCAA GAGCTACCAA CTCTTTTTCC GAAGGTAACT GGCTTCAGCA GAGCGCAGAT    4200
ACCAAATACT GTCCTTCTAG TGTAGCCGTA GTTAGGCCAC CACTTCAAGA ACTCTGTAGC    4260
ACCGCCTACA TACCTCGCTC TGCTAATCCT GTTACCAGTG GCTGCTGCCA GTGGCGATAA    4320
GTCGTGTCTT ACCGGGTTGG ACTCAAGACG ATAGTTACCG GATAAGGCGC AGCGGTCGGG    4380
CTGAACGGGG GGTTCGTGCA CACAGCCCAG CTTGGAGCGA ACGACCTACA CCGAACTGAG    4440
ATACCTACAG CGTGAGCATT GAGAAAGCGC CACGCTTCCC GAAGGGAGAA AGGCGGACAG    4500
```

```
GTATCCGGTA AGCGGCAGGG TCGGAACAGG AGAGCGCACG AGGGAGCTTC CAGGGGAAA       4560

CGCCTGGTAT CTTTATAGTC CTGTCGGGTT TCGCCACCTC TGACTTGAGC GTCGATTTTT      4620

GTGATGCTCG TCAGGGGGGC GGAGCCTATG GAAAAACGCC AGCAACGCGG CCTTTTTACG      4680

GTTCCTGGCC TTTTGCTGGC CTTTTGCTCA CATGTTCTTT CCTGCGTTAT CCCCTGATTC      4740

TGTGGATAAC CGTATTACCG CCTTTGAGTG AGCTGATACC GCTCGCCGCA GCCGAACGAC      4800

CGAGCGCAGC GAGTCAGTGA GCGAGGAAGC GGAAGAGCGC CAATACGCAA ACCGCCTCTC      4860

CCCGCGCGTT GGCCGATTCA TTAATGCAGC TGGCACGACA GGTTTCCCGA CTGGAAAGCG      4920

GGCAGTGAGC GCAACGCAAT TAATGTGAGT TACCTCACTC ATTAGGCACC CCAGGCTTTA      4980

CACTTTATGC TTCCGGCTCG TATGTTGTGT GGAATTGTGA GCGGATAACA ATTTCACACA      5040

GGAAACAGCT ATGACCATGA TTACGCC                                          5067

(2) INFORMATION FOR SEQ ID NO:21:

(i) SEQUENCE CHARACTERISTICS:
        (A) LENGTH: 8618 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TCGACGGTGC CCCCAGCAGA AGTATCGACT GCATGCTAAT TATTAACAAA CCAAAAGGCG        60

TTGCCACTTA CACCCTTACC TTTAGGTTTT TAAACTTTAA CAGACTAAGC GGAGGTACCC       120

TGTTTAAAAC TGATGTCTTA ACCTTTACCT ATGTAGGCGA AAATCAATAA AACCAGAAAA       180

AAATAAGTTT AAAAGCTTTA TTTTTCATAC ACGCGAGCGG TAAGGCTGCC GCCTTCAGGA       240

AAAGTTACTC TGTAAACAGT TCTTTCACAA CAGCACAAAA CATAGGTATT AGTTAACAGT       300

TCATTTGGGC TATAATAATA TACATTTTCT TGGGTGGCAA AGCAAGGGTC GGTAATCTCA       360

ACAAAACCAT CAACTGGAAT GCAAGAATAG TCCAGCACGT TGGGTTCAAT CTAAAAATGA       420

AGAAACGCTG TTGAGGTTCA CTAAGCACAG GTTTTGAATC TGTCGGCAGC GTCCATGCAT       480

CATAGCTTGT CTCAAAGCAG ATTGTCTTCT TTCCTCTGCC TTGGAAGTGG TTTGGTGAAG       540

CACTACAGGT GTCTTTTCAA CCTCTTTCAG CACCCGCTCT ATTACAGATC TCACCCACAC       600

AGCACAGTTT TTAAGAGAAC AATAGTTTTG AAGGCTACAA GATTTACACT TAAGCACCAG       660

CCAGTAATTA TAAGTGCTTT TAAGAACTAC CCCTAGCTCA GGGTTAATGC ACCTTTTAAT       720

GGCCTCCATG CAGGCTTTAT GGACAGTTCT AAAAAAAGAC AGTCTAAAAT AAATGTAGTG       780

AGTGTTTCTA AATATAATAC TCCCCACATA GTTAATTTCA TCAGGCCTGC TAGAATTTAC       840

AAACTCTCGG TACCACATAT ACTTTTTATT CATAGCCCCA CCCTTAATAA AGTCCTCAAT       900

CACTTTCTGA ACCACATGCT TGCTAGCCAT GCATTGTAAA GACAAGCTGT TAGAGCAGTG       960

ACAGTGTACT CGCCACGTTT GAGCCTCTGC CAGGCAGCAG TGCTTAGTTA CTATCAACTC      1020

AATACCCGCA TTGCATGTAA ACCCCCCAAA GAGCAGTTTT TCATGCCTGT GTAGCACATC      1080

ATCCACAAAA ATAGGAATTT CATAGCATAA AGCAAAGCAA TTACAATATT TAGGAACTCT      1140

CACCACAGCA GTCACGTGAC ATGTTGTCTC AGCAGTGCAG TTGCCTTCCA TCCTACAATT      1200

ATGAACAAAA ACTAAACACT TCTAACAAAG ATACAGTGAC AATCTCCCTT CCTCTAAAAG      1260

CATTGTTTAC ATTAGGGTGA TTATTAACAA CGTCAGAAAT TTCTTTAATT AAAGTGCCTT      1320

TAAAATGTGC AAGAGCATCA TCATACTCAA AACCAAGCTG AGAGTAAAAG ACCACCTTAA      1380
```

| | | |
|---|---|---|
| AAGTAATCCC AGGCTTGTTT TTATCAACAG CCTTAAACAT GCTTTCACAA AATATAGAAG | 1440 |
| CAGTAACATC ATCAATGGTG TCGAAGAGAA ACTCCATAGG AGACTCCAGC ATTGATCCAA | 1500 |
| GCTCTCTAAC AAAATCTTCC TCAAAATGAA TAATGCCCTT TACACAAACG CGGGGCAGAC | 1560 |
| GATGGTGGGC CATCGCGTCA ACCTGAAACA CATTTTACAG TAAACAAAGC TAGCTCCGCA | 1620 |
| GTGGTAAAGT CATGCCCATG GGTGAGGCCA AAATCCTTAA AAAAGCTATC TAAGTAGTTG | 1680 |
| GTCATCCCCT CAGTTAAAAA GTTTTGCAGC TGGGTGGTGC ATACCACATA GTGCCAGCTT | 1740 |
| ATAGCTACAA AGACCTGCAT CCCCTCCTTA GCAGACAGCT CTTGCACACA CGCAGTAACT | 1800 |
| ATCCACCGCT TAAGAAAAGC TTTAAGCCCA GCGCACATAA CAGCTCCAAT GTTTTTATCC | 1860 |
| AAGGAGAGCA AAATTTCAGC AAGCGCAGGC TCAACAGTAA TAGTGAAGCA GAGGCATTTC | 1920 |
| AGACGAGGCT CACTAGCTGC AGTCGCCATT TATGAGGTCT GCAATAAAAA ACAACTCATC | 1980 |
| AGCAGCTGAA AAAGTGCACT TTGACCTCAT TAAGCCACTG CATATGCAAG TCCTCATCTA | 2040 |
| TGCCGCAGCC CAGACCCTCA ATCCAGCCCC GAATGTACAC TTTAATAAGA GATTCAACCT | 2100 |
| CTTCTTTTAG CAAAGTACAC ATGCTGTTTG GACTAGTATA CACAATAGAA GTCACAATGA | 2160 |
| GGGGCCCGCT GTGGCTGGAA AGCCTGCGCA CAGCCCGAAG GTTAAAAATG GACTGTAACA | 2220 |
| GCATTGAAAC CCCGCGACAC AGGTCAGTCT CGCGGTCTTG ATCTCTTATT ATAGCGACCA | 2280 |
| AATGGTCCTT CAGAGTGATG TTGCACTCAT AGAAGTAGGC AGCTCCGGCA GCCATTCTGC | 2340 |
| AAAATAACAA AACACCACTA AGCATAGCAC CATCACCAAG CATGAAAACA GGTAAAAACA | 2400 |
| AAAGCAACAC TTACTTATTC AGCAGTCACA AGAATGTTGG GCTCCCAAGT GACAGACAAG | 2460 |
| CCTAATGCAA GGTGGGCACA GTCTCCGGAA TAAGTTGACA AAAGTCACGC CGCAAAGCTT | 2520 |
| CCTGAAGAGA AACGGCGGTA GCCTGGATAT CTGCAACGGA CCCAAAACCT TCAGTGTCAC | 2580 |
| TTCCAATAAA CAGATAAAAC TCTAAATAGT CCCCACTTAA AACCGAAACA GCCGCGGCAA | 2640 |
| AGGTAGGACA CGGACGCACT TCCTGAGCCC TAATAAGGCT AAACACCACA CGGCGCAGTT | 2700 |
| CAGAAGGCAA AAAGTCTGTA AGCTCTAGCT GAGCACACAC ACTCTCCACT AGACACTTGT | 2760 |
| GAAGCCTCAG ACAAAAACAT GCTCCCATAG ACACTCCTAA AGCTGCCATT GTACTCACGG | 2820 |
| ACGGCTGGCT GTCAGAGGAG AGCTATGAGG ATGAAATGCC AAGCACAGCG TTTATATAGT | 2880 |
| CCTCAAAGTA GGGCGTGTGG AAAACGAAAA GGAATATAAC GGGGCGTTTG AGGAAGTGGT | 2940 |
| GCCAAGTACA GTCATAAAAT GTGGGCGCGT GGTAAATGTT AAGTGCAGTT TCCCTTTGGC | 3000 |
| GGTTGGCCCG GAAAGTTCAC AAAAAGTACA GCACGTCCTT GTCACCGTGT CAACCACAAA | 3060 |
| ACCACAAATA GGCACAACGC CCAAAAACCC GGGTCGACAC GCGTGAATTC ACCGGTTCGA | 3120 |
| GCTTAATGTC GTAACAACTC CGCCCCGTTG ACGCAAATGG GCGGTAGGCG TGTACGGTGG | 3180 |
| GAGGTCTATA TAAGCAGAGC TCGTTTAGTG AACCGTCTGC AGACTCTCTT CCGCATCGCT | 3240 |
| GTCTGCGAGG GCCAGCTGTT GGGCTCGCGG TTGAGGACAA ACTCTTCGCG GTCTTTCCAG | 3300 |
| TACTCTTGGA TCGGAAACCC GTCGGCCTCC GAACGGTACT CCGCCACCGA GGGACCTGAG | 3360 |
| CGAGTCCGCA TCGACCGGAT CGGAAAACCT CTCGAGAAAG GCGTCTAACC AGTCACAGTC | 3420 |
| GCAAGTCTAG AATGCTCCCC TACCAAGACA AGGTGGGTGC CTTCTACAAG GATAATGCAA | 3480 |
| GAGCCAATTC AACCAAGCTG TCCTTAGTGA CAGAAGGACA TGGGGCAGG AGACCACCTT | 3540 |
| ATTTGTTGTT TGTCCTTCTC ATCTTATTGG TTGGTATCCT GGCCTTGCTT GCTATCACTG | 3600 |
| GAGTTCGATT TCACCAAGTA TCAACTAGTA ATATGGAATT TAGCAGATTG CTGAAAGAGG | 3660 |
| ATATGGAGAA ATCAGAGGCC GTACATCACC AAGTCATAGA TGTCTTGACA CCGCTCTTCA | 3720 |

```
-continued

AGATTATTGG AGATGAGATT GGGTTACGGT TGCCACAAAA GCTAAACGAG ATCAAACAAT    3780

TTATCCTTCA AAAGACAAAT TTCTTCAATC CGAACAGAGA ATTCGACTTC CGCGATCTCC    3840

ACTGGTGCAT TAACCCGCCT AGTACGGTCA AGGTGAATTT TACTAATTAC TGTGAGTCAA    3900

TTGGGATCAG AAAAGCTATT GCATCGGCAG CAAATCCTAT CCTTTTATCA GCCCTATCTG    3960

GGGGCAGAGG TGACATATTC CCACCACACA GATGCAGTGG AGCTACTACT TCAGTAGGCA    4020

AAGTTTTCCC CCTATCAGTC TCATTATCCA TGTCTTTGAT CTCAAGAACC TCAGAGGTAA    4080

TCAATATGCT GACCGCTATC TCAGACGGCG TGTATGGCAA AACTTACTTG CTAGTGCCTG    4140

ATGATATAGA AAGAGAGTTC GACACTCGAG AGATTCGAGT CTTTGAAATA GGGTTCATCA    4200

AAAGGTGGCT GAATGACATG CCATTACTCC AAACAACCAA CTATATGGTA CTCCCGAAGA    4260

ATTCCAAAGC CAAGGTATGT ACTATAGCAG TGGGTGAGTT GACACTGGCT TCCTTGTGTG    4320

TAGAAGAGAG CACTGTATTA TTATATCATG ACAGCAGTGG TTCACAAGAT GGTATTCTAG    4380

TAGTGACACT GGGGATATTT TGGGCAACAC CTATGGATCA CATTGAGGAA GTGATACCTG    4440

TCGCTCACCC ATCAATGAAG AAAATACATA TAACAAACCA CCGTGGTTTT ATAAAAGATT    4500

CAATTGCAAC CTGGATGGTG CCTGCCCTGG CCTCTGAGAA ACAAGAAGAA CAAAAAGGTT    4560

GTCTGGAGTC AGCTTGTCAA AGAAAAACCT ACCCCATGTG CAACCAAGCG TCATGGGAAC    4620

CCTTCGGAGG AAGACAGTTG CCATCTTATG GGCGGTTGAC ATTACCTCTA GATGCAAGTG    4680

TTGACCTTCA ACTTAACATA TCGTTCACAT ACGGTCCGGT TATACTGAAT GGAGATGGTA    4740

TGGATTATTA TGAAAGCCCA CTTTTGAACT CCGGATGGCT TACCATTCCC CCCAAAGACG    4800

GAACAATCTC TGGATTGATA AACAAAGCAG GTAGAGGAGA CCAGTTCACT GTACTCCCCC    4860

ATGTGTTAAC ATTTGCGCCC AGGGAATCAA GTGGAAATTG TTATTTACCT ATTCAAACAT    4920

CTCAAATTAG AGATAGAGAT GTCCTCATTG AGTCCAATAT AGTGGTGTTG CCTACACAGA    4980

GTATTAGATA TGTCATAGCA ACGTATGACA TATCACGAAG TGATCATGCT ATTGTTTATT    5040

ATGTTTATGA CCCAATCCGG ACGATTTCTT ATACGCACCC ATTTAGACTA ACTACCAAGG    5100

GTAGACCTGA TTTCCTAAGG ATTGAATGTT TTGTGTGGGA TGACAATTTG TGGTGTCACC    5160

AATTTTACAG ATTCGAGGCT GACATCGCCA ACTCTACAAC CAGTGTTGAG AATTTAGTCC    5220

GTATAAGATT CTCATGTAAC CGTTAACCGC GGCGTGATTA ATCAGCCATA CCACATTTGT    5280

AGAGGTTTTA CTTGCTTTAA AAAACCTCCC ACACCTCCCC CTGAACCTGA ACATAAAAT     5340

GAATGCAATT GTTGTTGTTA ACTTGTTTAT TGCAGCTTAT AATGGTTACA AATAAAGCAA    5400

TAGCATCACA AATTTCACAA ATAAAGCATT TTTTTCACTG CATTCTAGTT GTGGTTTGTC    5460

CAAACTCATC AATGTATCTT ATCATGTCTG GATCCGAAAC GCCCAAAAAC CCGGGGCGCC    5520

GGCCAAAAGT CCGCGGAACT CGCCCTGTCG TAAAACCACG CCTTTGACGT CACTGGACAT    5580

TCCCGTGGGA ACACCCTGAC CAGGGCGTGA CCTGAACCTG ACCGTCCCAT GACCCCGCCC    5640

CTTGCAACAC CCAAATTTAA GCCACACCTC TTTGTCCTGT ATATTATTGA TGATGGGGGG    5700

ATCCACTAGT TCTAGAGCGG CCGCCACCGC GGTGGAGCTC CAGCTTTTGT TCCCTTTAGT    5760

GAGGGTTAAT TCCGAGCTTG GCGTAATCAT GGTCATAGCT GTTTCCTGTG TGAAATTGTT    5820

ATCCGCTCAC AATTCCACAC AACATACGAG CCGGAAGCAT AAAGTGTAAA GCCTGGGGTG    5880

CCTAATGAGT GAGCTAACTC ACATTAATTG CGTTGCGCTC ACTGCCCGCT TCCAGTCGG    5940

GAAACCTGTC GTGCCAGCTG CATTAATGAA TCGGCCAACG CGCGGGGAGA GGCGGTTTGC    6000

GTATTGGGCG CTCTTCCGCT TCCTCGCTCA CTGACTCGCT GCGCTCGGTC GTTCGGCTGC    6060

GGCGAGCGGT ATCAGCTCAC TCAAAGGCGG TAATACGGTT ATCCACAGAA TCAGGGGATA    6120
```

```
ACGCAGGAAA GAACATGTGA GCAAAAGGCC AGCAAAAGGC CAGGAACCGT AAAAAGGCCG    6180

CGTTGCTGGC GTTTTTCCAT AGGCTCCGCC CCCCTGACGA GCATCACAAA AATCGACGCT    6240

CAAGTCAGAG GTGGCGAAAC CCGACAGGAC TATAAAGATA CCAGGCGTTT CCCCCTGGAA    6300

GCTCCCTCGT GCGCTCTCCT GTTCCGACCC TGCCGCTTAC CGGATACCTG TCCGCCTTTC    6360

TCCCTTCGGG AAGCGTGGCG CTTTCTCATA GCTCACGCTG TAGGTATCTC AGTTCGGTGT    6420

AGGTCGTTCG CTCCAAGCTG GGCTGTGTGC ACGAACCCCC CGTTCAGCCC GACCGCTGCG    6480

CCTTATCCGG TAACTATCGT CTTGAGTCCA ACCCGGTAAG ACACGACTTA TCGCCACTGG    6540

CAGCAGCCAC TGGTAACAGG ATTAGCAGAG CGAGGTATGT AGGCGGTGCT ACAGAGTTCT    6600

TGAAGTGGTG GCCTAACTAC GGCTACACTA GAAGGACAGT ATTTGGTATC TGCGCTCTGC    6660

TGAAGCCAGT TACCTTCGGA AAAAGAGTTG GTAGCTCTTG ATCCGGCAAA CAAACCACCG    6720

CTGGTAGCGG TGGTTTTTTT GTTTGCAAGC AGCAGATTAC GCGCAGAAAA AAGGATCTC    6780

AAGAAGATCC TTTGATCTTT TCTACGGGGT CTGACGCTCA GTGGAACGAA AACTCACGTT    6840

AAGGGATTTT GGTCATGAGA TTATCAAAAA GGATCTTCAC CTAGATCCTT TTAAATTAAA    6900

AATGAAGTTT TAAATCAATC TAAAGTATAT ATGAGTAAAC TTGGTCTGAC AGTTACCAAT    6960

GCTTAATCAG TGAGGCACCT ATCTCAGCGA TCTGTCTATT TCGTTCATCC ATAGTTGCCT    7020

GACTCCCCGT CGTGTAGATA ACTACGATAC GGGAGGGCTT ACCATCTGGC CCCAGTGCTG    7080

CAATGATACC GCGAGACCCA CGCTCACCGG CTCCAGATTT ATCAGCAATA AACCAGCCAG    7140

CCGGAAGGGC CGAGCGCAGA AGTGGTCCTG CAACTTTATC CGCCTCCATC CAGTCTATTA    7200

ATTGTTGCCG GGAAGCTAGA GTAAGTAGTT CGCCAGTTAA TAGTTTGCGC AACGTTGTTG    7260

CCATTGCTAC AGGCATCGTG GTGTCACGCT CGTCGTTTGG TATGGCTTCA TTCAGCTCCG    7320

GTTCCCAACG ATCAAGGCGA GTTACATGAT CCCCCATGTT GTGCAAAAAA GCGGTTAGCT    7380

CCTTCGGTCC TCCGATCGTT GTCAGAAGTA AGTTGGCCGC AGTGTTATCA CTCATGGTTA    7440

TGGCAGCACT GCATAATTCT CTTACTGTCA TGCCATCCGT AAGATGCTTT TCTGTGACTG    7500

GTGAGTACTC AACCAAGTCA TTCTGAGAAT AGTGTATGCG GCGACCGAGT TGCTCTTGCC    7560

CGGCGTCAAT ACGGGATAAT ACCGCGCCAC ATAGCAGAAC TTTAAAAGTG CTCATCATTG    7620

GAAAACGTTC TTCGGGGCGA AAACTCTCAA GGATCTTACC GCTGTTGAGA TCCAGTTCGA    7680

TGTAACCCAC TCGTGCACCC AACTGATCTT CAGCATCTTT TACTTTCACC AGCGTTTCTG    7740

GGTGAGCAAA AACAGGAAGG CAAAATGCCG CAAAAAAGGG AATAAGGGCG ACACGGAAAT    7800

GTTGAATACT CATACTCTTC CTTTTTCAAT ATTATTGAAG CATTTATCAG GGTTATTGTC    7860

TCATGAGCGG ATACATATTT GAATGTATTT AGAAAAATAA ACAAATAGGG GTTCCGCGCA    7920

CATTTCCCCG AAAAGTGCCA CCTGGGAAAT TGTAAACGTT AATATTTTGT TAAAATTCGC    7980

GTTAAATTTT TGTTAAATCA GCTCATTTTT TAACCAATAG GCCGAAATCG GCAAAATCCC    8040

TTATAAATCA AAAGAATAGA CCGAGATAGG GTTGAGTGTT GTTCCAGTTT GGAACAAGAG    8100

TCCACTATTA AGAACGTGG ACTCCAACGT CAAAGGGCGA AAAACCGTCT ATCAGGGCGA    8160

TGGCCCACTA CGTGAACCAT CACCCTAATC AAGTTTTTTG GGGTCGAGGT GCCGTAAAGC    8220

ACTAAATCGG AACCCTAAAG GGAGCCCCCG ATTTAGAGCT TGACGGGGAA AGCCGGCGAA    8280

CGTGGCGAGA AAGGAAGGGA AGAAAGCGAA AGGAGCGGGC GCTAGGGCGC TGGCAAGTGT    8340

AGCGGTCACG CTGCGCGTAA CCACCACACC CGCCGCGCTT AATGCGCCGC TACAGGGCGC    8400

GTCGCGCCAT TCGCCATTCA GGCTGCGCAA CTGTTGGGAA GGGCGATCGG TGCGGGCCTC    8460
```

```
TTCGCTATTA CGCCAGCTGG CGAAAGGGGG ATGTGCTGCA AGGCGATTAA GTTGGGTAAC      8520

GCCAGGGTTT TCCCAGTCAC GACGTTGTAA AACGACGGCC AGTGAATTGT AATACGACTC      8580

ACTATAGGGC GAATTGGGTA CCGGGCCCCC CCTCGAGG                              8618
```

(2) INFORMATION FOR SEQ ID NO:22:

(i) SEQUENCE CHARACTERISTICS:
        (A) LENGTH: 4965 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
TCGCGATATC CGTTAAGTTT GTATCGTAAA TGCACAAGGG AATCCCCAAA AGCTCCAAAA        60

CCCAAACACA TACCCAACAA GACCGCCCCC CACAACCCAG CACCGAACTC GAAGAGACCA       120

GGACCTCCCG AGCACGACAC AGCACAACAT CAGCTCAGCG ATCCACGCAC TACGATCCTC       180

GAACATCGGA CAGACCCGTC TCCTACACCA TGAACAGGAC CAGGTCCCGC AAGCAAACCA       240

GCCACAGATT GAAGAACATC CCAGTTCACG GAAACCACGA GGCCACCATC CAGCACATAC       300

CAGAGAGTGT CTCAAAAGGA GCGAGATCCC AGATCGAAAG GCGGCAACCC AATGCAATCA       360

ACTCAGGCTC TCATTGCACC TGGTTAGTCC TGTGGTGCCT CGGAATGGCC AGTCTCTTTC       420

TTTGTTCCAA GGCTCAGATA CATTGGAATA ATTTGTCAAC TATTGGGATT ATCGGGACTG       480

ATAGTGTCCA TTACAAGATC ATGACTAGGC CCAGTCACCA GTACTTGGTC ATAAAACTGA       540

TGCCTAATGT TTCACTTATA GAGAATTGTA CCAAAGCAGA ATTAGGTGAG TATGAGAAAT       600

TATTGAATTC AGTCCTCGAA CCAATCAACC AAGCTTTGAC TCTAATGACC AAGAATGTGA       660

AGCCCCTGCA GTCATTAGGG TCAGGTAGGA GACAAAGGCG TTTTGCAGGA GTGGTACTTG       720

CAGGTGTAGC TTTAGGAGTG GCTACAGCTG CACAAATCAC TGCAGGAATA GCTTTACATC       780

AATCCAACCT CAATGCTCAA GCAATCCAAT CTCTTAGAAC CAGCCTTGAA CAGTCTAACA       840

AAGCTATAGA AGAAATTAGG GAGGCTACCC AAGAAACCGT CATTGCCGTT CAGGGAGTCC       900

AGGACTACGT CAACAACGAA CTCGTCCCTG CCATGCAACA TATGTCATGT GAATTAGTTG       960

GGCAGAGATT AGGGTTAAGA CTGCTTCGGT ATTATACTGA GTTGTTGTCA ATATTTGGCC      1020

CGAGTTTACG TGACCCTATT TCAGCCGAGA TATCAATTCA GGCACTGATT TATGCTCTTG      1080

GAGGAGAAAT TCATAAGATA CTTGGGAAGT TGGGATATTC TGGAAGTGAT ATGATTGCAA      1140

TCTTGGAGAG TCGGGGGATA AAAACAAAAA TAACTCATGT TGATCTTCCC GGGAAATTCA      1200

TCATCCTAAG TATCTCATAC CCAACTTTAT CAGAAGTCAA GGGGGTTATA GTCCACAGAC      1260

TGGAAGCGGT TTCTTACAAC ATAGGATCAC AAGAGTGGTA CACCACTGTC CCGAGGTATA      1320

TTGCAACTAA TGGTTACTTA ATATCTAATT TTGATGAGTC ATCTTGTGTA TTCGTCTCAG      1380

AGTCAGCCAT TTGTAGCCAG AACTCCCTGT ATCCCATGAG CCCACTCTTA CAACAATGTA      1440

TTAGGGGCGA CACTTCATCT TGTGCTCGGA CCTTGGTATC TGGGACTATG GGCAACAAAT      1500

TTATTCTGTC AAAAGGTAAT ATCGTCGCAA ATTGTGCTTC TATACTATGT AAGTGTTATA      1560

GCACAAGCAC AATTATTAAT CAGAGTCCTG ATAAGTTGCT GACATTCATT GCCTCCGATA      1620

CCTGCCCACT GGTTGAAATA GATGGTGCTA CTATCCAAGT TGGAGGCAGG CAATACCCTG      1680

ATATGGTATA CGAAGGCAAA GTTGCCTTAG GCCCTGCTAT ATCACTTGAT AGGTTAGATG      1740

TAGGTACAAA CTTAGGGAAC GCCCTTAAGA AACTGGATGA TGCTAAGGTA CTGATAGACT      1800
```

-continued

```
CCTCTAACCA GATCCTTGAG ACGGTTAGGC GCTCTTCCTT CAATTTTGGC AGTCTCCTCA    1860

GCGTTCCTAT ATTAAGTTGT ACAGCCCTGG CTTTGTTGTT GCTGATTTAC TGTTGTAAAA    1920

GACGCTACCA ACAGACACTC AAGCAGCATA CTAAGGTCGA TCCGGCATTT AAACCTGATC    1980

TAACTGGAAC TTCGAAATCC TATGTGAGAT CACACTGACT CGAGATCCAC TAGTTCTAGA    2040

GCGGCCGCCA CCGCGGTGGA GCTCCAGCTT TTGTTCCCTT TAGTGAGGGT TAATTCCGAG    2100

CTTGGCGTAA TCATGGTCAT AGCTGTTTCC TGTGTGAAAT TGTTATCCGC TCACAATTCC    2160

ACACAACATA CGAGCCGGAA GCATAAAGTG TAAAGCCTGG GGTGCCTAAT GAGTGAGCTA    2220

ACTCACATTA ATTGCGTTGC GCTCACTGCC CGCTTTCCAG TCGGGAAACC TGTCGTGCCA    2280

GCTGCATTAA TGAATCGGCC AACGCGCGGG GAGAGGCGGT TTGCGTATTG GGCGCTCTTC    2340

CGCTTCCTCG CTCACTGACT CGCTGCGCTC GGTCGTTCGG CTGCGGCGAG CGGTATCAGC    2400

TCACTCAAAG GCGGTAATAC GGTTATCCAC AGAATCAGGG GATAACGCAG GAAAGAACAT    2460

GTGAGCAAAA GGCCAGCAAA AGGCCAGGAA CCGTAAAAAG GCCGCGTTGC TGGCGTTTTT    2520

CCATAGGCTC CGCCCCCCTG ACGAGCATCA CAAAAATCGA CGCTCAAGTC AGAGGTGGCG    2580

AAACCCGACA GGACTATAAA GATACCAGGC GTTTCCCCCT GGAAGCTCCC TCGTGCGCTC    2640

TCCTGTTCCG ACCCTGCCGC TTACCGGATA CCTGTCCGCC TTTCTCCCTT CGGGAAGCGT    2700

GGCGCTTTCT CATAGCTCAC GCTGTAGGTA TCTCAGTTCG GTGTAGGTCG TTCGCTCCAA    2760

GCTGGGCTGT GTGCACGAAC CCCCCGTTCA GCCCGACCGC TGCGCCTTAT CCGGTAACTA    2820

TCGTCTTGAG TCCAACCCGG TAAGACACGA CTTATCGCCA CTGGCAGCAG CCACTGGTAA    2880

CAGGATTAGC AGAGCGAGGT ATGTAGGCGG TGCTACAGAG TTCTTGAAGT GGTGGCCTAA    2940

CTACGGCTAC ACTAGAAGGA CAGTATTTGG TATCTGCGCT CTGCTGAAGC CAGTTACCTT    3000

CGGAAAAAGA GTTGGTAGCT CTTGATCCGG CAAACAAACC ACCGCTGGTA GCGGTGGTTT    3060

TTTTGTTTGC AAGCAGCAGA TTACGCGCAG AAAAAAAGGA TCTCAAGAAG ATCCTTTGAT    3120

CTTTTCTACG GGGTCTGACG CTCAGTGGAA CGAAAACTCA CGTTAAGGGA TTTTGGTCAT    3180

GAGATTATCA AAAAGGATCT TCACCTAGAT CCTTTTAAAT TAAAAATGAA GTTTTAAATC    3240

AATCTAAAGT ATATATGAGT AAACTTGGTC TGACAGTTAC CAATGCTTAA TCAGTGAGGC    3300

ACCTATCTCA GCGATCTGTC TATTTCGTTC ATCCATAGTT GCCTGACTCC CCGTCGTGTA    3360

GATAACTACG ATACGGGAGG GCTTACCATC TGGCCCCAGT GCTGCAATGA TACCGCGAGA    3420

CCCACGCTCA CCGGCTCCAG ATTTATCAGC AATAAACCAG CCAGCCGGAA GGGCCGAGCG    3480

CAGAAGTGGT CCTGCAACTT TATCCGCCTC CATCCAGTCT ATTAATTGTT GCCGGGAAGC    3540

TAGAGTAAGT AGTTCGCCAG TTAATAGTTT GCGCAACGTT GTTGCCATTG CTACAGGCAT    3600

CGTGGTGTCA CGCTCGTCGT TTGGTATGGC TTCATTCAGC TCCGGTTCCC AACGATCAAG    3660

GCGAGTTACA TGATCCCCCA TGTTGTGCAA AAAAGCGGTT AGCTCCTTCG GTCCTCCGAT    3720

CGTTGTCAGA AGTAAGTTGG CCGCAGTGTT ATCACTCATG GTTATGGCAG CACTGCATAA    3780

TTCTCTTACT GTCATGCCAT CCGTAAGATG CTTTTCTGTG ACTGGTGAGT ACTCAACCAA    3840

GTCATTCTGA GAATAGTGTA TGCGGCGACC GAGTTGCTCT TGCCCGGCGT CAATACGGGA    3900

TAATACCGCG CCACATAGCA GAACTTTAAA AGTGCTCATC ATTGGAAAAC GTTCTTCGGG    3960

GCGAAAACTC TCAAGGATCT TACCGCTGTT GAGATCCAGT TCGATGTAAC CCACTCGTGC    4020

ACCCAACTGA TCTTCAGCAT CTTTTACTTT CACCAGCGTT TCTGGGTGAG CAAAAACAGG    4080

AAGGCAAAAT GCCGCAAAAA AGGGAATAAG GGCGACACGG AAATGTTGAA TACTCATACT    4140

CTTCCTTTTT CAATATTATT GAAGCATTTA TCAGGGTTAT TGTCTCATGA GCGGATACAT    4200
```

```
ATTTGAATGT ATTTAGAAAA ATAAACAAAT AGGGGTTCCG CGCACATTTC CCCGAAAAGT      4260

GCCACCTGGG AAATTGTAAA CGTTAATATT TTGTTAAAAT TCGCGTTAAA TTTTTGTTAA      4320

ATCAGCTCAT TTTTTAACCA ATAGGCCGAA ATCGGCAAAA TCCCTTATAA ATCAAAAGAA      4380

TAGACCGAGA TAGGGTTGAG TGTTGTTCCA GTTTGGAACA AGAGTCCACT ATTAAAGAAC      4440

GTGGACTCCA ACGTCAAAGG GCGAAAAACC GTCTATCAGG GCGATGGCCC ACTACGTGAA      4500

CCATCACCCT AATCAAGTTT TTTGGGGTCG AGGTGCCGTA AAGCACTAAA TCGGAACCCT      4560

AAAGGGAGCC CCCGATTTAG AGCTTGACGG GGAAAGCCGG CGAACGTGGC GAGAAAGGAA      4620

GGGAAGAAAG CGAAAGGAGC GGGCGCTAGG GCGCTGGCAA GTGTAGCGGT CACGCTGCGC      4680

GTAACCACCA CACCCGCCGC GCTTAATGCG CCGCTACAGG GCGCGTCGCG CCATTCGCCA      4740

TTCAGGCTGC GCAACTGTTG GGAAGGGCGA TCGGTGCGGG CCTCTTCGCT ATTACGCCAG      4800

CTGGCGAAAG GGGGATGTGC TGCAAGGCGA TTAAGTTGGG TAACGCCAGG GTTTTCCCAG      4860

TCACGACGTT GTAAAACGAC GGCCAGTGAA TTGTAATACG ACTCACTATA GGGCGAATTG      4920

GGTACCGGGC CCCCCCTCGA GGTCGACGGT ATCGATAAGC TTGAT                     4965

(2) INFORMATION FOR SEQ ID NO:23:

(i) SEQUENCE CHARACTERISTICS:
        (A) LENGTH: 5241 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

AAGCTTAATG TCGTAACAAC TCCGCCCCGT TGACGCAAAT GGGCGGTAGG CGTGTACGGT        60

GGGAGGTCTA TATAAGCAGA GCTCGTTTAG TGAACCGTCT GCAGACTCTC TTCCGCATCG       120

CTGTCTGCGA GGGCCAGCTG TTGGGCTCGC GGTTGAGGAC AAACTCTTCG CGGTCTTTCC       180

AGTACTCTTG GATCGGAAAC CCGTCGGCCT CCGAACGGTA CTCCGCCACC GAGGGACCTG       240

AGCGAGTCCG CATCGACCGG ATCGGAAAAC CTCTCGAGAA AGGCGTCTAA CCAGTCACAG       300

TCGCAAGTCT AGAATGCACA AGGGAATCCC CAAAAGCTCC AAAACCCAAA CACATACCCA       360

ACAAGACCGC CCCCCACAAC CCAGCACCGA ACTCGAAGAG ACCAGGACCT CCCGAGCACG       420

ACACAGCACA ACATCAGCTC AGCGATCCAC GCACTACGAT CCTCGAACAT CGGACAGACC       480

CGTCTCCTAC ACCATGAACA GGACCAGGTC CCGCAAGCAA ACCAGCCACA GATTGAAGAA       540

CATCCCAGTT CACGGAAACC ACGAGGCCAC CATCCAGCAC ATACCAGAGA GTGTCTCAAA       600

AGGAGCGAGA TCCCAGATCG AAAGGCGGCA ACCCAATGCA ATCAACTCAG GCTCTCATTG       660

CACCTGGTTA GTCCTGTGGT GCCTCGGAAT GGCCAGTCTC TTTCTTTGTT CCAAGGCTCA       720

GATACATTGG AATAATTTGT CAACTATTGG GATTATCGGG ACTGATAGTG TCCATTACAA       780

GATCATGACT AGGCCCAGTC ACCAGTACTT GGTCATAAAA CTGATGCCTA ATGTTTCACT       840

TATAGAGAAT TGTACCAAAG CAGAATTAGG TGAGTATGAG AAATTATTGA ATTCAGTCCT       900

CGAACCAATC AACCAAGCTT TGACTCTAAT GACCAAGAAT GTGAAGCCCC TGCAGTCATT       960

AGGGTCAGGT AGGAGACAAA GGCGTTTTGC AGGAGTGGTA CTTGCAGGTG TAGCTTTAGG      1020

AGTGGCTACA GCTGCACAAA TCACTGCAGG AATAGCTTTA CATCAATCCA ACCTCAATGC      1080

TCAAGCAATC CAATCTCTTA GAACCAGCCT TGAACAGTCT AACAAAGCTA TAGAAGAAAT      1140

TAGGGAGGCT ACCCAAGAAA CCGTCATTGC CGTTCAGGGA GTCCAGGACT ACGTCAACAA      1200
```

-continued

```
CGAACTCGTC CCTGCCATGC AACATATGTC ATGTGAATTA GTTGGGCAGA GATTAGGGTT    1260

AAGACTGCTT CGGTATTATA CTGAGTTGTT GTCAATATTT GGCCCGAGTT TACGTGACCC    1320

TATTTCAGCC GAGATATCAA TTCAGGCACT GATTTATGCT CTTGGAGGAG AAATTCATAA    1380

GATACTTGGG AAGTTGGGAT ATTCTGGAAG TGATATGATT GCAATCTTGG AGAGTCGGGG    1440

GATAAAAACA AAAATAACTC ATGTTGATCT TCCCGGGAAA TTCATCATCC TAAGTATCTC    1500

ATACCCAACT TTATCAGAAG TCAAGGGGGT TATAGTCCAC AGACTGGAAG CGGTTTCTTA    1560

CAACATAGGA TCACAAGAGT GGTACACCAC TGTCCCGAGG TATATTGCAA CTAATGGTTA    1620

CTTAATATCT AATTTTGATG AGTCATCTTG TGTATTCGTC TCAGAGTCAG CCATTTGTAG    1680

CCAGAACTCC CTGTATCCCA TGAGCCCACT CTTACAACAA TGTATTAGGG GCGACACTTC    1740

ATCTTGTGCT CGGACCTTGG TATCTGGAC TATGGGCAAC AAATTTATTC TGTCAAAAGG    1800

TAATATCGTC GCAAATTGTG CTTCTATACT ATGTAAGTGT TATAGCACAA GCACAATTAT    1860

TAATCAGAGT CCTGATAAGT TGCTGACATT CATTGCCTCC GATACCTGCC CACTGGTTGA    1920

AATAGATGGT GCTACTATCC AAGTTGGAGG CAGGCAATAC CCTGATATGG TATACGAAGG    1980

CAAAGTTGCC TTAGGCCCTG CTATATCACT TGATAGGTTA GATGTAGGTA CAAACTTAGG    2040

GAACGCCCTT AAGAAACTGG ATGATGCTAA GGTACTGATA GACTCCTCTA ACCAGATCCT    2100

TGAGACGGTT AGGCGCTCTT CCTTCAATTT TGGCAGTCTC CTCAGCGTTC CTATATTAAG    2160

TTGTACAGCC CTGGCTTTGT TGTTGCTGAT TTACTGTTGT AAAAGACGCT ACCAACAGAC    2220

ACTCAAGCAG CATACTAAGG TCGATCCGGC ATTTAAACCT GATCTAACTG AACTTCGAA    2280

ATCCTATGTG AGATCACACT GACCGCGGCG TGATTAATCA GCCATACCAC ATTTGTAGAG    2340

GTTTTACTTG CTTTAAAAAA CCTCCCACAC CTCCCCCTGA ACCTGAAACA TAAAATGAAT    2400

GCAATTGTTG TTGTTAACTT GTTTATTGCA GCTTATAATG GTTACAAATA AAGCAATAGC    2460

ATCACAAATT TCACAAATAA AGCATTTTTT TCACTGCATT CTAGTTGTGG TTTGTCCAAA    2520

CTCATCAATG TATCTTATCA TGTCTGGATC CCCCGGAATT CACTGGCCGT CGTTTTACAA    2580

CGTCGTGACT GGGAAAACCC TGGCGTTACC CAACTTAATC GCCTTGCAGC ACATCCCCCC    2640

TTCGCCAGCT GGCGTAATAG CGAAGAGGCC CGCACCGATC GCCCTTCCCA ACAGTTGCGC    2700

AGCCTGAATG GCGAATGGCG CCTGATGCGG TATTTTCTCC TTACGCATCT GTGCGGTATT    2760

TCACACCGCA TATGGTGCAC TCTCAGTACA ATCTGCTCTG ATGCCGCATA GTTAAGCCAG    2820

TACACTCCGC TATCGCTACG TGACTGGGTC ATGGCTGCGC CCCGACACCC GCCAACACCC    2880

GCTGACGCGC CCTGACGGGC TTGTCTGCTC CCGGCATCCG CTTACAGACA AGCTGTGACC    2940

GTCTCCGGGA GCTGCATGTG TCAGAGGTTT TCACCGTCAT CACCGAAACG CGCGAGGCAG    3000

TTCTTGAAGA CGAAAGGGCC TCGTGATACG CCTATTTTTA TAGGTTAATG TCATGATAAT    3060

AATGGTTTCT TAGACGTCAG GTGGCACTTT TCGGGGAAAT GTGCGCGGAA CCCCTATTTG    3120

TTTATTTTTC TAAATACATT CAAATATGTA TCCGCTCATG AGACAATAAC CCTGATAAAT    3180

GCTTCAATAA TATTGAAAAA GGAAGAGTAT GAGTATTCAA CATTTCCGTG TCGCCCTTAT    3240

TCCCTTTTTT GCGGCATTTT GCCTTCCTGT TTTTGCTCAC CCAGAAACGC TGGTGAAAGT    3300

AAAAGATGCT GAAGATCAGT TGGGTGCACG AGTGGGTTAC ATCGAACTGG ATCTCAACAG    3360

CGGTAAGATC CTTGAGAGTT TTCGCCCCGA AGAACGTTTT CCAATGATGA GCACTTTTAA    3420

AGTTCTGCTA TGTGGCGCGG TATTATCCCG TATTGACGCC GGGCAAGAGC AACTCGGTCG    3480

CCGCATACAC TATTCTCAGA ATGACTTGGT TGAGTACTCA CCAGTCACAG AAAAGCATCT    3540
```

```
TACGGATGGC ATGACAGTAA GAGAATTATG CAGTGCTGCC ATAACCATGA GTGATAACAC    3600

TGCGGCCAAC TTACTTCTGA CAACGATCGG AGGACCGAAG GAGCTAACCG CTTTTTTGCA    3660

CAACATGGGG GATCATGTAA CTCGCCTTGA TCGTTGGGAA CCGGAGCTGA ATGAAGCCAT    3720

ACCAAACGAC GAGCGTGACA CCACGATGCC TGTAGCAATG GCAACAACGT TGCGCAAACT    3780

ATTAACTGGC GAACTACTTA CTCTAGCTTC CCGGCAACAA TTAATAGACT GGATGGAGGC    3840

GGATAAAGTT GCAGGACCAC TTCTGCGCTC GGCCCTTCCG GCTGGCTGGT TTATTGCTGA    3900

TAAATCTGGA GCCGGTGAGC GTGGGTCTCG CGGTATCATT GCAGCACTGG GGCCAGATGG    3960

TAAGCCCTCC CGTATCGTAG TTATCTACAC GACGGGGAGT CAGGCAACTA TGGATGAACG    4020

AAATAGACAG ATCGCTGAGA TAGGTGCCTC ACTGATTAAG CATTGGTAAC TGTCAGACCA    4080

AGTTTACTCA TATATACTTT AGATTGATTT AAAACTTCAT TTTTAATTTA AAAGGATCTA    4140

GGTGAAGATC CTTTTTGATA ATCTCATGAC CAAAATCCCT TAACGTGAGT TTTCGTTCCA    4200

CTGAGCGTCA GACCCCGTAG AAAAGATCAA AGGATCTTCT TGAGATCCTT TTTTTCTGCG    4260

CGTAATCTGC TGCTTGCAAA CAAAAAAACC ACCGCTACCA GCGGTGGTTT GTTTGCCGGA    4320

TCAAGAGCTA CCAACTCTTT TTCCGAAGGT AACTGGCTTC AGCAGAGCGC AGATACCAAA    4380

TACTGTCCTT CTAGTGTAGC CGTAGTTAGG CCACCACTTC AAGAACTCTG TAGCACCGCC    4440

TACATACCTC GCTCTGCTAA TCCTGTTACC AGTGGCTGCT GCCAGTGGCG ATAAGTCGTG    4500

TCTTACCGGG TTGGACTCAA GACGATAGTT ACCGGATAAG GCGCAGCGGT CGGGCTGAAC    4560

GGGGGGTTCG TGCACACAGC CCAGCTTGGA GCGAACGACC TACACCGAAC TGAGATACCT    4620

ACAGCGTGAG CATTGAGAAA GCGCCACGCT TCCCGAAGGG AGAAAGGCGG ACAGGTATCC    4680

GGTAAGCGGC AGGGTCGGAA CAGGAGAGCG CACGAGGGAG CTTCCAGGGG GAAACGCCTG    4740

GTATCTTTAT AGTCCTGTCG GGTTTCGCCA CCTCTGACTT GAGCGTCGAT TTTTGTGATG    4800

CTCGTCAGGG GGGCGGAGCC TATGGAAAAA CGCCAGCAAC GCGGCCTTTT TACGGTTCCT    4860

GGCCTTTTGC TGGCCTTTTG CTCACATGTT CTTTCCTGCG TTATCCCCTG ATTCTGTGGA    4920

TAACCGTATT ACCGCCTTTG AGTGAGCTGA TACCGCTCGC CGCAGCCGAA CGACCGAGCG    4980

CAGCGAGTCA GTGAGCGAGG AAGCGGAAGA GCGCCAATAC GCAAACCGCC TCTCCCCGCG    5040

CGTTGGCCGA TTCATTAATG CAGCTGGCAC GACAGGTTTC CCGACTGGAA AGCGGGCAGT    5100

GAGCGCAACG CAATTAATGT GAGTTACCTC ACTCATTAGG CACCCCAGGC TTTACACTTT    5160

ATGCTTCCGG CTCGTATGTT GTGTGGAATT GTGAGCGGAT AACAATTTCA CACAGGAAAC    5220

AGCTATGACC ATGATTACGC C                                              5241

(2) INFORMATION FOR SEQ ID NO:24:

(i) SEQUENCE CHARACTERISTICS:
        (A) LENGTH: 5147 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

AAGCTTAATG TCGTAACAAC TCCGCCCCGT TGACGCAAAT GGGCGGTAGG CGTGTACGGT     60

GGGAGGTCTA TATAAGCAGA GCTCGTTTAG TGAACCGTCT GCAGACTCTC TTCCGCATCG    120

CTGTCTGCGA GGGCCAGCTG TTGGGCTCGC GGTTGAGGAC AAACTCTTCG CGGTCTTTCC    180

AGTACTCTTG GATCGGAAAC CCGTCGGCCT CCGAACGGTA CTCCGCCACC GAGGGACCTG    240
```

-continued

```
AGCGAGTCCG CATCGACCGG ATCGGAAAAC CTCTCGAGAA AGGCGTCTAA CCAGTCACAG    300

TCGCAAGTCT AGAATGCACA AGGGAATCCC CAAAAGCTCC AAAACCCAAA CACATACCCA    360

ACAAGACCGC CCCCCACAAC CCAGCACCGA ACTCGAAGAG ACCAGGACCT CCCGAGCACG    420

ACACAGCACA ACATCAGCTC AGCGATCCAC GCACTACGAT CCTCGAACAT CGGACAGACC    480

CGTCTCCTAC ACCATGAACA GGACCAGGTC CCGCAAGCAA ACCAGCCACA GATTGAAGAA    540

CATCCCAGTT CACGGAAACC ACGAGGCCAC CATCCAGCAC ATACCAGAGA GTGTCTCAAA    600

AGGAGCGAGA TCCCAGATCG AAAGGCGGCA ACCCAATGCA ATCAACTCAG GCTCTCATTG    660

CACCTGGTTA GTCCTGTGGT GCCTCGGAAT GGCCAGTCTC TTTCTTTGTT CCAAGGCTCA    720

GATACATTGG AATAATTTGT CAACTATTGG GATTATCGGG ACTGATAGTG TCCATTACAA    780

GATCATGACT AGGCCCAGTC ACCAGTACTT GGTCATAAAA CTGATGCCTA ATGTTTCACT    840

TATAGAGAAT TGTACCAAAG CAGAATTAGG TGAGTATGAG AAATTATTGA ATTCAGTCCT    900

CGAACCAATC AACCAAGCTT TGACTCTAAT GACCAAGAAT GTGAAGCCCC TGCAGTCATT    960

AGGGTCAGGT AGGAGACAAA GGCGTTTTGC AGGAGTGGTA CTTGCAGGTG TAGCTTTAGG   1020

AGTGGCTACA GCTGCACAAA TCACTGCAGG AATAGCTTTA CATCAATCCA ACCTCAATGC   1080

TCAAGCAATC CAATCTCTTA GAACCAGCCT TGAACAGTCT AACAAAGCTA TAGAAGAAAT   1140

TAGGGAGGCT ACCCAAGAAA CCGTCATTGC CGTTCAGGGA GTCCAGGACT ACGTCAACAA   1200

CGAACTCGTC CCTGCCATGC AACATATGTC ATGTGAATTA GTTGGGCAGA GATTAGGGTT   1260

AAGACTGCTT CGGTATTATA CTGAGTTGTT GTCAATATTT GGCCCGAGTT TACGTGACCC   1320

TATTTCAGCC GAGATATCAA TTCAGGCACT GATTTATGCT CTTGGAGGAG AAATTCATAA   1380

GATACTTGGG AAGTTGGGAT ATTCTGGAAG TGATATGATT GCAATCTTGG AGAGTCGGGG   1440

GATAAAAACA AAAATAACTC ATGTTGATCT TCCCGGGAAA TTCATCATCC TAAGTATCTC   1500

ATACCCAACT TTATCAGAAG TCAAGGGGGT TATAGTCCAC AGACTGGAAG CGGTTTCTTA   1560

CAACATAGGA TCACAAGAGT GGTACACCAC TGTCCCGAGG TATATTGCAA CTAATGGTTA   1620

CTTAATATCT AATTTTGATG AGTCATCTTG TGTATTCGTC TCAGAGTCAG CCATTTGTAG   1680

CCAGAACTCC CTGTATCCCA TGAGCCCACT CTTACAACAA TGTATTAGGG GCGACACTTC   1740

ATCTTGTGCT CGGACCTTGG TATCTGGGAC TATGGGCAAC AAATTTATTC TGTCAAAAGG   1800

TAATATCGTC GCAAATTGTG CTTCTATACT ATGTAAGTGT TATAGCACAA GCACAATTAT   1860

TAATCAGAGT CCTGATAAGT TGCTGACATT CATTGCCTCC GATACCTGCC CACTGGTTGA   1920

AATAGATGGT GCTACTATCC AAGTTGGAGG CAGGCAATAC CCTGATATGG TATACGAAGG   1980

CAAAGTTGCC TTAGGCCCTG CTATATCACT TGATAGGTTA GATGTAGGTA CAAACTTAGG   2040

GAACGCCCTT AAGAAACTGG ATGATGCTAA GGTACTGATA GACTCCTCTA ACCAGATCCT   2100

TGAGACGGTT AGGCGCTCTT CCTTCAATTT TGGCAGTCTC CTCAGCGTTC CTATATTAAG   2160

TTGTACAGCC CTGGCTTTGT TGTTGCTGAT TTACTGTTGT AAAAGACGCT ACCAACAGAC   2220

ACTCAAGCAG CATACTAAGG TCGATCCGGC ATTTAAACCT GATCTAACTG GAACTTCGAA   2280

ATCCTATGTG AGATCACACT GACCGCGGAA TTGTTGTTGT TAACTTGTTT ATTGCAGCTT   2340

ATAATGGTTA CAAATAAAGC AATAGCATCA CAAATTTCAC AAATAAAGCA TTTTTTTCAC   2400

TGCATTCTAG TTGTGGTTTG TCCAAACTCA TCAATGTATC TTATCATGTC TGGATCCCCC   2460

GGAATTCACT GGCCGTCGTT TTACAACGTC GTGACTGGGA AAACCCTGGC GTTACCCAAC   2520

TTAATCGCCT TGCAGCACAT CCCCCCTTCG CCAGCTGGCG TAATAGCGAA GAGGCCCGCA   2580

CCGATCGCCC TTCCCAACAG TTGCGCAGCC TGAATGGCGA ATGGCGCCTG ATGCGGTATT   2640
```

```
TTCTCCTTAC GCATCTGTGC GGTATTTCAC ACCGCATATG GTGCACTCTC AGTACAATCT    2700

GCTCTGATGC CGCATAGTTA AGCCAGTACA CTCCGCTATC GCTACGTGAC TGGGTCATGG    2760

CTGCGCCCCG ACACCCGCCA ACACCCGCTG ACGCGCCCTG ACGGGCTTGT CTGCTCCCGG    2820

CATCCGCTTA CAGACAAGCT GTGACCGTCT CCGGGAGCTG CATGTGTCAG AGGTTTTCAC    2880

CGTCATCACC GAAACGCGCG AGGCAGTTCT TGAAGACGAA AGGGCCTCGT GATACGCCTA    2940

TTTTTATAGG TTAATGTCAT GATAATAATG GTTTCTTAGA CGTCAGGTGG CACTTTTCGG    3000

GGAAATGTGC GCGGAACCCC TATTTGTTTA TTTTTCTAAA TACATTCAAA TATGTATCCG    3060

CTCATGAGAC AATAACCCTG ATAAATGCTT CAATAATATT GAAAAAGGAA GAGTATGAGT    3120

ATTCAACATT TCCGTGTCGC CCTTATTCCC TTTTTTGCGG CATTTTGCCT TCCTGTTTTT    3180

GCTCACCCAG AAACGCTGGT GAAAGTAAAA GATGCTGAAG ATCAGTTGGG TGCACGAGTG    3240

GGTTACATCG AACTGGATCT CAACAGCGGT AAGATCCTTG AGAGTTTTCG CCCCGAAGAA    3300

CGTTTTCCAA TGATGAGCAC TTTTAAAGTT CTGCTATGTG GCGCGGTATT ATCCCGTATT    3360

GACGCCGGGC AAGAGCAACT CGGTCGCCGC ATACACTATT CTCAGAATGA CTTGGTTGAG    3420

TACTCACCAG TCACAGAAAA GCATCTTACG GATGGCATGA CAGTAAGAGA ATTATGCAGT    3480

GCTGCCATAA CCATGAGTGA TAACACTGCG GCCAACTTAC TTCTGACAAC GATCGGAGGA    3540

CCGAAGGAGC TAACCGCTTT TTTGCACAAC ATGGGGGATC ATGTAACTCG CCTTGATCGT    3600

TGGGAACCGG AGCTGAATGA AGCCATACCA AACGACGAGC GTGACACCAC GATGCCTGTA    3660

GCAATGGCAA CAACGTTGCG CAAACTATTA ACTGGCGAAC TACTTACTCT AGCTTCCCGG    3720

CAACAATTAA TAGACTGGAT GGAGGCGGAT AAAGTTGCAG GACCACTTCT GCGCTCGGCC    3780

CTTCCGGCTG GCTGGTTTAT TGCTGATAAA TCTGGAGCCG GTGAGCGTGG GTCTCGCGGT    3840

ATCATTGCAG CACTGGGGCC AGATGGTAAG CCCTCCCGTA TCGTAGTTAT CTACACGACG    3900

GGGAGTCAGG CAACTATGGA TGAACGAAAT AGACAGATCG CTGAGATAGG TGCCTCACTG    3960

ATTAAGCATT GGTAACTGTC AGACCAAGTT TACTCATATA TACTTTAGAT TGATTTAAAA    4020

CTTCATTTTT AATTTAAAAG GATCTAGGTG AAGATCCTTT TTGATAATCT CATGACCAAA    4080

ATCCCTTAAC GTGAGTTTTC GTTCCACTGA GCGTCAGACC CCGTAGAAAA GATCAAAGGA    4140

TCTTCTTGAG ATCCTTTTTT TCTGCGCGTA ATCTGCTGCT TGCAAACAAA AAAACCACCG    4200

CTACCAGCGG TGGTTTGTTT GCCGGATCAA GAGCTACCAA CTCTTTTTCC GAAGGTAACT    4260

GGCTTCAGCA GAGCGCAGAT ACCAAATACT GTCCTTCTAG TGTAGCCGTA GTTAGGCCAC    4320

CACTTCAAGA ACTCTGTAGC ACCGCCTACA TACCTCGCTC TGCTAATCCT GTTACCAGTG    4380

GCTGCTGCCA GTGGCGATAA GTCGTGTCTT ACCGGGTTGG ACTCAAGACG ATAGTTACCG    4440

GATAAGGCGC AGCGGTCGGG CTGAACGGGG GGTTCGTGCA CACAGCCCAG CTTGGAGCGA    4500

ACGACCTACA CCGAACTGAG ATACCTACAG CGTGAGCATT GAGAAAGCGC CACGCTTCCC    4560

GAAGGGAGAA AGGCGGACAG GTATCCGGTA AGCGGCAGGG TCGGAACAGG AGAGCGCACG    4620

AGGGAGCTTC CAGGGGGAAA CGCCTGGTAT CTTTATAGTC CTGTCGGGTT TCGCCACCTC    4680

TGACTTGAGC GTCGATTTTT GTGATGCTCG TCAGGGGGGC GGAGCCTATG GAAAAACGCC    4740

AGCAACGCGG CCTTTTTACG GTTCCTGGCC TTTTGCTGGC CTTTTGCTCA CATGTTCTTT    4800

CCTGCGTTAT CCCCTGATTC TGTGGATAAC CGTATTACCG CCTTTGAGTG AGCTGATACC    4860

GCTCGCCGCA GCCGAACGAC CGAGCGCAGC GAGTCAGTGA GCGAGGAAGC GGAAGAGCGC    4920

CAATACGCAA ACCGCCTCTC CCCGCGCGTT GGCCGATTCA TTAATGCAGC TGGCACGACA    4980
```

```
GGTTTCCCGA CTGGAAAGCG GGCAGTGAGC GCAACGCAAT TAATGTGAGT TACCTCACTC      5040

ATTAGGCACC CCAGGCTTTA CACTTTATGC TTCCGGCTCG TATGTTGTGT GGAATTGTGA      5100

GCGGATAACA ATTTCACACA GGAAACAGCT ATGACCATGA TTACGCC                   5147
```

(2) INFORMATION FOR SEQ ID NO:25:

(i) SEQUENCE CHARACTERISTICS:
        (A) LENGTH: 8792 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

```
GTCGACGGTG CCCCCAGCAG AAGTATCGAC TGCATGCTAA TTATTAACAA ACCAAAAGGC        60

GTTGCCACTT ACACCCTTAC CTTTAGGTTT TTAAACTTTA ACAGACTAAG CGGAGGTACC       120

CTGTTTAAAA CTGATGTCTT AACCTTTACC TATGTAGGCG AAAATCAATA AAACCAGAAA       180

AAAATAAGTT TAAAAGCTTT ATTTTTCATA CACGCGAGCG GTAAGGCTGC CGCCTTCAGG       240

AAAAGTTACT CTGTAAACAG TTCTTTCACA ACAGCACAAA ACATAGGTAT TAGTTAACAG       300

TTCATTTGGG CTATAATAAT ATACATTTTC TTGGGTGGCA AAGCAAGGGT CGGTAATCTC       360

AACAAAACCA TCAACTGGAA TGCAAGAATA GTCCAGCACG GTGGGTTCAA TCTAAAAATG       420

AAGAAACGCT GTTGAGGTTC ACTAAGCACA GGTTTTGAAT CTGTCGGCAG CGTCCATGCA       480

TCATAGCTTG TCTCAAAGCA GATTGTCTTC TTTCCTCTGC CTTGGAAGTG GTTTGGTGAA       540

GCACTACAGG TGTCTTTTCA ACCTCTTTCA GCACCCGCTC TATTACAGAT CTCACCCACA       600

CAGCACAGTT TTTAAGAGAA CAATAGTTTT GAAGGCTACA AGATTTACAC TTAAGCACCA       660

GCCAGTAATT ATAAGTGCTT TTAAGAACTA CCCCTAGCTC AGGGTTAATG CACCTTTTAA       720

TGGCCTCCAT GCAGGCTTTA TGGACAGTTC TAAAAAAGA CAGTCTAAAA TAAATGTAGT        780

GAGTGTTTCT AAATATAATA CTCCCCACAT AGTTAATTTC ATCAGGCCTG CTAGAATTTA       840

CAAACTCTCG GTACCACATA TACTTTTTAT TCATAGCCCC ACCCTTAATA AAGTCCTCAA       900

TCACTTTCTG AACCACATGC TTGCTAGCCA TGCATTGTAA AGACAAGCTG TTAGAGCAGT       960

GACAGTGTAC TCGCCACGTT TGAGCCTCTG CCAGGCAGCA GTGCTTAGTT ACTATCAACT      1020

CAATACCCGC ATTGCATGTA AACCCCCCAA AGAGCAGTTT TCATGCCTG TGTAGCACAT       1080

CATCCCACAA AATAGGAATT TCATAGCATA AAGCAAAGCA ATTACAATAT TTAGGAACTC      1140

TCACCACAGC AGTCACGTGA CATGTTGTCT CAGCAGTGCA GTTGCCTTCC ATCCTACAAT      1200

TATGAACAAA AACTAAACAC TTCTAACAAA GATACAGTGA CAATCTCCCT TCCTCTAAAA      1260

GCATTGTTTA CATTAGGGTG ATTATTAACA ACGTCAGAAA TTTCTTTAAT TAAAGTGCCT      1320

TTAAAATGTG CAAGAGCATC ATCATACTCA AAACCAAGCT GAGAGTAAAA GACCACCTTA      1380

AAAGTAATCC CAGGCTTGTT TTTATCAACA GCCTTAAACA TGCTTTCACA AAATATAGAA      1440

GCAGTAACAT CATCAATGGT GTCGAAGAGA AACTCCATAG GAGACTCCAG CATTGATCCA      1500

AGCTCTCTAA CAAAATCTTC CTCAAAATGA ATAATGCCCT TTACACAAAC GCGGGGCAGA      1560

CGATGGTGGG CCATCGCGTC AACCTGAAAC ACATTTTACA GTAAACAAAG CTAGCTCCGC      1620

AGTGGTAAAG TCATGCCCAT GGGTGAGGCC AAAATCCTTA AAAAAGCTAT CTAAGTAGTT      1680

GGTCATCCCC TCAGTTAAAA AGTTTTGCAG CTGGGTGGTG CATACCACAT AGTGCCAGCT      1740

TATAGCTACA AAGACCTGCA TCCCCTCCTT AGCAGACAGC TCTTGCACAC ACGCAGTAAC      1800
```

-continued

```
TATCCACCGC TTAAGAAAAG CTTTAAGCCC AGCGCACATA ACAGCTCCAA TGTTTTTATC      1860

CAAGGAGAGC AAAATTTCAG CAAGCGCAGG CTCAACAGTA ATAGTGAAGC AGAGGCATTT      1920

CAGACGAGGC TCACTAGCTG CAGTCGCCAT TTATGAGGTC TGCAATAAAA AACAACTCAT      1980

CAGCAGCTGA AAAAGTGCAC TTTGACCTCA TTAAGCCACT GCATATGCAA GTCCTCATCT      2040

ATGCCGCAGC CCAGACCCTC AATCCAGCCC CGAATGTACA CTTTAATAAG AGATTCAACC      2100

TCTTCTTTTA GCAAAGTACA CATGCTGTTT GGACTAGTAT ACACAATAGA AGTCACAATG      2160

AGGGGCCCGC TGTGGCTGGA AAGCCTGCGC ACAGCCCGAA GGTTAAAAAT GGACTGTAAC      2220

AGCATTGAAA CCCCGCGACA CAGGTCAGTC TCGCGGTCTT GATCTCTTAT TATAGCGACC      2280

AAATGGTCCT TCAGAGTGAT GTTGCACTCA TAGAAGTAGG CAGCTCCGGC AGCCATTCTG      2340

CAAAATAACA AAACACCACT AAGCATAGCA CCATCACCAA GCATGAAAAC AGGTAAAAAC      2400

AAAAGCAACA CTTACTTATT CAGCAGTCAC AAGAATGTTG GGCTCCCAAG TGACAGACAA      2460

GCCTAATGCA AGGTGGGCAC AGTCTCCGGA ATAAGTTGAC AAAAGTCACG CCGCAAAGCT      2520

TCCTGAAGAG AAACGGCGGT AGCCTGGATA TCTGCAACGG ACCCAAAACC TTCAGTGTCA      2580

CTTCCAATAA ACAGATAAAA CTCTAAATAG TCCCCACTTA AAACCGAAAC AGCCGCGGCA      2640

AAGGTAGGAC ACGGACGCAC TTCCTGAGCC CTAATAAGGC TAAACACCAC ACGGCGCAGT      2700

TCAGAAGGCA AAAAGTCTGT AAGCTCTAGC TGAGCACACA CACTCTCCAC TAGACACTTG      2760

TGAAGCCTCA GACAAAAACA TGCTCCCATA GACACTCCTA AAGCTGCCAT TGTACTCACG      2820

GACGGCTGGC TGTCAGAGGA GAGCTATGAG GATGAAATGC CAAGCACAGC GTTTATATAG      2880

TCCTCAAAGT AGGGCGTGTG GAAAACGAAA AGGAATATAA CGGGGCGTTT GAGGAAGTGG      2940

TGCCAAGTAC AGTCATAAAA TGTGGGCGCG TGGTAAATGT TAAGTGCAGT TTCCCTTTGG      3000

CGGTTGGCCC GGAAAGTTCA CAAAAAGTAC AGCACGTCCT TGTCACCGTG TCAACCACAA      3060

AACCACAAAT AGGCACAACG CCCAAAAACC CGGGTCGACA CGCGTGAATT CACCGGTTCG      3120

AGCTTAATGT CGTAACAACT CCGCCCCGTT GACGCAAATG GCGGTAGGC GTGTACGGTG       3180

GGAGGTCTAT ATAAGCAGAG CTCGTTTAGT GAACCGTCTG CAGACTCTCT TCCGCATCGC      3240

TGTCTGCGAG GGCCAGCTGT TGGGCTCGCG GTTGAGGACA AACTCTTCGC GGTCTTTCCA      3300

GTACTCTTGG ATCGGAAACC CGTCGGCCTC CGAACGGTAC TCCGCCACCG AGGGACCTGA      3360

GCGAGTCCGC ATCGACCGGA TCGGAAAACC TCTCGAGAAA GGCGTCTAAC CAGTCACAGT      3420

CGCAAGTCTA GAATGCACAA GGGAATCCCC AAAAGCTCCA AAACCCAAAC ACATACCCAA      3480

CAAGACCGCC CCCCACAACC CAGCACCGAA CTCGAAGAGA CCAGGACCTC CCGAGCACGA      3540

CACAGCACAA CATCAGCTCA GCGATCCACG CACTACGATC CTCGAACATC GGACAGACCC      3600

GTCTCCTACA CCATGAACAG GACCAGGTCC CGCAAGCAAA CCAGCCACAG ATTGAAGAAC      3660

ATCCCAGTTC ACGGAAACCA CGAGGCCACC ATCCAGCACA TACCAGAGAG TGTCTCAAAA      3720

GGAGCGAGAT CCCAGATCGA AAGGCGGCAA CCCAATGCAA TCAACTCAGG CTCTCATTGC      3780

ACCTGGTTAG TCCTGTGGTG CCTCGGAATG GCCAGTCTCT TCTTTGTTC CAAGGCTCAG       3840

ATACATTGGA ATAATTTGTC AACTATTGGG ATTATCGGGA CTGATAGTGT CCATTACAAG      3900

ATCATGACTA GGCCCAGTCA CCAGTACTTG GTCATAAAAC TGATGCCTAA TGTTTCACTT      3960

ATAGAGAATT GTACCAAAGC AGAATTAGGT GAGTATGAGA AATTATTGAA TTCAGTCCTC      4020

GAACCAATCA ACCAAGCTTT GACTCTAATG ACCAAGAATG TGAAGCCCCT GCAGTCATTA      4080

GGGTCAGGTA GGAGACAAAG GCGTTTTGCA GGAGTGGTAC TTGCAGGTGT AGCTTTAGGA      4140

GTGGCTACAG CTGCACAAAT CACTGCAGGA ATAGCTTTAC ATCAATCCAA CCTCAATGCT      4200
```

```
CAAGCAATCC AATCTCTTAG AACCAGCCTT GAACAGTCTA ACAAAGCTAT AGAAGAAATT    4260

AGGGAGGCTA CCCAAGAAAC CGTCATTGCC GTTCAGGGAG TCCAGGACTA CGTCAACAAC    4320

GAACTCGTCC CTGCCATGCA ACATATGTCA TGTGAATTAG TTGGGCAGAG ATTAGGGTTA    4380

AGACTGCTTC GGTATTATAC TGAGTTGTTG TCAATATTTG GCCCGAGTTT ACGTGACCCT    4440

ATTTCAGCCG AGATATCAAT TCAGGCACTG ATTTATGCTC TTGGAGGAGA AATTCATAAG    4500

ATACTTGGGA AGTTGGGATA TTCTGGAAGT GATATGATTG CAATCTTGGA GAGTCGGGGG    4560

ATAAAAACAA AAATAACTCA TGTTGATCTT CCCGGGAAAT TCATCATCCT AAGTATCTCA    4620

TACCCAACTT TATCAGAAGT CAAGGGGGTT ATAGTCCACA GACTGGAAGC GGTTTCTTAC    4680

AACATAGGAT CACAAGAGTG GTACACCACT GTCCCGAGGT ATATTGCAAC TAATGGTTAC    4740

TTAATATCTA ATTTTGATGA GTCATCTTGT GTATTCGTCT CAGAGTCAGC CATTTGTAGC    4800

CAGAACTCCC TGTATCCCAT GAGCCCACTC TTACAACAAT GTATTAGGGG CGACACTTCA    4860

TCTTGTGCTC GGACCTTGGT ATCTGGGACT ATGGGCAACA AATTTATTCT GTCAAAAGGT    4920

AATATCGTCG CAAATTGTGC TTCTATACTA TGTAAGTGTT ATAGCACAAG CACAATTATT    4980

AATCAGAGTC CTGATAAGTT GCTGACATTC ATTGCCTCCG ATACCTGCCC ACTGGTTGAA    5040

ATAGATGGTG CTACTATCCA AGTTGGAGGC AGGCAATACC CTGATATGGT ATACGAAGGC    5100

AAAGTTGCCT TAGGCCCTGC TATATCACTT GATAGGTTAG ATGTAGGTAC AAACTTAGGG    5160

AACGCCCTTA AGAAACTGGA TGATGCTAAG GTACTGATAG ACTCCTCTAA CCAGATCCTT    5220

GAGACGGTTA GGCGCTCTTC CTTCAATTTT GGCAGTCTCC TCAGCGTTCC TATATTAAGT    5280

TGTACAGCCC TGGCTTTGTT GTTGCTGATT TACTGTTGTA AAAGACGCTA CCAACAGACA    5340

CTCAAGCAGC ATACTAAGGT CGATCCGGCA TTTAAACCTG ATCTAACTGG AACTTCGAAA    5400

TCCTATGTGA GATCACACTG ACCGCGGCGT GATTAATCAG CCATACCACA TTTGTAGAGG    5460

TTTTACTTGC TTTAAAAAAC CTCCCACACC TCCCCCTGAA CCTGAAACAT AAAATGAATG    5520

CAATTGTTGT TGTTAACTTG TTTATTGCAG CTTATAATGG TTACAAATAA AGCAATAGCA    5580

TCACAAATTT CACAAATAAA GCATTTTTTT CACTGCATTC TAGTTGTGGT TTGTCCAAAC    5640

TCATCAATGT ATCTTATCAT GTCTGGATCC GAAACGCCCA AAAACCCGGG GCGCCGGCCA    5700

AAAGTCCGCG GAACTCGCCC TGTCGTAAAA CCACGCCTTT GACGTCACTG GACATTCCCG    5760

TGGGAACACC CTGACCAGGG CGTGACCTGA ACCTGACCGT CCCATGACCC CGCCCCTTGC    5820

AACACCCAAA TTTAAGCCAC ACCTCTTTGT CCTGTATATT ATTGATGATG GGGGGATCCA    5880

CTAGTTCTAG AGCGGCCGCC ACCGCGGTGG AGCTCCAGCT TTTGTTCCCT TTAGTGAGGG    5940

TTAATTCCGA GCTTGGCGTA ATCATGGTCA TAGCTGTTTC CTGTGTGAAA TTGTTATCCG    6000

CTCACAATTC CACACAACAT ACGAGCCGGA AGCATAAAGT GTAAAGCCTG GGGTGCCTAA    6060

TGAGTGAGCT AACTCACATT AATTGCGTTG CGCTCACTGC CCGCTTTCCA GTCGGGAAAC    6120

CTGTCGTGCC AGCTGCATTA ATGAATCGGC CAACGCGCGG GGAGAGGCGG TTTGCGTATT    6180

GGGCGCTCTT CCGCTTCCTC GCTCACTGAC TCGCTGCGCT CGGTCGTTCG GCTGCGGCGA    6240

GCGGTATCAG CTCACTCAAA GGCGGTAATA CGGTTATCCA CAGAATCAGG GGATAACGCA    6300

GGAAAGAACA TGTGAGCAAA AGGCCAGCAA AAGGCCAGGA ACCGTAAAAA GGCCGCGTTG    6360

CTGGCGTTTT TCCATAGGCT CCGCCCCCCT GACGAGCATC ACAAAAATCG ACGCTCAAGT    6420

CAGAGGTGGC GAAACCCGAC AGGACTATAA AGATACCAGG CGTTTCCCCC TGGAAGCTCC    6480

CTCGTGCGCT CTCCTGTTCC GACCCTGCCG CTTACCGGAT ACCTGTCCGC CTTTCTCCCT    6540
```

```
TCGGGAAGCG TGGCGCTTTC TCATAGCTCA CGCTGTAGGT ATCTCAGTTC GGTGTAGGTC    6600
GTTCGCTCCA AGCTGGGCTG TGTGCACGAA CCCCCCGTTC AGCCCGACCG CTGCGCCTTA    6660
TCCGGTAACT ATCGTCTTGA GTCCAACCCG GTAAGACACG ACTTATCGCC ACTGGCAGCA    6720
GCCACTGGTA ACAGGATTAG CAGAGCGAGG TATGTAGGCG GTGCTACAGA GTTCTTGAAG    6780
TGGTGGCCTA ACTACGGCTA CACTAGAAGG ACAGTATTTG GTATCTGCGC TCTGCTGAAG    6840
CCAGTTACCT TCGGAAAAAG AGTTGGTAGC TCTTGATCCG GCAAACAAAC CACCGCTGGT    6900
AGCGGTGGTT TTTTTGTTTG CAAGCAGCAG ATTACGCGCA GAAAAAAAGG ATCTCAAGAA    6960
GATCCTTTGA TCTTTTCTAC GGGGTCTGAC GCTCAGTGGA ACGAAAACTC ACGTTAAGGG    7020
ATTTTGGTCA TGAGATTATC AAAAAGGATC TTCACCTAGA TCCTTTTAAA TTAAAAATGA    7080
AGTTTTAAAT CAATCTAAAG TATATATGAG TAAACTTGGT CTGACAGTTA CCAATGCTTA    7140
ATCAGTGAGG CACCTATCTC AGCGATCTGT CTATTTCGTT CATCCATAGT TGCCTGACTC    7200
CCCGTCGTGT AGATAACTAC GATACGGGAG GGCTTACCAT CTGGCCCCAG TGCTGCAATG    7260
ATACCGCGAG ACCCACGCTC ACCGGCTCCA GATTTATCAG CAATAAACCA GCCAGCCGGA    7320
AGGGCCGAGC GCAGAAGTGG TCCTGCAACT TTATCCGCCT CCATCCAGTC TATTAATTGT    7380
TGCCGGGAAG CTAGAGTAAG TAGTTCGCCA GTTAATAGTT TGCGCAACGT TGTTGCCATT    7440
GCTACAGGCA TCGTGGTGTC ACGCTCGTCG TTTGGTATGG CTTCATTCAG CTCCGGTTCC    7500
CAACGATCAA GGCGAGTTAC ATGATCCCCC ATGTTGTGCA AAAAAGCGGT TAGCTCCTTC    7560
GGTCCTCCGA TCGTTGTCAG AAGTAAGTTG GCCGCAGTGT TATCACTCAT GGTTATGGCA    7620
GCACTGCATA ATTCTCTTAC TGTCATGCCA TCCGTAAGAT GCTTTTCTGT GACTGGTGAG    7680
TACTCAACCA AGTCATTCTG AGAATAGTGT ATGCGGCGAC CGAGTTGCTC TTGCCCGGCG    7740
TCAATACGGG ATAATACCGC GCCACATAGC AGAACTTTAA AAGTGCTCAT CATTGGAAAA    7800
CGTTCTTCGG GGCGAAAACT CTCAAGGATC TTACCGCTGT TGAGATCCAG TTCGATGTAA    7860
CCCACTCGTG CACCCAACTG ATCTTCAGCA TCTTTTACTT TCACCAGCGT TTCTGGGTGA    7920
GCAAAAACAG GAAGGCAAAA TGCCGCAAAA AAGGGAATAA GGGCGACACG GAAATGTTGA    7980
ATACTCATAC TCTTCCTTTT TCAATATTAT TGAAGCATTT ATCAGGGTTA TTGTCTCATG    8040
AGCGGATACA TATTTGAATG TATTTAGAAA AATAAACAAA TAGGGGTTCC GCGCACATTT    8100
CCCCGAAAAG TGCCACCTGG GAAATTGTAA ACGTTAATAT TTTGTTAAAA TTCGCGTTAA    8160
ATTTTTGTTA AATCAGCTCA TTTTTTAACC AATAGGCCGA AATCGGCAAA ATCCCTTATA    8220
AATCAAAAGA ATAGACCGAG ATAGGGTTGA GTGTTGTTCC AGTTTGGAAC AAGAGTCCAC    8280
TATTAAAGAA CGTGGACTCC AACGTCAAAG GGCGAAAAAC CGTCTATCAG GGCGATGGCC    8340
CACTACGTGA ACCATCACCC TAATCAAGTT TTTTGGGGTC GAGGTGCCGT AAAGCACTAA    8400
ATCGGAACCC TAAAGGGAGC CCCCGATTTA GAGCTTGACG GGGAAAGCCG GCGAACGTGG    8460
CGAGAAAGGA AGGGAAGAAA GCGAAAGGAG CGGGCGCTAG GGCGCTGGCA AGTGTAGCGG    8520
TCACGCTGCG CGTAACCACC ACACCCGCCG CGCTTAATGC GCCGCTACAG GGCGCGTCGC    8580
GCCATTCGCC ATTCAGGCTG CGCAACTGTT GGGAAGGGCG ATCGGTGCGG GCCTCTTCGC    8640
TATTACGCCA GCTGGCGAAA GGGGGATGTG CTGCAAGGCG ATTAAGTTGG GTAACGCCAG    8700
GGTTTTCCCA GTCACGACGT TGTAAAACGA CGGCCAGTGA ATTGTAATAC GACTCACTAT    8760
AGGGCGAATT GGGTACCGGG CCCCCCCTCG AG                                  8792
```

(2) INFORMATION FOR SEQ ID NO:26:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:26:

TCAGTCATAG CCATCGACAG A                                    21

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GTGCTGGCTG GCACGGGCAT T                                    21

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

ATGTCCACCA AAGTCCCCTC T                                    21

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CCCGGGGCGT CGTATGGATA T                                    21

(2) INFORMATION FOR SEQ ID NO:30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GATACGCGTT CCATTAGCAG ATCT                                 24

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:31:

GGACACCTTT CTGATCAGTT CATT                                                24

(2) INFORMATION FOR SEQ ID NO:32:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

GATACGCGTT CCATTAGCAG ATCTTTGAGG GGCCTGGAAA TAGGC                         45

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

GGTTGTGTGG AAGACCCGGG GGCG                                                24

(2) INFORMATION FOR SEQ ID NO:34:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

AGATCTGCTA ATGGAACGCG TATCGCTGCC CCCACAGTAC AGCAA                         45

(2) INFORMATION FOR SEQ ID NO:35:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

GATCTGTTAA CCCTAAGGCC ATGGCATATG TCGCGAGGCC ATCGTGGCCG CGGCCGCA           58

(2) INFORMATION FOR SEQ ID NO:36:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

CGCGTGCGGC CGCGGCCACG ATGGCCTCGC GACATATGCC ATGGCCTTAG GGTTAACA     58

(2) INFORMATION FOR SEQ ID NO:37:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

CTAGTCATCT TAACGCGTGT CCTCAACATC ACCCGCGA     38

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

CTTGCTTGTT ATTAAAAAAA G     21

(2) INFORMATION FOR SEQ ID NO:39:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

TCACGCCCTG GTCAGGGTGT T     21

(2) INFORMATION FOR SEQ ID NO:40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

GCCATCGCGT CAACCTGA     18

(2) INFORMATION FOR SEQ ID NO:41:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

ATGATGTCTG GGGACATG     18

(2) INFORMATION FOR SEQ ID NO:42:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

TCACGCCCTG GTCAGGGTGT T                                                 21

(2) INFORMATION FOR SEQ ID NO:43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

ACCACGCGCC CACATTTT                                                     18

(2) INFORMATION FOR SEQ ID NO:44:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

CCAGGACATA GCAAGCCAAC AGGTC                                             25

(2) INFORMATION FOR SEQ ID NO:45:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

CGATATCCGT TAAGTTTGTA TCGTAATGCT CCCCTACCAA GAC                         43

(2) INFORMATION FOR SEQ ID NO:46:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

GGGATAAAAA TTAACGGTTA CATGAGAATC TTATACGGAC                             40

(2) INFORMATION FOR SEQ ID NO:47:

(i) SEQUENCE CHARACTERISTICS:

(A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

GGGCTGAAGC TTGCTGGCCG CTCATTAGAC AAGCGAATGA GGGAC                45

(2) INFORMATION FOR SEQ ID NO:48:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

AGATCTCCCG GGCTCGAGTA ATTAATTAAT TTTTATTACA CCAGAAAAGA CGGCTTGAGA    60

TC                                                                  62

(2) INFORMATION FOR SEQ ID NO:49:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

TAATTACTCG AGCCCGGGAG ATCTAATTTA ATTTAATTTA TATAACTCAT TTTTTGAATA    60

TACT                                                                64

(2) INFORMATION FOR SEQ ID NO:50:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

TATCTCGAAT TCCCGCGGCT TTAAATGGAC GGAACTCTTT TCCCC                45

(2) INFORMATION FOR SEQ ID NO:51:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

GATCTTTTGT TAACAAAAAC TAATCAGCTA TCGCGAATCG ATTCCCGGGG GATCCGGTAC    60

CC                                                                  62

(2) INFORMATION FOR SEQ ID NO:52:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

TCGAGGGTAC CGGATCCCCC GGGAATCGAT TCGCGATAGC TGATTAGTTT TTGTTAACAA     60

AA                                                                  62

(2) INFORMATION FOR SEQ ID NO:53:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

CGATATCCGT TAAGTTTGTA TCGTAATCTG CAGCCCGGGG GGG                      43

(2) INFORMATION FOR SEQ ID NO:54:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

GATCCCCCGG GCTGCAGATT ACGATACAAA CTTAACGGAT ATCG                     44

(2) INFORMATION FOR SEQ ID NO:55:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

ATCATCAAGC TTGATTCTTT ATTCTATAC                                      29

(2) INFORMATION FOR SEQ ID NO:56:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

GTCTTGGTAG GGGAGCATTA CGATACAAAC TTAACG                              36

(2) INFORMATION FOR SEQ ID NO:57:

(i) SEQUENCE CHARACTERISTICS:

(A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

ATGCTCCCCT ACCAAGAC                                                       18

(2) INFORMATION FOR SEQ ID NO:58:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

GTAATTAGTA AAATTCACCT TG                                                  22

(2) INFORMATION FOR SEQ ID NO:59:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

TGGAGATCGC GGAAGTCG                                                       18

(2) INFORMATION FOR SEQ ID NO:60:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

TGGAGATCGC GGAAGTCG                                                       18

(2) INFORMATION FOR SEQ ID NO:61:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

TGTTTATGAC CCAATCG                                                        17

(2) INFORMATION FOR SEQ ID NO:62:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

ATGCTCCCGC GGTTAACGGT TACATGAGAA TCT                                        33

(2) INFORMATION FOR SEQ ID NO:63:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:63:

CATAAATTAT TTCATTATCG CGATATCCGT TAAGTTTGTA TCGTAATGCA CAAGGGAATC           60

CCCAAAAGC                                                                  69

(2) INFORMATION FOR SEQ ID NO:64:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:64:

ATCATCGGAT CCATAAAAAT CAGTGTGATC TCACATAGGA TTTCGAAG                        48

(2) INFORMATION FOR SEQ ID NO:65:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:65:

ATCATCGAAT TCTGAATGTT AAATGTTATA CTTTG                                      35

(2) INFORMATION FOR SEQ ID NO:66:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:66:

GGGGGTACCT TTGAGAGTAC CACTTCAG                                              28

(2) INFORMATION FOR SEQ ID NO:67:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:67:

GGGTCTAGAG CGGCCGCTTA TAAAGATCTA AAATGCATAA TTTC                44

(2) INFORMATION FOR SEQ ID NO:68:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:68:

ATCATCCTGC AGGTATTCTA AACTAGGAAT AGATG                          35

(2) INFORMATION FOR SEQ ID NO:69:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:69:

GTACGTGACT AATTAGCTAT AAAAAGGATC CGGTACCCTC GAGTCTAGAA TCGATCCCGG    60

GTTTTTATGA CTAGTTAATC AC                                            82

(2) INFORMATION FOR SEQ ID NO:70:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:70:

GGCCGTGATT AACTAGTCAT AAAAACCCGG GATCGATTCT AGACTCGAGG GTACCGGATC    60

CTTTTTATAG CTAATTAGTC AC                                            82

(2) INFORMATION FOR SEQ ID NO:71:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:71:

AGCTTCCCGG GTTAATTAAT TAGTCATCAG GCAGGGCGAG AACGAGACTA TCTGCTCGTT    60

AATTAATTAG                                                          70

(2) INFORMATION FOR SEQ ID NO:72:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:72:

AGCTCTAATT AATTAACGAG CAGATAGTCT CGTTCTCGCC CTGCCTGATG ACTAATTAAT      60

TAACCCGGGA                                                             70

(2) INFORMATION FOR SEQ ID NO:73:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:73:

ATCATCGAGC TCGCGGCCGC CTATCAAAAG TCTTAATGAG TT                         42

(2) INFORMATION FOR SEQ ID NO:74:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:74:

GAATTCCTCG AGCTGCAGCC CGGGTTTTTA TAGCTAATTA GTCATTTTTT CGTAAGTAAG      60

TATTTTTATT TAA                                                         73

(2) INFORMATION FOR SEQ ID NO:75:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:75:

CCCGGGCTGC AGCTCGAGGA ATTCTTTTTA TTGATTAACT AGTCAAATGA GTATATATAA      60

TTGAAAAAGT AA                                                          72

(2) INFORMATION FOR SEQ ID NO:76:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:76:

GATGATGGTA CCTTCATAAA TACAAGTTTG ATTAAACTTA AGTTG                      45

(2) INFORMATION FOR SEQ ID NO:77:

(i) SEQUENCE CHARACTERISTICS:
            (A) LENGTH: 42 base pairs
            (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:77:

ACTGTACTCG AGTCTAGAAT GCACAAGGGA ATCCCCAAAA GC                          42

(2) INFORMATION FOR SEQ ID NO:78:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:78:

ATTCCAATGT ATCTGAGC                                                     18

(2) INFORMATION FOR SEQ ID NO:79:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:79:

ACTGTACCGC GGTCAGTGTG ATCTCACATA GGATTTCGA                              39

(2) INFORMATION FOR SEQ ID NO:80:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:80:

GGTTGAAATA GATGGTG                                                      17

(2) INFORMATION FOR SEQ ID NO:81:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:81:

ATCGTAAAGC TTAATGTCGT AATAACCCCG C                                      31

(2) INFORMATION FOR SEQ ID NO:82:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:82:

TCTACTGCAG CCGGTGTCTT CTATGGAGGT CA                                       32

(2) INFORMATION FOR SEQ ID NO:83:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:83:

TCTTCGCCCC CGTTTTCACC ATGG                                                24

(2) INFORMATION FOR SEQ ID NO:84:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:84:

ATCACGCCGC GGCTTAAAAA AATTACGCCC CGCCCT                                   36

(2) INFORMATION FOR SEQ ID NO:85:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:85:

AATTCGGTAC CAAGCTTCTT TATTCTATAC TTAAAAAGTG AAAATAAATA CAAAGGTTCT         60

TGACTCTCTT C                                                             71

(2) INFORMATION FOR SEQ ID NO:86:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:86:

CGCATCGCTG TCTGCGAGGG CCAGCTGTTG GGCTCGCGGT TGAGGACAAA CTCTTCGCGG         60

TCTTTCCAGT                                                               70

(2) INFORMATION FOR SEQ ID NO:87:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:87:

ACTCTTGGAT CGGAAACCCG TCGGCCTCCG AACGTACTCC GCCACCGAGG GACCTGAGCG      60

AGTCCGCATC      70

(2) INFORMATION FOR SEQ ID NO:88:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:88:

GACCGGATCG GAAAACCTCT CGAGAAAGGC GTCTAACCAG TCACAGTCGC AAGCCCGGGT      60

(2) INFORMATION FOR SEQ ID NO:89:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:89:

CTTTGTATTT ATTTTCACTT TTTAAGTATA GAATAAAGAA GCTTGGTACC G      51

(2) INFORMATION FOR SEQ ID NO:90:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:90:

GAAGAGTTTG TCCTCAACCG CGAGCCCAAC AGCTGGCCCT CGCAGACAGC GATGCGGAAG      60

AGAGTCAAGA AC      72

(2) INFORMATION FOR SEQ ID NO:91:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:91:

GCTCAGGTCC CTCGGTGGCG GAGTACGTTC GGAGGCCGAC GGGTTTCCGA TCCAAGAGTA      60

CTGGAAAGAC CGC      73

(2) INFORMATION FOR SEQ ID NO:92:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:92:

CTAGACCCGG GCTTGCGACT GTGACTGGTT AGACGCCTTT CTCGAGAGGT TTTCCGATCC        60

GGTCGATGCG GACTC        75

(2) INFORMATION FOR SEQ ID NO:93:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:93:

ATCGTCCTGC AGACTCTCTT CCGCATCGCT GTCTGC        36

(2) INFORMATION FOR SEQ ID NO:94:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:94:

GCTCTAGACT TGCGACTGTG ACTGGTTAG        29

(2) INFORMATION FOR SEQ ID NO:95:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:95:

CGTTTAGTGA ACCGTCTGCA        20

(2) INFORMATION FOR SEQ ID NO:96:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:96:

GACGGTTCAC TAAACGAGCT        20

(2) INFORMATION FOR SEQ ID NO:97:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:97:

GTAAAACGAC GGCCAGT                                                    17

(2) INFORMATION FOR SEQ ID NO:98:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:98:

ATCGTCCCGC GGAATTGTTG TTGTTAACTT GTT                                  33

(2) INFORMATION FOR SEQ ID NO:99:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:99:

TTTTTGGGCG TT                                                         12

(2) INFORMATION FOR SEQ ID NO:100:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:100:

ACGACCCGTA GAGGGCGTTG GACAGCAACT TGGCCTCGCG GTTGAGGACA AACTCTT        57

(2) INFORMATION FOR SEQ ID NO:101:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:101:

ACGACCCGTA GAGGGCGTTG GACAGCAACT TGGCCTCGCG GTTGAGGACA AACTCTT        57

(2) INFORMATION FOR SEQ ID NO:102:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:102:

GGGTTTTTGG GCGTTTCGCG AACCGGTGAA TTCACGCGTG TCGACCCC                  48

(2) INFORMATION FOR SEQ ID NO:103:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:103:

CCCAAAAACC CGCAAAGCGC TTGGCCACTT AAGTGCGCAC AGCTGGGG                48

(2) INFORMATION FOR SEQ ID NO:104:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:104:

ATCGTACATA TGGAGAAAAA AATCACTGGA TAT                              33

(2) INFORMATION FOR SEQ ID NO:105:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:105:

ATCGTAGATA TCCTCGAGTT ACGCCCCGCC CTGCCACTC                      39

(2) INFORMATION FOR SEQ ID NO:106:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:106:

ATCTTAACGC GTCCCTCAGC CTTCTAATGG GAC                              33

(2) INFORMATION FOR SEQ ID NO:107:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:107:

CTTGCTTGTT ATTAAAAAAA G                                          21

(2) INFORMATION FOR SEQ ID NO:108:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:108:

GATACGCGTT CCATTAGCAG ATCT                                              24

(2) INFORMATION FOR SEQ ID NO:109:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:109:

CGCGCACAAA CTGGTAGGTG C                                                 21

(2) INFORMATION FOR SEQ ID NO:110:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:110:

AGATCTGCTA ATGGAACGCG TATCAAGTTT AATAATATTA TC                          42

(2) INFORMATION FOR SEQ ID NO:111:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:111:

GATACGCGTT CCATTAGCAG ATCTGTTTTA CAGCTACCA                              39

(2) INFORMATION FOR SEQ ID NO:112:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:112:

GTACAGTTAT GTTGAAGG                                                     18

(2) INFORMATION FOR SEQ ID NO:113:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:113:

ATCAGTACGC GTATGGGCCA CACACGGAGG                                              30

(2) INFORMATION FOR SEQ ID NO:114:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:114:

ATCAGTAGAT CTGTTATTAG TGATATCAAA                                              30

(2) INFORMATION FOR SEQ ID NO:115:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:115:

ATCGTCATTG CCACGCGTAT GGCAGAAGGA TTTGCAGCCA AT                                42

(2) INFORMATION FOR SEQ ID NO:116:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:116:

ATCGTCATTG CCACGCGTAA CCAGGGACAA TACTTGTTCA TC                                42

(2) INFORMATION FOR SEQ ID NO:117:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:117:

ATCAGTCACG GTGTGTAAAT GGGCCACACA CGGAGG                                       36

(2) INFORMATION FOR SEQ ID NO:118:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

-continued

```
    (xi) SEQUENCE DESCRIPTION: SEQ ID NO:118:

ATCAGTACGC GTGTTATTAG TGATATCAAA                                              30

(2) INFORMATION FOR SEQ ID NO:119:

(i) SEQUENCE CHARACTERISTICS:
          (A) LENGTH: 39 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:119:

ATCCGTACGC GTTAGAGGGC AAAGCCCGTG CAGCAGCGC                                    39

(2) INFORMATION FOR SEQ ID NO:120:

(i) SEQUENCE CHARACTERISTICS:
          (A) LENGTH: 39 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:120:

ATCCGTCACG GTGTGTAGAT GGGTTGTTTT GTGGAGAAT                                    39
```

TRUNCATED TRANSCRIPTIONALLY ACTIVE CYTOMEGALOVIRUS PROMOTERS

FIELD OF THE INVENTION

This invention relates to recombinant adenoviruses, methods of making them, uses for them (including as a vector for replicating DNA), expression products from them, and uses for the expression products. This invention also relates to promoters and expression cassettes, especially truncated promoters and expression cassettes containing the promoters.

More particularly, this invention relates to recombinant canine adenoviruses (CAV) and methods of making them, uses for them (including as a vector for replicating DNA), expression products from them, and uses for the expression products. Recombinant CAV2 viruses, especially those wherein the exogenous DNA has been inserted into the CAV2 E3 and/or into the right end of the genome between the right ITR and the E4 transcription unit, and methods of making them, uses for them (including in immunological, immunogenic, vaccine or therapeutic compositions, or as a vector for cloning, replicating or expressing DNA and methods of using the compositions or vector), expression products from them, and uses for the expression products are preferred.

However, the invention broadly relates to a CAV synthetically modified to contain therein exogenous DNA, wherein a non-essential region of the CAV genome or a portion thereof has been deleted from the CAV. The CAV is preferably packaged as an infectious CAV with respect to cells in which CAV naturally replicates. The non-essential region of the CAV genome or portion thereof deleted from the CAV is preferably the E3 region or a portion thereof. The exogenous DNA is preferably present in the E3 region, the E1 region, the E4 region, or the region located between the right ITR and the E4 region. And, the CAV can be a CAV2.

The recombinant CAV can be a vector for expression or cloning of heterologous DNA. The heterologous DNA can encode any desired expression product. Preferred expression products include: an epitope of interest, a biological response modulator, a growth factor, a recognition sequence, a therapeutic gene, or a fusion protein. Thus, the heterologous DNA can encode any or all of these products. Accordingly, the heterologous DNA can be a transgene.

The epitope of interest can be antigen or immunogen or epitope thereof of a human or veterinary pathogen or toxin. Therefore, the invention further relates to immunological, antigenic or vaccine compositions, containing the expression products. Further, since the CAV vector, in certain instances, can be administered directly to a suitable host, the invention relates to compositions containing the CAV vector. The compositions can be immunological, antigenic, vaccine, or therapeutic (e.g., compositions for stimulating an immunological response—local or systemic—including, but not limited to a protective response, or for gene therapy). The invention therefore futher relates to methods of inducing an immunological response, or of transferring genetic information (e.g., gene therapy) comprising administering the composition to a suitable vertebrate host (animal or human).

Additionally, since the expression product can be isolated from the CAV vector in vitro or from cells infected or transfected by the CAV vector in vitro, the invention relates to methods for expressing a product, e.g., comprising inserting the exogenous DNA into a CAV as a vector to obtain a recombinant CAV, e.g., by recombination or by cleaving and ligating and obtaining recombinant CAV therefrom, followed by infection or transfection of suitable cells in vitro with the recombinant CAV, and optionally extracting, purifying or isolating the expression product from the cells.

As the expression products can provide an antigenic, immunological or protective (vaccine) response, the invention further relates to products therefrom; namely, antibodies and uses thereof. More in particular, the expression products can elicit antibodies. The antibodies can be formed into monoclonal antibodies; and, the antibodies or expression products can be used in kits, assays, tests, and the like involving binding, so that the invention relates to these uses too.

Additionally, since the recombinants of the invention can be used to replicate DNA, the invention relates to recombinant CAV as a vector and methods for replicating DNA by infecting cells with the recombinant and harvesting DNA therefrom. The resultant DNA can be used as probes or primers or for amplification.

The invention still further relates to promoters and expression cassettes containing the promoters, for use in recombinant viruses or plasmids.

In this aspect, the invention specifically relates to a truncated transcriptionally active promoter for a recombinant virus or plasmid which comprises a region transactivated with a transactivating protein provided by the virus or a system into which the plasmid is inserted and the minimal promoter region of the promoter. The invention also relates to an expression cassette comprising the promoter, and to viruses or plasmids containing the promoter or expression cassette. The expression cassette can include a functional truncated polyadenylation signal.

Several publications are cited in the following text, with full citation of each set forth in the section headed References or with full citation occurring where cited. The publications cited throughout the text and the documents cited in those publications are hereby incorporated herein by reference.

BACKGROUND OP THE INVENTION

The patent and scientific literature includes various viral vector systems, uses therefor, and exogenous DNA for expression of protein by such systems, as well as uses for such proteins and uses for products from such proteins.

For instance, recombinant poxvirus (e.g., vaccinia, avipox virus) and exogenous DNA for expression in viral vector systems can be found in U.S. Pat. Nos. 5,174,993 and 5,505,941 (e.g., recombinant avipox virus, vaccinia virus; rabies glycoprotein (G), gene, turkey influenza hemagglutinin gene, gp51,30 envelope gene of bovine leukemia virus, Newcastle Disease Virus (NDV) antigen, FelV envelope gene, RAV-1 env gene, NP (nudeoprotein gene of Chicken/Pennsylvania/1/83 influenza virus), matrix and preplomer gene of infectious bronchitis virus; HSV gD; entomopox promoter, inter alia), U.S. Pat. No. 5,338,683, e.g., recombinant vaccinia virus, avipox virus; DNA encoding Herpesvirus glycoproteins, inter alia; U.S. Pat. No. 5,494,807 (e.g., recombinant vaccinia, avipox; exogenous DNA encoding antigens from rabies, Hepatitis B, JEV, YF, Dengue, measles, pseudorabies, Epstein-Barr, HSV, HIV, SIV, EHV, BHV, HCMV, canine parvovirus, equine influenza, FeLV, FHV, Hantaan, C. tetani, avian influenza, mumps, NDV, inter alia); U.S. Pat. No. 5,503,834 (e.g., recombinant vaccinia, avipox, Morbillivirus [e.g., measles F, hemagglutinin, inter alia]); U.S. Pat. No. 4,722,848 (e.g., recombinant vaccinia virus; HSV tk, glycoproteins [e.g., gB, gD], influenza HA, Hepatitis B [e.g., HBsAg], inter alia); U.K. Patent GB 2 269 820 B and U.S. Patent No. 5,514,375 (recombinant poxvirus; flavivirus structural proteins); WO 92/22641 (e.g., recombinant poxvirus; immunodeficiency virus, inter alia); WO 93/03145 (e.g., recombinant poxvirus; IBDV, inter alia); WO 94/16716 and U.S. application Ser. No. 08/184,009, filed Jan. 19, 1994 (e.g., recombinant poxvirus; cytokine and/or tumor associated antigens, inter alia); and PCT/US94/06652 (Plasmodium antigens such as from each stage of the Plasmodium life cycle).

Baculovirus expression systems, exogenous DNA for expression therein, and purification of recombinant proteins therefrom can be found in Richardson, C. D. (Editor), *Methods in Molecular Biology* 39, "Baculovirus Expression Protocols" (1995 Humana Press Inc.) (see, e.g., Ch.18 for influenza HA expression, Ch.19 for recombinant protein purification techniques), Smith et al., "Production of Huma Beta Interferon in Insect Cells Infected with a Baculovirus Expression Vector," Molecular and Cellular Biology, Dec., 1983, Vol. 3, No. 12, p. 2156–2165; Pennock et al., "Strong and Regulated Expression of *Escherichia coli* B-Galactosidase in Infect Cells with a Baculovirus vector," Molecular and Cellular Biology Mar. 1984, Vol. 4, No. 3, p. 399–406; EPA 0 370 573 (Skin test and test kit for AIDS, discussing baculovirus expression systems containing portion of HIV-1 env gene, and citing U.S. application Ser. No. 920,197, filed Oct. 16, 1986 and EP Patent publication No. 265785).

U.S. Pat. No. 4,769,331 relates to herpesvirus as a vector.

There are also poliovirus and adenovirus vector systems (see. e.g., Kitson et al., J. Virol. 65, 3068–3075, 1991; Grunhaus et al., 1992, "Adenovirus as cloning vectors," Seminars in Virology (Vol. 3) p. 237–52, 1993; Ballay et al. EMBO Journal, vol. 4, p. 3861–65; Graham, Tibtech 8, 85–87, April, 1990; Prevec et al., J. Gen Virol. 70, 429–434).

PCT WO91/11525 relates to CAV2 modified to contain a promoter-gene sequence within the region from the SmaI site close to the end of the inverted terminal repeat region up to the promoter for the early region 4 (E4).

CAV, and particularly CAV2, has numerous problems. Several of these problems are discussed below. A significant problem is that the CAV genome can only accept a limited amount of exogenous DNA. That is, only a limited amount of exogenous DNA can be inserted into the CAV genome. Thus, CAV is "insert size limited" and therefore presents a significant problem which must be addressed if CAV is to be a useful vector for a constellation of cloning and expression applications.

The efficient transmission of many viral infections via the oronasal route has provided the impetus for assessing the efficacy of viral vector-based vaccine candidates via the same route. However, since the spread of most live replicating vaccines within the vaccinee and their spread to or contacts with the general environment are well documented (for examples see Schwartz et al., 1974, Mueller et al., 1989, Oualikene et al., 1994), the choice of an adequate viral vector is not obvious.

To address legitimate safety concerns, vector selection preferably involves consideration of characterized live attenuated vaccines as the apparent safety thereof is established. For vaccination of humans, various vectors based on replicating live attenuated viruses are under consideration. To date, there are documented approaches based on human adenoviruses (HAVs) serotype 4 and 7 (Lubeck et al., 1989, Chanda et al., 1990, Chengalvala et al., 1991, 1994, Hsu et al., 1994 ), influenza viruses (for a review Garcia-Sastre and Palese, 1995) and poliovirus and related viruses (for a review Girard et al., 1995).

In the field of veterinary medicine, several vectors based on replicating live attenuated viruses are currently being analyzed with the objective to apply those recombinant vectors as vaccines either parenterally or via the natural route of infection, thereby stimulating local protection. Among the best characterized at this point are members of the poxviridae family [e.g., fowlpox-based vectors (Edbauer et al. 1990, Taylor et al., 1995 and ref. therein)], herpesviridae family [e.g., pseudorabies virus-based vectors (Sedegah et al. 1992, Mettenleiter et al. 1994, Hooft van Iddekinge et al., 1996 and ref. therein), turkey herpes virus-based vectors (Ross et al. 1993, Darteil et al. 1995 and ref. therein), feline herpes virus-based vectors (Cole et al., 1990, Wardley et al., 1992, Willense et al., 1996), infectious laryngotracheitis virus-based vectors (Guo et al., 1994), bovine herpes virus-based vectors (Kit et al. 1991)] and to a lesser extent members of the Adenoviridae family [bovine adenovirus 3-based vectors (Mittal et al., 1995)].

The canine species provides an appropriate model for oronasal immunizations. As such, the canine adenovirus serotype 2 (CAV2) for which attenuated vaccinal strains exist that can be safely administered either parenterally or via oronasal route, provides a viable immunization vehicle for canine vaccination. Canine distemper virus (CDV) infection of dogs provides a good example of a respiratory infection in this target species. Further, a relatively direct experimental CDV challenge system is accessible and allows a direct comparison between CAV2 based-vaccine candidates and previously developed classical CDV vaccines.

CAV2 was first isolated from an outbreak of upper respiratory tract infection in dogs by Ditchfield et al. (1962). Since then, the virus has been isolated from the respiratory tract of dogs with respiratory diseases both in the US and in Europe (Binn et al. 1967, Appel and Percy, 1970, Assaf et al. 1978, Danskin 1973). Experimental studies have resulted in mild respiratory disease following aerosol inoculation of CAV2 (Swango et al. 1970, Appel , 1970). Several CAV2-based vaccines have been developed and extensively used worldwide for the vaccination of puppies and adult dogs. Immunization with CAV2 has even been shown to protect against an experimental challenge exposure with a serologically related strain of CAV1, which is fatal to non-vaccinated dogs (Fairchild and Cohen, 1969, Appel et al. 1973, Bass et al. 1980). The apparent safety of CAV2 as a vaccine has been well evidenced by the lack of vaccine-induced and vaccine-associated complications in dogs and other animal species including man during its 30 years of utility. Further, results from field serological surveys indicate that many wild animals (foxes, raccoons, skunks and mongooses) are asymptomatically exposed to CAV2 or to an antigenically related virus infection (Summer et al., 1988). A vaccinal strain of canine adenovirus serotype 2 (CAV2), therefore, provides a unique example of a safe replication-competent, host-restricted virus which can be considered for the derivation of effective vector-based vaccine candidate for vaccination, especially of dogs.

HAVs have been shown to be valuable mammalian cell expression vectors (for a review see Graham et al. 1988) and are currently being evaluated both as recombinant viral vaccine candidates (for reviews see Randrianarison-Jewtoukoff and Perricaudet 1995, Imler 1995) and as vectors for gene therapy (for reviews see Perricaudet and Perricaudet 1995). There are two major groups of HAVs, and a third, less explored, group of recombinant HAVs.

The first group of these adenovirus vectors corresponds to replication-incompetent recombinant adenoviruses which are based on viruses deleted of their E1 region. The E1 region encodes proteins which are essential for virus replication in tissue culture. It has, however, been demonstrated that replication-incompetent recombinant adenoviruses deleted of their E1 region can be propagated in the 293 cell line (Graham et al., 1977) which constitutively expresses the E1 region (Haj-Ahmad et al., 1986).

Deletion of the E1 region not only increases the amount of foreign DNA which can be inserted into HAVs, but also limits their replication in human cells and thus considerably improves the safety characteristics of the corresponding recombinant HAVs in humans. Most of the HAV-based vaccine candidates against veterinary and humans pathogens are currently based on E1-deleted vectors. Despite their limited replicative capacity, protection data in challenge experiments have been described (Prevec et al., 1989, McDermott et al., 1989, Lubeck et al., 1989, Eloit et al., 1990, Ragot et al., 1993, Wesseling et al., 1993, Both et al., 1993, Gallichan et al., 1993, Hsu et al., 1994, Breker-Klasser et al., 1995). The property of inducing a protective immune response even in the absence of vector replication is shared by other host restricted viral vectors, the most promising of which being the canarypox virus-based vector ALVAC (Taylor et al., 1991, see Perkus et al., 1995 for a review).

When the goal is a replication competent adenovirus vector, the use of the E1 region as an insertion site is thus not desirable; and, the E1 region therefore has heretofore had deficiencies and presented problems. These deficiencies and problems are compounded when a replication competent adenovirus displaying safety characteristics with respect to humans is desired. In particular, while the E1 region deletion in HAVs may limit replication in human cells and improve safety characteristics with respect to humans, as discussed below, the possibility of recombination between E1 transformed cell lines and E1 deleted recombinant adenoviruses has been documented and thus the safety profile of E1 transformed cell lines appears questionable, thereby rendering any benefit from using E1 region deleted adenoviruses potentially illusory and exascerbating deficiencies and problems heretofore in the use of E1 region deleted adenoviruses (since propagation of E1 region deleted adenoviruses is in cells which constitutively express the E1 region).

The second group of adenovirus vectors corresponds to recombinant adenoviruses which are replication-competent in human cells but replication-incompetent in most non-human animal cells. Those viruses are characterized by a substitution of part of the E3 region with foreign gene expression cassettes. The E3 region has been shown to be non-essential both in vitro and in vivo for infectious virus formation (Kelly and Lewis 1973, Kapoor et al., 1981, Morin et al., 1987, Lubeck et al., 1989). Numerous recombinant HAVs have therefore been generated by replacement of part of the E3 region (Morin et al., 1987, Chengalvala et al., 1991, 1994, Prevec et al., 1989, Johnson et al., 1988, Lubeck et al., 1989, Dewar et al., 1989, Natuk et al., 1993, Hsu et al., 1994).

However, since proteins encoded by the E3 region have been shown to alter various aspects of the host immune responses (for a review see Wold and Gooding 1991), E3 deletion may have some impact on the pathogenic profile of corresponding recombinant viruses. Indeed, it has been demonstrated in a cotton rat model that deletion of the E3 region from HAV serotype 5 increases virus pulmonary pathogenicity (Ginsberg et al., 1989). However, it has also been demonstrated that a recombinant bovine Ad3, partially deleted within its E3 region, produces lesions in cotton rats similar to those observed with the parental wt bovine Ad3, therefore suggesting that safety of bovine Ad3-based vectors may be sufficient for the derivation of live recombinant virus vaccines for cattle (Mittal et al., 1996).

These results also show that the impact of deletions within the E3 region of any specific adenovirus should be considered on a case-by-case approach.

The CAV2 E3 region has been identified and characterized previously (Linne, 1992). However, based on the available published data (Linne 1992), the precise definition of an insertion site in the CAV2 E3 region is not obvious. DNA sequence analysis revealed that the organization of the CAV2 E3 region differs significantly from that described for HAVs. The human adenovirus E3 region corresponds to a stretch of at least 3 kbp containing at least 8 open reading frames (orf) whereas the CAV2 E3 region is only 1.5 kbp long and contains only 3 orfs. None of these orfs have a significant level of homology with HAV E3 orfs. From such preliminary comparative analyses, it appears reasonable to speculate that human and canine adenoviruses genomes have evolved differently.

The definition of an insertion site within the CAV2 E3 region is further complicated by the complex splicing and polyadenylation pattern which characterizes the adenovirus family (for a review Imperiale et al., 1995). RNA splicing donor and aceptor sites localized within the E3 region may be important for the maturation of several essential mRNAs even though their coding sequences are localized outside of the E3 region.

Further, since the E3 region is located within a genome region of high transcriptional activity (for a review Sharp et al., 1984), the insertion of foreign DNA at this site has a potential detrimental impact on the biology of the recombinant virus. Additionally, the E3 region is located downstream of the major late promoter (MLP), where interference between transcription of recombinant gene and transcription initiated at the MLP has been demonstrated (Zu et al., 1995).

Problems in the art to be addressed therefore include: minimizing phenotypic alterations of the recombinant virus, and the definition of an insertion site in a less transcriptionally active region. And, in general, it can be said that the E3 region presents problems in the art which should be addressed.

The less explored third group of recombinant HAVs is based on the insertion of recombinant DNA between the right inverted terminal repeat (ITR) and the E4 promoter. The ITRs contain sequences which are essential for viral DNA replication and efficient packaging of the viral genomic DNA. While a region between the right inverted terminal repeat (ITR) and the E4 promoter may accommodate exogenous DNA sequences (Saito et al., 1985, Chanda et al., 1990), adenoviruses-based vectors have severe limitations in the amount of foreign DNA they can carry, as the packaging capacity of recombinant hAd5 is limited to a genome of approximatively 105% of the wild-type genome (Bett et al. 1993); thus presenting a problem in the art.

While the region between the right ITR and the E4 region may represent an additional insertion site candidate for the generation of CAV2 recombinant viruses, and PCT WO 91/11525 may relate to a SmaI site close to the leftward extremity of the ITR as a potential insertion site. Contrary to the teachings of WO91/11525, there appears to be an upper limit for insertion at this site as Applicant attempted insertions at this site and was able to insert a 400 bp DNA fragment, but larger insertions such as a fragment approximately 1 kbp repeatedly failed to be introduced into the site. Hence, a problem in the art is the utility of this site.

Therefore, the E4 promoter region has heretofore had deficiencies and presented problems.

Initial characterization of the CAV2 genome at the molecular level has been described in the literature. Restriction analysis of several strains of both CAV2 and CAV1 (Jouvenne et al., 1987, Macartney et al., 1988, Spibey and Cavanagh 1989) and sequence analysis of the corresponding E1, E3 and ITRs regions have been reported (Cavanagh et al., 1991, Linne 1992). Although the overall genomic organization of canine adenoviruses is similar to those described for other Adenoviridae family members, the precise organisation of CAV2 genomic E3 region is unique.

Accordingly, one cannot merely extrapolate from one member to another member of the Adenoviridae family, thereby providing yet another problem in the art.

Further still, when addressing any or all of the aforementioned deficiencies or problems, it would be preferred to avoid any dependence on an endogenous promoter like the E3 or the MLP promoters. However, the pattern of expression of the recombinant gene may be a critical parameter in the overall expression and ergo in the efficacy of the recombinant in a vaccine or immunological composition (Darteil et al., 1995, Xu et al., 1995, Hooft van Iddekinge et al., 1996).

Several cellular and viral promoters have been involved in the derivation of recombinant HAVs. Among the best characterized are b-actin, SV40 early, SV40 late, hAD MLP, and hCMV-IE (Zu et al., 1995). The hCMV-IE promoter may have promise as an upstream regulatory region, since it is associated with the highest level and the longest persistence of recombinant protein expression in tissue culture. This promoter also appears to operate in almost every cell line tested thus far. A potential for cell type independent promoter activity can be regarded as a clear advantage.

It has been demonstrated that the hCMV-IE promoter can be transactivated by HAV infection (Gorman et al., 1989). The large size of this promoter (approximately 850 bp) is a problem with respect to the size limitations of recombinant CAV vector. Thus, one cannot merely extrapolate from past successes with this promoter to a recombinant CAV vector.

Adenoviruses are known to strongly repress the synthesis of cellular proteins after the onset of viral DNA replication (for a review Zhang and Schneider, 1993). Thus, replication-competent recombinant adenoviruses have heretofore had a potential for a strong limitation of the recombinant protein expression after the onset of DNA replication.

Similarly, Saito et al. (1985) demonstrated that a recombinant human adenovirus serotype 5 can produce high amounts of recombinant mRNA but that almost no recombinant protein is obtained.

Late adenovirus mRNAs are characterized by the presence of a tripartite leader (TPL) sequence in their 5' untranslated region (5'UTR). The presence of the TPL can be an important component of the translatability of late adenovirus mRNAs. Further, it has been demonstrated that in an hAd5 background, the presence of the TPL is a feature of the translational control of a recombinant SV40 T antigen expressed from adenovirus late promoter (Thummel et al. 1983).

Another important problem to address in the design of an expression cassette is the size of the polyadenylation signal.

Even still further, the problems in the art include establishing conditions to transfect CAV2 DNA into monolayers. The infectivity of purified naked adenovirus DNA is low. Using a calcium phosphate-based procedure, Graham and Van der Berg (1973) report a yield of 1 pfu/mg of purified DNA. This is not an efficient process for isolating recombinant viruses. Several approaches have been proposed to attempt to address this problem; but, none heretofore have fully addressed the problem, and particularly without raising additional issues such as safety.

For instance, DNA protein complexes have been purified and are reported to have an increased infectivity ($5 \times 10^3$ pfu/mg) (Sharp et al., 1976) over naked DNA. Similarly, covalently closed circles of adenovirus DNA have also been shown to be infectious (Graham, 1984).

A widely used procedure to derive recombinant HAVs is based on the utilization of the 293 cell line which has been transformed with the HAV E1 region (Graham et al., 1977). Previously, it has been reported that the derivation of bovine and canine adenovirus recombinants was dependent on the utilization of cell lines transformed with the corresponding adenovirus E1 region (PCT WO 91/11525, Mittal et al., 1995a). However, since the genes encoded by the E1 region of some adenoviruses have been shown to contribute to the transformation of rodent cells (reviewed by Grand, 1987), the safety profile of E1 transformed cell line appear questionable. The presence of potent transactivators within the adenovirus E1 region (for a review Nevins, 1993) is also well established and further extends safety concerns which can be raised regarding E1 transformed cell lines.

Thus, transfection conditions independent of use of an E1 transformed cell line, especially with good yields, would be a significant advance in the art.

Accordingly, it is believed that a recombinant CAV, preferably a recombinant CAV2, having exogenous DNA inserted therein and a non-essential region or portion thereof deleted therefrom, especially such a CAV which is packaged as an infectious CAV with respect to cells in which CAV naturally replicates, or a CAV containing exogenous DNA within the E3 and/or the right end of the genome between the right ITR and the E4 transcription unit, and methods for making such recombinants, and uses for such recombinants, as described herein (above and below), has not been taught or suggested. Further, it is believed that a truncated transcriptionally active promoter for a recombinant virus or plasmid which comprises a region transactivated with a transactivating protein provided by the virus or a system into which the plasmid is inserted and the minimal promoter region of the promoter, an expression cassette comprising the promoter, and viruses or plasmids containing the promoter or expression cassette, have not been heretofore described or suggested. And, such a recombinant CAV and methods of making and using such a recombinant CAV, and such a promoter, expression cassette and viruses and plasmids containing the promoter or expression cassette present an advancement over prior recombinants, especially since as to humans CAV is a non-replicating vector and the promoter and expression cassette address insert size limits of recombinant viruses.

OBJECTS AND SUMMARY OF THE INVENTION

It is an object of the invention to provide a recombinant adenovirus, preferably a recombinant canine adenovirus (CAV), such as a recombinant canine adenovirus-2 (CAV2).

It is a further object of the invention to provide such a recombinant which contains exogenous DNA, preferably in a non-essential region, and which has had a non-essential region of the CAV genome, or a portion thereof, deleted therefrom; and, preferably to provide such a recombinant which is packaged as an infectious CAV with respect to cells in which CAV naturally replicates.

It is also an object of the invention to provide such a recombinant CAV containing exogenous DNA wherein the exogenous DNA is inserted into the E3 or both the E3 and the region located between the right ITR and the E4 transcription unit.

It is another object of the invention to provide a transcritionally active truncated promoter, an expression cassette containing the promoter, and viruses and plasmids containing the promoter or the expression cassette; including to provide such an expression cassette containing a truncated polyadenylation signal.

Further objects of the invention include any or all of: to provide expression products from such recombinants, methods for expressing products from such recombinants, compositions containing the recombinants or the expression products, methods for using the expression products, methods for using the compositions, DNA from the recombinants, and methods for replicating DNA from the recombinants.

Another object of the invention is an adenovirus-based, e.g., CAV-based, preferably CAV2-based, vector, or compositions containing the vector, or methods for making or using the vector with consideration of any, any combination, or all, of the earlier-discussed deficiencies and/or problems in the art.

Accordingly, the invention surprisingly provides a CAV synthetically modified to contain therein exogenous DNA, wherein a non-essential region of the CAV genome or a portion thereof has been deleted from the CAV. The CAV is preferably packaged as an infectious CAV with respect to cells in which CAV naturally replicates. Any non-essential region or portion thereof can be deleted from the CAV genome, and the viability and stability of the recombinant CAV resulting from the deletion can be used to ascertain whether a deleted region or portion thereof is indeed non-essential. The non-essential region of the CAV genome or portion thereof deleted from the CAV is preferably the E3 region or a portion thereof. The exogenous DNA is present in any non-essential region (and viability and stability of the recombinant CAV resulting from the insertion of exogenous DNA can be used to ascertain whether a region into which exogenous DNA is inserted is non-essential). The E3 region, the E1 region, the E4 region, or a region located between the right ITR and the E4 region, are presently preferred as non-essential regions for insertion of exogenous DNA into the CAV genome.

Additionally, the invention surprisingly provides a recombinant CAV comprising heterologous DNA in a non-essential region of the CAV genome, wherein the heterologous DNA is in the E3 or both the E3 and the region located between the right ITR and the E4 transcription unit.

The CAV of these embodiments is preferably a CAV2.

The invention further provides a vector for cloning or expression of heterologous DNA comprising the recombinant CAV.

The heterologous DNA encodes an expression product comprising: an epitope of interest, a biological response modulator, a growth factor, a recognition sequence, a therapeutic gene, or a fusion protein.

An epitope of interest is an antigen or immunogen or immunologically active fragment thereof from a pathogen or toxin of veterinary or human interest.

An epitope of interest can be an antigen of a veterinary pathogen or toxin, or from an antigen of a veterinary pathogen or toxin, or another antigen or toxin which elicits a response with respect to the pathogen, of from another antigen or toxin which elicits a response with respect to the pathogen, such as, for instance: a Morbillivirus antigen, e.g., a canine distemper virus or measles or rinderpest antigen such a HA or F; a rabies glycoprotein, e.g., rabies glycoprotein G; an avian influenza antigen, e.g., turkey influenza HA, Chicken/Pennsylvania/1/83 influenza antigen such a nudeoprotein (NP); a bovine leukemia virus antigen, e.g., gp51,30 envelope; a Newcastle Disease Virus (NDV) antigen, e.g., HN or F; a feline leukemia virus antigen (FeLV), e.g., FeLV envelope protein; RAV-1 env; matrix and/or preplomer of infectious bronchitis virus; a Herpesvirus glycoprotein, e.g., a glycoprotein from feline herpesvirus, equine herpesvirus, bovine herpesvirus, pseudorabies virus, canine herpesvirus, or cytomegalovirus; a flavivirus antigen, e.g., a Japanese encephalitis virus (JEV) antigen; an immunodeficiency virus antigen, e.g., a feline immunodeficiency virus (FIV) antigen or a simian immunodeficiency virus (SIV) antigen; a parvovirus antigen, e.g., canine parvovirus; an equine influenza antigen; a Marek's Disease virus antigen; an poxvirus antigen, e.g., an ectromelia antigen, a canarypox virus antigen or a fowlpox virus antigen; or an infectious bursal disease virus antigen, e.g., VP2, VP3, VP4.

An epitope of interest can be an antigen of a human pathogen or toxin, or from an antigen of a human pathogen or toxin, or another antigen or toxin which elicits a response with respect to the pathogen, or from another antigen or toxin which elicits a response with respect to the pathogen, such as, for instance: a Morbillivirus antigen, e.g., a measles virus antigen such as HA or F; a rabies glycoprotein, e.g., rabies virus glycoprotein G; an influenza antigen, e.g., influenza virus HA or N; a Herpesvirus antigen, e.g., a glycoprotein of a herpes simplex virus (HSV), a human cytomegalovirus (HCMV), Epstein-Barr; a flavivirus antigen, a JEV, Yellow Fever virus or Dengue virus antigen; a Hepatitis virus antigen, e.g., HBsAg; an immunodeficiency virus antigen, e.g., an HIV antigen such as gp120, gp160; a Hantaan virus antigen; a *C. tetani* antigen; a mumps antigen; a pneumococcal antigen, e.g., PspA; a Borrelia antigen, e.g., OspA, OspB, OspC of Borrelia associated with Lyme disease such as *Borrelia burgdoreferi, Borrelia atzelli* and *Borrelia garinii;* a chicken pox (varicella zoster) antigen; or a Plasmodium antigen.

Of course, the foregoing lists are intended as exemplary, as the epitope of interest can be an antigen of any veterinary or human pathogen or from any antigen of any veterinary or human pathogen.

Since th e heterologous DNA can be a growth factor or therapeutic gene, the recombinant CAV can be used in gene therapy. Gene therapy involves transferring genetic information; and, with respect to gene therapy and immunotherapy, reference is made to U.S. Pat. No. 5,252, 479, which is incorporated herein by reference, together with the documents cited in it and on its face, and to WO 94/16716 and U.S. application Ser. No. 08/184,009, filed January 19, 1994, each of which is also incorporated herein by reference, together with the documents cited therein. The growth factor or therapeutic gene, for example, can encode a disease-fighting protein, a molecule for treating cancer, a tumor suppressor, a cytokine, a tumor associated antigen, or interferon; and, the growth factor or therapeutic gene can, for example, be selected from the group consisting of a gene encoding alpha-globin, beta-globin, gamma-globin, granulocyte macrophage-colony stimulating factor, tumor necrosis factor, an interleukin, macrophage colony stimulating factor, granulocyte colony stimulating factor, erythropoietin, mast cell growth factor, tumor suppressor p53, retinoblastoma, interferon, melanoma associated antigen or B7.

The invention still further provides an immunogenic, immunological or vaccine composition containing the recombinant CAV virus or vector, and a pharmaceutically acceptable carrier or diluent. An immunological composition containing the recombinant CAV virus or vector (or an expression product thereof) elicits an immunological response—local or systemic. The response can, but need not be, protective. An immunogenic composition containing the recombinant CAV virus or vector (or an expression product thereof) likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms can be protective compositions).

The invention therefore also provides a method of inducing an immunological response in a host vertebrate comprising administering to the host an immunogenic, immunological or vaccine composition comprising the recombinant CAV virus or vector and a pharmaceutically acceptable carrier or diluent. For purposes of this specification, "animal" includes all vertebrate species, except humans; and "vertebrate" includes all vertebrates, including animals (as "animal" is used herein) and humans. And, of course, a subset of "animal" is "mammal", which for purposes of this specification includes all mammals, except humans.

For human administration, recombinant CAV, especially CAV2, provides the advantage of expression without productive replication. This thus provides the ability to use recombinants of the invention in immunocompromised individuals; and, provides a level of safety to workers in contact with recombinants of the invention. Therefore, the invention comprehends methods for amplifying or expressing a protein by administering or inoculating a host with a recombinant CAV virus or vector, e.g., CAV2, whereby the host is not a canine or not a natural host of the recombinant virus or vector, and there is expression without productive replication.

Furthermore, since CAV, and especially CAV2, is used as vaccinial strains in dogs, the present invention provides a means for introducing additional epitope(s) of interest of antigen(s) of a canine pathogen(s) or toxin(s) into the vaccinial CAV, e.g., CAV2, strains for a recombinant CAV expressing those additional epitope(s) of interest and thereby providing a means to elicit in vivo responses to those epitope(s) of interest and canine adenovirus by inoculating a dog or pup with the vaccinial recombinant CAV. The additional epitope(s) of interest can be an antigen of a canine pathogen (other than adenovirus) or toxin, from an antigen of a canine pathogen (other than adenovirus) or toxin, another antigen which elicits a response in dogs or pups to the canine pathogen (other than adenovirus) or toxin, or from another antigen which elicits a response in dogs or pups to the canine pathogen (other than adenovirus) or toxin (an example of the latter two epitopes of interest are measles HA and F and epitopes thereon which elicit a protective response against canine distemper virus in dogs or pups; see U.S. Pat. No. 5,503,834).

Accordingly the present invention provides that the recombinant vaccinial CAV can contain heterologous DNA encoding an epitope of interest from any antigen of a canine pathogen or toxin, for instance: rabies, canine herpesvirus, canine distemper virus, canine parvovirus and the like. In this regard, reference is made to copending U.S. applications Ser. No. 08/413,118, filed Mar. 29, 1995 (canine herpesvirus DNA), Ser. No. 08/224,657, filed Apr. 6, 1994 (canine distemper), Ser. No. 08/416,646, filed Apr. 5, 1995 (canine distemper), and Ser. No. 08/486,969, filed Jun. 7, 1995 (rabies combination compositions) and U.S. Pat. No. 5,529,780 (canine herpesvirus DNA), all incorporated herein by reference, together with the documents cited therein. Thus, the invention envisions CAV recombinants containing exogenous DNA coding for more than one protein, e.g., coding for two or more epitopes such as antigens of canine pathogens. The invention also envisions compositions containing CAV recombinants in combination with other antigens.

The invention even further provides a therapeutic composition containing the recombinant CAV virus or vector and a pharmaceutically acceptable carrier or diluent. The therapeutic composition is useful in the gene therapy and immunotherapy embodiments of the invention, e.g., in a method for transferring genetic information to an animal or human in need of such comprising administering to the host the composition; and, the invention accordingly includes methods for transferring genetic information.

In yet another embodiment, the invention provides a method of expressing a protein or gene product or an expression product which comprises infecting or transfecting a cell in vitro with a recombinant CAV virus or vector of the invention and optionally extracting, purifying or isolating the protein, gene product or expression product or DNA from the cell. And, the invention provides a method for cloning or replicating a heterologous DNA sequence comprising infecting or transfecting a cell in vitro or in vivo with a recombinant CAV virus or vector of the invention and optionallly extracting, purifying or isolating the DNA from the cell or progeny virus The invention in another aspect provides a method for preparing the recombinant CAV virus or vector of the invention comprising inserting the exogenous DNA into a non-essential region of the CAV genome.

The method can further comprise deleting a non-essential region from the CAV genome, preferably prior to inserting the eogenous DNA.

The method can comprise in vivo recombination (even though CAV DNA is infectious). Thus, the method can comprise transfecting a cell with CAV DNA in a cell-compatible medium in the presence of donor DNA comprising the exogenous DNA flanked by DNA sequences homologous with portions of the CAV genome, whereby the exogenous DNA is introduced into the genome of the CAV, and optionally then recovering CAV modified by the in vivo recombination.

The method can also comprise cleaving CAV DNA to obtain cleaved CAV DNA, ligating the exogenous DNA to the cleaved CAV DNA to obtain hybrid CAV-exogenous DNA, tranfecting a cell with the hybrid CAV-exogenous DNA, and optionally then recovering CAV modified by the presence of the exogenous DNA.

Since in vivo recombination is comprehended, the invention accordingly also provides a plasmid comprising donor DNA not naturally occurring in CAV encoding a polypeptide foreign to CAV, the donor DNA is within a segment of CAV DNA which would otherwise be co-linear with a non-essential region of the CAV genome such that DNA from a non-essential region of CAV is flanking the donor DNA.

The exogenous DNA can be inserted into CAV to generate the recombinant CAV in any orientation which yields stable integration of that DNA, and expression thereof, when desired.

The exogenous DNA in the recombinant CAV virus or vector of the invention can include a promoter. The promoter can be from a herpesvirus. For instance, the promoter can be a cytomegalovirus (CMV) promoter, such as a human CMV (HCMV) or murine CMV promoter.

The promoter is preferably a truncated transcriptionally active promoter which comprises a region transactivated with a transactivating protein provided by the virus and the minimal promoter region of the full-length promoter from which the truncated transcriptionally active promoter is derived. For purposes of this specification, a "promoter" is composed of an association of DNA sequences corresponding to the minimal promoter and upstream regulatory sequences; a "minimal promoter" is composed of the CAP site plus TATA box (minimum sequences for basic level of transcription; unregulated level of transcription); and, "upstream regulatory sequences" are composed of the upstream element(s) and enhancer sequence(s). Further, the term "truncated" indicates that the full-length promoter is not completely present, i.e., that some portion of the full-length promoter has been removed. And, the truncated promoter can be derived from a herpesvirus such as MCMV or HCMV, e.g., HCMV-IE or MCMV-IE.

The promoter can truncated so that there is up to a 40% and even up to a 90% reduction in size, from a full-length promoter based upon base pairs; for instance, with the murine CMV-IE promoter, and HCMV-IE promoter, respectively. Indeed, a truncated promoter of the invention can consist essentially of an enhancer region which is transactivated by a transactivating protein provided by a virus or system into which the truncated promoter is inserted, and the mimimal promoter. Thus, as little as 60% and even as little as 10% of the original base pairs of the full-length promoter can be present in a truncated promoter of the invention.

Given that nature provided so many more base pairs for promoters than now has been discovered necessary, the promoters, and expression cassettes, viruses and plasmids containing the truncated promoters of the invention are indeed surprising. Indeed, the promoters of the invention obtain superior performance in comparison with full-length promoters, and, without necessarily wishing to be bound by any one particular theory, it is believed that this superior performance is due to the truncation. Further, truncation of promoters addresses the insert size limit problem of recombinant viruses and plasmids, particularly CAV.

Thus, the invention even still further provides, a truncated transcriptionally active promoter for a recombinant virus or plasmid which comprises a region transactivated with a transactivating protein provided by the virus or a system into which the plasmid is inserted and the minimal promoter region of a full-length promoter from which the truncated transcriptionally active promoter is derived.

Like the aforementioned promoter, the inventive promoter is preferably a herpesvirus, e.g., a MCMV or HCMV such as MCMV-IE or HCMV-IE promoter; and, there can be up to a 40% and even up to a 90% reduction in size, from a full-length promoter, based upon base pairs.

The invention thus also provides an expression cassette for insertion into a recombinant virus or plasmid comprising the truncated transcriptionally active promoter. The expression cassette can further include a functional truncated polyadenylation signal; for instance an SV40 polyadenylation signal which is truncated, yet functional. Considering that nature provided a larger signal, it is indeed surprising that a truncated polyadenylation signal is functional; and, a truncated polyadenylation signal addresses the insert size limit problems of recombinant viruses such as CAV. The expression cassette can also include exogenous or heterologous DNA with respect to the virus or system into which it is inserted; and that DNA can be exogenous or heterologous DNA as described herein.

Even further surprisingly, the present invention provides a recombinant CAV, preferably CAV2, wherein at least one non-essential loci, such as the E3 region, is employed for generation of the recombinant. Based on data derived from HAVs and bovine Ad3, part of this region may be non-essential both in vitro and in vivo for infectious virus formation and thus can be considered as an insertion region. Accordingly, in an aspect, the present invention provides the generation of a CAV E3 deletion or partial deletion mutant (e.g., E3 ORF1 and/or ORF2); and, this mutant additionally demonstrates that the entire CAV E3 region is not necessary in tissue culture and thus can be used as an insertion site in the generation of recombinant CAV. And therefore, the present invention encompasses a recombinant CAV wherein endogenous DNA is deleted and/or exogenous DNA introduced in the E3 region; preferably one or more non-essential domains within the E3 region, e.g., ORF2.

A deletion within the E3 region can also provide additional capacity for insertion of heterologous sequences into the CAV genome. For example, such deletions can compensate for the introduction of a large expression cassette into the right end of the genome. In this regard, by the methods herein taught, without undue experimentation, the skilled artisan can readily identify additional non-essential domains, preferably in the E3 region, and additional non-essential regions.

In another aspect, the invention surprisingly provides a recombinant CAV, preferably CAV2, wherein deletions within non-essential regions are relative to insertion of heterologous DNA. For instance, deletions within non-essential regions can be substantially similiar, e.g., compensatory, to the insertion of heterologous DNA in another region, such as, without limitation, the E4/right ITR region.

Nucleotide sequence comparisons between the ITRs from various CAV2 strains indicate some variability immediately upstream of the right ITR (Cavanagh et al., 1991, Spibey, 1991). Applicants' engineered a novel and nonobvious insertion site within this region; and therefore, the present invention in a further aspect encompasses CAV recombinants having exogenous DNA inserted therein. Further, the E4/right ITR region, as herein demonstrated, can surprisingly accept much larger fragments of heterologous DNA than the previously described SmaI site, further addressing the insert size limit of CAV.

Since the E4/right ITR site is localized in a region of the CAV genome with little transcriptional activity (for a review see Sharp et al., 1984), insertion thereinto does not significantly impact the biology of the CAV recombinant virus.

As discussed above, in an embodiment, the present invention provides novel and nonobvious expression cassette(s) for insertion of exogenous DNA into CAV; the cassette(s) comprising appropriate heterologous eukaryotic regulatory sequences. In a preferred embodiment, the invention provides expression cassette(s) rationally designed with consideration of packaging limitations and biological characteristics associated with viruses and plasmids such as adenovirus-based vectors. The ability to truncate MCMV and HCMV promoters to as small as an enhancer region which is transactivated with a transactivating protein provided by the virus or system into which the promoter is inserted and the mimimal promoter demonstrates that promoters from other eukaryotic viruses, and especially from other herpesviruses, can be similarly truncated, without undue experimentation from this disclosure and the knowledge in the art; and, the invention comprehends truncated promoters from such other viruses.

In a more specific aspect, the present invention encompasses CAV, preferably CAV2, recombinants comprising the HCMV-IE or MCMV-IE promoter, preferably a truncated promoter therefrom. Preferably, the HCMV-IE or MCMV-IE promoter or a truncated promoter therefrom is transactivated by CAV-induced gene products.

In the a spects of the present invention which include a truncated transcriptionally active (or competent) promoter (preferably a truncated transcriptionally active eukaryotic virus promoter such as a herpesvirus promoter, e.g., a HCMV or MCMV promoter), b y "active" (or competent), the truncated transcr ip tionally active promoter should exhibit at least 80%, preferably at least 85%, more preferably at least 90%, and most preferably at least 95% of the transcriptional activity of the pristine or full length promoter. Deletion of nucleotides or of portions or of regions of the full length promoter can be done from the herein teachings, without undue experimentatin, for generation of active fragments in addition to those exemplified.

The degree truncation, i.e., amount of base pairs deleted, from the original full length or pristine promoter, in terms of percentage, can be any amount up to 90%, so long as the truncated promoter remains "active" or "competent". Thus, a truncated transcriptionally active promoter can be, in terms of base pairs with respect to the full length or pristine promoter, about 5% to about 95%, preferably about 10% to about 90%, more peferably about 10% to about 60% and most preferably about 10% to about 40% of the full length or pristine promoter, with specific embodiments being about 10% and about 40% of the full length or pristine promoter (i.e., deletions from the full length or pristine promoter, in terms of base pairs, of about 95% to about 5%, preferably about 90% to about 10%, more preferably about 90% to about 40%, and most preferably about 90% to about 60% of the base pairs of the full length or pristine promoter, with deletions of about 90% and about 60% of base pairs of the full length or pristine promoter being specific embodiments). Indeed, all that need be retained of the original, full length or pristine promoter, at a minimum, is the minimal promoter and a region which is transactivated with a transactivating protein provided by the virus or system into which the promoter is inserted.

The deletion of portions of a promoter such as the HCMV-IE, is to reduce its size so as to address the deficiencies and/or problems of the size of promoters such as the HCMV-IE promoter and the packing limitations of adenoviruses.

In a particular aspect, the present invention provides an active fragment of the HCMV-IE having a size of 91 bp or an active fragment of the MCMV-IE having a size of 466 bp, i.e., a truncated transcriptionally active HCMV-IE of about 91 bp or a truncated transcriptionally active MCMV-IE of about 466 bp. (The present invention can encompass HCMV-IE or MCMV-IE fragments having substantial base pair size and/or homology with respect to the 91 bp or 466 bp fragment, e.g., as to base pair size and/or homology, at least 80%, preferably at least 85%, more preferably at least 90%, and most preferably at least 95% of the 91 bp or 466 bp fragment.) The fragment can be inserted into a CAV such as CAV2; and therefore, the invention encompasses a recombinant CAV such as CAV2 comprising an active fragment of HCMV-IE or MCMV-IE, i.e., a truncated transcriptionally active promoter derived from HCMV-IE or MCMV-IE, and preferably, the 91 bp or 466 bp fragment or an active fragment having substantial base pair size and/or homology to the 91 bp or 466 bp fragment.

Size reduction considerations for preparing the particular 91 bp or 466 bp fragment, or any other active fragment of the HCMV-IE or MCMV-IE promoter, can, as discussed above, be from the known molecular organization of the HCMV-IE or MCMV-IE promoter (Boshart et al., 1985).

It is surprising that such small versions of the full length or pristine promoter, such as the 91 bp or 466 bp fragment, are still able to be "active" (as the term is discussed above), and even drive an equivalent high level of transcription activity in CAV, particularly CAV2, infected cells as the 850 bp version of HCMV-IE and the 766 bp version of MCMV-IE, respectively.

The 91 bp fragment or an active fragment having substantial base pair size to the 91 bp fragment is especially surprising as it is believed to be the smallest promoter element which has been used in an adenovirus-based recombinant virus.

By following the herein considerations applied to the HCMV-IE and MCMV-IE promoter for generation of "active" fragments thereof, "active" fragments of promoters other than HCMV-IE or MCMV-IE, e.g., from other eukaryotic viruses such as other herpesviruses which are exogenous to adenovirus, e.g., CAV2, can be produced, without undue experimentation; and therefore, the present invention provides a fragment of a promoter exogenous to an adenovirus, i.e., a truncated transcriptionally active promoter, which is active like the full length promoter in the adenovirus when introduced into the adenovirus. The adenovirus is preferably CAV such as CAV2.

Thus, in another aspect the present invention provides a fragment of the murine CMV-IE (MCMV-IE) promoter (Dorsh-Hasler et al., 1985), i.e., a truncated transcriptionally active promoter derived from MCMV-IE, which is active in adenovirus, e.g., CAV2. Indeed, in adenovirus such as CAV2 infected cells the 466 bp MCMV-IE promoter element exhibits activity like the HCMV-IE 91 bp promoter element.

In yet another aspect, the invention provides a promoter which is active in adenovirus, e.g., CAV2, which has extended the translation of recombinant mRNAs into the late phase of the viral cycle; and, recombinants comprising the promoter, as well as compositions comprising the recombinants and methods for making and using the promoter, the recombinants and the compositions. Such a promoter can comprise an HCMV-IE promoter or active fragment thereof wherein the 5'UTR has been replaced with the human Ad2 TPL.

In still another aspect, the invention provides an insertion cassette for generating recombinant adenoviruses, e.g., CAV2, and to recombinants comprising the cassette, as well as compositions comprising the recombinants and methods for making and using the cassette, the recombinants and the compositions. This cassette preferably comprises a minimizd polyadenylation sequence ("minimized poly-A"), such as a minimized polyadenylation sequence from SV40 ("minimized SV40 poly-A"). The minimized SV40 poly-A can be any length less than the full length or native or pristine SV40 poly-A to as small as about 153 bp (plus or minus 10%).

It is demonstrated herein that such a minimized SV40 poly-A is still associated with the same high level of steady stable mRNA as the wild-type element in adenovirus, e.g., CAV2, infected cells. The minimized SV40 poly-A cassette can be used to minimize DNA inserted into adenovirus; and, this addresses the capacity deficiencies and problems of adenoviruses. Further, from the minimization of the SV40 polyadenylation signal, other similar sequences can be derived, from other sources, without undue experimentation.

Indeed, it is believed that heretofore an expression cassette having size and components which have been optimized for the expression of a recombinant protein by an adenovirus-based vector has not been described in the literature.

In an even further aspect, the present invention provides conditions and ergo methods to transfect purified adenovirus, e.g., CAV, preferably CAV2, DNA into canine mono layers.

In preferred embodiments of the invention, transfection conditions are independent of the utilization of a E1 transformed canine cell line. This procedure provides good yields, including yields of approximately $5 \times 10^3$ pfu/μg of purified CAV DNA. And, this procedure avoids the utilization of E1 transformed cells for the derivation and propagation of CAV recombinant viruses, thereby avoiding the safety issues surrounding E1 transformed cells.

The present invention thus provides recombinant adenoviruses, preferably CAV, more preferably CAV2, and methods for making a nd using them, and compositions containing them or expression products from them. Any suitable non-essential region can be used for insertion into the genome or deletion from the genome. Such sites include E4, E1, and E3. Two insertion sites are presently preferred: the first is within the E3 region and the second located between the right ITR and the E4 transcription unit (preferably the SmaI site); the former site or both sites (combined) are preferred. The CAV E3 ORF2, e.g., CAV2 E2 ORF2, is presently most preferred.

The results herein also demonstrate that the CAV E3 is non-essential for replication in tissue culture. This represents the first successful attempt to derive recombinant CAV viruses and thus constitutes a basis for products based upon recombinant CAV such as CAV2, e.g., immunological, antigenic or vaccine compositions containing the recombinant CAV or expression products therefrom.

Accordingly, the present invention comprehends a CAV such as CAV2 synthetically modified to contain therein exogenous DNA (DNA not naturally occurring in CAV, or not naturally occurring in CAV at the insertion site) in a non-essential region o f the CAV2 genome. The non-essential region is preferably the CAV E3 or both the CAV E3 and the right end of the genome such as the SmaI site.

The invention further comprehends antibodies elicited by the inventive compositions and/or recombinants and uses for such antibodies. The antibodies, or the product (epitopes of interest) which elicited them, or monoclonal antibodies from the antibodies, can be used in binding assays, tests or kits to determine the presence or absence of an antigen or antibody.

Flanking DNA used in the invention can be from the site of insertion or a portion of the genome adjacent thereto (wherein "adjacent" includes contiguous sequences, e.g., codon or codons, as well as up to as many sequences, e.g., codon or codons, before there is an intervening insertion site).

The exogenous or heterologous DNA (or DNA foreign to CAV, or DNA not naturally occurring in CAV) can be DNA encoding any of the aforementioned epitopes of interest, as listed above. In this regard, with respect to Borrelia DNA, reference is made to U.S. Pat. No. 5,523,089, WO93/08306, PCT/US92/08697, Molecular Microbiology (1989), 3(4), 479–486, and PCT publications WO 93/04175, and WO 96/06165, incorporated herein by reference. With respect to pneumococcal epitopes of interest, reference is made to Briles et al. WO 92/14488, incorporated herein by reference, with respect to tumor viruses reference is made to *Molecular Biology of Tumor Viruses, RNA TUMOR VIRUSES* (Second Edition, Edited by Weiss et al., Cold Spring Harbor Laboratory 1982) (e.g., page 44 et seq.—Taxonomy of Retroviruses), incorporated herein by reference. With respect to DNA encoding other epitopes of interest, attention is directed to the documents cited in the BACKGROUND OF THE INVENTION, for instance: U.S. Pat. Nos. 5,174, 993 and 5,505,941 (e.g., recombinant avipox virus, vaccinia virus; rabies glycoprotein (G), gene, turkey influenza hemagglutinin gene, gp51,30 envelope gene of bovine leukemia virus, Newcastle Disease Virus (NDV) antigen, FelV envelope gene, RAV-1 env gene, NP (nudeoprotein gene of Chicken/Pennsylvania/1/83 influenza virus), matrix and preplomer gene of infectious bronchitis virus; HSV gD; entomopox promoter, inter alia), U.S. Pat. No. 5,338,683, e.g., recombinant vaccinia virus, avipox virus; DNA encoding Herpesvirus glycoproteins, inter alia; U.S. Pat. No. 5,494, 807 (e.g., recombinant vaccinia, avipox; exogenous DNA encoding antigens from rabies, Hepatitis B, JEV, YF, Dengue, measles, pseudorabies, Epstein-Barr, HSV, HIV, SIV, EHV, BHV, HCMV, canine parvovirus, equine influenza, FeLV, FHV, Hantaan, *C. tetani*, avian influenza, mumps, NDV, inter alia); U.S. Pat. No. 5,503,834 (e.g., recombinant vaccinia, avipox, Morbillivirus [e.g., measles F, hemagglutinin, inter alia]); U.S. Pat. No. 4,722,848 (e.g., recombinant vaccinia virus; HSV tk, glycoproteins [e.g., gB, gD], influenza HA, Hepatitis B [e.g., HBsAg], inter alia); U.K. Patent GB 2 269 820 B and U.S. Pat. No. 5,514,375 (recombinant poxvirus; flavivirus structural proteins); WO 92/22641 (e.g., recombinant poxvirus; immunodeficiency virus, inter alia); WO 93/03145 (e.g., recombinant poxvirus; IBDV, inter alia); WO 94/16716 and U.S. application Ser. No. 08/184,009, filed Jan. 19, 1994 (e.g., recombinant poxvirus; cytokine and/or tumor associated antigens, inter alia); and PCT/US94/06652 (Plasmodium antigens such as from each stage of the Plasmodium life cycle).

In particular, since the tag and other exogenous DNA had been incorporated into CAV2, as in the recombinants described in the Examples, other exogenous DNA can be incorporated into CAV2. Therefore, instead of the exogenous DNA used to generate vCA1, vCA2, vCA3, vCA4, vCA5, vCA6, vCA7, vCA8, and vCA-CDVF1-@12bp-up-SmaI, the exogenous DNA of the above-listed documents and/or those otherwise cited herein are used to generate additional CAV2 recombinants with the exogenous DNA in regions as in vCA2 through vCA8 and vCA-CDVF1-@12bp-up-SmaI and deletions as in vCA2 through VCA8 and vCA-CDVF1-@12bp-up-SmaI (e.g., insertions in the E3 or at the region between the right ITR and the E4 transcription unit or at both sites and deletions in the E3 region) including recombinants containing coding for multiple antigens, as herein described (including with subfragment promoters, reduced or modified polyadenylation cassettes, and promoters with 5'UTR replaced). Analysis demonstrates expression. Compositions are prepared by admixture with a carrier or diluent for administration to a vertebrate (animal or human) hosts for generating responses, including antibody responses.

The exogenous DNA can include a marker, e.g., a color or light marker. The exogenous DNA can also code for a product which would be detrimental to an insect host such that the expression product can be a pesticide or insecticide. The exogenous DNA can also code for an anti-fungal polypeptide; and, for information on such a polypeptide and DNA therefor, reference is made to U.S. Pat. No. 5,421,839 and the documents cited therein, incorporated herein by reference.

In addition, the present invention provides a method for mapping a non-essential region in the adenovirus, preferably CAV, e.g., CAV2, genome, comprising preparing donor DNA comprising DNA not naturally occurring in CAV present within a segment of CAV DNA otherwise co-linear with a portion of the CAV genome such that by in vivo recombination the donor DNA can be introduced into a region of the CAV genome, introducing said donor DNA into the CAV genome by in vivo recombination, recovering recombinants, and determining stability and viability thereof and expression or presence of the DNA not naturally occurring in CAV and/or absence of endogenous CAV DNA in the recombinants, whereby viability and stability of recombinants and expression or presence of the DNA not naturally occurring in CAV and/or absence of endogenous CAV DNA indicates that the region into which the donor DNA was introduced is non-essential. This method is employed in the Examples below. The donor DNA can be marker DNA such that by hybridization one can determine whether it has been incorporated into the genome, e.g., hybridization to the marker DNA or failure to hybridize to endogenous DNA replaced by the marker.

These and other objects and embodiments within the present invention are described or are obvious from the following detailed description.

BRIEF DESCRIPTION OF DRAWINGS

In the following Detailed Description, reference will be made to the accompanying drawings, incorporated herein by reference, wherein:

FIG. 1 (FIGS. 1A–C) shows a complete DNA sequence of pLF027 ((6,995 bp) (SEQ ID NO: 1) CAV2 HindIII A fragment starts at nucleotide #689 and ends at nucleotide #4,725. CAV2 E3 region starts at nucleotide #1,414 and ends at nucleotide #2,945. CAV2 E3 ORF1 starts at nucleotide #8 and ends at nucleotide #346. CAV2 E3 ORF2 starts at nucleotide #384 and ends at nucleotide #1,478. CAV2 E3 ORF3 starts at nucleotide #1,019 and ends at nucleotide #483. The remaining nucleotides correspond to pBSSK+);

FIG. 3 (FIGS. 3A–C) shows a complete DNA sequence of pLF047A ((6,959 bp) (SEQ ID NO: 2) The 23 bp BlgII/MluI linker starts at nucleotide #1,485 and ends at nucleotide #1,508. The remaining sequences correspond to pLF027);

FIG. 5 (FIGS. 5A–C) shows a complete DNA sequence of pLF049A ((7,002 bp) (SEQ ID NO: 3) The 63 bp BlgII/MluI linker starts at VIR02890.37 2890.APP 47 nucleotide #2,138 and ends at nucleotide #2,201. The remaining sequences correspond to pLF047A);

FIG. 7 (FIGS. 7A–C) shows a complete DNA sequence of pLF086 ((6,581 bp) (SEQ ID NO: 4) The 63 bp BlgII/MluI linker starts at nucleotide #2,295 and ends at nucleotide #2,358. The remaining sequences correspond to pLF047A);

FIG. 9 (FIGS. 9A–C) shows a complete DNA sequence of pLF056 ((6,196 bp) (SEQ ID NO: 5) CAV2 SalI B fragment starts at nucleotide #1 and ends at nucleotide #3,274. The right ITR (196 bp) starts at nucleotide #3,078 and ends at nucleotide #3,274. The SmaI site is localized at position #3,088. The remaining nucleotides correspond to pBSSK+);

FIG. 11 (FIGS. 11A–C) shows a complete DNA sequence of pLF061 ((6,503 bp) (SEQ ID NO: 6) The 306 bp heterologous DNA tag starts at nucleotide #3,091 and ends at nucleotide #3,397. The remaining nucleotides correspond to pLF056);

FIG. 13 (FIGS. 13A–C) shows a complete DNA sequence of pLF022 ((4,504 bp) (SEQ ID NO: 7) The hCMV-IE (145 bp) promoter starts at nucleotide #2 and ends at nucleotide #147. All other nucleotides correspond to pCAT basic sequences and include: the CAT reporter gene which starts at nucleotide #209 and ends at nucleotide #868, the SV40 small t antigen and polyadenylation signal (856 bp) which starts at nucleotide #958 and ends at nucleotide #1,814 and the ampicillin resistance gene which starts at nucleotide #2,467 and ends at nucleotide #3,327);

FIG. 15 (FIGS. 15A–B) shows a complete DNA sequence of pLF062 ((3,812 bp) (SEQ ID NO: 8) The hCMV-IE (145 bp) promoter starts at nucleotide #2 and ends at nucleotide #147. The CAT reporter gene starts at nucleotide #209 and ends at nucleotide #868. The SV40 polyadenylation signal (241 bp) starts at nucleotide #881 and ends at nucleotide #1,122. The ampicillin resistance gene starts at nucleotide #1,775 and ends at nucleotide #2,635);

FIG. 17 (FIGS. 17A–B) shows a complete DNA sequence of pLF066 ((4,009 bp) (SEQ ID NO: 9) The hCMV-IE (145 bp) promoter starts at nucleotide #2 and ends at nucleotide #147. The Ad2 TPL (202 bp) starts at nucleotide #154 and ends at nucleotide #356. The CAT reporter gene starts at nucleotide #406 and ends at nucleotide #1,065. The SV40 polyadenylation signal (241 bp) starts at nucleotide #1,077 and ends at nucleotide #1,319. The ampicillin resistance gene starts at nucleotide #1,972 and ends at nucleotide #2,832);

FIG. 19 (FIGS. 19A–B) shows a complete DNA sequence of pLF069 ((3,955 bp) (SEQ ID NO: 10) The hCMV-IE (91 bp) promoter starts at nucleotide #2 and ends at nucleotide #93. The Ad2 TPL (202 bp) starts at nucleotide #100 and ends at nucleotide #302.The CAT reporter gene starts at nucleotide #352 and ends at nucleotide #1,011. The SV40 polyadenylation signal (241 bp) starts at nucleotide #1,024 and ends at nucleotide #1,265. The ampicillin resistance gene starts at nucleotide #1,918 and ends at nucleotide #2,778);

FIG. 20 shows a restriction map of pLF069;

FIG. 21 (FIGS. 21A–B) shows a complete DNA sequence of pLF077 ((3,861 bp) (SEQ ID NO: 11) The hCMV-IE (91 bp) promoter starts at nucleotide #2 and ends at nucleotide #93. The Ad2 TPL (202 bp) starts at nucleotide #100 and ends at nucleotide #302. The CAT reporter gene starts at nucleotide #352 and ends at nucleotide #1,011. The SV40 polyadenylation signal (153 bp) starts at nucleotide #1018 and ends at nucleotide #1,171. The ampicillin resistance gene starts at nucleotide #1,824 and ends at nucleotide #2,684);

FIG. 23 (FIGS. 23A–B) shows a complete DNA sequence of pLF091 ((3,888 bp) (SEQ ID NO: 12) The hCMV-IE (91 bp) promoter starts at nucleotide #2 and ends at nucleotide #93. The Ad2 TPL (202 bp) starts at nucleotide #100 and ends at nucleotide #302. The CAT reporter gene starts at nucleotide #352 and ends at nucleotide #1,011. The SV40 polyadenylation signal (153 bp) starts at nucleotide #1,018 and ends at nucleotide #1,164. The CAV2 12 nucleotides inserted at the 3' end of the SV40 polyadenylation signal are starting at nucleotide #1,165 and are finishing at nucleotide #1,176. The ampicillin resistance gene starts at nucleotide #1,851 and ends at nucleotide #2,711);

FIG. 25 (FIGS. 25A–C) shows a complete DNA sequence of pLF092 ((7,379 bp) (SEQ ID NO: 13) The CAT expression cassette (as defined in pLF091) starts at nucleotide #1 and ends at nucleotide #1,179. The CAV2 left flanking arm (182 bp) starts at nucleotide #1,180 and ends at nucleotide #1,362. The CAV2 right flanking arm (3,090 bp) starts at nucleotide #4,285 and ends at nucleotide #7,375. The remaining nucleotides corresponds to pBSSK+);

FIG. 27 (FIGS. 27A–C) shows a complete DNA sequence of pLF105 ((6,243 bp) (SEQ ID NO: 14) The polylinker starts at nucleotide #3,092 and ends at nucleotide #3,123. The CAV2 left flanking arm (182 bp) starts at nucleotide #3,123 and ends at nucleotide #3,321. The CAV2 right flanking arm (3,090 bp) starts at nucleotide #1 and ends at nucleotide #3,091. The remaining nucleotides correspond to pBSSK+);

FIG. 28 shows a restriction map of pLF105;

FIG. 29 (FIGS. 29A–C) shows a complete DNA sequence of pLF102 ((6,615 bp) (SEQ ID NO: 15) The 305 bp BlgII/MluI linker starts at nucleotide #1,471 and ends at nucleotide #1,776. The remaining sequences correspond to pLF086; VIR02890.37Z890.APP 51

FIG. 31 (FIGS. 31A–C) shows a complete DNA sequence of pLF1116A ((6,450 bp) (SEQ ID NO: 16) The 311 bp MluI/MluI linker starts at nucleotide #1,092 and ends at nucleotide #1,403. The remaining sequences correspond to pLF086);

FIG. 33 (FIGS. 33A–C) shows a complete DNA sequence of pLF100 ((6,247 bp) (SEQ ID NO: 17) The 302 bp DraIII/MluI linker starts at nucleotide #898 and ends at nucleotide #1,200. The remaining sequences correspond to pLF086);

FIG. 35 (FIGS. 35A–C) shows a complete DNA sequence of pLF120 ((6,048 bp) (SEQ ID NO: 18) The 311 bp DraIII/MluI linker starts at nucleotide #898 and ends at nucleotide #1,209. The remaining sequences correspond to pLF086);

FIG. 37 (FIGS. 37A–C) shows a complete DNA sequence of pLF043 ((5,109 bp) (SEQ ID NO: 19) CDV HA coding sequence starts at nucleotide #35 and ends at nucleotide #2175. CDV HA ORF stop codon is #1847. The partial vaccinia H6 promoter starts at nucleotide #7 and ends at nucleotide #35. The remaining sequences correspond to pBSSK+);

FIG. 38 shows a restriction map of pLF043;

FIG. 39 (FIGS. 39A–C) shows a complete DNA sequence of pLF098 ((5,070 bp) (SEQ ID NO: 20) CDV HA expression cassette starts at nucleotide #1 and ends at nucleotide #2372. The remaining sequences correspond to pLF069);

FIG. 41 (FIGS. 41A–D) shows a complete DNA sequence of pLF099A ((8,618 bp) (SEQ ID NO: 21) CDV HA expression cassette starts at nucleotide #3120 and ends at nucleotide #5,494. The remaining sequences correspond to pLF105);

FIG. 43 (FIGS. 43A–C) shows a complete DNA sequence of pLF108 ((4,965 bp) (SEQ ID NO: 22) the 3' most region of the vaccinia virus H6 promoter is located between position#1 and 29; the CDV F1 coding sequence begins at position#30 and terminates at position#2,018; the remaining sequences correspond to pBSSK+);

FIG. 44 shows a restriction map of pLF108;

FIG. 45 (FIGS. 45A–C) shows a complete DNA sequence of pLF111 ((5,241 bp) (SEQ ID NO: 23) CDV F1 expression cassette begins at position #1 and terminates at position #2,556; the remaining sequences correspond to pLF069);

FIG. 47 (FIGS. 47A–C) shows a complete DNA sequence of pLF128 ((5,147 bp) (SEQ ID NO: 24) CDV F1 expression cassette begins at position #1 and terminates at position #2,452; the remaining sequences correspond to pLF077);

FIG. 49 (FIGS. 49A–D) shows a complete DNA sequence of pLF130A ((8,792 bp) (SEQ ID NO: 25) CDV F1 expression cassette begins at position #3,126 and terminates at nucleotide #5,669; the CAV2 SalI.B left flanking arm (3,091 bp) is located between position #1 and 3,091; the CAV2 SalI.B right flanking arm (182 bp) is located between position #5,688 and 5,870; the remaining sequences correspond to pLF105); and, FIG. 50 shows a restriction map of pLF130A.

DETAILED DESCRIPTION

Figure 2:
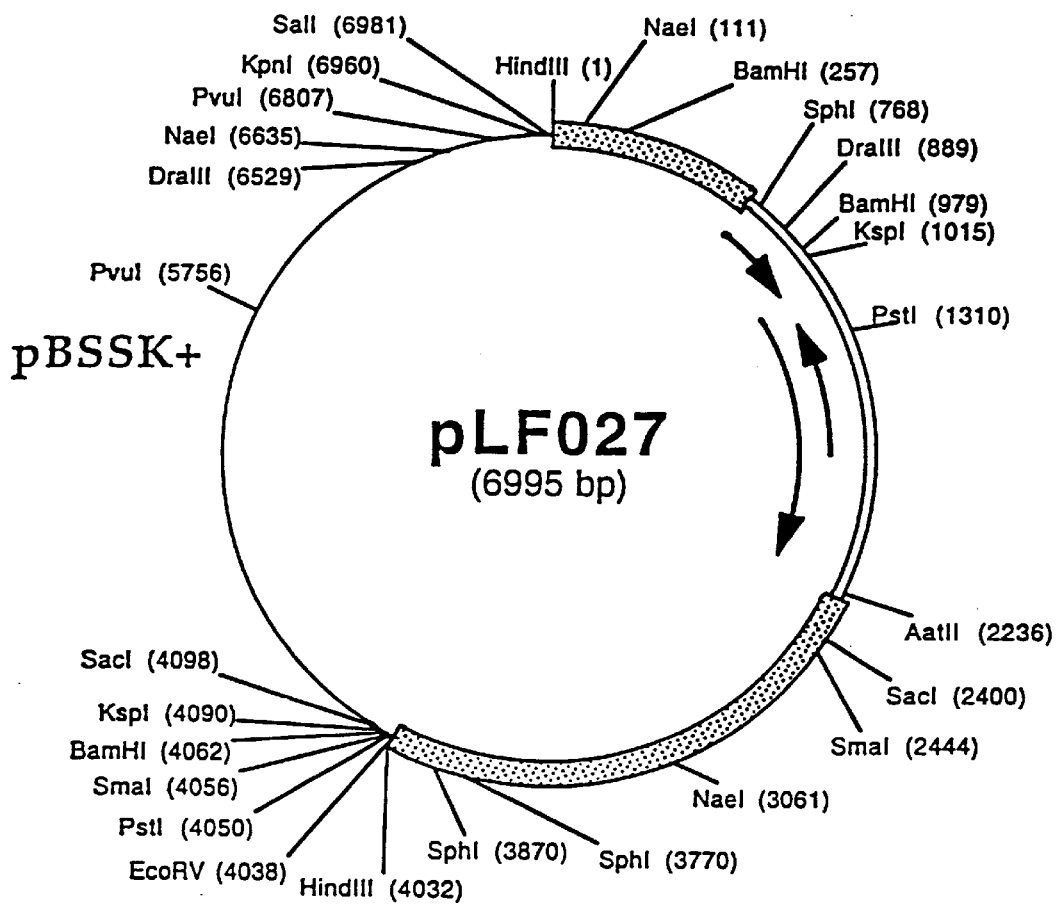
FIG. 2 shows a restriction map of pLF027.

As mentioned earlier, the present invention relates to recombinant adenovirus, such as CAV, preferably CAV2, methods for making and using them, and to compositions containing them or their expression products; and, to promoters and expression cassettes.

More specifically, this invention relates to recombinant CAV such as CAV2, especially those wherein exogenous DNA has been inserted into a non-essential region and/or a non-essential region is deleted and methods of making them, uses for them (including as a vector for replicating DNA), expression products from them, and uses for the expression products. The CAV E3 region, preferably ORF2, is preferred for insertion and/or deletion.

The uses for recombinant viruses, and for products therefrom can be determined without undue experimentation from the documents set forth in the BACKGROUND OF THE INVENTION and the discussion under the SUMMARY OF THE INVENTION.

The heterologous or exogenous DNA in recombinants of the invention preferably encodes an expression product comprising: an epitope of interest, a biological response modulator, a growth factor, a recognition sequence, a therapeutic gene, or a fusion protein. With respect to these terms, reference is made to the following discussion, and generally to Kendrew, THE ENCYCLOPEDIA OF MOLECULAR BIOLOGY (Blackwell Science Ltd 1995) and Sambrook, Fritsch, Maniatis, *Molecular Cloning, A LABORATORY MANUAL* (2d Edition, Cold Spring Harbor Laboratory Press, 1989).

As to antigens for use in vaccine or immunological compositions, reference is made to the documents and discussion set forth in the BACKGROUND OF THE INVENTION and the discussion under the SUMMARY OF THE INVENTION; see also Stedman's Medical Dictionary (24th edition, 1982, e.g., definition of vaccine (for a list of antigens used in vaccine formulations; such antigens or epitopes of interest from those antigens can be used in the invention, as either an expression product of the inventive recombinant virus, or in a multivalent composition containing an inventive recombinant virus or an expression product therefrom).

As to epitopes of interest, one skilled in the art can determine an epitope or immunodominant region of a peptide or polypeptide and ergo the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

A general method for determining which portions of a protein to use in an immunological composition focuses on the size and sequence of the antigen of interest. "In general, large proteins, because they have more potential determinants are better antigens than small ones. The more foreign an antigen, that is the less similar to self configurations which induce tolerance, the more effective it is in provoking an immune response." Ivan Roitt, *Essential Immunology*, 1988.

As to size: the skilled artisan can maximize the size of the protein encoded by the DNA sequence to be inserted into the viral vector (keeping in mind the packaging limitations of the vector). To minimize the DNA inserted while maximizing the size of the protein expressed, the DNA sequence can exclude introns (regions of a gene which are transcribed but which are subsequently excised from the primary RNA transcript).

At a minimum, the DNA sequence can code for a peptide at least 8 or 9 amino acids long. This is the minimum length that a peptide needs to be in order to stimulate a CD4+ T cell response (which recognizes virus infected cells or cancerous cells). A minimum peptide length of 13 to 25 amino acids is useful to stimulate a CD8+ T cell response (which recognizes special antigen presenting cells which have engulfed the pathogen). See Kendrew, supra. However, as these are minimum lengths, these peptides are likely to generate an immunological response, i.e., an antibody or T cell response; but, for a protective response (as from a vaccine composition), a longer peptide is preferred.

With respect to the sequence, the DNA sequence preferably encodes at least regions of the peptide that generate an antibody response or a T cell response. One method to determine T and B cell epitopes involves epitope mapping. The protein of interest "is fragmented into overlapping peptides with proteolytic enzymes. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules. The method is less effective for determining B-cell epitopes" since B cell epitopes are often not linear amino acid sequence but rather result from the tertiary structure of the folded three dimensional protein. Janis Kuby, *Immunology*, (1992) pp. 79–80.

Another method for determining an epitope of interest is to choose the regions of the protein that are hydrophilic. Hydrophilic residues are often on the surface of the protein and are therefore often the regions of the protein which are accessible to the antibody. Janis Kuby, *Immunology*, (1992) p. 81.

Yet another method for determining an epitope of interest is to perform an X-ray crystallographic analysis of the antigen (full length)-antibody complex. Janis Kuby, *Immunology,* (1992) p. 80.

Still another method for choosing an epitope of interest which can generate a T cell response is to identify from the protein sequence potential HLA anchor binding motifs which are peptide sequences which are known to be likely to bind to the MHC molecule.

The peptide which is a putative epitope of interest, to generate a T cell response, should be presented in a MHC complex. The peptide preferably contains appropriate anchor motifs for binding to the MHC molecules, and should bind with high enough affinity to generate an immune response. Factors which can be considered are: the HLA type of the patient (vertebrate, animal or human) expected to be immunized, the sequence of the protein, the presence of appropriate anchor motifs and the occurance of the peptide sequence in other vital cells.

An immune response is generated, in general, as follows: T cells recognize proteins only when the protein has been cleaved into smaller peptides and is presented in a complex called the "major histocompatability complex MHC" located on another cell's surface. There are two classes of MHC complexes—class I and class II, and each class is made up of many different alleles. Different patients have different types of MHC complex alleles; they are said to have a 'different HLA type.'

Class I MHC complexes are found on virtually every cell and present peptides from proteins produced inside the cell. Thus, Class I MHC complexes are useful for killing cells which when infected by viruses or which have become cancerous and as the result of expression of an oncogene. T cells which have a protein called CD4 on their surface, bind to the MHC class I cells and secrete lymphokines. The lymphokines stimulate a response; cells arrive and kill the viral infected cell.

Class II MHC complexes are found only on antigen-presenting cells and are used to present peptides from circulating pathogens which have been endocytosed by the antigen-presenting cells. T cells which have a protein called CD8 bind to the MHC class II cells and kill the cell by exocytosis of lytic granules.

Some guidelines in determining whether a protein is an epitopes of interest which will stimulate a T cell response, include: Peptide length—the peptide should be at least 8 or 9 ammino acids long to fit into the MHC class I complex and at least 13–25 amino acids long to fit into a class II MCH complex. This length is a minimum for the peptide to bind to the MHC complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia, M. et al, *Specific Binding of Leukemia Oncogene Fusion Protein Peptides to HLA Class I Molecules,* Blood 85:2680–2684; Englehard, V H, *Structure of peptides associated with class I and class II MHC molecules* Ann. Rev. Immunol. 12:181 (1994)). This can be done, without undue experimentation, by comparing the sequence of the protein of interest with published structures of peptides associated with the MHC molecules. Protein epitopes recognized by T cell receptors are peptides generated by enzymatic degradation of the protein molecule and are prestnted on the cell surface in association with class I or class II MHC molecules.

Further, the skilled artisan can ascertain an epitope of interest by comparing the protein sequence with sequences listed in the protein data base. Regions of the protein which share little or no homology are better choices for being an epitope of that protein and are therefore useful in a vaccine or immunological composition. Regions which share great homology with widely found sequences present in vital cells should be avoided.

Even further, another method is simply to generate or express portions of a protein of interest, generate monoclonal antibodies to those portions of the protein of interest, and then ascertain whether those antibodies inhibit growth in vitro of the pathogen from which the from which the protein was derived. The skilled artisan can use the other guidelines set forth in this disclosure and in the art for generating or expressing portions of a protein of interest for analysis as to whether antibodies thereto inhibit growth in vitro. For example, the skilled artisan can generate portions of a protein of interest by: selecting 8 to 9 or 13 to 25 amino acid length portions of the protein, selecting hydrophylic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid and corresponding DNA sequence of an epitope of interest for obtaining a T cell, B cell and/or antibody response. In addition, reference is made to Gefter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing antibodies are directed. Disclosures of such epitopes are in many of the references cited in the Relevant Literature section.")

With respect to expression of a biological response modulator, reference is made to Wohlstadter, "Selection Methods," WO 93/19170, published Sep. 30, 1993, and the documents cited therein, incorporated herein by reference.

For instance, a biological response modulator modulates biological activity; for instance, a biological response modulator is a modulatory component such as a high molecular weight protein associated with non-NMDA excitatory amino acid receptors and which allosterically regulates affinity of AMPA binding (See Kendrew, supra). The recombinant of the present invnention can express such a high molecular weight protein.

More generally, nature has provided a number of precedents of biological response modulators. Modulation of activity may be carried out through mechanisms as complicated and intricate as allosteric induced quaternary change to simple presence/absence, e.g., expression/degradation, systems. Indeed, the repression/activation of expression of many biological molecules is itself mediated by molecules whose activities are capable of being modulated through a variety of mechanisms.

Table 2 of Neidhardt et al *Physiology of the Bacterial Cell* (Sinauer Associates Inc., Publishers, 1990), at page 73, lists chemical modifications to bacterial proteins. As is noted in that table, some modifications are involved in proper assembly and other modifications are not, but in either case such modifications are capable of causing modulation of function. From that table, analogous chemical modulations for proteins of other cells can be determined, without undue experimentation.

In some instances modulation of biological functions may be mediated simply through the proper/improper localization of a molecule. Molecules may function to provide a growth advantage or disadvantage only if they are targeted to a particular location. For example, a molecule may be typically not taken up or used by a cell, as a function of that molecule being first degredaded by the cell by secretion of an enzyme for that degradation. Thus, production of the enzyme by a recombinant can regulate use or uptake of the molecule by a cell. Likewise, the recombinant can express a molecule which binds to the enzyme necessary for uptake or use of a molecule, thereby similarly regulating its uptake or use.

Localization targeting of proteins carried out through cleavage of signal peptides another type of modulation or regulation. In this case, a specific endoprotease catalytic activity can be expressed by the recombinant.

Other examples of mechanisms through which modulation of function may occur are RNA virus poly-proteins, allosteric effects, and general covalent and non-covalent steric hindrance. HIV is a well studied example of an RNA virus which expresses non-functional poly-protein constructs. In HIV "the gag, pol, and env poly-proteins are processed to yield, respectively, the viral structural proteins p17, p24, and p15—reverse transcriptase and integrase—and the two envelope proteins gp41 and gp120" (Kohl et al., PNAS USA 85:4686–90 (1988)). The proper cleavage of the poly-proteins is crucial for replication of the virus, and virions carrying inactive mutant HIV protease are non-infectious (Id.). This is another example of the fusion of proteins down-modulating their activity. Thus, it is possible to construct recombinant viruses which express molecules which interfere with endoproteases, or which provide endoproteases, for inhibiting or enhancing the natural expression of certain proteins (by interfering with or enhancing cleavage).

The functional usefulness of enzymes may also be modulated by altering their capability of catalyzing a reaction. Illustrative examples of modulated molecules are zymogens, formation/disassociation of multi-subunit functional complexes, RNA virus poly-protein chains, allosteric interactions, general steric hindrance (covalent and non-covalent) and a variety of chemical modifications such as phosphorylation, methylation, acetylation, adenylation, and uridenylation (see Table 1 of Neidhardt, supra, at page 315 and Table 2 at page 73).

Zymogens are examples of naturally occurring protein fusions which cause modulation of enzymatic activity. Zymogens are one class of proteins which are converted into their active state through limited proteolysis. See Table 3 of Reich, *Proteases and Biological Control,* Vol. 2, (1975) at page 54). Nature has developed a mechanism of down-modulating the activity of certain enzymes, such as trypsin, by expressing these enzymes with additional "leader" peptide sequences at their amino termini. With the extra peptide sequence the enzyme is in the inactive zymogen state. Upon cleavage of this sequence the zymogen is converted to its enzymatically active state. The overall reaction rates of the zymogen are "about $10^5$–$10^6$ times lower than those of the corresponding enzyme" (See Table 3 of Reich, supra at page 54).

It is therefore possible to down-modulate the function of certain enzymes simply by the addition of a peptide sequence to one of its termini. For example, with knowledge of this property, a recombinant can express peptide sequences containing additional amino acids at one or both terminii.

The formation or disassociation of multi-subunit enzymes is another way through which modulation may occur. Different mechanisms may be responsible for the modulation of activity upon formation or disassociation of multi-subunit enzymes.

Therefore, sterically hindering the proper specific subunit interactions will down-modulate the catalytic activity. And accordingly, the recombinant of the invention can express a molecule which sterically hinders a naturally occurring enzyme or enzyme complex, so as to modulate biological functions.

Certain enzyme inhibitors afford good examples of functional down-modulation through covalent steric hindrance or modification. Suicide substrates which irreversibly bind to the active site of an enzyme at a catalytically important amino acid in the active site are examples of covalent modifications which sterically block the enzymatic active site. An example of a suicide substrate is TPCK for chymotrypsin (Fritsch, *Enzyme Structure and Mechanism,* 2d ed; Freeman & Co. Publishers, 1984)). This type of modulation is possible by the recombinant expressing a suitable suicide substrate, to thereby modulate biological responses (e.g., by limiting enzyme activity).

There are also examples of non-covalent steric hindrance including many repressor molecules. The recombinant can express repressor molecules which are capable of sterically hindering and thus down-modulating the function of a DNA sequence by preventing particular DNA-RNA polymerase interactions.

Allosteric effects are another way through which modulation is carried out in some biological systems. Aspartate transcarbamoylase is a well characterized allosteric enzyme. Interacting with the catalytic subunits are regulatory domains. Upon binding to CTP or UTP the regulatory subunits are capable of inducing a quaternary structural change in the holoenzyme causing down-modulation of catalytic activity. In contrast, binding of ATP to the regulatory subunits is capable of causing up-modulation of catalytic activity (Fritsch, supra). Using methods of the invention, molecules can be expressed which are capable of binding and causing modulatory quaternary or tertiary changes.

In addition, a variety of chemical modifications, e.g., phosphorylation, methylation, acetylation, adenylation, and uridenylation may be carried out so as to modulate function. It is known that modifications such as these play important roles in the regulation of many important cellular components. Table 2 of Neidhardt, supra, at page 73, lists different bacterial enzymes which undergo such modifications. From that list, one skilled in the art can ascertain other enzymes of other systems which undergo the same or similar modifications, without undue experimentation. In addition, many proteins which are implicated in human disease also undergo such chemical modifications. For example, many oncogenes have been found to be modified by phosphorylation or to modify other proteins through phosphorylation or dephosphorylation. Therefore, the ability afforded by the invention to express modulators which can modify or alter function, e.g., phosphorylation, is of importance.

From the foregoing, the skilled artisan can use the present invention to express a biological response modulator, without any undue experimentation.

With respect to expression of fusion proteins by inventive recombinants, reference is made to Sambrook, Fritsch, Maniatis, *Molecular Cloning, A LABORATORY MANUAL* (2d Edition, Cold Spring Harbor Laboratory Press, 1989) (especially Volume 3), and Kendrew, supra, incorporated herein by reference. The teachings of Sambrook et al., can be suitably modified, without undue experiementation, from this disclosure, for the skilled artisan to generate recombinants expressing fusion proteins.

With regard to gene therapy and immunotherapy, reference is made to U.S. Pat. Nos. 4,690,915 and 5,252,479, which are incorporated herein by reference, together with the documents cited therein it and on their face, and to WO 94/16716 and U.S. application Ser. No. 08/184,009, filed Jan. 19, 1994, each of which is also incorporated herein by reference, together with the documents cited therein.

A growth factor can be defined as multifunctional, locally acting intercellular signalling peptides which control both ontogeny and maintenance of tissue and function (see Kendrew, especially at page 455 et seq.).

The growth factor or therapeutic gene, for example, can encode a disease-fighting protein, a molecule for treating cancer, a tumor suppressor, a cytokine, a tumor associated antigen, or interferon; and, the growth factor or therapeutic gene can, for example, be selected from the group consisting of a gene encoding alpha-globin, beta-globin, gamma-globin, granulocyte macrophage-colony stimulating factor, tumor necrosis factor, an interleukin (e.g., an interleukin selected from interleukins 1 to 14, or 1 to 11, or any combination thereof), macrophage colony stimulating factor, granulocyte colony stimulating factor, erythropoietin, mast cell growth factor, tumor suppressor p53, retinoblastoma, interferon, melanoma associated antigen or B7. U.S. Pat. No. 5,252,479 provides a list of proteins which can be expressed in an adenovirus system for gene therapy, and the skilled artisan is directed to that disclosure. WO 94/16716 and U.S. application Ser. No. 08/184,009, filed Jan. 19, 1994, provide genes for cytokines and tumor associated antigens and immunotherapy methods, including ex vivo methods, and the skilled artisan is directed to those disclosures.

Thus, one skilled in the art can create recombinants expressing a growth factor or therapeutic gene and use the recombinants, from this disclosure and the knowledge in the art, without undue experimentation.

Moreover, from the foregoing and the knowledge in the art, no undue experimentation is required for the skilled artisan to construct an inventive recombinant which expresses an epitope of interest, a biological response modulator, a growth factor, a recognition sequence, a therapeutic gene, or a fusion protein; or for the skilled artisan to use such a recombinant.

It is noted that the exogenous or heterologous DNA can itself include a promoter for driving expression in the recombinant CAV, or the exogenous DNA can simply be coding DNA and appropriately placed downstream from an endogenous promoter to drive expression. Further, multiple copies of coding DNA or use of a strong or early promoter or early and late promoter, or any combination thereof, can be done so as to amplify or increase expression. Thus, the exogenous or heterologous DNA can be suitably positioned with respect to an endogenous promoter like the E3 or the MLP promoters, or those promoters can be translocated to be inserted at another location, with the exogenous or heterologous DNA. The coding DNA can be DNA coding for more than one protein so as to have expression of more than one product from the recombinant CAV.

The expression products can be antigens, immunogens or epitopes of interest; and therefore, the invention further relates to immunological, antigenic or vaccine compositions containing the expression products. Further, since the CAV vector, in certain instances, can be administered directly to a suitable host, the invention relates to compositions containing the CAV, preferably CAV2, vector. Additionally, since the expression product can be isolated from the CAV, preferably CAV2, vector in vitro or from cells infected or transfected by the CAV vector in vitro, the invention relates to methods for expressing a product, e.g., comprising inserting the exogenous DNA into a CAV as a vector, e.g., by restriction/ligation or by recombination followed by infection or transfection of suitable cells in vitro with a recombinant CAV, and optionally extracting, purifying or isolating the expression product from the cells. Any suitable extraction, purification or isolation techniques can be employed; and reference is made to the discussion and documents in the BACKGROUND OF THE INVENTION and SUMMARY OF THE INVENTION.

In particular, after infecting cells with the recombinant CAV, the protein(s) from the expression of the exogenous DNA are collected by known techniques such as chromatography (see Robbins, EPA 0162738A1; Panicali, EPA 0261940A2); Richardson, supra; Smith et al., supra; Pennock et al., supra; EP Patent Publication No. 0265785). The collected protein(s) can then be employed in a vaccine, antigenic or immunological composition which also contains a suitable carrier.

Thus, the recombinant CAV can be used to prepare proteins such as antigens, immunogens, epitopes of interest, etc. which can be further used in immunological, antigenic or vaccine compositions. It is noted that a recombinant CAV expressing a product detrimental to growth or development of insects can be used to prepare an insecticide, and a recombinant CAV expressing a product detrimental to growth of plants can be used to prepare a herbicide (by isolating the expression product and admixing it with an insecticidally or herbicidally acceptable carrier or diluent) and a recombinant CAV expressing an anti-fungal polypeptide can be used to prepare an anti-fungal preparation (by isolating the expression product and admixing it with a suitable carrier or diluent).

As the expression products can provide an antigenic, immunological or protective (vaccine) response, the invention further relates to products therefrom; namely, antibodies and uses thereof. More in particular, the expression products can elicit antibodies. The antibodies can be formed into monoclonal antibodies; and, the antibodies or expression products can be used in kits, assays, tests, and the like involving binding, so that the invention relates to these uses too. Additionally, since the recombinants of the invention can be used to replicate DNA, the invention relates to recombinant CAV as a vector and methods for replicating DNA by infecting or transfecting cells with the recombinant and harvesting DNA therefrom. The resultant DNA can be used as probes or primers or for amplification.

The administration procedure for recombinant CAV or expression product thereof, compositions of the invention such as immunological, antigenic or vaccine compositions or therapeutic compositions can be via a parenteral route (intradermal, intramuscular or subcutaneous). Such an administration enables a systemic immune response. The administration can be via a mucosal route, e.g., oral, nasal, genital, etc. Such an administration enables a local immune response.

More generally, the inventive antigenic, immunological or vaccine compositions or therapeutic compositions (compositions containing the CAV, preferably CAV2, recombinants of the invention or expression products) can be prepared in accordance with standard techniques well known to those skilled in the pharmaceutical or vetinary arts. Such compositions can be administered in dosages and by techniques well known to those skilled in the medical arts taking into consideration such factors as the breed or species, age, sex, weight, and condition of the particular patient, and the route of administration. The compositions can be administered alone, or can be co-administered or sequentially administered with other compositions of the invention or with other immunological, antigenic or vaccine or therapeutic compositions. Such other compositions can include purified native antigens or epitopes or antigens or epitopes from the expression by a recombinant CAV or another vector system; and are administered taking into account the aforementioned factors.

Examples of compositions of the invention include liquid preparations for orifice, e.g., oral, nasal, anal, genital, e.g., vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant may be in admixture with a suitable carrier, diluent, or excipient such as sterile water, physiological saline, glucose or the like.

Antigenic, immunological or vaccine compositions typically can contain an adjuvant and an amount of the recombinant CAV or expression product to elicit the desired response. In human applications, alum (aluminum phosphate or aluminum hydroxide) is a typical adjuvant. Saponin and its purified component Quil A, Freund's complete adjuvant and other adjuvants used in research and veterinary applications have toxicities which limit their potential use in human vaccines. Chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the protein within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vescular Systems, Inc., Nashua, N.H.) can also be used.

The composition may be packaged in a single dosage form for immunization by parenteral (i.e., intramuscular, intradermal or subcutaneous) administration or orifice administration, e.g., perlingual (i.e., oral), intragastric, mucosal including intraoral, intraanal, intravaginal, and the like administration. And again, the effective dosage and route of administration are determined by the nature of the composition, by the nature of the expression product, by expression level if recombinant CAV2 is directly used, and by known factors, such as breed or species, age, sex, weight, condition and nature of host, as well as $LD_{50}$ and other screening procedures which are known and do not require undue experimentation. Dosages of expressed product can range from a few to a few hundred micrograms, e.g., 5 to 500 μg. The inventive recombinant can be administered in any suitable amount to achieve expression at these dosage levels. The vaccinal CAV2 is administered in an amount of about $10^{3.5}$ pfu; thus, the inventive recombinant is preferably administered in at least this amount; more preferably about $10^4$ pfu to about $10^6$ pfu. Other suitable carriers or diluents can be water or a buffered saline, with or without a preservative. The expression product or recombinant CAV may be lyophilized for resuspension at the time of administration or can be in solution.

The carrier may also be a polymeric delayed release system. Synthetic polymers are particularly useful in the formulation of a composition having controlled release. An early example of this was the polymerization of methyl methacrylate into spheres having diameters less than one micron to form so-called nano particles, reported by Kreuter, J., *Microcapsules and Nanoparticles in Medicine and Pharmacology*, M. Donbrow (Ed). CRC Press, p. 125–148.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters and polyamides, particularly those that are biodegradable.

A frequent choice of a carrier for pharmaceuticals and more recently for antigens is poly (d,1-lactide-co-glycolide) (PLGA). This is a biodegradable polyester that has a long history of medical use in erodible sutures, bone plates and other temporary prostheses where it has not exhibited any toxicity. A wide variety of pharmaceuticals including peptides and antigens have been formulated into PLGA microcapsules. A body of data has accumulated on the adaption of PLGA for the controlled release of antigen, for example, as reviewed by Eldridge, J. H., et al. *Current Topics in Microbiology and Immunology*. 1989, 146:59–66. The entrapment of antigens in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

Thus, solid, including solid-containing-liquid, liquid, and gel (including "gel caps") compositions are envisioned.

Additionally, the inventive vectors, e.g., recombinant CAV2, and the expression products therefrom can stimulate an immune or antibody response in animals. From those antibodies, by techniques well-known in the art, monoclonal antibodies can be prepared and, those monoclonal antibodies, can be employed in well known antibody binding assays, diagnostic kits or tests to determine the presence or absence of antigen(s) and therefrom the presence or absence of the natural causative agent of the antigen or, to determine whether an immune response to that agent or to the antigen(s) has simply been stimulated.

Monoclonal antibodies are immunoglobulin produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H., U.S. Pat. No. 4,376,110, issued Mar. 8, 1983, incorporated herein by reference.

Monoclonal antibodies have also been used to recover materials by immunoadsorption chromatography, e.g. Milstein, C., 1980, Scientific American 243:66, 70, incorporated herein by reference.

Furthermore, the inventive recombinant CAV or expression products therefrom can be used to stimulate a response in cells in vitro or ex vivo for subsequent reinfusion into a patient. If the patient is seronegative, the reinfusion is to stimulate an immune response, e.g., an immunological or antigenic response such as active immunization. In a seropositive individual, the reinfusion is to stimulate or boost the immune system against a pathogen.

The recombinant CAV of the invention are also useful for generating DNA for probes or for PCR primers which can be used to detect the presence or absence of hybridizable DNA or to amplify DNA, e.g., to detect a pathogen in a sample or for amplifying DNA.

Furthermore, as discussed above, the invention comprehends promoters and expression cassettes which are useful in adenovirus systems, as well as in any viral or cell system which provides a transactivating protein. The promoter is preferably a truncated transcriptionally active promoter for a recombinant virus or plasmid which comprises a region transactivated with a transactivating protein provided by the virus or a system into which the plasmid is inserted and the minimal promoter region of a full-length promoter from which the truncated transcriptionally active promoter is derived.

Like the inventive promoter is preferably a derived from a eukaryotic virus such as a herpesvirus, e.g., a MCMV or HCMV such as MCMV-IE or HCMV-IE promoter; and, there can be up to a 40% and even up to a 90% reduction in size, from a full-length promoter, based upon base pairs.

The expression cassette of the invention can further include a functional truncated polyadenylation signal; for instance an SV40 polyadenylation signal which is truncated, yet functional. The expression cassette can contain exogenous or heterologous DNA (with respect to the virus or system into which the promoter or expression cassette is being inserted); for instance exogenous or heterologous coding DNA as herein described above, and in the Examples. This DNA can be suitably positioned and operably linked to the promoter for expression. The expression cassette can be inserted in any orientation; preferably the orientation which obtains maximum expression from the system or virus into which the expression cassette is inserted.

While the promoter and expression cassette are specifically exemplified with reference to adenoviruses, the skilled artisan can adapt these embodiments of the invention to other viruses and to plasmids for cells such as eukaryotic cells, without undue experimentation, by simply ascertaining whether the virus, plasmid, cell or system provides the transactivating protein.

As to HCMV promoters, reference is made to U.S. Pat. Nos. 5,168,062 and 5,385,839, incorporated herein by reference. As to transfecting cells with plasmid DNA for expression therefrom, reference is made to Felgner et al. (1994), J. Biol. Chem. 269, 2550–2561, incorporated herein by reference. And, as to direct injection of plasmid DNA as a simple and effective method of vaccination against a variety of infectious diseases reference is made to Science, 259:1745–49, 1993, incorporated herein by reference. It is therefore within the scope of this invention that the inventive promoter and expression cassette be used in systems other than adenovirus; for example, in plasmids for the direct injection of plasmid DNA.

Other utilities also exist for embodiments of the invention.

The following non-limiting Examples are given by way of illustration only and are not to be considered a limitation of this invention.

EXAMPLES

Example 1

Virus and Cell Line Identifications

The described stock of canine adenovirus type 2 (CAV2) was produced at Rhone Merieux Inc. (Athens, Ga.) under the reference CAV2 Lot #0830 pool-033093, with a titer of $10^{7.4}$ $TCID_{50}$/ml. Madin and Darby canine kidney (MDCK) cell line was also provided by Rhone Merieux Inc. CAV2 is commercially available from Rhone Merieux Inc. as a canine vaccine.

Example 2

Virus Culture and Cloning

MDCK cell suspensions were seeded in MEM (Gibco, Grand Island, N.Y.) supplemented with 7.5% fetal bovine serum (Sigma, St Louis, Mo.), sodium pyruvate (Gibco, 1 mM final), glutamine (Gibco, 2 mM final), penicillin (Gibco, 50 U/ml), streptomycin (Gibco, 50 mg/ml) and non essential amino acids (NEA)(Gibco, 0.1 mM final) and cultured at $37^{itch}$ in 5% $CO_2$. Confluent MDCK cells were infected with serial dilutions of CAV2 and cultured under a 0.6% agarose overlay at $37^{itch}$ in 5% $CO_2$. CAV2 was subjected to several rounds of plaque purification. A plaque purified CAV2 was amplified in a T25 MDCK flask. When the culture CPE was complete, infected cells were collected and their CAV2 content was titrated on MDCK cell monolayers under agarose. The virus stock was further amplified by infecting a confluent T175 MDCK flask with a multiplicity of infection (MOI) of 0.1. The titer of the T175 MDCK flask amplified virus was established to be $10^8$ p.f.u/ml.

Example 3

Viral DNA Purification

Roller bottles containing confluent MDCK cell monolayers ($10^8$ cells/bottle) were infected at a MOI of 0.1 pfu/cell with plaque purified CAV2 virus. Three days later the infected monolayer were harvested and subjected to low speed centrifugation (1K g, 15 minutes, 15° C.). The cell pellets were stored at −70° C. The frozen pellets were subsequently thawed at 37° C. and carefully resuspended in 10 mM Tris HCl pH 8.0 and 10 mM EDTA buffer (35 ml/$10^8$ cells) to limit cellular DNA shearing. SDS was added to the resuspended pellets to a final concentration of 1%. After 15 minutes incubation at room temperature NaCl was added to a concentration of 1.25 M. After 3 hours incubation at 4° C. the material was centrifuged at 25K g for 20 minutes at 4° C. Dense white pellets containing salts and cellular DNA were discarded and supernatants were digested with Proteinase K (300 µg/ml final concentration) at 42° C. for 4 hours and subsequently heated at 65° C. for 30 minutes. Two cycles of phenol-chloroform and chloroform extractions were performed prior to recovery of viral DNA by ethanol precipitation in the presence of 0.3 M sodium acetate pH 6.0. The viral DNA pellet was washed with 70% ethanol before being air dried for 1 hour and subsequently resuspended in 2 ml of $H_2O$. This procedure typically yields approximatively 4 mg of purified CAV2 DNA. Purified viral DNA was stored at −20° C. until further utilization.

Example 4

Viral DNA Restriction Analysis

Aliquots of purified CAV2 DNA were digested with a set of restriction enzymes purchased from Boehringer Mannheim Corp. (Indianapolis, Ind.) accordingly to the manufacturer's specifications. Restricted DNA samples were fractionated by electrophoresis on a 1% agarose gel and the corresponding restriction fragments were visualized under UV light after staining of the gel with ethidium bromide (4 µg/ml). Table 1 summarizes the size of the various restriction fragments.

Example 5

Identification and Characterization of the Restriction Fragment Containing the E3 Region 1. Southern blot analysis of specific endonuclease restricted CAV2 DNA.

Four µg aliquots of purified CAV2 DNA were digested with BamHI, BqlI, HindII, HindIII and PstI, respectively, before being fractionated by electrophoresis through a 1% agarose gel. The gel was soaked in 0.25 M HCL for 30 minutes before being washed in $H_2O$ for 5 minutes. Viral DNA was subsequently denatured in 0.5 M NaOH and 0.9M NaCl solution for 30 minutes. After being rinsed with $H_2O$ for 5 minutes, DNA was renatured by two subsequent baths in 0.5 M tris HCl pH 7.5 containing 3 M NaCl. DNA was subsequently transferred overnight in 10× SSC (1.5M NaCl, 0.15M Na Citrate pH 7.4) buffer onto a nylon membrane (Hybond N, Amersham Life Sciences, Cleveland, Ohio). The nylon membrane was air dried for one hour before being submitted to UV cross-linking for 3 minutes. A 6 hours prehybridization was performed at 65° C. in 4× SSC, 25% Denhardt's solution (v/v), 0.1% SDS (v/v), 0.1% Na pyrophosphate and denatured hering sperm DNA (500 µg/ml) solution.

2. Preparation of the probes specific for CAV2 PVIII and Fiber genes.

Since in most adenoviruses the E3 region is comprised between the two structural genes, PVIII and fiber, Applicant took advantage of a previously published partial sequence of the CAV2 (Manhattan strain) genome (Linne, 1992) to design two specific primers pairs for each of these genes. Oligonucleotides LF189 (5'-TCAGTCATAGCCATCGACAGA-3') (SEQ ID NO: 26) and LF190 (5'-GTGCTGGCTGGCACGGGCATT-3') (SEQ ID NO: 27) were designed to correspond to sequences within the 3' end of the CAV2 PVIII gene whereas oligonucleotides LF191 (5'-ATGTCCACCAAAGTCCCCTCT-3') (SEQ ID NO: 28) and LF192 (5'-CCCGGGGCGTCGTATGGATAT3') (SEQ ID NO: 29) were designed to correspond to sequences within the 5' end of the CAV2 fiber gene.

A 302 bp DNA PVIII specific probe was generated by mixing 10 ng of purified CAV2 DNA with 5 μl of 10× PCR buffer, 3.75 μl of 2 mM dNTPs, 26 μl H2O, 0.25 μl of Taq polymerase (5.0 u/μl), 5 μl of 5 μM 5' end primer LF189 and 5 μl of 5 AM 3' end primer LF190. A 30 cycle PCR amplification was performed in a 0.5 ml tube containing 40 μl of mineral oil using the following profile: 94° C. 1 minute, 55° C. 1 minute and 72° C. 1 minute. A 190 bp DNA Fiber specific probe was generated by PCR by swapping primer LF189 with primer LF191 and primer LF190 with primer LF192 in the previously described protocol. Both PCR reactions were electrophoresed through a 1% agarose gel and the corresponding PCR products were isolated using the Gene Clean procedure according to the manufacturer (Bio 101, Inc., La Jolla, Calif.) specifications. 100 ng aliquots of each probe was labelled by mixing with 1 μg of random hexamers (Pharmacia, Piscataway, N.J.) in a total volume of 13 μl and subsequently boiled for 3 minutes before being incubated with 2.5 μl of a dCTP, dTTP and dGTP mixture (each at a concentration of 0.5M), 2.3 μl Klenow 10× buffer, 1.5 μl Klenow enzyme (2u/μl) and 5μl of $^{32}$P-a-DATP (3000 Ci/mmol, 10 mCi/ml, NEN, Boston, Mass.) at RT for 4 hours. The reaction was stopped by adding 100 μl of Stop solution (IBI Prime Time kit). 25 μl of each probe was heat denatured (100° C.) for 3 minutes before being incubated overnight at 65° C. with the previously described nylon membrane in a total volume of 50 ml of prehybridization solution. The nylon membrane was subsequently washed at 65° C. in 6× SSC, 0.1% SDS and 50 mM Na Pyrophosphate solution for 2 hours. Viral DNA restriction fragments complementary to the radiolabelled DNA probes were identified by autoradiography.

3. Identification and cloning of the restriction fragment containing the E3 region.

The HindIII fragment A (4.0 Kbp) was identified as the shortest well isolated restriction fragment recognized by both PVIII and Fiber probes, suggesting that it may contain the entire CAV2 E3 region. This fragment was isolated using Gene Clean procedure as previously described and subsequently subcloned into the HindIII site of the vector pBluescript SK+(Stratagene, La Jolla, Calif.) generating plasmid pLF027.

4. Characterization of the CAV2 E3 region.

The CAV2 E3 region was analyzed by restriction digestion of pLF027 and by sequencing pLF027 according to Sequenase 2.0 kit instructions (US Biochemical, Cleveland, Ohio). Sequence analysis was performed using the MacVector software (Eastman Kodak, Rochester, N.Y.). The pLF027 restriction map is shown in FIG. 2. The corresponding sequence of the pLF027 including the CAV2 E3 region [defined as the DNA stretch between the PVIII stop codon (#1,413 in pLF027) and the fiber ATG initiation codon (#2,945 in pLF027)] is represented in FIG. 1. Analysis of sequencing data revealed that the CAV2 E3 1,533 bps were 100% homologous with the previously identified CAV2 (Manhattan strain) E3 region (Linne, 1992). Analysis of the amino acid sequence deduced from the nucleotide sequence revealed that the rightward coding strand of the CAV2 E3 region encodes two potential polypeptides (ORF1 and ORF2) whereas the leftward coding strand encodes a single potential polypeptide (ORF3). The characteristics of these ORFs are presented in Table 2.

Example 6

Generation of Donor Plasmid pLF086.

1. Introduction of BglII and MluI restriction sites in the middle of the CAV2 E3 sequence.

Figure 4:
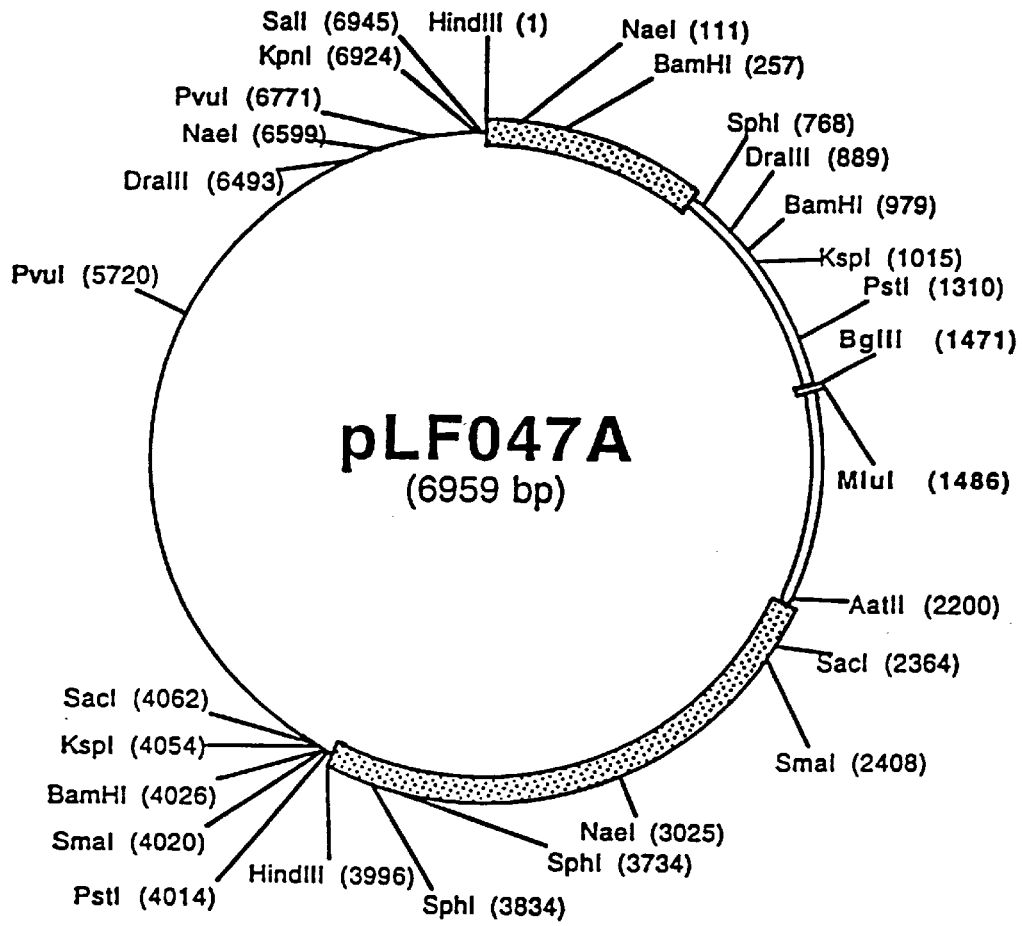
FIG. 4 shows a restriction map of pLF047A.
Figure 6:
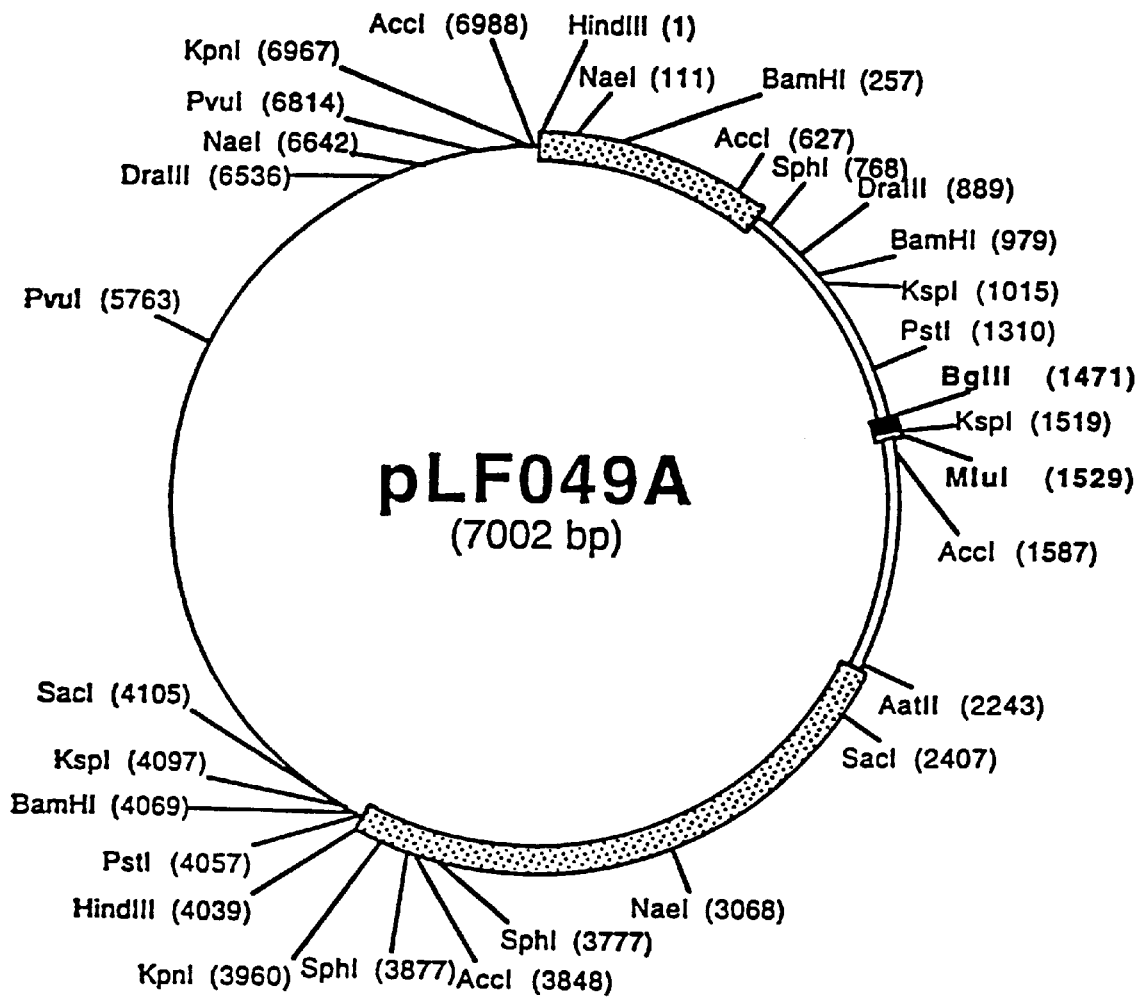
FIG. 6 shows a restriction map of pLF049A.

In order to facilitate further manipulations, a 24 bp DNA linker (5'-GATACGCGTTCCATTAGCAGATCT-3') (SEQ ID NO: 30) containing unique BalII and MluI restriction sites were introduced between nucleotide #1487 and #1966 of the CAV2 E3 region (as described in FIG. 1) by a double round PCR amplification procedure. Initial PCR amplifications was performed using pLF027 DNA as template and using the following primer couples (LF327(5'-GGACACCTTTCTGATCAGTTCATT-3')/LF324(5'-GATACGCGTTCCATTA GCAGATCTTTGAGGGGCCTGGAAATAGGC-3') (SEQ ID NO: 31, 32)] and [LF326(5'-GGTTGTGTGGAAGACCCGGGGGCG-3')/LF325(5'-AGATCTGCTAATGGAA CGCGTATCGCTGCCCCCACAGTACAGCAA-3') (SEQ ID NO: 33, 34)], to generate two partially overlapping DNA fragments of 838 bp and 956 bp, respectively. The second round of PCR amplification was performed in the presence of both partially overlapping purified DNA fragments and both external primers LF327 and LF326. The resultant 1,794 bp DNA fragment was digested with PstI and AatI and the resultant 890 bp PstI/AatII fragment was purified and ligated with the 6,069 bp PstI/AatII DNA fragment of pLF027, generating pLF047A (FIGS. 3 and 4). All PCR amplifications were performed using the conditions previously described. The 6,944 bp MluI/BglII pLF047A was subsequently ligated with preannealed oligonucleotides LF328 (5'-GATCTGTTAACCCTAAGGCCATGGCATATGTCGCGA-GGCCATCGTGGCCGCGGCCGCA-3') (SEQ ID NO: 35) and LF329 (5'-CGCGTGCGGCCGCGGCCACGATGGCCTCGCGACA-TATGCCATGGCCTTAGGGTTAACA-3') to (SEQ ID NO: 36) generate pLF049A (FIGS. 5 and 6).

This manipulation results in the exchanging of 60 bp of the CAV2 E3 region with a 60 bp BglII/MluI polylinker DNA fragment. The size of the E3 region has not been modified and E3 ORF1 remained unaffected. However, sequences corresponding to E3 ORF2 have been disrupted and those of the E3 ORF3 were completely eliminated.

2. Generation of donor plasmid pLF086.

Figure 8:
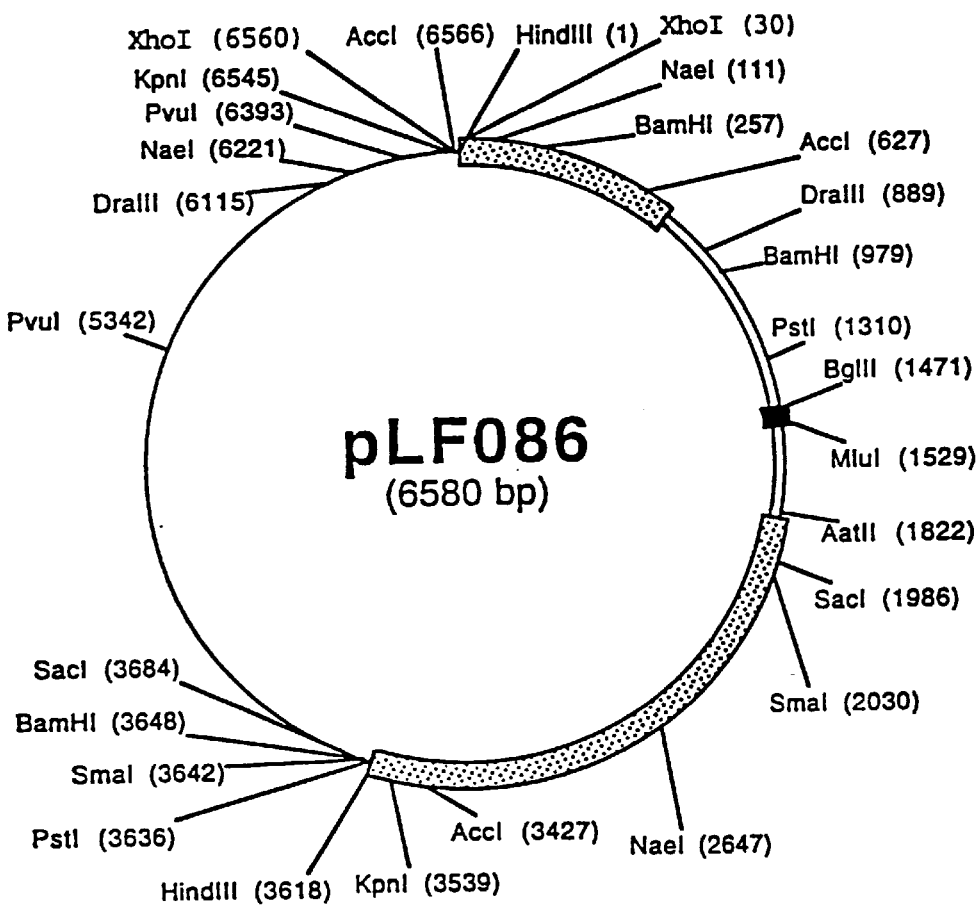
FIG. 8 shows a restriction map of pLF086.

In order to delete part of the CAV2 E3 region a 428 bp deletion was engineered 3' of the pLF049A MluI site. A 537 bp DNA fragment was generated by PCR as previously described using the pLF027 template and the primers pair LF361(5'-CTAGTCATCTTAACGCGTGTCC-TCAACATCACCCGCGA-3')/LF334(5'-CTT GCTTGTTATTAAAAAAAG-3') (SEQ ID NO: 37, 38). This 551 bp fragment was subsequently digested with MluI and AatI before being purified and ligated with the 6,284 bp MluI/AatII DNA fragment of pLF049A, generating pLF086 (FIGS. 7 and 8). This manipulation, which introduces a 27% (428 bp) deletion of the E3 region, further expands the deletion of E3 ORF2 towards its 3' end but does not interfere with E3 ORF1 coding sequence.

Example 7

Cloning and Characterization of the Restriction Fragment Containing the Right End of the Viral Genome 1. Cloning of the restriction fragment containing the right end of the viral genome.

Previously published restriction maps of the CAV2 (Glasgow strain) genome indicated the presence of a unique SalI restriction site located at 84.0 map units (Spibey and Cavanagh 1989). SalI digestion of CAV2 DNA (30 μg) generated the predicted 3.2 kbp and 29 kbp DNA fragments. The CAV2 DNA SalI B fragment (3.2 kbp) was gel purified using Gene Clean procedure as previously described and resuspended in 20 μl of $H_2O$.

Approximatively 3 μg of purified SalI B fragment was denatured by the addition of 2 μl of 1 N NaOH in a total volume of 22 μl for 90 minutes at RT to eliminate the known protein moiety (Robinson et al., 1973) which is covalently linked to the 5' termini of adenovirus genome. The DNA was subsequently renatured by the addition of 1.3 λl of 2M Tris HCl pH 7.5 and incubated successively at 65° C. for 1 hour and at RT for 1 hour before being ligated with the 2.919 bp SalI/SmaI fragment of pBluescript SK+ to generate pLF056.

2. Characterization of the restriction fragment containing the right end of the viral genome.

Figure 10:
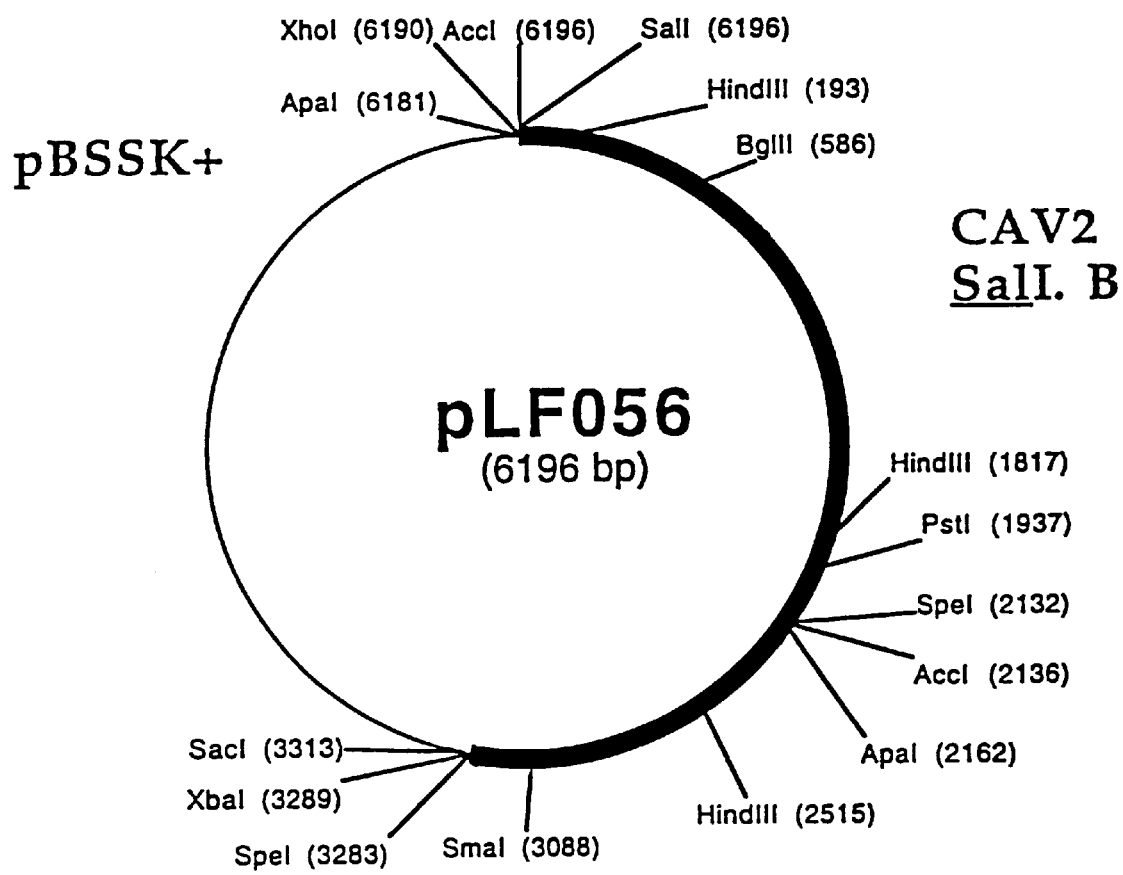
FIG. 10 shows a restriction map of pLF056.

The 3.2K bp right end of the CAV2 genome was analyzed by restriction digestion of pLF056 and by sequencing of the same plasmid according to Sequenase 2.0 kit instructions. Sequence analysis was performed using the MacVector software. The pLF056 restriction map is shown in FIG. 10, and FIG. 9 shows the DNA sequence. Sequencing data revealed that the CAV2 DNA SalI B fragment is 3,274 bp in length. Two unique restriction sites within the CAV2 genome have been localized within the CAV2 DNA SalI B fragment: BalII at position #587 and SpeI at position #2,133. The 196 bp ITR (FIG. 9) nucleotide sequence of CAV2 situated at the right termini is 100% homologous with the CAV2 right and left ITR sequences previously published for the CAV2 Vaxitas and Glasgow strains, respectively (Cavanagh et al. 1991). Analysis of the remainder of the CAV2 SalI-B fragment DNA versus the DNA sequence of the previously mentioned CAV2 strains shows significant divergence with only 45% homology.

Example 8

Generation of pLF061

Figure 12:
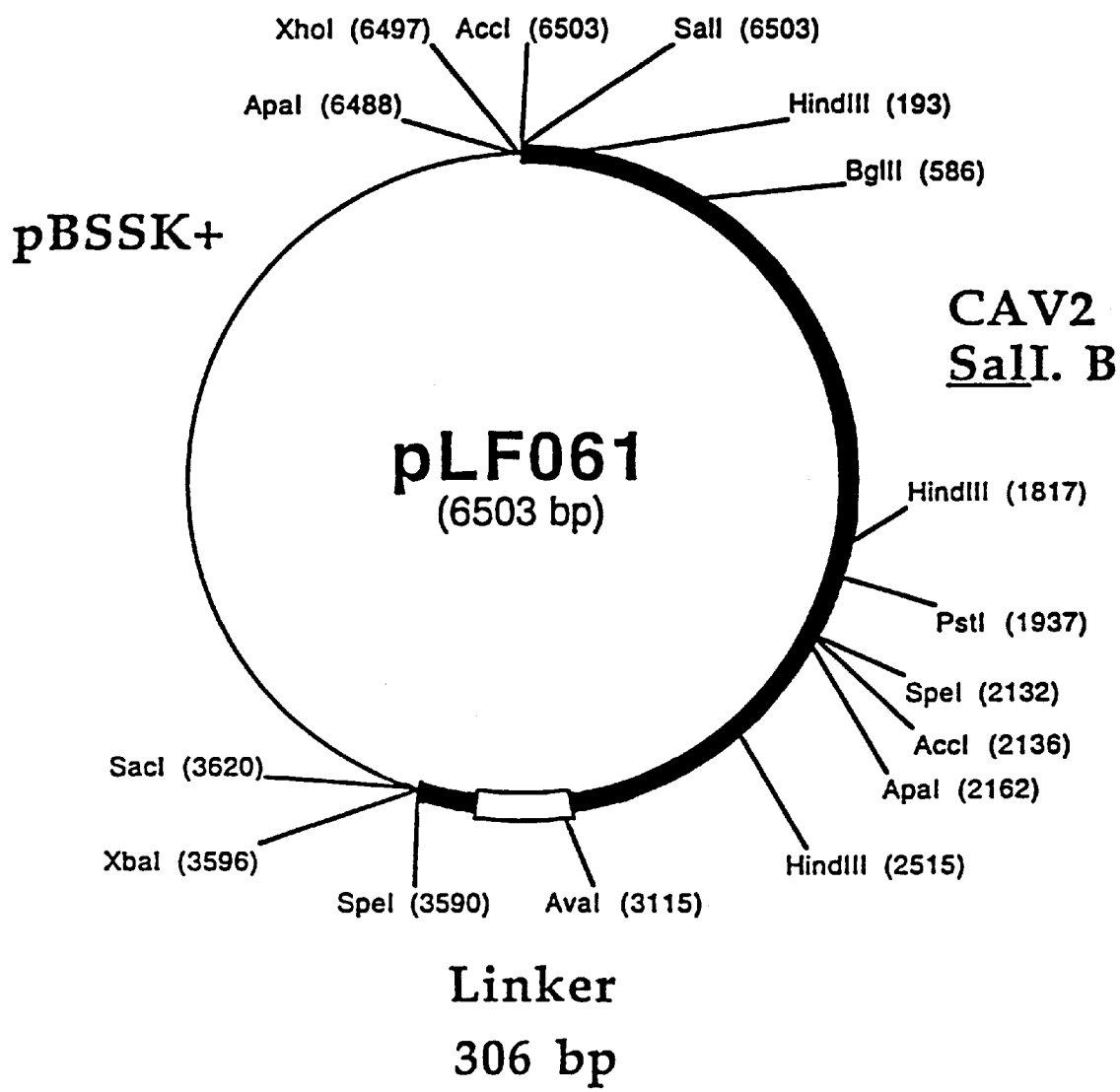
FIG. 12 shows a restriction map of pLF061.

A NruI/EcoRV 312 bp tag DNA fragment (FIG. 11) was ligated with SmaI linearized pLF056 to generate pLF061 (FIG. 11; restriction map shown in FIG. 12).

Example 9

Transfection of Purified Viral DNA into MDCK Cells

Solution A was prepared by mixing 5 μg of purified CAV2 DNA with serum free MEM, supplemented as previously described, to a final volume of 300 μl. Solution B was prepared by adding 40 μl of Lipofectamine reagent (Gibco) to 260 μl of supplemented but serum free MEM medium. Solutions A and B were mixed together and incubated at RT for 30 minutes. The CAV2 DNA/liposome complexes were gently mixed with 2.4 ml of supplemented MEM medium (serum free) before being added to MDCK cell monolayer that was 75% confluent. After 24 hour incubation at 37° C. in presence of 5% CO2, the serum free medium was removed and replaced by 3 ml of supplemented MEM medium containing 5% $CO_2$. The culture was incubated at 37° C. in presence of 5% $Co_2$ for 8 days with 2 ml of supplemented MEM medium being added to it on the third day. No CPE could be evidenced during this incubation. On day 8 the transfected MDCK cells were scraped off and harvested in a total volume of 5 ml. After 2 rounds of 2 minutes sonication on ice, 2 ml of the transfected culture were used to infect a 100% confluent MDCK monolayer in a 150 mm diameter tissue culture dish for 1 hour at 37° C. in presence of 5% $CO_2$. The culture was subsequently overlaid with medium containing 0.6% agarose. Plaques are appearing after 5 days at 37° C. in the presence of 5% $Co_2$. Typically, a yield of at least 2,000 pfu/10 μg of purified DNA is observed.

Example 10

Generation of Recombinant CAV2 Virus vCA1

1. In vitro generation of a recombinant CAV2 genome.

20 μg of purified CAV2 DNA was digested with 30 U of SalI overnight at 37° C. The digested DNA was phenol chloroform extracted and ethanol precipitated before being resuspended in $H_2O$ to a concentration of 370 ng/μl. 5 μgof SalI digested CAV2 DNA were in vitro ligated with 5 μg of the 3,557 bp SalI/SacI pLF061 DNA fragment overnight at 15° C. in the presence of 400 U of ligase (NEB, Beverly, Mass.) in a total volume of 50 μl.

2. Isolation of CAV2 recombinant virus vCAl.

The whole ligation reaction was subsequently used to transfect a 75% confluent MDCK monolayer as previously described. 4 ml of the harvested transfected culture were used to infect two 150 mm diameter tissue culture dishes. A total of 8 plaques became apparent after 10 days of incubation. All plaques were picked and resuspended in 1 ml of supplemented MEM medium before being sonicated for 2×2' on ice. The clarified culture medium was serially diluted and used to infect 100% confluent MDCK cells monolayer in 60 mm diameter tissue culture dishes. After 6 days of culture the agarose overlay was discarded and the infected monolayer was blotted onto nitrocellulose filters following the procedure described in Perkus et al. 1993. The filters were processed and subsequently hybridized with a labelled NruI/EcorV 312 bp tag DNA fragment following classical procedures previously described. Autoradiography experiments demonstrated that five out the initially detected 8 plaques contain recombinant CAV2 viruses. One well isolated plaque identified by plaque hybridization was picked and submitted to four additional rounds of plaque purification on MDCK cells. Hybridization with the probe was confirmed after each round of purification. The plaque purified recombinant CAV2 virus was named vCA1.

3. Characterization of VCA1.

To further characterize vCA1 a small scale DNA purification was performed. Briefly, purified vCA1 recombinant virus was used to infect a 100% confluent MDCK monolayer ($10^6$ cells). After 5 days, when CPE were completed, the infected culture was scraped and harvest. The sonicated and clarified culture medium was treated with proteinase K (500 μg/ml final concentration) for 2 hours at 42° C. The enzyme was inactivated by heating the reaction at 65° C. for 20 minutes and the total DNA was subsequently phenol chloroform extracted and ethanol precipitated before being resuspended in H$_2$O. Purified total DNA was subsequently treated with RNase T1, phenol chloroform extracted and ethanol precipitated before being resuspended in H$_2$O to a final concentration of 1.2 µg/ml. 5 µg aliquots of purified vCA1 were independently digested with BqlII and SpeI. Since those two sites are unique within the CAV2 genome a 29 kbp and 3 kbp fragments are expected from the BglII digestion, whereas a 30.5 kbp and a 1.5 kbp fragments are expected from the SpeI digestion. These restriction fragments are indeed observed demonstrating that vCA1 is a recombinant CAV2 virus which has incorporated 300 bp of heterologous DNA within the right end of its genome.

To further demonstrate that vCA1 has indeed incorporated the expected tag DNA fragment, the VCA1 DNA was analyzed by Southern blotting; and, this confirmed that vCA1 indeed incorporated the tag DNA fragment.

To confirm that the CAV2 SmaI has been used as the insertion site, a 1.9 kbp DNA fragment was amplified from purified vCA1 DNA with the couple of primers LF379 (5'-TCACGCCCTGGTCAGGGTGTT-3') (SEQ ID NO: 39) and LF407 (5'-GCCATCGCGTCAACCTGA-3') (SEQ ID NO: 40) using the conditions previously described. A partial sequence analysis of 1.940 bp DNA fragment conducted using primers LF63 (5'-ATGATGTCTGGGGACATG-3') (SEQ ID NO: 41), LF379 (5'-TCACGCCCTGGTCAGGGTGTT-3') (SEQ ID NO: 42) and LF384 (5'-ACCACGCGCCCACATTTT-3') (SEQ ID NO: 43) confirmed that the heterologous tag DNA was indeed inserted into the CAV2 SmaI site to yield vCA1.

Example 11

Generation of Recombinant CAV2 Virus vCA2

Ten pg of pLF086 were digested with HindIII and the resulting 3.6 kbp DNA fragment was isolated using Gene Clean procedure as previously described and resuspended in H$_2$O to a concentration of 100 ng/gl. MDCK cells were transfected using the Lipofectamine based procedure previously described. Solution A was prepared by mixing 0.5 µg of 3.600 bp HindIII DNA fragment with 3 µg of purified CAV2 DNA. Solution A total volume was brought to 300µl with supplemented serum free MEM medium. Transfected cells were harvested after 8 days and plate out on 150 mm diameter tissue culture dishes as previously described. Plaques were lifted as previously described and hybridized with 5' end labelled oligonucleotide LF328. Five viral plaques crossreacting with the probe were picked and subsequently submitted to 4 rounds of plaque purification as previously described. The plaque purified recombinant CAV2 virus was named vCA2. (Note that plaque purification is a use of the recombinant for replication of the DNA, or for replication of the virus, i.e., a vector use of the recombinant, thereby showing that there is no restriction or limit on the exogenous DNA).

2. Characterization of vCA2.

To characterize vCA2, a small scale DNA purification was performed as previously described for vCA1. Purified vCA2 DNA and wild-type CAV2 DNA were independently digested by HindIII and the restricted DNAs were subsequently fractionated by electrophoresis through a 1% agarose gel. A 3.6 kbp HindIII fragment was visualized in the vCA2 sample whereas a 4.0 kbp fragment was present in the wild-type CAV2 sample, proving that the E3 region has been deleted of 428 bp in vCA2 genome.

To further demonstrate that the expected tag (oligonucleotides LF328/LF329) has indeed been incorporated into the vCA2 E3 region, Southern blot was performed and this confirmed incorporation of the tag.

This result indicates that the complete CAV2 E3 ORF2 is not necessary in tissue culture. It also demonstrates that part of the CAV2 E3 ORF2 sequences can be exchanged with heterologous DNA and thus validates a second insertion site within the CAV2 genome. This results also proves that part of the CAV2 E3 region can be deleted to compensate for the introduction of foreign DNA into the SmaI site previously described in the derivation of vCA1.

Example 12

Figure 14:
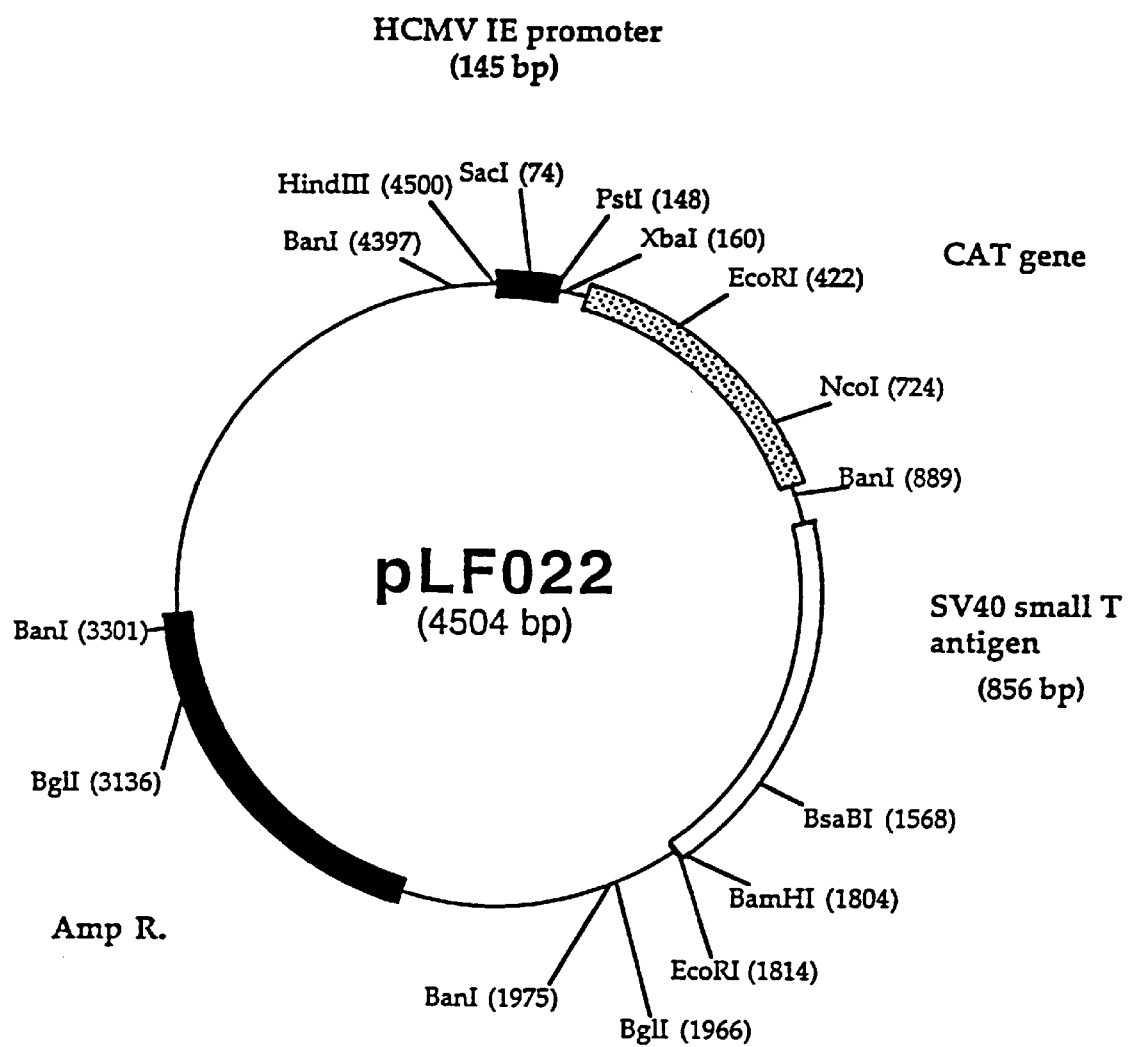
FIG. 14 shows a restriction map of pLF022.

Generation of Subfragment Promoters, Reduced or Modified Polyadenylation Cassettes, Promoters with 5'UTR Replaced, and Plasmids and Recombinants Containing Same 1.1 Generation of pLF022, an expression vector in which the CAT reporter gene has been placed under the control of a subfragment (145 bp) of the HCMV-IE promoter:

DNA from human cytomegalovirus (hCMV) (Towne strain) was prepared as described in Lafemina et al. (1989). Amplification of the 3' end of the human cytomegalovirus immediate early promoter (hCMV-IE) was performed by PCR as previously described, using the primers pair LF172 (5'-ATCGTAAAGCTTAATGTCGTAATAACCCCGC-3')/ LF159 (5'-TCTACTGCAGCCGGTGTCTTCTATGGAGGTCA-3') and hCMV DNA (10 ng) as template. The resulting 166 bp DNA fragment was subsequently digested with PstI and HindIII before being purified using Gene Clean procedure and directly ligated with the 4,348 bp PstI/HindIII DNA fragment of pCAT-Basic Vector (Promega, Madison, Wis.), generating pLF022 (FIGS. 13, 14, SEQ ID NO: 7). The regulatory sequences present in the pLF022 expression cassette are a 145 bp fragment of the hCMV IE promoter and a 856 bp cassette containing the SV40 small t antigen and polyadenylation signal.

Figure 16:
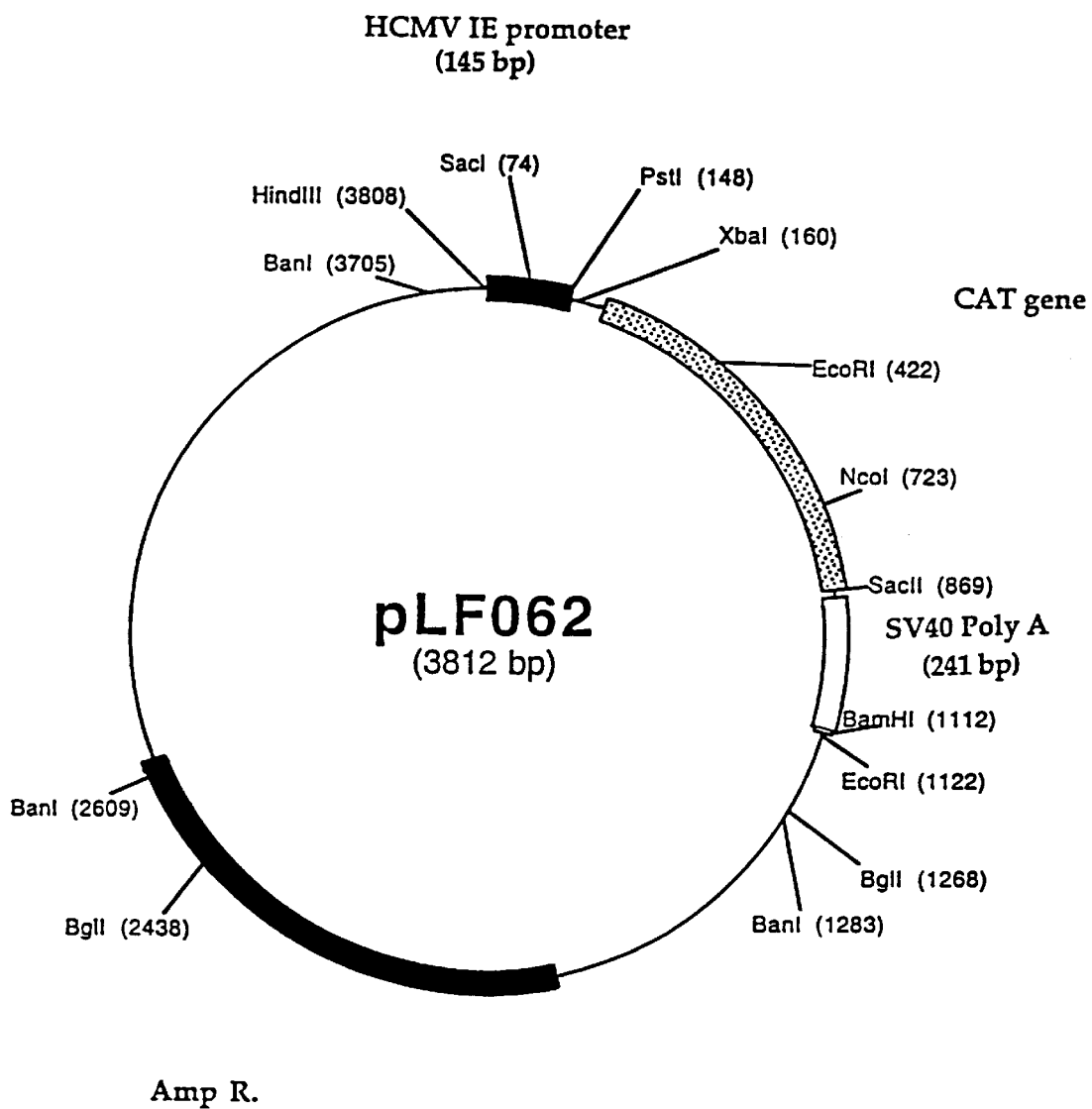
FIG. 16 shows a restriction map of pLF062.

1.2 Generation of pLF062, a derivative of pLF022 in which the SV40 polyadenylation cassette has been reduced to 241 bp:

In order to reduce the size of the SV40 small t antigen and polyadenylation signal cassette (856 bp) of pLF022, the following manipulations were performed. A 170 bp DNA fragment was amplified by PCR using primers LF377 (5'-TCTTCGCCCCCGTTTTCACCATGG-3') and LF378 (5'-ATCACGCCGCGGCTTAAAAAAATTACGCCCCGCC-CT-3') and pLF022 DNA (10 ng) as template. The purified amplified fragment was resuspended in 18 ml H$_2$O and incubated with 1 U of Klenow enzyme (Boehringer Mannheim, Indianapolis, Ind.) for 30 minutes at room temperature in the presence of 800 µM dNTPs. The modified DNA fragment was phenol-chloroform extracted and recovered by ethanol precipitation before being digested with NcoI. The resulting 136 bp fragment was ligated with the 3,655 bp NcoI/BsaBI DNA fragment of pLF022, generating pLF062 (FIGS. 15, 16, SEQ ID NO: 8). pLF062 contains two repeats of the consensus polyadenylation signal AATAAA downstream of the CAT gene. The size of the CAT expression cassette in pLF062 is 1,119 bp as compared to 1,804 bp in pLF022. Regulatory sequences in pLF062 expression cassette are a 145 bp fragment of the hCMV-IE promoter and a 241 bp cassette containing the SV40 polyadenylation signal.

1.3 Generation of pLF066, a derivative of pLF062 in which the Ad2 TPL has been cloned downstream of the HCMV-IE promoter:

In order to allow the expression of the reporter gene after the onset of CAV2 replication, pLF062 CAT expression cassette was modified by cloning the human Ad2 tripartite leader (Ad2 TPL) downstream of the hCMV-IE promoter transcription start site.

Oligonucleotides SPH6ETr1 (5'-AATTCGGTACCAAGCTTCTTTATTC-TATACTTAAAAAGTGAAAATAAATA-CAAAGGTTCTTGACT CTCTTC-3', SPH6ETr2 (5'-CGCATCGCTGTCTGCGAGGGCCAGCTGTTGGGCTC-GCGGTTGAGGACAAACTCTTCGCGGTCTTT CCAGT-3'), SPH6ETr3 (5'-ACTCTTGGATCGGAAACCCGTCGGCCTC-CGAACGTACTCCGCCACCGAGGGACCT-GAGCGAGTCC GCATC-3'), SPH6ETr4 (5'-GACCGGATCGGAAAACCTCTCGAGAAAGGCGTCTA-ACC AGTCACAGTCGCAAGCCCGGGT-3'), SPH6ETr5 (5'-CTTTGTATTTATTTTCAC TTTTTAAGTATAGAATAAAGAAGCTTGGTACCG-3'), SPH6ETr6(5'GAAGAGT TTGTCCTCAACCGCGAGC-CCAACAGCTGGCCCTCGCAGACAGCGAT-GCGGAAGAGAGTCAAGAAC -3'), SPH6ETr7 (5'-GCTCAGGTCCCTCGGTGGCGGAGTACGTTCGGAG-GCCGACGGGTTTCCGATCCAAGAGTACTGGA AAGACCGC-3'), and SPH6ETr8 (5'-CTAGACCCGGGCTTGCGACTGTGACTG-GTTAGACGCCTTTCTCGAGAGGTTTTC-CGATCCGGTCG ATGCGGACTC-3,) were kinased and annealed and the 271 bp product was gel purified.

The complete Ad2 TPL was subsequently amplified by PCR using primers LF394 (5'ATCGTCCTGCAGACTCTCTTCCGCATCGCTGTCT-GC-3') and LF395 (5'-GCTCTAGACTTGCGACTGTGACTGGTTAG-3') and the gel purified annealed oligonucleotides as template.

Figure 18:
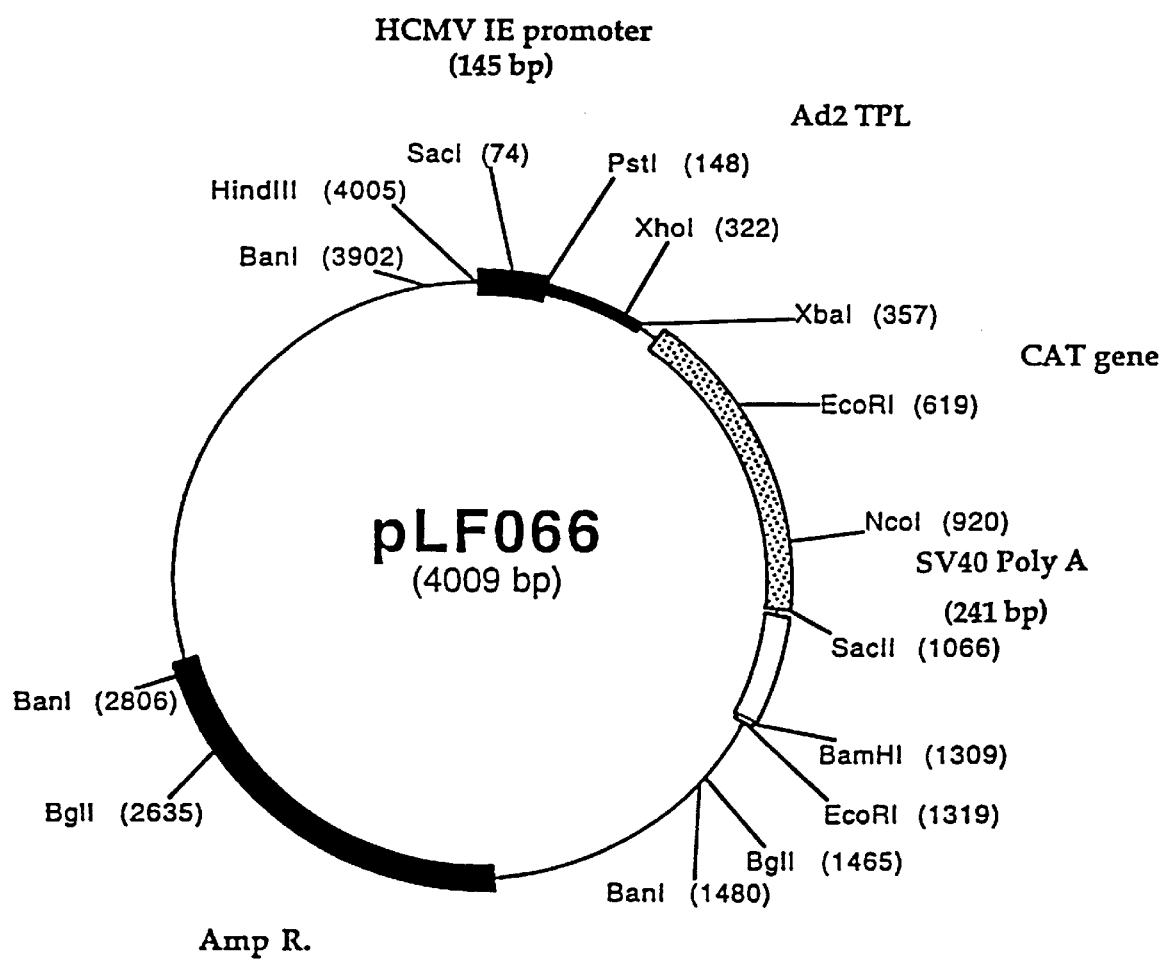
FIG. 18 shows a restriction map of pLF066.
Figure 22:
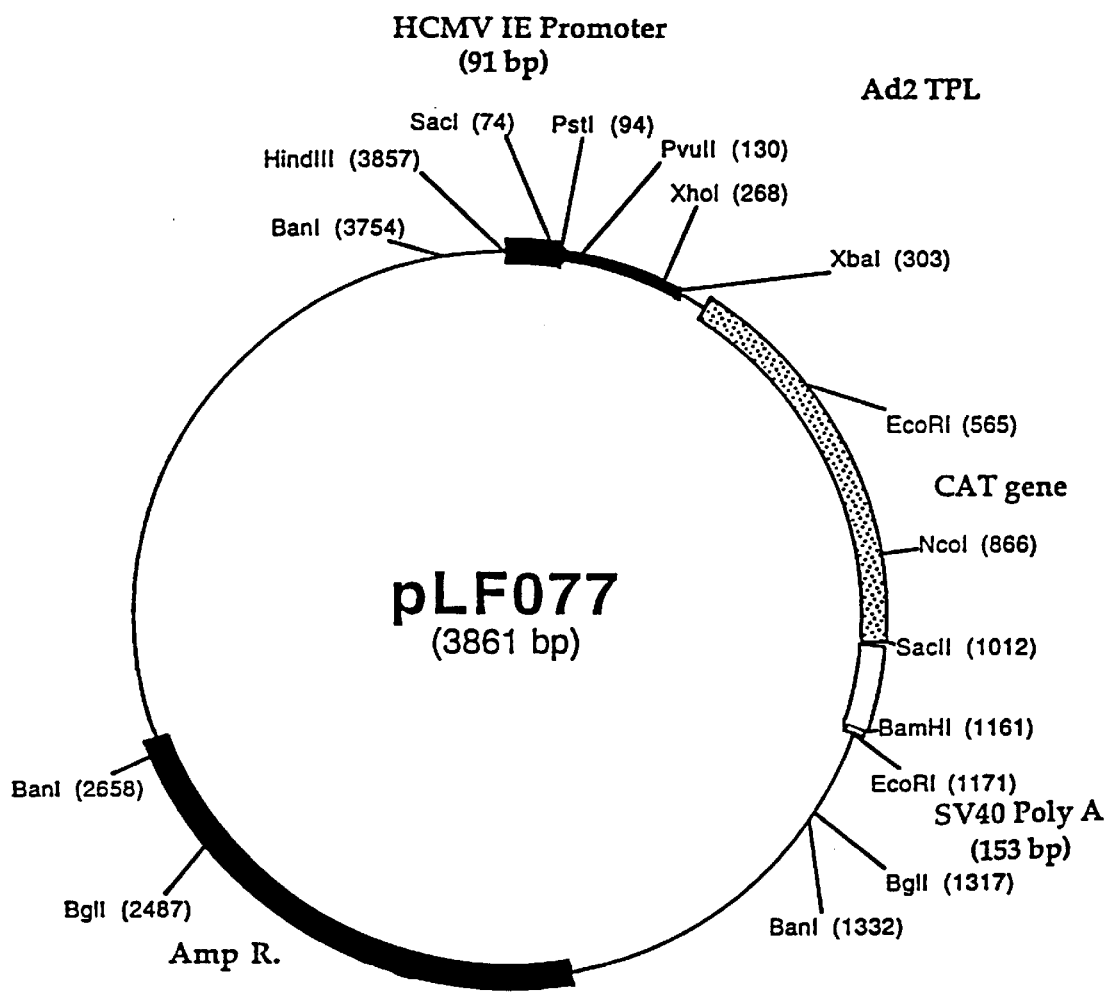
FIG. 22 shows a restriction map of pLF077.

The resulting 220 bp DNA fragment was subsequently digested by PstI and XbaI before being purified using Gene Clean procedure as previously described and directly ligated with the 3,800 bp PstI/XbaI pLF062 fragment, generating pLF066 (FIGS. 17, 18, SEQ ID NO: 9). Regulatory sequences in pLF066 expression cassette are a 145 bp fragment of the hCMV-IE promoter in which the 5'UTR has been replaced by the 202 bp Ad2 TPL and a 241 bp cassette containing the SV40 polyadenylation signal.

1.4 Generation of pLF069, a derivative of pLF066 in which the HCMV-IE 5'UTR has been replaced by the Ad2 TPL:

The HCMV-IE promoter 5'UTR (54 bp) present in pLF062 was deleted using the following procedure. Annealed oligonucleotides LF397 (5'-CGTTTAGTGAACCGTCTGCA-3') and LF398 (5'-GACGGTTCACTAAACGAGCT-3') were ligated with the 3,936 bp DNA fragment of pLF062, generating pLF069 (FIG. 19, 20, SEQ ID NO: 10). Regulatory sequences in pLF069 expression cassette are a 91 bp fragment of the HCMV-IE promoter in which the 5'UTR has been replaced by the 202 bp Ad2 TPL and a 241 bp cassette containing the SV40 polyadenylation signal.

1.5 Generation of pLF077, a derivative of pLF069 in which the SV40 polyadenylation cassette has been reduced to 153 bp:

A 160 bp subfragment of SV40 polyadenylation sequences was amplified by PCR using oligonucleotides M13R (5'-GTAAAACGACGGCCAGT-3') and LF409 (5'-ATCGTCCCGCGGAATTGTTGTTGTTAACTTGTT-3') and PCAT Basic DNA (long) as template. The resulting 145 bp DNA fragment was subsequently digested by KspI and BamHI before being purified using Gene Clean procedure and directly ligated with the 3,716 bp KspI/BamHI DNA fragment of pLF069, generating pLF077 (FIG. 21, 22, SEQ ID NO: 11). The CAT expression cassette size in pLF077 is 1,161 bp as compared to 1,804 bp in pLF022 (36% reduction). Regulatory sequences in pLF069 expression cassette are a 91 bp fragment of the HCMV-IE promoter in which the 5'UTR has been replaced by the 202 bp Ad2 TPL and a 153 bp cassette containing part of the SV40 polyadenylation signal.

Figure 24:
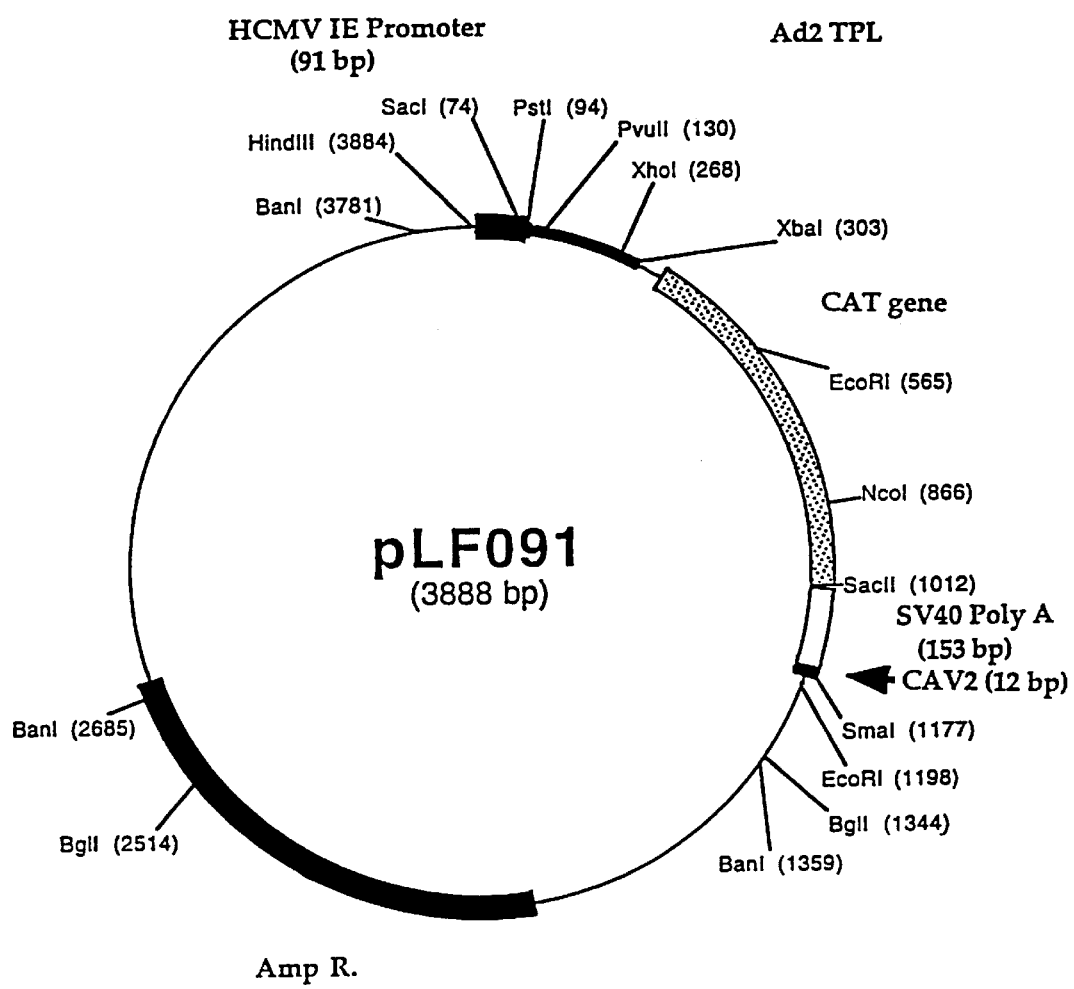
FIG. 24 shows a restriction map of pLF091.

1.6 Generation of pLF091, a derivative of pLF077 in which the 3' end of the polyadenylation signal has been modified:

The 12 bp (5'-TTTTTGGGCGTT-3') which are localised upstream of SmaI site at the 5' end of the right ITR sequence in the CAV2 genome were introduced downstream of the pLF077 polyadenylation cassette using the following procedure. A 1,000 bp DNA fragment was amplified by PCR using oligonucleotides LF423 (5'-ACGACCCGTAGAGGGCGTTGGACAGCAACTTGGC-CTCGCGGTTGAGGACAAACTCTT-3') and LF432 (5'-ATCGTCCCCGGGTTTTTGGGCGTTATCCAGACATG-ATAAGATACA-3') and pLF077 DNA (10 ng) as template. The 1,000 bp PCR DNA fragment was Gene Clean purified and modified by Klenow treatment before being digested by NcoI. The PCR reaction was electrophoresed through a 1.2% agarose gel and the 295 bp fragment was subsequently isolated using Gene Clean procedure. pLF077 was digested by BamHI and subsequently modified by the action of Klenow enzyme before being digested by NcoI. The digestion reaction was electrophoresed through a 1% agarose gel and the 3,567 bp restriction fragment was isolated using Gene Clean procedure, before being ligated with the aforementionned 295 bp DNA fragment, resulting in pLF091 (FIGS. 23, 24, SEQ ID NO: 12).

Figure 26:
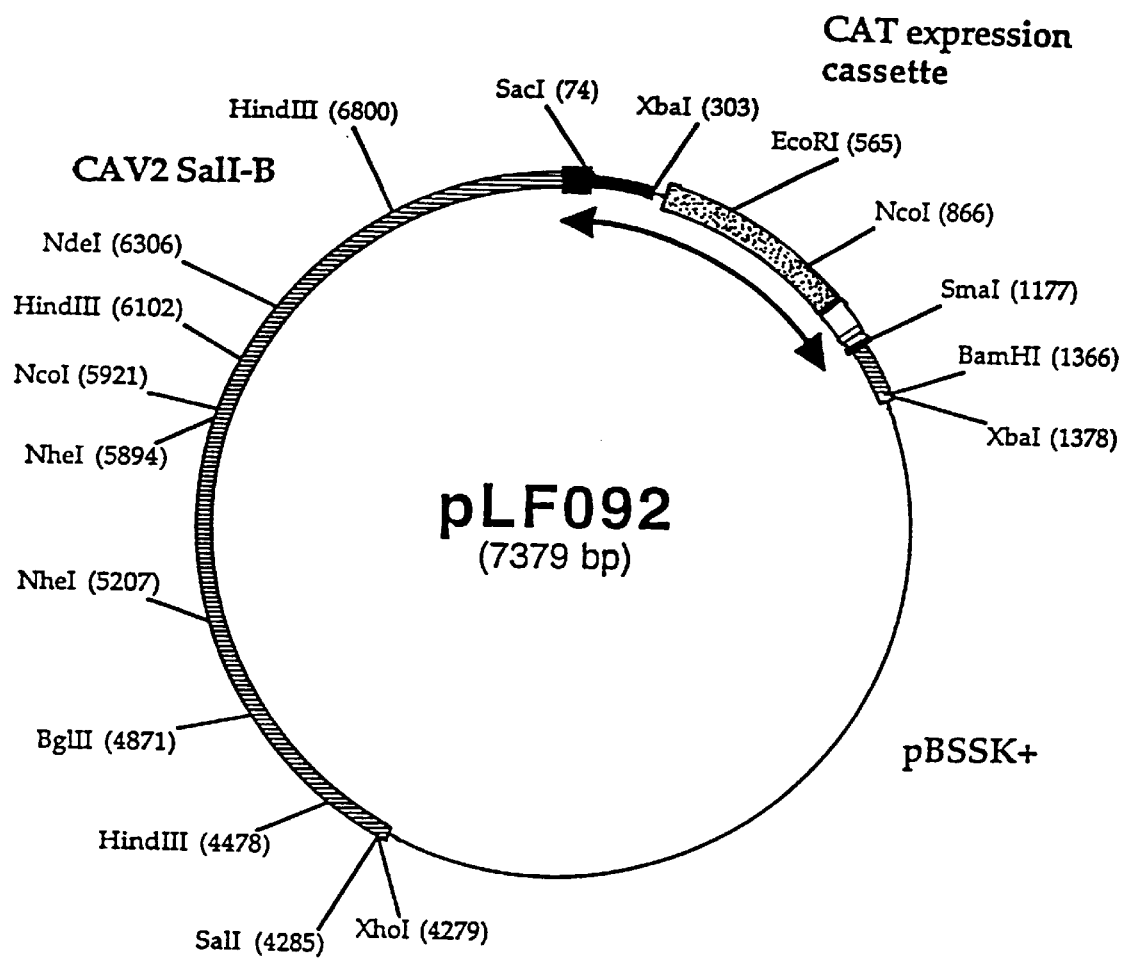
FIG. 26 shows a restriction map of pLF092.

1.7 Generation of pLF092, a CAT expression cassette donor plasmid:

The 1,180 bp HindIII/SmaI DNA fragment of pLF091, which contains the entire CAT expression cassette, was modified by the action of Klenov enzyme and subsequently ligated with the 6.2 kbp SmaI linearized pLF056 to generate pLF092 (FIGS. 25, 26, SEQ ID NO: 13). This plasmid corresponds to a donor plasmid for the insertion of the CAT expression cassette into an insertion site 12 bp upstream of the SmaI site at the CAV2 genome 5' end.

1.8 Generation of pLF105, a donor plasmid for the insertion of foreign DNA 12 bp upstream of the SmaI site at the 5' end of the right ITR sequence in the CAV2 genome:

A polylinker [NruI-AgeI-EcoRI-MluI-SalI-SmaI] constituted of preannealed oligonucleotides LF446 (5'-GGGTTTTTGGGCGTTTCGCGAACCGGTGAATTCAC-GCGTGTCGACCCC-3') and LF447 (5'-CCCAAAAACCCGCAAAGCGCTTGGCCACTTAAGT-GCGCACAGCTGGGG-3') was ligated with the 6.2 kbp SmaI linearized pLF056 to generate pLF105 (FIGS. 27, 28, SEQ ID NO: 14).

1.9 Generation of recombinant CAV2 virus vCA3, which contains a CAT expression cassette inserted into the right terminal end of the CAV2 genome:

Ten(10) µg of pLF092 were digested with HindIII and BamHI and the resulting 4.3 kbp DNA fragment was isolated using Gene Clean procedure and resuspended in $H_2O$ to a concentration of 100 ng/µl. MDCK cells were transfected using the Lipofectamine based procedure. Solution A was prepared by mixing 0.4 µg of 4.3 kbp HindIII/BamHI pLF092 fragment with 4.4 µg of purified CAV2 DNA. Solution A total volume was brought to 300 µl with supplemented serum free MEM medium. Transfected cells were harvested after 8 days and plated out on 150 mm diameter tissue culture dishes as previously described. A probe specific for the CAT reporter gene was generated by PCR using pCAT Basic DNA (10 ng) as template and primers pair LF218 (5'-ATCGTACATATGGAGAAAAAAATCACTGGATAT-3')/LF231 (5'-ATCGTAGATATCCTCGAGTTACGCCCCGCCCTGCC-ACTC-3'). The resultant 660 bp DNA fragment was labelled by random priming using a procedure previously described and subsequently hybridized with nitrocellulose membrane to lift viral plaques, as previously described. A plaque crossreacting with the probe was picked and subsequently submitted to 4 rounds of plaque purification, as previously described. The plaque purified recombinant CAV2 virus was named vCA3.

2. Characterization of vCA3.

2.1. Analysis of CAT gene expression by recombinant virus vCA3.

2.1.1. Detection of CAT enzymatique activity in vCA3 infected MDCK cells lysates.

Purified vCA3 recombinant virus and wild-type CAV2 were used to independently infect 100% confluent MDCK monolayer ($10^6$ cells) at a M.O.I. of 10. After 24 hours at 37° C. in the presence of 5% $CO_2$, the infected cultures were scraped and harvested. Cells pellets were washed 3 times with prewarmed (37° C.) PBS ($Ca^{2+}$ and $Mg^{2+}$ free) before being resuspended in 1 ml of 40 mM Tris-HCl, pH 7.5, 1 mM EDTA, pH 8.0 and 150 mM NaCl and incubated for 5 minutes at room temperature. The cells were subsequently centrifuged at 12 Kg for 30 seconds at 4° C. and the resulting pellet was resuspended in 100 ml of 0.25M Tris-HCl, pH 8.0 before being subjected to 3 rapid freeze/thaw cycles with vigorous vortexing after each thaw cycle. Endogenous deacetyl activity was inactivated by incubating the lysates at 65° C. for 10 minutes. The supernatants of a 12 Kg centrifugation for 2 minutes at RT were assayed in a chloramphenicol acetyltransferase (CAT) assay as follows. Twenty-five ml of cell lysate was incubated for 2 hours at 37° C. with 3 ml of [$^{14}$C] chloramphenicol (0.005 mCi/ml)(NEN, Boston, Mass.), 5 ml of n-Butyryl Coenzyme A (5 mg/ml) and 92 ml of 0.25 M Tris-HCl, pH 8.0. The reaction was terminated by adding 500 ml of ethyl acetate (Sigma, St Louis, Mo.) per tube. The reaction was vortexed with the mixed xylenes for 30 seconds and subsequently centrifuged at 12 K g for 1 minute. The upper, organic phase was transferred to a fresh tube and evaporated to dryness. The residue was resuspended in 25 ml of n-Butyryl Coenzyme A (5 mg/ml) and 10 ml of the resuspended material was subsequently dotted onto a silica gel thin layer chromatography (TCL) silica plate (Baker, Philisburg, N.Y.). The slica plate chromatography was run in a closed chamber for approximately 1 hour, until the solvent was half-way up the plate. The silica plate was subsequently dried and autoradiogramed. Butyrylated chloramphenicol was clearly detected in the vCA2 sample whereas no modified chloramphenicol could be evidenced in the control wild-type CAV2 sample. This result demonstrates that the recombinant virus vCA3 expresses a functional CAT activity and thus validates both the expression cassette we have engineered and the insertion site we have selected.

2.1.2. Detection of CAT protein by radioimmnuprecipitation from vCA3 infected MDCK cells lysates.

Radioimmunoprecipitation analyses were performed as previously described (Pincus et al., 1992) using [$^{35}$S] methionine (1000 Ci/mmol, NEN)-labelled lysates derived from vCA3-infected MDCK cells and CAT rabbit polyclonal serum (5'3'Inc, Boulder, CO). The immunoprecipitated CAT polypeptide was resolved by SDS-PAGE and visualized by fluorography using sodium salicylate.

Analysis of vCA3 genomic organisation by restriction enzyme activity:

vCA3 DNA was purified as previously described. Purified total DNA was subsequently resuspended in $H_2O$ to a final concentration of 1.3 g/ml. 2 μgaliquots of purified vCA3 were independently digested with BalII and SalI. Since those two sites are unique within the CAV2 genome a 28.2 kbp and 3.8 kbp fragments are expected from the BqlII digestion, whereas a 27.8 kbp and a 4.2 kbp fragments are expected from the SalI digestion. These restriction fragments are indeed observed demonstrating that vCA3 is a recombinant CAV2 virus which has incorporated 1,000 bp of the CAT expression cassette within the right end of its genome.

Example 13

Generation of Donor Plasmid PLF102

Figure 30:
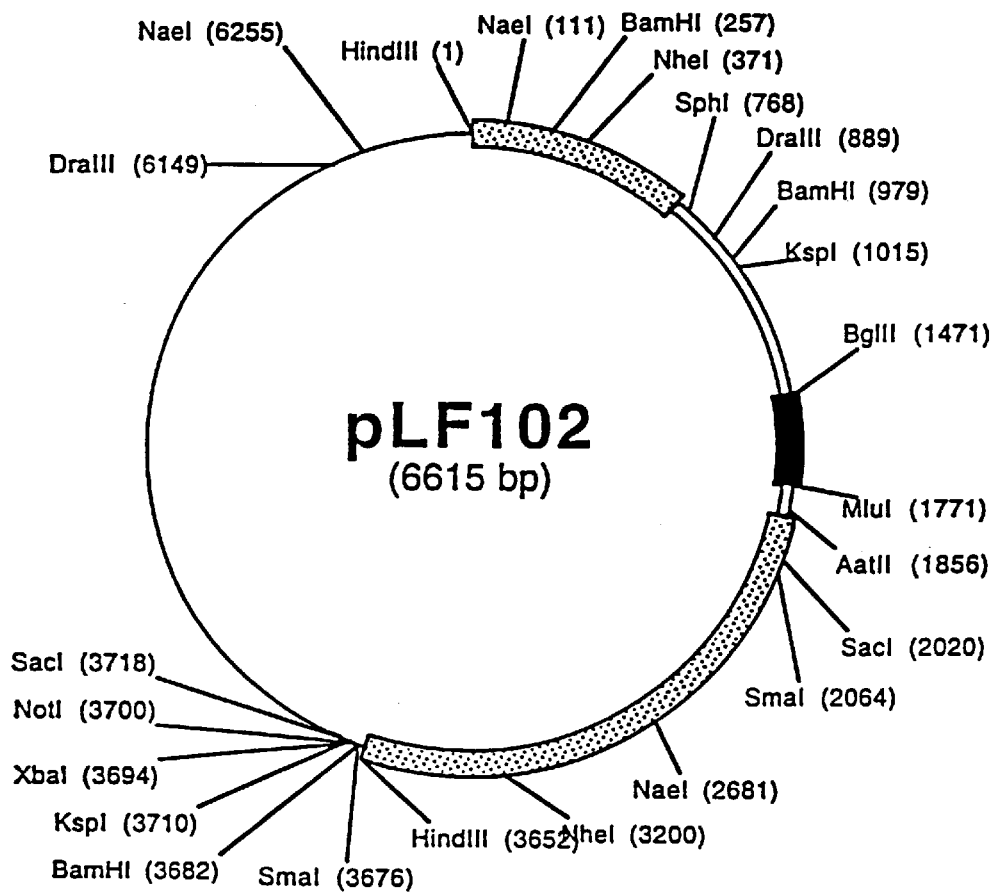
FIG. 30 shows a restriction map of pLF102)

In order to delete the 3' end of the E3 ORF2 without modifying the E3 ORF1, the following procedure was developed. A PCR amplification was set up using pLF027 DNA as a template and the primers pair LF437 (5'ATCTTAACGCGTCCCTCAGCCTTCTAATGGGAC 3') and LF334 (5° CTTGCTTGTTATTAAAAAAAG 3') as previously described. The 329 bp amplified DNA fragment was purified using the previously described Gene Clean procedure before being digested by MluI and SmaI. The resultant 287 bp MluI/SmaI DNA fragment was gel purified before being ligated with the 6,079 bp MluI/SmaI DNA fragment of pLF086, generating pLF095. The pLF095 63 bp BgII/MluI linker was subsequently swapped with a 305 bp BglII/MluI linker of unrelated foreign DNA using the following procedure. A 305 bp DNA fragment [nucleotide sequence described in FIGS. 29 and 30, see below] was obtained by digesting an unrelated plasmid with MluI and BglII. The MluI and BglII digested DNA fragment was gel purified and subsequently ligated with the 6,315 bp MluI/BalII DNA fragment of pLF095, generating pLF102 (FIG. 29, SEQ ID NO: 15).

The engineering of pLF102 results in the exchange of a 688 bp fragment of CAV2 E3 (which represents 45% of the total E3 size) with 305 bp of foreign DNA and is useful to further define the limits of non-essential subdomains within CAV2 E3 region.

Example 14

Generation of Donor Plasmid DLF116A

In order to delete a pLF027 EcoRV/AatII 1.8 kbp DNA fragment which contains two SphI restriction sites [at positions #3,770 and #3,870], the pLF027 EcoRV/AatII 5,163 bp fragment was gel purified and subsequently treated with Klenow enzyme before being religated on itself to generate pLF094.

A 24 bp DNA linker (5'-GATACGCGTTCCATTAGCAGATCT-3') containing unique BalII and MluI restriction sites was introduced into the pLF094 intergenic sequence between E3 ORF1 and E3 ORF2 by a double round PCR amplification procedure. Initial PCR amplifications were performed using pLF027 DNA as template and the following primer couples [LF243 (5' CGCGCACAAACTGGTAGGTGC 3')/LF436(5' AGATCTGCTAATGGAACGCGTAT- CAAGTTTAATAATATATTATC 3')] and [LF435(5' GATACGCGTTCCATTAGCAGATCTGTTT-TACAGCTACCA 3')/LF277(5' GTACAGTTATGT-TGAAGG 3')], to generate two partially overlapping DNA fragments of 487 bp and 698 bp, respectively. The second round of PCR amplification was performed in the presence of both partially overlapping purified DNA fragments and both external primers LF243 and LF277. The amplified 1,185 bp DNA fragment was digested with SohI and PstI and the resultant 566 bp PstI/SphI fragment was purified and ligated with the 4,653 bp SphI/PstI partial digest of pLF094, generating pLF093. All PCR amplifications were performed using the conditions previously described.

Figure 32:
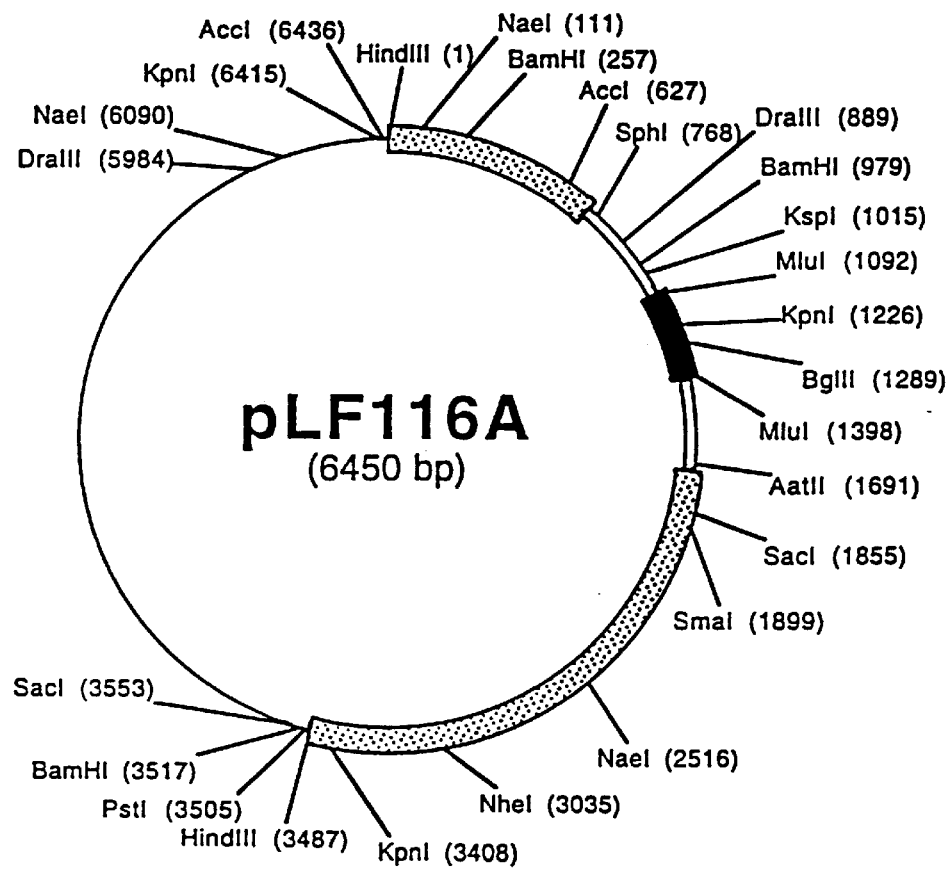
FIG. 32 shows a restriction map of pLF1116A.

A deletion of the 5' end of E3 ORF2 without modifying E3 ORF1 was engineered by the following procedure. The pLF093 XhoI/MluI 1,062 bp fragment was gel purified and subsequently ligated with the 5,081 bp XhoI/MluI fragment of pLF086, generating pLF115. MluI linearized pLF115 DNA was subsequently ligated with a 311 bp MluI/MluI fragment of unrelated foreign DNA, generating pLF116A and B. The complete DNA sequence of pLF116A including the sequence of the unrelated 311 bp MluI/MluI fragment of foreign DNA is presented in FIG. 31 (SEQ ID NO: 16), with the restriction map shown in FIG. 32.

The engineering of pLF116A results in the exchange of a 876 bp fragment of CAV2 E3 (which represents 57% of the total E3 size) with 311 bp of foreign DNA and is useful to further define the limits of non-essential subdomains within CAV2 E3 region.

Example 14

Generation of Donor Plasmid pLF100

In order to delete simultaneously the 5' end of the E3 ORF2, the 3' end of the E3 ORF1 and the complete E3 ORF3, a 634 bp fragment was deleted between the MluI (#1529) and DraIII(#889) restriction sites of pLF086 (FIGS. 7 and 8) and subsequently exchanged with a 302 bp fragment of unrelated foreign DNA using the following procedure.

Figure 34:
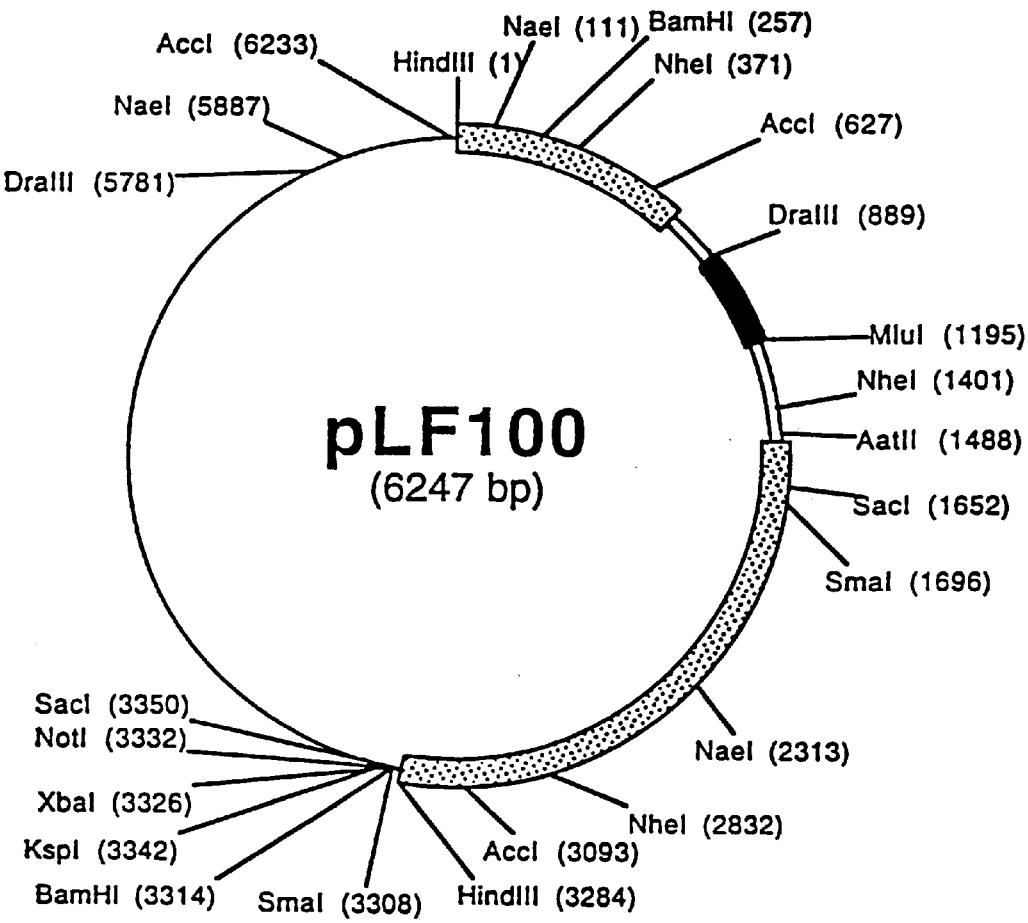
FIG. 34 shows a restriction map of pLF100.

The 302 bp DNA fragment was obtained by digesting an unrelated plasmid with MluI and DraIII. The MluI and DraIII digested DNA fragment was gel purified and subsequently ligated with the 5,946 bp MluI/DraIII DNA fragment of pLF086, generating pLF100 (FIGS. 33, 34 SEQ ID NO: 17). The nucleotide sequence of the 302 bp fragment is shown in FIG. 33, and the restriction map is shown in FIG. 34.

The engineering of pLF100 results in the exchange of a 1,060 bp fragment of CAV2 E3 (which represents 69% of the total E3 size) with 302 bp of foreign DNA and is useful to further define the limits of non-essential subdomains within CAV2 E3 region.

Example 15

Generation of Donor Plasmid pLF120

Figure 36:
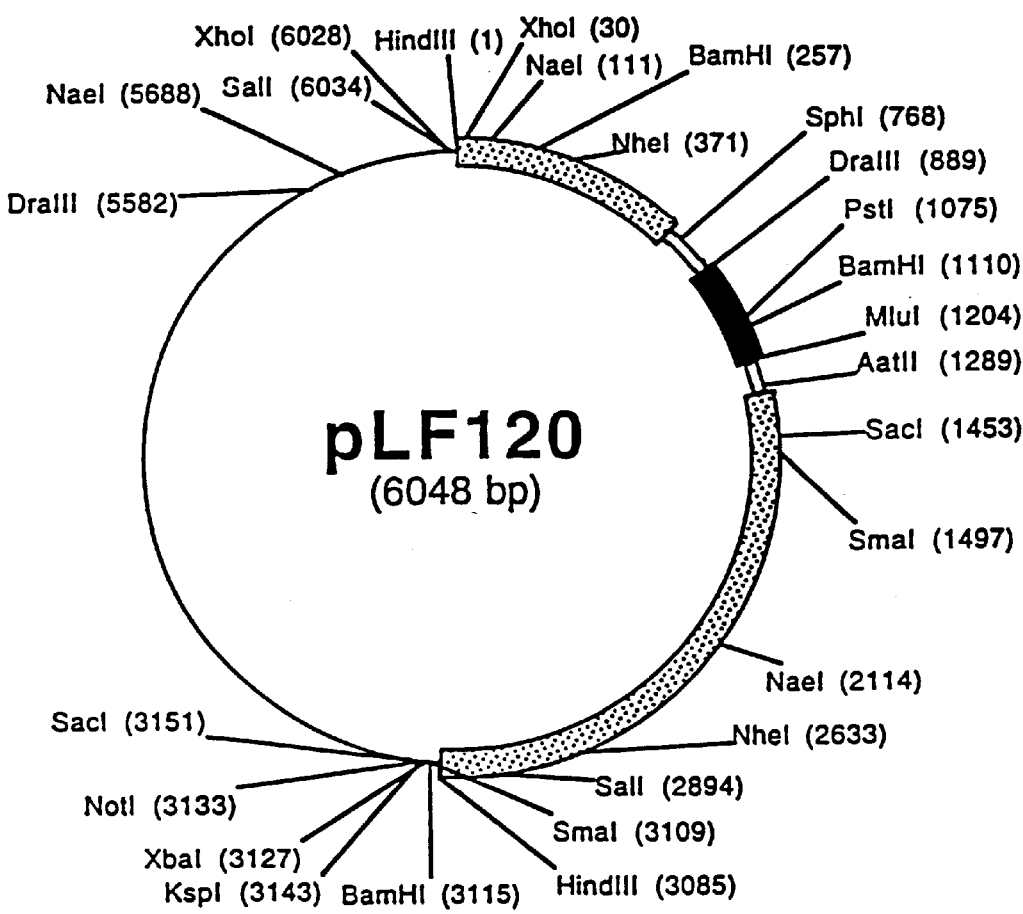
FIG. 36 shows a restriction map of pLF120.
Figure 40:
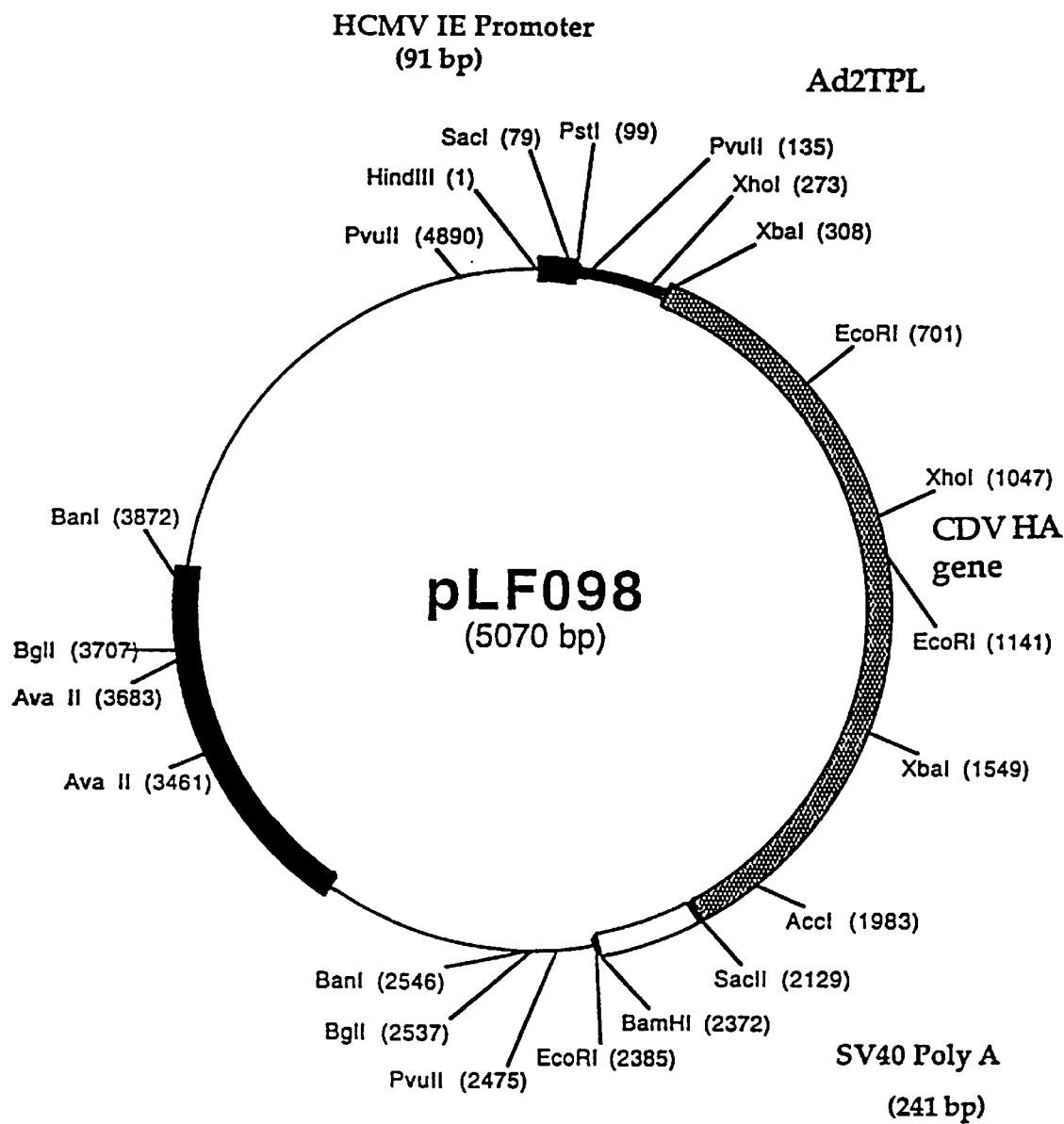
FIG. 40 shows a restriction map of pLF098.
Figure 42:
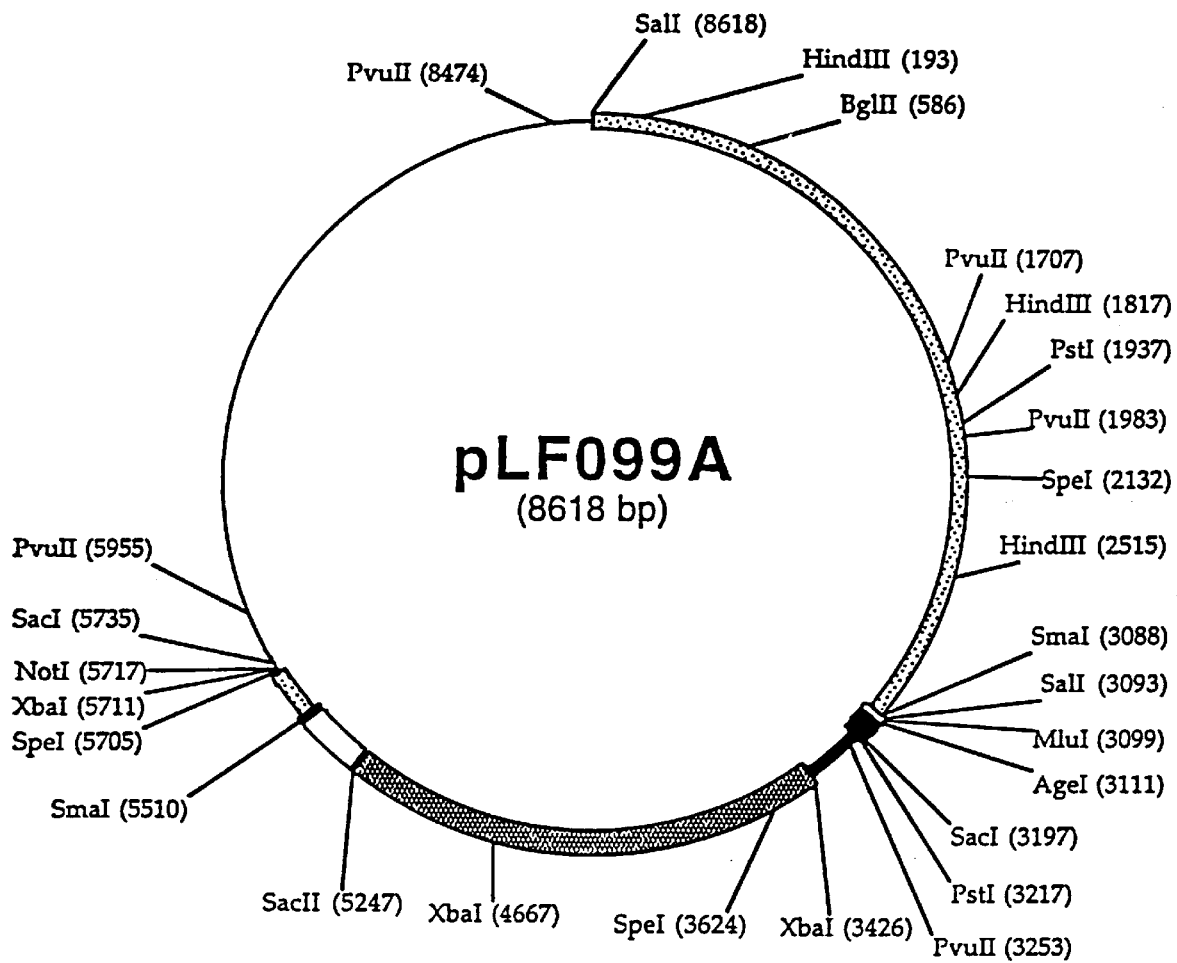
FIG. 42 shows a restriction map of pLF099A.

In order to delete simultaneously the 3' end of the E3 ORF1, the almost complete E3 ORF2 and the complete E3 ORF3, a 882 bp fragment was deleted between the MluI (#1,771) and DraIII(#889) restriction sites of pLF102 and subsequently exchanged with a 311 bp fragment of unrelated foreign DNA using the following procedure.

pLF102 DNA was linearized by MluI and subsequently partially digested with DraIII. The resultant 5,733 bp MluI/DraIII was subsequently ligated with a 311 bp MluI/DraIII fragment of unrelated foreign DNA, generating pLF120 (FIGS. 35, 36, SEQ ID NO: 18). The nucleotide sequence of the 311 bp MluI/DraIII fragment of unrelated foreign DNA is shown in FIG. 35, and the restriction map is shown in FIG. 36.

The engineering of pLF120 results in the exchange of a 1,261 bp fragment of CAV2 E3 (which represents 82% of the total E3 size) with 311 bp of foreign DNA and is useful to further define the limits of non-essential subdomains within CAV2 E3 region. This is the largest deletion and indicates that practically all of the E3 region, e.g., about 80% to about 100%, such as up to about 80 to about 95% or up to about 80% to 90% or up to about 80% to 85% of the E3 region can be deleted.

Example 16

Generation of pLF043, a pBSSK+ Which Contains the Canine Distemper Virus (CDV) Hemagalutinin (HA) Coding Sequence 1. Generation of plasmid PSDCDVHA.

The Onderstepoort strain of canine distemper virus (CDV) was obtained from Dr. M. Appel (Cornell University, Ithaca, NY). RNA was harvested from CDV infected Vero cells and cDNA was prepared in the following manner.

RNA from CDV infected Vero cells was isolated by the guanidium isothiocyanate-cesium chloride method of Chirgwin, et al., (1979). First strand cDNA was synthesized with AMV reverse transcriptase (Life Sciences, St. Petersburg, FL), the oligonucleotide primer CDVFSP (SEQ ID NO: 44) (5'-CCAGGACATAGCAAGCCAACAGGTC-3'), and RNA from CDV infected cells. CDVFSP (SEQ ID NO: 44) primes 80 bp upstream of the CDV fusion (F) start codon, yielding a positive sense single stranded CDNA product which contains the F and hemagglutinin (HA) coding sequences.

The HA-specific open reading frame (ORF) was amplified from the first strand cDNA product by polymerase chain reaction (PCR) as previously described. Oligonucleotide primers CDVHA1 (SEQ ID NO: 45) (5'-CGATATCCGTTAAGTTTGTATCGTAATGCTCCCCTA-CCAAGAC-3') and CDVHA2 (SEQ ID NO: 46) (5'-GGGATAAAAATTAACGGTTACATGAGAATCTTATAC-GGAC-3') were used in a PCR with the CDVFSP derived first strand cDNA as template. CDVHA1 contains the 3' most region of the vaccinia virus H6 promoter (Perkus, et al., 1989) followed by a sequence which primes from the translation initiation codon into the CDV HA ORF. CDVHA2 (SEQ ID NO: 46) primes from the stop codon of the HA ORF toward the CDV HA 5' end. The resultant 1.8 kbp PCR product was treated with the Klenow fragment from the E. coli DNA polymerase, in the presence of 20 mM dNTPs, to blunt end the fragment. The 1.8 kbp blunt-ended fragment was inserted between the NruI site within the H6 promoter, and the SmaI site 3' of the H6 promoter in pSD554 (see below). The resultant plasmid pCDVHA should have contained the H6 promoted CDV HA ORF, but there was an unexpected deletion at the CDV HA 5' end. Repair of the deletion is described below.

Plasmid pSD554 contains the vaccinia K1L host range gene (Gillard et al., 1986) and vaccinia H6 promoter followed by insertion sites, within flanking vaccinia arms. The flanking vaccinia arms replace the ATI region: open reading frames A25L and A26L (Goebel et al., 1990a,b). pSD554 was prepared in the following manner.

Left and right vaccinia flanking arms were constructed by PCR using the template pSD414 which contains vaccinia SalI B (Goebel et al., 1990a,b). The left arm was synthesized using oligonucleotide primers MPSYN267 (SEQ ID NO: 47) (5'-GGGCTGAAGCTTGCTGGCCGCTCATTAGACAAGC-GAATGAGGGAC-3') and MPSYN268 (SEQ ID NO: 48) (5'-AGATCTCCCGGGCTCGAGTAATTAAT-TAATTTTTATTACACCAGAAAAGACGGCTTGAGA TC-3') in a PCR with template pSD414. The right arm was synthesized using oligonucleotide primers MPSYN269 (SEQ ID NO: 49) (5'-TAATTACTCGAGCCCGGGAGATCTAATT-TAATTTAATTTATATAACTCATTTTTTGAATA T ACT-3') and MPSYN270 (SEQ ID NO: 50) (5'-TATCTCGAATTCCCGCGGCTTTAAATGGACGGAAC-TCTTTTCCCC-3') in a PCR with template pSD414. The two PCR-derived fragments containing the left and right arms were combined in a PCR. The resultant PCR product was digested with EcoRI and HindIII and a 0.9 kbp fragment was isolated. The 0.9 kb fragment was inserted between the pUC8 EcoRI and HindIII sites. The resultant plasmid pSD541 received the K1L gene, and additional insertion sites, in the following manner.

Plasmid pSD541 was digested with BglII and XhoI and ligated with annealed complementary oligonucleotides MPSYN333 (SEQ ID NO: 51) (5'-GATCTTTTGTTAACAAAAACTAATCAGC-TATCGCGAATCGATTCCCGGGGGATCCGGTACC C-3') and MPSYN334 (SEQ ID NO: 52) (5'-TCGAGGGTACCGGATCCCCCGGGAATC-GATTCGCGATAGCTGATTAGTTTTTGTTAACAA AA-3'), generating plasmid pSD552. pSD452 (Perkus et al., 1990) contains the K1L gene. pSD452 was digested with HpaI and partially digested with BglII and the resultant lkbp fragment containing the K1L gene was inserted between the pSD552 BglII and HpaI sites. The resultant plasmid pSD553 was digested with NruI and a SmaI/NruI fragment containing the vaccinia H6 promoter (Perkus et al., 1989) was inserted. The resultant plasmid, pMP553H6, contains the vaccinia H6 promoter downstream from the K1L gene within the A26L insertion locus.

Plasmid pMP553H6 was digested with NruI and BamHI and ligated with annealed synthetic oligonucleotides MPSYN347 (SEQ ID NO: 53) (5'-CGATATCCGTTAAGTTTGTATCGTAATCTGCAGCCC-GGGGGGG-3') and MPSYN348 (SEQ ID NO: 54) (5'-GATCCCCCGGGCTGCAGATTACGATACAAACTTAA-CGGATATCG-3'). The resultant plasmid pSD554 contains the K1L gene and the H6 promoter followed by insertion sites, within flanking vaccinia sequences which replace the ATI region.

The vaccinia virus H6 promoter and 5' end of the CDV HA ORF were added to PCDVHA as a PCR derived fragment. The ATG of the regulatory region H6 overlaps the CDV HA translation initiation codon in the PCR derived fragment. The vaccinia virus H6 promoter has been described in Perkus, et al., 1989.

pEIVC5L contains the modified H6 promoter and a non-pertinent gene. pEIVC5L was used in a polymerase chain reaction with oligonucleotide primers H65PH (SEQ ID NO: 55) (5'-ATCATCAAGCTTGATTCTTTATTCTATAC-3') and CDVHAH6 (SEQ ID NO: 56) (5'-GTCTTGGTAGGGGAGCATTACGATACAAACTTAACG-3') to generate a 156 bp fragment. CDVHAH6 contains the 5' 18 base pairs of CDV HA followed by a sequence which primes from the translation initiation codon toward the H6 promoter 5' end. H65PH (SEQ ID NO: 55) contains a HindIII site followed by a sequence which primes from the H6 promoter 5' end toward the 3' end. The 156 base pair PCR-derived H65PH/CDVHAH6 (SEQ ID NO: 55/SEQ ID NO: 56) product contains the H6 promoter and the 5' 18 base pairs of the CDV HA coding sequence.

The CDVFSP (SEQ ID NO: 44) first strand cDNA product was used in a PCR with oligonucleotide primers CDVHAATG (SEQ ID NO: 57) (5'-ATGCTCCCCTACCAAGAC-3') and CDVHAECO (SEQ ID NO: 58) (5'-GTAATTAGTAAAATTCACCTTG-3') to generate a 459 base pair fragment. CDVHAATG (SEQ ID NO: 57) primes from the translation initiation codon toward the CDV HA 3' end. CDVHAECO (SEQ ID NO: 58) primes from position 583 of the following H6 promoted CDV HA sequence toward the CDV HA 5' end. The 156 base pair and 459 base pair PCR-derived fragments were pooled and used in a PCR with H65PH (SEQ ID NO: 55) and CDVHAECO (SEQ ID NO: 58) to generate a 597 base pair fragment. The PCR-derived product was digested with HindIII and EcoRI, generating a 520 base pair fragment which contains the H6 promoter and 5' most 387 base pairs of the CDV HA coding sequence. The 520 base pair HindIII/EcoRI digested PCR fragment was inserted between the HindIII and EcoRI sites of PBSSK+, yielding pBSCDVHA5S. Plasmid pBSCDVHA5S contains the H6 promoted 5' end of the CDV HA ORF in pBSSK+, and the 3' end of the CDV HA ORF was added in the following manner.

Plasmid PCDVHA was digested with SmaI followed by partial digestion with EcoRI to generate a 1.4 kbp fragment containing the 3' end of the CDV HA ORF. The 1.4 kbp pCDVHA EcoRI/SmaI fragment was inserted between the EcoRI and SmaI sites of pBSCDVHA5S. The resultant plasmid pBSCDVHA was digested with BamHI and partially digested with XhoI to generate a 1.9 kbp fragment containing the H6 promoted CDV HA open reading frame. The 1.9 kbp BamHI/XhoI PBSCDVHA fragment was inserted between the BamHI and XhoI sites of pSD553 (see above). The resultant plasmid pSDCDVHA contains the H6 promoted CDV HA gene in the ATI insertion site.

2. Generation of pLF043.

The pSDCDVHA 1,975 bp HindIII/BamHI which contains the CDV HA coding sequence and the 3' most region of the vaccinia virus H6 promoter, was gel purified and subsequently inserted between the corresponding restrictions sites of pBSSK+, generating pLFO43 (FIGS. 37 and 38) (SEQ ID NO: 19).

Example 17

Generation of pLF098, Which Contains a Complete CDV HA Expression Cassette

A XbaI restriction site was engineered immediately upstream of the CDV HA initiation codon (ATG) in the following manner. A 409 bp DNA fragment was amplified by PCR using pLF043 DNA as a template and the primers pair LF412 (5' CTGATCTCTAGAATGCTCCCCTACCAA-GACAAG 3') (SEQ ID NO: 59) and LF413 (5' TGGAGATCGCGGAAGTCG 3') (SEQ ID NO: 60) as previously described. The PCR amplified fragment was isolated using the Gene Clean procedure as previously described before being treated with the Klenow fragment from the E. coli DNA polymerase, in the presence of 2OmM dNTPs and digested by SpeI and EcoRI. The resultant blunt-ended/SpeI 192 bp DNA fragment was subsequently ligated with the 4,891 bp NruI/SpeI fragment of pLF043, generating pLF096.

A KspI restriction site was engineered immediately downstream of pLF096 CDV HA stop codon (TAA) in the following manner. A 204 bp DNA fragment was amplified by PCR using pLF043 as a template and the primers pair LF438 (5' TGTTTATGACCCAATCG 3') (SEQ ID NO: 61) and LF439 (5' ATGCTCCCGCGGTTAACGGTTACATGAGAATCT 3') (SEQ ID NO: 62) as previously described. The PCR amplified fragment was isolated using the Gene Clean procedure as previously described before being digested with KspI and AccI. The resultant 143 bp DNA fragment was gel purified and subsequently ligated with the 4,594 bp KspI/AccI fragment of pLF096, generating pLF097.

The 1,821 bp pLF097 KspI/XbaI fragment which contains the CDV HA coding sequence was subsequently ligated with the 3,246 bp KspI/XbaI fragment of pLF069, generating pLF098 (FIGS. 39, 40) (SEQ ID NO: 20).

Example 18

Generation of pLF099A, a Donor Plasmid for the Insertion of CDV HA Expression Cassette 12 bp Upstream of the SmaI Site at the CAV2 Genome Right End The 2,372 bp BamHI/HindIII pLF098 fragment which contains the CDV HA coding sequence coupled to the regulatory sequences defined in pLF069 was treated with the Klenow fragment from the *E. coli* DNA polymerase before being ligated with the 6,243 bp NruI linearized pLF105, generating pLF099A and pLF099B. pLF099A corresponds to the rightward orientation of the expression cassette (FIGS. 41, 42) (SEQ ID NO: 21).

Example 19

Generation and Characterization of Recombinant CAV2 Virus vCA4

1. Generation of recombinant CAV2 virus vCA4 Ten μg of pLF102 were digested with HindIII and the resulting 3,652 bp DNA fragment was isolated using Gene Clean procedure as previously described and resuspended in $H_2O$ to a concentration of 100 ng/μl. MDCK cells were transfected using the Lipofectamine based procedure previously described. Solution A was prepared by mixing 0.5 μg of 3.6 kbp HindIII DNA fragment with 3 μg of purified vCA2 DNA. Solution A total volume was brought to 300 μl with supplemented serum free MEM medium. Transfected cells were harvested after 8 days and plate out on 150 mm diameter tissue culture dishes as previously described. A probe specific for the 305 bp fragment of foreign DNA inserted into pLF102 was generated by PCR using pLF102 DNA (10 ng) as template and primers pair LF440 (5'-ATCAGTACGCGTATGGGCCACACACGGAGG-3')/ LF441 (5'-ATCAGTAGATCTGTTATTAGTGATATCAAA-3'). The resultant 305 bp DNA fragment was labelled by random priming using a procedure previously described and subsequently hybridized with nitrocellulose membrane used to lift viral plaques as previously described. Five viral plaques crossreacting with the probe were picked and subsequently submitted to 4 rounds of plaque purification as previously described. The plaque purified recombinant CAV2 virus was named vCA4.

2. Characterization of vCA4 vCA4 DNA was purified as previously described. Purified total DNA was subsequently resuspended in $H_2O$ to a final concentration of 1.9 λg/ml. 2 μg aliquots of purified vCA4 were digested with HindIII. The expected 3, 667 bp HindIII fragment was visualized in the vCA4 sample whereas a 4.0 kbp fragment was present in the wild-type CAV2 sample, proving that vCA4 genomic DNA contains the partially deleted E3 region described in pLF102. VCA4 DNA was analyzed by Southern Blot which indicated that vCA4 has an E3 region 371 bp shorter than the wild-type E3 region.

This result futher demonstrates non-essential subdomains of CAV2 E3 region. More specifically, the derivation of vCA4 demonstrates that the CAV2 E3 sequences comprised between position #1,470 and position #2,157 [ie 45% of the E3 region], as in pLF027 (see FIG. 1, SEQ ID NO: 1) can be exchanged with heterologous DNA. It also further validates the CAV2 E3 as an insertion site within the CAV2 genome. This results also proves that part of the CAV2 E3 region can be deleted to compensate for the introduction of foreign DNA into the right end of CAV2 genome as previously described in the derivation of vCA3.

Example 20

Generation and Characterization of Recombinant CAV2 Virus vCA5

1. Generation of recombinant CAV2 virus vCA5

Ten μg of pLF116A were digested with HindIII and the resulting 3,487 bp DNA fragment was isolated using Gene Clean procedure as previously described and resuspended in $H_2O$ to a concentration of 100 ng/μl. MDCK cells were transfected using the Lipofectamine based procedure previously described. Solution A was prepared by mixing 0.5 μg of 3.5 kbp HindIII DNA fragment with 3 μg of purified vCA2 DNA. Solution A total volume was brought to 300l with supplemented serum free MEM medium. Transfected cells were harvested after 8 days and plate out on 150 mm diameter tissue culture dishes as previously described. A probe specific for the 311 bp fragment of foreign DNA inserted into pLF116A was generated by PCR using pLF116A DNA (10 ng) as template and primers pair LF453 (5'-ATCGTCATTGCCACGCGTATGGCAGAAGGATTTGCAGCCAAT-3')/ LF454 (5'-ATCGTCATTGCCACGCGTAACCAGGGACAATACTTGTTCATC-3'). The resultant 311 bp DNA fragment was labelled by random priming using a procedure previously described and subsequently hybridized with nitrocellulose membrane used to lift viral plaques as previously described. Five viral plaques crossreacting with the probe were picked and subsequently submitted to 4 rounds of plaque purification as previously described. The plaque purified recombinant CAV2 virus was named vCA5.

2. Characterization of vCA5 vCA5 DNA is purified as previously described. Purified total DNA is subsequently resuspended in HZO to a final concentration of 1.9 μg/ml. 2 μg aliquots of purified vCA5 are digested with HindIII. The expected 3,487 bp HindIII fragment is visualized in the vCA5 sample whereas a 4.0 kbp fragment is present in the wild-type CAV2 sample, proving that vCA5 genomic DNA contains the partially deleted E3 region described in pLF116A.

This result futher demonstrates non-essential subdomains of CAV2 E3 region. More specifically, the derivation of vCA5 demonstrates that the CAV2 E3 sequences comprised between position #1,088 and position #1,964 [ie 57% of the E3 region], as described in pLF027 (see FIG. 1, SEQ ID NO: 1) can be exchanged with heterologous DNA. It also further validates the CAV2 E3 as an insertion site within the CAV2 genome. This result also proves that part of the CAV2 E3 region can be deleted to compensate for the introduction of foreign DNA into the right end of CAV2 genome as previously described in the derivation of vCA3.

Example 21

Generation and Characterization of Recombinant CAV2 Virus vCA6

1. Generation of recombinant CAV2 virus vCA6

Ten μg of pLF100 were digested with HindIII and the resulting 3,284 bp DNA fragment was isolated using Gene Clean procedure as previously described and resuspended in H$_2$O to a concentration of 100 ng/μl. MDCK cells were transfected using the Lipofectamine based procedure previously described. Solution A was prepared by mixing 0.5 μg of 3.3 kbp HindIII DNA fragment with 3 μg of purified vCA2 DNA. Solution A total volume was brought to 300 μl with supplemented serum free MEM medium. Transfected cells were harvested after 8 days and plate out on 150 mm diameter tissue culture dishes as previously described. A probe specific for the 311 bp fragment of foreign DNA inserted into pLF100 was generated by PCR using pLF100 DNA (10 ng) as template and primers pair LF442(5'-ATCAGTCACGGTGTGTAAATGGGCCACACACGGA-GG-3')/ LF443 (5'-ATCAGTACGCGTGTTATTAGTGATATCAAA-3'). The resultant 302 bp DNA fragment was labelled by random priming using a procedure previously described and subsequently hybridized with nitrocellulose membrane used to lift viral plaques as previously described. Five viral plaques crossreacting with the probe were picked and subsequently submitted to 4 rounds of plaque purification as previously described. The plaque purified recombinant CAV2 virus was named vCA6.

2. Characterization of vCA6 vCA6 DNA is purified as previously described. Purified total DNA is subsequently resuspended in H$_2$O to a final concentration of 1.9 μg/ml. 24 g aliquots of purified vCA6 are digested with HindIII. The expected 3,284 bp HindIII fragment was visualized in the vCA6 sample whereas a 4.0 kbp fragment is present in the wild-type CAV2 sample, proving that vCA6 genomic DNA contains the partially deleted E3 region described in pLF100.

This result futher demonstrates non-essential subdomains of CAV2 E3 region. More specifically, the derivation of vCA6 demonstrates that the CAV2 E3 sequences comprised between position #898 and position #1,949 [ie 69% of the E3 region], as described in pLF027 (see FIG. 1, SEQ ID NO: 1) can be exchanged with heterologous DNA. It also further validates the CAV2 E3 as an insertion site within the CAV2 genome. This results also proves that part of the CAV2 E3 region can be deleted to compensate for the introduction of foreign DNA into the right end of CAV2 genome as previously described in the derivation of vCA3.

Example 22

Generation and Characterization of Recombinant CAV2 Virus vCA7

1. Generation of recombinant CAV2 virus vCA7

Ten μg of pLF120 were digested with HindIII and the resulting 3,085 bp DNA fragment was isolated using Gene Clean procedure as previously described and resuspended in H$_2$O to a concentration of 100 ng/μl. MDCK cells were transfected using the Lipofectamine based procedure previously described. Solution A was prepared by mixing 0.5 μg of 3.3 kbp HindIII DNA fragment with 3 μg of purified vCA2 DNA. Solution A total volume was brought to 300 μl with supplemented serum free MEM medium. Transfected cells were harvested after 8 days and plate out on 150 mm diameter tissue culture dishes as previously described. A probe specific for the 311 bp fragment of foreign DNA inserted into pLF100 was generated by PCR using pLF100 DNA (10 ng) as template and primers pair LF458(5'-ATCCGTACGCGTTAGAGGGCAAAGCCCGTGCAGC-AGCGC-3')/ LF459 (5'-ATCCGTCACGGTGTGTAGATGGGTTGTTTTGTGGA-GAAT-3'). The resultant 311 bp DNA fragment was labelled by random priming using a procedure previously described and subsequently hybridized with nitrocellulose membrane used to lift viral plaques as previously described. Cross reacivity between the probe and viral DNA has been evidenced.

This result indicates that a deletion of 1,259 bp between position #898 and position #2,157, as described in pLF027 (see FIG. 1, SEQ ID NO: 1) is compatible with viral replication in tissue culture, further showing that essentially all of the E3 region can be deleted.

Example 23

Generation of vCA8

Ten μg of pLF099A were digested with BqlII and NotI and the resulting 5,131 bp DNA fragment was isolated using Gene Clean procedure as previously described and resuspended in H$_2$O to a concentration of 100 ng/μl. MDCK cells were transfected using the Lipofectamine based procedure previously described. Solution A was prepared by mixing 0.5 μg of 5.1 kbp BqlII/NotI DNA fragment with 3 μg of purified vCA2 DNA. Solution A total volume was brought to 300 μl with supplemented serum free MEM medium. Transfected cells were harvested after 8 days and plate out on 150 mm diameter tissue culture dishes as previously described. The 440 bp EcoRI fragment of pSDCDVHA was labelled by random priming using a procedure previously described and subsequently hybridized with nitrocellulose membrane used to lift viral plaques as previously described. Two viral plaques cross-reacting with the probe were picked and are currently submitted to a plaque purification process as previously described. The plaque purified recombinant CAV2 virus is named vCA8.

2. Characterization of vCA8 vCA8 DNA purification, restriction digestion, Southern Blot, and CDV HA expression analysis by radioimmunoprecipitation confirm insertion and expression.

Example 24

Generation of pLF108, a pBSSK+ Derived Plasmid Which Contains the Canine Distemper Virus (CDV) Fusion (F1) Coding Sequence 1. Generation of pATICDVF1

The CDV fusion (F) specific open reading frame (ORF) was amplified from CDNA by PCR using oligonucleotide primers CDVATGF1 (SEQ ID NO: 63) (5'-CATAAATTATTTCATTATCGCGATATC-CGTTAAGTTTGTATCGTAATGCACAAGG-GAATCCCCAAAAGC-3') and CDVFT (SEQ ID NO: 64) (5'-ATCATCGGATCCATAAAAATCAGTGTGATCTCACAT-AGGATTTCGAAG-3') with CDVFSP (SEQ ID NO: 44) derived first strand CDNA as the template. CDVATGF1 (SEQ ID NO: 63) contains the 3' most region of the vaccinia virus H6 promoter (Perkus, et al., 1989) followed by a sequence which primes from the CDV F translation initiation codon into the CDV F ORF. CDVFT (SEQ ID NO: 64) contains a BamHI site followed by a sequence which primes from the CDV F stop codon toward the CDV F 5' end. The resultant PCR product was digested with NruI and BamHI, yielding a 2 kbp fragment which was inserted into pSD554 between the NruI and BamHI sites. The resultant plasmid pATICDVF1 contains the H6 promoted CDV F ORF in the vaccinia virus ATI insertion locus. 2. Generation of HC5LSP28

Figure 46:
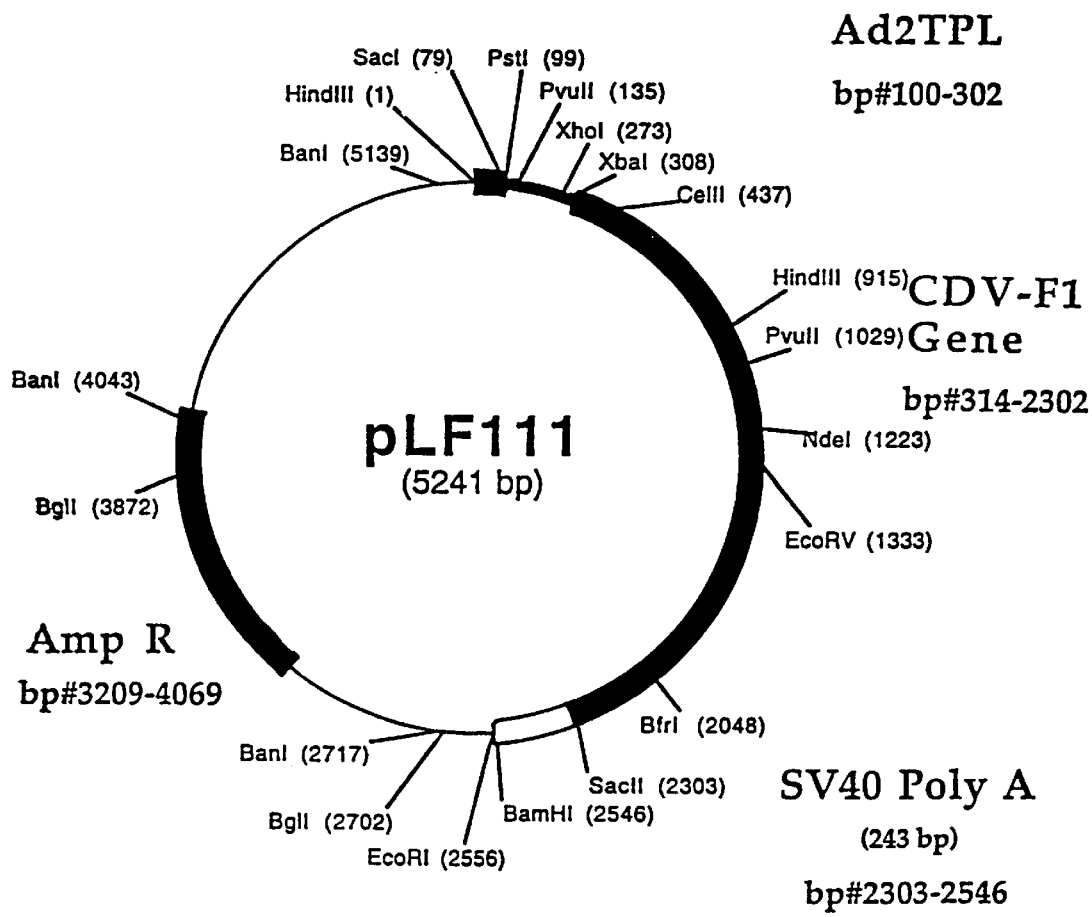
FIG. 46 shows a restriction map of pLF111.
Figure 48:
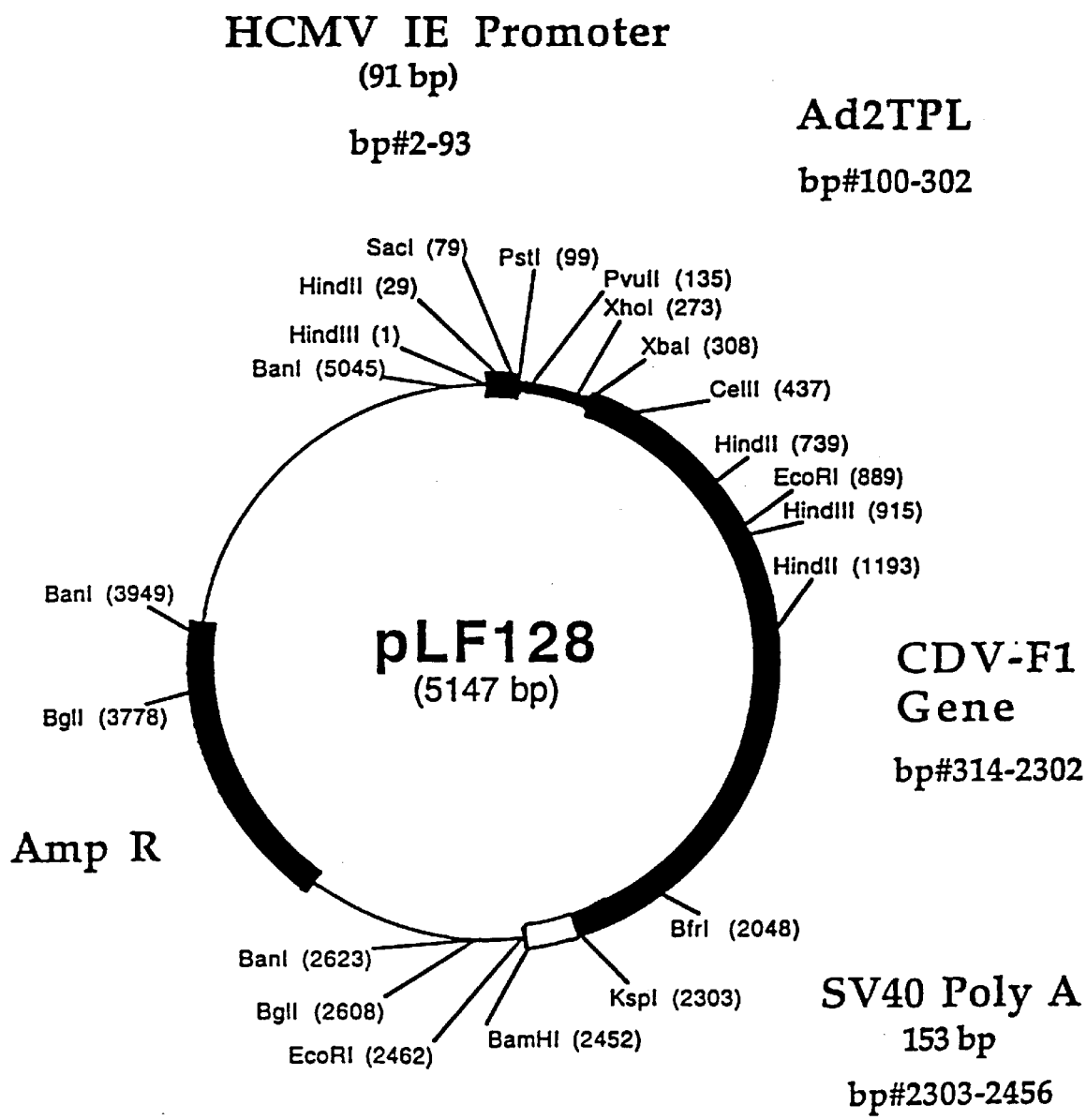
FIG. 48 shows a restriction map of pLF128.

The C5 vector plasmid HC5LSP28 was constructed to remove the C5 ORF in the following manner. Oligonucleotide primers C5A (SEQ ID NO: 65) (5'-ATCATCGAATTCTGAATGTTAAATGTTATACTTTG-3') and C5B (SEQ ID NO: 66) (5'-GGGGGTACCTTTGAGAGTACCACTTCAG-3') were used in a PCR with genomic canarypox DNA as the template. The resultant 1.5 kbp fragment was digested at the C5A end with EcoRI and the other end remained blunt for insertion between the EcoRI and SmaI sites of pUC8, yielding plasmid C5LAB. Oligonucleotide primers C5C (SEQ ID NO: 67) (5'-GGGTCTAGAGCGGCCGCTTATAAAGATCTAAAATG-CATAATTTC-3') and C5DA (SEQ ID NO: 68) (5'-ATCATCCTGCAGGTATTCTAAACTAGGAATAGATG-3') were used in a PCR with genomic canarypox DNA as template. The resultant 400 base pair fragment was digested at the C5DA end with PstI and the other end remained blunt for insertion between the SmaI and PstI sites of C5LAB, yielding plasmid pC5L. Annealed complementary oligonucleotides CP26 (SEQ ID NO: 69) (5'-GTACGTGACTAATTAGCTATAAAAAGGATCCGGTAC-CCTCGAGTCTAGAATCGATCCCGGG- TTTT TATGACTAGTTAATCAC-3') and CP27 (SEQ ID NO: 70) (5'-GGCCGTGATTAACTAGTCATAAAAAC-CCGGGATCGATTCTAGACTCGAGGGTAC-CGGATCCTTTT TATAGCTAATTAGTCAC-3') were inserted between the pC5L AsD7l8 and NotI sites. The resultant plasmid HC5LSP28 is a locus C5 vector plasmid.

3. Generation of pBSCDVHAVQ

Oligonucleotides RW132 (SEQ ID NO: 71) (5'-AGCTTCCCGGGTTAATTAATTAGTCAT-CAGGCAGGGCGAGAACGAGACTATCT-GCTCGTTAATTA ATTAG-3') and RW133 (SEQ ID NO: 72) (5'-AGCTCTAATTAATTAACGAGCAGAT-AGTCTCGTTCTCGCCCTGCCTGATGAC-TAATTAATTAACC CGGGA-3') were annealed to form a double-stranded linker sequence. The RW132/RW133 (SEQ ID NO: 71/SEQ ID NO: 72) double-stranded sequence was inserted into the HindIII site 5' of the H6 promoted CDV HA ORF in pBSCDVHA5S, generating plasmid pBSCDVHAVQ.

4. Generation of pC5CDVHAF1

The 2 kbp PBSCDVHAVQ SmaI fragment, which contains the H6 promoted CDV HA ORF, was inserted into the HC5LSP28 SmaI site, generating plasmid pC5LCDVHA. The 2.1 kbp pATICDVF1 HpaI/BamHI fragment, containing the H6 promoted CDV F ORF, was ligated with the pC5LCDVHA SmaI/BamHI 6.5 kbp DNA fragment, generating plasmid pC5LCDVHAF1 which contains the H6 promoted CDV F and H6 promoted CDV HA ORFs, with their transcripts directed away from each other, in the C5 locus.

6. Generation of vector plasmid pC6L

The C6 vector pC6L was constructed to remove the C6 ORF in the following manner. Oligonucleotide primers C6A1 (SEQ ID NO: 73) (5'-ATCATCGAGCTCGCGGCCGCCTATCAAAAGTCTTA-ATGAGTT-3'), C6B1 (SEQ ID NO: 74) (5'-GAATTCCTCGAGCTGCAGCCCGGGTTTT-TATAGCTAATTAGTCATTTTTTCGTAAGTAAGTATTT TTATTTAA-3'), C6C1 (SEQ ID NO: 75) (5'-CCCGGGCTGCAGCTCGAGGAATTCTTTT-TATTGATTAACTAGTCAAATGAGTATATATAATTGAA AAAGTAA-3') and C6D1 (SEQ ID NO: 76) (5'-GATGATGGTACCTTCATAAATACAAGTTTGATTAAA-CTTAAGTTG-3') were used to construct pC6L. Oligonucleotide primers C6A1 (SEQ ID NO: 73) and C6B1 (SEQ ID NO: 74) were used in a PCR with canarypox DNA template to generate a 380 base pair fragment. A second PCR reaction with the canarypox DNA template, and oligonucleotide primers C6C1 (SEQ ID NO: 75) and C6D1 (SEQ ID NO: 76), generated a 1,155 base pair fragment. The two PCR reaction products were pooled and primed for a final PCR with C6A1 (SEQ ID NO: 73) and C6D1 (SEQ ID NO: 76), yielding a 1,613 base pair fragment. The final PCR product was digested with SacI and KpnI, and inserted between the SacI and KDnI sites of pBSSK+. The resultant C6 insertion plasmid was designated as pC6L. 7. Generation of pMM103 pC5LCDVHAF1 was digested with BamHI and treated with the Klenow fragment from the *E. coli* DNA polymerase, in the presence of 20 $\mu$M dNTPs to blunt end the BamHI site, followed by digestion with SmaI. The 4.2 kbp blunt ended BamHI to SmaI fragment, containing the H6 promoted CDV F and H6 promoted CDV HA ORFs, was inserted into the SmaI site of pC6L, generating plasmid pMM103.

8. Generation of pLF108

The pMM103 HindIII/BamHI 1,961 bp DNA fragment which contains the CDV F1 coding sequence and the 3' most region of the vaccinia virus H6 promoter, was gel purified and subsequently inserted between the corresponding restrictions sites of pBSSK+, generating pLF108 (FIGS. 43, 44, SEQ ID NO: 22).

Example 25

Generation of pLF111, Which Contains a Complete CDV F1 Expression Cassette

A pLF108 XbaI restriction site was engineered immediately upstream of the CDV F1 initiation codon (ATG) in the following manner. A 473 bp DNA fragment was amplified by PCR using pLF108 DNA as a template and LF448A (5' ACTGTACTCGAGTCTAGAATGCACAAGG-GAATCCCCAAAAGC 3') (SEQ ID NO: 77) and RW830 (5' ATTCCAATGTATCTGAGC 3') (SEQ ID NO: 78) as primers. The PCR amplified fragment was isolated using the Gene Clean procedure as previously described before being digested by XhoI and CelII. The resultant XhoI/CelII 136 bp DNA fragment was subsequently ligated with the 4,783 bp XhoI/CelII fragment of pLF108, generating pLF109.

The XbaI (#2,035) was deleted and a KsPI restriction site was engineered immediately downstream of pLF108 CDV F1 stop codon (TGA#2,016) in the following manner. A 431 bp DNA fragment was amplified by PCR using pLF109 as a template and LF449 (5'ACTGTACCGCGGTCAGTGTGATCTCACATAGGAT-TTCGA 3') (SEQ ID NO: 79) and CDV-FG (5' GGT-TGAAATAGATGGTG 3') (SEQ ID NO: 80) as the primers. The PCR amplified fragment was isolated using the Gene Clean procedure as previously described before being digested with Ks I and BfrI. The resultant 255 bp DNA fragment was gel purified and subsequently ligated with the 4,631 bp KspI/BfrI fragment of pLF109, generating pLF110.

The 1,997 bp pLF110 KspI/XbaI fragment which contains the CDV F1 coding sequence was subsequently ligated with the 3,244 bp KspI/XbaI fragment of pLF069, generating pLF111 (FIGS. 45, 46, SEQ ID NO: 23).

Example 26

Generation of pLF128, Which Contains a Modified Complete CDV F1 Expression Cassette In order to reduce the size of the polyadenylation cassette in the CDV F1 expression cassette from 241 bp to 153 bp, the following manipulations were performed. The pLF077 KspI/BamHI 146 bp fragment was gel purified as previously described and subsequently ligated with the pLF111 KspI/BamHI 5,002 bp fragment in order to generate pLF128 (FIGS. 47, 48, SEQ ID NO: 24).

Example 27

Generation of pLF130A, a Donor Plasmid for Insertion of CDV F1 Expression Cassette 12 bp Upstream of SmaI Site at CAV2 Genome Right End Plasmid pLF128 was digested by BamHI and subsequently partially digested by HindIII. The BamHI/HindIII 2,451 bp fragment contains the CDV F1 coding sequence coupled to the regulatory sequences in pLF077, and was treated with the Klenow fragment from the *E. coli* DNA polymerase before being ligated with the 6,243 bp NruI linearized pLF105, generating pLF130A and pLF130B. pLF130A corresponds to the rightward orientation of the expression cassette (FIGS. 49, 50, SEQ ID NO: 25).

Example 28

Generation of vCA-CDVF1-@12bp-up-SmaI

Ten μg of pLF130A were digested with BglII and NotI and the resulting 5,305 bp DNA fragment was isolated using the Gene Clean procedure as previously described and resuspended in $H_2O$ to a concentration of 100 ng/μl. MDCK cells were transfected using the Lipofectamine based procedure as previously described. Solution A was prepared by mixing 0.5 μg of 5.3 kbp BglII/NotI DNA fragment with 3 μg of purified vCA2 DNA. Solution A total volume was brought to 300 μl with supplemented serum free MEM medium. Transfected cells were harvested after 8 days and plated out on 150 mm diameter tissue culture dishes as previously described. The 1.4 kbp EcoRI/BamHI DNA fragment of pATICDVF1 was labelled by random priming using the procedure previously described and subsequently hybridized with a nitrocellulose membrane to lift viral plaques, as previously described. Two viral plaques cross-reacting with the probe were picked and are subjected to a plaque purification process, as previously described to yield vCA-CDVF1-@12bp-up-SmaI. This virus is characterized by restriction digestion (DNA analysis) and Southern Blot radioimmunoprecipitation (expression analysis).

Example 29

Additional Recombinants

Since the tag and other exogenous DNA had been incorporated into CAV2, other exogenous DNA can be incorporated into CAV2. Therefore, instead of the exogenous DNA used to generate vCA1, vCA2, vCA3, vCA4, vCA5, vCA6, vCA7, vCA8, and vCA-CDVF1-@12-bp-up-SmaI, exogenous DNA as described in U.S. Pat. Nos. 5,174,993 and 5,505,941 (e.g., recombinant avipox virus, vaccinia virus; rabies glycoprotein (G), gene, turkey influenza hemagglutinin gene, gp51,30 envelope gene of bovine leukemia virus, Newcastle Disease Virus (NDV) antigen, FelV envelope gene, RAV-1 env gene, NP (nudeoprotein gene of Chicken/Pennsylvania/1/83 influenza virus), matrix and preplomer gene of infectious bronchitis virus; HSV gD; entomopox promoter, inter alia), U.S. Pat. No. 5,338,683, e.g., recombinant vaccinia virus, avipox virus; DNA encoding Herpesvirus glycoproteins, inter alia; U.S. Pat. No. 5,494,807 (e.g., recombinant vaccinia, avipox; exogenous DNA encoding antigens from rabies, Hepatitis B, JEV, YF, Dengue, measles, pseudorabies, Epstein-Barr, HSV, HIV, SIV, EHV, BHV, HCMV, canine parvovirus, equine influenza, FeLV, FHV, Hantaan, *C. tetani,* avian influenza, mumps, NDV, inter alia); U.S. Pat. No. 5,503,834 (e.g., recombinant vaccinia, avipox, Morbillivirus [e.g., measles F, hemagglutinin, inter alia]); U.S. Pat. No. 4,722,848 (e.g., recombinant vaccinia virus; HSV tk, glycoproteins [e.g., gB, gD], influenza HA, Hepatitis B [e.g., HBsAg], inter alia); U.K. Patent GB 2 269 820 B and U.S. Pat. No. 5,514,375 (recombinant poxvirus; flavivirus structural proteins); WO 92/22641 (e.g., recombinant poxvirus; immunodeficiency virus, inter alia); WO 93/03145 (e.g., recombinant poxvirus; IBDV, inter alia); WO 94/16716 and U.S. application Ser. No. 08/184,009, filed Jan. 19, 1994 (e.g., recombinant poxvirus; cytokine and/or tumor associated antigens, inter alia); PCT/US94/06652 (Plasmodium antigens such as from each stage of the Plasmodium life cycle); U.S. Pat. No. 5,523,089, WO93/08306, PCT/US92/08697, Molecular Microbiology (1989), 3(4), 479–486, PCT publications WO 93/04175, and WO 96/06165 (Borrelia antigens and DNA therefor); and Briles et al. WO 92/14488 (pneumococcal DNA), are used to generate additional CAV2 recombinants with the exogenous DNA in regions as in vCA2 through vCA8 and vCA-CDVF1-@12bp-up-SmaI and deletions as in vCA2 through vCA8 and vCA-CDVF1-@12bp-up-SmaI (e.g., insertions in the E3 or at the region between the right ITR and the E4 transcription unit or at both sites and deletions in the E3 region) including recombinants containing coding for multiple antigens, as herein described (including with subfragment promoters, reduced or modified polyadenylation cassettes, and promoters with 5'UTR replaced). Analysis demonstrates expression. Compositions are prepared by admixture with a carrier or diluent for administration to a vertebrate (animal or human) hosts for generating responses, including antibody responses.

TABLE 1

Sizes of CAV2 DNA restriction fragments.
CAV2 DNA restriction fragments sizes

| Fragment # | A | B | C | D | E | F | G | H | I | J | K |
|---|---|---|---|---|---|---|---|---|---|---|---|
| BamHI | 14 | 8.1 | 6.1 | 2.1 | 0.8 | 0.7 | | | | | |
| EcoRI | 20 | 8.2 | 3.8 | | | | | | | | |
| Asp718 | 9.5 | 4.8 | 3.8 | 3.2 | 3.2 | 3 | 2.5 | 0.85 | 0.75 | | |
| SalI | 29 | 3.2 | | | | | | | | | |
| BglII | 29 | 2.8 | | | | | | | | | |
| BglI | 6.1 | 5 | 4.1 | 3.2 | 2 | 1.7 | 1.5 | 1.5 | 1 | 0.7 | ND |

TABLE 2

Characteristics of CAV2 E3 region ORFs

|  | ORF1 | ORF2 | ORF3 |
|---|---|---|---|
| MW (KDa.) | 12.6 | 40.7 | 18.6 |
| pI | 6.48 | 7.45 | 9.68 |
| Limits in FIG. 3 | 8–346 | 384–1478 | 1019–483 |

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

ABLETT, R. E. and L. A. BAKER. 1960. Veterinary Record, 72, 1202.

APPEL, M. , S. I. BISTNER, M. MENEGUS, D. A. ALBERT and L. E. CARMICHAEL. 1973. Pathogenicity of low-virulence strains of two canine adenovirus types. Am. J. Vet. Res., 34, 543–550.

APPEL, M. J. G. and D. H. PERCY. 1970. SV-5-like parainfluenza virus in dogs. J.A.V.M.A., 156, 1778–1781.

APPEL, M. J. G., PICKERILL, R. G., M. MENEGUS, D. H. PERCY, D. H. PARSONSON and B. E. SHEFFY. 1970. 20$^{th}$ Ganes Veterinary Symposium, Manhattan, USA, pp 15–23.

ASSAF, R., C. MONPETIT, G. MARSOLAIS, M. AMINZADEHM, L. LAMONTAGNE and P. MAROIS. 1978. MV Quebec, 8, 10–12.

BASS, E. P., M. A. GILL and W. H. BECKENHAUER. 1980. Evaluation of canine adenovirus type 2 as a replacement for infectious canine hepatatis vaccine. J. Am. Vet. Med. Assoc., 177, 234–242.

BETT, A. J., L. PREVEC and F. L. GRAHAM. 1993. Packaging capacity and stability of human adenovirus type 5 vectors. J. Virol., 67, 5911–5921.

BINN, L. N., EDDY, G. A., LAZAR, E. C., HELMS, J. and T. MURNANE. 1967. Viruses recovered from laboratory dogs with respiratory disease. Proceedings of the Society of Experimental Biology and Medicine, 126, 140–145.

BOSHART, M., F. WEBER, G. JAHN, K. DORSH-HÄKSLER, B. FLECKENSTEIN and W. SCHAFFNER. 1985. A very strong enhancer is located upstream of an immediate early gene of human cytomegalovirus. Cell, 41, 521–530.

BOTH, G. W. , L. J. LOCKETT, V. JANARDHANA, S. J. EDWARDS, A. R. BELLAMY, F. L. GRAHAM, L. PREVEC and M. E. ANDREW. 1993. Protective immunuty to rotavirus-induced diarrhoea is passively transferred to newborn mice from naive dams vaccinated with single dose of a recombinant adenovirus expressing rotavirus VP7sc. Virology, 193, 940–950.

BREKER-KLASSEN, M., YOO, D., MITTAL, S. K., SORDEN, S. D., HAINES, D. M. and L. A. BABIUK. 1995. Recombinant type 5 adenovirus expressing bovine parainfluenza virus type 3 glycoproteins protect sigmodon hispidus cotton rat from bovine parainfluenza virus type 3 infection. J. Virol., 69, 4308–4315.

CABASSO, V. J., M. R. STEBBINS, T. W. NORTON and H. R. COX. 1954. Propagation of infectious canine hepatatis virus in tissue culture. Proceedings of the Society of Experimental Biology and Medicine, 85, 239–245.

CAVANAGH, H. M. A., C. F. GALLAGHER and N. SPIBEY. 1991. A mutant of canine adenovirus type 2 with a duplication of the Ela region exhibits altered expression of early region 4. J. Gen. Virol., 72, 2121–2127.

CHANDA, P. K., NATUK, R. J., B. B. MASON, B. M. BHAT, L. GREENBERG, S. K. DHEER, K. L. MOLNAR-KIMBER, S. MIZUTANI, M. D. LUBECK, A. R. DAVIS and P. P. HUNG. 1990. High level expression of the envelope glycoprotein of the human immunodeficiency virus type I in presence of rev gene using helper-independent adenovirus type 7 recombinants. Virology, 175, 535–547.

CHENGALVALA, M., M. D. LUBECK, A. R. DAVIS, S. MIZUTANI, K. MOLNAR-KIMBER, J. MORIN, and P. P. HUNG. 1991. Evaluation of adenovirus type 4 and type 7 recombinant hepatatis B vaccines in dogs. Vaccine, 9, 485–490.

CHENGALVALA, M. V. , B. M. BHAT, R. BHAT, M. D. LUBECK, S. MIZUTANI, A. R. DAVIS and P. P. HUNG. 1994. Immunogenicity of high expression adenovirushepatatis B virus recombinant vaccines in dogs. J. Gen. Virol., 75, 125–131.

DANSKIN, D. 1973. Isolation of canine adenovirus A26/61 (Toronto) using canine kidney (MDCK) cell line. The Veterinary Record, 126–127.

DARTEIL, R., BUBLOT, M., LAPLACE, E., J. -F. BOUQUET, J. -C. AUDONNET and M. RIVIERE. 1995. Herpesvirus of turkey recombinant viruses expressing infectious bursal disease virus (IBDV) VP2 immunogen induce protection against an IBDV virulent challenge in chickens. Virology 211, 481–490.

DEWAR, R. L. , V. NATARAJAN, M. B. VASUDEVA-CHARI and N. P. SALZMAN. 1989. Synthesis and processing of human immunodeficiency virus type 1 envelope proteins encoded by recombinant human adenovirus. J. Virol. , 63, 129–136.

DITCHFIELD, J., L. W. MACPERSON and A. ZBITNEW. 1962. Association of a canine adenovirus (Toronto A26/61) with an outbreak of laryngotracheitis ("kennel cough"). Can. Vet. Jour., 3, 238–247.

DORSCH-HÄKSLER, K., G. M. KEIL, F. WEBER, M. JASIN, W. SCHAFFNER and U. H. KOSZINOWSKI. 1985. A long and complex enhancer activates transcription of the gene coding for the highly abundant early mRNA in murine cytomegalovirus. Proc. Natl. Acad. Sci., 82, 8325–8329.

EDBAUER, C., R. WEINBERG, J. TAYLOR, A. REY-SENELONGE, J-F. BOUQUET, P. DESMETTRE and E. PAOLETTI. 1990. Protection of chickens with a recombinant fowlpox virus expressing the newcastle disease virus hemagglutinin-neuraminidase gene. Virology, 179, 901–904.

ELOIT, M. , P. GILARDI-HEBENSTREIT, B. TOMA and M. PERRICAUDET. 1990. Construction of a defective adenovirus vector expressing the pseudorabies virus glycoprotein gp50 and its use as a live vaccine. J. Gen. Virol., 71, 2425–2431.

FAIRCHILD, G. A. and D. COHEN. 1969. Serological study of a canine adenovirus (Toronto A26/61) infection in dogs. Am. J. Vet. Res., 30, 923–928.

GALLICHAN, W. S., D. C. JOHNSON, F. L. GRAHAM and K. L. ROSENTHAL. 1993. Mucosal immunity and protection after intranasal immunization with recombinant adenovirus expressing herpes simplex virus glycoprotein B. J. of Infect. Dis. 168, 622–629.

GARCÍA-SASTRE, A. and P. PALESE. 1995. Influenza virus vectors. Biologicals, 23, 171–178.

GILLARD, S., SPEHNER, D., DRILLIEN, R., AND KIRN, A., Proc. Natl. Acad. Sci. USA 83, 5573–5577 (1986).

GOEBEL, S. J., G. P. JOHNSON, M. E. PERKUS, S. W. DAVIS, J. P. WINSLOW AND E. PAOLETTI, Virology 179, 517–563 (1990b).

GOEBEL, S. J., JOHNSON, G. P., PERKUS, M. E., DAVIS, S. W., WINSLOW, J. P., PAOLETTI, E., Virology 179, 247–266 (1990a).

GINSBERG, H. S., U. LUNDHOLM-BEAUCHAMP, R. L. HORSWOOD, B. PERNIS, W. S. M. WOLD, R. M. CHANOCK and G. A. PRINCE. 1989. Role of early region 3 (E3) in pathogenesis of adenovirus disease. Proc. Natl. Acad. Sci. USA, 86, 3823–3827.

GIRARD, M., R. ALTMEYER, S. van der WERF, C. WYCHOWSKI and A. MARTIN. 1995. The use of picornaviruses as vectors for the engineering of live recombinant vaccines. Biologicals, 23, 165–169.

GORMAN, C. M., D. GIES, G. McCRAY and M. HUANG. 1989. The human cytomegalovirus major immediate early promoter can be trans-activated by adenovirus early proteins. Virology, 171, 377–385.

GRAHAM, F. L., L. A. PREVEC, M. SCHEIDER, G. GHOSH-CHOUDHURY, M. McDERMOTT, and D. C. JOHNSON. 1988. Cloning and expression of glycoprotein genes in human adenovirus vectors. In: Technological Advances in Vaccine Development, 243–253.

GRAHAM, F. L., J. SMILEY, W. C. RUSSELL and R. NAIRN. 1977. Characteristics of a human cell line transformed by human adenovirus 5. J. Gen. Virol., 36, 59–72.

GRAND, R. J. A. 1987. The structure and function of the adenovirus early region 1 proteins. Biochem. J., 241, 25–38.

HADDADA, H., B. KLONJKOWSKI and M. PERRICAUDET. 1994. Adenoviral vectors of animal origin and use in gene therapy. Patent # WO94/26914.

HAJ-AHMAD, Y. and F. L. GRAHAM. 1986. Development of a helper-independent human adenovirus vector and its use in the transfer of herpes simplex virus thymidine kinase gene. J. Virol., 57, 267–274.

HSU, K. -H. L., M. D. LUBECK, B. M. BHAT, R. A. BHAT, B. KOSTEK, B. H. SELLING, S. MIZUTANI, A. R. DAVIS and P. P. HUNG. 1994. Efficacy of adenovirus-vectored syncytial virus vaccines in a new ferret model. Vaccine, 12, 607–612.

IMLER, J-L. 1995. Adenovirus vectors as recombinant viral vaccines. Vaccine, 13, 1143–1151.

IMPERIALE, M., G. AKUSJARVI and K. LEPPARD. 1995. Post-transcriptional control of adenovirus gene expression. Curr. Top. Microbiol. Immunol., 199, 139–171.

JOHNSON, D. C., G. GHOSH-CHOUDHURY, J. R. SMILEY, L. FALLIS and F. L. GRAHAM. 1988. Abundant expression of herpes simplex virus glycoprotein gB using an adenovirus vector. Virology, 164, 1–14.

JOUVENNE, P., M. DION and C. HAMELIN. 1987. Cloning, physical mapping and cross-hybridization of the canine adenovirus types 1 and 2 genomes. Gene, 60, 21–28.

KELLY, T. J., JR. and A. M. LEWIS, JR. 1973. Use of nondefective adenovirus-simian virus 40 hybrids for mapping the simian virus 40 genome. J. Virol., 12, 643–652.

KIT, M., S. KIT, S. P. LITTLE, R. D. DI MARCHI, AND C. GALE. 1991. Bovine herpesvirus-1 (infectious bovine rhinotracheitis virus)-based viral vector which expresses foot-and-mouth disease epitopes. Vaccine, 9, 564–572.

KOPTOPOULOS, G. and H. J. C. CORNWELL. 1981. Veterinary bulletin, 51, 135–142.

LAFEMINA, R. L, M. C. PIZZORNO, J. D. MOSCA and G. S. HAYWARD. 1989. Expression of the acidic nuclear immediate early protein (IEI) of human cytomegalovirus in stable cell lines and its preferential association with metaphase chromosomes. Virology, 172, 584–600.

LINNÉ, T. 1992. Differences in E3 region of the canine adenovirus type 1 and type 2. Virus Research, 23, 119–133.

LUBECK, M. D., A. R. DAVIS, M. CHENGALVALA, R. J. NATUK, J. E. MORIN, K. MOLNAR-KIMBER, B. B. MASON, B. M. BHAT, S. MIZUTANI, P. P. HUNG and R. H. PURCELL. 1989. Immunogenicity and efficacy testing in chimpanzees of an oral hepatatis B vaccine based on a live recombinant adenovirus. Proc. Natl. Acad. Sci. USA, 86, 6763–6767.

LUBECK, M. D., R. J. NATUK, M. CHENGALVALA, P. K. CHANDA, K. K. MURTHY, S. MURTHY, S. MIZUTANI, S. -G. LEE, M. S. WADE, B. M. BHAT, R. BHAT, S. K. DHEER, J. W. EICHBERG, A. R. DAVIS and P. P. HUNG. 1994. Immunogenicity of recombinant adenovirus-human immunodeficiency virus vaccines in chimpanzees following intranasal administration. AIDS. Res. Hum. Retr., 10, 1443–1449.

MACARTNEY, L., H. M. A. CAVANAGH and N. SPIBEY. 1988. Isolationof canine adenovirus-2 from faeces of dogs with enteric disease and its unambigous typing by restriction endonuclease mapping. Research in Veterinary Science, 44, 9–14.

McDERMOTT, M. R., F. L. GRAHAM, T. HANKE and D. C. JOHNSON. 1989. Protectiuon of mice against lethal challenge with herpes simplex by vaccination with an adenovirus vector expressing HSV glycoprotein B. Virology, 169, 244–247.

METTENLEITER, T. C., B. G. KLUPP, F. WEILAND and N. VISSER. 1994. Characterization of a quadruple glycoprotein-deleted pseudorabies virus mutant for use as a biologically safe live virus vaccine. 75, 1723–1733.

MITTAL, S. K., A. J. BETT, L. PREVEC and F. L. GRAHAM. 1995b. Foreign gene expression by human adenovirus type 5-based vectors studied using firefly luciferase and bacterial 3-galactosidase genes as reporters. Virology, 210, 226–230.

MITTAL, S. K., L. PREVEC, F. L. GRAHAM and L. A. BABIUK. 1995a. Development of a bovine adenovirus type 3-based expression vector. J. Gen. Virol., 76, 93–102.

MORIN, J. E., M. D. LUBECK, J. E. BARTON, A. J. CONLEY, A. R. DAVIS and P. P. HUNG. 1987. Recombinant adenovirus induces antibody response to hepatatis B virus surface antigen in hamsters. Proc. Natl. Acad. Sci. USA, 84, 4626–4630.

MUELLER, R. E., R. L. MULDOON and G. G. JACKSON. 1969. Communicability of enteric live adenovirus type 4 vaccine in families. J. Infect. Dis., 119, 60–66.

NATUK, R. J., M. D. LUBECK, P. K. CHANDA, M. CHENGALVALA, M. S. WADE, S. C. S. MURTHY, J. WILHELM, S. K. VERNON, S. K. DHEER, S. MIZUTANI, S. -G. LEE, K. K. MURTHY, J. W. EICHBERG, A. R. DAVIS and P. P. HUNG. 1993. Immunogenicity of recombinant human adenovirus-human immunodeficiency virus vaccines in chimpanzees. AIDS. Res. Hum. Retr., 9, 395–404.

NEVINS, J. R. 1993. Transcriptional activation by the adenovirus E1A prteins. Seminars in Virology, 4, 25–31.

OUALIKENE, W., P. GONIN and M. ELOIT. 1994. Short and long term dissemination of deletion mutants of adenovirus in permissive (cotton rat) and non-permissive (mouse) species. J. Gen. Virol., 75, 2765–2768.

PERKUS, M. E., LIMBACH, K., AND PAOLETTI, E., J. Virol. 63, 3829–3836 (1989).

PERKUS, M. E., J. TARTAGLIA and E. PAOLETTI. 1995. Poxvirus-based vaccine candidates for cancer, AIDS, and other infectious diseases. J. Leuk. Biol., 58, 1–13.

PERKUS, M. E., E. B. KAUFFMAN, J. TAYLOR, S. MERCER, D. SMITH, J. VANDERHOEVEN, and E. PAOLETTI. 1993. Methodology of using vaccinia virus to express foreign genes in tissue culture. J. Tiss. Cult. Meth. 15:72–81.

PERRICAUDET, M. and L. D. STRATFORD-PERRICAUDET. 1995. Adenovirus-mediated in vivo gene therapy. In: Viruses in human gene therapy. Carolina Academic Press, 1–32.

PREVEC, L., M. SCHNEIDER, K. L. ROSENTHAL, L. W. BELBECK, J. B. DERBYSHIRE and F.L. GRAHAM. 1989. Use of human adenovirus-based vectors for antigen expression in animals. J. Gen. Virol., 70, 429–434.

RAGOT, T. , S. FINERTY, P. E. WATKINS, M. PERRICAUDET and A. J. MORGAN. 1993. Replication-defective recombinant adenovirus expressing the Epstein-Barr virus (EBV) envelope glycoprotein gp340/220 induces protective immunity against EBV-induced lymphomas in cottontop tamarin. J. Gen. Virol., 74, 501–507.

RANDRIANARISON-JEWTOUKOFF, V. and M. PERRICAUDET. 1995. Recombinant adenovirus as vaccines. Biologicals, 23, 145–157.

ROBINSON, A. J., H. B. YOUNDHUSBAND and A. J. D. BELLETT. 1973. A circular DNA-protein complex from adenoviruses. Virology, 56, 54–69.

ROSS, L. J. N., M. M. BINNS, P. TYERS, J. PASTOREK, V. ZELNIK and S. SCOTT. 1993. Construction and properties of a turkey herpesvirus recombinant expressing the Marek's disease virus homolgue of glycoprotein B of herpes simplex virus. J. Gen. Virol. 74, 371–377.

SAITO, I. , Y. OYA, K. YAMAMOTO, T. YUASA and H. SHIMOJO. 1985. Construction of nondefective adenovirus type 5 bearing a 2.8 kilobase hepatatis B virus DNA near the right end of its genome. J. Virol. , 54, 711–719.

SCHWARTZ, A. R., Y. TOGO and R. B. HORNICK. 1974. Clinical evaluation of live types 1, 2 and 5 adenovirus vaccines. Am. Rev. Resp. Dis., 109, 233-

SEDEGAH, M., C. H. CHIANG, W. R. WEISS, S. MELLOUK, M. D. COCHRAN, R. A. HOUGHTEN, the late R. L. BEUDOIN, D. SMITH, and S. L. HOFFMAN. 1992. recombinant pseudorabies virus carrying a plasmodium gene: herpesvirus as a new live viral vector for inducing T- and B-cell immunity. Vaccine, 10, 578–584

SHARP, P. 1984. Adenovirus transcription. In: The adenovirus, Ed. H. S. GINSBERG, Plenun Press, New-York and London. Pp. 173–204. SPIBEY, N. and H. M. A. CAVANAGH. 1989. Molecular cloning and restriction endonuclease mapping of two strains of canine adenovirus type 2. J. Gen. Virol., 70, 165–172.

SUMMER, J. W. , J. H. SHADDOCK, G. -J. WU and G. M. BAER. 1988. Oral administration of an attenuated strain of canine adenovirus (type 2) to raccoons, foxes, shunk and mongoose. Am. J. Vet. Res., 49, 169–171.

SWANGO, L. J., W. L. WOODING and L. N. BINN. 1970. A comparison of the pathogenesis of infectious canine hepatatis virus and the A26/61 virus strain (Toronto). J.A.V.M.A., 156, 1687–1696.

TAYLOR, J., C. TRIMARCHI, R. WEINBERG, B. LANGUET, F. GUILLEMIN, P. DESMETTRE and E. PAOLETTI. 1991. Efficacy studies on a canarypox-rabies recombinant virus. Vaccine, 9, 190–193.

THUMMEL, C., R. TJIAN, S. -L. HU, and T. GRODZICKER. 1983. Translational control of SV40 T antigen expressed from the adenovirus late promoter. Cell, 33, 455–464.

TOP, JR, F. H., R. A. GROSSMAN, P. J. BARTELLONI, H. E. SEGAL, B. A. DUDDING, P. K. RUSSELL and E. L. BUESCHER. 1971b. Immunization with live types 7 and 4 vaccines. I. Safety, infectivity, antigenicity and potency of adenovirus type 7 vaccine in humans. J. Inf. Dis., 124, 148–154.

TOP, JR., F. H. , E. L. BUESCHER, W. H. BANCROFT and P K. RUSSELL. 1971a. Immunization with live types 7 and 4 vaccines. II. Antibody response and protective effect against accutate respiratory disease due to adenovirus type 7. J. Inf. Dis., 124, 155–160.

WESSELING, J. G. , G. -J. GODEKE, V. E. C. J. SCHIJNS, L. PREVEC, F. L. GRAHAM, M. C. HORZINEK and P. J. M. ROTTIER. 1993. Mouse hepatitis virus spike and nucleocapsid proteins expressed by adenovirus vectors protect mice against a lethal infection. J. Virol., 74, 2061–2069.

WOLD, W. S. M. and L. R. GOODING. 1991. Minireview: Region E3 of adenovirus: A cassette of genes involved in host immunosurveillance and virus-cell interactions. Virology, 184, 1–8.

XU, Z. Z., V. KROUGLIAK, L. PREVEC, F. L. GRAHAM and G. W. BOTH. 1995. Investigation of promoter function in human and animal cells infected with human recombinant adenoviruses expressing rotavirus antigen VP7sc. J. Gen. Virol., 76, 1971–1980.

ZHANG, Y. and R. J. SCHNEIDER. 1993. Adenovirus inhibition of cellular protein synthesis and the specific translation of late viral mRNAs. Seminars in Virology, 4, 229–236.

What is claimed is:

1. A truncated transcriptionally active cytomegaloviruts immediate early promoter consisting essentially of a DNA sequence selected from the group consisting of (i) a DNA sequence of 91 base pairs in length and set forth in FIG. 21, and (ii) a DNA sequence of 145 base pairs in length and set forth in FIG. 13.

2. The truncated pronmoter of claim 1, wherein the DNA sequence is 91 base pairs in length and set forth in FIG. 21.

3. The truncated promoter of claim 1, wherein the DNA sequence is 145 base pairs in length and set forth in FIG. 13.

4. A recombinant canine adenovirus (CAV) comprising the promoter of claim 1.

5. A recombinant canine adenovirus type 2 (CAV2) comprising the promoter of claim 1.

6. The recombinant CAV2 of claim 5, further comprising a heterologous DNA operably linked to the promoter.

7. The recombinant CAV2 of claim 5, further comprising a functional truncated polyadenylation signal.

8. The recombinant CAV2 of claim 5, wherein the promoter comprises a region transactivated with a transactivating protein of CAV2.

9. A host cell transformed with the recombinant virus of claim 5.

10. An expression cassette for insertion into a recombinant virus comprising the promoter of claim 1.

11. The expression cassette of claim 10, further comprising a heterologous DNA operably linked to the truncated promoter.

12. The expression cassette of claim 11, further comprising a functional truncated polyadenylation signal.

13. A plasmid containing the promoter of claim 1.

14. The plasmid of claim 13, further comprising a heterologous DNA linked operably to the truncated promoter.

15. The plasmid of claim 14, further comprising a functional truncated polyadenylation signal.

* * * * *

UNITED STATES PATENT AND TRADEMARK OFFICE
CERTIFICATE OF CORRECTION

PATENT NO. : 6,156,567
DATED : December 5, 2000
INVENTOR(S) : Laurent Fischer

It is certified that error appears in the above-identified patent and that said Letters Patent is hereby corrected as shown below:

Claim 1,
Line 1, change "cytomegaloviruts" to -- cytomegalovirus --.

Claim 2,
Line 1, change "pronomoter" to -- promoter --.

Signed and Sealed this

Twenty-fifth Day of September, 2001

*Attest:*

NICHOLAS P. GODICI
*Attesting Officer*     *Acting Director of the United States Patent and Trademark Office*